US010350288B2

(12) United States Patent
Hetherington

(10) Patent No.: US 10,350,288 B2
(45) Date of Patent: Jul. 16, 2019

(54) METHODS AND COMPOSITIONS FOR TREATING HERPES

(71) Applicant: Genocea Biosciences, Inc., Cambridge, MA (US)

(72) Inventor: Seth Vollmer Hetherington, Chapel Hill, NC (US)

(73) Assignee: Genocea Biosciences, Inc., Cambridge, MA (US)

(*) Notice: Subject to any disclaimer, the term of this patent is extended or adjusted under 35 U.S.C. 154(b) by 0 days.

(21) Appl. No.: 15/717,849

(22) Filed: Sep. 27, 2017

(65) Prior Publication Data

US 2018/0133310 A1 May 17, 2018

Related U.S. Application Data

(60) Provisional application No. 62/401,148, filed on Sep. 28, 2016.

(51) Int. Cl.

| *C12N 7/04* | (2006.01) |
| *A61K 31/52* | (2006.01) |
| *A61K 38/00* | (2006.01) |
| *A61K 39/00* | (2006.01) |
| *A61K 39/12* | (2006.01) |
| *A61P 31/22* | (2006.01) |
| *A61K 31/522* | (2006.01) |
| *A61K 39/245* | (2006.01) |
| *C07K 14/035* | (2006.01) |
| *G01N 33/569* | (2006.01) |

(52) U.S. Cl.
CPC ............ *A61K 39/245* (2013.01); *A61K 31/52* (2013.01); *A61K 31/522* (2013.01); *A61K 38/00* (2013.01); *A61K 39/12* (2013.01); *A61P 31/22* (2018.01); *C07K 14/035* (2013.01); *C12N 7/04* (2013.01); *G01N 33/56994* (2013.01); *A61K 2039/545* (2013.01); *A61K 2039/55511* (2013.01); *A61K 2039/55577* (2013.01); *C12N 2710/16622* (2013.01); *C12N 2710/16634* (2013.01); *G01N 2333/035* (2013.01)

(58) Field of Classification Search
CPC ...... A61K 39/245; A61K 39/12; A61K 38/00; A61K 31/52; A61K 31/522; A61K 2039/55511; A61K 2039/545; A61K 2039/55577; A61K 39/00; A61K 35/763; A61K 35/76; A61K 2039/525; A61K 2039/6075; A61K 39/25; C07K 14/035; C07K 14/005; C07K 16/085; C07K 14/03; C12N 7/04; C12N 2710/16622; C12N 2710/16634; C12N 7/00; C12N 2710/16034; C12N 2710/16611; C12N 2710/16011; A61P 31/22; G01N 2333/035; G01N 33/56994
See application file for complete search history.

(56) References Cited

U.S. PATENT DOCUMENTS

| 4,818,694 A | 4/1989 | Watson et al. |
| 5,149,529 A | 9/1992 | Ho et al. |
| 5,612,041 A | 3/1997 | Burke et al. |
| 5,648,079 A | 7/1997 | Burke et al. |
| 5,654,174 A | 8/1997 | Cohen et al. |
| 5,656,457 A | 8/1997 | Parkes et al. |
| 5,679,348 A | 10/1997 | Nesburn et al. |
| 5,750,114 A | 5/1998 | Burke et al. |
| 5,763,406 A | 6/1998 | Pedersen et al. |
| 5,795,579 A | 8/1998 | Burke et al. |
| 5,807,557 A | 9/1998 | Dubin |
| 5,851,533 A | 12/1998 | Berman et al. |
| 5,876,923 A | 3/1999 | Leopardi et al. |
| 5,955,088 A | 9/1999 | Ghiasi et al. |
| 5,958,895 A | 9/1999 | Pachuk et al. |
| 5,962,428 A | 10/1999 | Carrano et al. |
| 6,027,730 A | 2/2000 | Francotte et al. |
| 6,156,319 A | 12/2000 | Cohen et al. |
| 6,197,497 B1 | 3/2001 | Goade et al. |
| 6,207,168 B1 | 3/2001 | Aurelian |
| 6,352,697 B1 | 3/2002 | Cox et al. |
| 6,413,518 B1 | 7/2002 | Koelle et al. |
| 6,468,982 B1 | 10/2002 | Weiner et al. |
| 6,537,555 B2 | 3/2003 | Hosken et al. |
| 6,635,258 B2 | 10/2003 | Burke et al. |
| 6,682,892 B2 | 1/2004 | Homa et al. |
| 6,692,752 B1 | 2/2004 | Slaoui et al. |
| 6,814,969 B2 | 11/2004 | Koelle et al. |
| 6,867,000 B2 | 3/2005 | Mishkin et al. |
| 6,932,972 B2 | 8/2005 | Stephenne et al. |
| 6,936,255 B1 | 8/2005 | Wettendorff |
| 6,962,709 B2 | 11/2005 | Koelle et al. |
| 7,037,509 B2 | 5/2006 | Koelle et al. |
| 7,078,041 B2 | 7/2006 | Koelle et al. |
| 7,094,767 B2 | 8/2006 | Armstrong et al. |

(Continued)

FOREIGN PATENT DOCUMENTS

| EP | 0139417 A1 | 5/1985 |
| WO | WO-94/29456 A2 | 12/1994 |

(Continued)

OTHER PUBLICATIONS

Wald A, Warren T, Fife K, et al. 1333—Therapeutic HSV-2 vaccine (GEN003) results in durable reduction in genital lesions at 1 year. Open Forum Infectious Diseases. 2014;1(Suppl 1):S55-S56. doi:10. 1093/ofid/ofu051.150.*

(Continued)

*Primary Examiner* — Rachel B Gill
(74) *Attorney, Agent, or Firm* — Choate, Hall & Stewart LLP; Brenda Herschbach Jarrell; Rolando Medina

(57) ABSTRACT

The present disclosure provides certain combinations of immunogenic compositions against HSV-2 and antiviral therapy. The vaccines can be used therapeutically and/or prophylactically.

27 Claims, 7 Drawing Sheets

Specification includes a Sequence Listing.

(56) References Cited

U.S. PATENT DOCUMENTS

| | | | |
|---|---|---|---|
| 7,157,437 | B2 | 1/2007 | Van Nest |
| 7,196,066 | B1 | 3/2007 | Swain et al. |
| 7,264,817 | B1 | 9/2007 | Berman et al. |
| 7,267,940 | B2 | 9/2007 | Chen et al. |
| 7,569,218 | B2 | 8/2009 | Weiner et al. |
| 7,628,993 | B2 | 12/2009 | Vilalta et al. |
| 7,666,434 | B2 | 2/2010 | Koelle et al. |
| 7,744,903 | B2 | 6/2010 | Koelle et al. |
| 8,197,824 | B2 | 6/2012 | Koelle et al. |
| 8,313,894 | B2 | 11/2012 | Flechtner et al. |
| 8,617,564 | B2 | 12/2013 | Long et al. |
| 9,624,273 | B2 | 4/2017 | Long et al. |
| 9,782,474 | B2 | 10/2017 | Long et al. |
| 9,895,436 | B2 | 2/2018 | Long et al. |
| 2002/0058021 | A1 | 5/2002 | Audonnet et al. |
| 2003/0017174 | A1 | 1/2003 | Burke et al. |
| 2003/0165537 | A1 | 9/2003 | Fehler et al. |
| 2003/0165819 | A1 | 9/2003 | McGowan et al. |
| 2003/0165820 | A1 | 9/2003 | Day et al. |
| 2004/0220076 | A1 | 11/2004 | Aurelian et al. |
| 2006/0280752 | A1 | 12/2006 | BenMohamed et al. |
| 2007/0196389 | A1 | 8/2007 | Caligiuri et al. |
| 2008/0145375 | A1 | 6/2008 | Bembridge et al. |
| 2008/0299140 | A1 | 12/2008 | Georges et al. |
| 2009/0148467 | A1 | 6/2009 | Friedman et al. |
| 2010/0203073 | A1 | 8/2010 | Koelle |
| 2010/0330112 | A1 | 12/2010 | Long et al. |
| 2011/0293664 | A1 | 12/2011 | Cohane et al. |
| 2012/0135025 | A1 | 5/2012 | Flechtner et al. |
| 2013/0171234 | A1 | 7/2013 | Fairman et al. |
| 2013/0337000 | A1 | 12/2013 | Long et al. |
| 2014/0227307 | A1 | 8/2014 | Long et al. |
| 2014/0328870 | A1* | 11/2014 | Long .................. A61K 39/245 424/186.1 |

FOREIGN PATENT DOCUMENTS

| | | |
|---|---|---|
| WO | WO-95/06055 A1 | 3/1995 |
| WO | WO-95/16779 A1 | 6/1995 |
| WO | WO-98/20016 A1 | 5/1998 |
| WO | WO-00/77043 A2 | 12/2000 |
| WO | WO-01/44477 A1 | 6/2001 |
| WO | WO-02/02131 A2 | 1/2002 |
| WO | WO-03/020108 A2 | 3/2003 |
| WO | WO-03/086308 A2 | 10/2003 |
| WO | WO-03/099860 A2 | 12/2003 |
| WO | WO-2004/009021 A2 | 1/2004 |
| WO | WO-2005/028496 A2 | 3/2005 |
| WO | WO-2007/106404 A2 | 9/2007 |
| WO | WO-2008/011609 A2 | 1/2008 |
| WO | WO-2008/027394 A2 | 3/2008 |
| WO | WO-2008/030560 A2 | 3/2008 |
| WO | WO-2008/085486 A1 | 7/2008 |
| WO | WO-2008/140478 A2 | 11/2008 |
| WO | WO-2009/006618 A2 | 1/2009 |
| WO | WO-2009/006680 A1 | 1/2009 |
| WO | WO-2010/02326 A1 | 1/2010 |
| WO | WO-2010/103017 A2 | 9/2010 |
| WO | WO-2010/135747 A1 | 11/2010 |
| WO | WO-2010/135749 A1 | 11/2010 |
| WO | WO-2011/112717 A1 | 9/2011 |
| WO | WO-2012/074881 A2 | 6/2012 |
| WO | WO-2013/078299 A1 | 5/2013 |
| WO | WO-2018/064232 A1 | 4/2018 |

OTHER PUBLICATIONS

United States Securities and Exchange Commission, Form S-1. Genocea Biosciences, Inc. Preliminary Prospectus, 2014. https://www.sec.gov/Archives/edgar/data/1457612/000104746913011353/a2217746zs-1.htm. Dec. 23, 2013.*

Genocea. Honeycomb Herpes Forum—Support Group Online for HSV. Comments by Chip Clark, CEO Genocea Biosciences, Inc. Oct. 7, 2015. https://honeyconnb.click/topic/61135-genocea-reports-good-results-one-year-later/?page=8&tab=comments#comment-365484.*

Press Release: "Genocea Reports Fourth Quarter and Year-End 2015 Financial Results." Published Feb. 11, 2016. Globe Newswire, https://www.cnbc.com/2016/02/11/globe-newswire-genocea-reports-fourth-quarter-and-year-end-2015-financial-results.html.*

"Genocea Reports Second Quarter 2016 Financial Results." Aug. 4, 2016. Globe Newswire. http://ir.genocea.com/releasedetail.cfm?releaseid=982898.*

Lawrence J. "Oral and genital herpes: four experimental treatment strategies." The Pharmaceutical Journal. Sep. 20, 2016. https://www.pharmaceutical-journal.com/news-and-analysis/features/oral-and-genital-herpes-four-experimental-treatment-strategies/20201735.fullarticle.*

Van Reenen M, Janssen B. EQ-5D-5L User Guide: Basic information on how to use the EQ-5D-5L instrument. Ver. 2.1. Apr. 2015.*

ClinicalTrials.gov. "Rollover Trial for Placebo Subjects Previously Enrolled Into GEN-003-002 Study". Genocea Biosciences, Inc. NCT02300142. Updated Jul. 1, 2015.*

International Search Report for PCT/US2017/053835, ISA/US, 4 pages (dated Nov. 21, 2017).

Kimberlin, D.W. et al., Human Herpesviruses: Biology, Therapy, and Immunoprophylaxis. Cmbridge: Cambridge University Press (2007). URL: <https://www.ncbi.nlm.gov/books/NBK47376/> [Retrieved from the Internet on Nov. 16, 2017].

Thermet, A. et al., DNA vaccination in combination or not with lamivudine treatment breaks humorl immune tolerance and enhances cccDNA clearance in the duck model of chronic hepatitis B virus infection, The Journal of General Virology, 89(5): 1192-1201 (2008).

Written Opinion for PCT/US2017/053835, ISA/US, 15 pages (dated Nov. 21, 2017).

Ashley, R. et al., Humoral Immune Response to Herpes Simplex Virus Type 2 Glycoproteins in Patients Receiving a Glycoprotein Subunit Vaccine, Journal of Virology, 56(2):475-481 (1985).

Awasthi, S. and Friedman, HM., Status of prophylactic and therapeutic genital herpes vaccines, Curr. Opin Virol., 6:6-12 (2014).

Baccari, A. et al., Both HSV-2 and HSV-1 neutralizing antibody titers are boosted in subjects with genital herpes after vaccination with GEN-0003, a novel HSV-2 immunotherapy, Paper Poster Session 1, Abstract, P0279 (2015).

Benedetti, J. et al, Recurrence rates in genital herpes after symptomatic first-episode infection, Ann Intern. Med., 121(11):847-54 (1994).

Bernstein, D.J. et al., Effects of herpes simplex virus type 2 glycoprotein vaccines and CLDC adjuvant on genital herpes infection in the guinea pig, Vaccine, 29: 2071-2078 (2011).

Birkmann, A. and Zimmermann, H., HSV antivirals—current and future treatment options, Curr. Opin. Virol., 18:9-13 (2016).

Boursnell, M. et al., A Genetically Inactivated Herpes Simplex Virus Type 2 (HSV-2) Vaccine Provides Effective Protection against Primary and Recurrent HSV-2 Disease, The Journal of Infectious Diseases, 175(1): 16-25 (1997).

Bowie, J.U. et al., Deciphering the message in protein sequences: tolerance to amino acid substitutions, Science, 247(4948): 1306-1310 (1990).

Braun, R.P. et al., Characterization of the IFN-γ T-cell responses to immediate early antigens in humans with genital herpes, Virology Journal, 3(54):1-15 (2006).

Braun, R.P. et al., Multi-antigenic DNA immunization using herpes simplex virus type 2 genomic fragments, Human Vaccines, 4(1): 36-43 (2008).

Cattamanchi, A. et al., Phase I Study of a Herpes Simplex Virus Type 2 (HSV-2) DNA Vaccine Administered to Healthy, HSV-2-Seronegative Adults by a Needle-Free Injection System, Clinical and Vaccine Immunology, 15(11):1638-1643 (2008).

Centers for Disease Control, Seroprevalence of herpes simplex virus type 2 among persons aged 14-49 years—United States, 2005-2008, MMWR Morb Mortal Wkly Rep., 59(50):456-9 (2010).

(56) References Cited

OTHER PUBLICATIONS

Corey, L. et al, Once-daily valacyclovir to reduce the risk of transmission of genital herpes, New England J. Med., 350:11-20 (2004).
Corey, L., Herpes simplex virus type 2 and HIV-1: the dialogue between the 2 organisms continues, J. Infect. Dis., 195:1242-4 (2007).
Dasgupta, G. et al., New Concepts in Herpes Simplex Virus Vaccine Development: Notes from the Battlefield, Expert Rev. Vaccines, 8(8):1023-1035 (2009).
Database EMBL P28278 (GL_HHV2H), Jan. 12, 1992 [retrieved on Sep. 1, 2013]. Retrieved from the internet: <URL:http//www.uniprot.org/uniprot/P28278>).
Database EMBL Q69467 (GD_HHV2H), Jan. 11, 1996 [retrieved on Sep. 1, 2013]. Retrieved from the internet: <URL:http//www.uniprot.org/uniprot/Q69467>).
De Bruyn, G. et al., A randomized controlled trial of a replication defective (gH deletion) herpes simplex virus vaccine for the treatment of recurrent genital herpes among immunocompetent subjects, Vaccine, 24:914-20 (2006).
Dolan, A., Herpes simplex virus type 2 (strain HG52), complete genome, GenBank Acc No. Z86099.2, Dep. Mar. 5, 1997, Rev. Nov. 14, 2006.
Dolan, A., Human herpesvirus 2, complete genome. NCBI Reference Sequence: NC_001798.1. Dep. Apr. 3, 2000.
Dolan, A., RS1 [human herpesvirus 2]. NCBI Reference Sequence: NC_044530.1. Dep. Apr. 3, 2000.
Dolan, A., Virion glycoprotein D [Human herpesvirus 2]. NCBI Reference Sequence: NC_044536.1. Dep. Apr. 3, 2000.
Dolan, A., Virion glycoprotein L [Human herpesvirus 2]. NCBI Reference Sequence: NC_044470.1. Dep. Apr. 3, 2000.
Dolan, et al., The Genome Sequence of Herpes Simplex Virus Type 2, J. Virol., 72(3):2010-2021 (1998).
Famvir® (famciclovir) tablets, Highlights of Prescribing Information, 16 pages. (2013).
Fife, K. H. et al, Effect of Valacyclovir on Viral Shedding in Immunocompetent Patients With Recurrent Herpes Simplex Virus 2 Genital Herpes: A US-Based Randomized, Double-Blind, Placebo-Controlled Clinical Trial, Mayo Clin. Proc., 81(10): 1321-7 (2006).
Fife, K.H. et al., An International, Randomized, Double-Blind, Placebo-Controlled, Study of Valacyclovir for the Suppression of Herpes Simplex Virus Type 2 Genital Herpes in Newly Diagnosed Patients, Sexually Transmitted Diseases 35(7): 668-673 (2008).
Fló, J., Co-immunization with plasmids coding the full length and a soluble form of glycoprotein D of HSV-2 induces protective cellular and humoral immune response in mice, Vaccine, 21(11-12): 1239-1245 (2003).
Fló, J., et al., Superiority of intramuscular route and full length glycoprotein D for DNA vaccination against herpes simplex 2. Enhancement of protection by the co-delivery of the GM-CSF gene. Vaccine, 18(28): 3242-3253 (2000).
Freeman, E.F. et al., Herpes simplex virus 2 infection increases HIV acquisition in men and women: systematic review and meta-analysis of longitudinal studies, AIDS, 73-83 (2006).
Garland, S.M. et al., Genital herpes, Best Practice & Research Clinical Obstetrics and Gynaecology, 28: 1098-1110 (2014).
GenBank ABU45435.1, glycoprotein D [Human herpesvirus 2] (Nov. 29, 2007).
Genbank BAA01264.1 (May 29, 2002).
Genbank CAB06713.1 (Nov. 14, 2006).
GenBank Direct Submission UniProtKB/Swiss-Prot: P28278.1, Envelope glycoprotein L; Short=gL; Flags: Precursor (2010).
Genocea Biosciences, Genocea Announces Positive Durability Data from 6-Month Analysis of Phase 2 Clinical Trial of Genital Herpes Immunotherapy GEN-003, Business Wire, Cambridge, MA, 3 pages (Oct. 7, 2015).
Grabowska, A.M. et al., Immunisation with Phage Displaying Peptides Representing Single Epitopes of the Glycoprotein G can give rise to Partial Protective Immunity to HSV-2, Virology, 269: 47-53 (2000).

Gupta, R. et al, Genital herpes, Lancet., 370:2127-37 (2007).
Gupta, R. et al., Valacyclovir and acyclovir for suppression of shedding of herpes simplex virus in the genital tract, J Infect Dis.,190:1374-81(2004).
Hook, L.M. et al, Vaccine-induced Antibodies to Herpes Simplex Virus Glycoprotein D Epitopes Involved in Virus Entry and Cell-to-Cell Spread Correlate with Protection Against Genital Disease in Guinea pigs, PLos Pathog., 14(5):e1007095 (2018).
International Search Report for PCT/US2010/035998, 7 pages. (dated Oct. 26, 2010).
International Search Report for PCT/US2010/036000, 7 pages (dated Sep. 7, 2010).
International Search Report for PCT/US2011/62120, 6 pages (dated Jul. 10, 2012).
International Search Report for PCT/US2012/066241, dated Feb. 28, 2013, published as WO 2013/078299 (2 pages).
Johnston, C. et al, Standard-dose and high-dose daily antiviral therapy for short episodes of genital HSV-2 reactivation: three randomised, open-label, cross-over trials, Lancet, 379:641-7 (2012).
Jones, C.A. et al., Vaccination strategies to prevent genital herpes and neonatal herpes simplex virus (HSV) disease, The Journal of the IHMF (England), 11(1):12-7 (2004). Abstract only.
Kern, E. Acyclovir Treatment of Experiment Genital Herpes Simplex Virus Infection, Amer J of Med, 73suppl:100-108 (1982).
Kern, E.R., Treatment of Genital Herpes Simplex Virus Infection in Guinea pigs. In Herpes Virus (UCLA Symposia on Molecular and Cellular Biology, New Series vol. 21: 617-636 (1984).
Kimberlin, D.W. and Rouse, D.J., Genital herpes, New Engl J Med., 350:1970-7 (2004).
Knipe, D.M. et al.,Summary and recommendations from a National Institute of Allergy and Infectious Diseases (NIAID) workshop on "Next Generation Herpes Simplex Virus Vaccines", Vaccine, 32: 1561-1562 (2014).
Koelle, D.M. et al., Antigenic Specificities of Human CD4+ T-Cell Clones Recovered from Recurrent Genital Herpes Simplex Virus Type 2 Lesions, Journal of Virology, 68(5):2803-2810 (1994).
Koelle, D.M. et al., Immunodominance among herpes simplex virus-specific CD8 T cells expressing a tissue-specific homing receptor, PNAS, 100(22):12899-12904 (2003).
Langenberg, A.G.M. et al., A Recombinant Glycoprotein Vaccine for Herpes Simplex Type 2: Safety and Efficacy, Annals of Internal Medicine, 122(12):889-898 (1995).
Lasky, L.A. et al., DNA Sequence Analysis of the Type-Common Glycoprotein-D Genes of Herpes Simplex Virus Types 1 and 2, DNA, 3(1): 23-29 (1984).
Liljeqvist, J.A. et al., Monoclonal antibodies and human sera directed to the secreted glycoprotein G of herpes simplex virus type 2 recognize type-specific antigenic determinants, Journal of General Virology, 83:157-165 (2002).
Martens, M.G. et al, Once daily valacyclovir for reducing viral shedding in subjects newly diagnosed with genital herpes, Infect. Dis. Obstet. Gynecol., 2009:105376 (2009).
McClements, W.L. et al., Immunization with DNA vaccines encoding glycoprotein D or glycoprotein B, alone or in combination, induces protective immunity in animal models of herpes simplex virus-2 disease, Proceedings of the National Academy of Sciences, National Academy of Sciences, 93(21): 11414-11420 (1996).
McGeoch, et al., Comparative sequence analysis of the long repeat regions and adjoining parts of the long unique regions in the genomes of herpes simplex viruses types 1 and 2, J. Gen. Virol., 71:3057-3075 (1991).
Mertz, G.J. Asymptomatic Shedding of Herpes Simplex Virus 1 and 2: Implications for Prevention of Transmission, The Journal of Infectious Diseases, 198:1-2 (2008).
Meseda, C.A. et al., A Prime-Boost Immunization with DNA and Modified Vaccinia Virus Ankara Vectors Expressing Herpes Simplex Virus-2 Glycoprotein D Elicits Greater Specific Antibody and Cytokine Responses than DNA Vaccine Alone, The Journal of Infectious Diseases, 186:1065-1073 (2002).
Mikloaska, Z. et al., Monophosphoryl Lipid A and QS21 Increa CD8 T Lymphocyte Cytotoxicity to Herpes implex Virus-2 Infected Cell Proteins 4 and 27 Through IFN-γ and IL-12 Production, J. Immuno., 164: 5167-5176 (2000).

(56) References Cited

OTHER PUBLICATIONS

Posavad, C.M. et al., Detailed Characterization of T Cell responses to herpes simplex virus-2 in immune seronegative persons, J. Immunol., 184(4): 3250-3259 (2010).

Pronovost, A.D. et al, Effect of Acyclovir on Genital Herpes in Guinea pigs, J Infect Dis, 145:904-908 (1982).

Rajaguru, S.C., Inhibition of Herpes Simplex Virus Replication Using Small Interfering RNA That Target ICP4 Gene of Herpes Simplex Type 2, Master of Science Thesis, University of Florida (2004).

Roth, K. et al., HSV-2 vaccine: Current state and insights into development of a vaccine that targets genital mucosal protection, Microbiol Pathogenesis, 1-10 (2012).

Schiffer, J.T. et al., Herpes simplex virus-2 transmission probability estimates based on quantity of viral shedding, Journal of the Royal Society Interface, 1-12 (2014).

Sedlackova, L. et al., Herpes Simplex Virus Type 1 Immediate-Early Protein ICP27 is Required for Efficient Incorporation of ICP0 and ICP4 into Virions, Journal of Virology, 82(1):268-277 (2008).

Shlapobersky, M. et al., Vaxfectin-adjuvanted plasmid DNA vaccine improves protection and immunogenecity in a murine model of genital herpes infection, Journal of General Virology, 93:1305-1315 (2012).

Sin, J-I. et al., DNA vaccines encoding interleukin-8 and RANTES enhance antigen-specific Th1-type CD4(+) T-cell-mediated protective immunity against herpes simplex virus type 2 in vivo, Journal of Virology, 74(23): 11173-11180 (2000).

Sin, J-I. et al., IL-12 gene as a DNA vaccine adjuvant in a herpes mouse model: 7-15 IL-12 enhances Th1-type CD4+ T cell-mediated protective immunity against herpes simplex virus-2 challenge, The Journal of Immunology, 162(5): 2912-2921 (1999).

Skoberne, M. et al., An adjuvanted herpes simplex virus 2 subunit vaccine elicits a T-cell response in mice and is an effective therapeutic vaccine in Guinea pigs, J Virol., 87:3930-42 (2013).

Sojikul, P. et al., A plant signal peptide-hepatitis B surface antigen fusion protein with enhanced stability and immunogenicity expressed in plant cells, PNAS, 100(5): 2209-2214 (2003).

Stanberry, L. R. et al., Glycoprotein-D-adjuvant vaccine to prevent genital herpes, N. Engl. J. Med., 347:1652-61 (2002).

Strasser, J.E. et al., Herpes Simplex Virus DNA Vaccine Efficacy: Effect of Glycoprotein D Plasmid Constructs, The Journal of Infectious Diseases, 182:1304-1310 (2000).

Tigges, M.A. et al., Human CD8+ Herpes Simplex Virus-Specific Cytotoxic T-Lymphocyte Clones Recognize Diverse Virion Protein Antigens, Journal of Virology, 66(3):1622-1634 (1992).

Valtrex® (valacyclovir hydrochloride) Caplets, Highlights of Prescribing Information, 27 pages (2008).

Vinh, D.C. and Aoki, F.Y., Famciclovir for the Treatment of Recurrent Genital Herpes: a Clinical and Pharmacological Perspective, Exp Opin on Pharmacother, 7(16):2271-2286 (2006).

Wald, A. et al., Suppression of subclinical shedding of herpes simplex virus type 2 with acyclovir, Ann Intern Med., 124(1 Pt 1):8-15 (1996).

Wald, A., Therapeutic HSV-2 Vaccine (GEN-003) Results in Durable Reduction in Genital Lesions at 1 Year, Phase 1/2a Clinical Trial: GEN-003-001, presented at IDWeek™ 2014 in Philadelphia, PA, USA, Oct. 8-12, 2014, powerpoint, 21 pages (Oct. 11, 2014).

Watari, E. et al., A synthetic peptide induces long-term protection from lethal infection with herpes simplex virus 2, The Journal of Experimental Medicine, 165:459-470 (1987).

World Health Organization (WHO), Status of Vaccine Research and Development of Vaccines for Herpes Simplex Virus Prepared for WHO PD-VAC, <http://www.who.int/immunization/research/meetings_workshops/HSV_vaccineRD_Sept2014.pdf> Pub. Sep. 24, 2014.

Written Opinion for PCT/US2010/035998 (Vaccines Against Herpes Simplex Virus Type 2: Compositions and Methods for Eliciting an Immune Response, filed May 24, 2010), issued by ISA/AU, 8 pages (dated Oct. 26, 2010).

Written Opinion for PCT/US2010/036000 (Herpes Simplex Virus Type 2: Compositions and Methods for Eliciting an Immune Response, filed May 24, 2010), issued by ISA/AU, 7 pages (dated Sep. 7, 2010).

Written Opinion for PCT/US2011/62120, 9 pages (dated Jul. 10, 2012).

Written Opinion for PCT/US2012/066241, dated Feb. 28, 2013, published as WO 2013/078299 (3 pages).

Yang, H. et al., High level expression of Glycoprotein D of Herpes Simplex Virus in *Escherichia coli*, Chinese Journal of Dermatology, 3:157-159 (1997). (English Abstract).

Zhou, J. et al., Research Progress of Envelope Glycoprotein gG-2 of HSV, Foreign Medical Sciences, 11(4):123-126 (2004). (English Abstract).

\* cited by examiner

Toxicity Grading Scale for Healthy Adult and Adolescent Volunteers Enrolled in Preventive Vaccine Clinical Trials

Clinical Abnormalities

| | Mild (Grade 1) | Moderate (Grade 2) | Severe (Grade 3) | Potentially Life-threatening (Grade 4) |
|---|---|---|---|---|
| Local Reaction to Injectable Product | | | | |
| Pain | Does not interfere with activity | Repeated use of non-narcotic pain reliever > 24 hours or interferes with activity | Any use of narcotic pain reliever or prevents daily activity | Emergency room (ER) visit or hospitalization |
| Tenderness | Mild discomfort to touch | Discomfort with movement | Significant discomfort at rest | ER visit or hospitalization |
| Erythema/Redness | 2.5 – 5 cm | 5.1 – 10 cm | > 10 cm | Necrosis or exfoliative dermatitis |
| Induration/Swelling | 2.5 – 5 cm and does not interfere with activity | 5.1 – 10 cm or interferes with activity | > 10 cm or prevents daily activity | Necrosis |
| Vital Signs | | | | |
| Fever (°C) / (°F) | 38.0 – 38.4 / 100.4 – 101.1 | 38.5 – 38.9 / 101.2 – 102.0 | 39.0 – 40 / 102.1 – 104 | >40 / >104 |
| Tachycardia – beats per minute | 101 – 115 | 116 – 130 | >130 | ER visit or hospitalization for arrhythmia |
| Bradycardia – beats per minute | 50 – 54 | 45 – 49 | <45 | ER visit or hospitalization for arrhythmia |
| Hypertension (systolic) – mmHg | 141 – 150 | 151 – 155 | >155 | ER visit or hospitalization for malignant hypertension |
| Hypertension (diastolic) – mmHg | 91 – 95 | 96 – 100 | >100 | ER visit or hospitalization for malignant hypertension |
| Hypotension (systolic) – mmHg | 85 – 89 | 80 – 84 | <80 | ER visit or hospitalization for hypotensive shock |
| Respiratory Rate – breaths per minute | 17 – 20 | 21 – 25 | >25 | Intubation |

Figure 1A

|  | Mild (Grade 1) | Moderate (Grade 2) | Severe (Grade 3) | Potentially Life-threatening (Grade 4) |
|---|---|---|---|---|
| Systemic (General) | | | | |
| Nausea/vomiting | No interference with activity or 1 - 2 episodes/24 hours | Some interference with activity or > 2 episodes/24 hours | Prevents daily activity, requires outpatient IV hydration | ER visit or hospitalization for hypotensive shock |
| Diarrhea | 2 - 3 loose stools or < 400 gms/24 hours | 4 - 5 stools or 400 - 800 gms/24 hours | 6 or more watery stools or > 800gms/24 hours or requires outpatient IV hydration | ER visit or hospitalization |
| Headache | No interference with activity | Repeated use of non-narcotic pain reliever > 24 hours or some interference with activity | Significant; any use of narcotic pain reliever or prevents daily activity | ER visit or hospitalization |
| Fatigue | No interference with activity | Some interference with activity | Significant; prevents daily activity | ER visit or hospitalization |
| Myalgia | No interference with activity | Some interference with activity | Significant; prevents daily activity | ER visit or hospitalization |
| Systemic Illness | | | | |
| Illness or clinical adverse event (as defined according to applicable regulations) | No interference with activity | Some interference with activity not requiring medical intervention | Prevents daily activity and requires medical intervention | ER visit or hospitalization |

Figure 1B

Tables for Laboratory Abnormalities

| | Mild (Grade 1) | Moderate (Grade 2) | Severe (Grade 3) | Potentially Life-threatening (Grade 4) |
|---|---|---|---|---|
| Serum | | | | |
| Sodium – Hyponatremia mEq/L | 132 – 134 | 130 – 131 | 125 – 129 | < 125 |
| Sodium – Hypernatremia mEq/L | 144 – 145 | 146 – 147 | 148 – 150 | > 150 |
| Potassium – Hyperkalemia mEq/L | 5.1 – 5.2 | 5.3 – 5.4 | 5.5 – 5.6 | > 5.6 |
| Potassium – Hypokalemia mEq/L | 3.5 – 3.6 | 3.3 – 3.4 | 3.1 – 3.2 | < 3.1 |
| Glucose – Hypoglycemia mg/dL | 65 – 69 | 55 – 64 | 45 – 54 | < 45 |
| Glucose – Hyperglycemia Fasting – mg/dL Random – mg/dL | 100 – 110 110 – 125 | 111 – 125 126 – 200 | >125 >200 | Insulin requirements or hyperosmolar coma |
| Blood Urea Nitrogen BUN mg/dL | 23–26 | 27 – 31 | > 31 | Requires dialysis |
| Creatinine – mg/dL | 1.5 – 1.7 | 1.8 – 2.0 | 2.1 – 2.5 | > 2.5 or requires dialysis |
| Calcium – hypocalcemia mg/dL | 8.0 – 8.4 | 7.5 – 7.9 | 7.0 – 7.4 | < 7.0 |
| Calcium – hypercalcemia mg/dL | 10.5 – 11.0 | 11.1 – 11.5 | 11.6 – 12.0 | > 12.0 |
| Magnesium – hypomagnesemia mg/dL | 1.3 – 1.5 | 1.1 – 1.2 | 0.9 – 1.0 | < 0.9 |
| Phosphorous – hypophosphatemia mg/dL | 2.3 – 2.5 | 2.0 – 2.2 | 1.6 – 1.9 | < 1.6 |
| CPK – mg/dL | 1.25 – 1.5 x ULN | 1.6 – 3.0 x ULN | 3.1 – 10 x ULN | > 10 x ULN |
| Albumin – Hypoalbuminemia g/dL | 2.8 – 3.1 | 2.5 – 2.7 | < 2.5 | -- |
| Total Protein – Hypoproteinemia g/dL | 5.5 – 6.0 | 5.0 – 5.4 | < 5.0 | -- |
| Alkaline phosphate – increase by factor | 1.1 – 2.0 x ULN | 2.1 – 3.0 x ULN | 3.1 – 10 x ULN | > 10 x ULN |
| Liver Function Tests –ALT, AST increase by factor | 1.1 – 2.5 x ULN | 2.6 – 5.0 x ULN | 5.1 – 10 x ULN | > 10 x ULN |
| Bilirubin – when accompanied by any increase in Liver Function Test increase by factor | 1.1 – 1.25 x ULN | 1.26 – 1.5 x ULN | 1.51 – 1.75 x ULN | > 1.75 x ULN |
| Bilirubin – when Liver Function Test is normal; increase by factor | 1.1 – 1.5 x ULN | 1.6 – 2.0 x ULN | 2.0 – 3.0 x ULN | > 3.0 x ULN |
| Cholesterol | 201 – 210 | 211 – 225 | > 226 | -- |
| Pancreatic enzymes – amylase, lipase | 1.1 – 1.5 x ULN | 1.6 – 2.0 x ULN | 2.1 – 5.0 x ULN | > 5.0 x ULN |

Figure 1C

| | Mild (Grade 1) | Moderate (Grade 2) | Severe (Grade 3) | Potentially Life-threatening (Grade 4) |
|---|---|---|---|---|
| Hematology | | | | |
| Hemoglobin (Female) - gm/dL | 11.0 – 12.0 | 9.5 – 10.9 | 8.0 – 9.4 | < 8.0 |
| Hemoglobin (Female) change from baseline value - gm/dL | Any decrease – 1.5 | 1.6 – 2.0 | 2.1 – 5.0 | > 5.0 |
| Hemoglobin (Male) - gm/dL | 12.5 – 13.5 | 10.5 – 12.4 | 8.5 – 10.4 | < 8.5 |
| Hemoglobin (Male) change from baseline value – gm/dL | Any decrease – 1.5 | 1.6 – 2.0 | 2.1 – 5.0 | > 5.0 |
| WBC Increase - cell/mm$^3$ | 10,800 – 15,000 | 15,001 – 20,000 | 20,001 – 25,000 | > 25,000 |
| WBC Decrease - cell/mm$^3$ | 2,500 – 3,500 | 1,500 – 2,499 | 1,000 – 1,499 | < 1,000 |
| Lymphocytes Decrease - cell/mm$^3$ | 750 – 1,000 | 500 – 749 | 250 – 499 | < 250 |
| Neutrophils Decrease - cell/mm$^3$ | 1,500 – 2,000 | 1,000 – 1,499 | 500 – 999 | < 500 |
| Eosinophils - cell/mm$^3$ | 650 – 1500 | 1501 – 5000 | > 5000 | Hypereosinophilic |
| Platelets Decreased - cell/mm$^3$ | 125,000 – 140,000 | 100,000 – 124,000 | 25,000 – 99,000 | < 25,000 |
| PT – increase by factor (prothrombin time) | 1.0 – 1.10 x ULN | 1.11 – 1.20 x ULN | 1.21 – 1.25 x ULN | > 1.25 ULN |
| PTT – increase by factor (partial thromboplastin time) | 1.0 – 1.2 x ULN | 1.21 – 1.4 x ULN | 1.41 – 1.5 x ULN | > 1.5 x ULN |
| Fibrinogen increase - mg/dL | 400 – 500 | 501 – 600 | > 600 | --- |
| Fibrinogen decrease - mg/dL | 150 – 200 | 125 – 149 | 100 – 124 | < 100 or associated with gross bleeding or disseminated intravascular coagulation (DIC) |
| Urine | | | | |
| Protein | Trace | 1+ | 2+ | Hospitalization or dialysis |
| Glucose | Trace | 1+ | 2+ | Hospitalization for hyperglycemia |
| Blood (microscopic) - red blood cells per high power field (rbc/hpf) | 1 – 10 | 11 – 50 | > 50 and/or gross blood | Hospitalization or packed red blood cells (PRBC) transfusion |

Figure 1D

SEQUENCE LISTING

<160> NUMBER OF SEQ ID NOS: 144

<210> SEQ ID NO 1
<211> LENGTH: 1317
<212> TYPE: PRT
<213> ORGANISM: Herpes simplex virus

<400> SEQUENCE: 1

```
Ser Ala Glu Gln Arg Lys Lys Lys Thr Thr Thr Thr Gln Gly
1               5                   10                  15

Arg Gly Ala Glu Val Ala Met Ala Asp Glu Asp Gly Gly Arg Leu Arg
            20                  25                  30

Ala Ala Ala Glu Thr Thr Gly Gly Pro Gly Ser Pro Asp Pro Ala Asp
            35                  40                  45

Gly Pro Pro Thr Pro Asn Pro Asp Arg Arg Pro Ala Ala Arg Pro
    50                  55                  60

Gly Phe Gly Trp His Gly Gly Pro Glu Glu Asn Glu Asp Glu Ala Asp
65                  70                  75                  80

Asp Ala Ala Ala Asp Ala Asp Ala Asp Glu Ala Ala Pro Ala Ser Gly
                85                  90                  95

Glu Ala Val Asp Glu Pro Ala Ala Asp Gly Val Val Ser Pro Arg Gln
                100                 105                 110

Leu Ala Leu Leu Ala Ser Met Val Asp Glu Ala Val Arg Thr Ile Pro
            115                 120                 125

Ser Pro Pro Glu Arg Asp Gly Ala Gln Glu Glu Ala Ala Arg Ser
    130                 135                 140

Pro Ser Pro Pro Arg Thr Pro Ser Met Arg Ala Asp Tyr Gly Glu Glu
145                 150                 155                 160

Asn Asp Asp Asp Asp Asp Asp Asp Asp Arg Asp Ala Gly
                165                 170                 175

Arg Trp Val Arg Gly Pro Glu Thr Thr Ser Ala Val Arg Gly Ala Tyr
            180                 185                 190

Pro Asp Pro Met Ala Ser Leu Ser Pro Arg Pro Pro Ala Pro Arg Arg
            195                 200                 205

His His His His His His Arg Arg Arg Ala Pro Arg Arg
            210                 215                 220

Ser Ala Ala Ser Asp Ser Ser Lys Ser Gly Ser Ser Ser Ala Ser
225                 230                 235                 240

Ser Ala Ser Ser Ala Ser Ser Ser Ser Ala Ser Ala Ser Ser
                245                 250                 255

Ser Asp Asp Asp Asp Asp Asp Ala Ala Arg Ala Pro Ala Ser Ala
            260                 265                 270

Ala Asp His Ala Ala Gly Gly Thr Leu Gly Ala Asp Asp Glu Glu Ala
            275                 280                 285

Gly Val Pro Ala Arg Ala Pro Gly Ala Ala Pro Arg Pro Ser Pro Pro
    290                 295                 300

Arg Ala Glu Pro Ala Pro Ala Arg Thr Pro Ala Ala Thr Ala Gly Arg
305                 310                 315                 320

Leu Glu Arg Arg Arg Ala Arg Ala Ala Val Ala Gly Arg Asp Ala Thr
                325                 330                 335
```

```
Gly Arg Phe Thr Ala Gly Arg Pro Arg Val Glu Leu Asp Ala Asp
                340                 345                 350
Ala Ala Ser Gly Ala Phe Tyr Ala Arg Tyr Arg Asp Gly Tyr Val Ser
                355                 360                 365
Gly Glu Pro Trp Pro Gly Ala Gly Pro Pro Pro Gly Arg Val Leu
        370                 375                 380
Tyr Gly Gly Leu Gly Asp Ser Arg Pro Gly Leu Trp Gly Ala Pro Glu
385                 390                 395                 400
Ala Glu Glu Ala Arg Ala Arg Phe Glu Ala Ser Gly Ala Pro Ala Pro
                405                 410                 415
Val Trp Ala Pro Glu Leu Gly Asp Ala Ala Gln Gln Tyr Ala Leu Ile
                420                 425                 430
Thr Arg Leu Leu Tyr Thr Pro Asp Ala Glu Ala Met Gly Trp Leu Gln
                435                 440                 445
Asn Pro Arg Val Ala Pro Gly Asp Val Ala Leu Asp Gln Ala Cys Phe
                450                 455                 460
Arg Ile Ser Gly Ala Ala Arg Asn Ser Ser Phe Ile Ser Gly Ser
465                 470                 475                 480
Val Ala Arg Ala Val Pro His Leu Gly Tyr Ala Met Ala Ala Gly Arg
                485                 490                 495
Phe Gly Trp Gly Leu Ala His Val Ala Ala Val Ala Met Ser Arg
        500                 505                 510
Arg Tyr Asp Arg Ala Gln Lys Gly Phe Leu Leu Thr Ser Leu Arg Arg
                515                 520                 525
Ala Tyr Ala Pro Leu Leu Ala Arg Glu Asn Ala Ala Leu Thr Gly Ala
                530                 535                 540
Arg Thr Pro Asp Asp Gly Gly Asp Ala Asn Arg His Asp Gly Asp Asp
545                 550                 555                 560
Ala Arg Gly Lys Pro Ala Ala Ala Ala Pro Leu Pro Ser Ala Ala
                565                 570                 575
Ala Ser Pro Ala Asp Glu Arg Ala Val Pro Ala Gly Tyr Gly Ala Ala
                580                 585                 590
Gly Val Leu Ala Ala Leu Gly Arg Leu Ser Ala Ala Pro Ala Ser Ala
                595                 600                 605
Pro Ala Gly Ala Asp Asp Asp Asp Asp Asp Gly Ala Gly Gly Gly
        610                 615                 620
Gly Gly Gly Arg Arg Ala Glu Gly Arg Val Ala Val Glu Cys Leu
625                 630                 635                 640
Ala Ala Cys Arg Gly Ile Leu Glu Ala Leu Glu Gly Phe Asp Gly
                645                 650                 655
Asp Leu Ala Ala Val Pro Gly Leu Gly Ala Arg Pro Ala Ala Pro
                660                 665                 670
Pro Arg Pro Gly Pro Ala Gly Ala Ala Pro Pro His Ala Asp Ala
                675                 680                 685
Pro Arg Leu Arg Ala Trp Leu Arg Glu Leu Arg Phe Val Arg Asp Ala
                690                 695                 700
Leu Val Leu Met Arg Leu Arg Gly Asp Leu Arg Val Ala Gly Gly Ser
705                 710                 715                 720
Glu Ala Ala Val Ala Ala Val Arg Ala Val Ser Leu Val Ala Gly Ala
                725                 730                 735
Leu Gly Pro Ala Leu Pro Arg Ser Pro Arg Leu Leu Ser Ser Ala Ala
                740                 745                 750
```

-continued

Ala Ala Ala Ala Asp Leu Leu Phe Gln Asn Gln Ser Leu Arg Pro Leu
            755                 760             765

Leu Ala Asp Thr Val Ala Ala Asp Ser Leu Ala Ala Pro Ala Ser
    770             775             780

Ala Pro Arg Glu Ala Arg Lys Arg Lys Ser Pro Ala Pro Ala Arg Ala
785             790             795                 800

Pro Pro Gly Gly Ala Pro Arg Pro Pro Lys Lys Ser Arg Ala Asp Ala
            805             810                 815

Pro Arg Pro Ala Ala Pro Pro Ala Gly Ala Ala Pro Pro Ala Pro
        820             825             830

Pro Thr Pro Pro Pro Arg Pro Pro Arg Pro Ala Ala Leu Thr Arg Arg
        835             840             845

Pro Ala Glu Gly Pro Asp Pro Gln Gly Gly Trp Arg Arg Gln Pro Pro
    850             855             860

Gly Pro Ser His Thr Pro Ala Pro Ser Ala Ala Ala Leu Glu Ala Tyr
865             870             875                 880

Cys Ala Pro Arg Ala Val Ala Glu Leu Thr Asp His Pro Leu Phe Pro
            885             890                 895

Ala Pro Trp Arg Pro Ala Leu Met Phe Asp Pro Arg Ala Leu Ala Ser
            900             905             910

Leu Ala Ala Arg Cys Ala Ala Pro Pro Gly Gly Ala Pro Ala Ala
    915             920             925

Phe Gly Pro Leu Arg Ala Ser Gly Pro Leu Arg Arg Ala Ala Ala Trp
    930             935             940

Met Arg Gln Val Pro Asp Pro Glu Asp Val Arg Val Ile Leu Tyr
945             950             955             960

Ser Pro Leu Pro Gly Glu Asp Leu Ala Ala Gly Arg Ala Gly Gly Gly
            965             970             975

Pro Pro Pro Glu Trp Ser Ala Glu Arg Gly Gly Leu Ser Cys Leu Leu
            980             985             990

Ala Ala Leu Gly Asn Arg Leu Cys Gly Pro Ala Thr Ala Ala Trp Ala
        995             1000            1005

Gly Asn Trp Thr Gly Ala Pro Asp Val Ser Ala Leu Gly Ala Gln
    1010            1015            1020

Gly Val Leu Leu Leu Ser Thr Arg Asp Leu Ala Phe Ala Gly Ala
    1025            1030            1035

Val Glu Phe Leu Gly Leu Leu Ala Gly Ala Cys Asp Arg Arg Leu
    1040            1045            1050

Ile Val Val Asn Ala Val Arg Ala Ala Asp Trp Pro Ala Asp Gly
    1055            1060            1065

Pro Val Val Ser Arg Gln His Ala Tyr Leu Ala Cys Glu Val Leu
    1070            1075            1080

Pro Ala Val Gln Cys Ala Val Arg Trp Pro Ala Ala Arg Asp Leu
    1085            1090            1095

Arg Arg Thr Val Leu Ala Ser Gly Arg Val Phe Gly Pro Gly Val
    1100            1105            1110

Phe Ala Arg Val Glu Ala Ala His Ala Arg Leu Tyr Pro Asp Ala
    1115            1120            1125

Pro Pro Leu Arg Leu Cys Arg Gly Ala Asn Val Arg Tyr Arg Val
    1130            1135            1140

Arg Thr Arg Phe Gly Pro Asp Thr Leu Val Pro Met Ser Pro Arg
    1145            1150            1155

```
Glu Tyr Arg Arg Ala Val Leu Pro Ala Leu Asp Gly Arg Ala Ala
    1160                1165                1170

Ala Ser Gly Ala Gly Asp Ala Met Ala Pro Gly Ala Pro Asp Phe
    1175                1180                1185

Cys Glu Asp Glu Ala His Ser His Arg Ala Cys Ala Arg Trp Gly
    1190                1195                1200

Leu Gly Ala Pro Leu Arg Pro Val Tyr Val Ala Leu Gly Arg Asp
    1205                1210                1215

Ala Val Arg Gly Gly Pro Ala Glu Leu Arg Gly Pro Arg Arg Glu
    1220                1225                1230

Phe Cys Ala Arg Ala Leu Leu Glu Pro Asp Gly Asp Ala Pro Pro
    1235                1240                1245

Leu Val Leu Arg Asp Asp Ala Asp Ala Gly Pro Pro Pro Gln Ile
    1250                1255                1260

Arg Trp Ala Ser Ala Ala Gly Arg Ala Gly Thr Val Leu Ala Ala
    1265                1270                1275

Ala Gly Gly Gly Val Glu Val Val Gly Thr Ala Ala Gly Leu Ala
    1280                1285                1290

Thr Pro Pro Arg Arg Glu Pro Val Asp Met Asp Ala Glu Leu Glu
    1295                1300                1305

Asp Asp Asp Asp Gly Leu Phe Gly Glu
    1310                1315

<210> SEQ ID NO 2
<211> LENGTH: 391
<212> TYPE: PRT
<213> ORGANISM: Herpes simplex virus

<400> SEQUENCE: 2

Met Val Leu Tyr Gly Gly Leu Gly Asp Ser Arg Pro Gly Leu Trp Gly
1               5                   10                  15

Ala Pro Glu Ala Glu Glu Ala Arg Ala Arg Phe Glu Ala Ser Gly Ala
            20                  25                  30

Pro Ala Pro Val Trp Ala Pro Glu Leu Gly Asp Ala Ala Gln Gln Tyr
        35                  40                  45

Ala Leu Ile Thr Arg Leu Leu Tyr Thr Pro Asp Ala Glu Ala Met Gly
    50                  55                  60

Trp Leu Gln Asn Pro Arg Val Ala Pro Gly Asp Val Ala Leu Asp Gln
65                  70                  75                  80

Ala Cys Phe Arg Ile Ser Gly Ala Ala Arg Asn Ser Ser Ser Phe Ile
                85                  90                  95

Ser Gly Ser Val Ala Arg Ala Val Pro His Leu Gly Tyr Ala Met Ala
            100                 105                 110

Ala Gly Arg Phe Gly Trp Gly Leu Ala His Val Ala Ala Val Ala
        115                 120                 125

Met Ser Arg Arg Tyr Asp Arg Ala Gln Lys Gly Phe Leu Leu Thr Ser
    130                 135                 140

Leu Arg Arg Ala Tyr Ala Pro Leu Leu Ala Arg Glu Asn Ala Ala Leu
145                 150                 155                 160

Thr Gly Ala Arg Thr Pro Asp Asp Gly Gly Asp Ala Asn Arg Arg Asp
                165                 170                 175

Gly Asp Asp Ala Arg Gly Lys Pro Ala Ala Ala Ala Pro Leu Pro
            180                 185                 190

Ser Ala Ala Ala Ser Pro Ala Asp Glu Arg Ala Val Pro Ala Gly Tyr
        195                 200                 205
```

```
Gly Ala Ala Gly Val Leu Ala Ala Leu Gly Arg Leu Ser Ala Pro
    210                 215                 220

Ala Ser Ala Pro Ala Gly Ala Asp Asp Asp Asp Asp Asp Asp Gly
225                 230                 235                 240

Ala Gly Gly Gly Gly Gly Gly Gly Gly Gly Gly Arg Arg Ala
                245                 250                 255

Glu Ala Gly Arg Val Ala Val Glu Cys Leu Ala Ala Cys Arg Gly Ile
                260                 265                 270

Leu Glu Ala Leu Ala Glu Gly Phe Asp Gly Asp Leu Ala Ala Val Pro
        275                 280                 285

Gly Leu Ala Gly Ala Arg Pro Ala Ala Pro Arg Pro Gly Pro Ala
    290                 295                 300

Gly Ala Ala Ala Pro Pro His Ala Asp Ala Pro Arg Leu Arg Ala Trp
305                 310                 315                 320

Leu Arg Glu Leu Arg Phe Val Arg Asp Ala Leu Val Leu Met Arg Leu
                325                 330                 335

Arg Gly Asp Leu Arg Val Ala Gly Gly Ser Glu Ala Ala Val Ala Ala
                340                 345                 350

Val Arg Ala Val Ser Leu Val Ala Gly Ala Leu Gly Pro Ala Leu Pro
                355                 360                 365

Arg Ser Pro Arg Leu Leu Ser Ser Ala Ala Ala Ala Ala Asp Leu
    370                 375                 380

Leu Phe Gln Asn Gln Ser Leu
385                 390

<210> SEQ ID NO 3
<211> LENGTH: 224
<212> TYPE: PRT
<213> ORGANISM: Herpes simplex virus

<400> SEQUENCE: 3

Met Gly Phe Val Cys Leu Phe Gly Leu Val Val Met Gly Ala Trp Gly
1               5                   10                  15

Ala Trp Gly Gly Ser Gln Ala Thr Glu Tyr Val Leu Arg Ser Val Ile
                20                  25                  30

Ala Lys Glu Val Gly Asp Ile Leu Arg Val Pro Cys Met Arg Thr Pro
            35                  40                  45

Ala Asp Asp Val Ser Trp Arg Tyr Glu Ala Pro Ser Val Ile Asp Tyr
    50                  55                  60

Ala Arg Ile Asp Gly Ile Phe Leu Arg Tyr His Cys Pro Gly Leu Asp
65                  70                  75                  80

Thr Phe Leu Trp Asp Arg His Ala Gln Arg Ala Tyr Leu Val Asn Pro
                85                  90                  95

Phe Leu Phe Ala Ala Gly Phe Leu Glu Asp Leu Ser His Ser Val Phe
            100                 105                 110

Pro Ala Asp Thr Gln Glu Thr Thr Thr Arg Arg Ala Leu Tyr Lys Glu
        115                 120                 125

Ile Arg Asp Ala Leu Gly Ser Arg Lys Gln Ala Val Ser His Ala Pro
    130                 135                 140

Val Arg Ala Gly Cys Val Asn Phe Asp Tyr Ser Arg Thr Arg Arg Cys
145                 150                 155                 160

Val Gly Arg Arg Asp Leu Arg Pro Ala Asn Thr Thr Ser Thr Trp Glu
                165                 170                 175

Pro Pro Val Ser Ser Asp Asp Glu Ala Ser Ser Gln Ser Lys Pro Leu
```

```
                       180                 185                 190
Ala Thr Gln Pro Pro Val Leu Ala Leu Ser Asn Ala Pro Pro Arg Arg
                195                 200                 205

Val Ser Pro Thr Arg Gly Arg Arg His Thr Arg Leu Arg Arg Asn
    210                 215                 220

<210> SEQ ID NO 4
<211> LENGTH: 347
<212> TYPE: PRT
<213> ORGANISM: Herpes simplex virus

<400> SEQUENCE: 4

Asn Arg Trp Lys Tyr Ala Leu Ala Asp Pro Ser Leu Lys Met Ala Asp
1               5                   10                  15

Pro Asn Arg Phe Arg Gly Lys Asn Leu Pro Val Leu Asp Gln Leu Thr
            20                  25                  30

Asp Pro Pro Gly Val Lys Arg Val Tyr His Ile Gln Pro Ser Leu Glu
        35                  40                  45

Asp Pro Phe Gln Pro Pro Ser Ile Pro Ile Thr Val Tyr Tyr Ala Val
    50                  55                  60

Leu Glu Arg Ala Cys Arg Ser Val Leu Leu His Ala Pro Ser Glu Ala
65                  70                  75                  80

Pro Gln Ile Val Arg Gly Ala Ser Asp Glu Ala Arg Lys His Thr Tyr
                85                  90                  95

Asn Leu Thr Ile Ala Trp Tyr Arg Met Gly Asp Asn Cys Ala Ile Pro
            100                 105                 110

Ile Thr Val Met Glu Tyr Thr Glu Cys Pro Tyr Asn Lys Ser Leu Gly
        115                 120                 125

Val Cys Pro Ile Arg Thr Gln Pro Arg Trp Ser Tyr Tyr Asp Ser Phe
    130                 135                 140

Ser Ala Val Ser Glu Asp Asn Leu Gly Phe Leu Met His Ala Pro Ala
145                 150                 155                 160

Phe Glu Thr Ala Gly Thr Tyr Leu Arg Leu Val Lys Ile Asn Asp Trp
                165                 170                 175

Thr Glu Ile Thr Gln Phe Ile Leu Glu His Arg Ala Arg Ala Ser Cys
            180                 185                 190

Lys Tyr Ala Leu Pro Leu Arg Ile Pro Pro Ala Ala Cys Leu Thr Ser
        195                 200                 205

Lys Ala Tyr Gln Gln Gly Val Thr Val Asp Ser Ile Gly Met Leu Pro
    210                 215                 220

Arg Phe Ile Pro Glu Asn Gln Arg Thr Val Ala Leu Tyr Ser Leu Lys
225                 230                 235                 240

Ile Ala Gly Trp His Gly Pro Lys Pro Pro Tyr Thr Ser Thr Leu Leu
                245                 250                 255

Pro Pro Glu Leu Ser Asp Thr Thr Asn Ala Thr Gln Pro Glu Leu Val
            260                 265                 270

Pro Glu Asp Pro Glu Asp Ser Ala Leu Leu Glu Asp Pro Ala Gly Thr
        275                 280                 285

Val Ser Ser Gln Ile Pro Pro Asn Trp His Ile Pro Ser Ile Gln Asp
    290                 295                 300

Val Ala Pro His His Ala Pro Ala Ala Pro Ser Asn Pro Arg Arg Arg
305                 310                 315                 320

Ala Gln Met Ala Pro Lys Arg Leu Arg Leu Pro His Ile Arg Asp Asp
                325                 330                 335
```

```
Asp Ala Pro Pro Ser His Gln Pro Leu Phe Tyr
            340                 345

<210> SEQ ID NO 5
<211> LENGTH: 393
<212> TYPE: PRT
<213> ORGANISM: Herpes simplex virus

<400> SEQUENCE: 5

Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
            35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
            340                 345                 350

Val Leu Val Ile Gly Gly Ile Ala Phe Trp Val Arg Arg Arg Ala Gln
        355                 360                 365
```

```
Met Ala Pro Lys Arg Leu Arg Leu Pro His Ile Arg Asp Asp Asp Ala
        370                 375                 380

Pro Pro Ser His Gln Pro Leu Phe Tyr
385                 390

<210> SEQ ID NO 6
<211> LENGTH: 261
<212> TYPE: PRT
<213> ORGANISM: Herpes simplex virus

<400> SEQUENCE: 6

Met Ser Arg Arg Arg Gly Pro Arg Arg Gly Pro Arg Arg Pro
1               5                   10                  15

Arg Pro Gly Ala Pro Ala Val Pro Arg Pro Gly Ala Pro Ala Val Pro
                20                  25                  30

Arg Pro Gly Ala Leu Pro Thr Ala Asp Ser Gln Met Val Pro Ala Tyr
            35                  40                  45

Asp Ser Gly Thr Ala Val Glu Ser Ala Pro Ala Ala Ser Ser Leu Leu
        50                  55                  60

Arg Arg Trp Leu Leu Val Pro Gln Ala Asp Asp Ser Asp Asp Ala Asp
65                  70                  75                  80

Tyr Ala Gly Asn Asp Asp Ala Glu Trp Ala Asn Ser Pro Pro Ser Glu
                85                  90                  95

Gly Gly Gly Lys Ala Pro Glu Ala Pro His Ala Ala Pro Ala Ala Ala
                100                 105                 110

Cys Pro Pro Pro Pro Arg Lys Glu Arg Gly Pro Gln Arg Pro Leu
            115                 120                 125

Pro Pro His Leu Ala Leu Arg Leu Arg Thr Thr Thr Glu Tyr Leu Ala
        130                 135                 140

Arg Leu Ser Leu Arg Arg Arg Pro Pro Ala Ser Pro Pro Ala Asp
145                 150                 155                 160

Ala Pro Arg Gly Lys Val Cys Phe Ser Pro Arg Val Gln Val Arg His
                165                 170                 175

Leu Val Ala Trp Glu Thr Ala Ala Arg Leu Ala Arg Arg Gly Ser Trp
            180                 185                 190

Ala Arg Glu Arg Ala Asp Arg Asp Arg Phe Arg Arg Val Ala Ala
        195                 200                 205

Ala Glu Ala Val Ile Gly Pro Cys Leu Glu Pro Glu Ala Arg Ala Arg
        210                 215                 220

Ala Arg Ala Arg Ala Arg Ala His Glu Asp Gly Gly Pro Ala Glu Glu
225                 230                 235                 240

Glu Glu Ala Ala Ala Ala Ala Arg Gly Ser Ser Ala Ala Ala Gly Pro
                245                 250                 255

Gly Arg Arg Ala Val
            260

<210> SEQ ID NO 7
<211> LENGTH: 825
<212> TYPE: PRT
<213> ORGANISM: Herpes simplex virus

<400> SEQUENCE: 7

Met Glu Pro Arg Pro Gly Thr Ser Ser Arg Ala Asp Pro Gly Pro Glu
1               5                   10                  15

Arg Pro Pro Arg Gln Thr Pro Gly Thr Gln Pro Ala Ala Pro His Ala
                20                  25                  30
```

-continued

```
Trp Gly Met Leu Asn Asp Met Gln Trp Leu Ala Ser Ser Asp Ser Glu
        35                  40                  45

Glu Glu Thr Glu Val Gly Ile Ser Asp Asp Asp Leu His Arg Asp Ser
 50                  55                  60

Thr Ser Glu Ala Gly Ser Thr Asp Thr Glu Met Phe Glu Ala Gly Leu
 65                  70                  75                  80

Met Asp Ala Ala Thr Pro Pro Ala Arg Pro Ala Glu Arg Gln Gly
                 85                  90                  95

Ser Pro Thr Pro Ala Asp Ala Gln Gly Ser Cys Gly Gly Pro Val
            100                 105                 110

Gly Glu Glu Ala Glu Ala Gly Gly Gly Asp Val Cys Ala Val
        115                 120                 125

Cys Thr Asp Glu Ile Ala Pro Pro Leu Arg Cys Gln Ser Phe Pro Cys
130                 135                 140

Leu His Pro Phe Cys Ile Pro Cys Met Lys Thr Trp Ile Pro Leu Arg
145                 150                 155                 160

Asn Thr Cys Pro Leu Cys Asn Thr Pro Val Ala Tyr Leu Ile Val Gly
                165                 170                 175

Val Thr Ala Ser Gly Ser Phe Ser Thr Ile Pro Ile Val Asn Asp Pro
            180                 185                 190

Arg Thr Arg Val Glu Ala Glu Ala Val Arg Ala Gly Thr Ala Val
        195                 200                 205

Asp Phe Ile Trp Thr Gly Asn Pro Arg Thr Ala Pro Arg Ser Leu Ser
    210                 215                 220

Leu Gly Gly His Thr Val Arg Ala Leu Ser Pro Thr Pro Pro Trp Pro
225                 230                 235                 240

Gly Thr Asp Asp Glu Asp Asp Asp Leu Ala Asp Val Asp Tyr Val Pro
                245                 250                 255

Pro Ala Pro Arg Arg Ala Pro Arg Arg Gly Gly Gly Ala Gly Ala
            260                 265                 270

Thr Arg Gly Thr Ser Gln Pro Ala Ala Thr Arg Pro Ala Pro Pro Gly
        275                 280                 285

Ala Pro Arg Ser Ser Ser Gly Gly Ala Pro Leu Arg Ala Gly Val
    290                 295                 300

Gly Ser Gly Ser Gly Gly Pro Ala Val Ala Ala Val Pro Arg
305                 310                 315                 320

Val Ala Ser Leu Pro Pro Ala Gly Gly Arg Ala Gln Ala Arg
                325                 330                 335

Arg Val Gly Glu Asp Ala Ala Ala Glu Gly Arg Thr Pro Pro Ala
            340                 345                 350

Arg Gln Pro Arg Ala Ala Gln Glu Pro Pro Ile Val Ile Ser Asp Ser
        355                 360                 365

Pro Pro Pro Ser Pro Arg Arg Pro Ala Gly Pro Gly Pro Leu Ser Phe
370                 375                 380

Val Ser Ser Ser Ser Ala Gln Val Ser Ser Gly Pro Gly Gly Gly
385                 390                 395                 400

Leu Pro Gln Ser Ser Gly Arg Ala Ala Arg Pro Arg Ala Ala Val Ala
                405                 410                 415

Pro Arg Val Arg Ser Pro Arg Ala Ala Ala Pro Val Val Ser
            420                 425                 430

Ala Ser Ala Asp Ala Ala Gly Pro Ala Pro Pro Ala Val Pro Val Asp
        435                 440                 445
```

-continued

Ala His Arg Ala Pro Arg Ser Arg Met Thr Gln Ala Gln Thr Asp Thr
450                 455                 460

Gln Ala Gln Ser Leu Gly Arg Ala Gly Ala Thr Asp Ala Arg Gly Ser
465                 470                 475                 480

Gly Gly Pro Gly Ala Glu Gly Gly Pro Gly Val Pro Arg Gly Thr Asn
                485                 490                 495

Thr Pro Gly Ala Ala Pro His Ala Ala Glu Gly Ala Ala Ala Arg Pro
            500                 505                 510

Arg Lys Arg Arg Gly Ser Asp Ser Gly Pro Ala Ala Ser Ser Ser Ala
        515                 520                 525

Ser Ser Ser Ala Ala Pro Arg Ser Pro Leu Ala Pro Gln Gly Val Gly
530                 535                 540

Ala Lys Arg Ala Ala Pro Arg Ala Pro Asp Ser Asp Ser Gly Asp
545                 550                 555                 560

Arg Gly His Gly Pro Leu Ala Pro Ala Ser Ala Gly Ala Ala Pro Pro
                565                 570                 575

Ser Ala Ser Pro Ser Ser Gln Ala Ala Val Ala Ala Ala Ser Ser Ser
            580                 585                 590

Ser Ala Ser Ser Ser Ser Ala Ser Ser Ser Ala Ser Ser Ser Ser
        595                 600                 605

Ala Ser Ser Ser Ser Ala Ser Ser Ser Ala Ser Ser Ser Ser Ala
610                 615                 620

Ser Ser Ser Ala Gly Gly Ala Gly Gly Ser Val Ala Ser Ala Ser Gly
625                 630                 635                 640

Ala Gly Glu Arg Arg Glu Thr Ser Leu Gly Pro Arg Ala Ala Ala Pro
                645                 650                 655

Arg Gly Pro Arg Lys Cys Ala Arg Lys Thr Arg His Ala Glu Gly Gly
            660                 665                 670

Pro Glu Pro Gly Ala Arg Asp Pro Ala Pro Gly Leu Thr Arg Tyr Leu
        675                 680                 685

Pro Ile Ala Gly Val Ser Val Val Ala Leu Ala Pro Tyr Val Asn
690                 695                 700

Lys Thr Val Thr Gly Asp Cys Leu Pro Val Leu Asp Met Glu Thr Gly
705                 710                 715                 720

His Ile Gly Ala Tyr Val Leu Val Asp Gln Thr Gly Asn Val Ala
                725                 730                 735

Asp Leu Leu Arg Ala Ala Ala Pro Ala Trp Ser Arg Arg Thr Leu Leu
            740                 745                 750

Pro Glu His Ala Arg Asn Cys Val Arg Pro Pro Asp Tyr Pro Thr Pro
        755                 760                 765

Pro Ala Ser Glu Trp Asn Ser Leu Trp Met Thr Pro Val Gly Asn Met
770                 775                 780

Leu Phe Asp Gln Gly Thr Leu Val Gly Ala Leu Asp Phe His Gly Leu
785                 790                 795                 800

Arg Ser Arg His Pro Trp Ser Arg Glu Gln Gly Ala Pro Ala Pro Ala
                805                 810                 815

Gly Asp Ala Pro Ala Gly His Gly Glu
            820                 825

<210> SEQ ID NO 8
<211> LENGTH: 400
<212> TYPE: PRT
<213> ORGANISM: Herpes simplex virus

<400> SEQUENCE: 8

```
Met Ser Ala Glu Gln Arg Lys Lys Lys Thr Thr Thr Thr Gln
1               5                   10                  15

Gly Arg Gly Ala Glu Val Ala Met Ala Asp Glu Asp Gly Arg Leu
            20                  25                  30

Arg Ala Ala Ala Glu Thr Thr Gly Gly Pro Gly Ser Pro Asp Pro Ala
                35                  40                  45

Asp Gly Pro Pro Pro Thr Pro Asn Pro Asp Arg Arg Pro Ala Ala Arg
    50                  55                  60

Pro Gly Phe Gly Trp His Gly Gly Pro Glu Glu Asn Glu Asp Glu Ala
65              70                  75                  80

Asp Asp Ala Ala Ala Asp Ala Asp Ala Asp Glu Ala Ala Pro Ala Ser
                85                  90                  95

Gly Glu Ala Val Asp Glu Pro Ala Ala Asp Gly Val Val Ser Pro Arg
                100                 105                 110

Gln Leu Ala Leu Leu Ala Ser Met Val Asp Glu Ala Val Arg Thr Ile
            115                 120                 125

Pro Ser Pro Pro Pro Glu Arg Asp Gly Ala Gln Glu Glu Ala Ala Arg
    130                 135                 140

Ser Pro Ser Pro Pro Arg Thr Pro Ser Met Arg Ala Asp Tyr Gly Glu
145                 150                 155                 160

Glu Asn Asp Asp Asp Asp Asp Asp Asp Asp Asp Arg Asp Ala
                165                 170                 175

Gly Arg Trp Val Arg Gly Pro Glu Thr Thr Ser Ala Val Arg Gly Ala
            180                 185                 190

Tyr Pro Asp Pro Met Ala Ser Leu Ser Pro Arg Pro Ala Pro Arg
    195                 200                 205

Arg His His His His His His Arg Arg Arg Ala Pro Arg Arg
    210                 215                 220

Arg Ser Ala Ala Ser Asp Ser Ser Lys Ser Gly Ser Ser Ser Ala
225             230                 235                 240

Ser Ser Ala Ser Ser Ser Ala Ser Ser Ser Ser Ala Ser Ala Ser
                245                 250                 255

Ser Ser Asp Asp Asp Asp Asp Ala Ala Arg Ala Pro Ala Ser
        260                 265                 270

Ala Ala Asp His Ala Ala Gly Gly Thr Leu Gly Ala Asp Asp Glu Glu
        275                 280                 285

Ala Gly Val Pro Ala Arg Ala Pro Gly Ala Ala Pro Arg Pro Ser Pro
    290                 295                 300

Pro Arg Ala Glu Pro Ala Pro Ala Arg Thr Pro Ala Ala Thr Ala Gly
305                 310                 315                 320

Arg Leu Glu Arg Arg Ala Arg Ala Ala Val Ala Gly Arg Asp Ala
            325                 330                 335

Thr Gly Arg Phe Thr Ala Gly Arg Pro Arg Arg Val Glu Leu Asp Ala
        340                 345                 350

Asp Ala Ala Ser Gly Ala Phe Tyr Ala Arg Tyr Arg Asp Gly Tyr Val
        355                 360                 365

Ser Gly Glu Pro Trp Pro Gly Ala Gly Pro Pro Pro Gly Arg Val
    370                 375                 380

Leu Tyr Gly Gly Leu Gly Asp Ser Arg Pro Gly Leu Trp Gly Ala Pro
385                 390                 395                 400

<210> SEQ ID NO 9
<211> LENGTH: 275
```

<212> TYPE: PRT
<213> ORGANISM: Herpes simplex virus

<400> SEQUENCE: 9

```
Ser Ser Ala Ala Ala Ala Ala Asp Leu Leu Phe Gln Asn Gln Ser
1               5                   10                  15

Leu Arg Pro Leu Leu Ala Asp Thr Val Ala Ala Asp Ser Leu Ala
            20                  25                  30

Ala Pro Ala Ser Ala Pro Arg Glu Ala Lys Arg Lys Ser Pro Ala
        35                  40                  45

Pro Ala Arg Ala Pro Pro Gly Gly Ala Pro Arg Pro Lys Lys Ser
    50                  55                  60

Arg Ala Asp Ala Pro Arg Pro Ala Ala Pro Pro Ala Gly Ala Ala
65                  70                  75                  80

Pro Pro Ala Pro Pro Thr Pro Pro Arg Pro Arg Pro Ala Ala
            85                  90                  95

Leu Thr Arg Arg Pro Ala Glu Gly Pro Asp Pro Gln Gly Gly Trp Arg
            100                 105                 110

Arg Gln Pro Pro Gly Pro Ser His Thr Pro Ala Pro Ser Ala Ala Ala
            115                 120                 125

Leu Glu Ala Tyr Cys Ala Pro Arg Ala Val Ala Glu Leu Thr Asp His
            130                 135                 140

Pro Leu Phe Pro Ala Pro Trp Arg Pro Ala Leu Met Phe Asp Pro Arg
145                 150                 155                 160

Ala Leu Ala Ser Leu Ala Ala Arg Cys Ala Pro Pro Gly Gly
                165                 170                 175

Ala Pro Ala Ala Phe Gly Pro Leu Arg Ala Ser Gly Pro Leu Arg Arg
                180                 185                 190

Ala Ala Ala Trp Met Arg Gln Val Pro Asp Pro Glu Asp Val Arg Val
                195                 200                 205

Val Ile Leu Tyr Ser Pro Leu Pro Gly Glu Asp Leu Ala Ala Gly Arg
            210                 215                 220

Ala Gly Gly Gly Pro Pro Glu Trp Ser Ala Glu Arg Gly Gly Leu
225                 230                 235                 240

Ser Cys Leu Leu Ala Ala Leu Gly Asn Arg Leu Cys Gly Pro Ala Thr
                245                 250                 255

Ala Ala Trp Ala Gly Asn Trp Thr Gly Ala Pro Asp Val Ser Ala Leu
                260                 265                 270

Gly Ala Gln
        275
```

<210> SEQ ID NO 10
<211> LENGTH: 311
<212> TYPE: PRT
<213> ORGANISM: Herpes simplex virus

<400> SEQUENCE: 10

```
Trp Ala Gly Asn Trp Thr Gly Ala Pro Asp Val Ser Ala Leu Gly Ala
1               5                   10                  15

Gln Gly Val Leu Leu Leu Ser Thr Arg Asp Leu Ala Phe Ala Gly Ala
            20                  25                  30

Val Glu Phe Leu Gly Leu Leu Ala Gly Ala Cys Asp Arg Arg Leu Ile
            35                  40                  45

Val Val Asn Ala Val Arg Ala Asp Trp Pro Ala Asp Gly Pro Val
        50                  55                  60
```

Val Ser Arg Gln His Ala Tyr Leu Ala Cys Glu Val Leu Pro Ala Val
65                  70                  75                  80

Gln Cys Ala Val Arg Trp Pro Ala Arg Asp Leu Arg Arg Thr Val
            85                  90                  95

Leu Ala Ser Gly Arg Val Phe Gly Pro Gly Val Phe Ala Arg Val Glu
            100                 105                 110

Ala Ala His Ala Arg Leu Tyr Pro Asp Ala Pro Leu Arg Leu Cys
            115                 120                 125

Arg Gly Ala Asn Val Arg Tyr Arg Val Arg Thr Arg Phe Gly Pro Asp
            130                 135                 140

Thr Leu Val Pro Met Ser Pro Arg Glu Tyr Arg Arg Ala Val Leu Pro
145                 150                 155                 160

Ala Leu Asp Gly Arg Ala Ala Ser Gly Ala Gly Asp Ala Met Ala
            165                 170                 175

Pro Gly Ala Pro Asp Phe Cys Glu Asp Glu Ala His Ser His Arg Ala
            180                 185                 190

Cys Ala Arg Trp Gly Leu Gly Ala Pro Leu Arg Pro Val Tyr Val Ala
            195                 200                 205

Leu Gly Arg Asp Ala Val Arg Gly Gly Pro Ala Glu Leu Arg Gly Pro
210                 215                 220

Arg Arg Glu Phe Cys Ala Arg Ala Leu Leu Glu Pro Asp Gly Asp Ala
225                 230                 235                 240

Pro Pro Leu Val Leu Arg Asp Asp Ala Asp Ala Gly Pro Pro Gln
            245                 250                 255

Ile Arg Trp Ala Ser Ala Ala Gly Arg Ala Gly Thr Val Leu Ala Ala
            260                 265                 270

Ala Gly Gly Gly Val Glu Val Val Gly Thr Ala Ala Gly Leu Ala Thr
            275                 280                 285

Pro Pro Arg Arg Glu Pro Val Asp Met Asp Ala Glu Leu Glu Asp Asp
            290                 295                 300

Asp Asp Gly Leu Phe Gly Glu
305                 310

<210> SEQ ID NO 11
<211> LENGTH: 569
<212> TYPE: PRT
<213> ORGANISM: Herpes simplex virus

<400> SEQUENCE: 11

Ser Ser Ala Ala Ala Ala Ala Asp Leu Leu Phe Gln Asn Gln Ser
1               5                   10                  15

Leu Arg Pro Leu Leu Ala Asp Thr Val Ala Ala Ala Asp Ser Leu Ala
            20                  25                  30

Ala Pro Ala Ser Ala Pro Arg Glu Ala Arg Lys Arg Lys Ser Pro Ala
            35                  40                  45

Pro Ala Arg Ala Pro Pro Gly Gly Ala Pro Arg Pro Pro Lys Lys Ser
            50                  55                  60

Arg Ala Asp Ala Pro Arg Pro Ala Ala Pro Pro Ala Gly Ala Ala
65                  70                  75                  80

Pro Pro Ala Pro Pro Thr Pro Pro Arg Pro Arg Pro Ala Ala
            85                  90                  95

Leu Thr Arg Arg Pro Ala Glu Gly Pro Asp Pro Gln Gly Gly Trp Arg
            100                 105                 110

Arg Gln Pro Pro Gly Pro Ser His Thr Pro Ala Pro Ser Ala Ala Ala
            115                 120                 125

```
Leu Glu Ala Tyr Cys Ala Pro Arg Ala Val Ala Glu Leu Thr Asp His
            130                 135                 140

Pro Leu Phe Pro Ala Pro Trp Arg Pro Ala Leu Met Phe Asp Pro Arg
145                 150                 155                 160

Ala Leu Ala Ser Leu Ala Arg Cys Ala Ala Pro Pro Gly Gly
            165                 170                 175

Ala Pro Ala Ala Phe Gly Pro Leu Arg Ala Ser Gly Pro Leu Arg Arg
            180                 185                 190

Ala Ala Ala Trp Met Arg Gln Val Pro Asp Pro Glu Asp Val Arg Val
            195                 200                 205

Val Ile Leu Tyr Ser Pro Leu Pro Gly Glu Asp Leu Ala Ala Gly Arg
210                 215                 220

Ala Gly Gly Pro Pro Glu Trp Ser Ala Glu Arg Gly Gly Leu
225                 230                 235                 240

Ser Cys Leu Leu Ala Ala Leu Gly Asn Arg Leu Cys Gly Pro Ala Thr
            245                 250                 255

Ala Ala Trp Ala Gly Asn Trp Thr Gly Ala Pro Asp Val Ser Ala Leu
            260                 265                 270

Gly Ala Gln Gly Val Leu Leu Leu Ser Thr Arg Asp Leu Ala Phe Ala
            275                 280                 285

Gly Ala Val Glu Phe Leu Gly Leu Leu Ala Gly Ala Cys Asp Arg Arg
            290                 295                 300

Leu Ile Val Val Asn Ala Val Arg Ala Ala Asp Trp Pro Ala Asp Gly
305                 310                 315                 320

Pro Val Val Ser Arg Gln His Ala Tyr Leu Ala Cys Glu Val Leu Pro
            325                 330                 335

Ala Val Gln Cys Ala Val Arg Trp Pro Ala Ala Arg Asp Leu Arg Arg
            340                 345                 350

Thr Val Leu Ala Ser Gly Arg Val Phe Gly Pro Gly Val Phe Ala Arg
            355                 360                 365

Val Glu Ala Ala His Ala Arg Leu Tyr Pro Asp Ala Pro Pro Leu Arg
370                 375                 380

Leu Cys Arg Gly Ala Asn Val Arg Tyr Arg Val Arg Thr Arg Phe Gly
385                 390                 395                 400

Pro Asp Thr Leu Val Pro Met Ser Pro Arg Glu Tyr Arg Arg Ala Val
            405                 410                 415

Leu Pro Ala Leu Asp Gly Arg Ala Ala Ser Gly Ala Gly Asp Ala
            420                 425                 430

Met Ala Pro Gly Ala Pro Asp Phe Cys Glu Asp Glu Ala His Ser His
            435                 440                 445

Arg Ala Cys Ala Arg Trp Gly Leu Gly Ala Pro Leu Arg Pro Val Tyr
450                 455                 460

Val Ala Leu Gly Arg Asp Ala Val Arg Gly Gly Pro Ala Glu Leu Arg
465                 470                 475                 480

Gly Pro Arg Arg Glu Phe Cys Ala Arg Ala Leu Leu Glu Pro Asp Gly
            485                 490                 495

Asp Ala Pro Pro Leu Val Leu Arg Asp Asp Ala Asp Ala Gly Pro Pro
            500                 505                 510

Pro Gln Ile Arg Trp Ala Ser Ala Ala Gly Arg Ala Gly Thr Val Leu
            515                 520                 525

Ala Ala Ala Gly Gly Gly Val Glu Val Val Gly Thr Ala Ala Gly Leu
530                 535                 540
```

Ala Thr Pro Pro Arg Arg Glu Pro Val Asp Met Asp Ala Glu Leu Glu
545                 550                 555                 560

Asp Asp Asp Asp Gly Leu Phe Gly Glu
                565

<210> SEQ ID NO 12
<211> LENGTH: 543
<212> TYPE: PRT
<213> ORGANISM: Herpes simplex virus

<400> SEQUENCE: 12

Thr Ala Gly Arg Pro Arg Arg Val Glu Leu Asp Ala Asp Ala Ala Ser
1               5                   10                  15

Gly Ala Phe Tyr Ala Arg Tyr Arg Asp Gly Tyr Val Ser Gly Glu Pro
            20                  25                  30

Trp Pro Gly Ala Gly Pro Pro Pro Gly Arg Val Leu Tyr Gly Gly
            35                  40                  45

Leu Gly Asp Ser Arg Pro Gly Leu Trp Gly Ala Pro Glu Ala Glu Glu
    50                  55                  60

Ala Arg Ala Arg Phe Glu Ala Ser Gly Ala Pro Ala Pro Val Trp Ala
65                  70                  75                  80

Pro Glu Leu Gly Asp Ala Ala Gln Gln Tyr Ala Leu Ile Thr Arg Leu
                85                  90                  95

Leu Tyr Thr Pro Asp Ala Glu Ala Met Gly Trp Leu Asn Pro Arg
            100                 105                 110

Val Ala Pro Gly Asp Val Ala Leu Asp Gln Ala Cys Phe Arg Ile Ser
            115                 120                 125

Gly Ala Ala Arg Asn Ser Ser Ser Phe Ile Ser Gly Ser Val Ala Arg
130                 135                 140

Ala Val Pro His Leu Gly Tyr Ala Met Ala Ala Gly Arg Phe Gly Trp
145                 150                 155                 160

Gly Leu Ala His Val Ala Ala Ala Val Ala Met Ser Arg Arg Tyr Asp
                165                 170                 175

Arg Ala Gln Lys Gly Phe Leu Leu Thr Ser Leu Arg Arg Ala Tyr Ala
            180                 185                 190

Pro Leu Leu Ala Arg Glu Asn Ala Ala Leu Thr Gly Ala Arg Thr Pro
    195                 200                 205

Asp Asp Gly Gly Asp Ala Asn Arg His Asp Gly Asp Asp Ala Arg Gly
210                 215                 220

Lys Pro Ala Ala Ala Ala Pro Leu Pro Ser Ala Ala Ala Ser Pro
225                 230                 235                 240

Ala Asp Glu Arg Ala Val Pro Ala Gly Tyr Gly Ala Ala Gly Val Leu
                245                 250                 255

Ala Ala Leu Gly Arg Leu Ser Ala Ala Pro Ala Ser Ala Pro Ala Gly
            260                 265                 270

Ala Asp Asp Asp Asp Asp Asp Gly Ala Gly Gly Gly Gly Gly
    275                 280                 285

Arg Arg Ala Glu Ala Gly Arg Val Ala Val Glu Cys Leu Ala Ala Cys
290                 295                 300

Arg Gly Ile Leu Glu Ala Leu Ala Glu Gly Phe Asp Gly Asp Leu Ala
305                 310                 315                 320

Ala Val Pro Gly Leu Ala Gly Ala Arg Pro Ala Ala Pro Arg Pro
                325                 330                 335

Gly Pro Ala Gly Ala Ala Ala Pro Pro His Ala Asp Ala Pro Arg Leu
            340                 345                 350

```
Arg Ala Trp Leu Arg Glu Leu Arg Phe Val Arg Asp Ala Leu Val Leu
        355                 360                 365

Met Arg Leu Arg Gly Asp Leu Arg Val Ala Gly Gly Ser Glu Ala Ala
370                 375                 380

Val Ala Ala Val Arg Ala Val Ser Leu Val Ala Gly Ala Leu Gly Pro
385                 390                 395                 400

Ala Leu Pro Arg Ser Pro Arg Leu Leu Ser Ala Ala Ala Ala
                405                 410                 415

Ala Asp Leu Leu Phe Gln Asn Gln Ser Leu Arg Pro Leu Leu Ala Asp
                420                 425                 430

Thr Val Ala Ala Asp Ser Leu Ala Ala Pro Ala Ser Ala Pro Arg
                435                 440                 445

Glu Ala Arg Lys Arg Lys Ser Pro Ala Pro Ala Arg Ala Pro Pro Gly
        450                 455                 460

Gly Ala Pro Arg Pro Lys Lys Ser Arg Ala Asp Ala Pro Arg Pro
465                 470                 475                 480

Ala Ala Ala Pro Pro Ala Gly Ala Ala Pro Pro Ala Pro Thr Pro
                485                 490                 495

Pro Pro Arg Pro Pro Arg Pro Ala Ala Leu Thr Arg Arg Pro Ala Glu
        500                 505                 510

Gly Pro Asp Pro Gln Gly Gly Trp Arg Arg Gln Pro Pro Gly Pro Ser
        515                 520                 525

His Thr Pro Ala Pro Ser Ala Ala Ala Leu Glu Ala Tyr Cys Ala
        530                 535                 540

<210> SEQ ID NO 13
<211> LENGTH: 544
<212> TYPE: PRT
<213> ORGANISM: Herpes simplex virus

<400> SEQUENCE: 13

Ala Ala Ala Asp Ser Leu Ala Ala Pro Ala Ser Ala Pro Arg Glu Ala
1               5                   10                  15

Arg Lys Arg Lys Ser Pro Ala Pro Ala Arg Ala Pro Pro Gly Gly Ala
            20                  25                  30

Pro Arg Pro Pro Lys Lys Ser Arg Ala Asp Ala Pro Arg Pro Ala Ala
        35                  40                  45

Ala Pro Pro Ala Gly Ala Ala Pro Pro Ala Pro Thr Pro Pro
        50                  55                  60

Arg Pro Pro Arg Pro Ala Ala Leu Thr Arg Arg Pro Ala Glu Gly Pro
65                  70                  75                  80

Asp Pro Gln Gly Gly Trp Arg Arg Gln Pro Pro Gly Pro Ser His Thr
                85                  90                  95

Pro Ala Pro Ser Ala Ala Ala Leu Glu Ala Tyr Cys Ala Pro Arg Ala
            100                 105                 110

Val Ala Glu Leu Thr Asp His Pro Leu Phe Pro Ala Pro Trp Arg Pro
        115                 120                 125

Ala Leu Met Phe Asp Pro Arg Ala Leu Ala Ser Leu Ala Ala Arg Cys
        130                 135                 140

Ala Ala Pro Pro Pro Gly Gly Ala Pro Ala Ala Phe Gly Pro Leu Arg
145                 150                 155                 160

Ala Ser Gly Pro Leu Arg Arg Ala Ala Ala Trp Met Arg Gln Val Pro
                165                 170                 175

Asp Pro Glu Asp Val Arg Val Val Ile Leu Tyr Ser Pro Leu Pro Gly
```

```
              180                 185                 190
Glu Asp Leu Ala Ala Gly Arg Ala Gly Gly Pro Pro Glu Trp
            195                 200                 205
Ser Ala Glu Arg Gly Gly Leu Ser Cys Leu Leu Ala Ala Leu Gly Asn
        210                 215                 220
Arg Leu Cys Gly Pro Ala Thr Ala Ala Trp Ala Gly Asn Trp Thr Gly
225                 230                 235                 240
Ala Pro Asp Val Ser Ala Leu Gly Ala Gln Gly Val Leu Leu Leu Ser
            245                 250                 255
Thr Arg Asp Leu Ala Phe Ala Gly Ala Val Glu Phe Leu Gly Leu Leu
            260                 265                 270
Ala Gly Ala Cys Asp Arg Arg Leu Ile Val Val Asn Ala Val Arg Ala
            275                 280                 285
Ala Asp Trp Pro Ala Asp Gly Pro Val Val Ser Arg Gln His Ala Tyr
        290                 295                 300
Leu Ala Cys Glu Val Leu Pro Ala Val Gln Cys Ala Val Arg Trp Pro
305                 310                 315                 320
Ala Ala Arg Asp Leu Arg Arg Thr Val Leu Ala Ser Gly Arg Val Phe
                325                 330                 335
Gly Pro Gly Val Phe Ala Arg Val Glu Ala Ala His Ala Arg Leu Tyr
            340                 345                 350
Pro Asp Ala Pro Pro Leu Arg Leu Cys Arg Gly Ala Asn Val Arg Tyr
            355                 360                 365
Arg Val Arg Thr Arg Phe Gly Pro Asp Thr Leu Val Pro Met Ser Pro
370                 375                 380
Arg Glu Tyr Arg Arg Ala Val Leu Pro Ala Leu Asp Gly Arg Ala Ala
385                 390                 395                 400
Ala Ser Gly Ala Gly Asp Ala Met Ala Pro Gly Ala Pro Asp Phe Cys
                405                 410                 415
Glu Asp Glu Ala His Ser His Arg Ala Cys Ala Arg Trp Gly Leu Gly
            420                 425                 430
Ala Pro Leu Arg Pro Val Tyr Val Ala Leu Gly Arg Asp Ala Val Arg
            435                 440                 445
Gly Gly Pro Ala Glu Leu Arg Gly Pro Arg Arg Glu Phe Cys Ala Arg
            450                 455                 460
Ala Leu Leu Glu Pro Asp Gly Asp Ala Pro Leu Val Leu Arg Asp
465                 470                 475                 480
Asp Ala Asp Ala Gly Pro Pro Gln Ile Arg Trp Ala Ser Ala Ala
                485                 490                 495
Gly Arg Ala Gly Thr Val Leu Ala Ala Ala Gly Gly Val Glu Val
            500                 505                 510
Val Gly Thr Ala Ala Gly Leu Ala Thr Pro Pro Arg Arg Glu Pro Val
            515                 520                 525
Asp Met Asp Ala Glu Leu Glu Asp Asp Asp Gly Leu Phe Gly Glu
530                 535                 540

<210> SEQ ID NO 14
<211> LENGTH: 1109
<212> TYPE: PRT
<213> ORGANISM: Herpes simplex virus

<400> SEQUENCE: 14

His His His His His His His Arg Arg Arg Ala Pro Arg Arg
1               5                   10                  15
```

-continued

```
Ser Ala Ala Ser Asp Ser Ser Lys Ser Gly Ser Ser Ser Ala Ser
            20                  25                  30

Ser Ala Ser Ser Ser Ala Ser Ser Ser Ser Ala Ser Ala Ser Ser
            35                  40                  45

Ser Asp Asp Asp Asp Asp Asp Ala Ala Arg Ala Pro Ala Ser Ala
50                  55                  60

Ala Asp His Ala Ala Gly Gly Thr Leu Gly Ala Asp Glu Glu Ala
65                  70                  75                  80

Gly Val Pro Ala Arg Ala Pro Gly Ala Ala Pro Arg Pro Ser Pro Pro
                85                  90                  95

Arg Ala Glu Pro Ala Pro Ala Arg Thr Pro Ala Ala Thr Ala Gly Arg
            100                 105                 110

Leu Glu Arg Arg Arg Ala Arg Ala Ala Val Ala Gly Arg Asp Ala Thr
            115                 120                 125

Gly Arg Phe Thr Ala Gly Arg Pro Arg Arg Val Glu Leu Asp Ala Asp
            130                 135                 140

Ala Ala Ser Gly Ala Phe Tyr Ala Arg Tyr Arg Asp Gly Tyr Val Ser
145                 150                 155                 160

Gly Glu Pro Trp Pro Gly Ala Gly Pro Pro Pro Gly Arg Val Leu
                165                 170                 175

Tyr Gly Gly Leu Gly Asp Ser Arg Pro Gly Leu Trp Gly Ala Pro Glu
            180                 185                 190

Ala Glu Glu Ala Arg Ala Arg Phe Glu Ala Ser Gly Ala Pro Ala Pro
            195                 200                 205

Val Trp Ala Pro Glu Leu Gly Asp Ala Ala Gln Gln Tyr Ala Leu Ile
210                 215                 220

Thr Arg Leu Leu Tyr Thr Pro Asp Ala Glu Ala Met Gly Trp Leu Gln
225                 230                 235                 240

Asn Pro Arg Val Ala Pro Gly Asp Val Ala Leu Asp Gln Ala Cys Phe
                245                 250                 255

Arg Ile Ser Gly Ala Ala Arg Asn Ser Ser Ser Phe Ile Ser Gly Ser
            260                 265                 270

Val Ala Arg Ala Val Pro His Leu Gly Tyr Ala Met Ala Ala Gly Arg
            275                 280                 285

Phe Gly Trp Gly Leu Ala His Val Ala Ala Val Ala Met Ser Arg
290                 295                 300

Arg Tyr Asp Arg Ala Gln Lys Gly Phe Leu Leu Thr Ser Leu Arg Arg
305                 310                 315                 320

Ala Tyr Ala Pro Leu Leu Ala Arg Glu Asn Ala Ala Leu Thr Gly Ala
                325                 330                 335

Arg Thr Pro Asp Asp Gly Gly Asp Ala Asn Arg His Asp Gly Asp Asp
            340                 345                 350

Ala Arg Gly Lys Pro Ala Ala Ala Ala Pro Leu Pro Ser Ala Ala
            355                 360                 365

Ala Ser Pro Ala Asp Glu Arg Ala Val Pro Ala Gly Tyr Gly Ala Ala
370                 375                 380

Gly Val Leu Ala Ala Leu Gly Arg Leu Ser Ala Ala Pro Ala Ser Ala
385                 390                 395                 400

Pro Ala Gly Ala Asp Asp Asp Asp Asp Gly Ala Gly Gly Gly
                405                 410                 415

Gly Gly Gly Arg Arg Ala Glu Ala Gly Arg Val Ala Val Glu Cys Leu
            420                 425                 430

Ala Ala Cys Arg Gly Ile Leu Glu Ala Leu Ala Glu Gly Phe Asp Gly
```

-continued

```
                435                 440                 445
Asp Leu Ala Ala Val Pro Gly Leu Ala Gly Ala Arg Pro Ala Ala Pro
    450                 455                 460
Pro Arg Pro Gly Pro Ala Gly Ala Ala Ala Pro Pro His Ala Asp Ala
465                 470                 475                 480
Pro Arg Leu Arg Ala Trp Leu Arg Glu Leu Arg Phe Val Arg Asp Ala
                485                 490                 495
Leu Val Leu Met Arg Leu Arg Gly Asp Leu Arg Val Ala Gly Gly Ser
                500                 505                 510
Glu Ala Ala Val Ala Ala Val Arg Ala Val Ser Leu Val Ala Gly Ala
            515                 520                 525
Leu Gly Pro Ala Leu Pro Arg Ser Pro Arg Leu Leu Ser Ser Ala Ala
    530                 535                 540
Ala Ala Ala Ala Asp Leu Leu Phe Gln Asn Gln Ser Leu Arg Pro Leu
545                 550                 555                 560
Leu Ala Asp Thr Val Ala Ala Asp Ser Leu Ala Ala Pro Ala Ser
                565                 570                 575
Ala Pro Arg Glu Ala Arg Lys Arg Lys Ser Pro Ala Pro Ala Arg Ala
                580                 585                 590
Pro Pro Gly Gly Ala Pro Arg Pro Lys Lys Ser Arg Ala Asp Ala
            595                 600                 605
Pro Arg Pro Ala Ala Ala Pro Pro Ala Gly Ala Ala Pro Pro Ala Pro
    610                 615                 620
Pro Thr Pro Pro Pro Arg Pro Pro Arg Pro Ala Ala Leu Thr Arg Arg
625                 630                 635                 640
Pro Ala Glu Gly Pro Asp Pro Gln Gly Gly Trp Arg Arg Gln Pro Pro
                645                 650                 655
Gly Pro Ser His Thr Pro Ala Pro Ser Ala Ala Ala Leu Glu Ala Tyr
                660                 665                 670
Cys Ala Pro Arg Ala Val Ala Glu Leu Thr Asp His Pro Leu Phe Pro
                675                 680                 685
Ala Pro Trp Arg Pro Ala Leu Met Phe Asp Pro Arg Ala Leu Ala Ser
    690                 695                 700
Leu Ala Ala Arg Cys Ala Ala Pro Pro Gly Gly Ala Pro Ala Ala
705                 710                 715                 720
Phe Gly Pro Leu Arg Ala Ser Gly Pro Leu Arg Arg Ala Ala Ala Trp
                725                 730                 735
Met Arg Gln Val Pro Asp Pro Glu Asp Val Arg Val Val Ile Leu Tyr
                740                 745                 750
Ser Pro Leu Pro Gly Glu Asp Leu Ala Ala Gly Arg Ala Gly Gly Gly
            755                 760                 765
Pro Pro Pro Glu Trp Ser Ala Glu Arg Gly Gly Leu Ser Cys Leu Leu
    770                 775                 780
Ala Ala Leu Gly Asn Arg Leu Cys Gly Pro Ala Thr Ala Ala Trp Ala
785                 790                 795                 800
Gly Asn Trp Thr Gly Ala Pro Asp Val Ser Ala Leu Gly Ala Gln Gly
                805                 810                 815
Val Leu Leu Leu Ser Thr Arg Asp Leu Ala Phe Ala Gly Ala Val Glu
                820                 825                 830
Phe Leu Gly Leu Leu Ala Gly Ala Cys Asp Arg Arg Leu Ile Val Val
                835                 840                 845
Asn Ala Val Arg Ala Ala Asp Trp Pro Ala Asp Gly Pro Val Val Ser
    850                 855                 860
```

```
Arg Gln His Ala Tyr Leu Ala Cys Glu Val Leu Pro Ala Val Gln Cys
865                 870                 875                 880

Ala Val Arg Trp Pro Ala Arg Asp Leu Arg Arg Thr Val Leu Ala
            885                 890                 895

Ser Gly Arg Val Phe Gly Pro Gly Val Phe Ala Arg Val Glu Ala Ala
            900                 905                 910

His Ala Arg Leu Tyr Pro Asp Ala Pro Pro Leu Arg Leu Cys Arg Gly
            915                 920                 925

Ala Asn Val Arg Tyr Arg Val Arg Thr Arg Phe Gly Pro Asp Thr Leu
930                 935                 940

Val Pro Met Ser Pro Arg Glu Tyr Arg Arg Ala Val Leu Pro Ala Leu
945                 950                 955                 960

Asp Gly Arg Ala Ala Ser Gly Ala Gly Asp Ala Met Ala Pro Gly
            965                 970                 975

Ala Pro Asp Phe Cys Glu Asp Glu Ala His Ser His Arg Ala Cys Ala
            980                 985                 990

Arg Trp Gly Leu Gly Ala Pro Leu Arg Pro Val Tyr Val Ala Leu Gly
            995                 1000                1005

Arg Asp Ala Val Arg Gly Gly Pro Ala Glu Leu Arg Gly Pro Arg
    1010                1015                1020

Arg Glu Phe Cys Ala Arg Ala Leu Leu Glu Pro Asp Gly Asp Ala
    1025                1030                1035

Pro Pro Leu Val Leu Arg Asp Asp Ala Asp Ala Gly Pro Pro Pro
    1040                1045                1050

Gln Ile Arg Trp Ala Ser Ala Ala Gly Arg Ala Gly Thr Val Leu
    1055                1060                1065

Ala Ala Ala Gly Gly Gly Val Glu Val Val Gly Thr Ala Ala Gly
    1070                1075                1080

Leu Ala Thr Pro Pro Arg Arg Glu Pro Val Asp Met Asp Ala Glu
    1085                1090                1095

Leu Glu Asp Asp Asp Asp Gly Leu Phe Gly Glu
    1100                1105

<210> SEQ ID NO 15
<211> LENGTH: 1164
<212> TYPE: PRT
<213> ORGANISM: Herpes simplex virus

<400> SEQUENCE: 15

Met Ser Ala Glu Gln Arg Lys Lys Lys Thr Thr Thr Thr Thr Gln
1               5                   10                  15

Gly Arg Gly Ala Glu Val Ala Met Ala Asp Glu Asp Gly Gly Arg Leu
            20                  25                  30

Arg Ala Ala Ala Glu Thr Thr Gly Gly Pro Gly Ser Pro Asp Pro Ala
            35                  40                  45

Asp Gly Pro Pro Pro Thr Pro Asn Pro Asp Arg Pro Ala Ala Arg
            50                  55                  60

Pro Gly Phe Gly Trp His Gly Gly Pro Glu Glu Asn Glu Asp Glu Ala
65                  70                  75                  80

Asp Asp Ala Ala Asp Ala Asp Ala Asp Glu Ala Pro Ala Ser
                85                  90                  95

Gly Glu Ala Val Asp Glu Pro Ala Ala Asp Gly Val Val Ser Pro Arg
            100                 105                 110

Gln Leu Ala Leu Leu Ala Ser Met Val Asp Glu Ala Val Arg Thr Ile
```

```
            115                 120                 125
Pro Ser Pro Pro Pro Glu Arg Asp Gly Ala Gln Glu Glu Ala Ala Arg
130                 135                 140
Ser Pro Ser Pro Pro Arg Thr Pro Ser Met Arg Ala Asp Tyr Gly Glu
145                 150                 155                 160
Glu Asn Asp Asp Asp Asp Asp Asp Asp Asp Asp Arg Asp Ala
                165                 170                 175
Gly Arg Trp Val Arg Gly Pro Glu Thr Thr Ser Ala Val Arg Gly Ala
                180                 185                 190
Tyr Pro Asp Pro Met Ala Ser Leu Ser Pro Arg Pro Ala Pro Arg
                195                 200                 205
Arg His His His His His His Arg Arg Arg Ala Pro Arg Arg
                210                 215                 220
Arg Ser Ala Ala Ser Asp Ser Ser Lys Ser Gly Ser Ser Ser Ala
225                 230                 235                 240
Ser Ser Ala Ser Ser Ala Ser Ser Ser Ser Ala Ser Ala Ser
                245                 250                 255
Ser Ser Asp Asp Asp Asp Asp Asp Ala Ala Arg Ala Pro Ala Ser
                260                 265                 270
Ala Ala Asp His Ala Ala Gly Gly Thr Leu Gly Ala Asp Asp Glu Glu
                275                 280                 285
Ala Gly Val Pro Ala Arg Ala Pro Gly Ala Ala Pro Arg Pro Ser Pro
290                 295                 300
Pro Arg Ala Glu Pro Ala Pro Ala Arg Thr Pro Ala Ala Thr Ala Gly
305                 310                 315                 320
Arg Leu Glu Arg Arg Arg Ala Arg Ala Ala Val Ala Gly Arg Asp Ala
                325                 330                 335
Thr Gly Arg Phe Thr Ala Gly Arg Pro Arg Arg Val Glu Leu Asp Ala
                340                 345                 350
Asp Ala Ala Ser Gly Ala Phe Tyr Ala Arg Tyr Arg Asp Gly Tyr Val
                355                 360                 365
Ser Gly Glu Pro Trp Pro Gly Ala Gly Pro Pro Pro Gly Arg Val
                370                 375                 380
Leu Tyr Gly Gly Leu Gly Ala Arg Thr Pro Asp Asp Gly Gly Asp Ala
385                 390                 395                 400
Asn Arg His Asp Gly Asp Asp Ala Arg Gly Lys Pro Ala Ala Ala
                405                 410                 415
Ala Pro Leu Pro Ser Ala Ala Ser Pro Ala Asp Glu Arg Ala Val
                420                 425                 430
Pro Ala Gly Tyr Gly Ala Ala Gly Val Leu Ala Ala Leu Gly Arg Leu
                435                 440                 445
Ser Ala Ala Pro Ala Ser Ala Pro Ala Gly Ala Asp Asp Asp Asp
                450                 455                 460
Asp Asp Gly Ala Gly Gly Gly Gly Gly Arg Arg Ala Glu Ala Gly
465                 470                 475                 480
Arg Val Ala Val Glu Cys Leu Ala Ala Cys Arg Gly Ile Leu Glu Ala
                485                 490                 495
Leu Ala Glu Gly Phe Asp Gly Asp Leu Ala Ala Val Pro Gly Leu Ala
                500                 505                 510
Gly Ala Arg Pro Ala Pro Pro Arg Pro Gly Pro Ala Gly Ala Ala
                515                 520                 525
Ala Pro Pro His Ala Asp Ala Pro Arg Leu Arg Ala Trp Leu Arg Glu
                530                 535                 540
```

```
Leu Arg Phe Val Arg Asp Ala Leu Val Leu Met Arg Leu Arg Gly Asp
545                 550                 555                 560

Leu Arg Val Ala Gly Gly Ser Glu Ala Ala Val Ala Ala Val Arg Ala
            565                 570                 575

Val Ser Leu Val Ala Gly Ala Leu Gly Pro Ala Leu Pro Arg Ser Pro
            580                 585                 590

Arg Leu Leu Ser Ser Ala Ala Ala Ala Ala Asp Leu Leu Phe Gln
        595                 600                 605

Asn Gln Ser Leu Arg Pro Leu Leu Ala Asp Thr Val Ala Ala Ala Asp
            610                 615                 620

Ser Leu Ala Ala Pro Ala Ser Ala Pro Arg Glu Ala Arg Lys Arg Lys
625                 630                 635                 640

Ser Pro Ala Pro Ala Arg Ala Pro Pro Gly Gly Ala Pro Arg Pro Pro
            645                 650                 655

Lys Lys Ser Arg Ala Asp Ala Pro Arg Pro Ala Ala Ala Pro Pro Ala
            660                 665                 670

Gly Ala Ala Pro Pro Ala Pro Pro Thr Pro Pro Arg Pro Pro Arg
            675                 680                 685

Pro Ala Ala Leu Thr Arg Arg Pro Ala Glu Gly Pro Asp Pro Gln Gly
            690                 695                 700

Gly Trp Arg Arg Gln Pro Pro Gly Pro Ser His Thr Pro Ala Pro Ser
705                 710                 715                 720

Ala Ala Ala Leu Glu Ala Tyr Cys Ala Pro Arg Ala Val Ala Glu Leu
            725                 730                 735

Thr Asp His Pro Leu Phe Pro Ala Pro Trp Arg Pro Ala Leu Met Phe
            740                 745                 750

Asp Pro Arg Ala Leu Ala Ser Leu Ala Ala Arg Cys Ala Ala Pro Pro
            755                 760                 765

Pro Gly Gly Ala Pro Ala Ala Phe Gly Pro Leu Arg Ala Ser Gly Pro
    770                 775                 780

Leu Arg Arg Ala Ala Ala Trp Met Arg Gln Val Pro Asp Pro Glu Asp
785                 790                 795                 800

Val Arg Val Val Ile Leu Tyr Ser Pro Leu Pro Gly Glu Asp Leu Ala
                805                 810                 815

Ala Gly Arg Ala Gly Gly Pro Pro Pro Glu Trp Ser Ala Glu Arg
            820                 825                 830

Gly Gly Leu Ser Cys Leu Leu Ala Ala Leu Gly Asn Arg Leu Cys Gly
            835                 840                 845

Pro Ala Thr Ala Ala Trp Ala Gly Asn Trp Thr Gly Ala Pro Asp Val
850                 855                 860

Ser Ala Leu Gly Ala Gln Gly Val Leu Leu Leu Ser Thr Arg Asp Leu
865                 870                 875                 880

Ala Phe Ala Gly Ala Val Glu Phe Leu Gly Leu Leu Ala Gly Ala Cys
                885                 890                 895

Asp Arg Arg Leu Ile Val Val Asn Ala Val Arg Ala Ala Asp Trp Pro
            900                 905                 910

Ala Asp Gly Pro Val Val Ser Arg Gln His Ala Tyr Leu Ala Cys Glu
            915                 920                 925

Val Leu Pro Ala Val Gln Cys Ala Val Arg Trp Pro Ala Ala Arg Asp
            930                 935                 940

Leu Arg Arg Thr Val Leu Ala Ser Gly Arg Val Phe Gly Pro Gly Val
945                 950                 955                 960
```

```
Phe Ala Arg Val Glu Ala His Ala Arg Leu Tyr Pro Asp Ala Pro
                965                 970                 975

Pro Leu Arg Leu Cys Arg Gly Ala Asn Val Tyr Arg Val Arg Thr
            980                 985                 990

Arg Phe Gly Pro Asp Thr Leu Val Pro Met Ser Pro Arg Glu Tyr Arg
        995                 1000                1005

Arg Ala Val Leu Pro Ala Leu Asp Gly Arg Ala Ala Ala Ser Gly
    1010                1015                1020

Ala Gly Asp Ala Met Ala Pro Gly Ala Pro Asp Phe Cys Glu Asp
    1025                1030                1035

Glu Ala His Ser His Arg Ala Cys Ala Arg Trp Gly Leu Gly Ala
    1040                1045                1050

Pro Leu Arg Pro Val Tyr Val Ala Leu Gly Arg Asp Ala Val Arg
    1055                1060                1065

Gly Gly Pro Ala Glu Leu Arg Gly Pro Arg Arg Glu Phe Cys Ala
    1070                1075                1080

Arg Ala Leu Leu Glu Pro Asp Gly Asp Ala Pro Pro Leu Val Leu
    1085                1090                1095

Arg Asp Asp Ala Asp Ala Gly Pro Pro Pro Gln Ile Arg Trp Ala
    1100                1105                1110

Ser Ala Ala Gly Arg Ala Gly Thr Val Leu Ala Ala Ala Gly Gly
    1115                1120                1125

Gly Val Glu Val Val Gly Thr Ala Ala Gly Leu Ala Thr Pro Pro
    1130                1135                1140

Arg Arg Glu Pro Val Asp Met Asp Ala Glu Leu Glu Asp Asp Asp
    1145                1150                1155

Asp Gly Leu Phe Gly Glu
    1160

<210> SEQ ID NO 16
<211> LENGTH: 1234
<212> TYPE: PRT
<213> ORGANISM: Herpes simplex virus

<400> SEQUENCE: 16

Met Ser Ala Glu Gln Arg Lys Lys Lys Thr Thr Thr Thr Thr Gln
1               5                   10                  15

Gly Arg Gly Ala Glu Val Ala Met Ala Asp Glu Asp Gly Gly Arg Leu
            20                  25                  30

Arg Ala Ala Ala Glu Thr Thr Gly Gly Pro Gly Ser Pro Asp Pro Ala
        35                  40                  45

Asp Gly Pro Pro Pro Thr Pro Asn Pro Asp Arg Arg Pro Ala Ala Arg
    50                  55                  60

Pro Gly Phe Gly Trp His Gly Gly Pro Glu Glu Asn Glu Asp Glu Ala
65                  70                  75                  80

Asp Asp Ala Ala Ala Asp Ala Asp Ala Asp Glu Ala Ala Pro Ala Ser
                85                  90                  95

Gly Glu Ala Val Asp Glu Pro Ala Ala Asp Gly Val Val Ser Pro Arg
            100                 105                 110

Gln Leu Ala Leu Leu Ala Ser Met Val Asp Glu Ala Val Arg Thr Ile
        115                 120                 125

Pro Ser Pro Pro Pro Glu Arg Asp Gly Ala Gln Glu Glu Ala Ala Arg
    130                 135                 140

Ser Pro Ser Pro Pro Arg Thr Pro Ser Met Arg Ala Asp Tyr Gly Glu
145                 150                 155                 160
```

-continued

```
Glu Asn Asp Asp Asp Asp Asp Asp Asp Asp Arg Asp Ala
            165                 170                 175

Gly Arg Trp Val Arg Gly Pro Glu Thr Thr Ser Ala Val Arg Gly Ala
            180                 185                 190

Tyr Pro Asp Pro Met Ala Ser Leu Ser Pro Arg Pro Ala Pro Arg
            195                 200                 205

Arg His His His His His His Arg Arg Arg Ala Pro Arg Arg
            210                 215                 220

Arg Ser Ala Ala Ser Asp Ser Ser Lys Ser Gly Ser Ser Ser Ala
225                 230                 235                 240

Ser Ser Ala Ser Ser Ser Ala Ser Ser Ser Ser Ala Ser Ala Ser
            245                 250                 255

Ser Ser Asp Asp Asp Asp Asp Asp Ala Ala Arg Ala Pro Ala Ser
            260                 265                 270

Ala Ala Asp His Ala Ala Gly Gly Thr Leu Gly Ala Asp Asp Glu Glu
            275                 280                 285

Ala Gly Val Pro Ala Arg Ala Pro Gly Ala Ala Pro Arg Pro Ser Pro
            290                 295                 300

Pro Arg Ala Glu Pro Ala Pro Ala Arg Thr Pro Ala Ala Thr Ala Gly
305                 310                 315                 320

Arg Leu Glu Arg Arg Ala Arg Ala Ala Val Ala Gly Arg Asp Ala
            325                 330                 335

Thr Gly Arg Phe Thr Ala Gly Arg Pro Arg Arg Val Glu Leu Asp Ala
            340                 345                 350

Asp Ala Ala Ser Gly Ala Phe Tyr Ala Arg Tyr Arg Asp Gly Tyr Val
            355                 360                 365

Ser Gly Glu Pro Trp Pro Gly Ala Gly Pro Pro Pro Gly Arg Val
            370                 375                 380

Leu Tyr Gly Gly Leu Gly Asp Ser Arg Pro Gly Leu Trp Gly Ala Pro
385                 390                 395                 400

Glu Ala Glu Glu Ala Arg Ala Arg Phe Glu Ala Ser Gly Ala Pro Ala
            405                 410                 415

Pro Val Trp Ala Pro Glu Leu Gly Asp Ala Ala Gln Gln Tyr Ala Leu
            420                 425                 430

Ile Thr Arg Leu Leu Tyr Thr Pro Asp Ala Glu Ala Met Gly Trp Leu
            435                 440                 445

Gln Asn Pro Arg Val Ala Pro Gly Asp Val Ala Leu Asp Gln Ala Cys
            450                 455                 460

Phe Arg Ile Ser Gly Ala Ala Arg Asn Ser Ser Phe Ile Ser Gly
465                 470                 475                 480

Ser Val Ala Arg Ala Val Pro His Leu Gly Tyr Ala Met Ala Ala Gly
            485                 490                 495

Arg Phe Gly Trp Gly Leu Ala His Val Ala Ala Val Ala Met Ser
            500                 505                 510

Arg Arg Tyr Asp Arg Ala Gln Lys Gly Phe Leu Leu Thr Ser Leu Arg
            515                 520                 525

Arg Ala Tyr Ala Pro Leu Leu Ala Arg Glu Asn Ala Ala Leu Thr Gly
            530                 535                 540

Ala Arg Thr Pro Asp Asp Gly Gly Asp Ala Asn Arg His Asp Gly Asp
545                 550                 555                 560

Asp Ala Arg Gly Lys Pro Ala Ala Ala Ala Pro Leu Pro Ser Ala
            565                 570                 575
```

```
Ala Ala Ser Pro Ala Asp Glu Arg Ala Val Pro Ala Gly Tyr Gly Ala
            580                 585                 590

Ala Gly Val Leu Ala Ala Leu Gly Arg Leu Ser Ala Ala Pro Ala Ser
        595                 600                 605

Ala Pro Ala Gly Ala Asp Asp Asp Asp Asp Asp Gly Ala Gly Gly
    610                 615                 620

Gly Gly Gly Gly Arg Arg Ala Glu Ala Gly Arg Val Ala Val Glu Cys
625                 630                 635                 640

Leu Ala Ala Cys Arg Gly Ile Leu Glu Ala Leu Ala Glu Gly Phe Asp
                645                 650                 655

Gly Asp Leu Ala Ala Val Pro Gly Leu Ala Gly Ala Arg Pro Ala Ala
            660                 665                 670

Pro Arg Pro Gly Pro Ala Gly Ala Ala Pro Pro His Ala Asp
        675                 680                 685

Ala Pro Arg Leu Arg Ala Trp Leu Arg Glu Leu Arg Phe Val Arg Asp
    690                 695                 700

Ala Leu Val Leu Met Arg Leu Arg Gly Asp Leu Arg Val Ala Gly Gly
705                 710                 715                 720

Ser Glu Ala Ala Val Ala Ala Val Arg Ala Val Ser Leu Val Ala Gly
                725                 730                 735

Ala Leu Gly Pro Ala Leu Pro Arg Ser Pro Arg Leu Leu Ser Ser Ala
            740                 745                 750

Ala Ala Ala Ala Asp Leu Leu Phe Gln Asn Gln Ser Leu Arg Pro
        755                 760                 765

Leu Leu Ala Asp Thr Val Ala Ala Asp Ser Leu Ala Ala Pro Ala
770                 775                 780

Ser Thr Pro Ala Pro Ser Ala Ala Ala Leu Glu Ala Tyr Cys Ala Pro
785                 790                 795                 800

Arg Ala Val Ala Glu Leu Thr Asp His Pro Leu Phe Pro Ala Pro Trp
                805                 810                 815

Arg Pro Ala Leu Met Phe Asp Pro Arg Ala Leu Ala Ser Leu Ala Ala
            820                 825                 830

Arg Cys Ala Ala Pro Pro Gly Gly Ala Pro Ala Ala Phe Gly Pro
        835                 840                 845

Leu Arg Ala Ser Gly Pro Leu Arg Arg Ala Ala Ala Trp Met Arg Gln
850                 855                 860

Val Pro Asp Pro Glu Asp Val Arg Val Ala Val Ile Leu Tyr Ser Pro Leu
865                 870                 875                 880

Pro Gly Glu Asp Leu Ala Ala Gly Arg Ala Gly Gly Gly Pro Pro
                885                 890                 895

Glu Trp Ser Ala Glu Arg Gly Gly Leu Ser Cys Leu Leu Ala Ala Leu
            900                 905                 910

Gly Asn Arg Leu Cys Gly Pro Ala Thr Ala Ala Trp Ala Gly Asn Trp
        915                 920                 925

Thr Gly Ala Pro Asp Val Ser Ala Leu Gly Ala Gln Val Leu Leu
930                 935                 940

Leu Ser Thr Arg Asp Leu Ala Phe Ala Gly Ala Val Glu Phe Leu Gly
945                 950                 955                 960

Leu Leu Ala Gly Ala Cys Asp Arg Leu Ile Val Val Asn Ala Val
                965                 970                 975

Arg Ala Ala Asp Trp Pro Ala Asp Gly Pro Val Val Ser Arg Gln His
            980                 985                 990

Ala Tyr Leu Ala Cys Glu Val Leu  Pro Ala Val Gln Cys  Ala Val Arg
```

```
           995                 1000                1005
Trp Pro Ala Ala Arg Asp Leu Arg Arg Thr Val Leu Ala Ser Gly
    1010                1015                1020

Arg Val Phe Gly Pro Gly Val Phe Ala Arg Val Glu Ala Ala His
    1025                1030                1035

Ala Arg Leu Tyr Pro Asp Ala Pro Pro Leu Arg Leu Cys Arg Gly
    1040                1045                1050

Ala Asn Val Arg Tyr Arg Val Arg Thr Arg Phe Gly Pro Asp Thr
    1055                1060                1065

Leu Val Pro Met Ser Pro Arg Glu Tyr Arg Arg Ala Val Leu Pro
    1070                1075                1080

Ala Leu Asp Gly Arg Ala Ala Ser Gly Ala Gly Asp Ala Met
    1085                1090                1095

Ala Pro Gly Ala Pro Asp Phe Cys Glu Asp Glu Ala His Ser His
    1100                1105                1110

Arg Ala Cys Ala Arg Trp Gly Leu Gly Ala Pro Leu Arg Pro Val
    1115                1120                1125

Tyr Val Ala Leu Gly Arg Asp Ala Val Arg Gly Gly Pro Ala Glu
    1130                1135                1140

Leu Arg Gly Pro Arg Arg Glu Phe Cys Ala Arg Ala Leu Leu Glu
    1145                1150                1155

Pro Asp Gly Asp Ala Pro Pro Leu Val Leu Arg Asp Asp Ala Asp
    1160                1165                1170

Ala Gly Pro Pro Pro Gln Ile Arg Trp Ala Ser Ala Ala Gly Arg
    1175                1180                1185

Ala Gly Thr Val Leu Ala Ala Ala Gly Gly Gly Val Glu Val Val
    1190                1195                1200

Gly Thr Ala Ala Gly Leu Ala Thr Pro Pro Arg Arg Glu Pro Val
    1205                1210                1215

Asp Met Asp Ala Glu Leu Glu Asp Asp Asp Asp Gly Leu Phe Gly
    1220                1225                1230

Glu
```

<210> SEQ ID NO 17
<211> LENGTH: 255
<212> TYPE: PRT
<213> ORGANISM: Herpes simplex virus

<400> SEQUENCE: 17

```
Met Phe Ser Ala Ser Thr Thr Pro Glu Gln Pro Leu Gly Leu Ser Gly
1               5                   10                  15

Asp Ala Thr Pro Pro Leu Pro Thr Ser Val Pro Leu Asp Trp Ala Ala
                20                  25                  30

Phe Arg Arg Ala Phe Leu Ile Asp Asp Ala Trp Arg Pro Leu Leu Glu
            35                  40                  45

Pro Glu Leu Ala Asn Pro Leu Thr Arg Leu Leu Ala Glu Tyr Asp
        50                  55                  60

Arg Arg Cys Gln Thr Glu Glu Val Leu Pro Arg Glu Asp Val Phe
65                  70                  75                  80

Ser Trp Thr Arg Tyr Cys Thr Pro Asp Asp Val Arg Val Ile Ile
                85                  90                  95

Gly Gln Asp Pro Tyr His His Pro Gly Gln Ala His Gly Leu Ala Phe
                100                 105                 110

Ser Val Arg Ala Asp Val Pro Val Pro Pro Ser Leu Arg Asn Val Leu
```

```
                115                 120                 125
Ala Ala Val Lys Asn Cys Tyr Pro Asp Ala Arg Met Ser Gly Arg Gly
    130                 135                 140

Cys Leu Glu Lys Trp Ala Arg Asp Gly Val Leu Leu Asn Thr Thr
145                 150                 155                 160

Leu Thr Val Lys Arg Gly Ala Ala Ser His Ser Lys Leu Gly Trp
                165                 170                 175

Asp Arg Phe Val Gly Val Val Gln Arg Leu Ala Arg Arg Pro
            180                 185                 190

Gly Leu Val Phe Met Leu Trp Gly Ala His Ala Gln Asn Ala Ile Arg
                195                 200                 205

Pro Asp Pro Arg Gln His Tyr Val Leu Lys Phe Ser His Pro Ser Pro
    210                 215                 220

Leu Ser Lys Val Pro Phe Gly Thr Cys Gln His Phe Leu Ala Ala Asn
225                 230                 235                 240

Arg Tyr Leu Glu Thr Arg Asp Ile Met Pro Ile Asp Trp Ser Val
                245                 250                 255

<210> SEQ ID NO 18
<211> LENGTH: 96
<212> TYPE: PRT
<213> ORGANISM: Herpes simplex virus

<400> SEQUENCE: 18

Met Gly Leu Ala Phe Ser Gly Ala Arg Pro Cys Cys Cys Arg His Asn
1               5                   10                  15

Val Ile Thr Thr Asp Gly Gly Glu Val Val Ser Leu Thr Ala His Glu
                20                  25                  30

Phe Asp Val Val Asp Ile Glu Ser Glu Glu Gly Asn Phe Tyr Val
            35                  40                  45

Pro Pro Asp Val Arg Val Val Thr Arg Ala Pro Gly Pro Gln Tyr Arg
    50                  55                  60

Arg Ala Ser Asp Pro Pro Ser Arg His Thr Arg Arg Arg Asp Pro Asp
65                  70                  75                  80

Val Ala Arg Pro Pro Ala Thr Leu Thr Pro Pro Leu Ser Asp Ser Glu
                85                  90                  95

<210> SEQ ID NO 19
<211> LENGTH: 226
<212> TYPE: PRT
<213> ORGANISM: Herpes simplex virus

<400> SEQUENCE: 19

Asn Arg Trp Gly Phe Val Cys Leu Phe Gly Leu Val Val Met Gly Ala
1               5                   10                  15

Trp Gly Ala Trp Gly Gly Ser Gln Ala Thr Glu Tyr Val Leu Arg Ser
                20                  25                  30

Val Ile Ala Lys Glu Val Gly Asp Ile Leu Arg Val Pro Cys Met Arg
            35                  40                  45

Thr Pro Ala Asp Asp Val Ser Trp Arg Tyr Glu Ala Pro Ser Val Ile
    50                  55                  60

Asp Tyr Ala Arg Ile Asp Gly Ile Phe Leu Arg Tyr His Cys Pro Gly
65                  70                  75                  80

Leu Asp Thr Phe Leu Trp Asp Arg His Ala Gln Arg Ala Tyr Leu Val
                85                  90                  95

Asn Pro Phe Leu Phe Ala Ala Gly Phe Leu Glu Asp Leu Ser His Ser
```

```
                    100                 105                 110
Val Phe Pro Ala Asp Thr Gln Glu Thr Thr Arg Arg Ala Leu Tyr
            115                 120                 125

Lys Glu Ile Arg Asp Ala Leu Gly Ser Arg Lys Gln Ala Val Ser His
            130                 135                 140

Ala Pro Val Arg Ala Gly Cys Val Asn Phe Asp Tyr Ser Arg Thr Arg
145                 150                 155                 160

Arg Cys Val Gly Arg Arg Asp Leu Arg Pro Ala Asn Thr Thr Ser Thr
                165                 170                 175

Trp Glu Pro Pro Val Ser Ser Asp Asp Glu Ala Ser Ser Gln Ser Lys
                180                 185                 190

Pro Leu Ala Thr Gln Pro Pro Val Leu Ala Leu Ser Asn Ala Pro Pro
            195                 200                 205

Arg Arg Val Ser Pro Thr Arg Gly Arg Arg Arg His Thr Arg Leu Arg
        210                 215                 220

Arg Asn
225

<210> SEQ ID NO 20
<211> LENGTH: 1388
<212> TYPE: PRT
<213> ORGANISM: Herpes simplex virus

<400> SEQUENCE: 20

Asp Tyr Asp Ile Pro Thr Thr Glu Asn Leu Tyr Phe Gln Gly Met Ala
1               5                   10                  15

Ala Pro Ala Arg Asp Pro Pro Gly Tyr Arg Tyr Ala Ala Ala Met Val
            20                  25                  30

Pro Thr Gly Ser Ile Leu Ser Thr Ile Glu Val Ala Ser His Arg Arg
        35                  40                  45

Leu Phe Asp Phe Phe Ala Arg Val Arg Ser Asp Glu Asn Ser Leu Tyr
    50                  55                  60

Asp Val Glu Phe Asp Ala Leu Leu Gly Ser Tyr Cys Asn Thr Leu Ser
65              70                  75                  80

Leu Val Arg Phe Leu Glu Leu Gly Leu Ser Val Ala Cys Val Cys Thr
                85                  90                  95

Lys Phe Pro Glu Leu Ala Tyr Met Asn Glu Gly Arg Val Gln Phe Glu
            100                 105                 110

Val His Gln Pro Leu Ile Ala Arg Asp Gly Pro His Pro Val Glu Gln
        115                 120                 125

Pro Val His Asn Tyr Met Thr Lys Val Ile Asp Arg Arg Ala Leu Asn
    130                 135                 140

Ala Ala Phe Ser Leu Ala Thr Glu Ala Ile Leu Leu Thr Gly Glu
145                 150                 155                 160

Ala Leu Asp Gly Thr Gly Ile Ser Leu His Arg Gln Leu Arg Ala Ile
                165                 170                 175

Gln Gln Leu Ala Arg Asn Val Gln Ala Val Leu Gly Ala Phe Glu Arg
            180                 185                 190

Gly Thr Ala Asp Gln Met Leu His Val Leu Glu Lys Ala Pro Pro
        195                 200                 205

Leu Ala Leu Leu Leu Pro Met Gln Arg Tyr Leu Asp Asn Gly Arg Leu
    210                 215                 220

Ala Thr Arg Val Ala Arg Ala Thr Leu Val Ala Glu Leu Lys Arg Ser
225                 230                 235                 240
```

```
Phe Cys Asp Thr Ser Phe Phe Leu Gly Lys Ala Gly His Arg Arg Glu
                245                 250                 255
Ala Ile Glu Ala Trp Leu Val Asp Leu Thr Thr Ala Thr Gln Pro Ser
        260                 265                 270
Val Ala Val Pro Arg Leu Thr His Ala Asp Thr Arg Gly Arg Pro Val
    275                 280                 285
Asp Gly Val Leu Val Thr Thr Ala Ala Ile Lys Gln Arg Leu Leu Gln
290                 295                 300
Ser Phe Leu Lys Val Glu Asp Thr Glu Ala Asp Val Pro Val Thr Tyr
305                 310                 315                 320
Gly Glu Met Val Leu Asn Gly Ala Asn Leu Val Thr Ala Leu Val Met
                325                 330                 335
Gly Lys Ala Val Arg Ser Leu Asp Asp Val Gly Arg His Leu Leu Glu
            340                 345                 350
Met Gln Glu Glu Gln Leu Glu Ala Asn Arg Glu Thr Leu Asp Glu Leu
        355                 360                 365
Glu Ser Ala Pro Gln Thr Thr Arg Val Arg Ala Asp Leu Val Ala Ile
    370                 375                 380
Gly Asp Arg Leu Val Phe Leu Glu Ala Leu Glu Lys Arg Ile Tyr Ala
385                 390                 395                 400
Ala Thr Asn Val Pro Tyr Pro Leu Val Gly Ala Met Asp Leu Thr Phe
                405                 410                 415
Val Leu Pro Leu Gly Leu Phe Asn Pro Ala Met Glu Arg Phe Ala Ala
            420                 425                 430
His Ala Gly Asp Leu Val Pro Ala Pro Gly His Pro Glu Pro Arg Ala
        435                 440                 445
Phe Pro Pro Arg Gln Leu Phe Phe Trp Gly Lys Asp His Gln Val Leu
    450                 455                 460
Arg Leu Ser Met Glu Asn Ala Val Gly Thr Val Cys His Pro Ser Leu
465                 470                 475                 480
Met Asn Ile Asp Ala Ala Val Gly Gly Val Asn His Asp Pro Val Glu
                485                 490                 495
Ala Ala Asn Pro Tyr Gly Ala Tyr Val Ala Ala Pro Ala Gly Pro Gly
            500                 505                 510
Ala Asp Met Gln Gln Arg Phe Leu Asn Ala Trp Arg Gln Arg Leu Ala
        515                 520                 525
His Gly Arg Val Arg Trp Val Ala Glu Cys Gln Met Thr Ala Glu Gln
    530                 535                 540
Phe Met Gln Pro Asp Asn Ala Asn Leu Ala Leu Glu Leu His Pro Ala
545                 550                 555                 560
Phe Asp Phe Phe Ala Gly Val Ala Asp Val Glu Leu Pro Gly Gly Glu
                565                 570                 575
Val Pro Pro Ala Gly Pro Gly Ala Ile Gln Ala Thr Trp Arg Val Val
            580                 585                 590
Asn Gly Asn Leu Pro Leu Ala Leu Cys Pro Val Ala Phe Arg Asp Ala
        595                 600                 605
Arg Gly Leu Glu Leu Gly Val Gly Arg His Ala Met Ala Pro Ala Thr
    610                 615                 620
Ile Ala Ala Val Arg Gly Ala Phe Glu Asp Arg Ser Tyr Pro Ala Val
625                 630                 635                 640
Phe Tyr Leu Leu Gln Ala Ala Ile His Gly Ser Glu His Val Phe Cys
                645                 650                 655
Ala Leu Ala Arg Leu Val Thr Gln Cys Ile Thr Ser Tyr Trp Asn Asn
```

-continued

```
                660                 665                 670
Thr Arg Cys Ala Ala Phe Val Asn Asp Tyr Ser Leu Val Ser Tyr Ile
                675                 680                 685
Val Thr Tyr Leu Gly Gly Asp Leu Pro Glu Glu Cys Met Ala Val Tyr
                690                 695                 700
Arg Asp Leu Val Ala His Val Glu Ala Leu Ala Gln Leu Val Asp Asp
705                 710                 715                 720
Phe Thr Leu Pro Gly Pro Glu Leu Gly Gly Gln Ala Gln Ala Glu Leu
                725                 730                 735
Asn His Leu Met Arg Asp Pro Ala Leu Leu Pro Pro Leu Val Trp Asp
                740                 745                 750
Cys Asp Gly Leu Met Arg His Ala Ala Leu Asp Arg His Arg Asp Cys
                755                 760                 765
Arg Ile Asp Ala Gly Glu His Glu Pro Val Tyr Ala Ala Ala Cys Asn
                770                 775                 780
Val Ala Thr Ala Asp Phe Asn Arg Asn Asp Gly Arg Leu Leu His Asn
785                 790                 795                 800
Thr Gln Ala Arg Ala Ala Asp Ala Ala Asp Asp Arg Pro His Arg Pro
                805                 810                 815
Ala Asp Trp Thr Val His His Lys Ile Tyr Tyr Val Leu Val Pro
                820                 825                 830
Ala Phe Ser Arg Gly Arg Cys Cys Thr Ala Gly Val Arg Phe Asp Arg
                835                 840                 845
Val Tyr Ala Thr Leu Gln Asn Met Val Val Pro Glu Ile Ala Pro Gly
                850                 855                 860
Glu Glu Cys Pro Ser Asp Pro Val Thr Asp Pro Ala His Pro Leu His
865                 870                 875                 880
Pro Ala Asn Leu Val Ala Asn Thr Val Asn Ala Met Phe His Asn Gly
                885                 890                 895
Arg Val Val Val Asp Gly Pro Ala Met Leu Thr Leu Gln Val Leu Ala
                900                 905                 910
His Asn Met Ala Glu Arg Thr Thr Ala Leu Leu Cys Ser Ala Ala Pro
                915                 920                 925
Asp Ala Gly Ala Asn Thr Ala Ser Thr Ala Asn Met Arg Ile Phe Asp
                930                 935                 940
Gly Ala Leu His Ala Gly Val Leu Leu Met Ala Pro Gln His Leu Asp
945                 950                 955                 960
His Thr Ile Gln Asn Gly Glu Tyr Phe Tyr Val Leu Pro Val His Ala
                965                 970                 975
Leu Phe Ala Gly Ala Asp His Val Ala Asn Ala Pro Asn Phe Pro Pro
                980                 985                 990
Ala Leu Arg Asp Leu Ala Arg His Val Pro Leu Val Pro Pro Ala Leu
                995                 1000                1005
Gly Ala Asn Tyr Phe Ser Ser Ile Arg Gln Pro Val Val Gln His
                1010                1015                1020
Ala Arg Glu Ser Ala Ala Gly Glu Asn Ala Leu Thr Tyr Ala Leu
                1025                1030                1035
Met Ala Gly Tyr Phe Lys Met Ser Pro Val Ala Leu Tyr His Gln
                1040                1045                1050
Leu Lys Thr Gly Leu His Pro Gly Phe Gly Phe Thr Val Val Arg
                1055                1060                1065
Gln Asp Arg Phe Val Thr Glu Asn Val Leu Phe Ser Glu Arg Ala
                1070                1075                1080
```

```
Ser Glu Ala Tyr Phe Leu Gly Gln Leu Gln Val Ala Arg His Glu
    1085                1090                1095

Thr Gly Gly Gly Val Ser Phe Thr Leu Thr Gln Pro Arg Gly Asn
    1100                1105                1110

Val Asp Leu Gly Val Gly Tyr Thr Ala Val Ala Ala Thr Ala Thr
    1115                1120                1125

Val Arg Asn Pro Val Thr Asp Met Gly Asn Leu Pro Gln Asn Phe
    1130                1135                1140

Tyr Leu Gly Arg Gly Ala Pro Pro Leu Leu Asp Asn Ala Ala Ala
    1145                1150                1155

Val Tyr Leu Arg Asn Ala Val Val Ala Gly Asn Arg Leu Gly Pro
    1160                1165                1170

Ala Gln Pro Leu Pro Val Phe Gly Cys Ala Gln Val Pro Arg Arg
    1175                1180                1185

Ala Gly Met Asp His Gly Gln Asp Ala Val Cys Glu Phe Ile Ala
    1190                1195                1200

Thr Pro Val Ala Thr Asp Ile Asn Tyr Phe Arg Arg Pro Cys Asn
    1205                1210                1215

Pro Arg Gly Arg Ala Ala Gly Gly Val Tyr Ala Gly Asp Lys Glu
    1220                1225                1230

Gly Asp Val Ile Ala Leu Met Tyr Asp His Gly Gln Ser Asp Pro
    1235                1240                1245

Ala Arg Pro Phe Ala Ala Thr Ala Asn Pro Trp Ala Ser Gln Arg
    1250                1255                1260

Phe Ser Tyr Gly Asp Leu Leu Tyr Asn Gly Ala Tyr His Leu Asn
    1265                1270                1275

Gly Ala Ser Pro Val Leu Ser Pro Cys Phe Lys Phe Phe Thr Ala
    1280                1285                1290

Ala Asp Ile Thr Ala Lys His Arg Cys Leu Glu Arg Leu Ile Val
    1295                1300                1305

Glu Thr Gly Ser Ala Val Ser Thr Ala Thr Ala Ala Ser Asp Val
    1310                1315                1320

Gln Phe Lys Arg Pro Pro Gly Cys Arg Glu Leu Val Glu Asp Pro
    1325                1330                1335

Cys Gly Leu Phe Gln Glu Ala Tyr Pro Ile Thr Cys Ala Ser Asp
    1340                1345                1350

Pro Ala Leu Leu Arg Ser Arg Asp Gly Glu Ala His Ala Arg
    1355                1360                1365

Glu Thr His Phe Thr Gln Tyr Leu Ile Tyr Asp Ala Ser Pro Leu
    1370                1375                1380

Lys Gly Leu Ser Leu
    1385

<210> SEQ ID NO 21
<211> LENGTH: 1374
<212> TYPE: PRT
<213> ORGANISM: Herpes simplex virus

<400> SEQUENCE: 21

Met Ala Ala Pro Ala Arg Asp Pro Pro Gly Tyr Arg Tyr Ala Ala Ala
1               5                   10                  15

Met Val Pro Thr Gly Ser Ile Leu Ser Thr Ile Glu Val Ala Ser His
                20                  25                  30

Arg Arg Leu Phe Asp Phe Phe Ala Arg Val Arg Ser Asp Glu Asn Ser
```

```
                35                  40                  45
Leu Tyr Asp Val Glu Phe Asp Ala Leu Leu Gly Ser Tyr Cys Asn Thr
 50                  55                  60
Leu Ser Leu Val Arg Phe Leu Glu Leu Gly Leu Ser Val Ala Cys Val
 65                  70                  75                  80
Cys Thr Lys Phe Pro Glu Leu Ala Tyr Met Asn Glu Gly Arg Val Gln
                 85                  90                  95
Phe Glu Val His Gln Pro Leu Ile Ala Arg Asp Gly Pro His Pro Val
                100                 105                 110
Glu Gln Pro Val His Asn Tyr Met Thr Lys Val Ile Asp Arg Arg Ala
            115                 120                 125
Leu Asn Ala Ala Phe Ser Leu Ala Thr Glu Ala Ile Ala Leu Leu Thr
130                 135                 140
Gly Glu Ala Leu Asp Gly Thr Gly Ile Ser Leu His Arg Gln Leu Arg
145                 150                 155                 160
Ala Ile Gln Gln Leu Ala Arg Asn Val Gln Ala Val Leu Gly Ala Phe
                165                 170                 175
Glu Arg Gly Thr Ala Asp Gln Met Leu His Val Leu Leu Glu Lys Ala
            180                 185                 190
Pro Pro Leu Ala Leu Leu Pro Met Gln Arg Tyr Leu Asp Asn Gly
            195                 200                 205
Arg Leu Ala Thr Arg Val Ala Arg Ala Thr Leu Val Ala Glu Leu Lys
210                 215                 220
Arg Ser Phe Cys Asp Thr Ser Phe Phe Leu Gly Lys Ala Gly His Arg
225                 230                 235                 240
Arg Glu Ala Ile Glu Ala Trp Leu Val Asp Leu Thr Ala Thr Gln
                245                 250                 255
Pro Ser Val Ala Val Pro Arg Leu Thr His Ala Asp Thr Arg Gly Arg
                260                 265                 270
Pro Val Asp Gly Val Leu Val Thr Thr Ala Ala Ile Lys Gln Arg Leu
            275                 280                 285
Leu Gln Ser Phe Leu Lys Val Glu Asp Thr Glu Ala Asp Val Pro Val
        290                 295                 300
Thr Tyr Gly Glu Met Val Leu Asn Gly Ala Asn Leu Val Thr Ala Leu
305                 310                 315                 320
Val Met Gly Lys Ala Val Arg Ser Leu Asp Asp Val Gly Arg His Leu
                325                 330                 335
Leu Glu Met Gln Glu Gln Leu Glu Ala Asn Arg Glu Thr Leu Asp
                340                 345                 350
Glu Leu Glu Ser Ala Pro Gln Thr Thr Arg Val Arg Ala Asp Leu Val
            355                 360                 365
Ala Ile Gly Asp Arg Leu Val Phe Leu Glu Ala Leu Glu Lys Arg Ile
            370                 375                 380
Tyr Ala Ala Thr Asn Val Pro Tyr Pro Leu Val Gly Ala Met Asp Leu
385                 390                 395                 400
Thr Phe Val Leu Pro Leu Gly Leu Phe Asn Pro Ala Met Glu Arg Phe
                405                 410                 415
Ala Ala His Ala Gly Asp Leu Val Pro Ala Pro Gly His Pro Glu Pro
            420                 425                 430
Arg Ala Phe Pro Pro Arg Gln Leu Phe Phe Trp Gly Lys Asp His Gln
            435                 440                 445
Val Leu Arg Leu Ser Met Glu Asn Ala Val Gly Thr Val Cys His Pro
450                 455                 460
```

Ser Leu Met Asn Ile Asp Ala Val Gly Gly Val Asn His Asp Pro
465                 470                475                 480

Val Glu Ala Ala Asn Pro Tyr Gly Ala Tyr Val Ala Ala Pro Ala Gly
                485                 490                 495

Pro Gly Ala Asp Met Gln Gln Arg Phe Leu Asn Ala Trp Arg Gln Arg
            500                 505                 510

Leu Ala His Gly Arg Val Arg Trp Val Ala Glu Cys Gln Met Thr Ala
        515                 520                 525

Glu Gln Phe Met Gln Pro Asp Asn Ala Asn Leu Ala Leu Glu Leu His
530                 535                 540

Pro Ala Phe Asp Phe Phe Ala Gly Val Ala Asp Val Glu Leu Pro Gly
545                 550                 555                 560

Gly Glu Val Pro Pro Ala Gly Pro Gly Ala Ile Gln Ala Thr Trp Arg
                565                 570                 575

Val Val Asn Gly Asn Leu Pro Leu Ala Leu Cys Pro Val Ala Phe Arg
            580                 585                 590

Asp Ala Arg Gly Leu Glu Leu Gly Val Gly Arg His Ala Met Ala Pro
        595                 600                 605

Ala Thr Ile Ala Ala Val Arg Gly Ala Phe Glu Asp Arg Ser Tyr Pro
610                 615                 620

Ala Val Phe Tyr Leu Leu Gln Ala Ala Ile His Gly Ser Glu His Val
625                 630                 635                 640

Phe Cys Ala Leu Ala Arg Leu Val Thr Gln Cys Ile Thr Ser Tyr Trp
                645                 650                 655

Asn Asn Thr Arg Cys Ala Ala Phe Val Asn Asp Tyr Ser Leu Val Ser
            660                 665                 670

Tyr Ile Val Thr Tyr Leu Gly Gly Asp Leu Pro Glu Glu Cys Met Ala
        675                 680                 685

Val Tyr Arg Asp Leu Val Ala His Val Glu Ala Leu Ala Gln Leu Val
690                 695                 700

Asp Asp Phe Thr Leu Pro Gly Pro Glu Leu Gly Gly Gln Ala Gln Ala
705                 710                 715                 720

Glu Leu Asn His Leu Met Arg Asp Pro Ala Leu Leu Pro Pro Leu Val
                725                 730                 735

Trp Asp Cys Asp Gly Leu Met Arg His Ala Ala Leu Asp Arg His Arg
            740                 745                 750

Asp Cys Arg Ile Asp Ala Gly Glu His Glu Pro Val Tyr Ala Ala Ala
        755                 760                 765

Cys Asn Val Ala Thr Ala Asp Phe Asn Arg Asn Asp Gly Arg Leu Leu
770                 775                 780

His Asn Thr Gln Ala Arg Ala Ala Asp Ala Ala Asp Arg Pro His
785                 790                 795                 800

Arg Pro Ala Asp Trp Thr Val His His Lys Ile Tyr Tyr Val Leu
                805                 810                 815

Val Pro Ala Phe Ser Arg Gly Arg Cys Cys Thr Ala Gly Val Arg Phe
            820                 825                 830

Asp Arg Val Tyr Ala Thr Leu Gln Asn Met Val Val Pro Glu Ile Ala
        835                 840                 845

Pro Gly Glu Glu Cys Pro Ser Asp Pro Val Thr Asp Pro Ala His Pro
850                 855                 860

Leu His Pro Ala Asn Leu Val Ala Asn Thr Val Asn Ala Met Phe His
865                 870                 875                 880

```
Asn Gly Arg Val Val Asp Gly Pro Ala Met Leu Thr Leu Gln Val
            885                 890                 895

Leu Ala His Asn Met Ala Glu Arg Thr Thr Ala Leu Leu Cys Ser Ala
            900                 905                 910

Ala Pro Asp Ala Gly Ala Asn Thr Ala Ser Thr Ala Asn Met Arg Ile
            915                 920                 925

Phe Asp Gly Ala Leu His Ala Gly Val Leu Leu Met Ala Pro Gln His
            930                 935                 940

Leu Asp His Thr Ile Gln Asn Gly Glu Tyr Phe Tyr Val Leu Pro Val
945                 950                 955                 960

His Ala Leu Phe Ala Gly Ala Asp His Val Ala Asn Ala Pro Asn Phe
            965                 970                 975

Pro Pro Ala Leu Arg Asp Leu Ala Arg His Val Pro Leu Val Pro Pro
            980                 985                 990

Ala Leu Gly Ala Asn Tyr Phe Ser Ser Ile Arg Gln Pro Val Val Gln
            995                 1000                1005

His Ala Arg Glu Ser Ala Ala Gly Glu Asn Ala Leu Thr Tyr Ala
            1010                1015                1020

Leu Met Ala Gly Tyr Phe Lys Met Ser Pro Val Ala Leu Tyr His
            1025                1030                1035

Gln Leu Lys Thr Gly Leu His Pro Gly Phe Gly Phe Thr Val Val
            1040                1045                1050

Arg Gln Asp Arg Phe Val Thr Glu Asn Val Leu Phe Ser Glu Arg
            1055                1060                1065

Ala Ser Glu Ala Tyr Phe Leu Gly Gln Leu Gln Val Ala Arg His
            1070                1075                1080

Glu Thr Gly Gly Gly Val Ser Phe Thr Leu Thr Gln Pro Arg Gly
            1085                1090                1095

Asn Val Asp Leu Gly Val Gly Tyr Thr Ala Val Ala Ala Thr Ala
            1100                1105                1110

Thr Val Arg Asn Pro Val Thr Asp Met Gly Asn Leu Pro Gln Asn
            1115                1120                1125

Phe Tyr Leu Gly Arg Gly Ala Pro Pro Leu Leu Asp Asn Ala Ala
            1130                1135                1140

Ala Val Tyr Leu Arg Asn Ala Val Val Ala Gly Asn Arg Leu Gly
            1145                1150                1155

Pro Ala Gln Pro Leu Pro Val Phe Gly Cys Ala Gln Val Pro Arg
            1160                1165                1170

Arg Ala Gly Met Asp His Gly Gln Asp Ala Val Cys Glu Phe Ile
            1175                1180                1185

Ala Thr Pro Val Ala Thr Asp Ile Asn Tyr Phe Arg Arg Pro Cys
            1190                1195                1200

Asn Pro Arg Gly Arg Ala Ala Gly Gly Val Tyr Ala Gly Asp Lys
            1205                1210                1215

Glu Gly Asp Val Ile Ala Leu Met Tyr Asp His Gly Gln Ser Asp
            1220                1225                1230

Pro Ala Arg Pro Phe Ala Ala Thr Ala Asn Pro Trp Ala Ser Gln
            1235                1240                1245

Arg Phe Ser Tyr Gly Asp Leu Leu Tyr Asn Gly Ala Tyr His Leu
            1250                1255                1260

Asn Gly Ala Ser Pro Val Leu Ser Pro Cys Phe Lys Phe Phe Thr
            1265                1270                1275

Ala Ala Asp Ile Thr Ala Lys His Arg Cys Leu Glu Arg Leu Ile
```

```
                    1280                1285                1290

Val Glu Thr Gly Ser Ala Val Ser Thr Ala Thr Ala Ala Ser Asp
            1295                1300                1305

Val Gln Phe Lys Arg Pro Pro Gly Cys Arg Glu Leu Val Glu Asp
            1310                1315                1320

Pro Cys Gly Leu Phe Gln Glu Ala Tyr Pro Ile Thr Cys Ala Ser
            1325                1330                1335

Asp Pro Ala Leu Leu Arg Ser Ala Arg Asp Gly Glu Ala His Ala
            1340                1345                1350

Arg Glu Thr His Phe Thr Gln Tyr Leu Ile Tyr Asp Ala Ser Pro
            1355                1360                1365

Leu Lys Gly Leu Ser Leu
            1370

<210> SEQ ID NO 22
<211> LENGTH: 3122
<212> TYPE: PRT
<213> ORGANISM: Herpes simplex virus

<400> SEQUENCE: 22

Met Ile Pro Ala Ala Leu Pro His Pro Thr Met Lys Arg Gln Gly Asp
1               5                   10                  15

Arg Asp Ile Val Val Thr Gly Val Arg Asn Gln Phe Ala Thr Asp Leu
                20                  25                  30

Glu Pro Gly Gly Ser Val Ser Cys Met Arg Ser Ser Leu Ser Phe Leu
            35                  40                  45

Ser Leu Leu Phe Asp Val Gly Pro Arg Asp Val Leu Ser Ala Glu Ala
50                  55                  60

Ile Glu Gly Cys Leu Val Glu Gly Gly Glu Trp Thr Arg Ala Ala Ala
65                  70                  75                  80

Gly Ser Gly Pro Pro Arg Met Cys Ser Ile Ile Glu Leu Pro Asn Phe
                85                  90                  95

Leu Glu Tyr Pro Ala Ala Arg Gly Gly Leu Arg Cys Val Phe Ser Arg
                100                 105                 110

Val Tyr Gly Glu Val Gly Phe Phe Gly Glu Pro Thr Ala Gly Leu Leu
            115                 120                 125

Glu Thr Gln Cys Pro Ala His Thr Phe Phe Ala Gly Pro Trp Ala Met
130                 135                 140

Arg Pro Leu Ser Tyr Thr Leu Leu Thr Ile Gly Pro Leu Gly Met Gly
145                 150                 155                 160

Leu Tyr Arg Asp Gly Asp Thr Ala Tyr Leu Phe Asp Pro His Gly Leu
                165                 170                 175

Pro Ala Gly Thr Pro Ala Phe Ile Ala Lys Val Arg Ala Gly Asp Val
                180                 185                 190

Tyr Pro Tyr Leu Thr Tyr Tyr Ala His Asp Arg Pro Lys Val Arg Trp
            195                 200                 205

Ala Gly Ala Met Val Phe Phe Val Pro Ser Gly Pro Gly Ala Val Ala
        210                 215                 220

Pro Ala Asp Leu Thr Ala Ala Ala Leu His Leu Tyr Gly Ala Ser Glu
225                 230                 235                 240

Thr Tyr Leu Gln Asp Glu Pro Phe Val Glu Arg Arg Val Ala Ile Thr
                245                 250                 255

His Pro Leu Arg Gly Glu Ile Gly Gly Leu Gly Ala Leu Phe Val Gly
                260                 265                 270
```

-continued

Val Val Pro Arg Gly Asp Gly Glu Gly Ser Gly Pro Val Pro Ala
            275                 280                 285

Leu Pro Ala Pro Thr His Val Gln Thr Pro Gly Ala Asp Arg Pro Pro
    290                 295                 300

Glu Ala Pro Arg Gly Ala Ser Gly Pro Pro Asp Thr Pro Gln Ala Gly
305                 310                 315                 320

His Pro Asn Arg Pro Pro Asp Asp Val Trp Ala Ala Leu Glu Gly
                325                 330                 335

Thr Pro Pro Ala Lys Pro Ser Ala Pro Asp Ala Ala Ser Gly Pro
            340                 345                 350

Pro His Ala Ala Pro Pro Gln Thr Pro Ala Gly Asp Ala Ala Glu
        355                 360                 365

Glu Ala Glu Asp Leu Arg Val Leu Glu Val Gly Ala Val Pro Val Gly
370                 375                 380

Arg His Arg Ala Arg Tyr Ser Thr Gly Leu Pro Lys Arg Arg Arg Pro
385                 390                 395                 400

Thr Trp Thr Pro Pro Ser Ser Val Glu Asp Leu Thr Ser Gly Glu Arg
                405                 410                 415

Pro Ala Pro Lys Ala Pro Pro Ala Lys Ala Lys Lys Ser Ala Pro
            420                 425                 430

Lys Lys Lys Ala Pro Val Ala Ala Glu Val Pro Ala Ser Ser Pro Thr
            435                 440                 445

Pro Ile Ala Ala Thr Val Pro Pro Ala Pro Asp Thr Pro Pro Gln Ser
    450                 455                 460

Gly Gln Gly Gly Gly Asp Asp Gly Pro Ala Ser Pro Ser Ser Pro Ser
465                 470                 475                 480

Val Leu Glu Thr Leu Gly Ala Arg Arg Pro Pro Glu Pro Pro Gly Ala
                485                 490                 495

Asp Leu Ala Gln Leu Phe Glu Val His Pro Asn Val Ala Ala Thr Ala
                500                 505                 510

Val Arg Leu Ala Ala Arg Asp Ala Ala Leu Ala Arg Glu Val Ala Ala
            515                 520                 525

Cys Ser Gln Leu Thr Ile Asn Ala Leu Arg Ser Pro Tyr Pro Ala His
530                 535                 540

Pro Gly Leu Leu Glu Leu Cys Val Ile Phe Phe Glu Arg Val Leu
545                 550                 555                 560

Ala Phe Leu Ile Glu Asn Gly Ala Arg Thr His Thr Gln Ala Gly Val
                565                 570                 575

Ala Gly Pro Ala Ala Ala Leu Leu Asp Phe Thr Leu Arg Met Leu Pro
            580                 585                 590

Arg Lys Thr Ala Val Gly Asp Phe Leu Ala Ser Thr Arg Met Ser Leu
        595                 600                 605

Ala Asp Val Ala Ala His Arg Pro Leu Ile Gln His Val Leu Asp Glu
610                 615                 620

Asn Ser Gln Ile Gly Arg Leu Ala Leu Ala Lys Leu Val Leu Val Ala
625                 630                 635                 640

Arg Asp Val Ile Arg Glu Thr Asp Ala Phe Tyr Gly Asp Leu Ala Asp
                645                 650                 655

Leu Asp Leu Gln Leu Arg Ala Ala Pro Ala Asn Leu Tyr Ala Arg
            660                 665                 670

Leu Gly Glu Trp Leu Leu Glu Arg Ser Arg Ala His Pro Asn Thr Leu
        675                 680                 685

Phe Ala Pro Ala Thr Pro Thr His Pro Glu Pro Leu Leu His Arg Ile

```
            690                 695                 700
Gln Ala Leu Ala Gln Phe Ala Arg Gly Glu Glu Met Arg Val Glu Ala
705                 710                 715                 720

Glu Ala Arg Glu Met Arg Glu Ala Leu Asp Ala Leu Ala Arg Gly Val
                725                 730                 735

Asp Ser Val Ser Gln Arg Ala Gly Pro Leu Thr Val Met Pro Val Pro
                740                 745                 750

Ala Ala Pro Gly Ala Gly Gly Arg Ala Pro Cys Pro Pro Ala Leu Gly
                755                 760                 765

Pro Glu Ala Ile Gln Ala Arg Leu Glu Asp Val Arg Ile Gln Ala Arg
                770                 775                 780

Arg Ala Ile Glu Ser Ala Val Lys Glu Tyr Phe His Arg Gly Ala Val
785                 790                 795                 800

Tyr Ser Ala Lys Ala Leu Gln Ala Ser Asp Ser His Asp Cys Arg Phe
                805                 810                 815

His Val Ala Ser Ala Ala Val Val Pro Met Val Gln Leu Leu Glu Ser
                820                 825                 830

Leu Pro Ala Phe Asp Gln His Thr Arg Asp Val Ala Gln Arg Ala Ala
                835                 840                 845

Leu Pro Pro Pro Pro Leu Ala Thr Ser Pro Gln Ala Ile Leu Leu
850                 855                 860

Arg Asp Leu Leu Gln Arg Gly Gln Pro Leu Asp Ala Pro Glu Asp Leu
865                 870                 875                 880

Ala Ala Trp Leu Ser Val Leu Thr Asp Ala Thr Gln Gly Leu Ile
                885                 890                 895

Glu Arg Lys Pro Leu Glu Glu Leu Ala Arg Ser Ile His Gly Ile Asn
                900                 905                 910

Asp Gln Gln Ala Arg Arg Ser Ser Gly Leu Ala Glu Leu Gln Arg Phe
                915                 920                 925

Asp Ala Leu Asp Ala Ala Leu Ala Gln Gln Leu Asp Ser Asp Ala Ala
                930                 935                 940

Phe Val Pro Ala Thr Gly Pro Ala Pro Tyr Val Asp Gly Gly Leu
945                 950                 955                 960

Ser Pro Glu Ala Thr Arg Met Ala Glu Asp Ala Leu Arg Gln Ala Arg
                965                 970                 975

Ala Met Glu Ala Ala Lys Met Thr Ala Glu Leu Ala Pro Glu Ala Arg
                980                 985                 990

Ser Arg Leu Arg Glu Arg Ala His Ala Leu Glu Ala Met Leu Asn Asp
                995                 1000                1005

Ala Arg Glu Arg Ala Lys Val Ala His Asp Ala Arg Glu Lys Phe
        1010                1015                1020

Leu His Lys Leu Gln Gly Val Leu Arg Pro Leu Pro Asp Phe Val
        1025                1030                1035

Gly Leu Lys Ala Cys Pro Ala Val Leu Ala Thr Leu Arg Ala Ser
        1040                1045                1050

Leu Pro Ala Gly Trp Thr Asp Leu Ala Asp Ala Val Arg Gly Pro
        1055                1060                1065

Pro Pro Glu Val Thr Ala Ala Leu Arg Ala Asp Leu Trp Gly Leu
        1070                1075                1080

Leu Gly Gln Tyr Arg Glu Ala Leu Glu His Pro Thr Pro Asp Thr
        1085                1090                1095

Ala Thr Ala Leu Ala Gly Leu His Pro Ala Phe Val Val Val Leu
        1100                1105                1110
```

-continued

Lys Thr Leu Phe Ala Asp Ala Pro Glu Thr Pro Val Leu Val Gln
1115                1120                1125

Phe Phe Ser Asp His Ala Pro Thr Ile Ala Lys Ala Val Ser Asn
1130                1135                1140

Ala Ile Asn Ala Gly Ser Ala Ala Val Ala Thr Ala Ser Pro Ala
1145                1150                1155

Ala Thr Val Asp Ala Ala Val Arg Ala His Gly Ala Leu Ala Asp
1160                1165                1170

Ala Val Ser Ala Leu Gly Ala Ala Arg Asp Pro Ala Ser Pro
1175                1180                1185

Leu Ser Phe Leu Ala Val Leu Ala Asp Ser Ala Ala Gly Tyr Val
1190                1195                1200

Lys Ala Thr Arg Leu Ala Leu Glu Ala Arg Gly Ala Ile Asp Glu
1205                1210                1215

Leu Thr Thr Leu Gly Ser Ala Ala Ala Asp Leu Val Val Gln Ala
1220                1225                1230

Arg Arg Ala Cys Ala Gln Pro Glu Gly Asp His Ala Ala Leu Ile
1235                1240                1245

Asp Ala Ala Arg Ala Thr Thr Ala Ala Arg Glu Ser Leu Ala
1250                1255                1260

Gly His Glu Ala Gly Phe Gly Gly Leu Leu His Ala Glu Gly Thr
1265                1270                1275

Ala Gly Asp His Ser Pro Ser Gly Arg Ala Leu Gln Glu Leu Gly
1280                1285                1290

Lys Val Ile Gly Ala Thr Arg Arg Arg Ala Asp Glu Leu Glu Ala
1295                1300                1305

Ala Val Ala Asp Leu Thr Ala Lys Met Ala Ala Gln Arg Ala Arg
1310                1315                1320

Gly Ser Ser Glu Arg Trp Ala Ala Gly Val Glu Ala Ala Leu Asp
1325                1330                1335

Arg Val Glu Asn Arg Ala Glu Phe Asp Val Val Glu Leu Arg Arg
1340                1345                1350

Leu Gln Ala Leu Ala Gly Thr His Gly Tyr Asn Pro Arg Asp Phe
1355                1360                1365

Arg Lys Arg Ala Glu Gln Ala Leu Ala Ala Asn Ala Glu Ala Val
1370                1375                1380

Thr Leu Ala Leu Asp Thr Ala Phe Ala Phe Asn Pro Tyr Thr Pro
1385                1390                1395

Glu Asn Gln Arg His Pro Met Leu Pro Pro Leu Ala Ala Ile His
1400                1405                1410

Arg Leu Gly Trp Ser Ala Ala Phe His Ala Ala Ala Glu Thr Tyr
1415                1420                1425

Ala Asp Met Phe Arg Val Asp Ala Glu Pro Leu Ala Arg Leu Leu
1430                1435                1440

Arg Ile Ala Glu Gly Leu Leu Glu Met Ala Gln Ala Gly Asp Gly
1445                1450                1455

Phe Ile Asp Tyr His Glu Ala Val Gly Arg Leu Ala Asp Asp Met
1460                1465                1470

Thr Ser Val Pro Gly Leu Arg Arg Tyr Val Pro Phe Phe Gln His
1475                1480                1485

Gly Tyr Ala Asp Tyr Val Glu Leu Arg Asp Arg Leu Asp Ala Ile
1490                1495                1500

```
Arg Ala Asp Val His Arg Ala Leu Gly Gly Val Pro Leu Asp Leu
    1505                1510                1515

Ala Ala Ala Ala Glu Gln Ile Ser Ala Ala Arg Asn Asp Pro Glu
1520                1525                1530

Ala Thr Ala Glu Leu Val Arg Thr Gly Val Thr Leu Pro Cys Pro
1535                1540                1545

Ser Glu Asp Ala Leu Val Ala Cys Ala Ala Leu Glu Arg Val
1550                1555                1560

Asp Gln Ser Pro Val Lys Asn Thr Ala Tyr Ala Glu Tyr Val Ala
1565                1570                1575

Phe Val Thr Arg Gln Asp Thr Ala Glu Thr Lys Asp Ala Val Val
1580                1585                1590

Arg Ala Lys Gln Gln Arg Ala Glu Ala Thr Glu Arg Val Met Ala
1595                1600                1605

Gly Leu Arg Glu Ala Leu Ala Ala Arg Glu Arg Ala Gln Ile
1610                1615                1620

Glu Ala Glu Gly Leu Ala Asn Leu Lys Thr Met Leu Lys Val Val
1625                1630                1635

Ala Val Pro Ala Thr Val Ala Lys Thr Leu Asp Gln Ala Arg Ser
1640                1645                1650

Val Ala Glu Ile Ala Asp Gln Val Glu Val Leu Leu Asp Gln Thr
1655                1660                1665

Glu Lys Thr Arg Glu Leu Asp Val Pro Ala Val Ile Trp Leu Glu
1670                1675                1680

His Ala Gln Arg Thr Phe Glu Thr His Pro Leu Ser Ala Ala Arg
1685                1690                1695

Gly Asp Gly Pro Gly Pro Leu Ala Arg His Ala Gly Arg Leu Gly
1700                1705                1710

Ala Leu Phe Asp Thr Arg Arg Val Asp Ala Leu Arg Arg Ser
1715                1720                1725

Leu Glu Glu Ala Glu Ala Glu Trp Asp Glu Val Trp Gly Arg Phe
1730                1735                1740

Gly Arg Val Arg Gly Gly Ala Trp Lys Ser Pro Glu Gly Phe Arg
1745                1750                1755

Ala Met His Glu Gln Leu Arg Ala Leu Gln Asp Thr Thr Asn Thr
1760                1765                1770

Val Ser Gly Leu Arg Ala Gln Pro Ala Tyr Glu Arg Leu Ser Ala
1775                1780                1785

Arg Tyr Gln Gly Val Leu Gly Ala Lys Gly Ala Glu Arg Ala Glu
1790                1795                1800

Ala Val Glu Glu Leu Gly Ala Arg Val Thr Lys His Thr Ala Leu
1805                1810                1815

Cys Ala Arg Leu Arg Asp Glu Val Val Arg Arg Val Pro Trp Glu
1820                1825                1830

Met Asn Phe Asp Ala Leu Gly Gly Leu Leu Ala Glu Phe Asp Ala
1835                1840                1845

Ala Ala Ala Asp Leu Ala Pro Trp Ala Val Glu Glu Phe Arg Gly
1850                1855                1860

Ala Arg Glu Leu Ile Gln Tyr Arg Met Gly Leu Tyr Ser Ala Tyr
1865                1870                1875

Ala Arg Ala Gly Gly Gln Thr Gly Ala Gly Ala Glu Ser Ala Pro
1880                1885                1890

Ala Pro Leu Leu Val Asp Leu Arg Ala Leu Asp Ala Arg Ala Arg
```

```
               1895                1900                1905
Ala  Ser  Ser  Ser  Pro  Glu  Gly  His  Glu  Val  Asp  Pro  Gln  Leu  Leu
          1910                1915                1920

Arg  Arg  Arg  Gly  Glu  Ala  Tyr  Leu  Arg  Ala  Gly  Gly  Asp  Pro  Gly
          1925                1930                1935

Pro  Leu  Val  Leu  Arg  Glu  Ala  Val  Ser  Ala  Leu  Asp  Leu  Pro  Phe
          1940                1945                1950

Ala  Thr  Ser  Phe  Leu  Ala  Pro  Asp  Gly  Thr  Pro  Leu  Gln  Tyr  Ala
          1955                1960                1965

Leu  Cys  Phe  Pro  Ala  Val  Thr  Asp  Lys  Leu  Gly  Ala  Leu  Leu  Met
          1970                1975                1980

Arg  Pro  Glu  Ala  Ala  Cys  Val  Arg  Pro  Pro  Leu  Pro  Thr  Asp  Val
          1985                1990                1995

Leu  Glu  Ser  Ala  Pro  Thr  Val  Thr  Ala  Met  Tyr  Val  Leu  Thr  Val
          2000                2005                2010

Val  Asn  Arg  Leu  Gln  Leu  Ala  Leu  Ser  Asp  Ala  Gln  Ala  Ala  Asn
          2015                2020                2025

Phe  Gln  Leu  Phe  Gly  Arg  Phe  Val  Arg  His  Arg  Gln  Ala  Thr  Trp
          2030                2035                2040

Gly  Ala  Ser  Met  Asp  Ala  Ala  Ala  Glu  Leu  Tyr  Val  Ala  Leu  Val
          2045                2050                2055

Ala  Thr  Thr  Leu  Thr  Arg  Glu  Phe  Gly  Cys  Arg  Trp  Ala  Gln  Leu
          2060                2065                2070

Gly  Trp  Ala  Ser  Gly  Ala  Ala  Ala  Pro  Arg  Pro  Pro  Pro  Gly  Pro
          2075                2080                2085

Arg  Gly  Ser  Gln  Arg  His  Cys  Val  Ala  Phe  Asn  Glu  Asn  Asp  Val
          2090                2095                2100

Leu  Val  Ala  Leu  Val  Ala  Gly  Val  Pro  Glu  His  Ile  Tyr  Asn  Phe
          2105                2110                2115

Trp  Arg  Leu  Asp  Leu  Val  Arg  Gln  His  Glu  Tyr  Met  His  Leu  Thr
          2120                2125                2130

Leu  Glu  Arg  Ala  Phe  Glu  Asp  Ala  Ala  Glu  Ser  Met  Leu  Phe  Val
          2135                2140                2145

Gln  Arg  Leu  Thr  Pro  His  Pro  Asp  Ala  Arg  Ile  Arg  Val  Leu  Pro
          2150                2155                2160

Thr  Phe  Leu  Asp  Gly  Gly  Pro  Pro  Thr  Arg  Gly  Leu  Leu  Phe  Gly
          2165                2170                2175

Thr  Arg  Leu  Ala  Asp  Trp  Arg  Arg  Gly  Lys  Leu  Ser  Glu  Thr  Asp
          2180                2185                2190

Pro  Leu  Ala  Pro  Trp  Arg  Ser  Ala  Leu  Glu  Leu  Gly  Thr  Gln  Arg
          2195                2200                2205

Arg  Asp  Val  Pro  Ala  Leu  Gly  Lys  Leu  Ser  Pro  Ala  Gln  Ala  Leu
          2210                2215                2220

Ala  Ala  Val  Ser  Val  Leu  Gly  Arg  Met  Cys  Leu  Pro  Ser  Ala  Ala
          2225                2230                2235

Leu  Ala  Ala  Leu  Trp  Thr  Cys  Met  Phe  Pro  Asp  Asp  Tyr  Thr  Glu
          2240                2245                2250

Tyr  Asp  Ser  Phe  Asp  Ala  Leu  Leu  Ala  Ala  Arg  Leu  Glu  Ser  Gly
          2255                2260                2265

Gln  Thr  Leu  Gly  Pro  Ala  Gly  Gly  Arg  Glu  Ala  Ser  Leu  Pro  Glu
          2270                2275                2280

Ala  Pro  His  Ala  Leu  Tyr  Arg  Pro  Thr  Gly  Gln  His  Val  Ala  Val
          2285                2290                2295
```

```
Leu Ala Ala Ala Thr His Arg Thr Pro Ala Ala Arg Val Thr Ala
2300                2305                2310

Met Asp Leu Val Leu Ala Ala Val Leu Leu Gly Ala Pro Val Val
2315                2320                2325

Val Ala Leu Arg Asn Thr Thr Ala Phe Ser Arg Glu Ser Glu Leu
2330                2335                2340

Glu Leu Cys Leu Thr Leu Phe Asp Ser Arg Pro Gly Gly Pro Asp
2345                2350                2355

Ala Ala Leu Arg Asp Val Val Ser Ser Asp Ile Glu Thr Trp Ala
2360                2365                2370

Val Gly Leu Leu His Thr Asp Leu Asn Pro Ile Glu Asn Ala Cys
2375                2380                2385

Leu Ala Ala Gln Leu Pro Arg Leu Ser Ala Leu Ile Ala Glu Arg
2390                2395                2400

Pro Leu Ala Asp Gly Pro Pro Cys Leu Val Leu Val Asp Ile Ser
2405                2410                2415

Met Thr Pro Val Ala Val Leu Trp Glu Ala Pro Glu Pro Pro Gly
2420                2425                2430

Pro Pro Asp Val Arg Phe Val Gly Ser Glu Ala Thr Glu Glu Leu
2435                2440                2445

Pro Phe Val Ala Thr Ala Gly Asp Val Leu Ala Ala Ser Ala Ala
2450                2455                2460

Asp Ala Asp Pro Phe Phe Ala Arg Ala Ile Leu Gly Arg Pro Phe
2465                2470                2475

Asp Ala Ser Leu Leu Thr Gly Glu Leu Phe Pro Gly His Pro Val
2480                2485                2490

Tyr Gln Arg Pro Leu Ala Asp Glu Ala Gly Pro Ser Ala Pro Thr
2495                2500                2505

Ala Ala Arg Asp Pro Arg Asp Leu Ala Gly Gly Asp Gly Gly Ser
2510                2515                2520

Gly Pro Glu Asp Pro Ala Ala Pro Pro Ala Arg Gln Ala Asp Pro
2525                2530                2535

Gly Val Leu Ala Pro Thr Leu Leu Thr Asp Ala Thr Thr Gly Glu
2540                2545                2550

Pro Val Pro Pro Arg Met Trp Ala Trp Ile His Gly Leu Glu Glu
2555                2560                2565

Leu Ala Ser Asp Asp Ala Gly Gly Pro Thr Pro Asn Pro Ala Pro
2570                2575                2580

Ala Leu Leu Pro Pro Pro Ala Thr Asp Gln Ser Val Pro Thr Ser
2585                2590                2595

Gln Tyr Ala Pro Arg Pro Ile Gly Pro Ala Ala Thr Ala Arg Glu
2600                2605                2610

Thr Arg Pro Ser Val Pro Pro Gln Gln Asn Thr Gly Arg Val Pro
2615                2620                2625

Val Ala Pro Arg Asp Asp Pro Arg Pro Ser Pro Thr Pro Ser
2630                2635                2640

Pro Pro Ala Asp Ala Ala Leu Pro Pro Pro Ala Phe Ser Gly Ser
2645                2650                2655

Ala Ala Ala Phe Ser Ala Ala Val Pro Arg Val Arg Arg Ser Arg
2660                2665                2670

Arg Thr Arg Ala Lys Ser Arg Ala Pro Arg Ala Ser Ala Pro Pro
2675                2680                2685
```

```
Glu Gly Trp Arg Pro Pro Ala Leu Pro Ala Pro Val Ala Pro Val
2690            2695            2700

Ala Ala Ser Ala Arg Pro Pro Asp Gln Pro Pro Thr Pro Glu Ser
2705            2710            2715

Ala Pro Pro Ala Trp Val Ser Ala Leu Pro Leu Pro Pro Gly Pro
2720            2725            2730

Ala Ser Ala Arg Gly Ala Phe Pro Ala Pro Thr Leu Ala Pro Ile
2735            2740            2745

Pro Pro Pro Pro Ala Glu Gly Ala Val Val Pro Gly Gly Asp Arg
2750            2755            2760

Arg Arg Gly Arg Arg Gln Thr Thr Ala Gly Pro Ser Pro Thr Pro
2765            2770            2775

Pro Arg Gly Pro Ala Ala Gly Pro Pro Arg Arg Leu Thr Arg Pro
2780            2785            2790

Ala Val Ala Ser Leu Ser Ala Ser Leu Asn Ser Leu Pro Ser Pro
2795            2800            2805

Arg Asp Pro Ala Asp His Ala Ala Val Ser Ala Ala Ala Ala
2810            2815            2820

Ala Val Pro Pro Ser Pro Gly Leu Ala Pro Pro Thr Ser Ala Val
2825            2830            2835

Gln Thr Ser Pro Pro Pro Leu Ala Pro Gly Pro Val Ala Pro Ser
2840            2845            2850

Glu Pro Leu Cys Gly Trp Val Val Pro Gly Gly Pro Val Ala Arg
2855            2860            2865

Arg Pro Pro Pro Gln Ser Pro Ala Thr Lys Pro Ala Ala Arg Thr
2870            2875            2880

Arg Ile Arg Ala Arg Ser Val Pro Gln Pro Pro Leu Pro Gln Pro
2885            2890            2895

Pro Leu Pro Gln Pro Pro Leu Pro Gln Pro Pro Leu Pro Gln Pro
2900            2905            2910

Pro Leu Pro Gln Pro Pro Leu Pro Gln Pro Pro Leu Pro Gln Pro
2915            2920            2925

Pro Leu Pro Gln Pro Pro Leu Pro Gln Pro Pro Leu Pro Gln Pro
2930            2935            2940

Pro Leu Pro Pro Val Thr Arg Thr Leu Thr Pro Gln Ser Arg Asp
2945            2950            2955

Ser Val Pro Thr Pro Glu Ser Pro Thr His Thr Asn Thr His Leu
2960            2965            2970

Pro Val Ser Ala Val Thr Ser Trp Ala Ser Ser Leu Ala Leu His
2975            2980            2985

Val Asp Ser Ala Pro Pro Pro Ala Ser Leu Leu Gln Thr Leu His
2990            2995            3000

Ile Ser Ser Asp Asp Glu His Ser Asp Ala Asp Ser Leu Arg Phe
3005            3010            3015

Ser Asp Ser Asp Asp Thr Glu Ala Leu Asp Pro Leu Pro Pro Glu
3020            3025            3030

Pro His Leu Pro Pro Ala Asp Glu Pro Pro Gly Pro Leu Ala Ala
3035            3040            3045

Asp His Leu Gln Ser Pro His Ser Gln Phe Gly Pro Leu Pro Val
3050            3055            3060

Gln Ala Asn Ala Val Leu Ser Arg Arg Tyr Val Arg Ser Thr Gly
3065            3070            3075

Arg Ser Ala Leu Ala Val Leu Ile Arg Ala Cys Arg Arg Ile Gln
```

```
                3080              3085              3090
Gln Gln Leu Gln Arg Thr Arg Ala Leu Phe Gln Arg Ser Asn
        3095              3100              3105
Ala Val Leu Thr Ser Leu His His Val Arg Met Leu Leu Gly
        3110              3115              3120

<210> SEQ ID NO 23
<211> LENGTH: 964
<212> TYPE: PRT
<213> ORGANISM: Herpes simplex virus

<400> SEQUENCE: 23

Ala Ala Gln Arg Ala Arg Gly Ser Ser Glu Arg Trp Ala Ala Gly Val
1               5                   10                  15

Glu Ala Ala Leu Asp Arg Val Glu Asn Arg Ala Glu Phe Asp Val Val
            20                  25                  30

Glu Leu Arg Arg Leu Gln Ala Leu Ala Gly Thr His Gly Tyr Asn Pro
        35                  40                  45

Arg Asp Phe Arg Lys Arg Ala Glu Gln Ala Leu Ala Ala Asn Ala Glu
    50                  55                  60

Ala Val Thr Leu Ala Leu Asp Thr Ala Phe Ala Phe Asn Pro Tyr Thr
65                  70                  75                  80

Pro Glu Asn Gln Arg His Pro Met Leu Pro Pro Leu Ala Ala Ile His
                85                  90                  95

Arg Leu Gly Trp Ser Ala Ala Phe His Ala Ala Ala Glu Thr Tyr Ala
            100                 105                 110

Asp Met Phe Arg Val Asp Ala Glu Pro Leu Ala Arg Leu Leu Arg Ile
        115                 120                 125

Ala Glu Gly Leu Leu Glu Met Ala Gln Ala Gly Asp Gly Phe Ile Asp
    130                 135                 140

Tyr His Glu Ala Val Gly Arg Leu Ala Asp Asp Met Thr Ser Val Pro
145                 150                 155                 160

Gly Leu Arg Arg Tyr Val Pro Phe Phe Gln His Gly Tyr Ala Asp Tyr
                165                 170                 175

Val Glu Leu Arg Asp Arg Leu Asp Ala Ile Arg Ala Asp Val His Arg
            180                 185                 190

Ala Leu Gly Gly Val Pro Leu Asp Leu Ala Ala Ala Glu Gln Ile
        195                 200                 205

Ser Ala Ala Arg Asn Asp Pro Glu Ala Thr Ala Glu Leu Val Arg Thr
    210                 215                 220

Gly Val Thr Leu Pro Cys Pro Ser Glu Asp Ala Leu Val Ala Cys Ala
225                 230                 235                 240

Ala Ala Leu Glu Arg Val Asp Gln Ser Pro Val Lys Asn Thr Ala Tyr
                245                 250                 255

Ala Glu Tyr Val Ala Phe Val Thr Arg Gln Asp Thr Ala Glu Thr Lys
            260                 265                 270

Asp Ala Val Val Arg Ala Lys Gln Gln Arg Ala Glu Ala Thr Glu Arg
        275                 280                 285

Val Met Ala Gly Leu Arg Glu Ala Leu Ala Ala Arg Glu Arg Arg Ala
    290                 295                 300

Gln Ile Glu Ala Glu Gly Leu Ala Asn Leu Lys Thr Met Leu Lys Val
305                 310                 315                 320

Val Ala Val Pro Ala Thr Val Ala Lys Thr Leu Asp Gln Ala Arg Ser
                325                 330                 335
```

```
Val Ala Glu Ile Ala Asp Gln Val Glu Val Leu Leu Asp Gln Thr Glu
                340                 345                 350

Lys Thr Arg Glu Leu Asp Val Pro Ala Val Ile Trp Leu Glu His Ala
            355                 360                 365

Gln Arg Thr Phe Glu Thr His Pro Leu Ser Ala Ala Arg Gly Asp Gly
        370                 375                 380

Pro Gly Pro Leu Ala Arg His Ala Gly Arg Leu Gly Ala Leu Phe Asp
385                 390                 395                 400

Thr Arg Arg Val Asp Ala Leu Arg Ser Leu Glu Glu Ala Glu
                405                 410                 415

Ala Glu Trp Asp Glu Val Trp Gly Arg Phe Gly Arg Val Arg Gly Gly
            420                 425                 430

Ala Trp Lys Ser Pro Glu Gly Phe Arg Ala Met His Glu Gln Leu Arg
        435                 440                 445

Ala Leu Gln Asp Thr Thr Asn Thr Val Ser Gly Leu Arg Ala Gln Pro
    450                 455                 460

Ala Tyr Glu Arg Leu Ser Ala Arg Tyr Gln Gly Val Leu Gly Ala Lys
465                 470                 475                 480

Gly Ala Glu Arg Ala Glu Ala Val Glu Glu Leu Gly Ala Arg Val Thr
            485                 490                 495

Lys His Thr Ala Leu Cys Ala Arg Leu Arg Asp Glu Val Val Arg Arg
        500                 505                 510

Val Pro Trp Glu Met Asn Phe Asp Ala Leu Gly Gly Leu Leu Ala Glu
    515                 520                 525

Phe Asp Ala Ala Ala Asp Leu Ala Pro Trp Ala Val Glu Glu Phe
530                 535                 540

Arg Gly Ala Arg Glu Leu Ile Gln Tyr Arg Met Gly Leu Tyr Ser Ala
545                 550                 555                 560

Tyr Ala Arg Ala Gly Gly Gln Thr Gly Ala Gly Ala Glu Ser Ala Pro
            565                 570                 575

Ala Pro Leu Leu Val Asp Leu Arg Ala Leu Asp Ala Arg Ala Arg Ala
        580                 585                 590

Ser Ser Ser Pro Glu Gly His Glu Val Asp Pro Gln Leu Leu Arg Arg
    595                 600                 605

Arg Gly Glu Ala Tyr Leu Arg Ala Gly Gly Asp Pro Gly Pro Leu Val
            610                 615                 620

Leu Arg Glu Ala Val Ser Ala Leu Asp Leu Pro Phe Ala Thr Ser Phe
625                 630                 635                 640

Leu Ala Pro Asp Gly Thr Pro Leu Gln Tyr Ala Leu Cys Phe Pro Ala
                645                 650                 655

Val Thr Asp Lys Leu Gly Ala Leu Leu Met Arg Pro Glu Ala Ala Cys
            660                 665                 670

Val Arg Pro Pro Leu Pro Thr Asp Val Leu Glu Ser Ala Pro Thr Val
        675                 680                 685

Thr Ala Met Tyr Val Leu Thr Val Val Asn Arg Leu Gln Leu Ala Leu
    690                 695                 700

Ser Asp Ala Gln Ala Ala Asn Phe Gln Leu Phe Gly Arg Phe Val Arg
705                 710                 715                 720

His Arg Gln Ala Thr Trp Gly Ala Ser Met Asp Ala Ala Ala Glu Leu
                725                 730                 735

Tyr Val Ala Leu Val Ala Thr Thr Leu Thr Arg Glu Phe Gly Cys Arg
            740                 745                 750

Trp Ala Gln Leu Gly Trp Ala Ser Gly Ala Ala Ala Pro Arg Pro Pro
```

-continued

```
                755                 760                 765
Pro Gly Pro Arg Gly Ser Gln Arg His Cys Val Ala Phe Asn Glu Asn
770                 775                 780

Asp Val Leu Val Ala Leu Val Ala Gly Val Pro Glu His Ile Tyr Asn
785                 790                 795                 800

Phe Trp Arg Leu Asp Leu Val Arg Gln His Glu Tyr Met His Leu Thr
                805                 810                 815

Leu Glu Arg Ala Phe Glu Asp Ala Ala Glu Ser Met Leu Phe Val Gln
                820                 825                 830

Arg Leu Thr Pro His Pro Asp Ala Arg Ile Arg Val Leu Pro Thr Phe
                835                 840                 845

Leu Asp Gly Gly Pro Pro Thr Arg Gly Leu Leu Phe Gly Thr Arg Leu
850                 855                 860

Ala Asp Trp Arg Arg Gly Lys Leu Ser Glu Thr Asp Pro Leu Ala Pro
865                 870                 875                 880

Trp Arg Ser Ala Leu Glu Leu Gly Thr Gln Arg Arg Asp Val Pro Ala
                885                 890                 895

Leu Gly Lys Leu Ser Pro Ala Gln Ala Leu Ala Ala Val Ser Val Leu
                900                 905                 910

Gly Arg Met Cys Leu Pro Ser Ala Ala Leu Ala Ala Leu Trp Thr Cys
                915                 920                 925

Met Phe Pro Asp Asp Tyr Thr Glu Tyr Asp Ser Phe Asp Ala Leu Leu
930                 935                 940

Ala Ala Arg Leu Glu Ser Gly Gln Thr Leu Gly Pro Ala Gly Gly Arg
945                 950                 955                 960

Glu Ala Ser Leu

<210> SEQ ID NO 24
<211> LENGTH: 870
<212> TYPE: PRT
<213> ORGANISM: Herpes simplex virus

<400> SEQUENCE: 24

Glu Tyr Asp Ser Phe Asp Ala Leu Leu Ala Ala Arg Leu Glu Ser Gly
1               5                   10                  15

Gln Thr Leu Gly Pro Ala Gly Gly Arg Glu Ala Ser Leu Pro Glu Ala
                20                  25                  30

Pro His Ala Leu Tyr Arg Pro Thr Gly Gln His Val Ala Val Leu Ala
                35                  40                  45

Ala Ala Thr His Arg Thr Pro Ala Ala Arg Val Thr Ala Met Asp Leu
                50                  55                  60

Val Leu Ala Ala Val Leu Leu Gly Ala Pro Val Val Ala Leu Arg
65                  70                  75                  80

Asn Thr Thr Ala Phe Ser Arg Glu Ser Glu Leu Glu Leu Cys Leu Thr
                85                  90                  95

Leu Phe Asp Ser Arg Pro Gly Gly Pro Asp Ala Ala Leu Arg Asp Val
                100                 105                 110

Val Ser Ser Asp Ile Glu Thr Trp Ala Val Gly Leu Leu His Thr Asp
                115                 120                 125

Leu Asn Pro Ile Glu Asn Ala Cys Leu Ala Ala Gln Leu Pro Arg Leu
                130                 135                 140

Ser Ala Leu Ile Ala Glu Arg Pro Leu Ala Asp Gly Pro Pro Cys Leu
145                 150                 155                 160

Val Leu Val Asp Ile Ser Met Thr Pro Val Ala Val Leu Trp Glu Ala
```

```
              165                 170                 175
Pro Glu Pro Pro Gly Pro Pro Asp Val Arg Phe Val Gly Ser Glu Ala
            180                 185                 190
Thr Glu Glu Leu Pro Phe Val Ala Thr Ala Gly Asp Val Leu Ala Ala
            195                 200                 205
Ser Ala Ala Asp Ala Asp Pro Phe Phe Ala Arg Ala Ile Leu Gly Arg
210                 215                 220
Pro Phe Asp Ala Ser Leu Leu Thr Gly Glu Leu Phe Pro Gly His Pro
225                 230                 235                 240
Val Tyr Gln Arg Pro Leu Ala Asp Glu Ala Gly Pro Ser Ala Pro Thr
            245                 250                 255
Ala Ala Arg Asp Pro Arg Asp Leu Ala Gly Gly Asp Gly Ser Gly
            260                 265                 270
Pro Glu Asp Pro Ala Ala Pro Pro Ala Arg Gln Ala Asp Pro Gly Val
            275                 280                 285
Leu Ala Pro Thr Leu Leu Thr Asp Ala Thr Thr Gly Glu Pro Val Pro
            290                 295                 300
Pro Arg Met Trp Ala Trp Ile His Gly Leu Glu Glu Leu Ala Ser Asp
305                 310                 315                 320
Asp Ala Gly Gly Pro Thr Pro Asn Pro Ala Pro Ala Leu Leu Pro Pro
            325                 330                 335
Pro Ala Thr Asp Gln Ser Val Pro Thr Ser Gln Tyr Ala Pro Arg Pro
            340                 345                 350
Ile Gly Pro Ala Ala Thr Ala Arg Glu Thr Arg Pro Ser Val Pro Pro
            355                 360                 365
Gln Gln Asn Thr Gly Arg Val Pro Val Ala Pro Arg Asp Asp Pro Arg
            370                 375                 380
Pro Ser Pro Pro Thr Pro Ser Pro Pro Ala Asp Ala Ala Leu Pro Pro
385                 390                 395                 400
Pro Ala Phe Ser Gly Ser Ala Ala Ala Phe Ser Ala Ala Val Pro Arg
            405                 410                 415
Val Arg Arg Ser Arg Arg Thr Arg Ala Lys Ser Arg Ala Pro Arg Ala
            420                 425                 430
Ser Ala Pro Pro Glu Gly Trp Arg Pro Pro Ala Leu Pro Ala Pro Val
            435                 440                 445
Ala Pro Val Ala Ala Ser Ala Arg Pro Pro Asp Gln Pro Pro Thr Pro
            450                 455                 460
Glu Ser Ala Pro Pro Ala Trp Val Ser Ala Leu Pro Leu Pro Pro Gly
465                 470                 475                 480
Pro Ala Ser Ala Arg Gly Ala Phe Pro Ala Pro Thr Leu Ala Pro Ile
            485                 490                 495
Pro Pro Pro Pro Ala Glu Gly Ala Val Val Pro Gly Gly Asp Arg Arg
            500                 505                 510
Arg Gly Arg Arg Gln Thr Thr Ala Gly Pro Ser Pro Thr Pro Pro Arg
            515                 520                 525
Gly Pro Ala Ala Gly Pro Pro Arg Arg Leu Thr Arg Pro Ala Val Ala
            530                 535                 540
Ser Leu Ser Ala Ser Leu Asn Ser Leu Pro Ser Pro Arg Asp Pro Ala
545                 550                 555                 560
Asp His Ala Ala Ala Val Ser Ala Ala Ala Ala Val Pro Pro Ser
            565                 570                 575
Pro Gly Leu Ala Pro Pro Thr Ser Ala Val Gln Thr Ser Pro Pro Pro
            580                 585                 590
```

```
Leu Ala Pro Gly Pro Val Ala Pro Ser Glu Pro Leu Cys Gly Trp Val
            595                 600                 605

Val Pro Gly Gly Pro Val Ala Arg Arg Pro Pro Gln Ser Pro Ala
610                 615                 620

Thr Lys Pro Ala Ala Arg Thr Arg Ile Arg Ala Arg Ser Val Pro Gln
625                 630                 635                 640

Pro Pro Leu Pro Gln Pro Pro Leu Pro Gln Pro Pro Leu Pro Gln Pro
                645                 650                 655

Pro Leu Pro Gln Pro Pro Leu Pro Gln Pro Pro Leu Pro Gln Pro Pro
                660                 665                 670

Leu Pro Gln Pro Pro Leu Pro Gln Pro Pro Leu Pro Gln Pro Pro Leu
                675                 680                 685

Pro Gln Pro Pro Leu Pro Pro Val Thr Arg Thr Leu Thr Pro Gln Ser
            690                 695                 700

Arg Asp Ser Val Pro Thr Pro Glu Ser Pro Thr His Thr Asn Thr His
705                 710                 715                 720

Leu Pro Val Ser Ala Val Thr Ser Trp Ala Ser Ser Leu Ala Leu His
                725                 730                 735

Val Asp Ser Ala Pro Pro Ala Ser Leu Leu Gln Thr Leu His Ile
                740                 745                 750

Ser Ser Asp Asp Glu His Ser Asp Ala Asp Ser Leu Arg Phe Ser Asp
            755                 760                 765

Ser Asp Asp Thr Glu Ala Leu Asp Pro Leu Pro Pro Glu Pro His Leu
770                 775                 780

Pro Pro Ala Asp Glu Pro Gly Pro Leu Ala Ala Asp His Leu Gln
785                 790                 795                 800

Ser Pro His Ser Gln Phe Gly Pro Leu Pro Val Gln Ala Asn Ala Val
                805                 810                 815

Leu Ser Arg Arg Tyr Val Arg Ser Thr Gly Arg Ser Ala Leu Ala Val
                820                 825                 830

Leu Ile Arg Ala Cys Arg Arg Ile Gln Gln Leu Gln Arg Thr Arg
                835                 840                 845

Arg Ala Leu Phe Gln Arg Ser Asn Ala Val Leu Thr Ser Leu His His
            850                 855                 860

Val Arg Met Leu Leu Gly
865                 870

<210> SEQ ID NO 25
<211> LENGTH: 337
<212> TYPE: PRT
<213> ORGANISM: Herpes simplex virus

<400> SEQUENCE: 25

Met Asp Pro Ala Val Ser Pro Ala Ser Thr Asp Pro Leu Asp Thr His
1               5                   10                  15

Ala Ser Gly Ala Gly Ala Ala Pro Ile Pro Val Cys Pro Thr Pro Glu
                20                  25                  30

Arg Tyr Phe Tyr Thr Ser Gln Cys Pro Asp Ile Asn His Leu Arg Ser
            35                  40                  45

Leu Ser Ile Leu Asn Arg Trp Leu Glu Thr Glu Leu Val Phe Val Gly
    50                  55                  60

Asp Glu Glu Asp Val Ser Lys Leu Ser Glu Gly Glu Leu Gly Phe Tyr
65                  70                  75                  80

Arg Phe Leu Phe Ala Phe Leu Ser Ala Ala Asp Asp Leu Val Thr Glu
```

```
                    85                  90                  95

Asn Leu Gly Gly Leu Ser Gly Leu Phe Glu Gln Lys Asp Ile Leu His
            100                 105                 110

Tyr Tyr Val Glu Gln Glu Cys Ile Glu Val Val His Ser Arg Val Tyr
        115                 120                 125

Asn Ile Ile Gln Leu Val Leu Phe His Asn Asn Asp Gln Ala Arg Arg
    130                 135                 140

Ala Tyr Val Ala Arg Thr Ile Asn His Pro Ala Ile Arg Val Lys Val
145                 150                 155                 160

Asp Trp Leu Glu Ala Arg Val Arg Glu Cys Asp Ser Ile Pro Glu Lys
                165                 170                 175

Phe Ile Leu Met Ile Leu Ile Glu Gly Val Phe Phe Ala Ala Ser Phe
            180                 185                 190

Ala Ala Ile Ala Tyr Leu Arg Thr Asn Asn Leu Leu Arg Val Thr Cys
        195                 200                 205

Gln Ser Asn Asp Leu Ile Ser Arg Asp Glu Ala Val His Thr Thr Ala
    210                 215                 220

Ser Cys Tyr Ile Tyr Asn Asn Tyr Leu Gly Gly His Ala Lys Pro Glu
225                 230                 235                 240

Ala Ala Arg Val Tyr Arg Leu Phe Arg Glu Ala Val Asp Ile Glu Ile
                245                 250                 255

Gly Phe Ile Arg Ser Gln Ala Pro Thr Asp Ser Ser Ile Leu Ser Pro
            260                 265                 270

Gly Ala Leu Ala Ala Ile Glu Asn Tyr Val Arg Phe Ser Ala Asp Arg
        275                 280                 285

Leu Leu Gly Leu Ile His Met Gln Pro Leu Tyr Ser Ala Pro Ala Pro
    290                 295                 300

Asp Ala Ser Phe Pro Leu Ser Leu Met Ser Thr Asp Lys His Thr Asn
305                 310                 315                 320

Phe Phe Glu Cys Arg Ser Thr Ser Tyr Ala Gly Ala Val Val Asn Asp
                325                 330                 335

Leu

<210> SEQ ID NO 26
<211> LENGTH: 86
<212> TYPE: PRT
<213> ORGANISM: Herpes simplex virus

<400> SEQUENCE: 26

Met Ser Trp Ala Leu Lys Thr Thr Asp Met Phe Leu Asp Ser Ser Arg
1               5                   10                  15

Cys Thr His Arg Thr Tyr Gly Asp Val Cys Ala Glu Ile His Lys Arg
            20                  25                  30

Glu Arg Glu Asp Arg Glu Ala Ala Arg Thr Ala Val Thr Asp Pro Glu
        35                  40                  45

Leu Pro Leu Leu Cys Pro Pro Asp Val Arg Ser Asp Pro Ala Ser Arg
    50                  55                  60

Asn Pro Thr Gln Gln Thr Arg Gly Cys Ala Arg Ser Asn Glu Arg Gln
65                  70                  75                  80

Asp Arg Val Leu Ala Pro
                85

<210> SEQ ID NO 27
<211> LENGTH: 467
<212> TYPE: PRT
```

<213> ORGANISM: Herpes simplex virus

<400> SEQUENCE: 27

| | | | | | | | | | | | | | | | |
|---|---|---|---|---|---|---|---|---|---|---|---|---|---|---|---|
| Met | Gly | Arg | Arg | Ala | Pro | Arg | Gly | Ser | Pro | Glu | Ala | Ala | Pro | Gly | Ala |
| 1 | | | | 5 | | | | | 10 | | | | | 15 | |
| Asp | Val | Ala | Pro | Gly | Ala | Arg | Ala | Ala | Trp | Trp | Val | Trp | Cys | Val | Gln |
| | | | 20 | | | | | 25 | | | | | 30 | | |
| Val | Ala | Thr | Phe | Ile | Val | Ser | Ala | Ile | Cys | Val | Val | Gly | Leu | Leu | Val |
| | | | 35 | | | | | 40 | | | | | 45 | | |
| Leu | Ala | Ser | Val | Phe | Arg | Asp | Arg | Phe | Pro | Cys | Leu | Tyr | Ala | Pro | Ala |
| | 50 | | | | | 55 | | | | | 60 | | | | |
| Thr | Ser | Tyr | Ala | Lys | Ala | Asn | Ala | Thr | Val | Glu | Val | Arg | Gly | Gly | Val |
| 65 | | | | | 70 | | | | | 75 | | | | | 80 |
| Ala | Val | Pro | Leu | Arg | Leu | Asp | Thr | Gln | Ser | Leu | Leu | Ala | Thr | Tyr | Ala |
| | | | | 85 | | | | | 90 | | | | | 95 | |
| Ile | Thr | Ser | Thr | Leu | Leu | Leu | Ala | Ala | Ala | Val | Tyr | Ala | Ala | Val | Gly |
| | | | 100 | | | | | 105 | | | | | 110 | | |
| Ala | Val | Thr | Ser | Arg | Tyr | Glu | Arg | Ala | Leu | Asp | Ala | Ala | Arg | Arg | Leu |
| | | | 115 | | | | | 120 | | | | | 125 | | |
| Ala | Ala | Ala | Arg | Met | Ala | Met | Pro | His | Ala | Thr | Leu | Ile | Ala | Gly | Asn |
| | 130 | | | | | 135 | | | | | 140 | | | | |
| Val | Cys | Ala | Trp | Leu | Leu | Gln | Ile | Thr | Val | Leu | Leu | Leu | Ala | His | Arg |
| 145 | | | | | 150 | | | | | 155 | | | | | 160 |
| Ile | Ser | Gln | Leu | Ala | His | Leu | Ile | Tyr | Val | Leu | His | Phe | Ala | Cys | Leu |
| | | | | 165 | | | | | 170 | | | | | 175 | |
| Val | Tyr | Leu | Ala | Ala | His | Phe | Cys | Thr | Arg | Gly | Val | Leu | Ser | Gly | Thr |
| | | | 180 | | | | | 185 | | | | | 190 | | |
| Tyr | Leu | Arg | Gln | Val | His | Gly | Leu | Ile | Asp | Pro | Ala | Pro | Thr | His | His |
| | | | 195 | | | | | 200 | | | | | 205 | | |
| Arg | Ile | Val | Gly | Pro | Val | Arg | Ala | Val | Met | Thr | Asn | Ala | Leu | Leu | Leu |
| | 210 | | | | | 215 | | | | | 220 | | | | |
| Gly | Thr | Leu | Leu | Cys | Thr | Ala | Ala | Ala | Val | Ser | Leu | Asn | Thr | Ile |
| 225 | | | | | 230 | | | | | 235 | | | | | 240 |
| Ala | Ala | Leu | Asn | Phe | Asn | Phe | Ser | Ala | Pro | Ser | Met | Leu | Ile | Cys | Leu |
| | | | | 245 | | | | | 250 | | | | | 255 | |
| Thr | Thr | Leu | Phe | Ala | Leu | Leu | Val | Val | Ser | Leu | Leu | Leu | Val | Val | Glu |
| | | | 260 | | | | | 265 | | | | | 270 | | |
| Gly | Val | Leu | Cys | His | Tyr | Val | Arg | Val | Leu | Val | Gly | Pro | His | Leu | Gly |
| | | | 275 | | | | | 280 | | | | | 285 | | |
| Ala | Ile | Ala | Ala | Thr | Gly | Ile | Val | Gly | Leu | Ala | Cys | Glu | His | Tyr | His |
| | 290 | | | | | 295 | | | | | 300 | | | | |
| Thr | Gly | Gly | Tyr | Tyr | Val | Val | Glu | Gln | Gln | Trp | Pro | Gly | Ala | Gln | Thr |
| 305 | | | | | 310 | | | | | 315 | | | | | 320 |
| Gly | Val | Arg | Val | Ala | Leu | Ala | Leu | Val | Ala | Phe | Ala | Leu | Ala | Met | |
| | | | | 325 | | | | | 330 | | | | | 335 | |
| Ala | Val | Leu | Arg | Cys | Thr | Arg | Ala | Tyr | Leu | Tyr | His | Arg | His | His | |
| | | | 340 | | | | | 345 | | | | | 350 | | |
| Thr | Lys | Phe | Phe | Val | Arg | Met | Arg | Asp | Thr | Arg | His | Arg | Ala | His | Ser |
| | | | 355 | | | | | 360 | | | | | 365 | | |
| Ala | Leu | Arg | Arg | Val | Arg | Ser | Ser | Met | Arg | Gly | Ser | Arg | Arg | Gly | Gly |
| | 370 | | | | | 375 | | | | | 380 | | | | |
| Pro | Pro | Gly | Asp | Pro | Gly | Tyr | Ala | Glu | Thr | Pro | Tyr | Ala | Ser | Val | Ser |
| 385 | | | | | 390 | | | | | 395 | | | | | 400 |

```
His His Ala Glu Ile Asp Arg Tyr Gly Asp Ser Asp Gly Asp Pro Ile
                405                 410                 415

Tyr Asp Glu Val Ala Pro Asp His Glu Ala Glu Leu Tyr Ala Arg Val
            420                 425                 430

Gln Arg Pro Gly Pro Val Pro Asp Ala Glu Pro Ile Tyr Asp Thr Val
        435                 440                 445

Glu Gly Tyr Ala Pro Arg Ser Ala Gly Glu Pro Val Tyr Ser Thr Val
    450                 455                 460

Arg Arg Trp
465

<210> SEQ ID NO 28
<211> LENGTH: 734
<212> TYPE: PRT
<213> ORGANISM: Herpes simplex virus

<400> SEQUENCE: 28

Met Phe Gly Gln Gln Leu Ala Ser Asp Val Gln Gln Tyr Leu Glu Arg
1               5                   10                  15

Leu Glu Lys Gln Arg Gln Gln Lys Val Gly Val Asp Glu Ala Ser Ala
            20                  25                  30

Gly Leu Thr Leu Gly Gly Asp Ala Leu Arg Val Pro Phe Leu Asp Phe
        35                  40                  45

Ala Thr Ala Thr Pro Lys Arg His Gln Thr Val Val Pro Gly Val Gly
    50                  55                  60

Thr Leu His Asp Cys Cys Glu His Ser Pro Leu Phe Ser Ala Val Ala
65              70                  75                  80

Arg Arg Leu Leu Phe Asn Ser Leu Val Pro Ala Gln Leu Arg Gly Arg
                85                  90                  95

Asp Phe Gly Gly Asp His Thr Ala Lys Leu Glu Phe Leu Ala Pro Glu
            100                 105                 110

Leu Val Arg Ala Val Ala Arg Leu Arg Phe Arg Glu Cys Ala Pro Glu
        115                 120                 125

Asp Ala Val Pro Gln Arg Asn Ala Tyr Tyr Ser Val Leu Asn Thr Phe
    130                 135                 140

Gln Ala Leu His Arg Ser Glu Ala Phe Arg Gln Leu Val His Phe Val
145                 150                 155                 160

Arg Asp Phe Ala Gln Leu Leu Lys Thr Ser Phe Arg Ala Ser Ser Leu
                165                 170                 175

Ala Glu Thr Thr Gly Pro Pro Lys Lys Arg Ala Lys Val Asp Val Ala
            180                 185                 190

Thr His Gly Gln Thr Tyr Gly Thr Leu Glu Leu Phe Gln Lys Met Ile
        195                 200                 205

Leu Met His Ala Thr Tyr Phe Leu Ala Ala Val Leu Leu Gly Asp His
    210                 215                 220

Ala Glu Gln Val Asn Thr Phe Leu Arg Leu Val Phe Glu Ile Pro Leu
225                 230                 235                 240

Phe Ser Asp Thr Ala Val Arg His Phe Arg Gln Arg Ala Thr Val Phe
                245                 250                 255

Leu Val Pro Arg Arg His Gly Lys Thr Trp Phe Leu Val Pro Leu Ile
            260                 265                 270

Ala Leu Ser Leu Ala Ser Phe Arg Gly Ile Lys Ile Gly Tyr Thr Ala
        275                 280                 285

His Ile Arg Lys Ala Thr Glu Pro Val Phe Asp Glu Ile Asp Ala Cys
    290                 295                 300
```

-continued

```
Leu Arg Gly Trp Phe Gly Ser Arg Val Asp His Val Lys Gly Glu
305                 310                 315                 320

Thr Ile Ser Phe Ser Phe Pro Asp Gly Ser Arg Ser Thr Ile Val Phe
                325                 330                 335

Ala Ser Ser His Asn Thr Asn Gly Ile Arg Gly Gln Asp Phe Asn Leu
            340                 345                 350

Leu Phe Val Asp Glu Ala Asn Phe Ile Arg Pro Asp Ala Val Gln Thr
        355                 360                 365

Ile Met Gly Phe Leu Asn Gln Ala Asn Cys Lys Ile Ile Phe Val Ser
370                 375                 380

Ser Thr Asn Thr Gly Lys Ala Ser Thr Ser Phe Leu Tyr Asn Leu Arg
385                 390                 395                 400

Gly Ala Ala Asp Glu Leu Leu Asn Val Val Thr Tyr Ile Cys Asp Asp
                405                 410                 415

His Met Pro Arg Val Val Thr His Thr Asn Ala Thr Ala Cys Ser Cys
            420                 425                 430

Tyr Ile Leu Asn Lys Pro Val Phe Ile Thr Met Asp Gly Ala Val Arg
        435                 440                 445

Arg Thr Ala Asp Leu Phe Leu Pro Asp Ser Phe Met Gln Glu Ile Ile
450                 455                 460

Gly Gly Gln Ala Arg Glu Thr Gly Asp Arg Pro Val Leu Thr Lys
465                 470                 475                 480

Ser Ala Gly Glu Arg Phe Leu Leu Tyr Arg Pro Ser Thr Thr Thr Asn
                485                 490                 495

Ser Gly Leu Met Ala Pro Glu Leu Tyr Val Tyr Val Asp Pro Ala Phe
            500                 505                 510

Thr Ala Asn Thr Arg Ala Ser Gly Thr Gly Ile Ala Val Val Gly Arg
        515                 520                 525

Tyr Arg Asp Asp Phe Ile Ile Phe Ala Leu Glu His Phe Phe Leu Arg
530                 535                 540

Ala Leu Thr Gly Ser Ala Pro Ala Asp Ile Ala Arg Cys Val Val His
545                 550                 555                 560

Ser Leu Ala Gln Val Leu Ala Leu His Pro Gly Ala Phe Arg Ser Val
                565                 570                 575

Arg Val Ala Val Glu Gly Asn Ser Ser Gln Asp Ser Ala Val Ala Ile
            580                 585                 590

Ala Thr His Val His Thr Glu Met His Arg Ile Leu Ala Ser Ala Gly
        595                 600                 605

Ala Asn Gly Pro Gly Pro Glu Leu Leu Phe Tyr His Cys Glu Pro Pro
610                 615                 620

Gly Gly Ala Val Leu Tyr Pro Phe Phe Leu Leu Asn Lys Gln Lys Thr
625                 630                 635                 640

Pro Ala Phe Glu Tyr Phe Ile Lys Lys Phe Asn Ser Gly Gly Val Met
                645                 650                 655

Ala Ser Gln Glu Leu Val Ser Val Thr Val Arg Leu Gln Thr Asp Pro
            660                 665                 670

Val Glu Tyr Leu Ser Glu Gln Leu Asn Asn Leu Ile Glu Thr Val Ser
        675                 680                 685

Pro Asn Thr Asp Val Arg Met Tyr Ser Gly Lys Arg Asn Gly Ala Ala
690                 695                 700

Asp Asp Leu Met Val Ala Val Ile Met Ala Ile Tyr Leu Ala Ala Pro
705                 710                 715                 720
```

```
Thr Gly Ile Pro Pro Ala Phe Phe Pro Ile Thr Arg Thr Ser
                725                 730

<210> SEQ ID NO 29
<211> LENGTH: 329
<212> TYPE: PRT
<213> ORGANISM: Herpes simplex virus

<400> SEQUENCE: 29

Met Asn Pro Val Ser Ala Ser Gly Ala Pro Pro Pro Pro Gly
1               5                   10                  15

Asp Gly Ser Tyr Leu Trp Ile Pro Ala Ser His Tyr Asn Gln Leu Val
            20                  25                  30

Thr Gly Gln Ser Ala Pro Arg His Pro Pro Leu Thr Ala Cys Gly Leu
        35                  40                  45

Pro Ala Ala Gly Thr Val Ala Tyr Gly His Pro Gly Ala Gly Pro Ser
    50                  55                  60

Pro His Tyr Pro Pro Pro Ala His Pro Tyr Pro Gly Met Leu Phe
65                  70                  75                  80

Ala Gly Pro Ser Pro Leu Glu Ala Gln Ile Ala Ala Leu Val Gly Ala
                85                  90                  95

Ile Ala Ala Asp Arg Gln Ala Gly Gly Leu Pro Ala Ala Gly Asp
                100                 105                 110

His Gly Ile Arg Gly Ser Ala Lys Arg Arg His Glu Val Glu Gln
            115                 120                 125

Pro Glu Tyr Asp Cys Gly Arg Asp Glu Pro Asp Arg Asp Phe Pro Tyr
    130                 135                 140

Tyr Pro Gly Glu Ala Arg Pro Glu Pro Arg Pro Val Asp Ser Arg Arg
145                 150                 155                 160

Ala Ala Arg Gln Ala Ser Gly Pro His Glu Thr Ile Thr Ala Leu Val
                165                 170                 175

Gly Ala Val Thr Ser Leu Gln Gln Glu Leu Ala His Met Arg Ala Arg
                180                 185                 190

Thr His Ala Pro Tyr Gly Pro Tyr Pro Pro Val Gly Pro Tyr His His
            195                 200                 205

Pro His Ala Asp Thr Glu Thr Pro Ala Gln Pro Pro Arg Tyr Pro Ala
    210                 215                 220

Lys Ala Val Tyr Leu Pro Pro His Ile Ala Pro Gly Pro Pro
225                 230                 235                 240

Leu Ser Gly Ala Val Pro Pro Ser Tyr Pro Pro Val Ala Val Thr
                245                 250                 255

Pro Gly Pro Ala Pro Pro Leu His Gln Pro Ser Pro Ala His Ala His
                260                 265                 270

Pro Pro Pro Pro Pro Gly Pro Thr Pro Pro Ala Ala Ser Leu
            275                 280                 285

Pro Gln Pro Glu Ala Pro Gly Ala Glu Ala Gly Ala Leu Val Asn Ala
    290                 295                 300

Ser Ser Ala Ala His Val Asn Val Asp Thr Ala Arg Ala Ala Asp Leu
305                 310                 315                 320

Phe Val Ser Gln Met Met Gly Ser Arg
                325

<210> SEQ ID NO 30
<211> LENGTH: 1240
<212> TYPE: PRT
<213> ORGANISM: Herpes simplex virus
```

<400> SEQUENCE: 30

Met Phe Cys Ala Ala Gly Gly Pro Ala Ser Pro Gly Gly Lys Pro Ala
1               5                   10                  15

Ala Arg Ala Ala Ser Gly Phe Phe Ala Pro His Asn Pro Arg Gly Ala
            20                  25                  30

Thr Gln Thr Ala Pro Pro Cys Arg Arg Gln Asn Phe Tyr Asn Pro
        35                  40                  45

His Leu Ala Gln Thr Gly Thr Gln Pro Lys Ala Leu Gly Pro Ala Gln
        50                  55                  60

Arg His Thr Tyr Tyr Ser Glu Cys Asp Glu Phe Arg Phe Ile Ala Pro
65                  70                  75                  80

Arg Ser Leu Asp Glu Asp Ala Pro Ala Glu Gln Arg Thr Gly Val His
                85                  90                  95

Asp Gly Arg Leu Arg Arg Ala Pro Lys Val Tyr Cys Gly Gly Asp Glu
            100                 105                 110

Arg Asp Val Leu Arg Val Gly Pro Glu Gly Phe Trp Pro Arg Arg Leu
            115                 120                 125

Arg Leu Trp Gly Gly Ala Asp His Ala Pro Glu Gly Phe Asp Pro Thr
130                 135                 140

Val Thr Val Phe His Val Tyr Asp Ile Leu Glu His Val Glu His Ala
145                 150                 155                 160

Tyr Ser Met Arg Ala Ala Gln Leu His Glu Arg Phe Met Asp Ala Ile
                165                 170                 175

Thr Pro Ala Gly Thr Val Ile Thr Leu Leu Gly Leu Thr Pro Glu Gly
            180                 185                 190

His Arg Val Ala Val His Val Tyr Gly Thr Arg Gln Tyr Phe Tyr Met
            195                 200                 205

Asn Lys Ala Glu Val Asp Arg His Leu Gln Cys Arg Ala Pro Arg Asp
210                 215                 220

Leu Cys Glu Arg Leu Ala Ala Ala Leu Arg Glu Ser Pro Gly Ala Ser
225                 230                 235                 240

Phe Arg Gly Ile Ser Ala Asp His Phe Glu Ala Glu Val Val Glu Arg
                245                 250                 255

Ala Asp Val Tyr Tyr Tyr Glu Thr Arg Pro Thr Leu Tyr Tyr Arg Val
            260                 265                 270

Phe Val Arg Ser Gly Arg Ala Leu Ala Tyr Leu Cys Asp Asn Phe Cys
            275                 280                 285

Pro Ala Ile Arg Lys Tyr Glu Gly Gly Val Asp Ala Thr Thr Arg Phe
290                 295                 300

Ile Leu Asp Asn Pro Gly Phe Val Thr Phe Gly Trp Tyr Arg Leu Lys
305                 310                 315                 320

Pro Gly Arg Gly Asn Ala Pro Ala Gln Pro Arg Pro Thr Ala Phe
                325                 330                 335

Gly Thr Ser Ser Asp Val Glu Phe Asn Cys Thr Ala Asp Asn Leu Ala
            340                 345                 350

Val Glu Gly Ala Met Cys Asp Leu Pro Ala Tyr Lys Leu Met Cys Phe
            355                 360                 365

Asp Ile Glu Cys Lys Ala Gly Gly Glu Asp Glu Leu Ala Phe Pro Val
        370                 375                 380

Ala Glu Arg Pro Glu Asp Leu Val Ile Gln Ile Ser Cys Leu Leu Tyr
385                 390                 395                 400

Asp Leu Ser Thr Thr Ala Leu Glu His Ile Leu Leu Phe Ser Leu Gly

```
                405                 410                 415
Ser Cys Asp Leu Pro Glu Ser His Leu Ser Asp Leu Ala Ser Arg Gly
            420                 425                 430

Leu Pro Ala Pro Val Val Leu Glu Phe Asp Ser Glu Phe Glu Met Leu
            435                 440                 445

Leu Ala Phe Met Thr Phe Val Lys Gln Tyr Gly Pro Glu Phe Val Thr
450                 455                 460

Gly Tyr Asn Ile Ile Asn Phe Asp Trp Pro Phe Val Leu Thr Lys Leu
465                 470                 475                 480

Thr Glu Ile Tyr Lys Val Pro Leu Asp Gly Tyr Gly Arg Met Asn Gly
                485                 490                 495

Arg Gly Val Phe Arg Val Trp Asp Ile Gly Gln Ser His Phe Gln Lys
                500                 505                 510

Arg Ser Lys Ile Lys Val Asn Gly Met Val Asn Ile Asp Met Tyr Gly
                515                 520                 525

Ile Ile Thr Asp Lys Val Lys Leu Ser Ser Tyr Lys Leu Asn Ala Val
        530                 535                 540

Ala Glu Ala Val Leu Lys Asp Lys Lys Asp Leu Ser Tyr Arg Asp
545                 550                 555                 560

Ile Pro Ala Tyr Tyr Ala Ser Gly Pro Ala Gln Arg Gly Val Ile Gly
                565                 570                 575

Glu Tyr Cys Val Gln Asp Ser Leu Leu Val Gly Gln Leu Phe Phe Lys
            580                 585                 590

Phe Leu Pro His Leu Glu Leu Ser Ala Val Ala Arg Leu Ala Gly Ile
            595                 600                 605

Asn Ile Thr Arg Thr Ile Tyr Asp Gly Gln Gln Ile Arg Val Phe Thr
        610                 615                 620

Cys Leu Leu Arg Leu Ala Gly Gln Lys Gly Phe Ile Leu Pro Asp Thr
625                 630                 635                 640

Gln Gly Arg Phe Arg Gly Leu Asp Lys Glu Ala Pro Lys Arg Pro Ala
            645                 650                 655

Val Pro Arg Gly Glu Gly Glu Arg Pro Gly Asp Gly Asn Gly Asp Glu
            660                 665                 670

Asp Lys Asp Asp Asp Glu Asp Gly Asp Glu Asp Gly Asp Glu Arg Glu
        675                 680                 685

Glu Val Ala Arg Glu Thr Gly Gly Arg His Val Gly Tyr Gln Gly Ala
        690                 695                 700

Arg Val Leu Asp Pro Thr Ser Gly Phe His Val Asp Pro Val Val
705                 710                 715                 720

Phe Asp Phe Ala Ser Leu Tyr Pro Ser Ile Ile Gln Ala His Asn Leu
            725                 730                 735

Cys Phe Ser Thr Leu Ser Leu Arg Pro Glu Ala Val Ala His Leu Glu
            740                 745                 750

Ala Asp Arg Asp Tyr Leu Glu Ile Glu Val Gly Gly Arg Arg Leu Phe
            755                 760                 765

Phe Val Lys Ala His Val Arg Glu Ser Leu Leu Ser Ile Leu Leu Arg
        770                 775                 780

Asp Trp Leu Ala Met Arg Lys Gln Ile Arg Ser Arg Ile Pro Gln Ser
785                 790                 795                 800

Thr Pro Glu Glu Ala Val Leu Leu Asp Lys Gln Gln Ala Ala Ile Lys
            805                 810                 815

Val Val Cys Asn Ser Val Tyr Gly Phe Thr Gly Val Gln His Gly Leu
            820                 825                 830
```

```
Leu Pro Cys Leu His Val Ala Ala Thr Val Thr Thr Ile Gly Arg Glu
        835                 840                 845

Met Leu Leu Ala Thr Arg Ala Tyr Val His Ala Arg Trp Ala Glu Phe
    850                 855                 860

Asp Gln Leu Leu Ala Asp Phe Pro Glu Ala Ala Gly Met Arg Ala Pro
865                 870                 875                 880

Gly Pro Tyr Ser Met Arg Ile Ile Tyr Gly Asp Thr Asp Ser Ile Phe
                885                 890                 895

Val Leu Cys Arg Gly Leu Thr Ala Ala Gly Leu Val Ala Met Gly Asp
                900                 905                 910

Lys Met Ala Ser His Ile Ser Arg Ala Leu Phe Leu Pro Pro Ile Lys
                915                 920                 925

Leu Glu Cys Glu Lys Thr Phe Thr Lys Leu Leu Leu Ile Ala Lys Lys
        930                 935                 940

Lys Tyr Ile Gly Val Ile Cys Gly Gly Lys Met Leu Ile Lys Gly Val
945                 950                 955                 960

Asp Leu Val Arg Lys Asn Asn Cys Ala Phe Ile Asn Arg Thr Ser Arg
                965                 970                 975

Ala Leu Val Asp Leu Leu Phe Tyr Asp Asp Thr Val Ser Gly Ala Ala
                980                 985                 990

Ala Ala Leu Ala Glu Arg Pro Ala Glu Glu Trp Leu Ala Arg Pro Leu
        995                 1000                1005

Pro Glu Gly Leu Gln Ala Phe Gly Ala Val Leu Val Asp Ala His
    1010                1015                1020

Arg Arg Ile Thr Asp Pro Glu Arg Asp Ile Gln Asp Phe Val Leu
    1025                1030                1035

Thr Ala Glu Leu Ser Arg His Pro Arg Ala Tyr Thr Asn Lys Arg
    1040                1045                1050

Leu Ala His Leu Thr Val Tyr Tyr Lys Leu Met Ala Arg Arg Ala
    1055                1060                1065

Gln Val Pro Ser Ile Lys Asp Arg Ile Pro Tyr Val Ile Val Ala
    1070                1075                1080

Gln Thr Arg Glu Val Glu Thr Val Ala Arg Leu Ala Ala Leu
    1085                1090                1095

Arg Glu Leu Asp Ala Ala Pro Gly Asp Glu Pro Ala Pro Pro
    1100                1105                1110

Ala Ala Leu Pro Ser Pro Ala Lys Arg Pro Arg Glu Thr Pro Ser
    1115                1120                1125

His Ala Asp Pro Pro Gly Gly Ala Ser Lys Pro Arg Lys Leu Leu
    1130                1135                1140

Val Ser Glu Leu Ala Glu Asp Pro Gly Tyr Ala Ile Ala Arg Gly
    1145                1150                1155

Val Pro Leu Asn Thr Asp Tyr Tyr Phe Ser His Leu Leu Gly Ala
    1160                1165                1170

Ala Cys Val Thr Phe Lys Ala Leu Phe Gly Asn Asn Ala Lys Ile
    1175                1180                1185

Thr Glu Ser Leu Leu Lys Arg Phe Ile Pro Glu Thr Trp His Pro
    1190                1195                1200

Pro Asp Asp Val Ala Ala Arg Leu Arg Ala Ala Gly Phe Gly Pro
    1205                1210                1215

Ala Gly Ala Gly Ala Thr Ala Glu Glu Thr Arg Arg Met Leu His
    1220                1225                1230
```

Arg Ala Phe Asp Thr Leu Ala
    1235            1240

<210> SEQ ID NO 31
<211> LENGTH: 881
<212> TYPE: PRT
<213> ORGANISM: Herpes simplex virus

<400> SEQUENCE: 31

Met Ala Ala Ser Gly Gly Glu Gly Ser Arg Asp Val Arg Ala Pro Gly
1               5                   10                  15

Pro Pro Pro Gln Gln Pro Gly Ala Arg Pro Ala Val Arg Phe Arg Asp
            20                  25                  30

Glu Ala Phe Leu Asn Phe Thr Ser Met His Gly Val Gln Pro Ile Ile
        35                  40                  45

Ala Arg Ile Arg Glu Leu Ser Gln Gln Gln Leu Asp Val Thr Gln Val
    50                  55                  60

Pro Arg Leu Gln Trp Phe Arg Asp Val Ala Ala Leu Glu Val Pro Thr
65                  70                  75                  80

Gly Leu Pro Leu Arg Glu Phe Pro Phe Ala Ala Tyr Leu Ile Thr Gly
                85                  90                  95

Asn Ala Gly Ser Gly Lys Ser Thr Cys Val Gln Thr Leu Asn Glu Val
            100                 105                 110

Leu Asp Cys Val Val Thr Gly Ala Thr Arg Ile Ala Ala Gln Asn Met
        115                 120                 125

Tyr Val Lys Leu Ser Gly Ala Phe Leu Ser Arg Pro Ile Asn Thr Ile
    130                 135                 140

Phe His Glu Phe Gly Phe Arg Gly Asn His Val Gln Ala Gln Leu Gly
145                 150                 155                 160

Gln His Pro Tyr Thr Leu Ala Ser Ser Pro Ala Ser Leu Glu Asp Leu
                165                 170                 175

Gln Arg Arg Asp Leu Thr Tyr Tyr Trp Glu Val Ile Leu Asp Ile Thr
            180                 185                 190

Lys Arg Ala Leu Ala Ala His Gly Gly Glu Asp Ala Arg Asn Glu Phe
        195                 200                 205

His Ala Leu Thr Ala Leu Glu Gln Thr Leu Gly Leu Gly Gln Gly Ala
    210                 215                 220

Leu Thr Arg Leu Ala Ser Val Thr His Gly Ala Leu Pro Ala Phe Thr
225                 230                 235                 240

Arg Ser Asn Ile Ile Val Ile Asp Glu Ala Gly Leu Leu Gly Arg His
                245                 250                 255

Leu Leu Thr Thr Val Val Tyr Cys Trp Trp Met Ile Asn Ala Leu Tyr
            260                 265                 270

His Thr Pro Gln Tyr Ala Gly Arg Leu Arg Pro Val Leu Val Cys Val
        275                 280                 285

Gly Ser Pro Thr Gln Thr Ala Ser Leu Glu Ser Thr Phe Glu His Gln
    290                 295                 300

Lys Leu Arg Cys Ser Val Arg Gln Ser Glu Asn Val Leu Thr Tyr Leu
305                 310                 315                 320

Ile Cys Asn Arg Thr Leu Arg Glu Tyr Thr Arg Leu Ser His Ser Trp
                325                 330                 335

Ala Ile Phe Ile Asn Asn Lys Arg Cys Val Glu His Glu Phe Gly Asn
            340                 345                 350

Leu Met Lys Val Leu Glu Tyr Gly Leu Pro Ile Thr Glu Glu His Met
        355                 360                 365

```
Gln Phe Val Asp Arg Phe Val Pro Glu Ser Tyr Ile Thr Asn Pro
    370                 375                 380

Ala Asn Leu Pro Gly Trp Thr Arg Leu Phe Ser Ser His Lys Glu Val
385                 390                 395                 400

Ser Ala Tyr Met Ala Lys Leu His Ala Tyr Leu Lys Val Thr Arg Glu
                405                 410                 415

Gly Glu Phe Val Val Phe Thr Leu Pro Val Leu Thr Phe Val Ser Val
            420                 425                 430

Lys Glu Phe Asp Glu Tyr Arg Arg Leu Thr Gln Gln Pro Thr Leu Thr
        435                 440                 445

Met Glu Lys Trp Ile Thr Ala Asn Ala Ser Arg Ile Thr Asn Tyr Ser
    450                 455                 460

Gln Ser Gln Asp Gln Asp Ala Gly His Val Arg Cys Glu Val His Ser
465                 470                 475                 480

Lys Gln Gln Leu Val Val Ala Arg Asn Asp Ile Thr Tyr Val Leu Asn
                485                 490                 495

Ser Gln Val Ala Val Thr Ala Arg Leu Arg Lys Met Val Phe Gly Phe
            500                 505                 510

Asp Gly Thr Phe Arg Thr Phe Glu Ala Val Leu Arg Asp Asp Ser Phe
        515                 520                 525

Val Lys Thr Gln Gly Glu Thr Ser Val Glu Phe Ala Tyr Arg Phe Leu
    530                 535                 540

Ser Arg Leu Met Phe Gly Gly Leu Ile His Phe Tyr Asn Phe Leu Gln
545                 550                 555                 560

Arg Pro Gly Leu Asp Ala Thr Gln Arg Thr Leu Ala Tyr Gly Arg Leu
                565                 570                 575

Gly Glu Leu Thr Ala Glu Leu Leu Ser Leu Arg Arg Asp Ala Ala Gly
            580                 585                 590

Ala Ser Ala Thr Arg Ala Ala Asp Thr Ser Asp Arg Ser Pro Gly Glu
        595                 600                 605

Arg Ala Phe Asn Phe Lys His Leu Gly Pro Arg Asp Gly Gly Pro Asp
    610                 615                 620

Asp Phe Pro Asp Asp Leu Asp Val Ile Phe Ala Gly Leu Asp Glu
625                 630                 635                 640

Gln Gln Leu Asp Val Phe Tyr Cys His Tyr Ala Leu Glu Glu Pro Glu
                645                 650                 655

Thr Thr Ala Ala Val His Ala Gln Phe Gly Leu Leu Lys Arg Ala Phe
            660                 665                 670

Leu Gly Arg Tyr Leu Ile Leu Arg Glu Leu Phe Gly Glu Val Phe Glu
        675                 680                 685

Ser Ala Pro Phe Ser Thr Tyr Val Asp Asn Val Ile Phe Arg Gly Cys
    690                 695                 700

Glu Leu Leu Thr Gly Ser Pro Arg Gly Gly Leu Met Ser Val Ala Leu
705                 710                 715                 720

Gln Thr Asp Asn Tyr Thr Leu Met Gly Tyr Thr Tyr Thr Arg Val Phe
                725                 730                 735

Ala Phe Ala Glu Glu Leu Arg Arg Arg His Ala Thr Ala Gly Val Ala
            740                 745                 750

Glu Phe Leu Glu Glu Ser Pro Leu Pro Tyr Ile Val Leu Arg Asp Gln
        755                 760                 765

His Gly Phe Met Ser Val Val Asn Thr Asn Ile Ser Glu Phe Val Glu
    770                 775                 780
```

```
Ser Ile Asp Ser Thr Glu Leu Ala Met Ala Ile Asn Ala Asp Tyr Gly
785                 790                 795                 800

Ile Ser Ser Lys Leu Ala Met Thr Ile Thr Arg Ser Gln Gly Leu Ser
            805                 810                 815

Leu Asp Lys Val Ala Ile Cys Phe Thr Pro Gly Asn Leu Arg Leu Asn
            820                 825                 830

Ser Ala Tyr Val Ala Met Ser Arg Thr Thr Ser Ser Glu Phe Leu His
            835                 840                 845

Met Asn Leu Asn Pro Leu Arg Glu Arg His Glu Arg Asp Asp Val Ile
850                 855                 860

Ser Glu His Ile Leu Ser Ala Leu Arg Asp Pro Asn Val Val Ile Val
865                 870                 875                 880

Tyr

<210> SEQ ID NO 32
<211> LENGTH: 752
<212> TYPE: PRT
<213> ORGANISM: Herpes simplex virus

<400> SEQUENCE: 32

Met Glu Ala Pro Gly Ile Val Trp Val Glu Ser Val Ser Ala Ile
1               5                   10                  15

Thr Leu Tyr Ala Val Trp Leu Pro Pro Arg Thr Arg Asp Cys Leu His
            20                  25                  30

Ala Leu Leu Tyr Leu Val Cys Arg Asp Ala Ala Gly Glu Ala Arg Ala
            35                  40                  45

Arg Phe Ala Glu Val Ser Val Gly Ser Ser Asp Leu Gln Asp Phe Tyr
50                  55                  60

Gly Ser Pro Asp Val Ser Ala Pro Gly Ala Val Ala Ala Ala Arg Ala
65                  70                  75                  80

Ala Thr Ala Pro Ala Ala Ser Pro Leu Glu Pro Leu Gly Asp Pro Thr
            85                  90                  95

Leu Trp Arg Ala Leu Tyr Ala Cys Val Leu Ala Ala Leu Glu Arg Gln
            100                 105                 110

Thr Gly Arg Trp Ala Leu Phe Val Pro Leu Arg Leu Gly Trp Asp Pro
            115                 120                 125

Gln Thr Gly Leu Val Val Arg Val Glu Arg Ala Ser Trp Gly Pro Pro
130                 135                 140

Ala Ala Pro Arg Ala Ala Leu Leu Asp Val Glu Ala Lys Val Asp Val
145                 150                 155                 160

Asp Pro Leu Ala Leu Ser Ala Arg Val Ala Glu His Pro Gly Ala Arg
            165                 170                 175

Leu Ala Trp Ala Arg Leu Ala Ala Ile Arg Asp Ser Pro Gln Cys Ala
            180                 185                 190

Ser Ser Ala Ser Leu Ala Val Thr Ile Thr Thr Arg Thr Ala Arg Phe
            195                 200                 205

Ala Arg Glu Tyr Thr Thr Leu Ala Phe Pro Pro Thr Arg Lys Glu Gly
            210                 215                 220

Ala Phe Ala Asp Leu Val Glu Val Cys Glu Val Gly Leu Arg Pro Arg
225                 230                 235                 240

Gly His Pro Gln Arg Val Thr Ala Arg Val Leu Leu Pro Arg Gly Tyr
            245                 250                 255

Asp Tyr Phe Val Ser Ala Gly Asp Gly Phe Ser Ala Pro Ala Leu Val
            260                 265                 270
```

```
Ala Leu Phe Arg Gln Trp His Thr Val His Ala Ala Pro Gly Ala
            275                 280                 285

Leu Ala Pro Val Phe Ala Phe Leu Gly Pro Gly Phe Glu Val Arg Gly
    290                 295                 300

Gly Pro Val Gln Tyr Phe Ala Val Leu Gly Phe Pro Gly Trp Pro Thr
305                 310                 315                 320

Phe Thr Val Pro Ala Ala Ala Ala Glu Ser Ala Arg Asp Leu Val
                325                 330                 335

Arg Gly Ala Ala Ala Thr His Ala Ala Cys Leu Gly Ala Trp Pro Ala
                340                 345                 350

Val Gly Ala Arg Val Val Leu Pro Pro Arg Ala Trp Pro Ala Val Ala
            355                 360                 365

Ser Glu Ala Ala Gly Arg Leu Leu Pro Ala Phe Arg Glu Ala Val Ala
    370                 375                 380

Arg Trp His Pro Thr Ala Thr Thr Ile Gln Leu Leu Asp Pro Pro Ala
385                 390                 395                 400

Ala Val Gly Pro Val Trp Thr Ala Arg Phe Cys Phe Ser Gly Leu Gln
                405                 410                 415

Ala Gln Leu Leu Ala Ala Leu Ala Gly Leu Gly Glu Ala Gly Leu Pro
            420                 425                 430

Glu Ala Arg Gly Arg Ala Gly Leu Glu Arg Leu Asp Ala Leu Val Ala
    435                 440                 445

Ala Ala Pro Ser Glu Pro Trp Ala Arg Ala Val Leu Glu Arg Leu Val
        450                 455                 460

Pro Asp Ala Cys Asp Ala Cys Pro Ala Leu Arg Gln Leu Leu Gly Gly
465                 470                 475                 480

Val Met Ala Ala Val Cys Leu Gln Ile Glu Gln Thr Ala Ser Ser Val
                485                 490                 495

Lys Phe Ala Val Cys Gly Gly Thr Gly Ala Ala Phe Trp Gly Leu Phe
            500                 505                 510

Asn Val Asp Pro Gly Asp Ala Asp Ala Ala His Gly Ala Ile Gln Asp
    515                 520                 525

Ala Arg Arg Ala Leu Glu Ala Ser Val Arg Ala Val Leu Ser Ala Asn
        530                 535                 540

Gly Ile Arg Pro Arg Leu Ala Pro Ser Leu Ala Pro Glu Gly Val Tyr
545                 550                 555                 560

Thr His Val Val Thr Trp Ser Gln Thr Gly Ala Trp Phe Trp Asn Ser
                565                 570                 575

Arg Asp Asp Thr Asp Phe Leu Gln Gly Phe Pro Leu Arg Gly Ala Ala
            580                 585                 590

Tyr Ala Ala Ala Ala Glu Val Met Arg Asp Ala Leu Arg Arg Ile Leu
    595                 600                 605

Arg Arg Pro Ala Ala Gly Pro Pro Glu Glu Ala Val Cys Ala Ala Arg
        610                 615                 620

Gly Val Met Glu Asp Ala Cys Asp Arg Phe Val Leu Ala Pro Phe Gly
625                 630                 635                 640

Arg Arg Leu Asp Ala Glu Tyr Trp Ser Val Leu Thr Pro Pro Gly Glu
                645                 650                 655

Ala Asp Asp Pro Leu Pro Gln Thr Ala Phe Arg Gly Gly Ala Leu Leu
            660                 665                 670

Asp Ala Glu Gln Tyr Trp Arg Arg Val Val Arg Val Cys Pro Gly Gly
    675                 680                 685

Gly Glu Ser Val Gly Val Pro Val Asp Leu Tyr Pro Arg Pro Leu Val
```

```
                690             695             700
Leu Pro Pro Val Asp Cys Ala His His Leu Arg Glu Ile Leu Arg Glu
705                 710             715                 720

Ile Gln Leu Val Phe Thr Gly Val Leu Glu Gly Val Trp Gly Glu Gly
                725             730             735

Gly Ser Phe Val Tyr Pro Phe Asp Glu Lys Ile Arg Phe Leu Phe Pro
                740             745             750
```

<210> SEQ ID NO 33
<211> LENGTH: 292
<212> TYPE: PRT
<213> ORGANISM: Herpes simplex virus

<400> SEQUENCE: 33

```
Met Asp Gly Ala Val Arg Arg Thr Ala Asp Leu Phe Leu Pro Asp Ser
1               5                   10                  15

Phe Met Gln Glu Ile Ile Gly Gly Gln Ala Arg Glu Thr Gly Asp Asp
                20                  25                  30

Arg Pro Val Leu Thr Lys Ser Ala Gly Glu Arg Phe Leu Leu Tyr Arg
            35                  40                  45

Pro Ser Thr Thr Thr Asn Ser Gly Leu Met Ala Pro Glu Leu Tyr Val
50                  55                  60

Tyr Val Asp Pro Ala Phe Thr Ala Asn Thr Arg Ala Ser Gly Thr Gly
65                  70                  75                  80

Ile Ala Val Val Gly Arg Tyr Arg Asp Asp Phe Ile Ile Phe Ala Leu
                85                  90                  95

Glu His Phe Phe Leu Arg Ala Leu Thr Gly Ser Ala Pro Ala Asp Ile
                100                 105                 110

Ala Arg Cys Val Val His Ser Leu Ala Gln Val Leu Ala Leu His Pro
            115                 120                 125

Gly Ala Phe Arg Ser Val Arg Val Ala Val Glu Gly Asn Ser Ser Gln
130                 135                 140

Asp Ser Ala Val Ala Ile Ala Thr His Val His Thr Glu Met His Arg
145                 150                 155                 160

Ile Leu Ala Ser Ala Gly Ala Asn Gly Pro Gly Pro Glu Leu Leu Phe
                165                 170                 175

Tyr His Cys Glu Pro Pro Gly Gly Ala Val Leu Tyr Pro Phe Phe Leu
                180                 185                 190

Leu Asn Lys Gln Lys Thr Pro Ala Phe Glu Tyr Phe Ile Lys Lys Phe
            195                 200                 205

Asn Ser Gly Gly Val Met Ala Ser Gln Glu Leu Val Ser Val Thr Val
210                 215                 220

Arg Leu Gln Thr Asp Pro Val Glu Tyr Leu Ser Glu Gln Leu Asn Asn
225                 230                 235                 240

Leu Ile Glu Thr Val Ser Pro Asn Thr Asp Val Arg Met Tyr Ser Gly
                245                 250                 255

Lys Arg Asn Gly Ala Ala Asp Asp Leu Met Val Ala Val Ile Met Ala
                260                 265                 270

Ile Tyr Leu Ala Ala Pro Thr Gly Ile Pro Pro Ala Phe Phe Pro Ile
            275                 280                 285

Thr Arg Thr Ser
290
```

<210> SEQ ID NO 34
<211> LENGTH: 598

<212> TYPE: PRT
<213> ORGANISM: Herpes simplex virus

<400> SEQUENCE: 34

```
Met Ala Thr Ser Ala Pro Gly Val Pro Ser Ala Ala Val Arg Glu
1               5                   10                  15

Glu Ser Pro Gly Ser Ser Trp Lys Glu Gly Ala Phe Glu Arg Pro Tyr
            20                  25                  30

Val Ala Phe Asp Pro Asp Leu Leu Ala Leu Asn Glu Ala Leu Cys Ala
            35                  40                  45

Glu Leu Leu Ala Ala Cys His Val Val Gly Val Pro Pro Ala Ser Ala
    50                  55                  60

Leu Asp Glu Asp Val Glu Ser Asp Val Ala Pro Ala Pro Pro Arg Pro
65                  70                  75                  80

Arg Gly Ala Ala Arg Glu Ala Ser Gly Gly Arg Gly Pro Gly Ser Ala
                85                  90                  95

Arg Gly Pro Pro Ala Asp Pro Thr Ala Glu Gly Leu Leu Asp Thr Gly
            100                 105                 110

Pro Phe Ala Ala Ala Ser Val Asp Thr Phe Ala Leu Asp Arg Pro Cys
        115                 120                 125

Leu Val Cys Arg Thr Ile Glu Leu Tyr Lys Gln Ala Tyr Arg Leu Ser
130                 135                 140

Pro Gln Trp Val Ala Asp Tyr Ala Phe Leu Cys Ala Lys Cys Leu Gly
145                 150                 155                 160

Ala Pro His Cys Ala Ala Ser Ile Phe Val Ala Phe Glu Phe Val
                165                 170                 175

Tyr Val Met Asp His His Phe Leu Arg Thr Lys Lys Ala Thr Leu Val
            180                 185                 190

Gly Ser Phe Ala Arg Phe Ala Leu Thr Ile Asn Asp Ile His Arg His
        195                 200                 205

Phe Phe Leu His Cys Cys Phe Arg Thr Asp Gly Gly Val Pro Gly Arg
210                 215                 220

His Ala Gln Lys Gln Pro Arg Pro Thr Pro Ser Pro Gly Ala Ala Lys
225                 230                 235                 240

Val Gln Tyr Ser Asn Tyr Ser Phe Leu Ala Gln Ser Ala Thr Arg Ala
                245                 250                 255

Leu Ile Gly Thr Leu Ala Ser Gly Gly Asp Asp Gly Ala Gly Ala Gly
            260                 265                 270

Ala Gly Gly Gly Ser Gly Thr Gln Pro Ser Leu Thr Thr Ala Leu Met
        275                 280                 285

Asn Trp Lys Asp Cys Ala Arg Leu Leu Asp Cys Thr Glu Gly Lys Arg
290                 295                 300

Gly Gly Gly Asp Ser Cys Cys Thr Arg Ala Ala Arg Asn Gly Glu
305                 310                 315                 320

Phe Glu Ala Ala Ala Gly Ala Leu Ala Gln Gly Gly Glu Pro Glu Thr
                325                 330                 335

Trp Ala Tyr Ala Asp Leu Ile Leu Leu Leu Ala Gly Thr Pro Ala
            340                 345                 350

Val Trp Glu Ser Gly Pro Arg Leu Arg Ala Ala Ala Asp Ala Arg Arg
        355                 360                 365

Ala Ala Val Ser Glu Ser Trp Glu Ala His Arg Gly Ala Arg Met Arg
370                 375                 380

Asp Ala Ala Pro Arg Phe Ala Gln Phe Ala Glu Pro Gln Pro Gln Pro
385                 390                 395                 400
```

```
Asp Leu Asp Leu Gly Pro Leu Met Ala Thr Val Leu Lys His Gly Arg
            405                 410                 415

Gly Arg Gly Arg Thr Gly Gly Glu Cys Leu Leu Cys Asn Leu Leu Leu
        420                 425                 430

Val Arg Ala Tyr Trp Leu Ala Met Arg Arg Leu Arg Ala Ser Val Val
        435                 440                 445

Arg Tyr Ser Glu Asn Asn Thr Ser Leu Phe Asp Cys Ile Val Pro Val
    450                 455                 460

Val Asp Gln Leu Glu Ala Asp Pro Glu Ala Gln Pro Gly Asp Gly Gly
465                 470                 475                 480

Arg Phe Val Ser Leu Leu Arg Ala Ala Gly Pro Glu Ala Ile Phe Lys
                485                 490                 495

His Met Phe Cys Asp Pro Met Cys Ala Ile Thr Glu Met Glu Val Asp
            500                 505                 510

Pro Trp Val Leu Phe Gly His Pro Arg Ala Asp His Arg Asp Glu Leu
        515                 520                 525

Gln Leu His Lys Ala Lys Leu Ala Cys Gly Asn Glu Phe Glu Gly Arg
        530                 535                 540

Val Cys Ile Ala Leu Arg Ala Leu Ile Tyr Thr Phe Lys Thr Tyr Gln
545                 550                 555                 560

Val Phe Val Pro Lys Pro Thr Ala Leu Ala Thr Phe Val Arg Glu Ala
                565                 570                 575

Gly Ala Leu Leu Arg Arg His Ser Ile Ser Leu Leu Ser Leu Glu His
                580                 585                 590

Thr Leu Cys Thr Tyr Val
            595

<210> SEQ ID NO 35
<211> LENGTH: 327
<212> TYPE: PRT
<213> ORGANISM: Herpes simplex virus

<400> SEQUENCE: 35

Met Glu Tyr Asp Ser Phe Asp Ala Leu Leu Ala Ala Arg Leu Glu Ser
1               5                   10                  15

Gly Gln Thr Leu Gly Pro Ala Gly Gly Arg Glu Ala Ser Leu Pro Glu
            20                  25                  30

Ala Pro His Ala Leu Tyr Arg Pro Thr Gly Gln His Val Ala Val Leu
        35                  40                  45

Ala Ala Ala Thr His Arg Thr Pro Ala Ala Arg Val Thr Ala Met Asp
    50                  55                  60

Leu Val Leu Ala Ala Val Leu Leu Gly Ala Pro Val Val Val Ala Leu
65                  70                  75                  80

Arg Asn Thr Thr Ala Phe Ser Arg Glu Ser Glu Leu Glu Leu Cys Leu
                85                  90                  95

Thr Leu Phe Asp Ser Arg Pro Gly Gly Pro Asp Ala Ala Leu Arg Asp
            100                 105                 110

Val Val Ser Ser Asp Ile Glu Thr Trp Ala Val Gly Leu Leu His Thr
        115                 120                 125

Asp Leu Asn Pro Ile Glu Asn Ala Cys Leu Ala Ala Gln Leu Pro Arg
    130                 135                 140

Leu Ser Ala Leu Ile Ala Glu Arg Pro Leu Ala Asp Gly Pro Pro Cys
145                 150                 155                 160

Leu Val Leu Val Asp Ile Ser Met Thr Pro Val Ala Val Leu Trp Glu
```

```
                165                 170                 175
Ala Pro Glu Pro Pro Gly Pro Pro Asp Val Arg Phe Val Gly Ser Glu
            180                 185                 190

Ala Thr Glu Glu Leu Pro Phe Val Ala Thr Ala Gly Asp Val Leu Ala
            195                 200                 205

Ala Ser Ala Ala Asp Ala Asp Pro Phe Phe Ala Arg Ala Ile Leu Gly
            210                 215                 220

Arg Pro Phe Asp Ala Ser Leu Leu Thr Gly Glu Leu Phe Pro Gly His
225                 230                 235                 240

Pro Val Tyr Gln Arg Pro Leu Ala Asp Glu Ala Gly Pro Ser Ala Pro
            245                 250                 255

Thr Ala Ala Arg Asp Pro Arg Asp Leu Ala Gly Gly Asp Gly Gly Ser
            260                 265                 270

Gly Pro Glu Asp Pro Ala Ala Pro Pro Ala Arg Gln Ala Asp Pro Gly
            275                 280                 285

Val Leu Ala Pro Thr Leu Leu Thr Asp Ala Thr Thr Gly Glu Pro Val
            290                 295                 300

Pro Pro Arg Met Trp Ala Trp Ile His Gly Leu Glu Glu Leu Ala Ser
305                 310                 315                 320

Asp Asp Ala Gly Gly Pro Thr
                325

<210> SEQ ID NO 36
<211> LENGTH: 512
<212> TYPE: PRT
<213> ORGANISM: Herpes simplex virus

<400> SEQUENCE: 36

Met Ala Thr Asp Ile Asp Met Leu Ile Asp Leu Gly Leu Asp Leu Ser
1               5                   10                  15

Asp Ser Glu Leu Glu Glu Asp Ala Leu Glu Arg Asp Glu Glu Gly Arg
            20                  25                  30

Arg Asp Asp Pro Glu Ser Asp Ser Ser Gly Glu Cys Ser Ser Ser Asp
            35                  40                  45

Glu Asp Met Glu Asp Pro Cys Gly Asp Gly Gly Ala Glu Ala Ile Asp
        50                  55                  60

Ala Ala Ile Pro Lys Gly Pro Pro Ala Arg Pro Glu Asp Ala Gly Thr
65                  70                  75                  80

Pro Glu Ala Ser Thr Pro Arg Pro Ala Ala Arg Arg Gly Ala Asp Asp
            85                  90                  95

Pro Pro Pro Ala Thr Thr Gly Val Trp Ser Arg Leu Gly Thr Arg Arg
            100                 105                 110

Ser Ala Ser Pro Arg Glu Pro His Gly Gly Lys Val Ala Arg Ile Gln
            115                 120                 125

Pro Pro Ser Thr Lys Ala Pro His Pro Arg Gly Gly Arg Gly Arg Gly
            130                 135                 140

Arg Arg Gly Arg Gly Arg Tyr Gly Pro Gly Gly Ala Asp Ser Thr Pro
145                 150                 155                 160

Lys Pro Arg Arg Arg Val Ser Arg Asn Ala His Asn Gln Gly Gly Arg
            165                 170                 175

His Pro Ala Ser Ala Arg Thr Asp Gly Pro Gly Ala Thr His Gly Glu
            180                 185                 190

Ala Arg Arg Gly Gly Glu Gln Leu Asp Val Ser Gly Gly Pro Arg Pro
            195                 200                 205
```

```
Arg Gly Thr Arg Gln Ala Pro Pro Leu Met Ala Leu Ser Leu Thr
    210                 215                 220

Pro Pro His Ala Asp Gly Arg Ala Pro Val Pro Glu Arg Lys Ala Pro
225                 230                 235                 240

Ser Ala Asp Thr Ile Asp Pro Ala Val Arg Ala Val Leu Arg Ser Ile
                245                 250                 255

Ser Glu Arg Ala Ala Val Glu Arg Ile Ser Glu Ser Phe Gly Arg Ser
            260                 265                 270

Ala Leu Val Met Gln Asp Pro Phe Gly Gly Met Pro Phe Pro Ala Ala
        275                 280                 285

Asn Ser Pro Trp Ala Pro Val Leu Ala Thr Gln Ala Gly Gly Phe Asp
    290                 295                 300

Ala Glu Thr Arg Arg Val Ser Trp Glu Thr Leu Val Ala His Gly Pro
305                 310                 315                 320

Ser Leu Tyr Arg Thr Phe Ala Ala Asn Pro Arg Ala Ala Ser Thr Ala
                325                 330                 335

Lys Ala Met Arg Asp Cys Val Leu Arg Gln Glu Asn Leu Ile Glu Ala
            340                 345                 350

Leu Ala Ser Ala Asp Glu Thr Leu Ala Trp Cys Lys Met Cys Ile His
        355                 360                 365

His Asn Leu Pro Leu Arg Pro Gln Asp Pro Ile Ile Gly Thr Ala Ala
    370                 375                 380

Ala Val Leu Glu Asn Leu Ala Thr Arg Leu Arg Pro Phe Leu Gln Cys
385                 390                 395                 400

Tyr Leu Lys Ala Arg Gly Leu Cys Gly Leu Asp Asp Leu Cys Ser Arg
                405                 410                 415

Arg Arg Leu Ser Asp Ile Lys Asp Ile Ala Ser Phe Val Leu Val Ile
            420                 425                 430

Leu Ala Arg Leu Ala Asn Arg Val Glu Arg Gly Val Ser Glu Ile Asp
        435                 440                 445

Tyr Thr Thr Val Gly Val Gly Ala Gly Glu Thr Met His Phe Tyr Ile
    450                 455                 460

Pro Gly Ala Cys Met Ala Gly Leu Ile Glu Ile Leu Asp Thr His Arg
465                 470                 475                 480

Gln Glu Cys Ser Ser Arg Val Cys Glu Leu Thr Ala Ser His Thr Ile
                485                 490                 495

Ala Pro Leu Tyr Val His Gly Lys Tyr Phe Tyr Cys Asn Ser Leu Phe
            500                 505                 510

<210> SEQ ID NO 37
<211> LENGTH: 87
<212> TYPE: PRT
<213> ORGANISM: Herpes simplex virus

<400> SEQUENCE: 37

Met Thr Gly Lys Pro Ala Arg Leu Gly Arg Trp Val Val Leu Leu Phe
1               5                   10                  15

Val Ala Leu Val Ala Gly Val Pro Gly Glu Pro Pro Asn Ala Ala Gly
                20                  25                  30

Ala Arg Gly Val Ile Gly Asp Ala Gln Cys Arg Gly Asp Ser Ala Gly
            35                  40                  45

Val Val Ser Val Pro Gly Val Leu Val Pro Phe Tyr Leu Gly Met Thr
        50                  55                  60

Ser Met Gly Val Cys Met Ile Ala His Val Tyr Gln Ile Cys Gln Arg
65                  70                  75                  80
```

Ala Leu Ala Ala Gly Ser Ala
                85

<210> SEQ ID NO 38
<211> LENGTH: 302
<212> TYPE: PRT
<213> ORGANISM: Herpes simplex virus

<400> SEQUENCE: 38

Asn Arg Trp Gly Ser Gly Val Pro Gly Pro Ile Asn Pro Pro Asn Ser
1               5                   10                  15

Asp Val Val Phe Pro Gly Gly Ser Pro Val Ala Gln Tyr Cys Tyr Ala
                20                  25                  30

Tyr Pro Arg Leu Asp Asp Pro Gly Pro Leu Gly Ser Ala Asp Ala Gly
            35                  40                  45

Arg Gln Asp Leu Pro Arg Arg Val Val Arg His Glu Pro Leu Gly Arg
        50                  55                  60

Ser Phe Leu Thr Gly Gly Leu Val Leu Leu Ala Pro Val Arg Gly
65                  70                  75                  80

Phe Gly Ala Pro Asn Ala Thr Tyr Ala Ala Arg Val Thr Tyr Arg
                85                  90                  95

Leu Thr Arg Ala Cys Arg Gln Pro Ile Leu Leu Arg Gln Tyr Gly Gly
            100                 105                 110

Cys Arg Gly Gly Glu Pro Pro Ser Pro Lys Thr Cys Gly Ser Tyr Thr
        115                 120                 125

Tyr Thr Tyr Gln Gly Gly Gly Pro Pro Thr Arg Tyr Ala Leu Val Asn
    130                 135                 140

Ala Ser Leu Leu Val Pro Ile Trp Asp Arg Ala Ala Glu Thr Phe Glu
145                 150                 155                 160

Tyr Gln Ile Glu Leu Gly Gly Glu Leu His Val Gly Leu Leu Trp Val
                165                 170                 175

Glu Val Gly Gly Glu Gly Pro Gly Pro Thr Ala Pro Pro Gln Ala Ala
            180                 185                 190

Arg Ala Glu Gly Gly Pro Cys Val Pro Pro Val Pro Ala Gly Arg Pro
        195                 200                 205

Trp Arg Ser Val Pro Pro Val Trp Tyr Ser Ala Pro Asn Pro Gly Phe
    210                 215                 220

Arg Gly Leu Arg Phe Arg Glu Arg Cys Leu Pro Gln Thr Pro Ala
225                 230                 235                 240

Ala Pro Ser Asp Leu Pro Arg Val Ala Phe Ala Pro Gln Ser Leu Leu
                245                 250                 255

Val Gly Ile Thr Gly Arg Thr Phe Ile Arg Met Ala Arg Pro Thr Glu
            260                 265                 270

Asp Val Gly Val Leu Pro Pro His Trp Ala Pro Gly Ala Leu Asp Asp
        275                 280                 285

Gly Pro Tyr Ala Pro Phe Pro Pro Arg Pro Arg Phe Arg Arg
    290                 295                 300

<210> SEQ ID NO 39
<211> LENGTH: 3987
<212> TYPE: DNA
<213> ORGANISM: Herpes simplex virus

<400> SEQUENCE: 39
atgtcgtact accatcacca tcaccatcac agtgccgaac agcgtaaaaa gaaaaaaacc         60

| | |
|---|---|
| accaccacga cccaaggacg tggagctgaa gttgctatgg cggatgagga tggaggccgc | 120 |
| ttgagagctg ctgctgagac tactggagga cctggatcac cggaccctgc cgatggaccc | 180 |
| cccctacac caaaccccga tcgtagaccg gctgctagac ctggattcgg atggcatgga | 240 |
| ggacccgagg aaaacgagga cgaggcggac gacgccgctg ccgacgccga cgccgatgag | 300 |
| gctgcccctg cttctggaga ggcggtagac gaacctgctg ccgatggagt tgttagccct | 360 |
| aggcaattgg cttttgttggc gagcatggta gacgaggctg tgagaacaat cccttcccct | 420 |
| cccctgaac gtgatggagc acaagaggag gcggctagga gtccctcacc accccgtaca | 480 |
| ccttctatga gagcggatta cggcgaggaa aacgacgacg acgacgatga tgatgacgac | 540 |
| gatgatcgtg atgccggacg ctgggttagg ggacctgaaa ccacttctgc tgtccgtgga | 600 |
| gcatacccg atcctatggc gagtttgagc cctagaccac ctgccccgag gagacaccac | 660 |
| caccaccacc atcataggcg tagacgtgct cctagacgtc gttctgccgc tagtgactct | 720 |
| tccaaatctg gctcttcttc atctgcctct tccgcttcat cttcggcctc atcgtcctct | 780 |
| tcggcatccg cttcgagtag tgatgatgat gatgacgacg acgctgctag agcccccgct | 840 |
| tctgctgccg accacgctgc tggcggaact ttgggagccg acgacgagga ggcgggagtt | 900 |
| cctgctcgtg ccccgggagc tgctccgagg ccttctccac cccgtgctga acctgctccg | 960 |
| gctagaacac cggccgctac tgctggtaga ctggagcgta gacgtgcccg tgctgctgtg | 1020 |
| gctggtagag atgctactgg ccgcttcact gctggccgtc ctagacgtgt tgaactggac | 1080 |
| gccgatgctg cttctggtgc tttctacgcc cgttaccgtg atggttacgt gtctggtgaa | 1140 |
| ccttggcctg gcgctggtcc acctccgccc ggacgtgtac tctacggtgg attgggcgat | 1200 |
| tctcgccctg gtctgtgggg cgctccggag gctgaggagg ctagagcccg tttcgaggct | 1260 |
| tctggtgccc ctgctcctgt ttgggctcct gaattgggcg acgctgctca acaatacgcc | 1320 |
| ctcatcacac gcttgctgta cactcccgac gccgaggcta tgggatggct ccaaaaccct | 1380 |
| agagttgccc ctggtgatgt tgctctggat caggcttgtt ccgtatctc cggcgctgct | 1440 |
| cgtaactctt cttcgttcat ctccggttct gtggctagag ctgtgcctca cttgggatac | 1500 |
| gccatggccg ctggacgttt cggctgggga ctggctcatg ttgctgccgc tgtagcaatg | 1560 |
| tctagacgct acgaccgtgc tcaaaaagga ttcttgctca cgtcactgag gcgtgcttac | 1620 |
| gccccttttgt tggcccgtga aaacgctgcc ctcactggcg cccgtacccc cgatgacggt | 1680 |
| ggcgacgcca accgccacga tggtgatgat gctagaggca aacccgctgc cgctgctgct | 1740 |
| cctttgcccct ctgccgccgc ttcccctgcc gatgaacgtg ctgttcctgc cggttacggt | 1800 |
| gccgctggtg tgttggctgc tttgggacgc ttgagtgctg ccccggctag tgccccgct | 1860 |
| ggtgccgatg acgatgacga tgacgatggt gctggcggag gcggtggcgg tagacgtgct | 1920 |
| gaggctggac gtgttgctgt tgaatgcctg gctgcctgta gaggaatctt ggaggctctg | 1980 |
| gccgagggat tcgacggaga cttggcggct gtacccggac tggcgggagc gaggcctgcc | 2040 |
| gctccacctc gccccggtcc tgctggtgct gccgctcctc ctcatgccga cgctcctaga | 2100 |
| ctccgtgctt ggctccgtga actccgtttc gttcgtgacg cttttggttct gatgagactg | 2160 |
| agaggcgact tgagagtggc tggaggatcc gaggctgctg ttgctgctgt ccgtgctgtt | 2220 |
| tctttggttg ctggtgcttt gggccctgct ttgccgagat ctcccgtttt gttgtcgagt | 2280 |
| gccgccgctc ctgccgccga tttgttgttc caaaaccaat ccctccgccc tctgctcgcc | 2340 |
| gacactgttg ccgctgccga ttctctggct gctccggctt ctgccccacg tgaagctcgt | 2400 |
| aaacgtaaat cacccgctcc ggctcgtgct ccccctggtg gcgcccctag acccctaaa | 2460 |

```
aaatcccgtg ccgatgcccc tagacctgct gctgctcccc ccgctggtgc tgctcccccc   2520 gctccccta ctcccccccc acgcccacct cgtcccgctg ccctcacacg ccgtcctgct    2580
gagggacccg atccacaagg cggctggcgt agacaacctc ctggcccatc ccatacaccg   2640
gcaccatctg ccgctgcttt ggaggcttac tgtgctcctc gtgctgtggc tgaactcacc   2700
gatcatccgc tgttccctgc tccctggcgt cccgccctca tgttcgatcc tagagctttg   2760
gcttccttgg ccgctcgttg tgctgcccct cccctggcg tgctccggc tgctttcggt     2820 cctctccgtg cctctggtcc actccgccgt gccgctgcct ggatgagaca agttcccgac   2880
cctgaggatg ttagagttgt gatcttgtac tcgcccttgc ctggcgagga tttggccgct   2940
ggtagagctg gcggtggccc ccctcctgaa tggtctgctg aacgtggtgg tttgtcttgc   3000
ttgttggccg ccctgggaaa ccgtctgtgt ggtcctgcta ctgctgcttg gctggaaac    3060 tggactggcg ctcccgatgt ttctgctctc ggtgctcaag gagttttgct gctctctact   3120
cgtgacttgg cattgctgg agctgttgaa ttcctgggac tcttggctgg cgcttgtgat    3180
aggagactca tcgtcgtaaa cgctgtgaga gctgccgatt ggcctgccga tggtcctgtt   3240
gtgtctcgtc aacacgctta cttggcttgt gaagtgttgc ccgctgtcca atgtgctgtt   3300
cgctggcctg ctgctcgtga tctgaggcgt actgttctgg ctagtggtcg tgttttcgga   3360
cctggtgttt tcgctcgtgt cgaagctgct cacgctagac tgtacccga tgccccaccc    3420 ctccgtttgt gtcgtggagc aaacgttcgc taccgtgtcc gtactcgttt cggacccgat   3480
actctggttc caatgtcccc tcgtgaatac cgtcgtgctg ttctgcctgc cctcgatgga   3540
cgtgctgccg cttctggcgc tggtgacgct atggctcctg gcgctccgga cttctgtgag   3600
gatgaggctc actcacatcg tgcctgtgcc cgctggggac tgggcgctcc attgaggcct   3660
gtatacgtgg cactgggccg tgatgctgtt agaggcggac ccgctgaatt gagaggccct   3720
cgtcgtgaat tctgtgctag ggctctgctc gaacccgatg gagatgctcc tcctttggta   3780
ctccgtgacg acgccgatgc tggtcctccc ccacaaattc gctgggctag tgctgctgga   3840
cgtgctggta ctgtattggc tgctgctggc ggtggcgttg aagttgttgg tactgccgct   3900
ggactcgcta cacctccccg ccgtgaacct gtagacatgg atgctgaact cgaggatgat   3960
gacgacggat tgttcggaga gtaatag                                       3987
```

<210> SEQ ID NO 40  
<211> LENGTH: 1128  
<212> TYPE: DNA  
<213> ORGANISM: Herpes simplex virus

<400> SEQUENCE: 40

```
atgaagttcc tcgtgaacgt ggccctggtg ttcatggtgg tgtacatcag ctacatctac     60
gccaaccgtt ggaagtacgc tctggctgac ccatccctga agatggctga ccccaaccgt    120
ttccgtggca agaacctgcc cgtgctggac cagctgaccg accccctgg cgtgaagcgt    180 gtgtaccaca tccagccatc cctcgaagac cccttccagc cccctccat ccccatcacc     240 gtgtactacg ctgtgctgga acgcgcttgc cgttccgtgc tgctgcacgc tccttccgag    300
gctccccaga tcgtgcgtgg tgcttccgac gaggctcgca agcacaccta caacctgact    360
atcgcttggt acaggatggg tgacaactgc gctatcccta tcaccgtcat ggaatacacc    420
gagtgcccct acaacaagtc cctgggcgtg tgccctatcc gtaccagcc ccgttggtcc     480 tactacgact ccttcagcgc tgtgtccgag gacaacctgg gtttcctgat gcacgctccc   540
```

```
gctttcgaga ctgctggcac ctacctgcgt ctggtcaaga tcaacgactg gaccgagatc    600
acccagttca tcctggaaca ccgtgctcgt gcttcgtgca agtacgccct gccctgcgt     660 atccctcctg ctgcttgcct gacctccaag gcttaccagc agggcgtgac cgtggactcc    720
atcggcatgc tgccccgttt catccccgag aaccagcgta ccgtggctct gtactctctg    780
aagatcgctg gctggcacgg tcctaagccc ccctacacct ccactctgct gcccctgag     840 ctgtccgaca ccaccaacgc tactcagccc gagttggtgc tgaggaccc  cgaggactcc    900 gctctgttgg aggacccgc  tggaaccgtg tcctcccaga tccccccaa  ctggcacatc    960 ccttccatcc aggacgtggc ccctcaccac gctccagctg ctccctccaa ccccgtcgt    1020 cgtgctcaga tggctcccaa gcgtctgcgt ctgccccaca tccgtgacga cgacgctcct   1080
ccatcccacc agcccctgtt ctaccaccac caccatcacc actaataa               1128

<210> SEQ ID NO 41
<211> LENGTH: 783
<212> TYPE: DNA
<213> ORGANISM: Herpes simplex virus

<400> SEQUENCE: 41
atgtctcgtc gtcgtggtcc tcgtcgtcgt ggtcctcgtc gtcgtccgcg tccgggtgcg    60
ccggcggtac cacgcccggg tgcgccggca gtgccgcgtc caggcgcact gcctaccgcg   120
gactctcaaa tggtgccggc gtatgattct ggtactgccg tcgaatctgc tccggcagcg   180
agctccctgc tgcgtcgttg gctgctggtc cctcaggcgg acgattccga tgacgcagac   240
tacgcgggca acgacgacgc ggagtgggct aacagcccgc caagcgaggg tggtggcaaa   300
gcgccggagg ctccgcacgc agcgcctgcc gcagcgtgcc cgcctccgcc tcctcgtaaa   360
gaacgtggcc ctcaacgtcc tctgccgcgcg cacctggctc tgcgtctgcg tactaccact   420
gagtacctgg cgcgtctgtc tctgcgtcgt cgccgtccgc cggctagccc gccggccgat   480
gcaccgcgtg gcaaagtgtg cttctctcca cgtgttcaag ttcgtcacct ggtggcttgg   540
gaaacggctg cccgtctggc tcgccgtggc agctgggcac gtgagcgcgc agaccgtgac   600
cgcttccgtc gccgtgtggc ggctgctgaa gccgttatcg gcccgtgcct ggaacctgag   660
gctcgcgctc gcgcgcgtgc gcgcgctcgt gcccacgaag atggcggtcc agcagaggaa   720
gaagaggcag ctgcagcagc gcgcggtagc tccgcggctg cgggtccagg tcgtcgtgcc   780
gta                                                                783

<210> SEQ ID NO 42
<211> LENGTH: 2523
<212> TYPE: DNA
<213> ORGANISM: Herpes simplex virus

<400> SEQUENCE: 42
atgtcgtact accatcacca tcaccatcac atggagccac gtcctggtac ttcttctcgc    60
gctgatcctg gtcctgaacg tccgccacgc cagactccgg gcacccagcc ggccgcccct   120
cacgcttggg gcatgctgaa cgatatgcag tggctggcgt cctctgattc cgaagaggag   180
actgaggttg gtatcagcga tgatgatctg caccgcgact ctaccagcga agcaggttcc   240
actgacaccg aaatgtttga agcgggcctg atggatgccg cgaccccgcc ggctcgtccg   300
ccggctgaac gtcagggtag ccctacgcct gcggatgcgc aaggctcttg tggtggtggt   360
ccagtaggcg aagaggaggc tgaggccggt ggcggcggta atgtgtgtgc ggtttgtacc   420
gatgaaatcg caccgccgct gcgttgtcag tctttccgt  gcctgcaccc gttttgcatt   480
```

```
ccgtgcatga aaacctggat cccgctgcgc aacacttgcc cgctgtgcaa cactccggtt    540
gcttatctga tcgttggtgt aaccgcatct ggttcctttt ctaccatccc gattgtcaac    600
gacccacgta cgcgtgttga ggcggaggcg gctgtacgtg cgggcaccgc ggtggacttt    660
atctggaccg gtaacccgcg caccgcgcca cgctccctgt ctctgggtgg ccataccgtt    720
cgtgctctga gcccgacccc accttggcca ggcaccgatg acgaagacga cgatctggct    780
gacgttgact atgttccgcc ggcaccgcgt cgcgcaccac gccgtggtgg cggtggcgcc    840
ggtgcgacgc gcggtaccct ccagccggca gcaactcgcc cagcaccgcc gggtgccccg    900
cgttctagca gctccggtgg cgcaccgctg cgtgctggcg tgggttctgg ttccggtggt    960
ggtccggccg tggcggctgt cgtcccgcgt gtggcttctc tgccaccggc agctggtggc   1020
ggtcgtgctc aagctcgtcg tgtcggcgag gacgcagcgg ctgctgaggg ccgtactcca   1080
ccggcccgtc aaccgcgcgc agcacaggaa ccgccgatcg tgatctccga ttccccgcca   1140
ccgagcccgc gtcgcccggc gggtccgggt ccgctgtctt ttgtatcctc cagctctgct   1200
caggtaagca gcggtcctgg cggtggcggc ctgccacagt cctctggtcg tgctgctcgt   1260
cctcgtgcgg cggttgctcc tcgtgtacgt tctccgccac gcgctgctgc cgcgccggtc   1320
gtttctgcct ctgctgacgc ggcaggtccg gctccgcctg cagttccggt tgatgcacac   1380
cgtgcaccgc gctctcgtat gacccaggcg cagactgata cccaggcaca atccctgggt   1440
cgcgcgggtg cgactgacgc tcgtggtagc ggtggtccgg gcgctgaagg tggcccgggt   1500 gttcacgcg gtactaacac tccgggcgct gcgccacacg cggctgaagg tgcggctgca    1560
cgtccgcgta acgtcgtgg ttccgacagc ggtccggctg caagcagcag cgcgagctct    1620
tccgctgcgc ctcgcagccc gctgcgccg caggtgttg cgccaagcg tgctgctccg      1680 cgtcgtgcac cggactccga ttctggcgac cgcggtcacg gcccgctggc ccctgctagc   1740
gcaggcgctg cgccgccatc cgccagcccg tcttctcagg cagctgtggc tgcggcgtcc   1800
tcttcttccg ctagcagctc ttccgcctct tctagcagcg cgtcctctag cagcgcatct   1860
tcctcttctg cttcttcttc tagcgcttct agctcttccg cgtcctcttc cgctggcggt   1920
gcaggcggct ctgttgcttc cgccagcggc gcaggtgagc gtcgtgaaac gagcctgggc   1980
ccacgtgctg ctgcaccgcg tggcccgcgt aagtgtgcgc gcaagacccg ccacgctgaa   2040
ggcggtccgg agccgggtgc gcgtgatccg gctccgggtc tgacccgtta cctgccgatt   2100
gcgggtgtgt cctccgttgt ggcactggcg ccgtatgtga acaaaactgt cacgggcgat   2160
tgcctgcctg ttctggacat ggaaaccggt catatcggcg cttacgtcgt tctggttgac   2220
caaaccggca acgtggcgga tctgctgcgt gcggccgctc cggcttggtc ccgtcgtacc   2280
ctgctgccga acatgctccg caactgtgta cgcccaccgg attacccaac ccgccggcc    2340 tccgagtgga actccctgtg gatgaccccg gttggtaaca tgctgttcga ccagggcacg   2400
ctggttggtg tctggactt tcacggcctg cgctcccgtc acccgtggtc ccgtgagcaa    2460
ggcgctccgg cccctgcggg cgatgccccg gctggccacg gcgagagtac tagaggatca   2520
taa                                                                 2523
```

<210> SEQ ID NO 43
<211> LENGTH: 2928
<212> TYPE: DNA
<213> ORGANISM: Herpes simplex virus

<400> SEQUENCE: 43

| | | |
|---|---|---|
| atgtcgtact accatcacca tcaccatcac gccgctcaac gtgctagggg atcctctgaa | 60 | |
| cgctgggctg ctggtgtcga ggctgctttg gatagagtgg agaaccgtgc cgaattcgat | 120 | |
| gttgtcgagc tgaggagact ccaagctttg gctggtactc acggctacaa ccctcgtgat | 180 | |
| ttccgtaaac gtgccgaaca ggctttggcg gcaaacgctg aggccgtaac attggctctg | 240 | |
| gacactgcct tcgctttcaa cccatacacg cccgaaaacc aacgtcatcc tatgctccca | 300 | |
| cctctcgctg ctattcaccg cctgggatgg agcgctgctt tccatgctgc tgctgaaact | 360 | |
| tacgccgaca tgttccgtgt cgatgccgaa ccactggcta gactgctccg tatcgctgag | 420 | |
| ggactgctgg agatggctca agctggcgac ggattcatcg attaccatga ggctgtcggt | 480 | |
| agactggccg atgatatgac ttctgtgccc ggattgaggc gctacgttcc tttcttccaa | 540 | |
| catggctacg ccgattacgt ggaactgaga gatcgcctgg atgctattag gccgacgtc | 600 | |
| catagagcac tcggtggtgt tccgctggat ttggcggctg ctgccgaaca aatttccgct | 660 | |
| gctcgtaacg atcctgaggc tactgctgaa ttggtccgta ctggtgtaac attgccttgc | 720 | |
| cctagtgagg acgctctcgt ggcttgtgct gctgccctgg agagagtcga tcaatctccc | 780 | |
| gtgaaaaaca cggcttacgc cgaatacgtt gccttcgtga cccgtcaaga cactgctgag | 840 | |
| actaaagacg ctgtggtccg tgctaaacaa caacgtgctg aggccactga acgtgttatg | 900 | |
| gctggcctga gagaggctct ggctgctaga aacgtcgtg ctcaaattga ggctgaggga | 960 | |
| ttggcaaacc tgaaaccat gctcaaagtc gtggctgtac cgctactgt tgctaaaact | 1020 | |
| ctcgaccagg ctcgtagtgt tgccgaaatt gccgatcaag tcgaagtgtt gctggatcaa | 1080 | |
| accgaaaaaa ctcgtgaact ggatgtgcct gctgtgatct ggctcgaaca cgcccaaaga | 1140 | |
| acattcgaga cacacccttt gtctgccgct cgtggtgatg gtcctggacc cttggctcgt | 1200 | |
| catgctggcc gctcggtgc cctcttcgat actcgtcgta gagtagacgc cttgaggaga | 1260 | |
| tccctggagg aggctgaggc tgaatgggac gaagtttggg gacgcttcgg tagagtgagg | 1320 | |
| ggcggagcgt ggaaatctcc ggagggattc cgtgcaatgc atgagcaact gagggccctc | 1380 | |
| caagacacaa caaacaccgt gtctggcctg agggctcaac ctgcttacga acgcttgtct | 1440 | |
| gctcgctacc aaggagtact cggagcgaaa ggcgctgaga gagctgaggc tgttgaggaa | 1500 | |
| ctcggtgctc gtgtcactaa acacaccgct ctgtgtgcta ggctgagaga tgaggtcgtc | 1560 | |
| cgtagagtgc cttgggaaat gaacttcgat gctctgggag gattgttggc tgagttcgat | 1620 | |
| gccgctgctg ccgatttggc accttgggct gtagaggaat ccgtggtgc tagagaactc | 1680 | |
| attcaatacc gtatgggcct gtactctgcc tacgctagag ctggaggaca aactggtgct | 1740 | |
| ggagctgaat ctgctcctgc tcctttgctc gtggatctga gggctttgga tgctcgtgct | 1800 | |
| cgtgcttctt cttcccctga gggacatgaa gtggaccac aactgctgag gaggcgtgga | 1860 | |
| gaggcttact tgagagctgg cggcgaccct ggacctctcg tgctccgtga agctgtttct | 1920 | |
| gctttggacc tgccattcgc cacatctttc ttggccccg atggaactcc cctccaatac | 1980 | |
| gctttgtgct cccctgccgt aacggacaaa ctcggagctt tgctcatgag gcccgaggcc | 2040 | |
| gcttgtgtta gacctccttt gcctaccgat gtgctggaat ctgccccaac tgtgactgcc | 2100 | |
| atgtacgtac tcactgtggt caaccgcctc caactggcat tgagtgatgc tcaagcggca | 2160 | |
| aacttccaac tgttcggtcg tttcgttcgt cataggcagg caacctgggg agcgtcaatg | 2220 | |
| gatgccgccg ctgaattgta cgttgccctg gtggctacaa ctctcacacg tgaattcggt | 2280 | |
| tgtcgctggg cacaattggg atgggctagt ggagctgctg ctcctagacc cccacctgga | 2340 | |
| ccccgtggct cacaacgtca ctgtgtggca ttcaacgaga acgatgtcct cgtcgctttg | 2400 | |

```
gttgccggtg ttcccgaaca catctacaac ttctggcgcc tggacttggt ccgtcaacac   2460
gagtacatgc acctcacact ggagcgtgcc ttcgaggatg ctgccgagtc tatgctcttc   2520
gttcaacgcc tcactccaca tcccgacgct cgtattagag ttctgccgac cttcttggat   2580
ggtggtcctc ctacacgtgg tctgttgttc ggaacccgct tggcggactg gcgtcgtggt   2640
aaactgtctg aaaccgaccc attggcccca tggagatctg ctttggaact cggaacccaa   2700
cgtcgtgacg tgcctgcttt gggaaaactg tcccctgctc aagctttggc cgctgtgtcg   2760
gtactgggcc gtatgtgctt gccctcggct gccttggctg ctttgtggac ctgtatgttc   2820
cccgacgact acactgaata cgactcattc gacgccctct ggcggctcg cctggaatcg    2880 ggacaaacat tgggacctgc tggcggtaga gaggcttcat tgtaatag               2928

<210> SEQ ID NO 44
<211> LENGTH: 2646
<212> TYPE: DNA
<213> ORGANISM: Herpes simplex virus

<400> SEQUENCE: 44
atgtcgtact accatcacca tcaccatcac gaatacgact ccttcgacgc tttgttggct     60
gctagactgg aatctggtca aaccttggga cccgctggcg gtagagaggc ttctttgccc    120
gaggctcctc atgctttgta ccgtccaacc ggacaacatg ttgctgtgtt ggcggctgct    180
actcatagaa cccctgctgc tcgtgttact gctatggacc tggtcttggc ggccgttttg    240
ctgggcgctc ctgtggtggt cgctctgaga aacactactg ccttctcccg tgaatccgaa    300
ttggaactgt gcctcaccct gttcgattct cgtcccggcg gaccggatgc tgccctgaga    360
gatgtggtat cctccgacat tgaaacctgg gctgtgggct tgctccacac cgatttgaac    420
cctattgaga acgcttgctt ggcggctcaa ctgccacgct tgtctgccct cattgctgaa    480 cgtccttttgg ccgatggacc cccttgtttg tgttggtgg acatttcgat tgacacctgtc   540 gctgttttgt gggaggcccc tgaaccacct ggccctcccg atgttcgttt cgtcggtagc    600
gaggccactg aggaattgcc tttcgtggct actgctggtg atgttttggc ggcgagtgct    660
gccgatgccg atcctttctt cgctcgtgct atcctgggcc gtccttttcga tgcttctctg    720 ctcactggtg aactgttccc tggtcacccc gtttaccaac gtccctggc ggatgaggct    780 ggtccttctg ctcctactgc cgctcgtgat cctagagatc tggctggagg cgacggtgga    840
tccggacctg aggatcccgc tgctccacct gctagacagg ccgatcctgg tgttttggct    900
cctactctgc tcaccgatgc tactactggc gaacctgtgc caccccgtat gtgggcttgg    960
attcatggac tggaggaact ggcttccgat gatgccggcg gtcctacccc aaaccctgcc   1020
ccggctttgc tgccccctcc tgctacggat caatctgtcc ccacttccca atacgcccct   1080
agaccaattg gccggctgc cactgctaga gaaactcgtc cttccgttcc cctcaacaa    1140 aacactggtc gtgtccctgt ggctccacgt gatgaccta gacttcccc ccctactcct    1200 tcccccctg ccgatgctgc tttgccacct cctgccttct ctggttctgc tgctgctttc    1260
tccgctgctg ttccacgtgt tcgtcgttct aggcgtactc gtgccaaatc ccgtgcccct   1320
cgtgcttctg ccccacccga gggatggcgt cccccgcctt gcctgccc tgttgctcct    1380 gtggcggctt ctgctcgtcc ccccgatcaa cctcctactc ccgaatctgc tcccccggct    1440
tgggtttccg ctctgccatt gccacccgga cctgctagtg ctcgtggtgc tttccctgct   1500
ccaaccttgg cccctattcc cccaccccccc gctgagggag ctgttgttcc cggtggtgat   1560
```

| | |
|---|---|
| cgtagacgtg gtcgccgtca acaactgct ggaccatccc ctacaccgcc acgtggcccg | 1620 |
| gctgctggtc ctcctcgtcg cctcactagg cctgctgttg ctagtctgtc cgcttctttg | 1680 |
| aactctctgc cttcccccg tgatcctgcc gatcatgctg ctgccgtttc tgctgccgcc | 1740 |
| gctgccgtac caccttcacc tggactggct ccccaactt ctgctgtcca aacctctcct | 1800 |
| cctcccttgg cgcctggtcc tgttgcccca tctgaaccett tgtgtggctg ggttgtgcct | 1860 |
| ggaggccctg ttgctagacg tcccccaccc caatctccgg ctactaaacc ggctgctcgt | 1920 |
| acccgtatta gggctcgttc tgtgccccaa ccacccttgc cccaacctcc actgcctcaa | 1980 |
| cccccttgc ctcaaccccc tctccccaa ccacctctgc ctcaacctcc gctgccccaa | 2040 |
| cctcctttgc cccaacctcc tttgcccaa cctcctttgc cccaacctcc gctgccccaa | 2100 |
| cctccgctgc cacctgttac tcgtacactc actcccaat tcgtgactc tgtgcctaca | 2160 |
| cctgagtctc caactcacac aaacacccac ttgcccgtta gtgctgtgac ttcttgggct | 2220 |
| tcgtccctgg ctctccatgt ggattctgcc cctcccctg cttcattgct ccaaactctc | 2280 |
| cacatttcct ccgatgatga acactccgac gccgactcac tccgcttctc cgattccgat | 2340 |
| gacactgagg ctctcgatcc tttgcctcct gaacctcact tgccacctgc cgatgaaccc | 2400 |
| cccggacctc tggctgccga ccatctccaa tcacctcact cacaattcgg tcctttgccc | 2460 |
| gttcaagcga acgctgttct gtctcgtcgt tacgtgagat caactggccg ttctgccttg | 2520 |
| gctgtgctca ttagagcttg tcgccgtatc caacaacaac tccagcgtac taggagagca | 2580 |
| ctcttccaac gctcaaacgc cgtgctcaca tcactccacc atgtccgtat gctcttggga | 2640 |
| taatag | 2646 |

<210> SEQ ID NO 45
<211> LENGTH: 261
<212> TYPE: DNA
<213> ORGANISM: Herpes simplex virus

<400> SEQUENCE: 45

| | |
|---|---|
| atgtcttggg ctctgaaaac caccgacatg ttcctggact cttctcgttg cacccaccgt | 60 |
| acctacggtg acgtttgcgc tgaaatccac aaacgtgaac gtgaagaccg tgaagctgct | 120 |
| cgtaccgctg ttaccgaccc ggaactgccg ctgctgtgcc cgccggacgt tcgttctgac | 180 |
| ccggcttctc gtaacccgac ccagcagacc cgtggttgcg ctcgttctaa cgaacgtcag | 240 |
| gaccgtgttc tggctccgtg a | 261 |

<210> SEQ ID NO 46
<211> LENGTH: 993
<212> TYPE: DNA
<213> ORGANISM: Herpes simplex virus

<400> SEQUENCE: 46

| | |
|---|---|
| atgaagttcc tcgtgaacgt ggccctggtg ttcatggtgg tgtacatcag ctacatctac | 60 |
| gctaaccgtt ggggttccgg cgtgcccggt cccatcaacc cccccaactc cgacgtggtg | 120 |
| ttccccggtg gttcccccgt ggctcagtac tgctacgctt accccgtct ggacgaccct | 180 |
| ggtcccctgg gttctgctga cgctggtcgt caggacctgc ccgtcgtgt cgtgcgtcac | 240 |
| gagcccctgg gtcgtagctt cctgaccggt ggcctggtgc tgttggctcc ccctgtgcgc | 300 |
| ggtttcggtg ctcccaacgc tacctacgct gtcgtgtga cctactaccg tctgacccgt | 360 |
| gcttgccgta gcccatcct gctgcgtcag tacggtggtt gccgtggtgg agagccccca | 420 |
| tcccccaaga cctgcggttc ttacacctac acctaccagg gtggtggtcc ccctaccgt | 480 |

-continued

```
tacgctctgg tcaacgcttc cctgctggtg cccatctggg accgtgctgc tgagactttc    540
gagtaccaga tcgagctggg tggcgagctg cacgtgggtc tgctgtgggt ggaagtgggt    600
ggagagggtc ccggtcctac cgctcctcct caggctgctc gtgctgaggg tggtccttgc    660
gtgccacccg tgcctgctgg tcgtccttgg cgttccgtgc cccccgtgtg gtactccgct    720
cccaaccccg gtttccgcgg tctgcgtttc cgtgagcgtt gcctgcctcc ccagacccct    780
gctgctcctt ccgacctgcc tcgtgtggct ttcgctcccc agtccctgct cgtgggtatc    840
accggtcgta ccttcatccg tatggctcgt cccaccgagg acgtgggtgt cctgcctcct    900
cactgggctc caggtgctct ggacgacggt ccctacgctc ccttccccccc tcgtccccgt    960 ttccgtcgtc accaccacca tcaccactaa taa                                 993
```

<210> SEQ ID NO 47  
<211> LENGTH: 9  
<212> TYPE: PRT  
<213> ORGANISM: Herpes simplex virus

<400> SEQUENCE: 47

Gly Leu Ala His Val Ala Ala Ala Val  
1               5

<210> SEQ ID NO 48  
<211> LENGTH: 9  
<212> TYPE: PRT  
<213> ORGANISM: Herpes simplex virus

<400> SEQUENCE: 48

Phe Ile Ser Gly Ser Val Ala Arg Ala  
1               5

<210> SEQ ID NO 49  
<211> LENGTH: 9  
<212> TYPE: PRT  
<213> ORGANISM: Herpes simplex virus

<400> SEQUENCE: 49

Gln Tyr Ala Leu Ile Thr Arg Leu Leu  
1               5

<210> SEQ ID NO 50  
<211> LENGTH: 9  
<212> TYPE: PRT  
<213> ORGANISM: Herpes simplex virus

<400> SEQUENCE: 50

Arg Tyr Asp Arg Ala Gln Lys Gly Phe  
1               5

<210> SEQ ID NO 51  
<211> LENGTH: 9  
<212> TYPE: PRT  
<213> ORGANISM: Herpes simplex virus

<400> SEQUENCE: 51

Gly Tyr Ala Met Ala Ala Gly Arg Phe  
1               5

<210> SEQ ID NO 52  
<211> LENGTH: 9  
<212> TYPE: PRT  
<213> ORGANISM: Herpes simplex virus

<400> SEQUENCE: 52

Pro Pro His Ala Asp Ala Pro Arg Leu
1               5

<210> SEQ ID NO 53
<211> LENGTH: 9
<212> TYPE: PRT
<213> ORGANISM: Herpes simplex virus

<400> SEQUENCE: 53

Lys Pro Ala Ala Ala Ala Ala Pro Leu
1               5

<210> SEQ ID NO 54
<211> LENGTH: 8
<212> TYPE: PRT
<213> ORGANISM: Herpes simplex virus

<400> SEQUENCE: 54

Ser Glu Ala Ala Val Ala Ala Val
1               5

<210> SEQ ID NO 55
<211> LENGTH: 8
<212> TYPE: PRT
<213> ORGANISM: Herpes simplex virus

<400> SEQUENCE: 55

Phe Gly Trp Gly Leu Ala His Val
1               5

<210> SEQ ID NO 56
<211> LENGTH: 9
<212> TYPE: PRT
<213> ORGANISM: Herpes simplex virus

<400> SEQUENCE: 56

Tyr Ala Leu Ile Thr Arg Leu Leu Tyr
1               5

<210> SEQ ID NO 57
<211> LENGTH: 9
<212> TYPE: PRT
<213> ORGANISM: Herpes simplex virus

<400> SEQUENCE: 57

Ala Leu Pro Arg Ser Pro Arg Leu Leu
1               5

<210> SEQ ID NO 58
<211> LENGTH: 9
<212> TYPE: PRT
<213> ORGANISM: Herpes simplex virus

<400> SEQUENCE: 58

Asp Leu Leu Phe Gln Asn Gln Ser Leu
1               5

<210> SEQ ID NO 59
<211> LENGTH: 9
<212> TYPE: PRT
<213> ORGANISM: Herpes simplex virus

<400> SEQUENCE: 59

```
Ala Asp Leu Leu Phe Gln Asn Gln Ser
1               5

<210> SEQ ID NO 60
<211> LENGTH: 9
<212> TYPE: PRT
<213> ORGANISM: Herpes simplex virus

<400> SEQUENCE: 60

Ala Arg Asn Ser Ser Ser Phe Ile Ser
1               5

<210> SEQ ID NO 61
<211> LENGTH: 9
<212> TYPE: PRT
<213> ORGANISM: Herpes simplex virus

<400> SEQUENCE: 61

Gln Ala Cys Phe Arg Ile Ser Gly Ala
1               5

<210> SEQ ID NO 62
<211> LENGTH: 9
<212> TYPE: PRT
<213> ORGANISM: Herpes simplex virus

<400> SEQUENCE: 62

Phe Val Arg Asp Ala Leu Val Leu Met
1               5

<210> SEQ ID NO 63
<211> LENGTH: 9
<212> TYPE: PRT
<213> ORGANISM: Herpes simplex virus

<400> SEQUENCE: 63

Phe Asp Gly Asp Leu Ala Ala Val Pro
1               5

<210> SEQ ID NO 64
<211> LENGTH: 9
<212> TYPE: PRT
<213> ORGANISM: Herpes simplex virus

<400> SEQUENCE: 64

Gly Leu Gly Asp Ser Arg Pro Gly Leu
1               5

<210> SEQ ID NO 65
<211> LENGTH: 9
<212> TYPE: PRT
<213> ORGANISM: Herpes simplex virus

<400> SEQUENCE: 65

Trp Ala Pro Glu Leu Gly Asp Ala Ala
1               5

<210> SEQ ID NO 66
<211> LENGTH: 9
<212> TYPE: PRT
<213> ORGANISM: Herpes simplex virus

<400> SEQUENCE: 66

Glu Cys Leu Ala Ala Cys Arg Gly Ile
```

```
1               5

<210> SEQ ID NO 67
<211> LENGTH: 9
<212> TYPE: PRT
<213> ORGANISM: Herpes simplex virus

<400> SEQUENCE: 67

Arg Ala Trp Leu Arg Glu Leu Arg Phe
1               5

<210> SEQ ID NO 68
<211> LENGTH: 9
<212> TYPE: PRT
<213> ORGANISM: Herpes simplex virus

<400> SEQUENCE: 68

Ala Leu Ala Gly Ser Thr Leu Ala Val
1               5

<210> SEQ ID NO 69
<211> LENGTH: 9
<212> TYPE: PRT
<213> ORGANISM: Herpes simplex virus

<400> SEQUENCE: 69

Leu Leu Glu Asp Pro Ala Gly Thr Val
1               5

<210> SEQ ID NO 70
<211> LENGTH: 9
<212> TYPE: PRT
<213> ORGANISM: Herpes simplex virus

<400> SEQUENCE: 70

Val Ile Gly Gly Ile Ala Phe Trp Val
1               5

<210> SEQ ID NO 71
<211> LENGTH: 9
<212> TYPE: PRT
<213> ORGANISM: Herpes simplex virus

<400> SEQUENCE: 71

Thr Val Tyr Tyr Ala Val Leu Glu Arg
1               5

<210> SEQ ID NO 72
<211> LENGTH: 9
<212> TYPE: PRT
<213> ORGANISM: Herpes simplex virus

<400> SEQUENCE: 72

Lys Tyr Ala Leu Ala Asp Pro Ser Leu
1               5

<210> SEQ ID NO 73
<211> LENGTH: 9
<212> TYPE: PRT
<213> ORGANISM: Herpes simplex virus

<400> SEQUENCE: 73

Ala Phe Glu Thr Ala Gly Thr Tyr Leu
1               5
```

```
<210> SEQ ID NO 74
<211> LENGTH: 9
<212> TYPE: PRT
<213> ORGANISM: Herpes simplex virus

<400> SEQUENCE: 74

Ala Pro Ser Asn Pro Gly Leu Ile Ile
1               5

<210> SEQ ID NO 75
<211> LENGTH: 9
<212> TYPE: PRT
<213> ORGANISM: Herpes simplex virus

<400> SEQUENCE: 75

Ile Pro Ile Thr Val Tyr Tyr Ala Val
1               5

<210> SEQ ID NO 76
<211> LENGTH: 9
<212> TYPE: PRT
<213> ORGANISM: Herpes simplex virus

<400> SEQUENCE: 76

Ala Pro Pro Ser His Gln Pro Leu Phe
1               5

<210> SEQ ID NO 77
<211> LENGTH: 9
<212> TYPE: PRT
<213> ORGANISM: Herpes simplex virus

<400> SEQUENCE: 77

Phe Leu Met His Ala Pro Ala Phe Glu
1               5

<210> SEQ ID NO 78
<211> LENGTH: 9
<212> TYPE: PRT
<213> ORGANISM: Herpes simplex virus

<400> SEQUENCE: 78

Phe Ser Ala Val Ser Glu Asp Asn Leu
1               5

<210> SEQ ID NO 79
<211> LENGTH: 8
<212> TYPE: PRT
<213> ORGANISM: Herpes simplex virus

<400> SEQUENCE: 79

Val Tyr Tyr Ala Val Leu Glu Arg
1               5

<210> SEQ ID NO 80
<211> LENGTH: 8
<212> TYPE: PRT
<213> ORGANISM: Herpes simplex virus

<400> SEQUENCE: 80

Ile Gly Met Leu Pro Arg Phe Ile
1               5

<210> SEQ ID NO 81
```

```
<211> LENGTH: 9
<212> TYPE: PRT
<213> ORGANISM: Herpes simplex virus

<400> SEQUENCE: 81

Tyr Thr Glu Cys Pro Tyr Asn Lys Ser
1               5

<210> SEQ ID NO 82
<211> LENGTH: 9
<212> TYPE: PRT
<213> ORGANISM: Herpes simplex virus

<400> SEQUENCE: 82

Phe Leu Met His Ala Pro Ala Phe Glu
1               5

<210> SEQ ID NO 83
<211> LENGTH: 9
<212> TYPE: PRT
<213> ORGANISM: Herpes simplex virus

<400> SEQUENCE: 83

Asn Leu Gly Phe Leu Met His Ala Pro
1               5

<210> SEQ ID NO 84
<211> LENGTH: 9
<212> TYPE: PRT
<213> ORGANISM: Herpes simplex virus

<400> SEQUENCE: 84

Val Ile Gly Gly Ile Ala Phe Trp Val
1               5

<210> SEQ ID NO 85
<211> LENGTH: 9
<212> TYPE: PRT
<213> ORGANISM: Herpes simplex virus

<400> SEQUENCE: 85

Gly Ile Ala Phe Trp Val Arg Arg Arg
1               5

<210> SEQ ID NO 86
<211> LENGTH: 9
<212> TYPE: PRT
<213> ORGANISM: Herpes simplex virus

<400> SEQUENCE: 86

Ser Glu Asp Asn Leu Gly Phe Leu Met
1               5

<210> SEQ ID NO 87
<211> LENGTH: 9
<212> TYPE: PRT
<213> ORGANISM: Herpes simplex virus

<400> SEQUENCE: 87

Arg Thr Gln Pro Arg Trp Ser Tyr Tyr
1               5

<210> SEQ ID NO 88
<211> LENGTH: 9
<212> TYPE: PRT
```

-continued

<213> ORGANISM: Herpes simplex virus

<400> SEQUENCE: 88

Ile Ala Phe Trp Val Arg Arg Ala
1               5

<210> SEQ ID NO 89
<211> LENGTH: 9
<212> TYPE: PRT
<213> ORGANISM: Herpes simplex virus

<400> SEQUENCE: 89

Leu Val Ile Gly Gly Ile Ala Phe Trp
1               5

<210> SEQ ID NO 90
<211> LENGTH: 9
<212> TYPE: PRT
<213> ORGANISM: Herpes simplex virus

<400> SEQUENCE: 90

Phe Trp Val Arg Arg Arg Ala Gln Met
1               5

<210> SEQ ID NO 91
<211> LENGTH: 9
<212> TYPE: PRT
<213> ORGANISM: Herpes simplex virus

<400> SEQUENCE: 91

Pro Tyr Thr Ser Thr Leu Leu Pro Pro
1               5

<210> SEQ ID NO 92
<211> LENGTH: 9
<212> TYPE: PRT
<213> ORGANISM: Herpes simplex virus

<400> SEQUENCE: 92

Val Gly Thr Ala Ala Leu Leu Val Val
1               5

<210> SEQ ID NO 93
<211> LENGTH: 9
<212> TYPE: PRT
<213> ORGANISM: Herpes simplex virus

<400> SEQUENCE: 93

Thr Ala Ala Leu Leu Val Val Ala Val
1               5

<210> SEQ ID NO 94
<211> LENGTH: 9
<212> TYPE: PRT
<213> ORGANISM: Herpes simplex virus

<400> SEQUENCE: 94

Thr Ser Thr Leu Leu Pro Pro Glu Leu
1               5

<210> SEQ ID NO 95
<211> LENGTH: 9
<212> TYPE: PRT
<213> ORGANISM: Herpes simplex virus

<400> SEQUENCE: 95

Gly Thr Val Ser Ser Gln Ile Pro Pro
1               5

<210> SEQ ID NO 96
<211> LENGTH: 9
<212> TYPE: PRT
<213> ORGANISM: Herpes simplex virus

<400> SEQUENCE: 96

Thr Ala Gly Thr Tyr Leu Arg Leu Val
1               5

<210> SEQ ID NO 97
<211> LENGTH: 9
<212> TYPE: PRT
<213> ORGANISM: Herpes simplex virus

<400> SEQUENCE: 97

Gly Val Thr Val Asp Ser Ile Gly Met
1               5

<210> SEQ ID NO 98
<211> LENGTH: 9
<212> TYPE: PRT
<213> ORGANISM: Herpes simplex virus

<400> SEQUENCE: 98

Ala Phe Trp Val Arg Arg Arg Ala Gln
1               5

<210> SEQ ID NO 99
<211> LENGTH: 9
<212> TYPE: PRT
<213> ORGANISM: Herpes simplex virus

<400> SEQUENCE: 99

Arg Val Tyr His Ile Gln Pro Ser Leu
1               5

<210> SEQ ID NO 100
<211> LENGTH: 9
<212> TYPE: PRT
<213> ORGANISM: Herpes simplex virus

<400> SEQUENCE: 100

Ala Tyr Leu Val Asn Pro Phe Leu Phe
1               5

<210> SEQ ID NO 101
<211> LENGTH: 9
<212> TYPE: PRT
<213> ORGANISM: Herpes simplex virus

<400> SEQUENCE: 101

Pro Phe Leu Phe Ala Ala Gly Phe Leu
1               5

<210> SEQ ID NO 102
<211> LENGTH: 9
<212> TYPE: PRT
<213> ORGANISM: Herpes simplex virus

<400> SEQUENCE: 102

```
Thr Glu Tyr Val Leu Arg Ser Val Ile
1               5

<210> SEQ ID NO 103
<211> LENGTH: 9
<212> TYPE: PRT
<213> ORGANISM: Herpes simplex virus

<400> SEQUENCE: 103

Gly Ser Gln Ala Thr Glu Tyr Val Leu
1               5

<210> SEQ ID NO 104
<211> LENGTH: 9
<212> TYPE: PRT
<213> ORGANISM: Herpes simplex virus

<400> SEQUENCE: 104

Arg Ile Asp Gly Ile Phe Leu Arg Tyr
1               5

<210> SEQ ID NO 105
<211> LENGTH: 9
<212> TYPE: PRT
<213> ORGANISM: Herpes simplex virus

<400> SEQUENCE: 105

Phe Leu Glu Asp Leu Ser His Ser Val
1               5

<210> SEQ ID NO 106
<211> LENGTH: 9
<212> TYPE: PRT
<213> ORGANISM: Herpes simplex virus

<400> SEQUENCE: 106

Tyr Val Leu Arg Ser Val Ile Ala Lys
1               5

<210> SEQ ID NO 107
<211> LENGTH: 9
<212> TYPE: PRT
<213> ORGANISM: Herpes simplex virus

<400> SEQUENCE: 107

Tyr Val Leu Arg Ser Val Ile Ala Lys
1               5

<210> SEQ ID NO 108
<211> LENGTH: 9
<212> TYPE: PRT
<213> ORGANISM: Herpes simplex virus

<400> SEQUENCE: 108

Ala Tyr Leu Val Asn Pro Phe Leu Phe
1               5

<210> SEQ ID NO 109
<211> LENGTH: 9
<212> TYPE: PRT
<213> ORGANISM: Herpes simplex virus

<400> SEQUENCE: 109

Glu Thr Thr Thr Arg Arg Ala Leu Tyr
1               5
```

<210> SEQ ID NO 110
<211> LENGTH: 9
<212> TYPE: PRT
<213> ORGANISM: Herpes simplex virus

<400> SEQUENCE: 110

Arg Ile Asp Gly Ile Phe Leu Arg Tyr
1               5

<210> SEQ ID NO 111
<211> LENGTH: 9
<212> TYPE: PRT
<213> ORGANISM: Herpes simplex virus

<400> SEQUENCE: 111

Tyr Leu Val Asn Pro Phe Leu Phe Ala
1               5

<210> SEQ ID NO 112
<211> LENGTH: 9
<212> TYPE: PRT
<213> ORGANISM: Herpes simplex virus

<400> SEQUENCE: 112

Phe Val Cys Leu Phe Gly Leu Val Val
1               5

<210> SEQ ID NO 113
<211> LENGTH: 9
<212> TYPE: PRT
<213> ORGANISM: Herpes simplex virus

<400> SEQUENCE: 113

Leu Tyr Lys Glu Ile Arg Asp Ala Leu
1               5

<210> SEQ ID NO 114
<211> LENGTH: 9
<212> TYPE: PRT
<213> ORGANISM: Herpes simplex virus

<400> SEQUENCE: 114

Gly Leu Asp Thr Phe Leu Trp Asp Arg
1               5

<210> SEQ ID NO 115
<211> LENGTH: 9
<212> TYPE: PRT
<213> ORGANISM: Herpes simplex virus

<400> SEQUENCE: 115

Arg Val Ser Pro Thr Arg Gly Arg Arg
1               5

<210> SEQ ID NO 116
<211> LENGTH: 9
<212> TYPE: PRT
<213> ORGANISM: Herpes simplex virus

<400> SEQUENCE: 116

Gly Leu Asp Thr Phe Leu Trp Asp Arg
1               5

<210> SEQ ID NO 117
<211> LENGTH: 1221
<212> TYPE: DNA
<213> ORGANISM: Herpes simplex virus

<400> SEQUENCE: 117

```
atgtcgtact accatcacca tcaccatcac atggtgctgt acggcgggct gggcgacagc      60
cgccccggcc tctgggggggc gcccgaggcg gaggaggcgc gggcccggtt cgaggcctcg     120
ggcgccccgg cgcccgtgtg ggcgcccgag ctgggcgacg cggcgcagca gtacgccctg     180
atcacgcggc tgctgtacac gccggacgcg gaggcgatgg ggtggctcca gaacccgcgc     240
gtggcgcccg ggacgtggc gctggaccag gcctgcttcc ggatctcggg cgcggcgcgc      300
aacagcagct ccttcatctc cggcagcgtg gcgcgggccg tgccccacct ggggtacgcc     360
atggcggcgg ccgcttcgg ctggggcctg gcgcacgtgg cggccgccgt ggccatgagc      420
cgccgctacg accgcgcgca gagggcttc ctgctgacca gcctgcgccg cgcctacgcg      480
cccctgctgg cgcgcgagaa cgcggcgctg accggggcgc ggaccccga cgacggcggc     540
gacgccaacc gccgcgacgg cgacgacgcc cgcgggaagc ccgccgccgc cgccgccccg     600
ttgccgtcgg cggcggcgtc gccggccgac gagcgcgcgg tgcccgccgg ctacggcgcc     660
gcggggggtgc tcgccgccct ggggcgcctg agcgccgcgc ccgcctccgc gccggccggg    720
gccgacgacg acgacgacga cgacgacggc gccggcggtg gtggcggtgg tggcggtggt    780
ggcggcggcc ggcgcgcgga ggcgggccgc gtggccgtgg agtgcctggc cgcctgccgc    840
gggatcctgg aggcgctggc ggagggcttc gacggcgacc tggcggccgt gccggggctg    900
gccggagccc ggcccgccgc gccccgcgc ccgggggccg cgggcgcggc cgccccgccg    960
cacgccgacg cgccccgcct gcgcgcctgg ctgcgcgagc tgcggttcgt gcgcgacgcg   1020
ctggtgctga tgcgcctgcg cggggacctg cgcgtggccg gcggcagcga ggccgccgtg   1080
gccgccgtgc gcgccgtgag cctggtcgcc ggggccctgg gccgcgcgt gccgcggagc   1140
ccgcgcctgc tgagctccgc cgccgccgcc gccgcggacc tgctcttcca gaaccagagc   1200
ctgagtacta gaggatcata a                                              1221
```

<210> SEQ ID NO 118
<211> LENGTH: 705
<212> TYPE: DNA
<213> ORGANISM: Herpes simplex virus

<400> SEQUENCE: 118

```
atgtcgtact accatcacca tcaccatcac atggggttcg tctgtctgtt tgggcttgtc      60
gttatgggag cctggggggc gtgggtggg tcacaggcaa ccgaatatgt tcttcgtagt      120
gttattgcca aagaggtggg ggacatacta agagtgcctt gcatgcggac ccccgcggac     180
gatgtttctt ggcgctacga ggccccgtcc gttattgact atgcccgcat agacggaata     240
tttcttcgct atcactgccc ggggttggac acgttttttgt gggataggca cgcccagagg     300
gcgtatcttg ttaacccctt tctctttgcg gcgggatttt tggaggactt gagtcactct     360
gtgtttccgg ccgacaccca ggaaacaacg acgcgccggg cccttttataa agagatacgc     420
gatgcgttgg gcagtcgaaa acaggccgtc agccacgcac ccgtcagggc cggtgtgta      480
aactttgact actcacgcac tcgccgctgc gtcgggcgac gcgatttacg gcctgccaac     540
accacgtcaa cgtgggaacc gcctgtgtcg tcggacgatg aagcgagctc gcagtcgaag     600
cccctcgcca cccagccgcc cgtcctcgcc ctttcgaacg cccccccacg gcgggtctcc     660
```

```
ccgacgcgag gtcggcgccg gcatactcgc ctccgacgca actga                 705

<210> SEQ ID NO 119
<211> LENGTH: 762
<212> TYPE: DNA
<213> ORGANISM: Herpes simplex virus

<400> SEQUENCE: 119
atgaagttcc tcgtgaacgt ggccctggtg ttcatggtgg tgtacatcag ctacatctac   60
gccaaccgtt gggggttcgt ctgtctgttt gggcttgtcg ttatgggagc ctgggggggcg  120 tgggggtgggt cacaggcaac cgaatatgtt cttcgtagtg ttattgccaa agaggtgggg  180
gacatactaa gagtgccttg catgcggacc cccgcgacg atgtttcttg gcgctacgag   240
gccccgtccg ttattgacta tgcccgcata gacggaatat tcttcgcta tcactgcccg   300 gggttggaca cgttttttgtg ggataggcac gcccagaggg cgtatcttgt taaccccttt   360
ctctttgcgg cgggattttt ggaggacttg agtcactctg tgtttccggc cgacacccag  420
gaaacaacga cgcgccgggc cctttataaa gagatacgcg atgcgttggg cagtcgaaaa  480
caggccgtca gccacgcacc cgtcagggcc gggtgtgtaa actttgacta ctcacgcact  540
cgccgctgcg tcgggcgacg cgatttacgg cctgccaaca ccacgtcaac gtgggaaccg  600
cctgtgtcgt cggacgatga agcgagctcg cagtcgaagc ccctcgccac ccagccgccc  660
gtcctcgccc tttcgaacgc ccccccacg cgggtctccc cgacgcgagg tcggcgccgg  720
catactcgcc tccgacgcaa ccatcaccat caccatcact ga                    762

<210> SEQ ID NO 120
<211> LENGTH: 4155
<212> TYPE: DNA
<213> ORGANISM: Herpes simplex virus

<400> SEQUENCE: 120
atgtcgtact accatcacca tcaccatcac atggccgctc ctgcccgcga ccccccgggt   60
taccggtacg ccgcggccat ggtgcccacc ggctccatcc tgagtacgat cgaggtggcg  120
tcccaccgca gactctttga ttttttcgcc cgcgtgcgct ccgacgaaaa cagcctgtat  180
gacgtagagt ttgacgcccct gctggggtcc tactgcaaca ccctgtcgct cgtgcgcttt  240
ctggagctcg gcctgtccgt ggcgtgcgtg tgcaccaagt tcccggagct ggcttacatg  300
aacgaagggc gtgtgcagtt cgaggtccac cagcccctca tcgcccgcga cggcccgcac  360
cccgtcgagc agcccgtgca taattacatg acgaaggtca tcgaccgccg ggccctgaac  420
gccgccttca gcctggccac cgaggccatt gccctgctca cgggggaggc cctggacggg  480
acgggcatta gcctgcatcg ccagctgcgc gccatccagc agctcgcgcg caacgtccag  540
gccgtcctgg ggcgtttga gcgcggcacg gccgaccaga tgctgcacgt gctgttggag  600
aaggcgcctc ccctgcccct gctgttgccc atgcaacgat atctcgacaa cgggcgcctg  660
gcgaccaggg ttgcccgggc gaccctggtc gccgagctga gcggagctt ttgcgacacg  720 agcttcttcc tgggcaaggc gggccatcgc cgcgaggcca tcgaggcctg gtcgtggac   780 ctgaccacgg cgacgcagcc gtccgtggcc gtgccccgcc tgacgcacgc cgacacgcgc  840
gggcggccgg tcgacggggt gctggtcacc accgccgcca tcaaacagcg cctcctgcag  900
tccttcctga aggtggagga caccgaggcc gacgtgccgg tgacctacgg cgagatggtc  960
ttgaacgggg ccaacctcgt cacggcgctg gtgatgggca aggccgtgcg gagcctggac 1020 gacgtggggcc gccacctgct ggagatgcag gaggagcaac tcgaggcgaa ccgggagacg 1080
```

```
ctggatgaac tcgaaagcgc cccccagaca acgcgcgtgc gcgcggatct ggtggccata    1140
ggcgacaggc tggtcttcct ggaggccctg gagaagcgca tctacgccgc caccaacgtg    1200
ccctacccccc tggtgggcgc catggacctg acgttcgtcc tgcccctggg gctgttcaac    1260
ccggccatgg agcgcttcgc cgcgcacgcc ggggacctgg tgcccgcccc cggccacccg    1320
gagccccgcg cgttccctcc ccggcagctg ttttttggg gaaaggacca ccaggttctg     1380
cggctgtcca tggagaacgc ggtcgggacc gtgtgtcatc cttcgctcat gaacatcgac    1440
gcggccgtcg ggggcgtgaa ccacgacccc gtcgaggccg cgaatccgta cggggcgtac    1500
gtcgcggccc cggccggccc cggcgcggac atgcagcagc gttttctgaa cgcctggcgg    1560
cagcgcctcg cccacggccg ggtccggtgg gtcgccgagt gccagatgac cgcggagcag    1620
ttcatgcagc ccgacaacgc caacctggct ctggagctgc accccgcgtt cgacttcttc    1680
gcgggcgtgg ccgacgtcga gcttcccggc ggcgaagtcc ccccggccgg tccgggggcg    1740
atccaggcca cctggcgcgt ggtcaacggc aacctgcccc tggcgctgtg tccggtggcg    1800
tttcgtgacg cccgggggcct ggagctcggc gttggccgcc acgccatggc gccggctacc    1860
atagccgccg tccgcggggc gttcgaggac cgcagctacc cggcggtgtt ctacctgctg    1920
caagccgcga ttcacggcag cgagcacgtg ttctgcgccc tggcgcggct cgtgactcag    1980
tgcatcacca gctactggaa caacacgcga tgcgcggcgt tcgtgaacga ctactcgctg    2040
gtctcgtaca tcgtgaccta cctcgggggc gacctccccg aggagtgcat ggccgtgtat    2100
cgggacctgg tggcccacgt cgaggccctg gcccagctgg tggacgactt tacccctgccg    2160
ggcccggagc tgggcgggca ggctcaggcc gagctgaatc acctgatgcg cgaccgggcg    2220
ctgctgccgc cctcgtgtgt ggactgcgac ggccttatgc gacacgcggc cctggaccgc    2280
caccgagact gccggattga cgcggggag cacgagcccg tctacgcggc ggcgtgcaac    2340
gtggcgacgg ccgactttaa ccgcaacgac ggccggctgc tgcacaacac ccaggccccgc    2400
gcggccgacg ccgccgacga ccggccgcac cggccggccg actggaccgt ccaccacaaa    2460
atctactatt acgtgctggt gccggccttc tcgcggggc gctgctgcac cgcggggtc     2520
cgcttcgacc gcgtgtacgc cacgctgcag aacatggtgg tcccggagat cgcccccggc    2580
gaggagtgcc cgagcgatcc cgtgaccgac cccgcccacc cgctgcatcc cgccaatctg    2640
gtggccaaca cggtcaacgc catgttccac aacgggcgc tcgtcgtcga cgggcccgcc    2700
atgctcacgc tgcaggtgct ggcgcacaac atggccgagc gcacgacggc gctgctgtgc    2760
tccgcggcgc ccgacgcggg cgccaacacc gcgtcgacgg ccaacatgcg catcttcgac    2820
ggggcgctgc acgccggcgt gctgctcatg gcccccagc acctggacca caccatccaa    2880
aatggcgaat acttctacgt cctgcccgtc cacgcgctgt tgcgggcgc cgaccacgtg    2940
gccaacgcgc ccaacttccc cccggccctg cgcgacctgg cgcgccacgt cccccctggtc   3000
cccccggccc tggggccaa ctacttctcc tccatccgcc agcccgtggt gcagcacgcc    3060
cgcgagagcg cggcgggga aacgcgctg acctacgcgc tcatggcggg gtacttcaag    3120
atgagccccg tggccctgta tcaccagctc aagacgggcc tccacccccgg gttcgggttc    3180
accgtcgtgc ggcaggaccg cttcgtgacc gagaacgtg tgttttccga gcgcgcgtcg    3240
gaggcgtact ttctgggcca gctccaggtg gcccgccacg aaacgggcgg ggggtcagc    3300
ttcacgctca cccagccgcg cggaaacgtg gacctgggtg tgggctacac cgccgtcgcg    3360
gccacggcca ccgtccgcaa cccccgttacg gacatgggca acctcccccca aaacttttac   3420
```

-continued

| | |
|---|---|
| ctcggccgcg gggcccccc gctgctagac aacgcggccg ccgtgtacct gcgcaacgcg | 3480 |
| gtcgtggcgg gaaaccggct ggggccggcc cagcccctcc cggtctttgg ctgcgcccag | 3540 |
| gtgccgcggc gcgccggcat ggaccacggg caggatgccg tgtgtgagtt catcgccacc | 3600 |
| cccgtggcca cggacatcaa ctactttcgc cggccctgca cccgcgggg acgcgcggcc | 3660 |
| ggcggcgtgt acgcggggga caaggagggg gacgtcatag ccctcatgta cgaccacggc | 3720 |
| cagagcgacc cggcgcggcc cttcgcggcc acggccaacc cgtgggcgtc gcagcggttc | 3780 |
| tcgtacgggg acctgctgta caacggggcc tatcacctca cggggcctc gcccgtcctc | 3840 |
| agccctgct tcaagttctt caccgcggcc gacatcacgg ccaaacatcg ctgcctggag | 3900 |
| cgtcttatcg tggaaacggg atcggcggta ccacggcca ccgctgccag cgacgtgcag | 3960 |
| tttaagcgcc cgccggggtg ccgcgagctc gtggaagacc cgtgcggcct gtttcaggaa | 4020 |
| gcctacccga tcacctgcgc cagcgacccc gccctgctac gcagcgcccg cgatggggag | 4080 |
| gcccacgcgc gagagaccca ctttacgcag tatctcatct acgacgcctc cccgctaaag | 4140 |
| ggcctgtctc tgtaa | 4155 |

<210> SEQ ID NO 121
<211> LENGTH: 1200
<212> TYPE: DNA
<213> ORGANISM: Herpes simplex virus

<400> SEQUENCE: 121

| | |
|---|---|
| atgagtgccg aacagcgtaa aaagaaaaaa accaccacca cgacccaagg acgtggagct | 60 |
| gaagttgcta tggcggatga ggatggaggc cgcttgagag ctgctgctga gactactgga | 120 |
| ggacctggat caccggaccc tgccgatgga cccccccta caccaaaccc cgatcgtaga | 180 |
| ccggctgcta gacctggatt cggatggcat ggaggaccg aggaaaacga ggacgaggcg | 240 |
| gacgacgccg ctgccgacgc cgacgccgat gaggctgccc ctgcttctgg agaggcggta | 300 |
| gacgaacctg ctgccgatgg agttgttagc cctaggcaat tggctttgtt ggcgagcatg | 360 |
| gtagacgagg ctgtgagaac aatcccttcc cctccccctg aacgtgatgg agcacaagag | 420 |
| gaggcggcta ggagtccctc accaccccgt acaccttcta tgagagcgga ttacggcgag | 480 |
| gaaaacgacg acgacgacga tgatgatgac gacgatgatc gtgatgccgg acgctgggtt | 540 |
| aggggacctg aaaccacttc tgctgtccgt ggagcatacc ccgatcctat ggcgagtttg | 600 |
| agccctagac cacctgcccc gaggagacac caccaccacc accatcatag gcgtagacgt | 660 |
| gctcctagac gtcgttctgc cgctagtgac tcttccaaat ctggctcttc ttcatctgcc | 720 |
| tcttccgctt catcttcggc ctcatcgtcc tcttcggcat ccgcttcgag tagtgatgat | 780 |
| gatgatgacg acgacgctgc tagagccccc gcttctgctg ccgaccacgc tgctggcgga | 840 |
| actttgggag ccgacgacga ggaggcggga gttcctgctc gtgccccggg agctgctccg | 900 |
| aggccttctc caccccgtgc tgaacctgct ccggctagaa caccggccgc tactgctggt | 960 |
| agactggagc gtagacgtgc ccgtgctgct gtggctggta gagatgctac tggccgcttc | 1020 |
| actgctggcc gtcctagacg tgttgaactg gacgccgatg ctgcttctgg tgctttctac | 1080 |
| gcccgttacc gtgatggtta cgtgtctggt gaacttggc ctggcgctgg tccacctccg | 1140 |
| cccggacgtg tactctacgg tggattgggc gattctcgcc ctggtctgtg gggcgctccg | 1200 |

<210> SEQ ID NO 122
<211> LENGTH: 825
<212> TYPE: DNA
<213> ORGANISM: Herpes simplex virus

<400> SEQUENCE: 122

```
tcgagtgccg ccgctgctgc cgccgatttg ttgttccaaa accaatccct ccgccctctg      60
ctcgccgaca ctgttgccgc tgccgattct ctggctgctc cggcttctgc cccacgtgaa     120
gctcgtaaac gtaaatcacc cgctccggct cgtgctcccc ctggtggcgc cctagaccc     180
cctaaaaaat cccgtgccga tgcccctaga cctgctgctg ctcccccgc tggtgctgct     240
cccccgctc ccctactcc ccccccacgc ccacctcgtc ccgctgccct cacacgccgt     300
cctgctgagg gacccgatcc acaaggcggc tggcgtagac aacctcctgg cccatcccat     360
acaccggcac catctgccgc tgctttggag gcttactgtg ctcctcgtgc tgtggctgaa     420
ctcaccgatc atccgctgtt ccctgctccc tggcgtcccg ccctcatgtt cgatcctaga     480
gctttggctt ccttggccgc tcgttgtgct gcccctcccc ctggcggtgc tccggctgct     540
ttcggtcctc tccgtgcctc tggtccactc cgccgtgccg ctgcctggat gagacaagtt     600
cccgaccctg aggatgttag agttgtgatc ttgtactcgc ccttgcctgg cgaggatttg     660
gccgctggta gagctggcgg tggccccct cctgaatggt ctgctgaacg tggtggtttg     720
tcttgcttgt tggccgccct gggaaaccgt ctgtgtggtc ctgctactgc tgcttgggct     780
ggaaactgga ctggcgctcc cgatgtttct gctctcggtg ctcaa                    825
```

<210> SEQ ID NO 123
<211> LENGTH: 933
<212> TYPE: DNA
<213> ORGANISM: Herpes simplex virus

<400> SEQUENCE: 123

```
tgggctggaa actggactgg cgctcccgat gtttctgctc tcggtgctca aggagttttg      60
ctgctctcta ctcgtgactt ggcattcgct ggagctgttg aattcctggg actcttggct     120
ggcgcttgtg ataggagact catcgtcgta aacgctgtga gagctgccga ttggcctgcc     180
gatggtcctg ttgtgtctcg tcaacacgct tacttggctt gtgaagtgtt gcccgctgtc     240
caatgtgctg ttcgctggcc tgctgctcgt gatctgaggc gtactgttct ggctagtggt     300
cgtgttttcg gacctggtgt tttcgctcgt gtcgaagctg ctcacgctag actgtacccc     360
gatgccccac ccctccgttt gtgtcgtgga gcaaacgttc gctaccgtgt ccgtactcgt     420
ttcggacccg atactctggt tccaatgtcc cctcgtgaat accgtcgtgc tgttctgcct     480
gccctcgatg gacgtgctgc cgcttctggc gctggtgacg ctatggctcc tggcgctccg     540
gacttctgtg aggatgaggc tcactcacat cgtgcctgtg cccgctgggg actgggcgct     600
ccattgaggc ctgtatacgt ggcactgggc cgtgatgctg ttagaggcgg acccgctgaa     660
ttgagaggcc ctcgtcgtga attctgtgct agggctctgc tcgaacccga tggagatgct     720
cctcctttgg tactccgtga cgacgccgat gctggtcctc ccccacaaat tcgctgggct     780
agtgctgctg gacgtgctgg tactgtattg gctgctgctg gcggtggcgt tgaagttgtt     840
ggtactgccg ctggactcgc tacacctccc cgccgtgaac ctgtagacat ggatgctgaa     900
ctcgaggatg atgacgacgg attgttcgga gag                                 933
```

<210> SEQ ID NO 124
<211> LENGTH: 1707
<212> TYPE: DNA
<213> ORGANISM: Herpes simplex virus

<400> SEQUENCE: 124

| | |
|---|---:|
| tcgagtgccg ccgctgctgc cgccgatttg ttgttccaaa accaatccct ccgccctctg | 60 |
| ctcgccgaca ctgttgccgc tgccgattct ctggctgctc cggcttctgc cccacgtgaa | 120 |
| gctcgtaaac gtaaatcacc cgctccggct cgtgctcccc ctggtggcgc ccctagaccc | 180 |
| cctaaaaaat cccgtgccga tgcccctaga cctgctgctg ctcccccgc tggtgctgct | 240 |
| cccccgctc cccctactcc ccccacgc ccacctcgtc ccgctgccct cacacgccgt | 300 |
| cctgctgagg gacccgatcc acaaggcggc tggcgtagac aacctcctgg cccatcccat | 360 |
| acaccggcac catctgccgc tgctttggag gcttactgtg ctcctcgtgc tgtggctgaa | 420 |
| ctcaccgatc atccgctgtt ccctgctccc tggcgtcccg ccctcatgtt cgatcctaga | 480 |
| gctttggctt ccttggccgc tcgttgtgct gcccctcccc ctggcggtgc tccggctgct | 540 |
| ttcggtcctc tccgtgcctc tggtccactc cgccgtgccg ctgcctggat gagacaagtt | 600 |
| cccgaccctg aggatgttag agttgtgatc ttgtactcgc ccttgcctgg cgaggatttg | 660 |
| gccgctggta gagctggcgg tggcccccct cctgaatggt ctgctgaacg tggtggtttg | 720 |
| tcttgcttgt tggccgccct gggaaaccgt ctgtgtggtc ctgctactgc tgcttgggct | 780 |
| ggaaactgga ctggcgctcc cgatgttct gctctcggtg ctcaaggagt tttgctgctc | 840 |
| tctactcgtg acttggcatt cgctggagct gttgaattcc tgggactctt ggctggcgct | 900 |
| tgtgatagga gactcatcgt cgtaaacgct gtgagagctg ccgattggcc tgccgatggt | 960 |
| cctgttgtgt ctcgtcaaca cgcttacttg gcttgtgaag tgttgcccgc tgtccaatgt | 1020 |
| gctgttcgct ggcctgctgc tcgtgatctg aggcgtactg ttctggctag tggtcgtgtt | 1080 |
| ttcggacctg gtgttttcgc tcgtgtcgaa gctgctcacg ctagactgta ccccgatgcc | 1140 |
| ccacccctcc gtttgtgtcg tggagcaaac gttcgctacc gtgtccgtac tcgtttcgga | 1200 |
| cccgatactc tggttccaat gtcccctcgt gaataccgtc gtgctgttct gcctgccctc | 1260 |
| gatggacgtg ctgccgcttc tggcgctggt gacgctatgg ctcctggcgc tccggacttc | 1320 |
| tgtgaggatg aggctcactc acatcgtgcc tgtgcccgct ggggactggg cgctccattg | 1380 |
| aggcctgtat acgtggcact gggccgtgat gctgttagag gcggaccccgc tgaattgaga | 1440 |
| ggccctcgtc gtgaattctg tgctagggct ctgctcgaac ccgatggaga tgctcctcct | 1500 |
| ttggtactcc gtgacgacgc cgatgctggt cctcccccac aaaattcgctg gctagtgct | 1560 |
| gctgacgtg ctggtactgt attggctgct gctggcggtg gcgttgaagt tgttggtact | 1620 |
| gccgctggac tcgctacacc tccccgccgt gaacctgtag acatggatgc tgaactcgag | 1680 |
| gatgatgacg acggattgtt cggagag | 1707 |

<210> SEQ ID NO 125
<211> LENGTH: 1629
<212> TYPE: DNA
<213> ORGANISM: Herpes simplex virus

<400> SEQUENCE: 125

| | |
|---|---:|
| actgctggcc gtcctagacg tgttgaactg gacgccgatg ctgcttctgg tgctttctac | 60 |
| gcccgttacc gtgatggtta cgtgtctggt gaaccttggc ctggcgctgg tccacctccg | 120 |
| cccgacgtg tactctacgg tggattgggc gattctcgcc ctggtctgtg gggcgctccg | 180 |
| gaggctgagg aggctagagc ccgtttcgag gcttctggtg cccctgctcc tgtttgggct | 240 |
| cctgaattgg gcgacgctgc tcaacaatac gccctcatca cacgcttgct gtacactccc | 300 |
| gacgccgagg ctatgggatg gctccaaaac cctagagttg cccctggtga tgttgctctg | 360 |
| gatcaggctt gtttccgtat ctccggcgct gctcgtaact cttcttcgtt catctccggt | 420 |

```
tctgtggcta gagctgtgcc tcacttggga tacgccatgg ccgctggacg tttcggctgg     480
ggactggctc atgttgctgc cgctgtagca atgtctagac gctacgaccg tgctcaaaaa     540
ggattcttgc tcacgtcact gaggcgtgct tacgcccctt tgttggcccg tgaaaacgct     600
gccctcactg gcgcccgtac ccccgatgac ggtggcgacg ccaaccgcca cgatggtgat     660
gatgctagag gcaaacccgc tgccgctgct gctcctttgc cctctgccgc cgcttcccct     720
gccgatgaac gtgctgttcc tgccggttac ggtgccgctg gtgtgttggc tgctttggga     780
cgcttgagtg ctgccccggc tagtgccccc gctggtgccg atgacgatga cgatgacgat     840
ggtgctggcg gaggcggtgg cggtagacgt gctgaggctg gacgtgttgc tgttgaatgc     900
ctggctgcct gtagaggaat cttggaggct ctggccgagg gattcgacgg agacttggcg     960
gctgtaccgg gactggcggg agcgaggcct gccgctccac ctcgccccgg tcctgctggt    1020
gctgccgctc ctcctcatgc cgacgctcct agactccgtg cttggctccg tgaactccgt    1080
ttcgttcgtg acgctttggt tctgatgaga ctgagaggcg acttgagagt ggctggagga    1140
tccgaggctg ctgttgctgc tgtccgtgct gtttctttgg ttgctggtgc tttgggccct    1200
gctttgccga gatctccccg tttgttgtcg agtgccgccg ctgctgccgc cgatttgttg    1260
ttccaaaacc aatccctccg ccctctgctc gccgacactg ttgccgctgc cgattctctg    1320
gctgctccgg cttctgcccc acgtgaagct cgtaaacgta aatcacccgc tccggctcgt    1380 gctcccctg gtggcgcccc tagacccct aaaaaatccc gtgccgatgc ccctagacct    1440
gctgctgctc ccccgctgg tgctgctccc ccgctcccc ctactccccc cccacgccca    1500
cctcgtcccg ctgccctcac acgccgtcct gctgagggac ccgatccaca aggcggctgg    1560
cgtagacaac ctcctggccc atcccataca ccggcaccat ctgccgctgc tttggaggct    1620
tactgtgct                                                            1629
```

<210> SEQ ID NO 126
<211> LENGTH: 1632
<212> TYPE: DNA
<213> ORGANISM: Herpes simplex virus

<400> SEQUENCE: 126

```
gccgctgccg attctctggc tgctccggct tctgccccac gtgaagctcg taaacgtaaa      60
tcacccgctc cggctcgtgc tccccctggt ggcgccccta gaccccctaa aaatcccgt     120 gccgatgccc ctagacctgc tgctgctccc ccgctggtg ctgctccccc cgctccccct     180
actccccccc cacgcccacc tcgtcccgct gccctcacac gccgtcctgc tgagggaccc     240
gatccacaag gcggctggcg tagacaacct cctggcccat ccatacacc ggcaccatct     300 gccgctgctt tggaggctta ctgtgctcct cgtgctgtgg ctgaactcac cgatcatccg     360
ctgttccctg ctccctggcg tcccgccctc atgttcgatc ctagagcttt ggcttccttg     420
gccgctcgtt gtgctgcccc tccccctggc ggtgctccgg ctgctttcgg tcctctccgt     480
gcctctggtc cactccgccg tgccgctgcc tgatgagac aagttcccga ccctgaggat     540
gttagagttg tgatcttgta ctcgcccttg cctggcgagg atttggccgc tggtagagct     600
ggcggtggcc cccctcctga atggtctgct gaacgtggtg gtttgtcttg cttgttggcc     660
gccctgggaa accgtctgtg tggtcctgct actgctgctt gggctggaaa ctggactggc     720
gctcccgatg tttctgctct cggtgctcaa ggagttttgc tgctctctac tcgtgacttg     780
gcattcgctg gagctgttga attcctggga ctcttggctg gcgcttgtga taggagactc     840
```

| | | | |
|---|---|---|---|
| atcgtcgtaa | acgctgtgag | agctgccgat tggcctgccg atggtcctgt tgtgtctcgt | 900 |
| caacacgctt | acttggcttg | tgaagtgttg cccgctgtcc aatgtgctgt tcgctggcct | 960 |
| gctgctcgtg | atctgaggcg | tactgttctg gctagtggtc gtgttttcgg acctggtgtt | 1020 |
| ttcgctcgtg | tcgaagctgc | tcacgctaga ctgtacccg atgccccacc cctccgtttg | 1080 |
| tgtcgtggag | caaacgttcg | ctaccgtgtc cgtactcgtt tcggacccga tactctggtt | 1140 |
| ccaatgtccc | ctcgtgaata | ccgtcgtgct gttctgcctg ccctcgatgg acgtgctgcc | 1200 |
| gcttctggcg | ctggtgacgc | tatggctcct ggcgctccgg acttctgtga ggatgaggct | 1260 |
| cactcacatc | gtgcctgtgc | ccgctgggga ctgggcgctc cattgaggcc tgtatacgtg | 1320 |
| gcactgggcc | gtgatgctgt | tagaggcgga cccgctgaat tgagaggccc tcgtcgtgaa | 1380 |
| ttctgtgcta | gggctctgct | cgaacccgat ggagatgctc ctcctttggt actccgtgac | 1440 |
| gacgccgatg | ctggtcctcc | cccacaaatt cgctgggcta gtgctgctgg acgtgctggt | 1500 |
| actgtattgg | ctgctgctgg | cggtggcgtt gaagttgttg gtactgccgc tggactcgct | 1560 |
| acacctcccc | gccgtgaacc | tgtagacatg gatgctgaac tcgaggatga tgacgacgga | 1620 |
| ttgttcggag | ag | | 1632 |

<210> SEQ ID NO 127
<211> LENGTH: 3330
<212> TYPE: DNA
<213> ORGANISM: Herpes simplex virus

<400> SEQUENCE: 127

| | | | |
|---|---|---|---|
| caccaccacc | accaccatca | taggcgtaga cgtgctccta gacgtcgttc tgccgctagt | 60 |
| gactcttcca | aatctggctc | ttcttcatct gcctcttccg cttcatcttc ggcctcatcg | 120 |
| tcctcttcgg | catccgcttc | gagtagtgat gatgatgatg acgacgacgc tgctagagcc | 180 |
| cccgcttctg | ctgccgacca | cgctgctggc ggaactttgg gagccgacga cgaggaggcg | 240 |
| ggagttcctg | ctcgtgcccc | gggagctgct ccgaggcctt ctccaccccg tgctgaacct | 300 |
| gctccggcta | gaacaccggc | cgctactgct ggtagactgg agcgtagacg tgcccgtgct | 360 |
| gctgtggctg | gtagagatgc | tactggccgc ttcactgctg gccgtcctag acgtgttgaa | 420 |
| ctggacgccg | atgctgcttc | tggtgctttc tacgcccgtt accgtgatgg ttacgtgtct | 480 |
| ggtgaacctt | ggcctggcgc | tggtccacct ccgcccggac gtgtactcta cggtggattg | 540 |
| ggcgattctc | gccctggtct | gtggggcgct ccggaggctg aggaggctag agcccgtttc | 600 |
| gaggcttctg | gtgcccctgc | tcctgttttgg gctcctgaat tgggcgacgc tgctcaacaa | 660 |
| tacgccctca | tcacacgctt | gctgtacact cccgacgccg aggctatggg atggctccaa | 720 |
| aaccctagag | ttgcccctgg | tgatgttgct ctggatcagg cttgtttccg tatctccggc | 780 |
| gctgctcgta | actcttcttc | gttcatctcc ggttctgtgg ctagagctgt gcctcacttg | 840 |
| ggatacgcca | tggccgctgg | acgtttcggc tggggactgg ctcatgttgc tgccgctgta | 900 |
| gcaatgtcta | gacgctacga | ccgtgctcaa aaaggattct tgctcacgtc actgaggcgt | 960 |
| gcttacgccc | ctttgttggc | ccgtgaaaac gctgccctca ctggcgcccg tacccccgat | 1020 |
| gacggtggca | acgccaaccg | ccacgatggt gatgatgcta gaggcaaacc cgctgccgct | 1080 |
| gctgctcctt | tgccctctgc | cgccgcttcc cctgccgatg aacgtgctgt tcctgccggt | 1140 |
| tacggtgccg | ctggtgtgtt | ggctgctttg gacgcttga gtgctgcccc ggctagtgcc | 1200 |
| cccgctggtg | ccgatgacga | tgacgatgac gatggtgctg gcggaggcgg tggcggtaga | 1260 |
| cgtgctgagg | ctggacgtgt | tgctgttgaa tgcctggctg cctgtagagg aatcttggag | 1320 |

```
gctctggccg agggattcga cggagacttg gcggctgtac cgggactggc gggagcgagg    1380
cctgccgctc cacctcgccc cggtcctgct ggtgctgccg ctcctcctca tgccgacgct    1440
cctagactcc gtgcttggct ccgtgaactc cgtttcgttc gtgacgcttt ggttctgatg    1500
agactgagag gcgacttgag agtggctgga ggatccgagg ctgctgttgc tgctgtccgt    1560
gctgtttctt tggttgctgg tgctttgggc cctgctttgc cgagatctcc ccgtttgttg    1620
tcgagtgccg ccgctgctgc cgccgatttg ttgttccaaa accaatccct ccgccctctg    1680
ctcgccgaca ctgttgccgc tgccgattct ctggctgctc cggcttctgc cccacgtgaa    1740
gctcgtaaac gtaaatcacc cgctccggct cgtgctcccc ctggtggcgc cctagaccc     1800
cctaaaaaat cccgtgccga tgcccctaga cctgctgctg ctcccccgc tggtgctgct     1860
ccccccgctc ccctactcc ccccacgc ccacctcgtc ccgctgccct cacacgccgt       1920
cctgctgagg gacccgatcc acaaggcggc tggcgtagac aacctcctgg cccatcccat    1980
acaccggcac catctgccgc tgcttttggag gcttactgtg ctcctcgtgc tgtggctgaa   2040
ctcaccgatc atccgctgtt ccctgctccc tggcgtcccg ccctcatgtt cgatcctaga    2100
gctttggctt ccttggccgc tcgttgtgct gcccctcccc ctggcggtgc tccggctgct    2160
ttcggtcctc tccgtgcctc tggtccactc cgccgtgccg ctgcctggat gagacaagtt    2220
cccgaccctg aggatgttag agttgtgatc ttgtactcgc ccttgcctgg cgaggatttg    2280
gccgctggta gagctggcgg tggcccccct cctgaatggt ctgctgaacg tggtggtttg    2340
tcttgcttgt tggccgccct gggaaaccgt ctgtgtggtc ctgctactgc tgcttgggct    2400
ggaaactgga ctggcgctcc cgatgtttct gctctcggtg ctcaaggagt tttgctgctc   2460
tctactcgtg acttggcatt cgctggagct gttgaattcc tgggactctt ggctggcgct    2520
tgtgatagga gactcatcgt cgtaaacgct gtgagagctg ccgattggcc tgccgatggt    2580
cctgttgtgt ctcgtcaaca cgcttacttg gcttgtgaag tgttgcccgc tgtccaatgt    2640
gctgttcgct ggcctgctgc tcgtgatctg aggcgtactg ttctggctag tggtcgtgtt    2700
ttcggacctg gtgttttcgc tcgtgtcgaa gctgctcacg ctagactgta ccccgatgcc    2760
ccacccctcc gtttgtgtcg tggagcaaac gttcgctacc gtgtccgtac tcgtttcgga    2820
cccgatactc tggttccaat gtcccctcgt gaataccgtc gtgctgttct gcctgccctc    2880
gatgacgtg ctgccgcttc tggcgctggt gacgctatgg ctcctggcgc tccggacttc     2940
tgtgaggatg aggctcactc acatcgtgcc tgtgcccgct ggggactggg cgctccattg    3000
aggcctgtat acgtggcact gggccgtgat gctgttagag gcggacccgc tgaattgaga    3060
ggccctcgtc gtgaattctg tgctagggct ctgctcgaac ccgatggaga tgctcctcct    3120
ttggtactcc gtgacgacgc cgatgctggt cctccccccac aaattcgctg ggctagtgct   3180
gctggacgtg ctggtactgt attggctgct gctggcggtg gcgttgaagt tgttggtact    3240
gccgctggac tcgctacacc tccccgccgt gaacctgtag acatggatgc tgaactcgag    3300
gatgatgacg acggattgtt cggagagtaa                                    3330
```

<210> SEQ ID NO 128
<211> LENGTH: 3492
<212> TYPE: DNA
<213> ORGANISM: Herpes simplex virus

<400> SEQUENCE: 128

```
atgagtgccg aacagcgtaa aaagaaaaaa accaccacca cgacccaagg acgtggagct    60
```

-continued

```
gaagttgcta tggcggatga ggatggaggc cgcttgagag ctgctgctga gactactgga    120
ggacctggat caccggaccc tgccgatgga cccccccta caccaaaccc cgatcgtaga     180
ccggctgcta gacctggatt cggatggcat ggaggacccg aggaaaacga ggacgaggcg    240
gacgacgccg ctgccgacgc cgacgccgat gaggctgccc ctgcttctgg agaggcggta    300
gacgaacctg ctgccgatgg agttgttagc cctaggcaat tggctttgtt ggcgagcatg    360
gtagacgagg ctgtgagaac aatcccttcc cctcccctg aacgtgatgg agcacaagag     420
gaggcggcta ggagtccctc accacccgt acaccttcta tgagagcgga ttacggcgag     480
gaaaacgacg acgacgacga tgatgatgac gacgatgatc gtgatgccgg acgctgggtt    540
aggggacctg aaaccacttc tgctgtccgt ggagcatacc ccgatcctat ggcgagtttg    600
agccctagac cacctgcccc gaggagacac caccaccacc accatcatag gcgtagacgt    660
gctcctagac gtcgttctgc cgctagtgac tcttccaaat ctggctcttc ttcatctgcc    720
tcttccgctt catcttcggc ctcatcgtcc tcttcggcat ccgcttcgag tagtgatgat    780
gatgatgacg acgacgctgc tagagccccc gcttctgctg ccgaccacgc tgctggcgga    840
actttgggag ccgacgacga ggaggcggga gttcctgctc gtgccccggg agctgctccg    900
aggccttctc caccccgtgc tgaacctgct ccggctagaa caccgccgc tactgctggt     960 agactggagc gtagacgtgc ccgtgctgct gtggctggta gagatgctac tggccgcttc    1020
actgctggcc gtcctagacg tgttgaactg gacgccgatg ctgcttctgg tgctttctac    1080
gcccgttacc gtgatggtta cgtgtctggt gaaccttggc ctggcgctgg tccacctccg    1140 cccgacgtg tactctacgg tggattgggc gcccgtaccc ccgatgacgg tggcgacgcc     1200
aaccgccacg atggtgatga tgctagaggc aaacccgctg ccgctgctgc tcctttgccc    1260
tctgccgccg cttcccctgc cgatgaacgt gctgttcctg ccggttacgg tgccgctggt    1320
gtgttggctg cttgggacg cttgagtgct gccccggcta gtgccccgc tggtgccgat      1380 gacgatgacg atgacgatgg tgctggcgga ggcggtggcg tagacgtgc tgaggctgga     1440 cgtgttgctg ttgaatgcct ggctgcctgt agaggaatct tggaggctct ggccgaggga    1500
ttcgacggag acttggcggc tgtaccggga ctggcgggag cgaggcctgc cgctccacct    1560
cgccccggtc ctgctggtgc tgccgctcct cctcatgccg acgctcctag actccgtgct    1620
tggctccgtg aactccgttt cgttcgtgac gcttttggttc tgatgagact gagaggcgac    1680
ttgagagtgg ctggaggatc cgaggctgct gttgctgctg tccgtgctgt ttctttggtt    1740
gctggtgctt tgggccctgc tttgccgaga tctccccgtt tgttgtcgag tgccgccgct    1800
gctgccgccg atttgttgtt ccaaaaccaa tccctccgcc ctctgctcgc cgacactgtt    1860
gccgctgccg attctctggc tgctccggct tctgccccac gtgaagctcg taaacgtaaa    1920
tcacccgctc cggctcgtgc tccccctggt ggcgcccta gaccccctaa aaaatcccgt     1980
gccgatgccc ctagacctgc tgctgctccc ccgctggtg ctgctccccc cgctccccct     2040 actcccccc cacgcccacc tcgtcccgct gccctcacac gccgtcctgc tgagggaccc     2100
gatccacaag gcggctggcg tagacaacct cctggcccat ccatacacc ggcaccatct     2160 gccgctgctt tggaggctta ctgtgctcct cgtgctgtgg ctgaactcac cgatcatccg    2220
ctgttccctg ctccctggcg tccgccctc atgttcgatc ctagagcttt ggcttccttg     2280
gccgctcgtt gtgctgcccc tcccctggc ggtgctccgg ctgctttcgg tcctctccgt     2340
gcctctggtc cactccgccg tgccgctgcc tggatgagac aagttcccga ccctgaggat    2400
gttagagttg tgatcttgta ctcgcccttg cctggcgagg atttggccgc tggtagagct    2460
```

-continued

```
ggcggtggcc ccctcctga atggtctgct gaacgtggtg gtttgtcttg cttgttggcc    2520
gccctgggaa accgtctgtg tggtcctgct actgctgctt gggctggaaa ctggactggc    2580
gctcccgatg tttctgctct cggtgctcaa ggagttttgc tgctctctac tcgtgacttg    2640
gcattcgctg gagctgttga attcctggga ctcttggctg gcgcttgtga taggagactc    2700
atcgtcgtaa acgctgtgag agctgccgat tggcctgccg atggtcctgt tgtgtctcgt    2760
caacacgctt acttggcttg tgaagtgttg cccgctgtcc aatgtgctgt tcgctggcct    2820
gctgctcgtg atctgaggcg tactgttctg gctagtggtc gtgttttcgg acctggtgtt    2880
ttcgctcgtg tcgaagctgc tcacgctaga ctgtacccg atgccccacc cctccgtttg     2940
tgtcgtggag caaacgttcg ctaccgtgtc cgtactcgtt tcggacccga tactctggtt    3000
ccaatgtccc ctcgtgaata ccgtcgtgct gttctgcctg ccctcgatgg acgtgctgcc    3060
gcttctggcg ctggtgacgc tatggctcct ggcgctccgg acttctgtga ggatgaggct    3120
cactcacatc gtgcctgtgc ccgctgggga ctgggcgctc cattgaggcc tgtatacgtg    3180
gcactgggcc gtgatgctgt tagaggcgga cccgctgaat tgagaggccc tcgtcgtgaa    3240
ttctgtgcta gggctctgct cgaacccgat ggagatgctc ctccttggt actccgtgac     3300
gacgccgatg ctggtcctcc cccacaaatt cgctgggcta gtgctgctgg acgtgctggt    3360
actgtattgg ctgctgctgg cggtggcgtt gaagttgttg gtactgccgc tggactcgct    3420
acacctcccc gccgtgaacc tgtagacatg gatgctgaac tcgaggatga tgacgacgga    3480
ttgttcggag ag                                                        3492
```

<210> SEQ ID NO 129
<211> LENGTH: 3702
<212> TYPE: DNA
<213> ORGANISM: Herpes simplex virus

<400> SEQUENCE: 129

```
atgagtgccg aacagcgtaa aaagaaaaaa accaccacca cgacccaagg acgtggagct    60
gaagttgcta tggcggatga ggatggaggc cgcttgagag ctgctgctga gactactgga    120
ggacctggat caccggaccc tgccgatgga cccccccta caccaaaccc cgatcgtaga    180
ccggctgcta gacctggatt cggatggcat ggaggacccg aggaaaacga ggacgaggcg    240
gacgacgccg ctgccgacgc cgacgccgat gaggctgccc ctgcttctgg agaggcggta    300
gacgaacctg ctgccgatgg agttgttagc cctaggcaat tggctttgtt ggcgagcatg    360
gtagacgagg ctgtgagaac aatcccttcc cctcccctg aacgtgatgg agcacaagag     420
gaggcggcta ggagtccctc accaccccgt acaccttcta tgagagcgga ttacggcgag    480
gaaaacgacg acgacgacga tgatgatgac gacgatgatc gtgatgccgg acgctgggtt    540
aggggacctg aaaccacttc tgctgtccgt ggagcatacc ccgatcctat ggcgagtttg    600
agccctagac cacctgcccc gaggagacac caccaccacc accatcatag gcgtagacgt    660
gctcctagac gtcgttctgc cgctagtgac tcttccaaat ctggctcttc ttcatctgcc    720
tcttccgctt catcttcggc ctcatcgtcc tcttcggcat ccgcttcgag tagtgatgat    780
gatgatgacg acgacgctgc tagagccccc gcttctgctg ccgaccacgc tgctggcgga    840
actttgggag ccgacgacga ggaggcggga gttcctgctc gtgccccggg agctgctccg    900
aggccttctc caccccgtgc tgaacctgct ccggctagaa caccggccgc tactgctggt    960
agactggagc gtagacgtgc ccgtgctgct gtggctggta gagatgctac tggccgcttc    1020
```

-continued

```
actgctggcc gtcctagacg tgttgaactg gacgccgatg ctgcttctgg tgctttctac    1080
gcccgttacc gtgatggtta cgtgtctggt gaaccttggc ctggcgctgg tccacctccg    1140
cccggacgtg tactctacgg tggattgggc gattctcgcc ctggtctgtg ggcgctccg     1200
gaggctgagg aggctagagc ccgtttcgag gcttctggtg ccctgctcc tgtttgggct     1260
cctgaattgg gcgacgctgc tcaacaatac gccctcatca cacgcttgct gtacactccc    1320
gacgccgagg ctatgggatg gctccaaaac cctagagttg ccctggtga tgttgctctg     1380
gatcaggctt gtttccgtat ctccggcgct gctcgtaact cttcttcgtt catctccggt    1440
tctgtggcta gagctgtgcc tcacttggga tacgccatgg ccgctggacg tttcggctgg    1500
ggactggctc atgttgctgc cgctgtagca atgtctagac gctacgaccg tgctcaaaaa    1560
ggattcttgc tcacgtcact gaggcgtgct tacgcccctt tgttggcccg tgaaaacgct    1620
gccctcactg gcgcccgtac ccccgatgac ggtggcgacg ccaaccgcca cgatggtgat    1680
gatgctagag gcaaacccgc tgccgctgct gctcctttgc cctctgccgc cgcttcccct    1740
gccgatgaac gtgctgttcc tgccggttac ggtgccgctg gtgtgttggc tgctttggga    1800
cgcttgagtg ctgccccggc tagtgccccc gctggtgccg atgacgatga cgatgacgat    1860
ggtgctggcg gaggcggtgg cggtagacgt gctgaggctg acgtgttgc tgttgaatgc     1920
ctggctgcct gtagaggaat cttggaggct ctggccgagg gattcgacgg agacttggcg    1980
gctgtaccgg gactggcggg agcgaggcct gccgctccac ctcgcccccgg tcctgctggt   2040
gctgccgctc ctcctcatgc cgacgctcct agactccgtg cttggctccg tgaactccgt    2100
ttcgttcgtg acgctttggt tctgatgaga ctgagaggcg acttgagagt ggctggagga    2160
tccgaggctg ctgttgctgc tgtccgtgct gtttctttgg ttgctggtgc tttgggccct   2220
gctttgccga gatctccccg tttgttgtcg agtgccgccg ctgctgccgc cgatttgttg   2280
ttccaaaacc aatccctccg ccctctgctc gccgacactg ttgccgctgc cgattctctg   2340
gctgctccgg cttctacacc ggcaccatct gccgctgctt tggaggctta ctgtgctcct   2400
cgtgctgtgg ctgaactcac cgatcatccg ctgttccctg ctccctggcg tcccgccctc   2460
atgttcgatc ctagagcttt ggcttccttg gccgctcgtt gtgctgcccc tcccctggc    2520
ggtgctccgg ctgctttcgg tcctctccgt gcctctggtc cactccgccg tgccgctgcc   2580
tggatgagac aagttcccga ccctgaggat gttagagttg tgatcttgta ctcgcccttg    2640
cctggcgagg atttggccgc tggtagagct ggcggtggcc cccctcctga atggtctgct    2700
gaacgtggtg gtttgtcttg cttgttggcc gccctgggaa accgtctgtg tggtcctgct    2760
actgctgctt gggctggaaa ctggactggc gctcccgatg tttctgctct cggtgctcaa    2820
ggagttttgc tgctctctac tcgtgacttg gcattgctg gagctgttga attcctggga    2880
ctcttggctg gcgcttgtga taggagactc atcgtcgtaa acgctgtgag agctgccgat    2940
tggcctgccg atggtcctgt tgtgtctcgt caacacgctt acttggcttg tgaagtgttg    3000
cccgctgtcc aatgtgctgt tcgctggcct gctgctcgta tctgaggcg tactgttctg     3060
gctagtggtc gtgttttcgg aacctggtgtt ttcgctcgtg tcgaagctgc tcacgctaga   3120
ctgtaccccg atgccccacc cctccgttttg tgtcgtggag caaacgttcg ctaccgtgtc   3180
cgtactcgtt tcggacccga tactctggtt ccaatgtccc ctcgtgaata ccgtcgtgct   3240
gttctgcctg ccctcgatgg acgtgctgcc gcttctggcg ctggtgacgc tatggctcct   3300
ggcgctccgg acttctgtga ggatgaggct cactcacatc gtgcctgtgc ccgctgggga   3360
ctgggcgctc cattgaggcc tgtatacgtg gcactgggcc gtgatgctgt tagaggcgga   3420
```

```
cccgctgaat tgagaggccc tcgtcgtgaa ttctgtgcta gggctctgct cgaacccgat   3480
ggagatgctc ctcctttggt actccgtgac gacgccgatg ctggtcctcc cccacaaatt   3540
cgctgggcta gtgctgctgg acgtgctggt actgtattgg ctgctgctgg cggtggcgtt   3600
gaagttgttg gtactgccgc tggactcgct acacctcccc gccgtgaacc tgtagacatg   3660
gatgctgaac tcgaggatga tgacgacgga ttgttcggag ag                      3702
```

```
<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 130

His His His His His His
1               5
```

```
<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Met Ser Tyr Tyr His His His His His His
1               5                   10
```

```
<210> SEQ ID NO 132
<211> LENGTH: 21
<212> TYPE: PRT
<213> ORGANISM: Unknown
<220> FEATURE:
<223> OTHER INFORMATION: Description of Unknown:
      Secretion signal peptide

<400> SEQUENCE: 132

Met Lys Phe Leu Val Asn Val Ala Leu Val Phe Met Val Val Tyr Ile
1               5                   10                  15

Ser Tyr Ile Tyr Ala
            20
```

```
<210> SEQ ID NO 133
<211> LENGTH: 294
<212> TYPE: DNA
<213> ORGANISM: Herpes simplex virus

<400> SEQUENCE: 133
atgtcgtact accatcacca tcaccatcac atgacgggga aacccgcaag actgggccgc    60
tgggtggtgc tgttgttcgt cgcgctcgtc gcgggcgtgc ccggggagcc gccgaacgcg   120
gcaggcgcac gcggcgttat cggggacgcg caatgccggg gcgacagcgc cggtgtggtg   180
tccgtcccgg gggtcctggt gcccttttat ctaggcatga cctcgatggg cgtatgtatg   240
atcgcgcacg tgtatcagat atgccagcgg gcactggccg ccgggtcagc ctga         294
```

```
<210> SEQ ID NO 134
<211> LENGTH: 1404
<212> TYPE: DNA
<213> ORGANISM: Herpes simplex virus
```

<400> SEQUENCE: 134

```
atgggacgcc gggcccccag gggatccccc gaggccgcgc cgggcgccga cgtcgcgccc      60
ggggcgcggg cggcgtggtg ggtctggtgt gtgcaggtgg cgacgttcat cgtctcggcc     120
atctgcgtcg tggggctcct ggtgctggcc tctgtgttcc gggacaggtt tccctgcctt     180
tacgccccog cgacctctta tgcgaaggcg aacgccacgg tcgaggtgcg cgggggtgta     240
gccgtccccc tccggttgga cacgcagagc ctgctggcca cgtacgcaat tacgtctacg     300
ctgttgctgg cggcggccgt gtacgccgcg gtgggcgcgg tgacctcgcg ctacgagcgc     360
gcgctggatg cggcccgtcg cctggcggcg cccgtatgg cgatgccaca cgccacgcta     420
atcgccggaa acgtctgcgc gtggctgttg cagatcacag tcctgctgct ggcccaccgc     480
atcagccagc tggcccacct tatctacgtc ctgcactttg cgtgcctcgt gtatctcgcg     540
gcccatttt gcaccagggg ggtcctgagc gggacgtacc tgcgtcaggt tcacggcctg     600
attgacccgg cgccgacgca ccatcgtatc gtcggtccgg tgcgggcagt aatgacaaac     660
gccttattac tgggcaccct cctgtgcacg gccgccgccg cggtctcgtt gaacacgatc     720
gccgccctga acttcaactt ttccgccccg agcatgctca tctgcctgac gacgctgttc     780
gccctgcttg tcgtgtcgct gttgttggtg gtcgagggg tgctgtgtca ctacgtgcgc     840
gtgttggtgg cccccacct cggggccatc gccgccaccg gcatcgtcgg cctggcctgc     900
gagcactacc acaccggtgg ttactacgtg gtggagcagc agtggccggg ggcccagacg     960
ggagtccgcg tcgccctggc gctcgtcgcc gcctttgccc tcgccatggc cgtgcttcgg    1020
tgcacgcgcg cctacctgta tcaccggcga caccacacta aattttcgt gcgcatgcgc    1080
gacaccggc accgcgccca ttcggcgctt cgacgcgtac gcagctccat gcgcggttct    1140
aggcgtggcg ggccgcccgg agacccgggc tacgcggaaa ccccctacgc gagcgtgtcc    1200
caccacgccg agatcgaccg gtatggggat tccgacgggg acccgatcta cgacgaagtg    1260
gccccgacc acgaggccga gctctacgcc cgagtgcaac gccccgggcc tgtgcccgac    1320
gccgagccca tttacgacac cgtggagggg tatgcgccaa ggtccgcggg ggagccggtg    1380
tacagcaccg ttcggcgatg gtag                                          1404
```

<210> SEQ ID NO 135
<211> LENGTH: 334
<212> TYPE: PRT
<213> ORGANISM: Herpes simplex virus

<400> SEQUENCE: 135

```
Met Lys Arg Ala Arg Ser Arg Ser Pro Ser Pro Ser Arg Pro Ser
  1               5                  10                  15

Ser Pro Phe Arg Thr Pro Pro His Gly Gly Ser Pro Arg Arg Glu Val
                 20                  25                  30

Gly Ala Gly Ile Leu Ala Ser Asp Ala Thr Ser His Val Cys Ile Ala
             35                  40                  45

Ser His Pro Gly Ser Gly Ala Gly Gln Pro Thr Arg Leu Ala Ala Gly
         50                  55                  60

Ser Ala Val Gln Arg Arg Arg Pro Arg Gly Cys Pro Pro Gly Val Met
 65                  70                  75                  80

Phe Ser Ala Ser Thr Thr Pro Glu Gln Pro Leu Gly Leu Ser Gly Asp
                 85                  90                  95

Ala Thr Pro Pro Leu Pro Thr Ser Val Pro Leu Asp Trp Ala Ala Phe
            100                 105                 110
```

-continued

```
Arg Arg Ala Phe Leu Ile Asp Asp Ala Trp Arg Pro Leu Leu Glu Pro
            115                 120                 125

Glu Leu Ala Asn Pro Leu Thr Ala Arg Leu Leu Ala Glu Tyr Asp Arg
130                 135                 140

Arg Cys Gln Thr Glu Glu Val Leu Pro Arg Glu Asp Val Phe Ser
145                 150                 155                 160

Trp Thr Arg Tyr Cys Thr Pro Asp Asp Val Arg Val Val Ile Ile Gly
                    165                 170                 175

Gln Asp Pro Tyr His His Pro Gly Gln Ala His Gly Leu Ala Phe Ser
                    180                 185                 190

Val Arg Ala Asp Val Pro Val Pro Pro Ser Leu Arg Asn Val Leu Ala
                    195                 200                 205

Ala Val Lys Asn Cys Tyr Pro Asp Ala Arg Met Ser Gly Arg Gly Cys
            210                 215                 220

Leu Glu Lys Trp Ala Arg Asp Gly Val Leu Leu Leu Asn Thr Thr Leu
225                 230                 235                 240

Thr Val Lys Arg Gly Ala Ala Ser His Ser Lys Leu Gly Trp Asp
                    245                 250                 255

Arg Phe Val Gly Gly Val Val Gln Arg Leu Ala Ala Arg Pro Gly
                    260                 265                 270

Leu Val Phe Met Leu Trp Gly Ala His Ala Gln Asn Ala Ile Arg Pro
            275                 280                 285

Asp Pro Arg Gln His Tyr Val Leu Lys Phe Ser His Pro Ser Pro Leu
            290                 295                 300

Ser Lys Val Pro Phe Gly Thr Cys Gln His Phe Leu Ala Ala Asn Arg
305                 310                 315                 320

Tyr Leu Glu Thr Arg Asp Ile Met Pro Ile Asp Trp Ser Val
                    325                 330

<210> SEQ ID NO 136
<211> LENGTH: 206
<212> TYPE: PRT
<213> ORGANISM: Herpes simplex virus

<400> SEQUENCE: 136

Ala Gly Ser Gln Ala Thr Glu Tyr Val Leu Arg Ser Val Ile Ala Lys
1               5                   10                  15

Glu Val Gly Asp Ile Leu Arg Val Pro Cys Met Arg Thr Pro Ala Asp
                    20                  25                  30

Asp Val Ser Trp Arg Tyr Glu Ala Pro Ser Val Ile Asp Tyr Ala Arg
            35                  40                  45

Ile Asp Gly Ile Phe Leu Arg Tyr His Cys Pro Gly Leu Asp Thr Phe
50                  55                  60

Leu Trp Asp Arg His Ala Gln Arg Ala Tyr Leu Val Asn Pro Phe Leu
65                  70                  75                  80

Phe Ala Ala Gly Phe Leu Glu Asp Leu Ser His Ser Val Phe Pro Ala
                85                  90                  95

Asp Thr Gln Glu Thr Thr Thr Arg Arg Ala Leu Tyr Lys Glu Ile Arg
            100                 105                 110

Asp Ala Leu Gly Ser Arg Lys Gln Ala Val Ser His Ala Pro Val Arg
            115                 120                 125

Ala Gly Cys Val Asn Phe Asp Tyr Ser Arg Thr Arg Arg Cys Val Gly
            130                 135                 140

Arg Arg Asp Leu Arg Pro Ala Asn Thr Thr Ser Thr Trp Glu Pro Pro
```

```
                145                 150                 155                 160
Val Ser Ser Asp Asp Glu Ala Ser Ser Gln Ser Lys Pro Leu Ala Thr
                    165                 170                 175

Gln Pro Pro Val Leu Ala Leu Ser Asn Ala Pro Pro Arg Arg Val Ser
                180                 185                 190

Pro Thr Arg Gly Arg Arg Arg His Thr Arg Leu Arg Arg Asn
                195                 200                 205
```

<210> SEQ ID NO 137
<211> LENGTH: 702
<212> TYPE: DNA
<213> ORGANISM: Herpes simplex virus

<400> SEQUENCE: 137

```
atgaagttcc tcgtgaacgt ggccctggtg ttcatggtgg tgtacatcag ctacatctac     60
gccgccgggt cacaggcaac cgaatatgtt cttcgtagtg ttattgccaa agaggtgggg    120
gacatactaa gagtgccttg catgcggacc cccgcggacg atgtttcttg gcgctacgag    180
gccccgtccg ttattgacta tgcccgcata gacggaatat tcttcgctat tcactgcccg    240
gggttggaca cgttttttgtg ggataggcac gcccagaggg cgtatcttgt taacccctt    300
ctctttgcgg cgggattttt ggaggacttg agtcactctg tgtttccggc cgacacccag    360
gaaacaacga cgcgccgggc cctttataaa gagatacgcg atgcgttggg cagtcgaaaa    420
caggccgtca gccacgcacc cgtcagggcc gggtgtgtaa actttgacta ctcacgcact    480
cgccgctgcg tcgggcgacg cgatttacgg cctgccaaca ccacgtcaac gtgggaaccg    540
cctgtgtcgt cggacgatga agcgagctcg cagtcgaagc ccctcgccac ccagccgccc    600
gtcctcgccc tttcgaacgc ccccccacgg cgggtctccc cgacgcgagg tcggcgccgg    660
catactcgcc tccgacgcaa ccatcaccat caccatcact ga                      702
```

<210> SEQ ID NO 138
<211> LENGTH: 1128
<212> TYPE: PRT
<213> ORGANISM: Herpes simplex virus

<400> SEQUENCE: 138

```
Met Ser Ala Glu Gln Arg Lys Lys Lys Thr Thr Thr Thr Thr Gln
1               5                   10                  15

Gly Arg Gly Ala Glu Val Ala Met Ala Asp Glu Asp Gly Gly Arg Leu
                20                  25                  30

Arg Ala Ala Ala Glu Thr Thr Gly Gly Pro Gly Ser Pro Asp Pro Ala
            35                  40                  45

Asp Gly Pro Pro Pro Thr Pro Asn Pro Asp Arg Arg Pro Ala Ala Arg
        50                  55                  60

Pro Gly Phe Gly Trp His Gly Gly Pro Glu Glu Asn Glu Asp Glu Ala
65                  70                  75                  80

Asp Asp Ala Ala Ala Asp Ala Asp Ala Asp Glu Ala Pro Ala Ser
                85                  90                  95

Gly Glu Ala Val Asp Glu Pro Ala Ala Asp Gly Val Val Ser Pro Arg
                100                 105                 110

Gln Leu Ala Leu Leu Ala Ser Met Val Asp Glu Ala Val Arg Thr Ile
            115                 120                 125

Pro Ser Pro Pro Pro Glu Arg Asp Gly Ala Gln Glu Glu Ala Ala Arg
        130                 135                 140

Ser Pro Ser Pro Pro Arg Thr Pro Ser Met Arg Ala Asp Tyr Gly Glu
```

-continued

```
            145                 150                 155                 160
        Glu Asn Asp Asp Asp Asp Asp Asp Asp Asp Asp Arg Asp Ala
                        165                 170                 175
        Gly Arg Trp Val Arg Gly Pro Glu Thr Thr Ser Ala Val Arg Gly Ala
                        180                 185                 190
        Tyr Pro Asp Pro Met Ala Ser Leu Ser Pro Arg Pro Pro Ala Pro Arg
                        195                 200                 205
        Arg His His His His His His His Arg Arg Arg Ala Pro Arg Arg
                        210                 215                 220
        Arg Ser Ala Ala Ser Asp Ser Ser Lys Ser Gly Ser Ser Ser Ser Ala
        225                 230                 235                 240
        Ser Ser Ala Ser Ser Ala Ser Ser Ser Ser Ala Ser Ala Ser
                        245                 250                 255
        Ser Ser Asp Asp Asp Asp Asp Asp Ala Ala Arg Ala Pro Ala Ser
                        260                 265                 270
        Ala Ala Asp His Ala Ala Gly Gly Thr Leu Gly Ala Asp Asp Glu Glu
                        275                 280                 285
        Ala Gly Val Pro Ala Arg Ala Pro Gly Ala Ala Pro Arg Pro Ser Pro
        290                 295                 300
        Pro Arg Ala Glu Pro Ala Pro Ala Arg Thr Pro Ala Ala Thr Ala Gly
        305                 310                 315                 320
        Arg Leu Glu Arg Arg Ala Arg Ala Ala Val Ala Gly Arg Asp Ala
                        325                 330                 335
        Thr Gly Arg Phe Thr Ala Gly Arg Pro Arg Arg Val Glu Leu Asp Ala
                        340                 345                 350
        Asp Ala Ala Ser Gly Ala Phe Tyr Ala Arg Tyr Arg Asp Gly Tyr Val
                        355                 360                 365
        Ser Gly Glu Pro Trp Pro Gly Ala Gly Pro Pro Pro Gly Arg Val
        370                 375                 380
        Leu Tyr Gly Gly Leu Gly Arg Thr Pro Asp Asp Gly Gly Asp Ala Asn
        385                 390                 395                 400
        Arg His Asp Gly Asp Asp Ala Arg Gly Lys Pro Ala Ala Ala Ala
                        405                 410                 415
        Pro Leu Pro Ser Ala Ala Ala Ser Pro Ala Asp Glu Arg Ala Val Pro
                        420                 425                 430
        Ala Gly Tyr Gly Ala Ala Gly Val Leu Ala Ala Leu Gly Arg Leu Ser
                        435                 440                 445
        Ala Ala Pro Ala Ser Ala Pro Ala Gly Ala Asp Asp Asp Asp Asp
                        450                 455                 460
        Asp Gly Ala Gly Gly Gly Gly Gly Arg Arg Ala Glu Ala Gly Arg
        465                 470                 475                 480
        Val Ala Val Glu Cys Leu Ala Ala Cys Arg Gly Ile Leu Glu Ala Leu
                        485                 490                 495
        Ala Glu Gly Phe Asp Gly Asp Leu Ala Ala Val Pro Gly Leu Ala Gly
                        500                 505                 510
        Ala Arg Pro Ala Ala Pro Pro Arg Pro Gly Pro Ala Gly Ala Ala Ala
                        515                 520                 525
        Pro Pro His Ala Asp Ala Pro Arg Leu Arg Ala Trp Leu Arg Glu Leu
                        530                 535                 540
        Arg Phe Val Arg Asp Ala Leu Val Leu Met Arg Leu Arg Gly Asp Leu
        545                 550                 555                 560
        Arg Val Ala Gly Gly Ser Glu Ala Ala Val Ala Ala Val Arg Ala Val
                        565                 570                 575
```

```
Ser Leu Val Ala Gly Ala Leu Gly Pro Ala Leu Pro Arg Ser Pro Arg
            580                 585                 590

Leu Leu Ser Ser Ala Ala Ala Ala Ala Asp Leu Leu Phe Gln Asn
        595                 600                 605

Gln Ser Leu Arg Pro Leu Leu Ala Asp Thr Val Ala Ala Asp Ser
    610                 615                 620

Leu Ala Ala Pro Ala Ser Ala Ala Pro Ala Gly Ala Ala Pro
625                 630                 635                 640

Pro Ala Pro Pro Thr Pro Pro Arg Pro Arg Pro Ala Ala Leu
                645                 650                 655

Thr Arg Arg Pro Ala Glu Gly Pro Asp Pro Gln Gly Gly Trp Arg Arg
            660                 665                 670

Gln Pro Pro Gly Pro Ser His Thr Pro Ala Pro Ser Ala Ala Ala Leu
            675                 680                 685

Glu Ala Tyr Cys Ala Pro Arg Ala Val Ala Glu Leu Thr Asp His Pro
            690                 695                 700

Leu Phe Pro Ala Pro Trp Arg Pro Ala Leu Met Phe Asp Pro Arg Ala
705                 710                 715                 720

Leu Ala Ser Leu Ala Ala Arg Cys Ala Ala Pro Pro Gly Gly Ala
                725                 730                 735

Pro Ala Ala Phe Gly Pro Leu Arg Ala Ser Gly Pro Leu Arg Arg Ala
            740                 745                 750

Ala Ala Trp Met Arg Gln Val Pro Asp Pro Glu Asp Val Arg Val Val
            755                 760                 765

Ile Leu Tyr Ser Pro Leu Pro Gly Glu Asp Leu Ala Ala Gly Arg Ala
            770                 775                 780

Gly Gly Gly Pro Pro Pro Glu Trp Ser Ala Glu Arg Gly Gly Leu Ser
785                 790                 795                 800

Cys Leu Leu Ala Ala Leu Gly Asn Arg Leu Cys Gly Pro Ala Thr Ala
                805                 810                 815

Ala Trp Ala Gly Asn Trp Thr Gly Ala Pro Asp Val Ser Ala Leu Gly
            820                 825                 830

Ala Gln Gly Val Leu Leu Leu Ser Thr Arg Asp Leu Ala Phe Ala Gly
            835                 840                 845

Ala Val Glu Phe Leu Gly Leu Leu Ala Gly Ala Cys Asp Arg Arg Leu
            850                 855                 860

Ile Val Val Asn Ala Val Arg Ala Ala Asp Trp Pro Ala Asp Gly Pro
865                 870                 875                 880

Val Val Ser Arg Gln His Ala Tyr Leu Ala Cys Glu Val Leu Pro Ala
                885                 890                 895

Val Gln Cys Ala Val Arg Trp Pro Ala Ala Arg Asp Leu Arg Arg Thr
            900                 905                 910

Val Leu Ala Ser Gly Arg Val Phe Gly Pro Gly Val Phe Ala Arg Val
            915                 920                 925

Glu Ala Ala His Ala Arg Leu Tyr Pro Asp Ala Pro Pro Leu Arg Leu
            930                 935                 940

Cys Arg Gly Ala Asn Val Arg Tyr Arg Val Arg Thr Arg Phe Gly Pro
945                 950                 955                 960

Asp Thr Leu Val Pro Met Ser Pro Arg Glu Tyr Arg Arg Ala Val Leu
                965                 970                 975

Pro Ala Leu Asp Gly Arg Ala Ala Ser Gly Ala Gly Asp Ala Met
            980                 985                 990
```

```
Ala Pro Gly Ala Pro Asp Phe Cys Glu Asp Glu Ala His Ser His Arg
            995                 1000                1005

Ala Cys Ala Arg Trp Gly Leu Gly Ala Pro Leu Arg Pro Val Tyr
    1010                1015                1020

Val Ala Leu Gly Arg Asp Ala Val Arg Gly Gly Pro Ala Glu Leu
    1025                1030                1035

Arg Gly Pro Arg Arg Glu Phe Cys Ala Arg Ala Leu Leu Glu Pro
    1040                1045                1050

Asp Gly Asp Ala Pro Pro Leu Val Leu Arg Asp Asp Ala Asp Ala
    1055                1060                1065

Gly Pro Pro Pro Gln Ile Arg Trp Ala Ser Ala Ala Gly Arg Ala
    1070                1075                1080

Gly Thr Val Leu Ala Ala Ala Gly Gly Gly Val Glu Val Val Gly
    1085                1090                1095

Thr Ala Ala Gly Leu Ala Thr Pro Pro Arg Arg Glu Pro Val Asp
    1100                1105                1110

Met Asp Ala Glu Leu Glu Asp Asp Asp Gly Leu Phe Gly Glu
    1115                1120                1125

<210> SEQ ID NO 139
<211> LENGTH: 1164
<212> TYPE: PRT
<213> ORGANISM: Herpes simplex virus

<400> SEQUENCE: 139

Met Ser Ala Glu Gln Arg Lys Lys Lys Thr Thr Thr Thr Thr Gln
1               5                   10                  15

Gly Arg Gly Ala Glu Val Ala Met Ala Asp Glu Asp Gly Gly Arg Leu
                20                  25                  30

Arg Ala Ala Ala Glu Thr Thr Gly Gly Pro Gly Ser Pro Asp Pro Ala
        35                  40                  45

Asp Gly Pro Pro Pro Thr Pro Asn Pro Asp Arg Pro Ala Ala Arg
50                  55                  60

Pro Gly Phe Gly Trp His Gly Gly Pro Glu Glu Asn Glu Asp Glu Ala
65          70                  75                  80

Asp Asp Ala Ala Ala Asp Ala Asp Ala Glu Ala Ala Pro Ala Ser
                85                  90                  95

Gly Glu Ala Val Asp Glu Pro Ala Ala Asp Gly Val Val Ser Pro Arg
                100                 105                 110

Gln Leu Ala Leu Leu Ala Ser Met Val Asp Glu Ala Val Arg Thr Ile
        115                 120                 125

Pro Ser Pro Pro Pro Glu Arg Asp Gly Ala Gln Glu Glu Ala Ala Arg
130                 135                 140

Ser Pro Ser Pro Pro Arg Thr Pro Ser Met Arg Ala Asp Tyr Gly Glu
145                 150                 155                 160

Glu Asn Asp Asp Asp Asp Asp Asp Asp Asp Asp Arg Asp Ala
                165                 170                 175

Gly Arg Trp Val Arg Gly Pro Glu Thr Thr Ser Ala Val Arg Gly Ala
            180                 185                 190

Tyr Pro Asp Pro Met Ala Ser Leu Ser Pro Arg Pro Ala Pro Arg
        195                 200                 205

Arg His His His His His His Arg Arg Arg Ala Pro Arg Arg
    210                 215                 220

Arg Ser Ala Ala Ser Asp Ser Ser Lys Ser Gly Ser Ser Ser Ser Ala
225                 230                 235                 240
```

```
Ser Ser Ala Ser Ser Ala Ser Ser Ser Ala Ser Ala Ser
            245                 250                 255

Ser Ser Asp Asp Asp Asp Asp Ala Ala Arg Ala Pro Ala Ser
            260                 265                 270

Ala Ala Asp His Ala Ala Gly Gly Thr Leu Gly Ala Asp Glu Glu
            275                 280                 285

Ala Gly Val Pro Ala Arg Ala Pro Gly Ala Ala Pro Arg Pro Ser Pro
290                 295                 300

Pro Arg Ala Glu Pro Ala Pro Ala Arg Thr Pro Ala Ala Thr Ala Gly
305                 310                 315                 320

Arg Leu Glu Arg Arg Ala Arg Ala Ala Val Ala Gly Arg Asp Ala
            325                 330                 335

Thr Gly Arg Phe Thr Ala Gly Arg Pro Arg Arg Val Glu Leu Asp Ala
            340                 345                 350

Asp Ala Ala Ser Gly Ala Phe Tyr Ala Arg Tyr Arg Asp Gly Tyr Val
            355                 360                 365

Ser Gly Glu Pro Trp Pro Gly Ala Gly Pro Pro Pro Gly Arg Val
            370                 375                 380

Leu Tyr Gly Gly Leu Gly Ala Met Ser Arg Arg Tyr Asp Arg Ala Gln
385                 390                 395                 400

Lys Gly Phe Leu Leu Thr Ser Leu Arg Arg Ala Tyr Ala Pro Leu Leu
            405                 410                 415

Ala Arg Glu Asn Ala Ala Leu Thr Gly Ala Arg Thr Pro Asp Asp Gly
            420                 425                 430

Gly Asp Ala Asn Arg His Asp Gly Asp Ala Arg Gly Lys Pro Ala
            435                 440                 445

Ala Ala Ala Ala Pro Leu Pro Ser Ala Ala Ala Ser Pro Ala Asp Glu
450                 455                 460

Arg Ala Val Pro Ala Gly Tyr Gly Ala Ala Gly Val Leu Ala Ala Leu
465                 470                 475                 480

Gly Arg Leu Ser Ala Ala Pro Ala Ser Ala Pro Ala Gly Ala Asp Asp
            485                 490                 495

Asp Asp Asp Asp Asp Gly Ala Gly Gly Gly Gly Gly Arg Arg Ala
            500                 505                 510

Glu Ala Gly Arg Val Ala Val Glu Cys Leu Ala Ala Cys Arg Gly Ile
            515                 520                 525

Leu Glu Ala Leu Ala Glu Gly Phe Asp Gly Asp Leu Ala Ala Val Pro
530                 535                 540

Gly Leu Ala Gly Ala Arg Pro Ala Ala Pro Pro Arg Pro Gly Pro Ala
545                 550                 555                 560

Gly Ala Ala Ala Pro Pro His Ala Asp Ala Pro Arg Leu Arg Ala Trp
            565                 570                 575

Leu Arg Glu Leu Arg Phe Val Arg Asp Ala Leu Val Leu Met Arg Leu
            580                 585                 590

Arg Gly Asp Leu Arg Val Ala Gly Gly Ser Glu Ala Ala Val Ala Ala
            595                 600                 605

Val Arg Ala Val Ser Leu Val Ala Gly Ala Leu Gly Pro Ala Leu Pro
            610                 615                 620

Arg Ser Pro Arg Leu Leu Ser Ser Ala Ala Ala Ala Ala Asp Leu
625                 630                 635                 640

Leu Phe Gln Asn Gln Ser Leu Arg Pro Leu Leu Ala Asp Thr Val Ala
            645                 650                 655
```

```
Ala Ala Asp Ser Leu Ala Ala Pro Ser Ala Ala Pro Pro Ala
            660                 665                 670

Gly Ala Ala Pro Pro Ala Pro Thr Pro Pro Arg Pro Pro Arg
        675                 680                 685

Pro Ala Ala Leu Thr Arg Arg Pro Ala Glu Gly Pro Asp Pro Gln Gly
        690                 695                 700

Gly Trp Arg Arg Gln Pro Pro Gly Pro Ser His Thr Pro Ala Pro Ser
705                 710                 715                 720

Ala Ala Ala Leu Glu Ala Tyr Cys Ala Pro Arg Ala Val Ala Glu Leu
            725                 730                 735

Thr Asp His Pro Leu Phe Pro Ala Pro Trp Arg Pro Ala Leu Met Phe
            740                 745                 750

Asp Pro Arg Ala Leu Ala Ser Leu Ala Ala Arg Cys Ala Ala Pro Pro
            755                 760                 765

Pro Gly Gly Ala Pro Ala Ala Phe Gly Pro Leu Arg Ala Ser Gly Pro
        770                 775                 780

Leu Arg Arg Ala Ala Ala Trp Met Arg Gln Val Pro Asp Pro Glu Asp
785                 790                 795                 800

Val Arg Val Val Ile Leu Tyr Ser Pro Leu Pro Gly Glu Asp Leu Ala
            805                 810                 815

Ala Gly Arg Ala Gly Gly Pro Pro Glu Trp Ser Ala Glu Arg
            820                 825                 830

Gly Gly Leu Ser Cys Leu Leu Ala Ala Leu Gly Asn Arg Leu Cys Gly
            835                 840                 845

Pro Ala Thr Ala Ala Trp Ala Gly Asn Trp Thr Gly Ala Pro Asp Val
        850                 855                 860

Ser Ala Leu Gly Ala Gln Gly Val Leu Leu Ser Thr Arg Asp Leu
865                 870                 875                 880

Ala Phe Ala Gly Ala Val Glu Phe Leu Gly Leu Ala Gly Ala Cys
            885                 890                 895

Asp Arg Arg Leu Ile Val Val Asn Ala Val Arg Ala Ala Asp Trp Pro
            900                 905                 910

Ala Asp Gly Pro Val Val Ser Arg Gln His Ala Tyr Leu Ala Cys Glu
            915                 920                 925

Val Leu Pro Ala Val Gln Cys Ala Val Arg Trp Pro Ala Ala Arg Asp
        930                 935                 940

Leu Arg Arg Thr Val Leu Ala Ser Gly Arg Val Phe Gly Pro Gly Val
945                 950                 955                 960

Phe Ala Arg Val Glu Ala Ala His Ala Arg Leu Tyr Pro Asp Ala Pro
            965                 970                 975

Pro Leu Arg Leu Cys Arg Gly Ala Asn Val Arg Tyr Arg Val Arg Thr
        980                 985                 990

Arg Phe Gly Pro Asp Thr Leu Val Pro Met Ser Pro Arg Glu Tyr Arg
        995                 1000                1005

Arg Ala Val Leu Pro Ala Leu Asp Gly Arg Ala Ala Ser Gly
        1010                1015                1020

Ala Gly Asp Ala Met Ala Pro Gly Ala Pro Asp Phe Cys Glu Asp
        1025                1030                1035

Glu Ala His Ser His Arg Ala Cys Ala Arg Trp Gly Leu Gly Ala
        1040                1045                1050

Pro Leu Arg Pro Val Tyr Val Ala Leu Gly Arg Asp Ala Val Arg
        1055                1060                1065

Gly Gly Pro Ala Glu Leu Arg Gly Pro Arg Arg Glu Phe Cys Ala
```

```
                    1070               1075               1080
Arg Ala Leu Leu Glu Pro Asp Gly Asp Ala Pro Pro Leu Val Leu
        1085               1090               1095

Arg Asp Asp Ala Asp Ala Gly Pro Pro Pro Gln Ile Arg Trp Ala
        1100               1105               1110

Ser Ala Ala Gly Arg Ala Gly Thr Val Leu Ala Ala Ala Gly Gly
        1115               1120               1125

Gly Val Glu Val Val Gly Thr Ala Ala Gly Leu Ala Thr Pro Pro
        1130               1135               1140

Arg Arg Glu Pro Val Asp Met Asp Ala Glu Leu Glu Asp Asp Asp
        1145               1150               1155

Asp Gly Leu Phe Gly Glu
        1160

<210> SEQ ID NO 140
<211> LENGTH: 3384
<212> TYPE: DNA
<213> ORGANISM: Herpes simplex virus

<400> SEQUENCE: 140
atgagtgccg aacagcgtaa aaagaaaaaa accaccacca cgacccaagg acgtggagct    60
gaagttgcta tggcggatga ggatggaggc cgcttgagag ctgctgctga gactactgga   120
ggacctggat caccggaccc tgccgatgga ccccccccta caccaaaccc cgatcgtaga   180
ccggctgcta gacctggatt cggatggcat ggaggacccg aggaaaacga ggacgaggcg   240
gacgacgccg ctgccgacgc cgacgccgat gaggctgccc ctgcttctgg agaggcggta   300
gacgaacctg ctgccgatgg agttgttagc cctaggcaat tggctttgtt ggcgagcatg   360
gtagacgagg ctgtgagaac aatcccttcc cctcccccctg aacgtgatgg agcacaagag   420
gaggcggcta ggagtccctc accacccgt acacccttcta tgagagcgga ttacggcgag   480
gaaaacgacg acgacgacga tgatgatgac gacgatgatc gtgatgccgg acgctgggtt   540
aggggacctg aaaccacttc tgctgtccgt ggagcatacc ccgatcctat ggcgagtttg   600
agccctagac cacctgcccc gaggagacac caccaccacc accatcatag cgtagacgt    660
gctcctagac gtcgttctgc cgctagtgac tcttccaaat ctggctcttc ttcatctgcc   720
tcttccgctt catcttcggc ctcatcgtcc tcttcggcat ccgcttcgag tagtgatgat   780
gatgatgacg acgacgctgc tagagccccc gcttctgctg ccgaccacgc tgctggcgga   840
actttgggag ccgacgacga ggaggcggga gttcctgctc gtgccccggg agctgctccg   900
aggccttctc caccccgtgc tgaacctgct ccggctagaa caccggccgc tactgctggt   960
agactggagc gtagacgtgc ccgtgctgct gtggctggta gagatgctac tggccgcttc  1020
actgctggcc gtcctagacg tgttgaactg gacgccgatg ctgcttctgg tgctttctac  1080
gcccgttacc gtgatggtta cgtgtctggt gaaccttggc ctggcgctgg tccacctccg  1140
cccgacgtg tactctacgg tggattgggc cgtaccccccg atgacggtgg cgacgccaac  1200
cgccacgatg gtgatgatgc tagaggcaaa cccgctgccg ctgctgctcc tttgccctct  1260
gccgccgctt cccctgccga tgaacgtgct gttcctgccg gttacggtgc cgctggtgtg  1320
ttggctgctt tgggacgctt gagtgctgcc ccggctagtg ccccgctgg tgccgatgac  1380
gatgacgatg acgatggtgc tggcggaggc ggtggcggta acgtgctga ggctggacgt  1440
gttgctgttg aatgcctggc tgcctgtaga ggaatcttgg aggctctggc cgagggattc  1500
gacggagact ggcggctgt accggactg gcgggagcga ggcctgccgc tccacctcgc  1560
```

| | |
|---|---:|
| cccggtcctg ctggtgctgc cgctcctcct catgccgacg ctcctagact ccgtgcttgg | 1620 |
| ctccgtgaac tccgtttcgt tcgtgacgct ttggttctga tgagactgag aggcgacttg | 1680 |
| agagtggctg gaggatccga ggctgctgtt gctgctgtcc gtgctgtttc tttggttgct | 1740 |
| ggtgctttgg gccctgcttt gccgagatct ccccgtttgt tgtcgagtgc cgccgctgct | 1800 |
| gccgccgatt tgttgttcca aaaccaatcc ctccgccctc tgctcgccga cactgttgcc | 1860 |
| gctgccgatt ctctggctgc tccggcttct gctgctgctc ccccgctgg tgctgctccc | 1920 |
| cccgctcccc ctactccccc cccacgccca cctcgtcccg ctgccctcac acgccgtcct | 1980 |
| gctgagggac ccgatccaca aggcggctgg cgtagacaac ctcctggccc atcccataca | 2040 |
| ccggcaccat ctgccgctgc tttggaggct tactgtgctc ctcgtgctgt ggctgaactc | 2100 |
| accgatcatc cgctgttccc tgctccctgg cgtcccgccc tcatgttcga tcctagagct | 2160 |
| ttggcttcct tggccgctcg ttgtgctgcc cctcccctg gcggtgctcc ggctgctttc | 2220 |
| ggtcctctcc gtgcctctgg tccactccgc cgtgccgctg cctggatgag acaagttccc | 2280 |
| gaccctgagg atgttagagt tgtgatcttg tactcgccct tgcctggcga ggatttggcc | 2340 |
| gctggtagag ctggcggtgg cccccctcct gaatggtctg ctgaacgtgg tggttttgtct | 2400 |
| tgcttgttgg ccgccctggg aaaccgtctg tgtggtcctg ctactgctgc ttgggctgga | 2460 |
| aactggactg gcgctcccga tgtttctgct ctcggtgctc aaggagtttt gctgctctct | 2520 |
| actcgtgact tggcattcgc tggagctgtt gaattcctgg actcttggc tggcgcttgt | 2580 |
| gataggagac tcatcgtcgt aaacgctgtg agagctgccg attggcctgc cgatggtcct | 2640 |
| gttgtgtctc gtcaacacgc ttacttggct tgtgaagtgt tgcccgctgt ccaatgtgct | 2700 |
| gttcgctggc ctgctgctcg tgatctgagg cgtactgttc tggctagtgg tcgtgttttc | 2760 |
| ggacctggtg ttttcgctcg tgtcgaagct gctcacgcta actgtaccc cgatgcccca | 2820 |
| cccctccgtt tgtgtcgtgg agcaaacgtt cgctaccgtg tccgtaccctcg tttcggaccc | 2880 |
| gatactctgg ttccaatgtc ccctcgtgaa taccgtcgtg ctgttctgcc tgccctcgat | 2940 |
| ggacgtgctg ccgcttctgg cgctggtgac gctatggctc ctggcgctcc ggacttctgt | 3000 |
| gaggatgagg ctcactcaca tcgtgcctgt gcccgctggg gactgggcgc tccattgagg | 3060 |
| cctgtatacg tggcactggg ccgtgatgct gttagaggcg gacccgctga attgagaggc | 3120 |
| cctcgtcgtg aattctgtgc tagggctctg ctcgaacccg atggagatgc tcctcctttg | 3180 |
| gtactccgtg acgacgccga tgctggtcct ccccacaaa ttcgctgggc tagtgctgct | 3240 |
| ggacgtgctg gtactgtatt ggctgctgct ggcggtggc ttgaagttgt tggtactgcc | 3300 |
| gctggactcg ctacacctcc ccgccgtgaa cctgtagaca tggatgctga actcgaggat | 3360 |
| gatgacgacg gattgttcgg agag | 3384 |

<210> SEQ ID NO 141
<211> LENGTH: 3492
<212> TYPE: DNA
<213> ORGANISM: Herpes simplex virus

<400> SEQUENCE: 141

| | |
|---|---:|
| atgagtgccg aacagcgtaa aaagaaaaaa accaccacca cgacccaagg acgtggagct | 60 |
| gaagttgcta tggcggatga ggatggaggc cgcttgagag ctgctgctga gactactgga | 120 |
| ggacctggat caccggaccc tgccgatgga ccccccccta caccaaaccc cgatcgtaga | 180 |
| ccggctgcta gacctggatt cggatggcat ggaggacccg aggaaaacga ggacgaggcg | 240 |

```
gacgacgccg ctgccgacgc cgacgccgat gaggctgccc ctgcttctgg agaggcggta    300
gacgaacctg ctgccgatgg agttgttagc cctaggcaat tggctttgtt ggcgagcatg    360
gtagacgagg ctgtgagaac aatcccttcc cctcccnctg aacgtgatgg agcacaagag    420
```
*(note: line 420 as printed)*
```
gaggcggcta ggagtccctc accacccngt acaccttcta tgagagcgga ttacggcgag    480
gaaaacgacg acgacgacga tgatgatgac gacgatgatc gtgatgccgg acgctgggtt    540 agggacctg aaaccacttc tgctgtccgt ggagcatacc ccgatcctat ggcgagtttg    600
agccctagac cacctgcccc gaggagacac caccaccacc accatcatag gcgtagacgt    660
gctcctagac gtcgttctgc cgctagtgac tcttccaaat ctggctcttc ttcatctgcc    720
tcttccgctt catcttcggc ctcatcgtcc tcttcggcat ccgcttcgag tagtgatgat    780
gatgatgacg acgacgctgc tagagccccc gcttctgctg ccgaccacgc tgctggcgga    840
actttgggag ccgacgacga ggaggcggga gttcctgctc gtgccccggg agctgctccg    900
aggccttctc caccccgtgc tgaacctgct ccggctagaa caccggccgc tactgctggt    960
agactggagc gtagacgtgc ccgtgctgct gtggctggta gagatgctac tggccgcttc   1020
actgctggcc gtcctagacg tgttgaactg gacgccgatg ctgcttctgg tgctttctac   1080
gcccgttacc gtgatggtta cgtgtctggt gaaccttggc ctggcgctgg tccacctccg   1140
cccggacgtg tactctacgg tggattgggc gcaatgtcta gacgctacga ccgtgctcaa   1200
aaaggattct tgctcacgtc actgaggcgt gcttacgccc ctttgttggc ccgtgaaaac   1260
gctgccctca ctggcgcccg taccccgat gacggtggcg acgccaaccg ccacgatggt   1320
gatgatgcta gaggcaaacc cgctgccgct gctgctcctt tgccctctgc cgccgcttcc   1380
cctgccgatg aacgtgctgt tcctgccggt tacggtgccg ctggtgtgtt ggctgctttg   1440
ggacgcttga gtgctgcccc ggctagtgcc ccgctggtg ccgatgacga tgacgatgac   1500
gatggtgctg gcggaggcgg tggcggtaga cgtgctgagg ctggacgtgt tgctgttgaa   1560
tgcctggctg cctgtagagg aatcttggag gctctggccg agggattcga cggagacttg   1620
gcggctgtac cggactggc gggagcgagg cctgccgctc cacctcgccc cggtcctgct   1680
ggtgctgccg ctcctcctca tgccgacgct cctagactcc gtgcttggct ccgtgaactc   1740
cgtttcgttc gtgacgcttt ggttctgatg agactgagag gcgacttgag agtggctgga   1800
ggatccgagg ctgctgttgc tgctgtccgt gctgttcctt tggttgctgg tgctttgggc   1860
cctgctttgc cgagatctcc ccgtttgttg tcgagtgccg ccgctgctgc cgccgatttg   1920
ttgttccaaa accaatccct ccgccctctg ctcgccgaca ctgttgccgc tgccgattct   1980
ctggctgctc cggcttctgc tgctgctccc ccgctggtg ctgctccccc cgctcccct   2040 actccccccc cacgccccacc tcgtcccgct gccctcacac gccgtcctgc tgagggaccc   2100
gatccacaag gcggctggcg tagacaacct cctggcccat cccatacacc ggcaccatct   2160
gccgctgctt tggaggctta ctgtgctcct cgtgctgtgg ctgaactcac cgatcatccg   2220
ctgttccctg ctccctggcg tcccgccctc atgttcgatc ctagagcttt ggcttccttg   2280
gccgctcgtt gtgctgcccc tcccctggc ggtgctccgg ctgctttcgg tcctctccgt   2340
gcctctggtc cactccgccg tgccgctgcc tggatgagac aagttcccga ccctgaggat   2400
gttagagttg tgatcttgta ctcgcccttg cctggcgagg atttggccgc tggtagagct   2460
ggcggtggcc cccctcctga atggtctgct gaacgtggtg gtttgtcttg cttgttggcc   2520
gccctgggaa accgtctgtg tggtcctgct actgctgctt gggctggaaa ctggactggc   2580
gctcccgatg tttctgctct cggtgctcaa ggagttttgc tgctctctac tcgtgacttg   2640
```

```
gcattcgctg gagctgttga attcctggga ctcttggctg gcgcttgtga taggagactc    2700
atcgtcgtaa acgctgtgag agctgccgat tggcctgccg atggtcctgt tgtgtctcgt    2760
caacacgctt acttggcttg tgaagtgttg cccgctgtcc aatgtgctgt tcgctggcct    2820
gctgctcgtg atctgaggcg tactgttctg gctagtggtc gtgttttcgg acctggtgtt    2880
ttcgctcgtg tcgaagctgc tcacgctaga ctgtaccccg atgccccacc cctccgtttg    2940
tgtcgtggag caaacgttcg ctaccgtgtc cgtactcgtt tcggacccga tactctggtt    3000
ccaatgtccc ctcgtgaata ccgtcgtgct gttctgcctg ccctcgatgg acgtgctgcc    3060
gcttctggcg ctggtgacgc tatggctcct ggcgctccgg acttctgtga ggatgaggct    3120
cactcacatc gtgcctgtgc ccgctgggga ctgggcgctc cattgaggcc tgtatacgtg    3180
gcactgggcc gtgatgctgt tagaggcgga cccgctgaat tgagaggccc tcgtcgtgaa    3240
ttctgtgcta gggctctgct cgaacccgat ggagatgctc ctcctttggt actccgtgac    3300
gacgccgatg ctggtcctcc cccacaaatt cgctgggcta gtgctgctgg acgtgctggt    3360
actgtattgg ctgctgctgg cggtggcgtt gaagttgttg gtactgccgc tggactcgct    3420
acacctcccc gccgtgaacc tgtagacatg gatgctgaac tcgaggatga tgacgacgga    3480
ttgttcggag ag                                                        3492

<210> SEQ ID NO 142
<211> LENGTH: 9
<212> TYPE: PRT
<213> ORGANISM: Herpes simplex virus

<400> SEQUENCE: 142

Tyr Val Leu Arg Ser Val Ile Ala Lys
1               5

<210> SEQ ID NO 143
<211> LENGTH: 9
<212> TYPE: PRT
<213> ORGANISM: Herpes simplex virus

<400> SEQUENCE: 143

Asp Ile Leu Arg Val Pro Cys Met Arg
1               5

<210> SEQ ID NO 144
<211> LENGTH: 9
<212> TYPE: PRT
<213> ORGANISM: Herpes simplex virus

<400> SEQUENCE: 144

Asp Arg His Ala Gln Arg Ala Tyr Leu
1               5
```

METHODS AND COMPOSITIONS FOR TREATING HERPES

CROSS REFERENCE TO RELATED APPLICATION

This application claims benefit under 35 U.S.C. 119(e) of U.S. Provisional Application No. 62/401,148 filed Sep. 28, 2016, the contents of which are incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 27, 2017, is named 2007781-0180_SL.txt and is 322,611 bytes in size.

BACKGROUND

Herpes simplex viruses (HSVs) are a main cause of genital ulcers worldwide, (see, the world wide web at the hypertext protocol transfer address of "who.int/bulletin/volumes/86/10/07-046128/en/index"). Of the 2 types of HSV, type 2 (HSV-2) is a more common cause of genital herpes and one of the most common sexually transmitted diseases with nearly 500 million people affected worldwide. Evidence of infection, by serologic studies, is present in 1 out of every 6 people aged 14 to 49 in the United States (see, the world wide web at the hypertext protocol transfer address of "niaid.nih.gov/topics/genitalherpes/Pages/default"; Centers for Disease Control, MMWR Morb Mortal Wkly Rep. (2010) 59:456-9). Women are more commonly infected than men, with 1 out of every 5 women in the US having evidence of infection. Certain groups, such as people with human immunodeficiency virus (HIV) and commercial sex workers, have high rates of infection ranging from 60% to 95%, (Kimberlin & Rouse, New Engl J Med. (2004) 350:1970-7; Gupta et al., Lancet. (2007) 370:2127-37).

To date, there are no known curative treatments or approved therapeutic vaccines for HSV-2 infection. Current therapy is directed at reducing the duration of primary disease or reducing the duration or frequency of secondary outbreaks. Accordingly, there remains a need for effective therapies to treat HSV-2 infection.

SUMMARY

The invention is based, at least in part, on the discovery that administration of an immunogenic composition and an antiviral therapy is effective therapy for herpes, e.g., herpes infection. Accordingly, in one aspect, the disclosure features a method of treating herpes infection. In some embodiments, the method comprises administering an antiviral therapy (e.g., an antiviral therapy described herein, e.g., famciclovir, valacyclovir, acyclovir or a combination thereof) to a subject. In some embodiments, the subject is receiving and/or has received an immunogenic composition (e.g., a vaccine composition described herein).

In some embodiments, efficacy of the immunogenic composition (e.g., vaccine composition) is improved in the subject, e.g., over a time period, relative to a subject receiving neither the immunogenic composition (e.g., vaccine composition) nor the antiviral therapy, relative to a subject receiving only the immunogenic composition (e.g., vaccine composition), or relative to a subject receiving only the antiviral therapy. In some embodiments, efficacy of the antiviral therapy is improved in the subject, e.g., over a time period, relative to a subject receiving neither the immunogenic composition (e.g., vaccine composition) nor the antiviral therapy, relative to a subject receiving only the immunogenic composition (e.g., vaccine composition) or only the antiviral therapy. In some embodiments, efficacy of the immunogenic composition (e.g., vaccine composition) and efficacy of the antiviral therapy is improved in the subject, e.g., over a time period, relative to a subject receiving neither the immunogenic composition (e.g., vaccine composition) nor the antiviral therapy, relative to a subject receiving only the immunogenic composition (e.g., vaccine composition) or only the antiviral therapy.

In some embodiments, the immunogenic composition (e.g., vaccine composition) comprises an HSV-2 gD2 polypeptide (or immunogenic fragment) and/or an HSV-2 ICP4 polypeptide (or immunogenic fragment). In some embodiments, the gD2 polypeptide has an internal deletion of all or part of the transmembrane domain. In some embodiments, the ICP4 polypeptide comprises at least 8 contiguous amino acids of an ICP4 polypeptide. In some embodiments, the immunogenic composition comprises an HSV-2 gD2 polypeptide comprising (i) an amino acid sequence having at least 85%, 90%, 95%, 97%, 98%, 99%, or 100% identity to SEQ ID NO:4, or an amino acid sequence having at least 85%, 90%, 95%, 97%, 98%, 99%, or 100% identity to SEQ ID NO:4 and lacking 1, 2, 3, 4, 5, 6, 7, 8, 9, or 10 amino acids from the amino terminus and/or carboxyl terminus of SEQ ID NO:4; and (ii) an HSV-2 ICP4 polypeptide comprising an amino acid sequence having at least 85%, 90%, 95%, 97%, 98%, 99%, or 100% identity to SEQ ID NO:2, or an amino acid sequence having at least 85%, 90%, 95%, 97%, 98%, 99%, or 100% identity to SEQ ID NO:2 and lacking 1, 2, 3, 4, 5, 6, 7, 8, 9, or 10 amino acids from the amino terminus and/or carboxyl terminus of SEQ ID NO:2. In some embodiments, the immunogenic composition comprises an adjuvant, e.g., one or more purified fractions of *Quillaja saponins*.

In some embodiments, efficacy of the immunogenic composition (e.g., vaccine composition) and/or the antiviral therapy is measured or indicated by one or more of: a genital herpes recurrence-free period, an increase in time to first herpes recurrence, an increase in time to next herpes recurrence, a decrease in genital herpes lesion rate, a decrease in genital herpes lesion frequency, a decrease in genital herpes lesion duration, a decrease in rate of genital herpes outbreaks, a decrease in duration of genital herpes outbreaks, a decrease in anogenital HSV shedding rate, a decrease in anogenital HSV shedding magnitude, a decrease or no increase in antiviral dose, a decrease in one or more herpes signs or symptoms, an increase in health-related quality of life, a decrease in time to lesion healing, a decrease in time to cessation of pain, a decrease in time to cessation of viral shedding, a decrease in herpes recurrence rate, a decrease in rate of symptomatic acquisition of herpes in a susceptible partner, an increase in humoral response, and an increase in cellular response.

In some embodiments, the method further comprises administering the antiviral therapy (e.g., an antiviral therapy described herein, e.g., famciclovir, valacyclovir, acyclovir or a combination thereof) to a population of subjects receiving and/or who have received an immunogenic composition (e.g., a vaccine composition described herein). In some embodiments, efficacy of the immunogenic composition (e.g., vaccine composition) is improved in the population (or a subset of the population), e.g., over a time period, relative to a subject or population of subjects receiving neither the immunogenic composition (e.g., vaccine composition) nor the antiviral therapy, relative to a subject or population of subjects receiving only the immunogenic composition (e.g., vaccine composition), or relative to a subject or population of subjects receiving only the antiviral therapy. In some embodiments, efficacy of the antiviral therapy is improved in the population (or a subset of the population), e.g., over a time period, relative to a subject or population of subjects receiving neither the immunogenic composition (e.g., vaccine composition) nor the antiviral therapy, relative to a subject or population of subjects receiving only the immunogenic composition (e.g., vaccine composition), or relative to a subject or population of subjects receiving only the antiviral therapy. In some embodiments, efficacy of the immunogenic composition (e.g., vaccine composition) and efficacy of the antiviral therapy is improved in the population (or a subset of the population), e.g., over a time period, relative to a subject or population of subjects receiving neither the immunogenic composition (e.g., vaccine composition) nor the antiviral therapy, relative to a subject or population of subjects receiving only the immunogenic composition (e.g., vaccine composition), or relative to a subject or population of subjects receiving only the antiviral therapy.

In some embodiments, efficacy of the immunogenic composition (e.g., vaccine composition) and/or the antiviral therapy is measured or indicated by one or more of: a genital herpes recurrence-free period, an increase in time to first herpes recurrence, an increase in time to next herpes recurrence, a decrease in genital herpes lesion rate, a decrease in genital herpes lesion frequency, a decrease in genital herpes lesion duration, a decrease in rate of genital herpes outbreaks, a decrease in duration of genital herpes outbreaks, a decrease in anogenital HSV shedding rate, a decrease in anogenital HSV shedding magnitude, a decrease or no increase in antiviral dose, a decrease in one or more herpes signs or symptoms, an increase in health-related quality of life, a decrease in time to lesion healing, a decrease in time to cessation of pain, a decrease in time to cessation of viral shedding, a decrease in herpes recurrence rate, a decrease in rate of symptomatic acquisition of herpes in a susceptible partner, an increase in humoral response, and an increase in cellular response.

In another aspect, the disclosure features a method of treating herpes infection. In some embodiments, the method comprises administering an antiviral therapy (e.g., an antiviral therapy described herein, e.g., famciclovir, valacyclovir, acyclovir or a combination thereof) to a population of subjects. In some embodiments, the population of subjects is receiving and/or has received an immunogenic composition (e.g., a vaccine composition described herein).

In some embodiments, efficacy of the immunogenic composition (e.g., vaccine composition) is improved in the population (or a subset of the population), e.g., over a time period, relative to a subject or population of subjects receiving neither the immunogenic composition (e.g., vaccine composition) nor the antiviral therapy, relative to a subject or population of subjects receiving only the immunogenic composition (e.g., vaccine composition), or relative to a subject or population of subjects receiving only the antiviral therapy. In some embodiments, efficacy of the antiviral therapy is improved in the population (or a subset of the population), e.g., over a time period, relative to a subject or population of subjects receiving neither the immunogenic composition (e.g., vaccine composition) nor the antiviral therapy, relative to a subject or population of subjects receiving only the immunogenic composition (e.g., vaccine composition), or relative to a subject or population of subjects receiving only the antiviral therapy. In some embodiments, efficacy of the immunogenic composition (e.g., vaccine composition) and efficacy of the antiviral therapy is improved in the population (or a subset of the population), e.g., over a time period, relative to a subject or population of subjects receiving neither the immunogenic composition (e.g., vaccine composition) nor the antiviral therapy, relative to a subject or population of subjects receiving only the immunogenic composition (e.g., vaccine composition), or relative to a subject or population of subjects receiving only the antiviral therapy.

In some embodiments, the immunogenic composition (e.g., vaccine composition) comprises an HSV-2 gD2 polypeptide (or immunogenic fragment) and/or an HSV-2 ICP4 polypeptide (or immunogenic fragment). In some embodiments, the gD2 polypeptide has an internal deletion of all or part of the transmembrane domain. In some embodiments, the ICP4 polypeptide comprises at least 8 contiguous amino acids of an ICP4 polypeptide. In some embodiments, the immunogenic composition comprises an HSV-2 gD2 polypeptide comprising (i) an amino acid sequence having at least 85%, 90%, 95%, 97%, 98%, 99%, or 100% identity to SEQ ID NO:4, or an amino acid sequence having at least 85%, 90%, 95%, 97%, 98%, 99%, or 100% identity to SEQ ID NO:4 and lacking 1, 2, 3, 4, 5, 6, 7, 8, 9, or 10 amino acids from the amino terminus and/or carboxyl terminus of SEQ ID NO:4; and (ii) an HSV-2 ICP4 polypeptide comprising an amino acid sequence having at least 85%, 90%, 95%, 97%, 98%, 99%, or 100% identity to SEQ ID NO:2, or an amino acid sequence having at least 85%, 90%, 95%, 97%, 98%, 99%, or 100% identity to SEQ ID NO:2 and lacking 1, 2, 3, 4, 5, 6, 7, 8, 9, or 10 amino acids from the amino terminus and/or carboxyl terminus of SEQ ID NO:2. In some embodiments, the immunogenic composition comprises an adjuvant, e.g., one or more purified fractions of *Quillaja saponins*.

In some embodiments, efficacy of the immunogenic composition (e.g., vaccine composition) and/or the antiviral therapy is measured or indicated by one or more of: a genital herpes recurrence-free period, an increase in time to first herpes recurrence, an increase in time to next herpes recurrence, a decrease in genital herpes lesion rate, a decrease in genital herpes lesion frequency, a decrease in genital herpes lesion duration, a decrease in rate of genital herpes outbreaks, a decrease in duration of genital herpes outbreaks, a decrease in anogenital HSV shedding rate, a decrease in anogenital HSV shedding magnitude, a decrease or no increase in antiviral dose, a decrease in one or more herpes signs or symptoms, an increase in health-related quality of life, a decrease in time to lesion healing, a decrease in time to cessation of pain, a decrease in time to cessation of viral shedding, a decrease in herpes recurrence rate, a decrease in rate of symptomatic acquisition of herpes in a susceptible partner, an increase in humoral response, and an increase in cellular response.

In another aspect, the disclosure features a method of treating herpes infection. In some embodiments, the method comprises administering to a subject an immunogenic composition (e.g., a vaccine composition described herein). In some embodiments, the subject is receiving and/or has received an antiviral therapy (e.g., an antiviral therapy described herein, e.g., famciclovir, valacyclovir, acyclovir or a combination thereof).

In some embodiments, efficacy of the immunogenic composition (e.g., vaccine composition) is improved in the subject, e.g., over a time period, relative to a subject receiving neither the immunogenic composition (e.g., vaccine composition) nor the antiviral therapy, relative to a subject receiving only the immunogenic composition (e.g., vaccine composition), or relative to a subject receiving only the antiviral therapy. In some embodiments, efficacy of the antiviral therapy is improved in the subject, e.g., over a time period, relative to a subject receiving neither the immunogenic composition (e.g., vaccine composition) nor the antiviral therapy, relative to a subject receiving only the immunogenic composition (e.g., vaccine composition) or only the antiviral therapy. In some embodiments, efficacy of the immunogenic composition (e.g., vaccine composition) and efficacy of the antiviral therapy is improved in the subject, e.g., over a time period, relative to a subject receiving neither the immunogenic composition (e.g., vaccine composition) nor the antiviral therapy, relative to a subject receiving only the immunogenic composition (e.g., vaccine composition) or only the antiviral therapy.

In some embodiments, the immunogenic composition (e.g., vaccine composition) comprises an HSV-2 gD2 polypeptide (or immunogenic fragment) and/or an HSV-2 ICP4 polypeptide (or immunogenic fragment). In some embodiments, the gD2 polypeptide has an internal deletion of all or part of the transmembrane domain. In some embodiments, the ICP4 polypeptide comprises at least 8 contiguous amino acids of an ICP4 polypeptide. In some embodiments, the immunogenic composition comprises an HSV-2 gD2 polypeptide comprising (i) an amino acid sequence having at least 85%, 90%, 95%, 97%, 98%, 99%, or 100% identity to SEQ ID NO:4, or an amino acid sequence having at least 85%, 90%, 95%, 97%, 98%, 99%, or 100% identity to SEQ ID NO:4 and lacking 1, 2, 3, 4, 5, 6, 7, 8, 9, or 10 amino acids from the amino terminus and/or carboxyl terminus of SEQ ID NO:4; and (ii) an HSV-2 ICP4 polypeptide comprising an amino acid sequence having at least 85%, 90%, 95%, 97%, 98%, 99%, or 100% identity to SEQ ID NO:2, or an amino acid sequence having at least 85%, 90%, 95%, 97%, 98%, 99%, or 100% identity to SEQ ID NO:2 and lacking 1, 2, 3, 4, 5, 6, 7, 8, 9, or 10 amino acids from the amino terminus and/or carboxyl terminus of SEQ ID NO:2. In some embodiments, the immunogenic composition comprises an adjuvant, e.g., one or more purified fractions of *Quillaja saponins*.

In some embodiments, efficacy of the immunogenic composition (e.g., vaccine composition) and/or the antiviral therapy is measured or indicated by one or more of: a genital herpes recurrence-free period, an increase in time to first herpes recurrence, an increase in time to next herpes recurrence, a decrease in genital herpes lesion rate, a decrease in genital herpes lesion frequency, a decrease in genital herpes lesion duration, a decrease in rate of genital herpes outbreaks, a decrease in duration of genital herpes outbreaks, a decrease in anogenital HSV shedding rate, a decrease in anogenital HSV shedding magnitude, a decrease or no increase in antiviral dose, a decrease in one or more herpes signs or symptoms, an increase in health-related quality of life, a decrease in time to lesion healing, a decrease in time to cessation of pain, a decrease in time to cessation of viral shedding, a decrease in herpes recurrence rate, a decrease in rate of symptomatic acquisition of herpes in a susceptible partner, an increase in humoral response, and an increase in cellular response.

In some embodiments, the method further comprises administering the immunogenic composition (e.g., vaccine composition) to a population of subjects receiving and/or who have received antiviral therapy (e.g., an antiviral therapy described herein, e.g., famciclovir, valacyclovir, acyclovir or a combination thereof). In some embodiments, efficacy of the immunogenic composition (e.g., vaccine composition) is improved in the population (or a subset of the population), e.g., over a time period, relative to a subject or population of subjects receiving neither the immunogenic composition (e.g., vaccine composition) nor the antiviral therapy, relative to a subject or population of subjects receiving only the immunogenic composition (e.g., vaccine composition), or relative to a subject or population of subjects receiving only the antiviral therapy. In some embodiments, efficacy of the antiviral therapy is improved in the population (or a subset of the population), e.g., over a time period, relative to a subject or population of subjects receiving neither the immunogenic composition (e.g., vaccine composition) nor the antiviral therapy, relative to a subject or population of subjects receiving only the immunogenic composition (e.g., vaccine composition), or relative to a subject or population of subjects receiving only the antiviral therapy. In some embodiments, efficacy of the immunogenic composition (e.g., vaccine composition) and efficacy of the antiviral therapy is improved in the population (or a subset of the population), e.g., over a time period, relative to a subject or population of subjects receiving neither the immunogenic composition (e.g., vaccine composition) nor the antiviral therapy, relative to a subject or population of subjects receiving only the immunogenic composition (e.g., vaccine composition), or relative to a subject or population of subjects receiving only the antiviral therapy.

In some embodiments, efficacy of the immunogenic composition (e.g., vaccine composition) and/or the antiviral therapy is measured or indicated by one or more of: a genital herpes recurrence-free period, an increase in time to first herpes recurrence, an increase in time to next herpes recurrence, a decrease in genital herpes lesion rate, a decrease in genital herpes lesion frequency, a decrease in genital herpes lesion duration, a decrease in rate of genital herpes outbreaks, a decrease in duration of genital herpes outbreaks, a decrease in anogenital HSV shedding rate, a decrease in anogenital HSV shedding magnitude, a decrease or no increase in antiviral dose, a decrease in one or more herpes signs or symptoms, an increase in health-related quality of life, a decrease in time to lesion healing, a decrease in time to cessation of pain, a decrease in time to cessation of viral shedding, a decrease in herpes recurrence rate, a decrease in rate of symptomatic acquisition of herpes in a susceptible partner, an increase in humoral response, and an increase in cellular response.

In another aspect, the disclosure features a method of treating herpes infection. In some embodiments, the method comprises administering an immunogenic composition (e.g., vaccine composition) to a population of subjects. In some embodiments, the population of subjects is receiving and/or has received antiviral therapy (e.g., an antiviral therapy described herein, e.g., famciclovir, valacyclovir, acyclovir or a combination thereof).

In some embodiments, efficacy of the immunogenic composition (e.g., vaccine composition) is improved in the population (or a subset of the population), e.g., over a time period, relative to a subject or population of subjects receiving neither the immunogenic composition (e.g., vaccine composition) nor the antiviral therapy, relative to a subject or population of subjects receiving only the immunogenic composition (e.g., vaccine composition), or relative to a subject or population of subjects receiving only the antiviral therapy. In some embodiments, efficacy of the antiviral therapy is improved in the population (or a subset of the population), e.g., over a time period, relative to a subject or population of subjects receiving neither the immunogenic composition (e.g., vaccine composition) nor the antiviral therapy, relative to a subject or population of subjects receiving only the immunogenic composition (e.g., vaccine composition), or relative to a subject or population of subjects receiving only the antiviral therapy. In some embodiments, efficacy of the immunogenic composition (e.g., vaccine composition) and efficacy of the antiviral therapy is improved in the population (or a subset of the population), e.g., over a time period, relative to a subject or population of subjects receiving neither the immunogenic composition (e.g., vaccine composition) nor the antiviral therapy, relative to a subject or population of subjects receiving only the immunogenic composition (e.g., vaccine composition), or relative to a subject or population of subjects receiving only the antiviral therapy.

In some embodiments, the immunogenic composition (e.g., vaccine composition) comprises an HSV-2 gD2 polypeptide (or immunogenic fragment) and/or an HSV-2 ICP4 polypeptide (or immunogenic fragment). In some embodiments, the gD2 polypeptide has an internal deletion of all or part of the transmembrane domain. In some embodiments, the ICP4 polypeptide comprises at least 8 contiguous amino acids of an ICP4 polypeptide. In some embodiments, the immunogenic composition comprises an HSV-2 gD2 polypeptide comprising (i) an amino acid sequence having at least 85%, 90%, 95%, 97%, 98%, 99%, or 100% identity to SEQ ID NO:4, or an amino acid sequence having at least 85%, 90%, 95%, 97%, 98%, 99%, or 100% identity to SEQ ID NO:4 and lacking 1, 2, 3, 4, 5, 6, 7, 8, 9, or 10 amino acids from the amino terminus and/or carboxyl terminus of SEQ ID NO:4; and (ii) an HSV-2 ICP4 polypeptide comprising an amino acid sequence having at least 85%, 90%, 95%, 97%, 98%, 99%, or 100% identity to SEQ ID NO:2, or an amino acid sequence having at least 85%, 90%, 95%, 97%, 98%, 99%, or 100% identity to SEQ ID NO:2 and lacking 1, 2, 3, 4, 5, 6, 7, 8, 9, or 10 amino acids from the amino terminus and/or carboxyl terminus of SEQ ID NO:2. In some embodiments, the immunogenic composition comprises an adjuvant, e.g., one or more purified fractions of *Quillaja saponins*.

In some embodiments, efficacy of the immunogenic composition (e.g., vaccine composition) and/or the antiviral therapy is measured or indicated by one or more of: a genital herpes recurrence-free period, an increase in time to first herpes recurrence, an increase in time to next herpes recurrence, a decrease in genital herpes lesion rate, a decrease in genital herpes lesion frequency, a decrease in genital herpes lesion duration, a decrease in rate of genital herpes outbreaks, a decrease in duration of genital herpes outbreaks, a decrease in anogenital HSV shedding rate, a decrease in anogenital HSV shedding magnitude, a decrease or no increase in antiviral dose, a decrease in one or more herpes signs or symptoms, an increase in health-related quality of life, a decrease in time to lesion healing, a decrease in time to cessation of pain, a decrease in time to cessation of viral shedding, a decrease in herpes recurrence rate, a decrease in rate of symptomatic acquisition of herpes in a susceptible partner, an increase in humoral response, and an increase in cellular response.

In another aspect, the disclosure features a method of treating herpes infection. In some embodiments, the method comprises administering to a subject (i) an antiviral therapy (e.g., an antiviral therapy described herein, e.g., famciclovir, valacyclovir, acyclovir or a combination thereof); and (ii) an immunogenic composition (e.g., a vaccine composition described herein). In some embodiments, the antiviral therapy and the immunogenic composition are administered concurrently. In some embodiments, the antiviral therapy and the immunogenic composition are administered sequentially.

In some embodiments, efficacy of the immunogenic composition (e.g., vaccine composition) is improved in the subject, e.g., over a time period, relative to a subject receiving neither the immunogenic composition (e.g., vaccine composition) nor the antiviral therapy, relative to a subject receiving only the immunogenic composition (e.g., vaccine composition), or relative to a subject receiving only the antiviral therapy. In some embodiments, efficacy of the antiviral therapy is improved in the subject, e.g., over a time period, relative to a subject receiving neither the immunogenic composition (e.g., vaccine composition) nor the antiviral therapy, relative to a subject receiving only the immunogenic composition (e.g., vaccine composition) or only the antiviral therapy. In some embodiments, efficacy of the immunogenic composition (e.g., vaccine composition) and efficacy of the antiviral therapy is improved in the subject, e.g., over a time period, relative to a subject receiving neither the immunogenic composition (e.g., vaccine composition) nor the antiviral therapy, relative to a subject receiving only the immunogenic composition (e.g., vaccine composition) or only the antiviral therapy.

In some embodiments, the immunogenic composition (e.g., vaccine composition) comprises an HSV-2 gD2 polypeptide (or immunogenic fragment) and/or an HSV-2 ICP4 polypeptide (or immunogenic fragment). In some embodiments, the gD2 polypeptide has an internal deletion of all or part of the transmembrane domain. In some embodiments, the ICP4 polypeptide comprises at least 8 contiguous amino acids of an ICP4 polypeptide. In some embodiments, the immunogenic composition comprises an HSV-2 gD2 polypeptide comprising (i) an amino acid sequence having at least 85%, 90%, 95%, 97%, 98%, 99%, or 100% identity to SEQ ID NO:4, or an amino acid sequence having at least 85%, 90%, 95%, 97%, 98%, 99%, or 100% identity to SEQ ID NO:4 and lacking 1, 2, 3, 4, 5, 6, 7, 8, 9, or 10 amino acids from the amino terminus and/or carboxyl terminus of SEQ ID NO:4; and (ii) an HSV-2 ICP4 polypeptide comprising an amino acid sequence having at least 85%, 90%, 95%, 97%, 98%, 99%, or 100% identity to SEQ ID NO:2, or an amino acid sequence having at least 85%, 90%, 95%, 97%, 98%, 99%, or 100% identity to SEQ ID NO:2 and lacking 1, 2, 3, 4, 5, 6, 7, 8, 9, or 10 amino acids from the amino terminus and/or carboxyl terminus of SEQ ID NO:2. In some embodiments, the immunogenic composition comprises an adjuvant, e.g., one or more purified fractions of *Quillaja saponins*.

In some embodiments, efficacy of the immunogenic composition (e.g., vaccine composition) and/or the antiviral therapy is measured or indicated by one or more of: a genital herpes recurrence-free period, an increase in time to first herpes recurrence, an increase in time to next herpes recurrence, a decrease in genital herpes lesion rate, a decrease in genital herpes lesion frequency, a decrease in genital herpes lesion duration, a decrease in rate of genital herpes outbreaks, a decrease in duration of genital herpes outbreaks, a decrease in anogenital HSV shedding rate, a decrease in anogenital HSV shedding magnitude, a decrease or no increase in antiviral dose, a decrease in one or more herpes signs or symptoms, an increase in health-related quality of life, a decrease in time to lesion healing, a decrease in time to cessation of pain, a decrease in time to cessation of viral shedding, a decrease in herpes recurrence rate, a decrease in rate of symptomatic acquisition of herpes in a susceptible partner, an increase in humoral response, and an increase in cellular response.

In some embodiments, the method comprises administering (i) an antiviral therapy (e.g., an antiviral therapy described herein, e.g., famciclovir, valacyclovir, acyclovir or a combination thereof); and (ii) an immunogenic composition (e.g., a vaccine composition described herein to a population of subjects. In some embodiments, efficacy of the immunogenic composition (e.g., vaccine composition) is improved in the population (or a subset of the population), e.g., over a time period, relative to a subject or population of subjects receiving neither the immunogenic composition (e.g., vaccine composition) nor the antiviral therapy, relative to a subject or population of subjects receiving only the immunogenic composition (e.g., vaccine composition), or relative to a subject or population of subjects receiving only the antiviral therapy. In some embodiments, efficacy of the antiviral therapy is improved in the population (or a subset of the population), e.g., over a time period, relative to a subject or population of subjects receiving neither the immunogenic composition (e.g., vaccine composition) nor the antiviral therapy, relative to a subject or population of subjects receiving only the immunogenic composition (e.g., vaccine composition), or relative to a subject or population of subjects receiving only the antiviral therapy. In some embodiments, efficacy of the immunogenic composition (e.g., vaccine composition) and efficacy of the antiviral therapy is improved in the population (or a subset of the population), e.g., over a time period, relative to a subject or population of subjects receiving neither the immunogenic composition (e.g., vaccine composition) nor the antiviral therapy, relative to a subject or population of subjects receiving only the immunogenic composition (e.g., vaccine composition), or relative to a subject or population of subjects receiving only the antiviral therapy.

In some embodiments, efficacy of the immunogenic composition (e.g., vaccine composition) and/or the antiviral therapy is measured or indicated by one or more of: a genital herpes recurrence-free period, an increase in time to first herpes recurrence, an increase in time to next herpes recurrence, a decrease in genital herpes lesion rate, a decrease in genital herpes lesion frequency, a decrease in genital herpes lesion duration, a decrease in rate of genital herpes outbreaks, a decrease in duration of genital herpes outbreaks, a decrease in anogenital HSV shedding rate, a decrease in anogenital HSV shedding magnitude, a decrease or no increase in antiviral dose, a decrease in one or more herpes signs or symptoms, an increase in health-related quality of life, a decrease in time to lesion healing, a decrease in time to cessation of pain, a decrease in time to cessation of viral shedding, a decrease in herpes recurrence rate, a decrease in rate of symptomatic acquisition of herpes in a susceptible partner, an increase in humoral response, and an increase in cellular response.

In any of the aspects described herein, a subject or population of subjects is receiving, has received, or is administered about 100 mg, 150 mg, 200 mg, 250 mg, 300 mg, 350 mg, 400 mg, 450 mg, 500 mg, 600 mg, 700 mg, 800 mg, 900 mg, 1 g, 1.1 g, 1.2 g, 1.3 g, 1.4 g, 1.5 g, 100-300 mg, 200-400 mg, 300-500 mg, 400-600 mg, 500-700 mg, 600-800 mg, 700-900 mg, 800-1000 mg, or more, of antiviral therapy per dose.

In any of the aspects described herein, a subject or population of subjects is receiving, has received, or is administered an immunogenic composition described herein comprising about 10 µg, 20 µg, 30 µg, 60 µg, or 100 µg of each of a gD2 polypeptide described herein and an ICP4 polypeptide described herein and/or about 25 µg, 50 µg or 75 µg of adjuvant described herein.

In any of the aspects described herein, efficacy of the immunogenic composition and/or antiviral therapy is assessed at, e.g., at least 3 months, 6 months, 12 months, 18 months, 24 months, 3 years, 4 years, 5 years, 6 years, 7 years, 8 years, 9 years, or 10 years after administration of the immunogenic composition and/or antiviral therapy.

In any of the aspects described herein, the subject or population of subjects: have not received and/or are not receiving therapy comprising tenofovir, lysine, a supplement or medication, other than valacyclovir, e.g., a therapy known to or purported to affect herpes outbreak frequency or intensity; do not have a history of ocular herpes infection, herpes-related erythema multiforme, herpes meningitis or herpes encephalitis; do not have active genital HSV-2 lesions; are not immunocompromised; are not receiving systemic immunosuppressive medication; do not have an autoimmune disease; have not previously had an autoimmune disease; do not have HIV, hepatitis B or hepatitis C; do not have history of hypersensitivity to any component of the vaccine formulation; do not have a clinically significant laboratory abnormality except for (i) creatinine kinase in subjects with an identified exercise regimen and hepatic and renal enzyme levels within normal limits or (ii) isolated Grade 2 unconjugated bilirubin in fasting subjects with a history of Gilbert's syndrome; have not received any other vaccine containing an HSV-2 antigen; have not received an investigational product within 30 days prior to the first dose of the vaccine formulation; have not received a blood product within 90 days prior to the first dose of the vaccine formulation; have not received a live vaccine within 28 days prior to the first dose of the vaccine formulation; have not received any other vaccine within 14 days prior to the first dose of the vaccine formulation; do not receive any other vaccine from the first dose until 28 days after the third dose; are not pregnant or nursing; or any combination thereof.

In any of the aspects described herein, the subject or population of subjects: is male, female or non-pregnant female; is at least 18 years old and less than 51 years old, is at least 10, 11, 12, 13, 14, 15, 16, 17, 18, 19, 20, 25, 30, 35, 40, 45, 50, 55, or 60 years old, are 51 years or older; are receiving antiviral therapy; have a history of at least one genital herpes outbreak while on antiviral therapy within about 1, 2, 3, 4, 5, 6, 7, 8, 9, 10, 11, or 12 months of treatment; have a history of greater than 1, 2, 3, 4, 5, 6, 7, 8, 9, 10, or more outbreaks of genital herpes within one year if not receiving antiviral therapy; have been diagnosed with genital herpes infection for greater than 6, 7, 8, 9, 10, 11, 12, 13, 14, 15, 16, 17, 18, or more months; use contraception for about 1, 7, 14, 21, 28, 35, or 42 days before and/or about 15, 30, 45, 60, 75, 90, 105, or 120 days after treatment with the immunogenic composition; or any combination thereof.

In any of the aspects described herein, the immunogenic composition treats infection by HSV-1, HSV-2, or HSV-1 and HSV-2 in the subject.

BRIEF DESCRIPTION OF THE DRAWINGS

The Figures described below, that together make up the Drawing, are for illustration purposes only, not for limitation.

FIGS. 1A-1D depict exemplary Toxicity Grading Scale for Healthy Adult and Adolescent Volunteers Enrolled in Preventive Vaccine Clinical Trials.

DEFINITIONS

Figure 2:
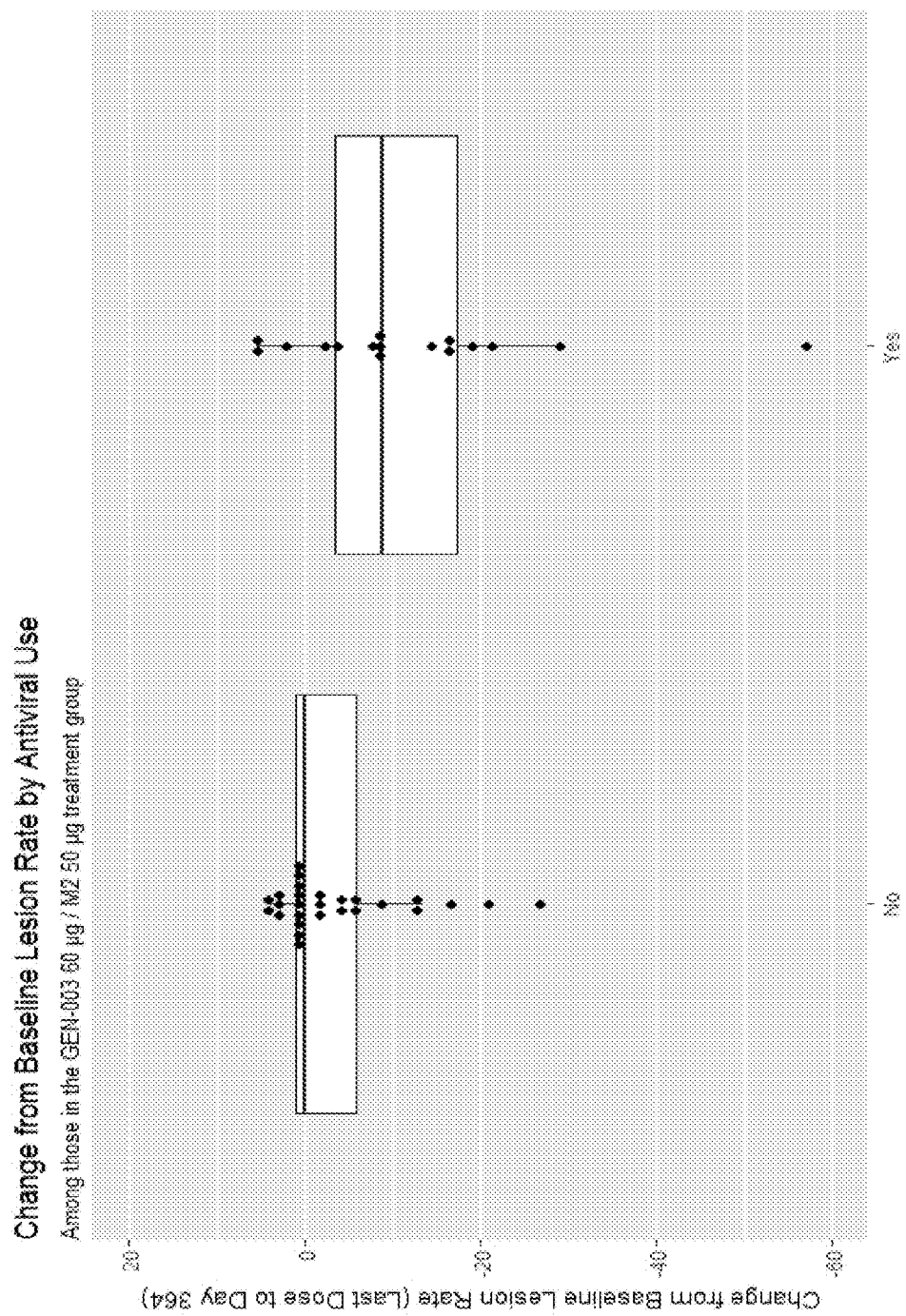
FIG. 2 depicts exemplary data showing the change from baseline genital lesion rates for those in the 60 μg GEN-003+50 μg Matrix-M2 treatment group who never took antiviral therapy during the study period and those who took antiviral therapy at least once.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Amelioration: as used herein, refers to the prevention, reduction or palliation of a state, or improvement of the state of a subject. Amelioration includes, but does not require complete recovery or complete prevention of a disease, disorder or condition (e.g., radiation injury).

Inhibitor: As used herein, the term "inhibitor" refers to an agent, condition, or event whose presence, level, degree, type, or form correlates with decreased level or activity of another agent (i.e., the inhibited agent, or target). In general, an inhibitor may be or include an agent of any chemical class including, for example, small molecules, polypeptides, nucleic acids, carbohydrates, lipids, metals, and/or any other entity, condition or event that shows the relevant inhibitory activity. In some embodiments, an inhibitor may be direct (in which case it exerts its influence directly upon its target, for example by binding to the target); in some embodiments, an inhibitor may be indirect (in which case it exerts its influence by interacting with and/or otherwise altering a regulator of the target, so that level and/or activity of the target is reduced).

Antiviral agent: As used herein, the term "antiviral agent" refers to a class of medication used specifically for treating viral infections by inhibiting, deactivating, or destroying virus particles. In general, an antiviral agent may be or comprises a compound of any chemical class (e.g., a small molecule, metal, nucleic acid, polypeptide, lipid and/or carbohydrate). In some embodiments, an antiviral agent is or comprises an antibody or antibody mimic. In some embodiments, an antiviral agent is or comprises a nucleic acid agent (e.g., an antisense oligonucleotide, a siRNA, a shRNA, etc) or mimic thereof. In some embodiments, an antiviral agent is or comprises a small molecule. In some embodiments, an antiviral agent is or comprises a naturally-occurring compound (e.g., small molecule). In some embodiments, an antiviral agent has a chemical structure that is generated and/or modified by the hand of man.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biologically active: as used herein, refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

Combination therapy: As used herein, the term "combination therapy" refers to those situations in which a subject is simultaneously exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agents or modalities to a subject receiving the other agents or modalities in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Comparable: As used herein, the term "comparable" refers to two or more agents, entities, situations, sets of conditions, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Corresponding to: As used herein designates the position/identity of a structural element in a compound or composition through comparison with an appropriate reference compound or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids.

Determine: Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Diagnostic information: As used herein, "diagnostic information" or "information for use in diagnosis" is information that is useful in determining whether a patient has a disease, disorder or condition and/or in classifying a disease, disorder or condition into a phenotypic category or any category having significance with regard to prognosis of a disease, disorder or condition, or likely response to treatment (either treatment in general or any particular treatment) of a disease, disorder or condition. Similarly, "diagnosis" refers to providing any type of diagnostic information, including, but not limited to, whether a subject is likely to have or develop a disease, disorder or condition, state, staging or characteristic of a disease, disorder or condition as manifested in the subject, information related to the nature or classification of a tumor, information related to prognosis and/or information useful in selecting an appropriate treatment. Selection of treatment may include the choice of a particular therapeutic agent or other treatment modalitiy such as surgery, radiation, etc., a choice about whether to withhold or deliver therapy, a choice relating to dosing regimen (e.g., frequency or level of one or more doses of a particular therapeutic agent or combination of therapeutic agents), etc.

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer o a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

Fragment: A "fragment" of a material or entity as described herein has a structure that includes a discrete portion of the whole, but lacks one or more moieties found in the whole. In some embodiments, a fragment consists of such a discrete portion. In some embodiments, a fragment consists of or comprises a characteristic structural element or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer. The whole material or entity may in some embodiments be referred to as the "parent" of the whole.

Functional: As used herein, a "functional" biological molecule is a biological molecule in a form in which it exhibits a property and/or activity by which it is characterized. A biological molecule may have two functions (i.e., bifunctional) or many functions (i.e., multifunctional).

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgap-dna.CMP matrix.

Improve," "increase" or "reduce: As used herein or grammatical equivalents thereof, indicate values that are relative to a baseline measurement, such as a measurement in the same individual prior to initiation of a treatment described herein, or a measurement in a control individual (or multiple control individuals) in the absence of the treatment described herein. In some embodiments, a "control individual" is an individual afflicted with the same form of disease or injury as an individual being treated.

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the patient is receiving or has received certain therapy to diagnose and/or to treat a disease, disorder, or condition.

Peptide: The term "peptide" as used herein refers to a polypeptide that is typically relatively short, for example having a length of less than about 100 amino acids, less than about 50 amino acids, less than about 40 amino acids less than about 30 amino acids, less than about 25 amino acids, less than about 20 amino acids, less than about 15 amino acids, or less than 10 amino acids.

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces. In some embodiments, a pharmaceutical composition is intended and suitable for administration to a human subject. In some embodiments, a pharmaceutical composition is sterile and substantially pyrogen-free.

Pharmaceutically acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Polypeptide: As used herein refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Prevent or Prevention: The term "prevent" or "prevention", as used herein, refers to a delay of onset, and/or reduction in frequency and/or severity of one or more symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition. Prevention may be considered complete when onset of a disease, disorder or condition has been delayed for a predefined period of time.

Prognostic and predictive information: As used herein, the terms "prognostic information" and "predictive information" are used to refer to any information that may be used to indicate any aspect of the course of a disease or condition either in the absence or presence of treatment. Such information may include, but is not limited to, the average life expectancy of a patient, the likelihood that a patient will survive for a given amount of time (e.g., 6 months, 1 year, 5 years, etc.), the likelihood that a patient will be cured of a disease, the likelihood that a patient's disease will respond to a particular therapy (wherein response may be defined in any of a variety of ways). Prognostic and predictive information are included within the broad category of diagnostic information.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Reference: As used herein, the term "reference" refers to a standard or control relative to which a comparison is performed. For example, in some embodiments, an agent, animal, individual, population, sample, sequence, or value of interest is compared to a reference or control agent, animal, individual, population, sample, sequence, or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Response: As used herein, a response to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a tumor's response. Tumor or subject response may be measured according to a wide variety of criteria, including clinical criteria and objective criteria. Techniques for assessing response include, but are not limited to, clinical examination, positron emission tomatography, chest X-ray CT scan, MRI, ultrasound, endoscopy, laparoscopy, presence or level of tumor markers in a sample obtained from a subject, cytology, and/or histology. Many of these techniques attempt to determine the size of a tumor or otherwise determine the total tumor burden. Methods and guidelines for assessing response to treatment are discussed in Therasse et. al., "New guidelines to evaluate the response to treatment in solid tumors", European Organization for Research and Treatment of Cancer, National Cancer Institute of the United States, National Cancer Institute of Canada, *J. Natl. Cancer Inst.,* 2000, 92(3):205-216. The exact response criteria can be selected in any appropriate manner, provided that when comparing groups of tumors and/or patients, the groups to be compared are assessed based on the same or comparable criteria for determining response rate. One of ordinary skill in the art will be able to select appropriate criteria.

Sample: As used herein, the term "sample" refers to a biological sample obtained or derived from a source of interest, as described herein. In some embodiments, a source of interest comprises an organism, such as a microbe, a plant, an animal or a human. In some embodiments, a biological sample comprises biological tissue or fluid. In some embodiments, a biological sample may comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; other body fluids, secretions, and/or excretions; and/or cells therefrom. In some embodiments, a biological sample comprises cells obtained from an individual, e.g., from a human or animal subject. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces). In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or polypeptides extracted from a sample or obtained by subjecting a primary sample to techniques such as amplification or reverse transcription of mRNA, isolation and/or purification of certain components.

Subject: As used herein, the term "subject" refers to an organism, for example, a mammal (e.g., a human, a non-human mammal, a non-human primate, a primate, a laboratory animal, a mouse, a rat, a hamster, a gerbil, a cat, a dog). In some embodiments a human subject is an adult, adolescent, or pediatric subject. In some embodiments, a subject is suffering from a disease, disorder or condition, e.g., a disease, disorder or condition that can be treated as provided herein, e.g., a cancer or a tumor listed herein. In some embodiments, a subject is susceptible to a disease, disorder, or condition; in some embodiments, a susceptible subject is predisposed to and/or shows an increased risk (as compared to the average risk observed in a reference subject or population) of developing the disease, disorder or condition. In some embodiments, a subject displays one or more symptoms of a disease, disorder or condition. In some embodiments, a subject does not display a particular symptom (e.g,. clinical manifestation of disease) or characteristic of a disease, disorder, or condition. In some embodiments, a subject does not display any symptom or characteristic of a disease, disorder, or condition. In some embodiments, a subject is a patient. In some embodiments, a subject is an individual to whom diagnosis and/or therapy is and/or has been administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Susceptible to: An individual who is "susceptible to" a disease, disorder, or condition (e.g., influenza) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from the disease, disorder, or condition).

Symptoms are reduced: According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom.

Therapeutic regimen: A "therapeutic regimen", as that term is used herein, refers to a dosing regimen whose administration across a relevant population may be correlated with a desired or beneficial therapeutic outcome.

Therapeutic agent: As used herein, the term "therapeutic agent" in general refers to any agent that elicits a desired effect (e.g., a desired biological, clinical, or pharmacological effect) when administered to a subject. In some embodiments, an agent is considered to be a therapeutic agent if it demonstrates a statistically significant effect across an appropriate population. In some embodiments, an appropriate population is a population of subjects suffering from and/or susceptible to a disease, disorder or condition. In some embodiments, an appropriate population is a population of model organisms. In some embodiments, an appropriate population may be defined by one or more criterion such as age group, gender, genetic background, preexisting clinical conditions, prior exposure to therapy. In some embodiments, a therapeutic agent is a substance that alleviates, ameliorates, relieves, inhibits, prevents, delays onset of, reduces severity of, and/or reduces incidence of one or more symptoms or features of a disease, disorder, and/or condition in a subject when administered to the subject in an effective amount. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutically effective amount: As used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treatment: As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Vaccination: As used herein, the term "vaccination" refers to the administration of a composition intended to generate an immune response, for example to a disease-causing agent. For the purposes of the present invention, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

DETAILED DESCRIPTION OF THE INVENTION

This application describes a combination therapy comprising an immunogenic composition against HSV-2 and an antiviral therapy. HSV-2 is a common cause of genital herpes and one of the most common sexually transmitted diseases with nearly 500 million people affected worldwide. Evidence of infection, by serologic studies, is present in 1 out of every 6 people aged 14 to 49 in the United States. Women are more commonly infected than men, with 1 out of every 5 women in the US having evidence of infection. Certain groups, such as people with human immunodeficiency virus (HIV) and commercial sex workers, have high rates of infection ranging from 60% to 95%, (Kimberlin & Rouse, New Engl J Med. (2004) 350:1970-7; Gupta et al., Lancet. (2007) 370:2127-37)

HSV-2 infection is associated with a 3-fold increase in risk of acquiring HIV infection, due in part to the presence of herpetic lesions (which may result in breach of the genital epithelium) and is considered to be a substantial contributor to the worldwide AIDS epidemic (Corey, J Infect Dis. (2007) 195:1242-4; Freeman et al., AIDS (2006) 20:73-83). Most HSV-2 seropositive people are unaware of their infection status, probably because of mild and atypical symptoms and signs, and this lack of awareness contributes to the continued spread of HSV-2 infection among susceptible populations.

In people with recognized genital herpes, the disease is characterized by the development of vesicles at the site of infection, usually the anogenital region (defined as the area covered by boxer shorts). Vesicles persist for days and evolve to ulcers that eventually crust and heal. The initial clinical manifestations occur approximately 4 days after acquisition of infection and are referred to as the primary outbreak or infection (or nonprimary initial, for the first episode of HSV-2 in a patient who is herpes simplex type 1 [HSV-1] seropositive). In the absence of antiviral therapy, lesions resolve over the course of 1 to 3 weeks. The virus migrates in a retrograde process to become latent in the sensory nerve ganglia. At varying intervals, recurrences (secondary outbreaks or infections) develop when the virus travels anterograde to the skin or mucosal surfaces. During the first year after primary infection, the median recurrence rate in the absence of therapy is 4 per year, and 20% of patients experience more than 10 recurrences (Benedetti et al., Ann Intern Med (1994) 121:847-54).

HSV-2 infection is transmitted by contact with the mucosal membranes of an infected person who is shedding the virus. During clinically active recurrences (presence of genital ulcers) HSV-2 can frequently be detected in ulcers and the surrounding skin and mucosa. However, during asymptomatic periods, shedding of HSV-2 from the ano-genital regions of an infected person can be detected on approximately 10% to 13% of days (subclinical shedding) by polymerase chain reaction (PCR) (Fife et al., Mayo Clin Proc. (2006) 81:1321-7; Martens et al., Infect Dis Obstet Gynecol (2009) 105376). Most transmission occurs during such periods of subclinical shedding. Transmission may also occur from pregnant mother to infant at birth, resulting in a severe form of disseminated infection leading to permanent neurologic damage or death of the infant (Whitley, Curr Opin Infect Dis. (2004) 17:243-6).

For these indications, acyclovir, valacyclovir, or famciclovir can be effective. Both clinical and subclinical shedding of HSV-2 are reduced, but not eliminated, during periods of therapy (Wald et al., Ann Intern Med. (1996) 124:8-15; Gupta et al., J Infect Dis. (2004) 190:1374-81; Fife et al., Mayo Clin Proc. (2006) 81:1321-7; Martens et al., Infect Dis Obstet Gynecol (2009) 105376; Johnston et al., Lancet. (2012) 379:641-7). However, in a clinical trial valacyclovir reduced transmission of HSV-2 from infected persons to uninfected partners by only 48% (Corey et al., J Infect Dis. (2007) 195:1242-4). The limitations of antiviral therapy include the requirement for daily treatment, potentially incomplete compliance leading to breakthrough of viral shedding or clinical disease, inability to completely suppress clinical recurrences, and limited prevention of transmission of infection. Consequently, there have been a number of attempts to develop effective vaccines either for prevention or treatment of infection with HSV-2 (Stanberry et al., N Engl J Med. (2002) 347:1652-61; de Bruyn et al., Vaccine. (2006) 24:914-20), but none is currently available. Thus, new and improved methodologies for herpesvirus vaccine discovery are needed to protect against herpes diseases.

Immunogenic Compositions

Immunogenic compositions for use in combination with antiviral therapy may include a polypeptide comprising a sequence from Table 1 or an immunogenic fragment thereof, or a combination of at least two polypeptides comprising sequences from Table 1 or immunogenic fragments thereof. In certain embodiments, the polypeptide(s) of an immunogenic composition comprise the entire sequence of at least one of SEQ ID NOS: 1-26, 135, 136, 138 and 139, or consist of the entire sequence of any one of SEQ ID NOS: 1-26, 135, 136, 138 and 139. Immunogenic compositions may include a polypeptide comprising a sequence from Table 1 or Table 2 or an immunogenic fragment thereof or a combination of at least two polypeptides comprising sequences from Table 1 or Table 2, or immunogenic fragments thereof. In certain embodiments, the polypeptide(s) of the immunogenic compositions comprise the entire sequence of any one of SEQ ID NOS: 1-38, 135, 136, 138 and 139 or consist of the entire sequence of any one of SEQ ID NO: 1-38, 135, 136, 138 and 139. The polypeptides in Tables 1 or 2 may be encoded by SEQ ID NOS: 39-46 and 117-134, 137, 140 and 141 as indicated and/or by cDNA sequences publically available (on the NCBI NIH web site on the World Wide Web, at the hypertext protocol transfer address of "ncbi.nlm.nih.gov/sites/entrez"). cDNA and protein sequences may also be obtained from any known strains of HSV-2, including HG52, 333, and Strain G. Accordingly, cDNA sequences may be accessed by gene or protein name from genomic sequence at NC_001798.1, and may be approximately 97% conserved with sequences disclosed at NC_001798.1. As described herein, the polypeptides may be referred to by protein name, by SEQ ID NO, and/or by the name of the gene encoding the protein.

The polypeptides can be prepared in a variety of expression systems. Suitable expression systems include *E. coli* and Baculovirus-based expression systems (e.g., in insect cells). Polypeptides prepared using *E. coli* are typically full-length and unglycosylated, although truncated variants can be prepared. In certain embodiments, these truncated variants retain all or part of the signal domain. Polypeptides prepared using a Baculovirus system typically lack the N-terminal signal sequence, but are fully or partially glycosylated.

In some embodiments, the polypeptides are prepared in non-mammalian cell systems. When an exogenous signal sequence is used, polypeptides may contain one or more amino acids at the N-terminal end which correspond to the exogenous signal sequence. An exogenous signal sequence commonly used in insect expression systems is the honey bee mellitin signal sequence. In other embodiments, the polypeptides may contain one or more amino acids corresponding to a signal sequence that has been cleaved. Exemplary polypeptides may contain one or more amino acids from a mammalian signal sequence that has been left intact or cleaved off, depending on the system used to prepare the polypeptides.

TABLE 1

HSV-2 antigens for immunogenic compositions

| Protein SEQ ID No. | DNA SEQ ID No. | Gene or Construct Name Protein Name | GeneID No. | GenBank Accession Nos. |
|---|---|---|---|---|
| 1 | 39 | RS TABLE 1-continued HSV-2 antigens for immunogenic compositions

| Protein SEQ ID No. | DNA SEQ ID No. | Gene or Construct Name Protein Name | GeneID No. | GenBank Accession Nos. |
|---|---|---|---|---|
| 6 | 41 | RL1<br>ICP34.5 | 1487287 | NP_044529.1 |
| 7 | 42 | RL2<br>ICP0 | 1487289 | NP_044528.2 |
| 8 | 121 | RS1.1<br>ICP4 internal fragment | 1487291 | NP_044530.1<br>RS1.1 corresponds to residues 1-400 of RS1 |
| 9 | 122 | RS1.3.1<br>ICP4 internal fragment | 1487291 | NP_044530.1<br>RS1.3.1 corresponds to residues 750-1024 of RS1 |
| 10 | 123 | RS1.3.2<br>ICP4 internal fragment | 1487291 | NP_044530.1<br>RS1.3.2 corresponds to residues 1008-1319 of RS1 |
| 11 | 124 | RS1.3<br>ICP4 internal fragment | 1487291 | NP_044530.1<br>RS1.3 corresponds to residues 750-1319_of RS1 |
| 12 | 125 | RS1.4<br>ICP4 internal fragment | 1487291 | NP_044530.1<br>RS1.4 corresponds to residues 340-883 of RS1 |
| 13 | 126 | RS1.5<br>ICP4 internal fragment | 1487291 | NP_044530.1<br>RS1.5 corresponds to residues 775-1318 of RS1 |
| 14 | 127 | RS1.6<br>ICP4 internal fragment | 1487291 | NP_044530.1<br>RS1.6 corresponds to residues 210-1318 of RS1 |
| 15 | 128 | RS1.7<br>ICP4 internal fragment | 1487291 | NP_044530.1<br>RS1.7 has a deletion of residues 391-544 of RS1 |
| 16 | 129 | RS1.8<br>ICP4 internal fragment | 1487291 | NP_044530.1<br>RS1.8 has a deletion of residues 786-868 of RS1 |
| 17 | | UL2 v.1<br>uracil DNA glycosylase | 1487303 | NP_044471.2 |
| 135 | | UL2 v.2<br>uracil DNA glycosylase | 1487303 | NP_044471.2 |
| 18 | | UL11<br>myristylated tegument protein | 1487294 | NP_044480.1 |
| 19 | 119 | UL1s v.1<br>gL2 secreted | 1487292 | NP_044470.1 |
| 136 | 137 | UL1s v.2<br>gL2 secreted | 1487292 | NP_044470.1 |
| 20 | | UL19a<br>VP5 | 1487302 | NP_044488.1 |
| 21 | 120 | UL19ΔTEV<br>VP5 | 1487302 | NP_044488.1 |
| 22 | | UL36<br>ICP1/2 | 1487322 | NP_044506.1 |
| 23 | 43 | UL36.3.4.1<br>ICP1/2 internal fragment | 1487322 | NP_044506.1<br>UL 36.3.4.1 corresponds to residues 1318-2280 of UL36 |
| 24 | 44 | UL36.4.2.5<br>ICP1/2 internal fragment | 1487322 | NP_044506.1<br>UL 36.4.2.5 corresponds to residues 2253-3122 of UL36 |
| 25 | | UL40<br>ribonucleoside reductase | 1487327 | NP_044510.1 |
| 26 | 45 | US12<br>ICP47 | 1487353 | NP_044543.1 |
| 138 | 140 | RS1.9<br>ICP4 internal fragment | 1487291 | NP_044530.1<br>RS1.9 has a deletion of residues 391-544 and 786-821 of RS1 |
| 139 | 141 | RS1.10<br>ICP4 internal fragment | 1487291 | NP_044530.1<br>RS1.10 has a deletion of residues 391-508 and 786-821 of RS1 |

TABLE 2

Additional HSV-2 antigens for immunogenic compositions

| Protein SEQ ID No. | DNA SEQ ID No. | Gene or Construct Name Protein Name | GeneID No. | GenBank Accession Nos. |
|---|---|---|---|---|
| 27 | 134 | UL10 gM2 | 1487293 | NP_044479.1 |
| 28 | | UL15 DNA cleavage/packaging protein | 1487298 | NP_044484.1 |
| 29 | | UL26.5 ICP35 | 1487311 | NP_044496.1 |
| 30 | | UL30 DNA-directed polymerase | 1487316 | NP_044500.1 |
| 31 | | UL5 DNA helicase/primase complex | 1487338 | NP_044474.1 |
| 32 | | UL8 DNA helicase/primase complex | 1487348 | NP_044477.1 |
| 33 | | UL15.5 unknown | 1487298 | NP_044484.1 UL15.5 is an alternate translation of UL15 |
| 34 | | UL32 cleavage/packaging protein | 1487318 | NP_044502.1 |
| 35 | | UL36.4.2 ICP1/2 fragment | 1487322 | NP_044506.1 |
| 36 | | UL54 ICP27 | 1487343 | NP_044525.1 |
| 37 | 133 | UL49.5 membrane-associated virion protein | 1487337 | NP_044520.1 |
| 38 | 46 | US4 gG2 | 1487356 | NP_044534.1 |

Immunogenic HSV-2 Polypeptides

Immunogenic polypeptides or polynucleotides as indicated in Table 1 and/or Table 2 may be used in immunogenic compositions, e.g., pharmaceutical compositions. The disclosure provides immunogenic compositions containing immunogenic polypeptides or polynucleotides encoding these immunogenic polypeptides, e.g., together with a pharmaceutical carrier. Antigens from HSV-2 may be identified by screening immune cells from patients exposed to or infected with HSV-2. Briefly, a library of HSV-2 antigens was expressed by bacteria and mixed with APCs. The APCs, in turn, processed and presented HSV-2-derived peptides to lymphocytes that had been isolated from human patients exposed to or infected with HSV-2. The patients belonged to several populations: (1) exposed to HSV-2 but seronegative for infection, (2) infected with HSV-2 but asymptomatic, (3) infected with HSV-2 and experiencing infrequent outbreaks, (4) infected with HSV-2 and experiencing frequent outbreaks, (5) naive and (6) seronegative for HSV-2 (HSV-2$^-$) but seropositive for HSV-1 (HSV-1$^+$). Lymphocyte responses from each population were compared for reactivity to HSV-2-derived polypeptides, and the screen detected antigens that induced reactive lymphocytes with greater frequency in one patient population as compared to the others. Infected but asymptomatic, and exposed but seronegative patients may activate protective immune responses that patients who experience frequent outbreaks do not; in particular, exposed but seronegative patients are presumed to have mounted sterilizing immunity to HSV-2 infection. It is believed that a unique set of polypeptides will activate lymphocytes from these patient populations. Thus, the present invention contemplates compositions of the specific HSV-2 polypeptides that activate the lymphocytes of infected but asymptomatic, or exposed but seronegative patients or a combination of these polypeptides for inhibiting or counteracting infection by HSV-2.

Antigens identified on the basis of their immunogenicity in infected but asymptomatic, or exposed but seronegative patients, are similarly expected to be immunogenic in any subject.

In some embodiments, a polypeptide may induce an innate immune response, a humoral immune response, or a cell-mediated immune response. The cell-mediated immune response may involve CD4+ and/or CD8+ T cells, and in certain embodiments, the immune response involving CD4+ T cells is an immune response in which TH1 cells are activated. In some embodiments, an immunogenic polypeptide avoids induction of TH2 cytokines. In some embodiments, the immune response involving CD4+ T cells is an immune response in which TH17 cells are activated.

Polypeptides (or immunogenic fragments thereof) in immunogenic compositions of the disclosure may induce T cell responses in multiple individuals, regardless of the HLA haplotype of the individuals. Specifically, epitopes in the polypeptides may induce T cell responses in individuals with one or more of the following HLA supertypes: HLA-A2, -A3, -A24, -A1, -B7, -B8, -B27, -B44, -B58, and B62, and HLA-DQB01, -DQB02, -DQB03, -DQB-04, and -DQB05.

In some embodiments, one or more, e.g. two, three, four, or more polypeptides from Table 1 and/or Table 2 (or immunogenic fragments thereof) are provided in an immunogenic composition. In some embodiments, two polypeptides from Table 1 and/or Table 2 are provided in an immunogenic composition. In other embodiments, three polypeptides from Table 1 and/or Table 2 are provided in an immunogenic composition. In other embodiments, four polypeptides from Table 1 and/or Table 2 are provided in an immunogenic composition.

In some embodiments, two, three, four, or more polypeptides from Table 1 and/or Table 2 (or immunogenic fragments thereof) are provided together as a conjugate. In some embodiments, two polypeptides from Table 1 and/or Table 2, or three polypeptides from Table 1 and/or Table 2, or four polypeptides from Table 1 and/or Table 2, are provided as a conjugate. In some embodiments, two, three, four, or more polypeptides from Table 1 and/or Table 2 are covalently bound to each other, e.g., as a fusion protein. In some embodiments, two polypeptides from Table 1 and/or Table 2, or three polypeptides from Table 1 and/or Table 2, or four polypeptides from Table 1 and/or Table 2, are covalently bound to each other, e.g. as a fusion protein.

In some embodiments, an immunogenic composition comprises two, three, four, or more polypeptides selected from the group consisting of SEQ ID NOS: 1-38, 135, 136, 138 and 139, and may contain or may not contain any other HSV-2 polypeptides.

In certain embodiments, an immunogenic composition comprises one or more polypeptides that are at least 70%, 80%, 90%, 95%, 96%, 97%, 98%, 99%, or 100% identical to a polypeptide encoded by a gene in Table 1 and/or Table 2, or a portion of said polypeptide. In certain embodiments, the homologous polypeptide is at least 8, 10, 15, 20, 30, 40, 50, 60, 80, 100, 120, 140, 160, 180, 200, 220, 240, 260, 280, 300, 350, 400, 450, or 500 amino acids in length. In some embodiments, such as those described immediately above, the polypeptide is no more than 300, 350, 400, 450, or 500 amino acids in length.

An immunogenic composition may also comprise portions of said polypeptides and genes, for example deletion mutants, truncation mutants, oligonucleotides, and peptide fragments. In some embodiments, the portions of said proteins are immunogenic.

The immunogenicity of a portion of a protein or a homolog thereof can be readily determined using the same assays that are used to determine the immunogenicity of the full-length protein. In some embodiments, the portion of the protein has substantially the same immunogenicity as the full-length proteins. In some embodiments, the immunogenicity is no more than 10%, 20%, 30%, 40%, or 50% less than that of the full-length protein. The protein fragments may be, for example, linear, circular, or branched. In some embodiments, a protein or protein fragment comprises one or more non-natural amino acids (e.g. an amino acid other than the 20 typically found in natural proteins). A non-natural amino acid may have an atypical side chain. In addition, peptidomimetics may be used; these may incorporate alterations to the peptide backbone.

In some embodiments, an immunogenic composition described herein includes an immunogenic polypeptide that contains a membrane translocating sequence (MTS), to facilitate introduction of the polypeptide into the mammalian cell and subsequent stimulation of the cell-mediated immune response. Exemplary membrane translocating sequences include hydrophobic region in the signal sequence of Kaposi fibroblast growth factor, the MTS of α-synuclein, β-synuclein, or γ-synuclein, the third helix of the Antennapedia homeodomain, SN50, integrin β3 h-region, HIV Tat, pAntp, PR-39, abaecin, apidaecin, Bac5, Bac7, P. berghei CS protein, and those MTSs described in U.S. Pat. Nos. 6,248,558, 6,432,680 and 6,248,558.

In certain embodiments, an immunogenic polypeptide is conjugated (e.g., covalently bound) to another molecule. This may, for example, increase the half-life, solubility, bioavailability, or immunogenicity of the antigen. Molecules that may be conjugated to an immunogenic polypeptide include a carbohydrate, biotin, poly(ethylene glycol) (PEG), polysialic acid, N-propionylated polysialic acid, nucleic acids, polysaccharides, and PLGA. There are many different types of PEG, ranging from molecular weights of below 300 g/mol to over 10,000,000 g/mol. PEG chains can be linear, branched, or with comb or star geometries.

Immunogenic HSV-2 Polypeptides and Nucleic Acids for Use in Immunogenic Compositions In certain embodiments, one or more, e.g. two, three, four, or more immunogenic fragments or variants thereof are provided in a mixture. For example, an immunogenic composition may comprise any one or more of SEQ ID NOS: 1-26, 136, 138 or 139.

In certain embodiments, an immunogenic composition may comprise any one, two, three, or four of ICP4, ICP4.2, ICP4.5, ICP4.9, ICP4.10, gL2, gL2s v.2, gD2ΔTMR and gD2 (SEQ ID NOS: 1-5, 13, 136, 138 and 139), or immunogenic fragment(s) thereof. In certain embodiments, combinations contain polypeptides or immunogenic fragments from only one of ICP4 (SEQ ID NO: 1), ICP4.2 (SEQ ID NO: 2), ICP4.5 (SEQ ID NO: 13), ICP4.9 (SEQ ID NO: 138) and ICP4.10 (SEQ ID NO: 139). In other embodiments, combinations contain polypeptides or immunogenic fragments from only one of gD2ΔTMR (SEQ ID NO: 4) and gD2 (SEQ ID NO: 5). In yet other embodiments, combinations contain polypeptides or immunogenic fragments from only one of gL2 (SEQ ID NO: 3) and gL2s v.2s (SEQ ID NO: 136). In some embodiments, combinations contain polypeptides or immunogenic fragments from any two of ICP4.2 (SEQ ID NO: 2), ICP4.5 (SEQ ID NO: 13), ICP4.9 (SEQ ID NO: 138) and ICP4.10 (SEQ ID NO: 139).

In some embodiments, an immunogenic composition may comprise at least one polypeptide fragment of SEQ ID NO: 1, such as the polypeptides of SEQ ID NOS: 2, 8-16, 138 and 139. In some embodiments, an immunogenic composition may comprise at least two polypeptide fragments of SEQ ID NO: 1, such as the polypeptides of SEQ ID NOS: 2, 8-16, 138 and 139. One or more polypeptide fragments of SEQ ID NO: 1 may replace SEQ ID NO: 1 in any of the immunogenic compositions as described herein.

Exemplary combinations of ICP4, ICP4.2, ICP4.5, ICP4.9, ICP4.10, gL2, gL2s v.2, gD2ΔTMR and gD2 include:

| Two antigen combinations | |
|---|---|
| ICP4 | gL2 or gL2s v.2 |
| SEQ ID NO: 1 | SEQ ID NO: 3 or SEQ ID NO: 136 |
| ICP4 | gD2ΔTMR |
| SEQ ID NO: 1 | SEQ ID NO: 4 |
| ICP4 | gD2 |
| SEQ ID NO: 1 | SEQ ID NO: 5 |
| ICP4.2 | gL2 or gL2s v.2 |
| SEQ ID NO: 2 | SEQ ID NO: 3 or SEQ ID NO: 136 |
| ICP4.2 | gD2ΔTMR |
| SEQ ID NO: 2 | SEQ ID NO: 4 |
| ICP4.2 | gD2 |
| SEQ ID NO: 2 | SEQ ID NO: 5 |
| gL2 or gL2s v.2 | gD2ΔTMR |

-continued

| | |
|---|---|
| SEQ ID NO: 3 or SEQ ID NO: 136 | SEQ ID NO: 4 |
| gL2 or gL2s v.2 | gD2 |
| SEQ ID NO: 3 or SEQ ID NO: 136 | SEQ ID NO: 5 |
| ICP4.5 | gL2 or gL2s v.2 |
| SEQ ID NO: 13 | SEQ ID NO: 3 or SEQ ID NO: 136 |
| ICP4.5 | gD2ΔTMR |
| SEQ ID NO: 13 | SEQ ID NO: 4 |
| ICP4.5 | gD2 |
| SEQ ID NO: 13 | SEQ ID NO: 5 |
| ICP4.9 | gL2 or gL2s v.2 |
| SEQ ID NO: 138 | SEQ ID NO: 3 or SEQ ID NO: 136 |
| ICP4.9 | gD2ΔTMR |
| SEQ ID NO: 138 | SEQ ID NO: 4 |
| ICP4.9 | gD2 |
| SEQ ID NO: 138 | SEQ ID NO: 5 |
| ICP4.10 | gL2 or gL2s v.2 |
| SEQ ID NO: 139 | SEQ ID NO: 3 or SEQ ID NO: 136 |
| ICP4.10 | gD2ΔTMR |
| SEQ ID NO: 139 | SEQ ID NO: 4 |
| ICP4.10 | gD2 |
| SEQ ID NO: 139 | SEQ ID NO: 5 |

| Three antigen combinations | | |
|---|---|---|
| ICP4 | gL2 | gD2ΔTMR |
| SEQ ID NO: 1 | SEQ ID NO: 3 | SEQ ID NO: 4 |
| ICP4.2 | gL2 | gD2ΔTMR |
| SEQ ID NO: 2 | SEQ ID NO: 3 | SEQ ID NO: 4 |
| ICP4.5 | gL2 | gD2ΔTMR |
| SEQ ID NO: 13 | SEQ ID NO: 3 | SEQ ID NO: 4 |
| ICP4.9 | gL2 | gD2ΔTMR |
| SEQ ID NO: 138 | SEQ ID NO: 3 | SEQ ID NO: 4 |
| ICP4.10 | gL2 | gD2ΔTMR |
| SEQ ID NO: 139 | SEQ ID NO: 3 | SEQ ID NO: 4 |
| ICP4 | gL2 | gD2 |
| SEQ ID NO: 1 | SEQ ID NO: 3 | SEQ ID NO: 5 |
| ICP4.2 | gL2 | gD2 |
| SEQ ID NO: 2 | SEQ ID NO: 3 | SEQ ID NO: 5 |
| ICP4.5 | gL2 | gD2 |
| SEQ ID NO: 13 | SEQ ID NO: 3 | SEQ ID NO: 5 |
| ICP4.9 | gL2 | gD2 |
| SEQ ID NO: 138 | SEQ ID NO: 3 | SEQ ID NO: 5 |
| ICP4.10 | gL2 | gD2 |
| SEQ ID NO: 139 | SEQ ID NO: 3 | SEQ ID NO: 5 |
| ICP4 | gL2s v.2 | gD2ΔTMR |
| SEQ ID NO: 1 | SEQ ID NO: 136 | SEQ ID NO: 4 |
| ICP4.2 | gL2s v.2 | gD2ΔTMR |
| SEQ ID NO: 2 | SEQ ID NO: 136 | SEQ ID NO: 4 |
| ICP4.5 | gL2s v.2 | gD2ΔTMR |
| SEQ ID NO: 13 | SEQ ID NO: 136 | SEQ ID NO: 4 |
| ICP4.9 | gL2s v.2 | gD2ΔTMR |
| SEQ ID NO: 138 | SEQ ID NO: 136 | SEQ ID NO: 4 |
| ICP4.10 | gL2s v.2 | gD2ΔTMR |
| SEQ ID NO: 139 | SEQ ID NO: 136 | SEQ ID NO: 4 |
| ICP4 | gL2s v.2 | gD2 |
| SEQ ID NO: 1 | SEQ ID NO: 136 | SEQ ID NO: 5 |
| ICP4.2 | gL2s v.2 | gD2 |
| SEQ ID NO: 2 | SEQ ID NO: 136 | SEQ ID NO: 5 |
| ICP4.5 | gL2s v.2 | gD2 |
| SEQ ID NO: 13 | SEQ ID NO: 136 | SEQ ID NO: 5 |
| ICP4.9 | gL2s v.2 | gD2 |
| SEQ ID NO: 138 | SEQ ID NO: 136 | SEQ ID NO: 5 |
| ICP4.10 | gL2s v.2 | gD2 |
| SEQ ID NO: 139 | SEQ ID NO: 136 | SEQ ID NO: 5 |

| Four antigen combinations | | | |
|---|---|---|---|
| ICP4.2 | ICP4.5 | gL2 | gD2ΔTMR |
| SEQ ID NO: 2 | SEQ ID NO: 13 | SEQ ID NO: 3 | SEQ ID NO: 4 |
| ICP4.2 | ICP4.9 | gL2 | gD2ΔTMR |
| SEQ ID NO: 2 | SEQ ID NO: 138 | SEQ ID NO: 3 | SEQ ID NO: 4 |
| ICP4.2 | ICP4.10 | gL2 | gD2ΔTMR |
| SEQ ID NO: 2 | SEQ ID NO: 139 | SEQ ID NO: 3 | SEQ ID NO: 4 |
| ICP4.2 | ICP4.5 | gL2 | gD2 |
| SEQ ID NO: 2 | SEQ ID NO: 13 | SEQ ID NO: 3 | SEQ ID NO: 5 |
| ICP4.2 | ICP4.9 | gL2 | gD2 |
| SEQ ID NO: 2 | SEQ ID NO: 138 | SEQ ID NO: 3 | SEQ ID NO: 5 |
| ICP4.2 | ICP4.10 | gL2 | gD2 |
| SEQ ID NO: 2 | SEQ ID NO: 139 | SEQ ID NO: 3 | SEQ ID NO: 5 |
| ICP4.2 | ICP4.5 | gL2s v.2 | gD2ΔTMR |
| SEQ ID NO: 2 | SEQ ID NO: 13 | SEQ ID NO: 136 | SEQ ID NO: 4 |
| ICP4.2 | ICP4.9 | gL2s v.2 | gD2ΔTMR |
| SEQ ID NO: 2 | SEQ ID NO: 138 | SEQ ID NO: 136 | SEQ ID NO: 4 |
| ICP4.2 | ICP4.10 | gL2s v.2 | gD2ΔTMR |
| SEQ ID NO: 2 | SEQ ID NO: 139 | SEQ ID NO: 136 | SEQ ID NO: 4 |
| ICP4.2 | ICP4.5 | gL2s v.2 | gD2 |
| SEQ ID NO: 2 | SEQ ID NO: 13 | SEQ ID NO: 136 | SEQ ID NO: 5 |
| ICP4.2 | ICP4.9 | gL2s v.2 | gD2 |
| SEQ ID NO: 2 | SEQ ID NO: 138 | SEQ ID NO: 136 | SEQ ID NO: 5 |
| ICP4.2 | ICP4.10 | gL2s v.2 | gD2 |
| SEQ ID NO: 2 | SEQ ID NO: 139 | SEQ ID NO: 136 | SEQ ID NO: 5 |

The individual antigens and combinations described above can also include additional peptides from or derived from HSV-2, such as polypeptides comprising sequences selected from SEQ ID NOS: 6-12, 14-26, and SEQ ID NO: 135, or immunogenic fragments thereof.

In some embodiments, the individual antigens and combinations described above are provided as isolated nucleic acids. In certain aspects, the nucleic acids have the nucleotide sequence of at least one of SEQ ID NOS: 39-45, 117-129, 137, 140, 141, or an immunogenic fragment thereof. Nucleic acids can be present in compositions of the invention singly or in combinations. Exemplary combinations include nucleic acids encoding for two or more of ICP4 (SEQ ID NO: 1), ICP4.9 (SEQ ID NO: 138), gL2 (SEQ ID NO: 3), gG2 (SEQ ID NO: 38) and gD2 (SEQ ID NO: 5).

ICP4 (SEQ ID NO: 1) Encoded by RS1

RS1 encodes ICP4, a transcriptional transactivator that may interact with and recruit specific components of the general transcription machinery to viral promoters and stabilize their formation for transcription initiation. ICP4 contains distinct domains for transactivation/phosphorylation (approximately spanning amino acid residues 150-200 of SEQ ID NO: 1), DNA binding (approximately spanning residues 380-540 of SEQ ID NO: 1), nuclear localization (approximately spanning residues 630-730 of SEQ ID NO: 1), and late regulatory transactivation (approximately spanning residues 1220-1319 of SEQ ID NO: 1). The DNA and protein sequence of RS1 may be found by searching for RS1 in the publicly available database, Entrez Gene (on the NCBI NIH web site on the World Wide Web, at the hypertext protocol transfer address of "ncbi.nlm.nih.gov/sites/entrez?db=gene"), in the Human herpesvirus 2 complete genome.

In some embodiments, an immunogenic composition described herein includes a polypeptide containing at least 20 consecutive amino acid residues selected from residues 383-766 of ICP4 (SEQ ID NO: 1), but no more than 1000 amino acids of ICP4 (SEQ ID NO: 1). The polypeptide may also be a variant of the at least 20 residue fragment.

In certain embodiments, the polypeptide includes no more than 950, 900, 850, 800, 750, 700, 650, 600, 550, 500, 450 or even 400 consecutive amino acids from ICP4. Exemplary polypeptides correspond approximately to amino acids residues of full-length ICP4 as follows: 383-766; 1-400 (RS1.1); 750-1024 (RS1.3.1); 1008-1319 (RS1.3.2); 750-1319 (RS1.3); 280-785 (RS1.4 comprising the full DNA binding region); 680-1319 (RS1.5 comprising the glycosylase/C-terminal region); 208-1319 (RS1.6 which may also comprise a Met residue at the N-term end); 1-380 plus 545-1319 (RS1.7, in which a region spanning approximately residues 381-544 is deleted, removing the DNA binding regions); 1-785 plus 870-1319 (RS1.8, in which a region spanning approximately residues 786-869 is deleted, removing the nuclear localization domain), or 1-766, 383-1318, 100-750, 400-1300, 250-766, 383-900 of ICP4 (SEQ ID NO: 1) and the like.

ICP4 Internal Fragment ICP4.2 (SEQ ID NO: 2) Encoded by RS1.2

RS1.2 encodes a 391 amino acid fragment denoted ICP4.2.

In specific embodiments, an immunogenic composition described herein includes a polypeptide containing from 50 to all 391 amino acids residues of ICP4.2 (SEQ ID NO: 2), such as from 100 to 391, 200 to 391 or 250 to 350 residues. In particular embodiments, the polypeptide includes all of ICP4.2 (SEQ ID NO: 2) or is ICP4.2 (SEQ ID NO: 2) itself. These polypeptides may, for example, include the full length or fragments of ICP4.2 (SEQ ID NO: 2) described herein with amino acid residues 1-382 or 767-1318 of ICP4 (SEQ ID NO: 1) or fragments thereof, which, in certain embodiments, are consecutive with the amino acid residues of ICP4.2 being used. Exemplary fragments that combine the residues of SEQ ID NO: 2 with select residues from 1-382 or 767-1318 of SEQ ID NO: 1 are described above.

An immunogenic fragment of ICP4.2 comprises at least one immunogenic portion, as measured experimentally or identified by algorithm. Peptides identified by such methods include the following:

| | |
|---|---|
| GLAHVAAAV | (SEQ ID NO: 47) |
| FISGSVARA | (SEQ ID NO: 48) |
| QYALITRLL | (SEQ ID NO: 49) |
| RYDRAQKGF | (SEQ ID NO: 50) |
| GYAMAAGRF | (SEQ ID NO: 51) |
| PPHADAPRL | (SEQ ID NO: 52) |
| KPAAAAAPL | (SEQ ID NO: 53) |
| SEAAVAAV | (SEQ ID NO: 54) |
| FGWGLAHV | (SEQ ID NO: 55) |
| YALITRLLY | (SEQ ID NO: 56) |
| ALPRSPRLL | (SEQ ID NO: 57) |
| DLLFQNQSL | (SEQ ID NO: 58) |
| ADLLFQNQS | (SEQ ID NO: 59) |
| ARNSSSFIS | (SEQ ID NO: 60) |
| QACFRISGA | (SEQ ID NO: 61) |
| FVRDALVLM | (SEQ ID NO: 62) |
| FDGDLAAVP | (SEQ ID NO: 63) |
| GLGDSRPGL | (SEQ ID NO: 64) |
| WAPELGDAA | (SEQ ID NO: 65) |
| ECLAACRGI | (SEQ ID NO: 66) |
| RAWLRELRF. | (SEQ ID NO: 67) |

Thus, in some aspects, this disclosure provides an immunogenic fragment of ICP4.2. The fragments, in some instances, are close in size to the full-length polypeptide. For example, they may lack at most one, two, three, four, five, ten, or twenty amino acids from one or both termini. In other embodiments, the fragment is 100-391 amino acids in length, or 150-391, or 200-391, or 250-391 amino acids in length. Other exemplary fragments are amino acid residues 1-350, 1-300, 1-250, 1-200, 1-150, 1-100, 1-50, 50-391, 50-350, 50-300, 50-250, 50-200, 50-150, 50-100, 100-391, 100-350, 100-300, 100-250, 100-200, 100-150, 150-391, 150-350, 150-300, 150-250, 150-200, 200-391, 200-350, 200-300, 200-250, 250-391, 250-350, 250-300, 300-391 and 350-391. The fragments described above or sub-fragments thereof (e.g., fragments of 8-50, 8-30, or 8-20 amino acid residues) preferably have one of the biological activities described below, such as increasing the T cell response by at least 1.5 fold or 2 fold. A fragment may be used as the polypeptide in the vaccines described herein or may be fused to another protein, protein fragment or a polypeptide.

In certain aspects, this application provides immunogenic polypeptides with at least 90%, 95%, 97%, 98%, 99%, or 99.5% identity to ICP4.2 or an immunogenic fragment thereof.

Glycoprotein L-2 (SEQ ID NO: 3 or SEQ ID NO: 136) Encoded by UL1

UL1 encodes Glycoprotein L-2 (gL2), a heterodimer glycoprotein that is required for the fusion of viral and cellular membranes and enables the virus to enter the host cell. The DNA and protein sequence of UL1 may be found by searching in the publicly available database, Entrez Gene (on the NCBI NIH web site on the World Wide Web, at the hypertext protocol transfer address of "ncbi.nlm.nih.gov/sites/entrez?db=gene"), in the Human herpesvirus 2 complete genome.

In some embodiments, the polypeptide may be a cytoplasmic form of UL1 (SEQ ID NO:3). In other embodiments, the polypeptide may be a secreted form of UL1, which lacks one or more amino acids of the signal sequence. An exemplary polypeptide of the secreted form of UL1 is the polypeptide of SEQ ID NO: 136. In certain embodiments, this polypeptide will not form an aggregate after it is substantially purified. In some embodiments, the polypeptide will contain one or more amino acids corresponding to a signal sequence that has been cleaved. The signal sequence may be a mammalian signal sequence or may be a non-mammalian signal sequence, depending on the system from which the polypeptide was purified.

In some embodiments, an immunogenic composition described herein includes a polypeptide containing at least 20 consecutive amino acid residues selected from residues 1-224 or 1-200 of gL2 (SEQ ID NO: 3 or SEQ ID NO: 136), but no more than 224 or 200 amino acids of gL2 (SEQ ID NO: 3 or SEQ ID NO: 136). The polypeptide may also be a variant of the at least 20 residue fragment.

In some embodiments, the polypeptide is at least 85% identical to a fragment of 150-200 or 200-250 amino acids of SEQ ID NO: 3 or SEQ ID NO: 136.

In certain embodiments, the polypeptide includes no more than 200 or 100 consecutive amino acids from gL2. Exemplary polypeptides are amino acids residues 1-20, 21-40, 41-60, of 61-80, 81-100, 101-120, 121-140, 141-160, 161-180, 181-200, 201-221 of gL2 (SEQ ID NO: 3 or amino acids residues 1-20, 21-40, 41-60, of 61-80, 81-100, 101-120, 121-140, 141-160, 161-180, or 181-200 SEQ ID NO: 136) and the like.

In other aspects, the disclosure provides an immunogenic fragment of gL2. An immunogenic fragment of gL2 comprises at least one immunogenic portion, as measured experimentally or identified by algorithm. Peptides identified by such methods include the following:

| | |
|---|---|
| AYLVNPFLF | (SEQ ID NO: 100) |
| PFLFAAGFL | (SEQ ID NO: 101) |
| TEYVLRSVI | (SEQ ID NO: 102) |
| GSQATEYVL | (SEQ ID NO: 103) |
| RIDGIFLRY | (SEQ ID NO: 104) |
| FLEDLSHSV | (SEQ ID NO: 105) |
| YVLRSVIAK | (SEQ ID NO: 106) |
| YVLRSVIAK | (SEQ ID NO: 107) |
| AYLVNPFLF | (SEQ ID NO: 108) |
| ETTTRRALY | (SEQ ID NO: 109) |
| RIDGIFLRY | (SEQ ID NO: 110) |
| YLVNPFLFA | (SEQ ID NO: 111) |
| FVCLFGLVV | (SEQ ID NO: 112) |
| LYKEIRDAL | (SEQ ID NO: 113) |
| GLDTFLWDR | (SEQ ID NO: 114) |
| RVSPTRGRR | (SEQ ID NO: 115) |
| YVLRSVIAK | (SEQ ID NO: 142) |
| GLDTFLWDR | (SEQ ID NO: 116) |
| DILRVPCMR | (SEQ ID NO: 143) |
| DRHAQRAYL | (SEQ ID NO: 144) |

Glycoprotein D-2 (SEQ ID NO: 5) Encoded by US6 and Internally-Deleted Glycoprotein D-2 (SEQ ID NO: 4) Encoded by US6ΔTMR US6 encodes envelope glycoprotein D-2 (gD2), an envelope glycoprotein that binds to host cell entry receptors and may trigger fusion of the virus with the host membrane. The gD2 protein has several distinct domains, including a signal domain (amino acid residues 1-25) which is cleaved from the mature protein, and a transmembrane domain (spanning approximately amino acids residues 340-363). The DNA and protein sequence of US6 may be found by searching in the publicly available database, Entrez Gene (on the NCBI NIH web site on the World Wide Web, at the hypertext protocol transfer address of "ncbi.nlm.nih.gov/sites/entrez?db=gene"), in the Human herpesvirus 2 complete genome.

In some embodiments, an immunogenic composition described herein includes a polypeptide comprising gD2 that is missing all or part of the transmembrane domain (which spans approximately amino acids residues 340-363 inclusive) as well as the signal sequence. In other embodiments, the deleted region may additionally include 5-10 amino acids of the sequence flanking the transmembrane domain. The deleted region may also comprise a portion of the transmembrane domain, for example at least 3 amino acids between residues 340-363. In some embodiments, at least one residue in the transmembrane domain has been modified, deleted or substituted, such that the transmembrane domain is no longer functional. For example, a variant may have its internal deletion begin at amino acid residue 336, 337, 338, 339, 340, 341, 342, 343, 344, 345 or 346 and end at amino acid residue 358, 359, 360, 361, 362, 363, 364, 365, 366, 367 or 368.

A construct encoding gD2 which is missing amino acid residues 340-363 (the transmembrane domain) is called US6ΔTMR (SEQ ID NO: 40). The corresponding protein is denoted gD2ΔTMR (SEQ ID NO: 4). In other embodiments, an immunogenic fragment of gD2 or gD2ΔTMR may comprise a deletion in a portion of the transmembrane domain, and/or may comprise a deletion in the flanking sequence outside of the transmembrane domain.

In other aspects, the disclosure provides an immunogenic fragment of gD2 or gD2ΔTMR. An immunogenic fragment of gD2 or gD2ΔTMR comprises at least one immunogenic portion, as measured experimentally or identified by algorithm. Peptides identified by such methods include the following:

| | |
|---|---|
| ALAGSTLAV | (SEQ ID NO: 68) |
| LLEDPAGTV | (SEQ ID NO: 69) |
| VIGGIAFWV | (SEQ ID NO: 70) |
| TVYYAVLER | (SEQ ID NO: 71) |
| KYALADPSL | (SEQ ID NO: 72) |
| AFETAGTYL | (SEQ ID NO: 73) |
| APSNPGLII | (SEQ ID NO: 74) |
| IPITVYYAV | (SEQ ID NO: 75) |
| APPSHQPLF | (SEQ ID NO: 76) |
| FLMHAPAFE | (SEQ ID NO: 77) |
| FSAVSEDNL | (SEQ ID NO: 78) |
| VYYAVLER | (SEQ ID NO: 79) |
| IGMLPRFI | (SEQ ID NO: 80) |
| YTECPYNKS | (SEQ ID NO: 81) |
| FLMHAPAFE | (SEQ ID NO: 82) |
| NLGFLMHAP | (SEQ ID NO: 83) |
| VIGGIAFWV | (SEQ ID NO: 84) |
| GIAFWVRRR | (SEQ ID NO: 85) |
| SEDNLGFLM | (SEQ ID NO: 86) |
| RTQPRWSYY | (SEQ ID NO: 87) |
| IAFWVRRRA | (SEQ ID NO: 88) |
| LVIGGIAFW | (SEQ ID NO: 89) |
| FWVRRRAQM | (SEQ ID NO: 90) |
| PYTSTLLPP | (SEQ ID NO: 91) |
| VGTAALLVV | (SEQ ID NO: 92) |
| TAALLVVAV | (SEQ ID NO: 93) |
| TSTLLPPEL | (SEQ ID NO: 94) |
| GTVSSQIPP | (SEQ ID NO: 95) |
| TAGTYLRLV | (SEQ ID NO: 96) |
| GVTVDSIGM | (SEQ ID NO: 97) |
| AFWVRRRAQ | (SEQ ID NO: 98) |
| RVYHIQPSL | (SEQ ID NO: 99) |

Thus, in some aspects, the disclosure provides an immunogenic fragment of gD2 (SEQ ID NO: 5) or gD2ΔTMR (SEQ ID NO: 4). The fragments, in some instances, are close in size to the full-length polypeptide. For example, they may lack at most one, two, three, four, five, ten, or twenty amino acids from one or both termini. In other embodiments, the fragment is 100-393 amino acids in length, or 150-393, or 200-393, or 250-393 amino acids in length. Other exemplary fragments are amino acid residues 1-350, 1-300, 1-250, 1-200, 1-150, 1-100, 1-50, 50-393, 50-350, 50-300, 50-250, 50-200, 50-150, 50-100, 100-393, 100-350, 100-300, 100-250, 100-200, 100-150, 150-393, 150-350, 150-300, 150-250, 150-200, 200-393, 200-350, 200-300, 200-250, 250-393, 250-350, 250-300, 300-393 and 350-393. The fragments described above or sub-fragments thereof (e.g., fragments of 8-50, 8-30, or 8-20 amino acid residues) preferably have one of the biological activities described below, such as increasing the T cell response by at least 1.5 fold or 2 fold. A fragment may be used as the polypeptide in the vaccines described herein or may be fused to another protein, protein fragment or a polypeptide.

In other embodiments, the polypeptide comprises the entire sequence of SEQ ID NO: 4 or SEQ ID NO: 5, or consists of the entire sequence of SEQ ID NO: 4 or SEQ ID NO: 5. In certain embodiments, an immunogenic fragment of gD2 retains all or part of the signal domain (amino acid residues 1-25) and/or the transmembrane domain (amino acids residues 340-363).

In certain embodiments, polypeptides have less than 20%, 30%, 40%, 50%, 60% or 70% homology with human autoantigens. Examples of such autoantigens include UL6 from HSV-1 and gK or UL53 from HSV-2.

In certain aspects, this application provides immunogenic polypeptides with at least 90%, 95%, 97%, 98%, 99%, or 99.5% identity to gD2ΔTMR, or an immunogenic fragment thereof.

ICP4 Internal Fragment ICP4.5 (SEQ ID NO: 13) Encoded by RS1.5

RS1.5 encodes a 544 amino acid fragment corresponding to residues 775-1318 of ICP4, denoted ICP4.5. The DNA and protein sequences of RS1.5 may be found by searching for RS1 in the publicly available database, Entrez Gene (on the NCBI NIH web site on the World Wide Web, at the hypertext protocol transfer address of "ncbi.nlm.nih.gov/sites/entrez?db=gene"), in the Human herpes virus 2 complete genome.

In specific embodiments, an immunogenic composition described herein includes a polypeptide containing from 50 to all 544 amino acids residues of ICP4.5 (SEQ ID NO: 13), such as 50, 100, 150, 200, 250, 300, 350, 400, 450, 500, or 544 residues. In particular embodiments, the polypeptide includes all of ICP4.5 (SEQ ID NO: 13) or is ICP4.5 (SEQ ID NO: 13) itself. These polypeptides may, for example, include the full length or fragments of ICP4.5 (SEQ ID NO: 13) described herein with amino acid residues 1-774 of ICP4 (SEQ ID NO: 1) or fragments thereof, which, in certain embodiments, are consecutive with the amino acid residues of ICP4.5 being used. Exemplary fragments that combine the residues of SEQ ID NO: 13 with select residues from 1-774 of SEQ ID NO: 1 are described above.

An immunogenic fragment of ICP4.5 comprises at least one immunogenic portion, as measured experimentally or identified by algorithm. Thus, in some aspects, this application provides an immunogenic fragment of ICP4.5. The fragments, in some instances, are close in size to the full-length polypeptide. For example, they may lack at most one, two, three, four, five, ten, or twenty amino acids from one or both termini. In other embodiments, the fragment is 50-544 amino acids in length, or 100-544, or 150-544, or 200-544, or 250-544, or 300-544, or 350-544, or 400-544, or 450-544, or 500-544 amino acids in length. Other exemplary fragments are amino acid residues 1-500, 1-450, 1-400, 1-350, 1-300, 1-250, 1-200, 1-150, 1-100, 1-50, 50-544, 50-500, 50-450, 50-400, 50-350, 50-300, 50-250, 50-200, 50-150, 50-100, 100-544, 100-500, 100-450, 100-400, 100-350, 100-300, 100-250, 100-200, 100-150, 150-544, 150-500, 150-450, 150-400, 150-350, 150-300, 150-250, 150-200, 200-544, 200-500, 200-450, 200-400, 200-350, 200-300, 200-250, and so forth. The fragments described above or sub-fragments thereof (e.g., fragments of 8-50, 8-30, or 8-20 amino acid residues) preferably have one of the biological activities described below, such as increasing the T cell response by at least 1.5 fold or 2 fold. A fragment may be used as the polypeptide in the vaccines described herein or may be fused to another protein, protein fragment or a polypeptide.

In certain aspects, the disclosure provides immunogenic polypeptides with at least 90%, 95%, 97%, 98%, 99%, or 99.5% identity to ICP4.5 or an immunogenic fragment thereof.

ICP4 Fragment ICP4.9 (SEQ ID NO: 138) Encoded by RS1.9, and ICP4 Fragment ICP4. 10 (SEQ ID NO: 139) Encoded by RS1.10

RS1.9 encodes a 1130 amino acid fragment of ICP4, carrying a double internal deletion of residues 391-544 and residues 786-821 of ICP4, denoted ICP4.9. RS1.10 encodes a 1166 amino acid fragment of ICP4, carrying a double internal deletion of residues 391-508 and residues 786-821 of ICP4, denoted ICP4.10. The DNA and protein sequences of RS1.9 and RS1.10 may be found by searching for RS1 in the publicly available database, Entrez Gene (on the NCBI NIH web site on the World Wide Web, at the hypertext protocol transfer address of "ncbi.nlm.nih.gov/sites/entrez?db=gene"), in the Human herpesvirus 2 complete genome.

In specific embodiments, an immunogenic composition described herein includes a polypeptide containing from 50 to all 1130 or 1166 amino acids residues of ICP4.9 (SEQ ID NO: 138) or ICP4.10 (SEQ ID NO: 139), such as 50, 100, 150, 200, 250, 300, 350, 400, 450, 500, 550, 600, 650, 700, 750, 800, 850, 900, 950, 1000, 1050, 1100, 1130 or 1166 residues. In particular embodiments, the polypeptide includes all of ICP4.9 (SEQ ID NO: 138) or ICP4.10 (SEQ ID NO: 139), or is ICP4.9 (SEQ ID NO: 138) or ICP4.10 (SEQ ID NO: 139) itself. These polypeptides may, for example, include the full length or fragments of ICP4.9 (SEQ ID NO: 138) or ICP4.10 (SEQ ID NO: 139) described herein.

An immunogenic fragment of ICP4.9 or ICP4.10 comprises at least one immunogenic portion, as measured experimentally or identified by algorithm. Thus, in some aspects, this application provides an immunogenic fragment of ICP4.9 or ICP4.10. The fragments, in some instances, are close in size to the full-length polypeptide. For example, they may lack at most one, two, three, four, five, ten, or twenty amino acids from one or both termini. In other embodiments, the fragment is 50-1130 amino acids in length, or 100-1130, 150-1130, or 200-1130, or 250-1130, or 300-1130, or 400-1130, or 500-1130, or 600-1130, or 700-1130, or 800-1130, or 900-1130, or 1000-1130 amino acids in length. Other exemplary fragments are amino acid residues 1-1130, 1-1000, 1-900, 1-800, 1-700, 1-600, 1-500, 1-400, 1-300, 1-200, 1-150, 1-100, 1-50, 50-1130, 50-1000, 50-900, 50-800, 50-700, 50-600, 50-500, 50-400, 50-300, 50-250, 50-200, 50-150, 50-100, 100-1130, 100-1000, 100-900, 100-800, 100-700, 100-600, 100-500, 100-400, 100-

300, 100-250, 100-200, 100-150, and so forth. The fragments described above or sub-fragments thereof (e.g., fragments of 8-50, 8-30, or 8-20 amino acid residues) preferably have one of the biological activities described below, such as increasing the T cell response by at least 1.5 fold or 2 fold. A fragment may be used as the polypeptide in the vaccines described herein or may be fused to another protein, protein fragment or a polypeptide.

In certain embodiments, an analog of ICP4.9 is based on SEQ ID NO: 1, where at least 50, 75, 100, 125, 130, 140, 145 or 150 residues from residues 391-544 are deleted. Separately or in combination, at least 20, 25, or 30 residues from residues 786-821 are deleted.

In certain embodiments, an analog of ICP4.10 is based on SEQ ID NO: 1, where at least 25, 50, 75, 90, 95, 100, 105, 110 or 115 residues from residues 391-508 are deleted. Separately or in combination, at least 25, 50, 60, 65, 70 or 75 residues from residues 786-821 are deleted.

In certain aspects, the disclosure provides immunogenic polypeptides with at least 90%, 95%, 97%, 98%, 99%, or 99.5% identity to ICP4.9 or ICP4.10, or an immunogenic fragment or analog thereof.

Additional Features of HSV-2 Polypeptides

Typically, the polypeptides present in an immunogenic composition described herein are immunogenic, either alone or as a variant, which includes polypeptides fused to another polypeptide or mixed with or complexed to an adjuvant. Variants also include sequences with less than 100% sequence identity, as described herein. In addition, one may use fragments, precursors and analogs that have an appropriate immunogenicity.

These polypeptides may be immunogenic in mammals, for example, mice, guinea pigs, or humans. An immunogenic polypeptide is typically one capable of raising a significant immune response in an assay or in a subject. Alternatively, an immunogenic polypeptide may (i) induce production of antibodies, e.g., neutralizing antibodies, that bind to the polypeptide (ii) induce $T_H1$ immunity, (iii) activate the $CD8^+$ T cell response, for example by increasing the number of $CD8^+$ T cells, increasing localization of $CD8^+$ T cells to the site of infection or reinfection, (iv) induce $T_H17$ immunity, and/or (v) activate innate immunity. In some embodiments, an immunogenic polypeptide causes the production of a detectable amount of antibody specific to that antigen.

In certain embodiments, polypeptides have less than 20%, 30%, 40%, 50%, 60% or 70% homology with human autoantigens.

A polypeptide may comprise one or more immunogenic portions and one or more non-immunogenic portions. The immunogenic portions may be identified by various methods, including protein microarrays, ELISPOT/ELISA techniques, and/or specific assays on different deletion mutants (e.g., fragments) of the polypeptide in question. Immunogenic portions may also be identified by computer algorithms. Some such algorithms, like EpiMatrix (produced by EpiVax), use a computational matrix approach. Other computational tools for identifying antigenic epitopes include PEPVAC (Promiscuous EPitope-based VACcine, hosted by Dana Farber Cancer Institute on the world wide web at the hypertext protocol transfer address of "immunax.dfci.harvard.edu/PEPVAC"), MHCPred (which uses a partial least squares approach and is hosted by The Jenner Institute on the world wide web at the hypertext protocol transfer address of "jenner.ac.uk/MHCPred"), and Syfpeithi, hosted on the world wide web at the hypertext protocol transfer address of "syfpeithi.de/".

In some embodiments, an immunogenic composition described herein may comprise fusion proteins and/or fusion DNA constructs. The underlying DNA sequences above may be modified in ways that do not affect the sequence of the protein product. For instance, the DNA sequence may be codon-optimized to improve expression in a host such as *E. coli* or an insect cell line (e.g., using the baculovirus expression system) or mammalian (e.g., Chinese Hamster Ovary) cell line. In certain embodiments, the DNA sequence may comprise an exogenous sequence, such as an exogenous signal sequence, for expression in non-mammalian cells. In particular embodiments, such as when smaller related polypeptides, including those having a molecular weight less than about 5000 daltons, e.g., 1500 to 5000 daltons, are used, modification may be useful in eliciting the desired immune response. For example, the smaller polypeptides can be conjugated to an appropriate immunogenic carrier such as proteins from other pathogenic organisms or viruses (e.g., tetanus toxoid), large proteins (e.g., keyhole limpet hemocyanin) or the like. Conjugation may be direct or indirect (e.g., via a linker). In other particular embodiments, a fusion protein may comprise a polypeptide disclosed above or an immunogenic fragment or variant thereof and a tag. A tag may be N-terminal or C-terminal. For instance, tags may be added to the nucleic acid or polypeptide to facilitate purification, detection, solubility, or confer other desirable characteristics on the protein or nucleic acid. For instance, a purification tag may be a peptide, oligopeptide, or polypeptide that may be used in affinity purification. Examples include His, GST, TAP, FLAG, myc, HA, MBP, VSV-G, thioredoxin, V5, avidin, streptavidin, BCCP, Calmodulin, Nus, S tags, lipoprotein D, and β galactosidase. In some embodiments, the fused portion is short. Thus, in some instances, the fusion protein comprises no more than 1, 2, 3, 4, 5, 10, 20, or 50 additional amino acids on one or both termini of a polypeptide described above, such as consecutive amino acids from any of the polypeptides in Table 1.

In some embodiments, tags, secretion signals, or other signal sequences may be added to the C-terminal end and/or to the N-terminal end of the polypeptide. Tags may be used to aid in purification of expressed polypeptides. Exemplary tags include HHHHHH (SEQ ID NO: 130) and MSYYHHHHHH (SEQ ID NO: 131). Secretion signals may be optimized for use with non-mammalian cells, such as insect cells. An exemplary secretion signal is MKFLVNVALVFMVVYISYIYA (SEQ ID NO: 132).

A detection tag may be used to detect the tag and, consequently, any amino acid sequence fused to it. Detection tags include fluorescent proteins, proteins that bind a fluorescent label, and proteins that bind an electron-dense moeity. Examples of fluorescent proteins include dsRed, mRFP, YFP, GFP, CFP, BFP, and Venus. An example of a protein that binds a fluorescent or electron-dense label is FlAsH.

Another aspect disclosed herein is an antibody preparation generated against a composition of the invention (e.g., a composition comprising one or more, or two or more of the polypeptides listed in Table 1). Any of a variety of antibodies are included. Such antibodies include, e.g., polyclonal, monoclonal, recombinant, humanized or partially humanized, single chain, Fab, and fragments thereof, etc. The antibodies can be of any isotype, e.g., IgA, IgG, various IgG isotypes such as $IgG_1$, $IgG_2$, $IgG_{2a}$, $IgG_{2b}$, $IgG_3$, $IgG_4$, etc.; and they can be from any animal species that produces antibodies, including goat, rabbit, mouse, chicken or the like. In some embodiments, Fab molecules are expressed and assembled in a genetically transformed host like *E. coli*.

A lambda vector system is available thus to express a population of Fab's with a potential diversity equal to or exceeding that of the subject generating the predecessor antibody. See Huse et al. (1989), Science 246, 1275-81.

Components of Immunogenic and Pharmaceutical Compositions

In certain embodiments, an immunogenic composition e.g., a vaccine, vaccine formulation, and/or a pharmaceutical composition described herein, comprises one or more of the polypeptides and nucleic acids described above and one or more of the following: an adjuvant, stabilizer, buffer, surfactant, controlled-release component, salt, preservative, and an antibody specific to said antigen.

Adjuvants

Immunogenic compositions described herein may include an adjuvant. Adjuvants can be broadly separated into two classes, based on their principal mechanisms of action: vaccine delivery systems and immunostimulatory adjuvants (see, e.g., Singh et al., Curr. HIV Res. 1:309-20, 2003). Vaccine delivery systems are often particulate formulations, e.g., emulsions, microparticles, immune-stimulating complexes (ISCOMs), which may be, for example, particles and/or matrices, and liposomes. In contrast, immunostimulatory adjuvants are sometimes derived from pathogens and can represent pathogen associated molecular patterns (PAMP), e.g., lipopolysaccharides (LPS), monophosphoryl lipid (MPL), or CpG-containing DNA, which activate cells of the innate immune system.

Alternatively, adjuvants may be classified as organic and inorganic. Inorganic adjuvants include aluminum salts such as aluminum phosphate, amorphous aluminum hydroxyphosphate sulfate, and aluminum hydroxide, which are commonly used in human vaccines. Organic adjuvants comprise organic molecules including macromolecules. An example of an organic adjuvant is cholera toxin.

Adjuvants may also be classified by the response they induce, and adjuvants can activate more than one type of response. In some embodiments, the adjuvant induces the activation of CD4+ T cells. The adjuvant may induce activation of $T_H1$ cells and/or activation of $T_H17$ cells and/or activation of $T_H2$ cells. Alternately, the adjuvant may induce activation of $T_H1$ cells and/or $T_H17$ cells but not activation of $T_H2$ cells, or vice versa. In some embodiments, the adjuvant induces activation of CD8+T cells. In further embodiments, the adjuvant may induce activation of Natural Killer T (NKT) cells. In some embodiments, the adjuvant induces the activation of $T_H1$ cells or $T_H17$ cells or $T_H2$ cells. In other embodiments, the adjuvant induces the activation of B cells. In yet other embodiments, the adjuvant induces the activation of APCs. These categories are not mutually exclusive; in some cases, an adjuvant activates more than one type of cell.

In certain embodiments, an adjuvant is a substance that increases the numbers or activity of APCs such as dendritic cells. In certain embodiments, an adjuvant promotes the maturation of APCs such as dendritic cells. In some embodiments, the adjuvant is or comprises a saponin. Typically, the saponin is a triterpene glycoside, such as those isolated from the bark of the *Quillaja saponaria* tree. A saponin extract from a biological source can be further fractionated (e.g., by chromatography) to isolate the portions of the extract with the best adjuvant activity and with acceptable toxicity. Typical fractions of extract from *Quillaja saponaria* tree used as adjuvants are known as fractions A and C. An exemplary saponin adjuvant is QS-21 (fraction C), which is available from Antigenics. QS-21 is an oligosaccharide-conjugated small molecule. Optionally, QS-21 may be admixed with a lipid such as 3D-MPL or cholesterol.

A particular form of saponins that may be used in vaccine formulations described herein is immunostimulating complexes (ISCOMs). ISCOMs are an art-recognized class of adjuvants, that generally comprise *Quillaja* saponin fractions and lipids (e.g., cholesterol and phospholipids such as phosphatidyl choline). In certain embodiments, an ISCOM is assembled together with a polypeptide or nucleic acid of interest. However, different saponin fractions may be used in different ratios. In addition, the different saponin fractions may either exist together in the same particles or have substantially only one fraction per particle (such that the indicated ratio of fractions A and C are generated by mixing together particles with the different fractions). In this context, "substantially" refers to less than 20%, 15%, 10%, 5%, 4%, 3%, 2% or even 1%. Such adjuvants may comprise fraction A and fraction C mixed into a ratio of 70-95 A:30-5 C, such as 70 A:30 C to 75 A:25 C; 75 A:25 C to 80 A:20 C; 80 A:20 C to 85 A:15 C; 85 A:15 C to 90 A:10 C; 90 A:10 C to 95 A:5 C; or 95 A:5 C to 99 A:1 C. ISCOMatrix, produced by CSL, and AbISCO 100 and 300, produced by Isconova, are ISCOM matrices comprising saponin, cholesterol and phospholipid (lipids from cell membranes), which form cage-like structures typically 40-50 nm in diameter. Posintro, produced by Nordic Vaccines, is an ISCOM matrix where the immunogen is bound to the particle by a multitude of different mechanisms, e.g., electrostatic interaction by charge modification, incorporation of chelating groups, or direct binding.

In some embodiments, the adjuvant is a TLR ligand. TLRs are proteins that may be found on leukocyte membranes, and recognize foreign antigens (including microbial antigens). An exemplary TLR ligand is IC-31, which is available from Intercell. IC-31 comprises an anti-microbial peptide, KLK, and an immunostimulatory oligodeoxynucleotide, ODN1a. IC-31 has TLR9 agonist activity. Another example is CpG-containing DNA. Different varieties of CpG-containing DNA are available from Prizer (Coley): Vaxlmmune is CpG 7909 (a (CpG)-containing oligodeoxynucleotide), and Actilon is CpG 10101 (a (CpG)-containing oligodeoxy-nucleotide).

In some embodiments, the adjuvant is a nanoemulsion. One exemplary nanoemulsion adjuvant is Nanostat Vaccine, produced by Nanobio. This nanoemulsion is a high-energy, oil-in-water emulsion. This nanoemulsion typically has a size of 150-400 nanometers, and includes surfactants to provide stability. More information about Nanostat can be found in U.S. Pat. Nos. 6,015,832, 6,506,803, 6,559,189, 6,635,676, and 7,314,624.

In some embodiments, an adjuvant includes a cytokine. In some embodiments, the cytokine is an interleukin such as IL-1, IL-6, IL-12, IL-17 and IL-23. In some embodiments, the cytokine is granulocyte-macrophage colony-stimulating factor (GM-CSF). The adjuvant may include cytokine as a purified polypeptide. Alternatively, the adjuvant may include nucleic acids encoding the cytokine.

Adjuvants may be covalently bound to antigens (e.g., the polypeptides described above). In some embodiments, the adjuvant may be a protein which induces inflammatory responses through activation of APCs. In some embodiments, one or more of these proteins can be recombinantly fused with an antigen of choice, such that the resultant fusion molecule promotes dendritic cell maturation, activates dendritic cells to produce cytokines and chemokines, and ultimately, enhances presentation of the antigen to T cells and initiation of T cell responses (see Wu et al., Cancer Res 2005; 65(11), pp 4947-4954). Other exemplary adjuvants that may be covalently bound to antigens comprise polysaccharides, synthetic peptides, lipopeptides, and nucleic acids.

The adjuvant can be used alone or in combination of two or more kinds. Adjuvants may be directly conjugated to antigens. Adjuvants may also be combined to increase the magnitude of the immune response to the antigen. Typically, the same adjuvant or mixture of adjuvants is present in each dose of a vaccine. Optionally, however, an adjuvant may be administered with a first dose of vaccine and not with subsequent doses (e.g., booster shots). Alternatively, a strong adjuvant may be administered with the first dose of vaccine and a weaker adjuvant or lower dose of the strong adjuvant may be administered with subsequent doses. The adjuvant can be administered before the administration of the antigen, concurrent with the administration of the antigen or after the administration of the antigen to a subject (sometimes within 1, 2, 6, or 12 hours, and sometimes within 1, 2, or 5 days). Certain adjuvants are appropriate for human patients, non-human animals, or both.

Additional Components of Immunogenic and Pharmaceutical Compositions

In addition to the antigens and the adjuvants described above, an immunogenic composition, e.g., a vaccine, a vaccine formulation and/or a pharmaceutical composition, may include one or more additional components.

In certain embodiments, an immunogenic composition may include one or more stabilizers such as sugars (such as sucrose, glucose, or fructose), phosphate (such as sodium phosphate dibasic, potassium phosphate monobasic, dibasic potassium phosphate, or monosodium phosphate), glutamate (such as monosodium L-glutamate), gelatin (such as processed gelatin, hydrolyzed gelatin, or porcine gelatin), amino acids (such as arginine, asparagine, histidine, L-histidine, alanine, valine, leucine, isoleucine, serine, threonine, lysine, phenylalanine, tyrosine, and the alkyl esters thereof), inosine, or sodium borate.

In certain embodiments, an immunogenic composition includes one or more buffers such as a mixture of sodium bicarbonate and ascorbic acid. In some embodiments, an immunogenic composition may be administered in saline, such as phosphate buffered saline (PBS), or distilled water.

In certain embodiments, an immunogenic composition includes one or more surfactants such as polysorbate 80 (Tween 80), Polyethylene glycol tert-octylphenyl ether t-Octylphenoxypolyethoxyethanol 4-(1,1,3,3-Tetramethylbutyl) phenyl-polyethylene glycol (TRITON X-100); Polyoxyethylenesorbitan monolaurate Polyethylene glycol sorbitan monolaurate (TWEEN 20); and 4-(1,1,3,3-Tetramethylbutyl)phenol polymer with formaldehyde and oxirane (TYLOXAPOL). A surfactant can be ionic or nonionic.

In certain embodiments, an immunogenic composition includes one or more salts such as sodium chloride, ammonium chloride, calcium chloride, or potassium chloride.

In certain embodiments, a preservative is included in an immunogenic composition. In other embodiments, no preservative is used. A preservative is most often used in multi-dose vaccine vials, and is less often needed in single-dose vaccine vials. In certain embodiments, the preservative is 2-phenoxyethanol, methyl and propyl parabens, benzyl alcohol, and/or sorbic acid.

In certain embodiments, an immunogenic composition is a controlled-release formulation.

DNA Immunogenic Compositions

In certain aspects, an immunogenic composition, e.g., a vaccine, a vaccine formulation and/or a pharmaceutical composition, comprises one or more of the nucleic acids disclosed herein. When a nucleic acid vaccine is administered to a patient, the corresponding gene product (such as a desired antigen) is produced in the patient's body. In some embodiments, nucleic acid vaccine vectors that include optimized recombinant polynucleotides can be delivered to a mammal (including humans) to induce a therapeutic or prophylactic immune response. The nucleic acid may be, for example, DNA, RNA, or a synthetic nucleic acid. The nucleic acid may be single stranded or double-stranded.

Nucleic acid vaccine vectors (e.g., adenoviruses, liposomes, papillomaviruses, retroviruses, etc.) can be administered directly to the mammal for transduction of cells in vivo. The nucleic acid vaccines can be formulated as pharmaceutical compositions for administration in any suitable manner, including parenteral administration. Plasmid vectors are typically more efficient for gene transfer to muscle tissue. The potential to deliver DNA vectors to mucosal surfaces by oral administration has also been reported (PLGA encapsulated Rotavirus and Hepatitis B) and DNA plasmids have been utilized for direct introduction of genes into other tissues. DNA vaccines have been introduced into animals primarily by intramuscular injection, by gene gun delivery, or by electroporation. After being introduced, the plasmids are generally maintained episomally without replication. Expression of the encoded proteins has been shown to persist for extended time periods, providing stimulation of B and T cells.

In determining the effective amount of the vector to be administered in the treatment or prophylaxis of an infection or other condition, the physician evaluates vector toxicities, progression of the disease, and the production of anti-vector antibodies, if any. Often, the dose equivalent of a naked nucleic acid from a vector is from about 1 µg to 1 mg for a typical 70 kilogram patient, and doses of vectors used to deliver the nucleic acid are calculated to yield an equivalent amount of therapeutic nucleic acid. Administration can be accomplished via single or divided doses. The toxicity and therapeutic efficacy of the nucleic acid vaccine vectors can be determined using standard pharmaceutical procedures in cell cultures or experimental animals.

A nucleic acid vaccine can contain DNA, RNA, a modified nucleic acid, or a combination thereof. In some embodiments, the vaccine comprises one or more cloning or expression vectors; for instance, the vaccine may comprise a plurality of expression vectors each capable of autonomous expression of a nucleotide coding region in a mammalian cell to produce at least one immunogenic polypeptide. An expression vector often includes a eukaryotic promoter sequence, such as the nucleotide sequence of a strong eukaryotic promoter, operably linked to one or more coding regions. The compositions and methods herein may involve the use of any particular eukaryotic promoter, and a wide variety are known, such as a CMV or RSV promoter. The promoter can be, but need not be, heterologous with respect to the host cell. The promoter used may be a constitutive promoter.

A vector useful in the present compositions and methods can be circular or linear, single-stranded or double stranded and can be a plasmid, cosmid, or episome. In a suitable embodiment, each nucleotide coding region is on a separate vector; however, it is to be understood that one or more coding regions can be present on a single vector, and these coding regions can be under the control of a single or multiple promoters.

Numerous plasmids may be used for the production of nucleic acid vaccines. Suitable embodiments of the nucleic acid vaccine employ constructs using the plasmids VR1012 (Vical Inc., San Diego Calif.), pCMVI.UBF3/2 (S. Johnston, University of Texas) or pcDNA3.1 (InVitrogen Corporation, Carlsbad, Calif.) as the vector. In addition, the vector construct can contain immunostimulatory sequences (ISS), such as unmethylated dCpG motifs, that stimulate the animal's immune system. The nucleic acid vaccine can also encode a fusion product containing the immunogenic polypeptide. Plasmid DNA can also be delivered using attenuated bacteria as delivery system, a method that is suitable for DNA vaccines that are administered orally. Bacteria are transformed with an independently replicating plasmid, which becomes released into the host cell cytoplasm following the death of the attenuated bacterium in the host cell.

DNA vaccines, including the DNA encoding the desired antigen, can be introduced into a host cell in any suitable form including, the fragment alone, a linearized plasmid, a circular plasmid, a plasmid capable of replication, an episome, RNA, etc. Preferably, the gene is contained in a plasmid. In certain embodiments, the plasmid is an expression vector. Individual expression vectors capable of expressing the genetic material can be produced using standard recombinant techniques. See e.g., Maniatis et al., 1985 Molecular Cloning: A Laboratory Manual or DNA Cloning, Vol. I and II (D. N. Glover, ed., 1985) for general cloning methods.

Routes of administration include, but are not limited to, intramuscular, intranasal, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Typical routes of administration include intramuscular, intraperitoneal, intradermal and subcutaneous injection. Genetic constructs may be administered by means including, but not limited to, traditional syringes, needleless injection devices, "microprojectile bombardment gene guns", or other physical methods such as electroporation ("EP"), "hydrodynamic method", or ultrasound. DNA vaccines can be delivered by any method that can be used to deliver DNA as long as the DNA is expressed and the desired antigen is made in the cell.

In some embodiments, a DNA vaccine is delivered via known transfection reagents such as cationic liposomes, fluorocarbon emulsion, cochleate, tubules, gold particles, biodegradable microspheres, or cationic polymers. Cochleate delivery vehicles are stable phospholipid calcium precipitants consisting of phosphatidyl serine, cholesterol, and calcium; this nontoxic and noninflammatory transfection reagent can be present in a digestive system. Biodegradable microspheres comprise polymers such as poly(lactide-co-glycolide), a polyester that can be used in producing microcapsules of DNA for transfection. Lipid-based microtubes often consist of a lipid of spirally wound two layers packed with their edges joined to each other. When a tubule is used, the nucleic acid can be arranged in the central hollow part thereof for delivery and controlled release into the body of an animal.

In some embodiments, DNA vaccine is delivered to mucosal surfaces via microspheres. Bioadhesive microspheres can be prepared using different techniques and can be tailored to adhere to any mucosal tissue including those found in eye, nasal cavity, urinary tract, colon and gastrointestinal tract, offering the possibilities of localized as well as systemic controlled release of vaccines. Application of bioadhesive microspheres to specific mucosal tissues can also be used for localized vaccine action. In some embodiments, an alternative approach for mucosal vaccine delivery is the direct administration to mucosal surfaces of a plasmid DNA expression vector which encodes the gene for a specific protein antigen.

The DNA plasmid vaccines according to the present invention are formulated according to the mode of administration to be used. In some embodiments where DNA plasmid vaccines are injectable compositions, they are sterile, and/or pyrogen free and/or particulate free. In some embodiments, an isotonic formulation is preferably used. Generally, additives for isotonicity can include sodium chloride, dextrose, mannitol, sorbitol and lactose. In some embodiments, isotonic solutions such as phosphate buffered saline are preferred. In some embodiments, stabilizers include gelatin and albumin. In some embodiments, a vasoconstriction agent is added to the formulation. In some embodiments, a stabilizing agent that allows the formulation to be stable at room or ambient temperature for extended periods of time, such as LGS or other polycations or polyanions is added to the formulation.

In some embodiments, the DNA vaccine may further comprise a pharmacologically acceptable carrier or diluent. Suitable carriers for the vaccine are well known to those skilled in the art and include but are not limited to proteins, sugars, etc. Such carriers may be aqueous or non-aqueous solutions, suspensions, and emulsions. Examples of non-aqueous carriers are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's or fixed oils. Intravenous vehicles include fluid and nutrient replenishers, electrolyte replenishers such as those based on Ringer's dextrose, and the like. Preservatives and antimicrobials include antioxidants, chelating agents, inert gases and the like. Preferred preservatives include formalin, thimerosal, neomycin, polymyxin B and amphotericin B.

An alternative approach to delivering the nucleic acid to an animal involves the use of a viral or bacterial vector. Examples of suitable viral vectors include adenovirus, polio virus, pox viruses such as alphaviruses, vaccinia, canary pox, and fowl pox, herpes viruses, including catfish herpes virus, adenovirus-associated vector, and retroviruses. Virus-like vectors include virosomes and virus-like particles. Exemplary bacterial vectors include attenuated forms of *Salmonella, Shigella, Edwardsiella ictaluri, Yersinia ruckerii,* and *Listeria monocytogenes*. In some embodiments, the nucleic acid is a vector, such as a plasmid, that is capable of autologous expression of the nucleotide sequence encoding the immunogenic polypeptide.

Use of Immunogenic Compositions

The immunogenic compositions, e.g., vaccines, vaccine formulations and/or pharmaceutical compositions, described herein, may be used for prophylactic and/or therapeutic treatment of herpes, including HSV-1 and particularly HSV-2. In some embodiments, such compositions are used in immunotherapy. The subject receiving the vaccination may be a male or a female, and may be a child or adult. In some embodiments, the subject being treated is a human. In other embodiments, the subject is a non-human animal.

Prophylactic Use

In prophylactic embodiments, an immunogenic composition described herein (e.g., a vaccine) is administered to a subject to induce an immune response that can help protect against the establishment of HSV-2.

In some embodiments, an immunogenic composition (e.g., vaccine composition) confers protective immunity, allowing a vaccinated individual to exhibit delayed onset of symptoms or reduced severity of symptoms (e.g., reduced number of lesions at the onset of infection), as the result of his/her exposure to the vaccine (e.g., a memory response). In certain embodiments, the reduction in severity of symptoms is at least 25%, 40%, 50%, 60%, 70%, 80% or even 90%. Some vaccinated individuals may display no symptoms upon contact with, HSV-2, or even no infection by HSV-2. Protective immunity is typically achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes, that result in sIGA production by B lymphocytes on mucosa-lined tissues of the body. Humoral immunity is typically the result of IgG antibodies and IgM antibodies in serum. For example, the IgG titer can be raised by 1.5-fold, 2-fold, 3-fold, 4-fold, 5-fold, 10-fold, 20-fold, 50-fold, or even 100-fold or more following administration of a vaccine formulation described herein. Cellular immunity can be achieved through cytotoxic T lymphocytes or through delayed-type hypersensitivity that involves macrophages and T lymphocytes, as well as other mechanisms involving T cells without a requirement for antibodies. In particular, cellular immunity may be mediated by $T_H1$ cells or $T_H17$ cells. Activation of $T_H1$ cells can be measured by secretion of IFN-γ, relative to the level of IFN-γ released in response to a polypeptide that does not generate an immunologic response. In certain embodiments, the amount of IFN-γ released is 1.5-fold, 2-fold, 3-fold, 4-fold, 5-fold, 10-fold, 20-fold, 50-fold or even 100-fold greater. The primary result of protective immunity is the destruction of HSV-2 viral particles or inhibition of HSV-2's ability to replicate. In some embodiments, the protective immunity conferred by presentation of antigen before exposure to HSV-2 will reduce the likelihood of seroconversion to an HSV-2-positive status.

The duration of protective immunity is preferably as long as possible. In certain embodiments, an immunogenic composition (e.g., vaccine) produces protective immunity lasting six months, one year, two years, five years, ten years, twenty years or even a lifetime.

In some embodiments, a combination of specific polypeptides may prove efficacious for inhibiting HSV-2 infection or the onset of symptoms described above. An exemplary immunogenic composition (e.g., vaccine) for prophylactic use may comprise a pharmaceutically-acceptable carrier, a first polypeptide consisting of SEQ ID NOS: 136, a second polypeptide consisting of SEQ ID NO: 1 or 4, and optionally a third polypeptide consisting of the other of SEQ ID NOS: 1 and 4, or immunogenic fragments thereof. In some embodiments, the second or third polypeptide consists of polypeptide fragments of SEQ ID NO: 1, such as the polypeptides of SEQ ID NOS: 2, 8-16, 138 and 139, or immunogenic fragments thereof. In some embodiments, an immunogenic composition (e.g., vaccine) for prophylactic use may comprise a first polypeptide consisting of SEQ ID NO: 136, a second polypeptide consisting of SEQ ID NO: 4 or SEQ ID NO: 5, a third polypeptide selected from the group consisting of SEQ ID NOS: 2, 8-16, 138 and 139, and optionally a fourth polypeptide selected from the group consisting of SEQ ID NOS: 2, 8-16, 138 and 139, or immunogenic fragments thereof.

In other embodiments, an immunogenic composition (e.g., vaccine) for prophylactic use comprises a pharmaceutically-acceptable carrier and a nucleic acid having a nucleotide sequence that encodes at least one of SEQ ID NOS: 1, 3, 5, 38, 136 or 138, or an immunogenic fragment thereof. For example, the nucleic acids can have a nucleotide sequence comprising at least one of SEQ ID NOS: 39, 46, 118, 137 or 140, or a fragment thereof that encodes an immunogenic polypeptide.

Therapeutic Use

In therapeutic applications, an immunogenic composition (e.g., vaccine) comprising a polypeptide or nucleic acid described herein may be administered to a patient suffering from HSV-2, in an amount sufficient to treat the patient. Treating the patient, in this case, may refer to delaying or reducing symptoms of HSV-2 in an infected individual. In some embodiments, treating the patient refers to reducing the duration of lesions, reducing the number of lesions, reducing the duration of symptoms per episode, and/or otherwise reducing the intensity of symptoms per episode. In certain embodiments, the vaccine reduces the duration or severity of mild symptoms; in some embodiments, the vaccine reduces the duration or severity of serious symptoms. In some embodiments, the vaccine reduces viral shedding and therefore the transmissibility of HSV-2 from the vaccinated patient. In certain embodiments, the reductions described above are at least 25%, 30%, 40%, 50%, 60%, 70%, 80% or even 90%. In certain embodiments, the reductions described above include the complete cessation of symptoms, viral shedding and/or future outbreaks (e.g., by blocking the ability of the virus to establish latency in sensory ganglia).

In therapeutic embodiments, an immunogenic composition (e.g., vaccine) is administered to an individual post-infection. The immunogenic composition (e.g., vaccine) may be administered shortly after infection, e.g. before symptoms manifest, or may be administered during or after manifestation of symptoms. In some embodiments, the immunogenic composition (e.g., vaccine) may prevent endogenous reactivation of earlier infection. In some embodiments, a post-infection vaccine could be administered to patients in high-risk groups.

The duration of therapeutic effects of an immunogenic composition (e.g., vaccine) disclosed herein is preferably as long as possible. In certain embodiments, an immunogenic composition (e.g., vaccine) produces therapeutic effects lasting one month, two months, three months, six months, one year, two years, five years, ten years, twenty years or even a lifetime.

In some embodiments, a combination of specific polypeptides may prove efficacious for treating a patient suffering from HSV-2 as described above. An exemplary immunogenic composition (e.g., vaccine) for therapeutic use may comprise a pharmaceutically-acceptable carrier, a first polypeptide consisting of SEQ ID NOS: 136, a second polypeptide consisting of SEQ ID NO: 1 or 4, and optionally a third polypeptide consisting of the other of SEQ ID NOS: 1 and 4, or immunogenic fragments thereof. In some embodiments, the second or third polypeptide consists of polypeptide fragments of SEQ ID NO: 1, such as the polypeptides of SEQ ID NOS: 2, 8-16, 138 and 139, or immunogenic fragments thereof. In some embodiments, immunogenic composition (e.g., vaccine) for therapeutic use may comprise a first polypeptide consisting of SEQ ID NO: 136, a second polypeptide consisting of SEQ ID NO: 4 or SEQ ID NO: 5, a third polypeptide selected from the group consisting of SEQ ID NOS: 2, 8-16, 138 and 139, and optionally a fourth polypeptide selected from the group consisting of SEQ ID NOS: 2, 8-16, 138 and 139, or immunogenic fragments thereof.

In other embodiments, an immunogenic composition (e.g., vaccine) for therapeutic use comprises a pharmaceutically-acceptable carrier and a nucleic acid having a nucleotide sequence that encodes at least one of SEQ ID NOS: 1, 3, 5, 38, 136 or 138 or an immunogenic fragment thereof. For example, the nucleic acids can have a nucleotide sequence comprising at least one of SEQ ID NOS: 39, 46, 118, 137 or 140, or a fragment thereof that encodes an immunogenic polypeptide.

Assaying Vaccination Efficacy

The efficacy of vaccination with an immunogenic composition (e.g., vaccine) disclosed herein may be determined in a number of ways.

Efficacy may be assayed in various model systems. Suitable model systems used to study HSV-2 include a guinea pig model and a mouse model, as described in the examples below. Briefly, the animals are vaccinated with immunogenic composition (e.g., vaccine) and then challenged with HSV-2 or the immunogenic composition (e.g., vaccine) is administered to already-infected animals. The response of the animals to the HSV-2 challenge or the immunogenic composition (e.g., vaccine) is then compared with control animals, using one of the measures described above. A similar assay could be used for clinical testing of humans. The treatment and prophylactic effects described above represent additional ways of determining efficacy of an immunogenic composition (e.g., vaccine).

In addition, efficacy may be evaluated by in vitro immunization of naive human peripheral blood mononuclear cells (PBMC), where APCs are exposed to the immunogenic composition (e.g., vaccine) and then the APCs are co-cultured with naive T cells from the same donor to evaluate the primary response to immunization in a test tube. An activation of the T-cells by 1.5-fold, 2-fold, 5-fold, 10-fold, 20-fold, 50-fold or 100-fold or more relative to activation of T-cells using APCs not exposed to an immunogenic composition (e.g., vaccine), in certain embodiments, is considered an adequate response.

Efficacy may further be determined by viral neutralization assays. Briefly, animals are immunized and serum is collected on various days post-immunization. Serial dilutions of serum are pre-incubated with virus during which time antibodies in the serum that are specific for the virus will bind to it. The virus/serum mixture is then added to permissive cells to determine infectivity by a plaque assay. If antibodies in the serum neutralize the virus, there are fewer plaques compared to the control group.

Antiviral Therapy

Methods described herein include combination of an immunogenic composition described herein and antiviral therapy. Any antiviral therapy can be combined with an immunogenic composition described herein. Antiviral therapy is a class of medications used specifically for treating viral infections. Most antivirals are used to treat specific viral infections; however, broad spectrum antivirals are effective against a wide range of viruses. Antivirals typically do not destroy a target pathogen, but instead inhibits its replication or development. Most antiviral therapeutics available are used to treat HIV, herpes viruses, hepatitis B and C viruses, and influenza A and B viruses.

Valacyclovir

Valacyclovir (or valaciclovir) is an antiviral drug approved for use in adult patients with, among other things, cold sores (e.g., herpes labialis), genital herpes (including initial episode, recurrent episodes, suppressive therapy and reduction of transmission) and herpes zoster. Valacyclovir is a prodrug converted in vivo to acyclovir. It is sold under the name Valtrex® (valacyclovir hydrochloride).

To treat cold sores in an adult, the current approved dosage of valacyclovir is 2 g twice daily for 1 day taken 12 hours apart. Therapy is initiated at the earliest symptom of a cold sore (e.g., tingling, itching or burning). To treat an initial episode of genital herpes in an adult the current approved dosage of valacyclovir is 1 g twice daily for 10 days. The therapy is most effective when administered within 48 hours of the onset of signs and symptoms. To treat a recurrent episode of genital herpes in an adult, the current approved dosage of valacyclovir is 50 mg twice daily for 3 days. Treatment is initiated at the first sign or symptom of an episode. To provide suppressive therapy for recurrent genital herpes in an adult, the current approved dosage of valacyclovir is 1 g once daily in patients with normal immune function. In patients with a history of 9 or fewer recurrences per year, an alternative dose is 500 mg once daily. In HIV-1-infected patients with a CD4+ cell count greater than or equal to 100 cells/mm$^3$, the current approved dosage of valacyclovir for chronic suppressive therapy of recurrent genital herpes is 500 mg twice daily. To reduce transmission of genital herpes in adults with a history of 9 or fewer recurrences per year, the current approved dosage of valacyclovir is 500 mg once daily for the source partner. The current approved dosage of valacyclovir for treatment of herpes zoster is 1 gram 3 times daily for 7 days. Therapy should be initiated at the earliest sign or symptom of herpes zoster and is most effective when started within 48 hours of the onset of rash.

Valacyclovir is also approved for use in pediatric patients for the treatment of cold sores (e.g., herpes labialis) and chicken pox. The current approved dosage of valacyclovir for the treatment of cold sores in pediatric patients aged greater than or equal to 12 years is 2 grams twice daily for 1 day taken 12 hours apart. Therapy should be initiated at the earliest symptom of a cold sore (e.g., tingling, itching, or burning). The current approved dosage of valacyclovir for treatment of chickenpox in immunocompetent pediatric patients aged 2 to less than 18 years is 20 mg/kg administered 3 times daily for 5 days. The total dose should not exceed 1 gram 3 times daily. Therapy should be initiated at the earliest sign or symptom.

Famciclovir

Famciclovir is an antiviral drug approved for use in immunocompetent adult patients with, among other things, cold sores (e.g., herpes labialis), genital herpes (including recurrent episodes and suppressive therapy), and herpes zoster. Famciclovir is also approved for use in HIV infected adult patients with recurrent orolabial or genital herpes. Famciclovir is sold under the name FAMVIR®.

To treat recurrent cold sores in an immunocompetent adult, the current approved dosage of famciclovir is 1500 mg as a single dose. Therapy is initiated at the earliest symptom of a cold sore (e.g., tingling, itching, burning, pain or lesion). To treat a recurrent episode of genital herpes in an immunocompetent adult the current approved dosage of famciclovir is 100 mg twice daily for 1 day. Therapy should be initiated at the first sign or symptom of a recurrent episode (e.g., tingling, itching, burning pain or lesion). To provide suppressive therapy for recurrent genital herpes in an immunocompetent adult, the current approved dosage of 250 mg twice daily. To treat herpes zoster in an immunocompetent adult, the current approved dosage of famciclovir is 500 mg every 8 hours for 7 days. Therapy should be initiated as soon as herpes zoster is diagnosed.

To treat recurrent orolabial or genital herpes in HIV-infected adult patients, the current approved dosage of famciclovir is 500 mg twice daily for 7 days. Therapy should be initiated at the first sign or symptom of a recurrent episode (e.g., tingling, itching, burning, pain or lesion).

Acyclovir

Acyclovir is guanosine analog approved for use in immunocompromised adult patients with, among other things, initial and recurrent mucosal and cutaneous herpes simplex (due to HSV-1 and HSV-2), severe initial clinical episodes of herpes genitalis, and varicella-zoster (shingles). It is also approved for use in adult patients with, among other things, herpes simplex encephalitis and in neonatal herpes simplex virus infection. Acyclovir is sold under the name ZOVIRAX.

To treat mucosal and cutaneous herpes simplex (HSV-1 and HSV-2) infection in immunocompromised patients, the current approved dosage of acyclovir for adults and adolescents (12 years of age and older) is 5 mg/kg infused at a constant rate over 1 hour, every 8 hours for 7 days. In children less than 12 years of age the current approved dosage of acyclovir is 10 mg/kg infused at a constant rate over 1 hour, every 8 hours for 7 days. To treat severe initial clinical episodes of herpes genitalis infection in adults and adolescents (12 years of age and older) the current approved dosage of acyclovir is 5 mg/kg infused at a constant rate over 1 hour, every 8 hours for 5 days.

To treat herpes simplex encephalitis in adults and adolescents (12 years of age and older) the recommended dosage of acyclovir is 10 mg/kg infused at a constant rate over 1 hour, every 8 hours for 10 days. The current approved pediatric (3 months to 12 years of age) dosage of acyclovir for the treatment of herpes simplex encephalitis is 20 mg/kg infused at a constant rate over 1 hour, every 8 hours for 10 days. To treat neonatal herpes simplex virus infection (birth to 3 months) the current approved dosage of acyclovir is 10 mg/kg infused at a constant rate over 1 hour, every 8 hours for 10 days.

To treat varicella zoster infection in immunocompromised adult or adolescent (12 years of age and older) patients, the current approved dosage is of acyclovir 10 mg/kg infused at a constant rate over 1 hour, every 8 hours for 7 days. For the treatment of pediatric (under 12 years of age) patients, the current approved dosage of acyclovir is 20 mg/kg infused at a constant rate over 1 hour, every 8 hours for 7 days.

Other Antiviral Therapies for HSV

In addition to acyclovir and its prodrug valacyclovir, the nucleoside analogs penciclovir and trifluridine are approved for treatment of HSV. Penciclovir is not orally bioavailable and as such is only used as a topical formulation for labial herpes. The nucleoside analog trifluridine, a modified form of deoxyuridine, is used to treat herpes keratitis and is also active against other viruses such as vaccinia virus and some adenovirus strains. Docosanol is a saturated fatty alcohol used for topical treatment of recurrent labial herpes; its proposed mode of action is the prevention of viral envelope fusion with the host cell membrane. Treatment with acyclovir, in combination with hydrocortisone, results in an increase in the number of prodrome only episodes of recurrent labial herpes such that outbreak is prevented.

Small molecule compounds are being developed for the treatment of genital or labial HSV infections. Two compounds of interest, amenamevir and pritelivir belong to a class of helicase-primase inhibitors. The viral helicase-primase enzyme complex is a heterotrimer consisting of viral UL5 helicase, UL52 primase, and ULB, an accessory protein without enzymatic function. It is required for DNA unwinding at the replication fork and synthesis of primers during virus replication. Since there is no eukaryotic homologue of the helicase-primase complex and since it is essential for viral replication, the helicase-primase complex represents an attractive target for new drug development. Furthermore, helicase-primase inhibitors do not need to become activated by viral enzymes and therefore, can protect both infected and uninfected cells from infection. Amenamevir is a helicase-primase inhibitor with activity against both HSV and VZV. In early studies, the efficacy of once-daily amenamevir was comparable to that of valacyclovir administered twice daily for 3 days with time to lesion healing shortened by 1-2 days. Pritelivir has shown efficacy in reduction of viral shedding and lesion rate in patients with genital herpes. Additional antivirals are described in, e.g., Birkmann et al., Curr Opin. Virol. 18:9-13 (2016)).

Uses of Immunogenic Compositions

Defense against HSV Infection

Immunogenic compositions of the present disclosure are designed to elicit an immune response against HSV-2. Compositions described herein may stimulate an innate immune response, an antibody response or a cell-mediated immune response, or a combination of these responses, in the subject to which it is administered. In some embodiments, the composition stimulates immune cells at the peripheral site of infection or sensory ganglia, such as neutrophils, macrophages, and NK cells. The composition may stimulate infiltration by macrophages; production of antiviral compounds such as nitric oxide, TNF-α, interferons (IFN), and interleukin 12 (IL-12) by neutrophils; and/or stimulation of NK cells to produce IFN-γ. IL-2, IFN-α and IFN-β production may also be triggered by the polypeptides of the present composition, and are believed to aid in controlling infection.

In some embodiments, the composition comprises antigens that stimulate production of neutralizing antibodies. Neutralizing antibodies may target the glycoproteins of the viral envelope, which mediate the interaction of virions with host cell and are responsible for attachment, binding, and entry of HSV-2 into cells. Accordingly, an exemplary composition comprises one or more glycoproteins described above or encoded by nucleic acids described above. Immunogenic antigens and/or epitopes as described herein may be administered separately, in series, or in combination with one another.

In some embodiments, the composition elicits a cell-mediated response, which may involve $CD4^+$ T cells, $CD8^+$ T cells and/or production of antiviral cytokines. The composition may trigger IL-17 secretion by $T_H17$ cells. The composition may trigger IFN-γ secretion, for example through the activation of the innate immune response, and mediate $CD8^+$ T cell clearing of the virus. IFN-γ is also secreted by $T_H1$ cells, $T_C$ cells, dendritic cells, and NK cells, and the composition may trigger IFN-γ secretion by any of these cell types. Such activity of $CD8^+$ T cells may be cytolytic, or, alternately, may be regulated by inhibitor molecules on the surface of the neurons which prevent neuronal killing. $CD4^+$ and/or $CD8^+$ T cells may play a role in maintaining latency of the virus, thus preventing reactivation. In some embodiments, the composition boosts a $CD4^+$ T cell response and/or a $CD8^+$ T cell response that prevents reactivation of the virus from its latent state.

In some embodiments, the composition blocks the ability of HSV to evade the host immune response, or, alternatively, boosts immune responses normally evaded by HSV. In some embodiments, the composition inhibits HSV-2 from shifting the immunological balance towards tolerance of HSV antigens. HSV-2 may mediate tolerance through $T_H2$ cells. First, HSV-2 may induce suppressor T cells, such as $CD4^+$ $CD25^+$ T cells and Tr1 cells that secrete IL-10, a $T_H2$ cytokine. $T_H2$ cytokines downregulate costimulatory molecules and inhibit the maturation and function of antigen-presenting dendritic cells. In addition, infection with HSV-2 inhibits the maturation and migration of dendritic cells, which are essential for efficient induction of $CD8^+$ killer T cells. Notably, $T_H2$ cytokines are produced during recurrence of HSV-2 infection, in contrast to $T_H1$ cytokines, which are produced during recurrence-free episodes. Thus, in certain embodiments, the compositions of the invention repress suppressor T cells and/or induce maturation or migration or both of dendritic cells.

In some embodiments, methods of inducing an immune response against HSV-2 in a mammal comprise administering the compositions described above. The composition may be used to induce an immune response at different time points, such as before exposure to HSV-2, after initial infection with HSV-2, before or after HSV-2 has established latency, before or after HSV-2 shedding occurs, and/or before or after recurrent outbreaks occur. In some embodiments, an immune response against HSV-2 may be induced at one or more of the timepoints above. The composition may induce a $T_H1$ response and/or a $T_H17$ response but not a $T_H2$ response, or may activate the responses at the same time or at different times.

In some embodiments, administration of the composition reduces symptoms associated with initial infection, latency, or recurrent infection with HSV. Such a composition may reduce incidence and/or severity of lesions, sores, pain, irritation, itching, fever, malaise, headache, viral shedding, or prodromes associated with HSV infection or outbreak.

In some embodiments, one or more antibodies to antigens of HSV-2 may be administered to individuals in order to produce passive immunity. Passive immunity results from the transfer of active humoral immunity in the form of ready-made antibodies, from one individual to another. Passive immunization may be used when there is a high risk of infection and insufficient time for the body to develop its own immune response, or to reduce the symptoms of ongoing or immunosuppressive diseases. Adoptive transfer of T cells may provide another method of eliciting an immune response to HSV-2 antigens in patients. In one embodiment, autologous T cells may be expanded on APCs presenting the antigens derived from the polypeptides described above. Subsequently, the expanded HSV-2-specific T cells are transferred back into the patient from which the T cells were derived.

Diagnostic Uses

This application provides, inter alia, a rapid, inexpensive, sensitive, and specific method for detection of HSV-2 in patients. In this respect it should be useful to hospitals and physicians examining and treating patients with or at risk for HSV-2 infection. As used herein, "patient" refers to an individual (such as a human) that either has an HSV-2 infection or has the potential to contract an HSV-2 infection.

In some embodiments, one may use an antibody against one of the polypeptides described herein, such as those of Table 1 and/or Table 2, to detect HSV-2 in an individual. The instant disclosure also provides a method of phenotyping biological samples from patients suspected of having a HSV-2 infection that involves: (a) rendering a biological sample amenable to immunoassay, if necessary; (b) contacting the sample with an appropriate HSV-2-specific antibody or antigen-binding portion thereof under conditions that allow for binding of the antibody or antigen-binding portion to an epitope of HSV-2; and (c) determining if the sample shows the presence of HSV-2 as compared to a control tissue; where if the test tissue shows the presence of HSV-2, the patient is identified as likely having a HSV-2 infection.

Alternatively, one may use the polypeptides described above to detect anti-HSV-2 antibodies in an individual. The instant disclosure also provides a method of phenotyping biological samples from patients suspected of having a HSV-2 infection: (a) rendering a biological sample amenable to an affinity assay such as ELISA, if necessary; (b) contacting the sample with a HSV-2-specific antigen or portion thereof under conditions that allow for binding of the antigen to any host antibodies present in the sample; and (c) determining if the sample shows the presence of HSV-2 as compared to a control tissue; where if the test tissue shows the presence of HSV-2, the patient is identified as likely having a HSV-2 infection. The aforementioned test may be appropriately adjusted to detect other viral infections, for instance by using a homolog (from another viral species) of the proteins described above, such as in Table 1 and/or Table 2.

A number of methods for measuring antibody-antigen binding are known in the art, including ELISA (enzyme-linked immunosorbent assay), Western blotting, competition assay, and spot-blot. The detection step may be, for instance, chemiluminescent, fluorescent, or colorimetric. One suitable method for measuring antibody-protein binding is the Luminex xMAP system, where peptides are conjugated to a dye-containing microsphere. Certain systems, including the xMAP system, are amenable to measuring several different markers in multiplex, and could be used to measure levels of antibodies at once. In some embodiments, other systems are used to assay a plurality of markers in multiplex. For example, profiling may be performed using any of the following systems: antigen microarrays, bead microarrays, nanobarcodes particle technology, arrayed proteins from cDNA expression libraries, protein in situ array, protein arrays of living transformants, universal protein array, lab-on-a-chip microfluidics, and peptides on pins. Another type of clinical assay is a chemiluminescent assay to detect antibody binding. In some such assays, including the VITROS Eci anti-HCV assay, antibodies are bound to a solid-phase support made up of microparticles in liquid suspension, and a surface fluorometer is used to quantify the enzymatic generation of a fluorescent product.

In other embodiments, one may use the polypeptides described above, such as those of Table 1 and/or Table 2, to detect T cells that are specific to HSV-2. The instant disclosure provides a method of phentoyping biological samples from patients suspected of having a HSV-2 infection, involving (a) rendering a biological sample amenable to an assay for activation of T cells, if necessary, (b) contacting the sample with a HSV-2-specific polypeptide or portion thereof under conditions that allow APCs to process the polypeptide, and (c) determining activation of the T cells in response to the HSV-2-specific polypeptide, where an elevated T cell activation relative to an uninfected patient indicates HSV-2 infection. This diagnostic assay is intended to detect the presence of HSV-2-specific T cells in any patients, including those patients who have been exposed to HSV-2 but have not seroconverted to produce detectable levels of anti-HSV-2 antibodies.

T cell activation may be measured using many assays, including cytokine-specific ELISA, cell proliferation measured by tritiated thymidine incorporation or membrane intercolating (PKH-67) or cytoplasmic (CFSE) dyes, ELISPOT, flow cytometry, and bead arrays. In addition, one may measure the T cell response in T cell lines or in T cell hybridomas from mice or humans that are specific for the antigens. Readouts for activated T cells include proliferation, cytokine production, or readout of a surrogate enzyme expressed by the hybridoma that is induced when the T cell or T cell hybridoma is activated in response to an antigen. For example, activation of a T cell response may be detected by T cell hybridoma that is engineered to produce β-galactosidase. β-galactosidase may be detected through the use of colorimetric • • galactosidase substrates such as chlorophenyl red •-D galactopyranoside (CPRG).

Infection with HSV-2 may be acute or latent. In some embodiments, if the biological sample shows the presence of HSV-2, one may administer a therapeutically effective amount of the compositions and therapies described herein to the patient. The biological sample may comprise, for example, blood, semen, urine, vaginal fluid, mucus, saliva, feces, urine, cerebrospinal fluid, or a tissue sample. In some embodiments, the biological sample is an organ intended for transplantation. In certain embodiments, before the detection step, the biological sample is subject to culture conditions that promote the growth of HSV-2.

The diagnostic tests herein may be used to detect HSV-2 in a variety of samples, including samples taken from patients and samples obtained from other sources. For example, the diagnostic tests may be used to detect HSV-2 on objects such as medical instruments. In some embodiments, the tests herein may be performed on samples taken from animals such as agricultural animals (cows, pigs, chickens, goats, horses and the like), companion animals (dogs, cats, birds, and the like), or wild animals. In certain embodiments, the tests herein may be performed on samples taken from cell cultures such as cultures of human cells that produce a therapeutic protein, cultures of bacteria intended to produce a useful biological molecule, or cultures of cells grown for research purposes.

The invention also includes a method of determining the location of a HSV-2 infection in a patient comprising: (a) administering a pharmaceutical composition comprising a labeled HSV-2 antibody or antigen-binding portion thereof to the patient, (b) detecting the label, and (c) determining if the patient has HSV-2 compared to a control. In certain embodiments, the method further comprises, if the patient has an HSV-2 infection, administering a therapeutically effective amount of a composition described herein to the patient. The method may further comprise determining the infected cell types and/or volume of the HSV-2 in the patient. This method may be used to evaluate the spread of HSV-2 in the patient and determine whether a localized therapy is appropriate.

In some embodiments, the polypeptides described herein may be used to make a prognosis of the course of infection. In some embodiments, T cell or antibody responses specific for the polypeptides herein may be detected in a sample taken from a patient. If antibodies or T cells are present at normal levels, it would indicate that the patient has raised an effective immune response against the pathogen. If antibodies or T cells are absent, or present at reduced levels, it would indicate that the patient is failing to raise a sufficient response against the pathogen, and a more aggressive treatment would be recommended. In some embodiments, antibody or T cells present at reduced levels refers to responses that are present at less than 50%, 20%, 10%, 5%, 2%, or 1% the typical level in a patient with a protective immune response. T cell responses may be detected by methods known in the art such as T cell proliferation, ELISPOT or ELISA, and antibodies may be detected by affinity for any of the antigens described herein, using methods known in the art such as ELISA.

In some embodiments, detection of T cells specific for HSV-2 antigens may be used to predict the progress and symptoms of HSV-2 infection in a patient. After infection with HSV-2, some patients remain asymptomatic, although the virus may establish latency. Other patients exhibit symptoms of HSV-2 infection, and may experience recurrent outbreaks. The HSV-2 antigens found in asymptomatic patients may differ from those antigens found in patients who present symptoms and/or recurrent outbreaks. Accordingly, the detection methods of the present invention may be used to distinguish between subgroups within the population of patients infected with HSV-2. Subgroups may be further divided into patients who experience frequent outbreaks and those who infrequently or never experience outbreaks, or patients who shed high levels of virus and those who shed low levels or do not shed. The categorization of patients, based on the presence and levels of T cell responses to certain HSV-2 antigens but not others, may help health care practitioners to determine appropriate treatment regimens. Similarly, differences in the magnitude of T cell responses and/or differences in the combination and levels of cytokines produced by T cells may also be used to predict the progress and symptoms of HSV-2 infection in a patient. Thus, an infected patient whose complement of HSV-2 antigens to which T cells respond predicts severe symptoms, frequent outbreaks, and/or high levels of viral shedding may require more intensive antiviral therapy and/or a longer course of therapeutic treatment than a patient whose complement of HSV-2 antigens predicts an asymptomatic infection.

It will be understood by one of skill in the art that the methods herein are not limited to detection of HSV-2. Other embodiments include the detection of related viruses including viruses with proteins homologous to the proteins described above, such as those in Table 1 and/or Table 2. Such related viruses include, for example, other members of the Herpesviridae family. Depending on the homology, these related viruses may also include viruses that are not members of the Herpesviridae family.

Use in Groups with Increased Risk for Infection by HSV-2

Essentially any individual has a certain risk of infection with HSV-2. However, certain sub-populations have an increased risk of infection. In some embodiments, patients receiving an immunogenic composition and/or antiviral therapy are immunocompromised.

An immunocompromising condition arising from a medical treatment is likely to expose the individual in question to a higher risk of infection. It is possible to treat an infection prophylactically in an individual having the immunocompromised condition before or during treatments known to generate such a condition. By prophylactically treating with the antigen before or during a treatment known to generate such a condition it is possible to prevent a subsequent infection or to reduce the risk of the individual contracting an infection due to the immunocompromised condition. Should the individual contract an infection, e.g., following a treatment leading to an immunocompromised condition, it is also possible to treat the infection by administering to the individual an antigen composition.

In certain embodiments, the compositions are administered to children or adult patients. In other embodiments, compositions are appropriate for pregnant women who were infected before becoming pregnant, or who became infected during pregnancy, such as to inhibit infection of a fetus or baby. The compositions may also be administered to neonates and infants who became infected in utero or during delivery.

Doses and Routes of Administration

Dosage Amounts and Timing

The amount of antigen in each vaccine dose is selected as an effective amount, which induces a prophylactic or therapeutic response, as described above, in either a single dose or over multiple doses. Preferably, the dose is without significant adverse side effects in typical vaccines. Such amount will vary depending upon which specific antigen is employed. Generally, it is expected that a dose will comprise 1-1000 µg of protein, in some instances 2-100 µg, for instance 4-40 µg. Alternatively, a dose will comprise 10-6000 µg of nucleic acid, in some instances 20-4000 µg, for instance 30-4000 µg. An optimal amount for a particular vaccine can be ascertained by standard studies involving observation of antibody titers, T cell activation levels, and other responses in subjects. In some embodiments, the appropriate amount of antigen to be delivered will depend on the age, weight, and health (e.g., immunocompromised status) of a subject. When present, typically an adjuvant will be present in amounts from 1-250 µg per dose, for example 50-150 µg, 75-125 µg or 100 µg.

In some embodiments, only one dose of the vaccine is administered to achieve the results described above. In other embodiments, following an initial vaccination, subjects receive one or more boost vaccinations, for a total of two, three, four or five vaccinations.

Advantageously, the number is three or fewer. A boost vaccination may be administered, for example, about 1 month, 2 months, 4 months, 6 months, or 12 months after the initial vaccination, such that one vaccination regimen involves administration at 0, 0.5-2 and 4-8 months. It may be advantageous to administer split doses of vaccines which may be administered by the same or different routes.

In some embodiments, the invention supplies a treatment regimen comprising a first dose of vaccine and a second, third or fourth dose of vaccine (a boost vaccine). In exemplary embodiments, a first dose of vaccine comprises one or more polypeptide antigens, or nucleic acids encoding one or more polypeptide antigens, or a combination of one or more polypeptide antigens and nucleic acids encoding the same or other protein antigens. In some embodiments, a boost vaccine is formulated with the same polypeptide antigens, nucleic acids, or polypeptide antigens and nucleic acids as the first dose. In some embodiments, a boost vaccine is formulated with different polypeptide antigens, nucleic acids, or polypeptide antigens and nucleic acids from the first dose. In some embodiments, the first dose may comprise only polypeptide antigens and boost vaccine may comprise only nucleic acids, or the first dose may comprise only nucleic acids and boost vaccine may comprise only polypeptide. In some embodiments, the first dose may comprise polypeptide antigens and nucleic acids, and boost vaccine may comprise only protein antigens or only nucleic acids. In some embodiments, the first dose may comprise only protein antigens or only nucleic acids, and boost vaccine may comprise protein antigens and nucleic acids. In certain embodiments where the boost vaccine is a polypeptide, the polypeptide is gL2 (SEQ ID NO: 3) or ICP4 (SEQ ID NO: 1) or an immunogenic fragment thereof (e.g., ICP4.2, and gL2s v.2, SEQ ID NOS: 2 and 136), optionally in combination with one or more of the adjuvants described above, particularly one or more of the ISCOMs. Such polypeptide boost vaccines are particularly useful in conjunction with any one of the nucleic acid vaccines described above (e.g., nucleic acids having nucleotide sequences that encode at least one of SEQ ID NOS: 1, 3, 5, 38, 136 or 138, or an immunogenic fragment thereof).

The pharmaceutical compositions described herein may take on a variety of dosage forms. In certain embodiments, the composition is provided in solid or powdered (e.g., lyophilized) form; it also may be provided in solution form. In certain embodiments, a dosage form is provided as a dose of lyophilized composition and at least one separate sterile container of diluent.

In some embodiments, the antigen is delivered to a patient at an amount of 1 µmol per dose. In some embodiments, the antigen is delivered at a dose ranging from 10 nmol to 100 nmol per dose. The appropriate amount of antigen to be delivered may be determined by one of skill in the art. In some embodiments, the appropriate amount of antigen to be delivered will depend on the age, weight, and health (e.g., immunocompromised status) of a subject.

Pharmaceutical compositions disclosed herein are (in some embodiments) administered in amounts sufficient to elicit production of antibodies as part of an immunogenic response. In some embodiments, the composition may be formulated to contain 5 µg/0.5 ml or an amount ranging from 10 µg/1 ml to 200 µg/1 ml of an antigen. In other embodiments, the composition may comprise a combination of antigens. The plurality of antigens may each be the same concentration, or may be different concentrations.

In some embodiments, the composition will be administered in a dose escalation manner, such that successive administrations of the composition contain a higher concentration of composition than previous administrations. In some embodiments, the composition will be administered in a manner such that successive administrations of the composition contain a lower concentration of composition than previous administrations.

In therapeutic applications, compositions are administered to a patient suffering from a disease in an amount sufficient to cure or at least partially arrest the disease and its complications.

Therapeutic applications of a composition described herein include reducing transmissibility, slowing disease progression, reducing viral shedding, or eliminating recurrent infections in patients that have been infected with HSV-2, such as by 90%, 80%, 70%, 60%, 50%, 40%, 30%, 20% or 10% of the levels at which they would occur in individuals who are not treated with the composition. The composition may also reduce the quantity of HSV-2 shed by infected individuals, inhibit the expression of proteins required for reactivation of HSV-2 from the latent stage in infected patients, and/or inhibit replication of HSV-2 in neurons of infected patients, such as by 90%, 80%, 70%, 60%, 50%, 40%, 30%, 20%, or 10% of the levels at which they would occur in individuals not treated with the composition.

In prophylactic embodiments, compositions are administered to a human or other mammal to induce an immune response that can inhibit the establishment of an infectious disease or other condition. In some embodiments, a composition may partially block the virus from establishing latency or reduce the efficiency with which latency is established.

In some embodiments, only one dose (administration) of the composition is given. In other embodiments, the composition is administered in multiple doses. In various embodiments, the composition is administered once, twice, three times, or more than three times. The number of doses administered to a subject is dependent upon the antigen, the extent of the disease or the expected exposure to the disease, and the response of a subject to the composition.

In some embodiments, the compositions are administered in combination with antimicrobial molecules. Antimicrobial molecules may include antiviral molecules. Many antiviral molecules are currently known in the art, and target one or more stage of the viral life cycle, including viral attachment to host cells, release of viral genes and/or enzymes into the host cell, replication of viral components using host-cell machinery, assembly of viral components into complete viral particles, and release of viral particles to infect new hosts.

Routes of Administration

The vaccine formulations and pharmaceutical compositions herein can be delivered by administration to an individual, typically by systemic administration (e.g., intravenous, intraperitoneal, intramuscular, intradermal, subcutaneous, transdermal, subdermal, intracranial, intranasal, mucosal, anal, vaginal, oral, sublingual, buccal route or they can be inhaled) or they can be administered by topical application.

In some embodiments, the composition may be administered directly to the likely sites of infection. In female patients, the composition may be applied topically to mucosal membranes, or delivered vaginally or rectally using devices and methods known in the art. The vaginal and rectal routes of delivery permit extended, continuous or pulsed delivery and administration of composition dosages, and may be administered either before or after exposure to HSV, depending on the use of a prophylactic or therapeutic composition. In male patients, the composition may be applied topically to the skin or mucosal membranes, or delivered rectally. In both patient populations, the composition may also be targeted to the sensory ganglia.

An HSV-2 vaccine or pharmaceutical composition is often administered via the intramuscular route. Typically, in this route, the vaccine is injected into an accessible area of muscle tissue. Intramuscular injections are, in some embodiments, given in the deltoid, vastus lateralis, ventrogluteal or dorsogluteal muscles. The injection is typically given at an approximately 90° angle to the surface of the skin, so the vaccine penetrates the muscle.

An HSV-2 vaccine may also be administered subcutaneously. The injection is typically given at a 45° angle to the surface of the skin, so the vaccine is administered to the subcutis and not the muscle.

In some embodiments, the HSV-2 vaccine is administered intradermally. Intradermal administration is similar to subcutaneous administration, but the injection is not as deep and the target skin layer is the dermis. The injection is typically given at a 10-15° angle to the surface of the skin, so the vaccine is delivered just beneath the epidermis.

In some embodiments, the HSV-2 vaccine is administered by electroporation. Delivery by electroporation may be intramuscular or intradermal. Suitable devices for electroporation include devices made by Inovio Pharmaceuticals, Inc. (Blue Bell, Pa.) and the TriGrid™ Delivery System made by Ichor Medical Systems, Inc. (San Diego, Calif.).

Formulations

The vaccine formulation may be suitable for administration to a human patient, and vaccine preparation may conform to USFDA guidelines. In some embodiments, the vaccine formulation is suitable for administration to a non-human animal. In some embodiments, the vaccine is substantially free of either endotoxins or exotoxins. Endotoxins include pyrogens, such as lipopolysaccharide (LPS) molecules. The vaccine may also be substantially free of inactive protein fragments. In some embodiments, the vaccine has lower levels of pyrogens than industrial water, tap water, or distilled water. Other vaccine components may be purified using methods known in the art, such as ion-exchange chromatography, ultrafiltration, or distillation. In other embodiments, the pyrogens may be inactivated or destroyed prior to administration to a patient. Raw materials for vaccines, such as water, buffers, salts and other chemicals may also be screened and depyrogenated. All materials in the vaccine may be sterile, and each lot of the vaccine may be tested for sterility. Thus, in certain embodiments the endotoxin levels in the vaccine fall below the levels set by the USFDA, for example 0.2 endotoxin (EU)/kg of product for an intrathecal injectable composition; 5 EU/kg of product for a non-intrathecal injectable composition, and 0.25-0.5 EU/ml for sterile water.

In some embodiments, the vaccine comprising a polypeptide contains less than 5%, 2%, 1%, 0.5%, 0.2%, 0.1% of other, undesired unpolypeptides, relative to the amount of desired polypeptides. In some embodiments, the vaccine contains less than 5%, less than 2%, less than 1%, less than 0.5%, less than 0.2%, or less than 0.1% DNA and/or RNA.

It is preferred that the vaccine has low or no toxicity, within a reasonable risk-benefit ratio.

The formulations suitable for introduction of the pharmaceutical composition vary according to route of administration. Formulations suitable for parenteral administration, such as, for example, by intraarticular (in the joints), intravenous, intramuscular, intradermal, intraperitoneal, intranasal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials.

Injection solutions and suspensions can be prepared from sterile powders, granules, and tablets of the kind previously described. Cells transduced by the packaged nucleic acid can also be administered intravenously or parenterally.

Formulations suitable for oral administration can consist of (a) liquid solutions, such as an effective amount of the polypeptides or packaged nucleic acids suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. The pharmaceutical compositions can be encapsulated, e.g., in liposomes, or in a formulation that provides for slow release of the active ingredient.

The antigens, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Suitable formulations for vaginal or rectal administration include, for example, suppositories, which consist of the polypeptides or packaged nucleic acids with a suppository base. Suitable suppository bases include natural or synthetic triglycerides or paraffin hydrocarbons. In addition, it is also possible to use gelatin rectal capsules which consist of a combination of the polypeptides or packaged nucleic acids with a base, including, for example, liquid triglycerides, polyethylene glycols, and paraffin hydrocarbons. The formulation may be suitable for administration to a human patient, and the preparation may conform to US FDA guidelines. In some embodiments, the formulation is suitable for administration to a non-human animal. In some embodiments, the composition is substantially free of either endotoxins or exotoxins. Endotoxins may include pyrogens, such as lipopolysaccharide (LPS) molecules. The composition may also be substantially free of inactive protein fragments which may cause a fever or other side effects. In some embodiments, the composition contains less than 1%, lessthan 0.1%, less than 0.01%, less than 0.001%, or less than 0.0001% of endotoxins, exotoxins, and/or inactive protein fragments. In some embodiments, the composition has lower levels of pyrogens than industrial water, tap water, or distilled water. Other components may be purified using methods known in the art, such as ion-exchange chromatography, ultrafiltration, or distillation. In other embodiments, the pyrogens may be inactivated or destroyed prior to administration to a patient. Raw materials for compositions, such as water, buffers, salts and other chemicals may also be screened and depyrogenated. All materials in the composition may be sterile, and each lot of the composition may be tested for sterility. Thus, in certain embodiments the endotoxin levels in the composition fall below the levels set by the USFDA: 0.2 endotoxin (EU)/kg of product for an intrathecal injectable composition; 5 EU/kg of product for a non-intrathecal injectable composition, and 0.25-0.5 EU/ml for sterile water.

In certain embodiments, the preparation comprises less than 50%, 20%, 10%, or 5% (by dry weight) contaminating protein. In certain embodiments, the desired molecule is present in the substantial absence of other biological macromolecules, such as other proteins (particularly other proteins which may substantially mask, diminish, confuse or alter the characteristics of the component proteins, either as purified preparations or in their function in the subject reconstituted mixture). In certain embodiments, at least 80%, 90%, 95%, 99%, or 99.8% (by dry weight) of biological macromolecules of the same type present (but water, buffers, and other small molecules, especially molecules having a molecular weight of less than 5000, can be present).

It is preferred that the composition has low or no toxicity, within a reasonable risk-benefit ratio. In certain embodiments, the composition comprises ingredients at concentrations that are less than $LD_{50}$ measurements for the animal being treated with the composition. $LD_{50}$ measurements may be obtained in mice or other experimental model systems, and extrapolated to humans and other animals. Methods for estimating the $LD_{50}$ of compounds in humans and other animals are well-known in the art. A composition, and any component within it, might have an $LD_{50}$ value in rats of greater than 100 g/kg, greater than 50 g/kg, greater than 20 g/kg, greater than 10 g/kg, greater than 5 g/kg, greater than 2 g/kg, greater than 1 g/kg, greater than 500 mg/kg, greater than 200 mg/kg, greater than 100 mg/kg, greater than 50 mg/kg, greater than 20 mg/kg, or greater than 10 mg/kg. In some embodiments, the therapeutic index of the composition (measured as the toxic dose for 50% of the population ($TD_{50}$) divided by the minimum effective dose for 50% of the population ($ED_{50}$)), is greater than 1, greater than 10, or greater than 100.

Preparation and Storage of Vaccines Formulations and Immunogenic Compositions

The immunogenic compositions described herein may be produced using a variety of techniques. For example, a polypeptide may be produced using recombinant DNA technology in a suitable host cell. A suitable host cell may be bacterial, yeast, mammalian, or other type of cell. The host cell may be modified to express an exogenous copy of one of the relevant polypeptide genes. Typically, the gene is operably linked to appropriate regulatory sequences such as a strong promoter and a polyadenylation sequence. In some embodiments, the promoter is inducible or repressible. Other regulatory sequences may provide for secretion or excretion of the polypeptide of interest or retention of the polypeptide of interest in the cytoplasm or in the membrane, depending on how one wishes to purify the polypeptide. The gene may be present on an extrachromosomal plasmid, or may be integrated into the host genome. One of skill in the art will recognize that it is not necessary to use a nucleic acid 100% identical to the naturally-occurring sequence. Rather, some alterations to these sequences are tolerated and may be desirable. For instance, the nucleic acid may be altered to take advantage of the degeneracy of the genetic code such that the encoded polypeptide remains the same. In some embodiments, the gene is codon-optimized to improve expression in a particular host. The nucleic acid may be produced, for example, by PCR or by chemical synthesis.

Once a recombinant cell line has been produced, a polypeptide may be isolated from it. The isolation may be accomplished, for example, by affinity purification techniques or by physical separation techniques (e.g., a size column).

In a further aspect of the present disclosure, there is provided a method of manufacture comprising mixing one or more polypeptides or an immunogenic fragment or variant thereof with a carrier and/or an adjuvant. In some embodiments, the adjuvant is one that stimulates a $T_H1$ cell response.

In some embodiments, antigens for inclusion in compositions of the invention may be produced in cell culture. One method comprises providing one or more mammalian expression vectors and cloning nucleotides encoding two or more polypeptides selected from polypeptides having an amino acid sequence of any one of SEQ ID NOS: 1-38, 135, 136, 138 or 139, then expressing and isolating the polypeptides.

In some embodiments, nucleic acids for inclusion in compositions of the invention may be produced by replication in a bacterial host such as *E. coli* and purified by standard RNA or DNA purification methods.

The immunogenic polypeptides described herein, and nucleic acid compositions that express the polypeptides, can be packaged in packs, dispenser devices, and kits for administering nucleic acid compositions to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition, such as those disclosed herein.

Combination Therapy

Combination therapy refers to those situations in which a subject or population of subjects is simultaneously exposed to two or more therapeutic regimens (e.g., two or more therapeutic agents such as antiviral therapy and an immunogenic composition). In some embodiments, the two or more therapies may be administered simultaneously (e.g., concurrently). In some embodiments, such therapies may be administered sequentially (e.g., all "doses" of a first regimen are administered prior to administration of any doses of a second regimen).

The present disclosure teaches methods of treating herpes using two or more therapeutic regimens, such as antiviral therapy and immunogenic composition, administered in overlapping dosing regimens. In some embodiments, a dosing regimen for one or more agents may comprise a plurality of "cycles" of doses administered according to a specified pattern. In some embodiments, specified pattern of administration for antiviral therapy is daily, about every other day, about every 3 days, about every 4 days, about every 5 days, about every 6 days, about every 7 days (e.g., weekly), about every 14 days (e.g., biweekly), about every 21 days, about every 28 days, about every 35 days, about every 42 days, about every 49 days, about every 2 months, about every 6 months or longer. In some embodiments, antiviral therapy is administered daily. In some embodiments, herpes is genital herpes.

In some embodiments, specified pattern of administration for immunogenic composition is at about every 7 days, about every 14 days, about every 21 days, about every 28 days, about every 35 days, about every 42 days, about every 49 days, about every 56 days or longer. In some embodiments, immunogenic composition is administered in at least one dose, at least two doses, at least three doses, at least four doses, at least 5 doses or more. In some embodiments, immunogenic composition is administered on about day 1, on about day 22 and on about day 43 of a therapeutic regimen. In some embodiments, a therapeutic regimen comprises daily administration of antiviral therapy. In some embodiments, a therapeutic regimen comprises daily administration of antiviral therapy beginning at least 14 days prior to administration of vaccine formulation wherein the vaccine formulation is administered in three doses about 21 days apart.

In some embodiments, the immunogenic composition comprises an HSV-2 gD2 polypeptide, wherein the gD2 polypeptide has an internal deletion of all or part of the transmembrane domain, and an HSV-2 ICP4 polypeptide or an immunogenic fragment comprising at least 8 contiguous amino acids of HSV-2 ICP4 polypeptide. In some embodiments, immunogenic composition comprises about 10 µg, 20 µg, 30 µg, 60 µg, or 100 µg of each of a gD2 polypeptide and a ICP4 polypeptide and/or about 25 µg, 50 µg or 75 µg of adjuvant. In some embodiments, immunogenic composition comprises about 60 µg of the gD2 polypeptide, about 60 µg of the ICP4 polypeptide and about 50 µg of adjuvant.

In some embodiments, antiviral therapy is selected from the group consisting of famciclovir, valacyclovir, acyclovir, penciclovir, trifluridine, acyclovir in combination with hydrocortisone, helicase-primase inhibitors (e.g., amenamevir and pritelivir) and combinations thereof. In some embodiments, antiviral therapy is valacyclovir. In some embodiments, a subject or population of subjects receives about 500 mg to about 1 g of antiviral therapy per dose.

In some embodiments, "administration" of combination therapy may involve administration of one or more agents or modalities to a subject receiving the other agents or modalities in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

In some embodiments, immunogenic composition and/or antiviral therapy treats infection by HSV-1, HSV-2, or HSV-1 and HSV-2 in a subject or population of subjects.

Patient Populations

Among other things, the present disclosure includes methods of treating herpes infection in certain patient populations using combination therapy comprising an immunogenic composition described herein and an antiviral therapy described herein. In some embodiments, herpes is genital herpes. In some embodiments, a subject or subjects use contraception for 28 days before and 90 days after treatment with the immunogenic composition. In some embodiments, a subject or a population of subjects is male. In some embodiments, a subject or population of subjects is female. In some embodiments, a subject or population of subjects is non-pregnant female. In some embodiments, a subject or population of subjects is 10, 11, 12, 13, 14, 15, 16, or 17 years of old. In some embodiments, a subject or population of subjects is at least 18 years old and less than 51 years old. In some embodiments, a subject or population of subjects is 51 years or older.

In some embodiments, a subject or a population of subjects has been diagnosed with genital herpes infection for greater than 1 year. In some embodiments, diagnosis of genital herpes infection comprises Western blot analysis for one or more HSV-2 antigens; PCR (e.g., type-specific PCR); viral culture (e.g., type-specific viral culture); or compatible clinical history and positive HerpeSelect® 2 enzyme-linked immunosorbent assay IgG with an index value >3.5 or a positive LIAISON® HSV-2 Type Specific IgG.

In some embodiments, the immunogenic composition is administered to subjects or populations of subjects that have been receiving antiviral therapy. In some embodiments, antiviral therapy is valacyclovir, acyclovir or famciclovir. In some embodiments, a subject or population of subjects has been taking a stable dose of antiviral therapy for 6 or more months prior to administration of a immunogenic composition. In some embodiments, a subject or population of subjects has had at least one outbreak of genital herpes within 6 months of administration of a immunogenic composition. In some embodiments, a subject or population of subjects has been taking a stable dose of antiviral therapy for 6 or more months and has had at least one outbreak of genital herpes within 6 months of administration of a vaccine formulation. In some embodiments, a stable dose of antiviral is 500 mg per day or 1 g per day.

In some embodiments, the immunogenic composition is administered to subjects or populations of subjects that have not been receiving antiviral therapy. In some embodiments, a subject or population of subjects has been taking a stable dose of antiviral therapy for about 14 days prior to administration of a immunogenic composition. In some embodiments, a subject or population of subjects has had greater than 5 outbreaks of genital herpes within 12 months of administration of a immunogenic composition. In some embodiments, a subject or population of subjects has been taking a stable dose of antiviral therapy of about 14 days and has had greater than 5 outbreaks of genital herpes within 12 months of administration of a immunogenic composition. In some embodiments, a stable dose of antiviral therapy is 500 mg once a day or 1 g once a day.

In some embodiments, a subject or population of subjects treated with antiviral therapy and immunogenic composition is not receiving therapy comprising tenofovir, lysine, a supplement or medication, other than valacyclovir, e.g., a therapy known to or purported to affect herpes outbreak frequency or intensity. In some embodiments, a subject or population of subjects treated with antiviral therapy and immunogenic composition does not have a history of ocular herpes infection, herpes-related erythema multiforme, herpes meningitis or herpes encephalitis. In some embodiments, a subject or population of subjects treated with antiviral therapy and immunogenic composition does not have active genital HSV-2 lesions.

In some embodiments, a subject or population of subjects treated with antiviral therapy and immunogenic composition is not immunocompromised. In some embodiments, a subject or population of subjects treated with antiviral therapy and immunogenic composition is not receiving systemic immunosuppressive medication. In some embodiments, a subject or population of subjects treated with antiviral therapy and immunogenic composition does not have an autoimmune disease. In some embodiments, a subject or population of subjects treated with antiviral therapy and immunogenic composition has not previously had an autoimmune disease. In some embodiments, a subject or population of subjects treated with antiviral therapy and immunogenic composition does not have HIV, hepatitis B or hepatitis C.

In some embodiments, a subject or population of subjects treated with antiviral therapy and immunogenic composition does not have history of hypersensitivity to any component of a vaccine formulation. In some embodiments, a subject or population of subjects treated with antiviral therapy and immunogenic composition does not have a clinically significant laboratory abnormality except for (i) creatinine kinase in subjects with an identified exercise regimen and hepatic and renal enzyme levels within normal limits or (ii) isolated Grade 2 unconjugated bilirubin in fasting subjects with a history of Gilbert's syndrome.

In some embodiments, a subject or population of subjects treated with antiviral therapy and immunogenic composition has not received any other vaccine containing an HSV-2 antigen. In some embodiments, a subject or population of subjects treated with antiviral therapy and immunogenic composition has not received an investigational product within 30 days prior to the first dose of immunogenic composition. In some embodiments, a subject or population of subjects treated with antiviral therapy and immunogenic composition has not received a blood product within 90 days prior to a first dose of vaccine formulation. In some embodiments, a subject or population of subjects treated with antiviral therapy and immunogenic composition has not received a live vaccine within 28 days prior to a first dose of vaccine formulation. In some embodiments, a subject or population of subjects treated with antiviral therapy and immunogenic composition has not received any other vaccine within 14 days prior to a first dose of vaccine formulation. In some embodiments, a subject or population of subjects treated with antiviral therapy and immunogenic composition has received any other vaccine from the first dose until 28 days after a third dose.

In some embodiments, a subject or population of subjects treated with antiviral therapy and immunogenic composition is not pregnant or nursing.

Efficacy of Combination Therapies

Among other things, the present disclosure includes methods of treating herpes infection using combination therapy comprising immunogenic composition described herein and antiviral therapy so that efficacy of immunogenic composition and/or antiviral therapy is improved in a subject or population of subjects over a specified time period relative to a subject or population of subjects receiving only immunogenic composition or antiviral therapy, or receiving neither immunogenic composition or antiviral therapy. In some embodiments, antiviral therapy is administered to a subject or population of subjects receiving immunogenic composition. In some embodiments, immunogenic composition is administered to a subject or population of subjects receiving antiviral therapy.

In some embodiments, combined administration of an immunogenic composition described herein and an antiviral therapy described herein results in an improvement in a disease or disorder described herein or a symptom thereof to an extent that is greater than one produced by either the immunogenic composition or the antiviral therapy alone. The difference between the combined effect and the effect of the immunogenic composition or antiviral therapy alone can be a statistically significant difference. In some embodiments, the combined result is synergistic.

In some embodiments, combined administration of immunogenic composition and antiviral therapy allows administration of the antiviral therapy at a reduced dose, at a reduced number of doses, and/or at a reduced frequency of dosage compared to a standard dosing regimen approved for the antiviral therapy, such as an approved regimen for an antiviral therapy described herein. In some embodiments, combined administration of immunogenic composition and the antiviral therapy allows administration of the immunogenic composition at a reduced dose, at a reduced number of doses, and/or at a reduced frequency of dosage compared to an effective dosing regimen for the immunogenic composition.

In some embodiments, antiviral therapy is selected from the group consisting of famciclovir, valacyclovir, acyclovir and combinations thereof. In some embodiments, antiviral therapy is valacyclovir. In some embodiments, subjects receive about 500 mg to about 1 g of antiviral therapy per dose. In some embodiments, efficacy of immunogenic composition and/or antiviral therapy is assessed at, at least 3 months, 6 months, 12 months, 18 months, 24 months, 3 years, 4 years, 5 years, 6 years, 7 years, 8 years, 9 years, 10 years after administration of therapy. In some embodiments, efficacy of immunogenic composition and/or efficacy of antiviral therapy is assessed at least 6 months after administration of therapy.

In some embodiments, efficacy of immunogenic composition and/or antiviral formulation is measured or indicated by a genital herpes recurrence-free period relative to a subject or population of subjects receiving only immunogenic composition or antiviral therapy. In some embodiments, efficacy of immunogenic composition and/or antiviral formulation is measured or indicated by increased time to first herpes recurrence relative to a subject or population of subjects receiving only immunogenic composition or antiviral therapy. In some embodiments, efficacy of immunogenic composition and/or antiviral therapy is measured or indicated by increased time to next herpes recurrence relative to a subject or population of subjects receiving only immunogenic composition or antiviral therapy.

In some embodiments, efficacy of immunogenic composition and/or antiviral therapy is measured or indicated by decreased genital herpes lesion rate relative to a subject or population of subjects receiving only immunogenic composition or antiviral therapy. In some embodiments, efficacy of immunogenic composition and/or antiviral therapy is measured or indicated by decreased genital herpes lesion frequency relative to a subject or population of subjects receiving only immunogenic composition or antiviral therapy. In some embodiments, efficacy of immunogenic composition and/or antiviral therapy is measured or indicated by decreased genital herpes lesion duration relative to a subject or population of subjects receiving only immunogenic composition or antiviral therapy.

In some embodiments, efficacy of immunogenic composition and/or antiviral therapy is measured or indicated by decreased rate of genital herpes outbreaks relative to a subject or population of subjects receiving only immunogenic composition or antiviral therapy. In some embodiments, efficacy of immunogenic composition and/or antiviral therapy is measured or indicated by decreased anogenital HSV shedding rate relative to a subject or population of subjects receiving only immunogenic composition or antiviral therapy. In some embodiments, efficacy of immunogenic composition and/or antiviral therapy is measured or indicated by decreased anogenital HSV shedding magnitude relative to a subject or population of subjects receiving only immunogenic composition or antiviral therapy. In some embodiments, viral shedding is measured is by real-time quantitative polymerase chain reaction (PCR).

In some embodiments, efficacy of immunogenic composition and/or antiviral therapy is measured or indicated by decreased or no increase of antiviral (e.g.,valacyclovir) dose relative to a subject or population of subjects receiving only immunogenic composition or antiviral therapy.

In some embodiments, efficacy of immunogenic composition and/or antiviral therapy is measured or indicated by decrease of one or more herpes signs or symptoms relative to a subject or population of subjects receiving only immunogenic composition or antiviral therapy. In some embodiments, a decrease in one or more herpes signs or symptoms is a decrease in the percentage of days with herpes-related signs or symptoms and/or a decrease in the magnitude of herpes-related signs or symptoms.

In some embodiments, efficacy of immunogenic composition and/or antiviral therapy is measured or indicated by increased health-related quality of life relative to a subject or population of subjects receiving only immunogenic composition or antiviral therapy. In some embodiments, health related quality of life is measured by the EuroQoL-5 Domains-5 Levels (EQ-5D-5L) questionnaire. In some embodiments, a subject or population of subjects completes the EQ-5D-5L questionnaire when not experiencing a genital herpes outbreak and or/on about each day of an outbreak.

In some embodiments, efficacy of immunogenic composition and/or antiviral therapy is measured or indicated by decreasing time to lesion healing relative to a subject or population of subjects receiving only immunogenic composition or antiviral therapy. In some embodiments, efficacy of immunogenic composition and/or antiviral therapy is measured or indicated by decreasing time to cessation of pain relative to a subject or population of subjects receiving only immunogenic composition or antiviral therapy. In some embodiments, efficacy of immunogenic composition and/or antiviral therapy is measured or indicated by decreasing rate of symptomatic acquisition of herpes in susceptible partners relative to a subject or population of subjects receiving only immunogenic composition or antiviral therapy.

In some embodiments, efficacy of immunogenic composition and/or antiviral therapy is measured or indicated by increase in humoral response and/or an increase in cellular response relative to a subject or population of subjects receiving only immunogenic composition or antiviral therapy. In some embodiments, increase in humoral response is measured or indicated by an increase in magnitude of response or fold rise from baseline of HSV-2 immunoglobulin G (IgG) levels and/or of HSV-2 neutralizing antibody levels. In some embodiments, baseline is a value, level, amount or quantity measured or indicated in a subject with herpes prior to administration of antiviral therapy and/or immunogenic composition. In some embodiments, baseline is a value, level, amount or quantity measured or indicated in a population of subjects with herpes prior to administration of antiviral therapy and/or immunogenic composition. In some embodiments, baseline is a value, level, amount or quantity measured or indicated in a subject or population of subjects without herpes.

In some embodiments, increase in humoral response is indicated by a 4-fold or greater rise in IgG titer from baseline. In some embodiments, increase in humoral response is indicated by a 2-fold or greater rise in 50% neutralizing antibody titer from baseline. In some embodiments, cellular response is an increase in secretion of granzyme B (GrB) levels. In some embodiments, increase in cellular response is measured or indicated by increase in magnitude of response or fold rise from baseline of granzyme B (GrB) levels. In some embodiments, cellular response is an increase in IFNγ secretion from T cells.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

The disclosure is further illustrated by the following examples. The examples are provided for illustrative purposes only. They are not to be construed as limiting the scope or content of the disclosure in any way.

EXEMPLIFICATION

Example 1

GEN-003-004 Clinical Study: A Randomized, Placebo-Controlled, Double-Blind Study to Assess the Efficacy and Safety of GEN-003 in Subjects with Genital HSV-2 Infection taking Valacyclovir Suppressive Therapy Formulations GEN-003 is an HSV-2 protein subunit vaccine consisting of two recombinant T-cell antigens (GB208 and GB217), Matrix-M2 adjuvant (M2) and diluent (0.9% normal saline). GB208 is an approximately 39 kDa T-cell antigen and internal fragment of the immediate early protein ICP4. ICP4 was identified as one of the most frequent proteins recognized by the T-cells of immune seronegative subjects studied by AnTigen Lead Acquisition System (ATLAS™), suggesting its potential role in control of viral replication and utility as a vaccine candidate. GB217 is a B-cell antigen and a recombinant version of the glycoprotein D, or gD, modified by deletion of the transmembrane region. This surface glycoprotein is a target of HSV-2 neutralizing antibodies and of T-cell responses. M2 is an immune stimulating complex-based adjuvant containing saponin fractions purified from fractionated *Quillaja saponins* (soapbark tree) bark, phosphatidylcholine, and cholesterol.

Summaries of the nonclinical pharmacology and toxicology studies are provided below.

Nonclinical Models of Immunogenicity and Efficacy

Immune responses to components of GEN-003 were evaluated in mice and monkeys. The study results indicated that GB208 and GB217 prime potent and functional T-cell and B-cell responses, including HSV-2 neutralizing antibodies, when administered with M2.

In a guinea pig model of vaginal HSV-2 infection, GEN-003 induced increases in GB208- and GB217-specific immunoglobulin G (IgG) titer and HSV-2 neutralizing antibodies (Skoberne et al 2013). The post-treatment mean number of days with genital HSV-2 lesions was reduced among animals receiving GEN-003 compared to those in the placebo group. In this model, HSV-2 infected animals administered GB208 with M2 or GB204 (a form of GB217) with M2 had significant reductions in the number of days of viral shedding compared to animals administered placebo. No viral shedding was observed in 33% of animals administered GB204 and 50% of the animals administered GB208.

Nonclinical Toxicology Studies

Repeat-dose toxicology studies of GEN-003 antigens and M2 were performed in accordance with Good Laboratory Practice in mice, rabbits, and monkeys, and a local tolerance study was performed in rabbits. No safety signals believed to be relevant to potential risks to humans receiving GEN-003 were identified.

Clinical Trials of GEN-003

Two clinical trials of GEN-003 have been completed, and 3 trials are ongoing. Summaries of four trials are provided below.

GEN-003-001: A Phase I/IIa, Randomized, Double-Blind, Dose-Ranging, Placebo-Controlled Study of the Safety and Immunogenicity of a HSV-2 Vaccine Containing Matrix M-2 Adjuvant in Individuals with Documented HSV-2 Genital Infection Subjects aged 18 to 50 years with documented diagnosis of genital HSV-2 infection for >1 year but who were otherwise healthy were enrolled sequentially into 1 of 3 dose cohorts defined by the antigen dose (10, 30, or 100 µg for each of the 2 protein antigens) and randomized within each cohort in a ratio of 3:1:1 to receive 3 intramuscular (IM) doses of GEN-003 antigens with M2, GEN-003 antigens without M2, or placebo at intervals of 21 days. The study is complete; 143 subjects were enrolled.

GEN-003 antigens with or without M2 exhibited an acceptable safety and tolerability profile for use as a therapeutic vaccine. Five serious adverse events (SAEs) in 5 subjects (femur fracture, suicide attempt, complicated migraine, myocardial infraction, abortion spontaneous) were reported during the course of the study, and none was considered associated with treatment. No adverse events of special interest (AESIs) were reported.

GEN-003 antigens generated a reduction in HSV-2 shedding rates that was maintained for at least 6 months after treatment, and the greatest reduction was achieved in the adjuvanted 30 µg dose group. No reduction in HSV-2 shedding occurred in the absence of M2. Thirty (30) µg GEN-003 reduced lesion rates for at least 6 months post-treatment. One hundred (100) µg GEN-003 also reduced HSV-2 shedding and lesion rates (number of days with lesions divided by the 28-day duration of the swab collection period) but less durably.

GEN-003 antigens elicited strong and durable antibody and T-cell immune responses to both vaccine-specific antigens and production of HSV-2 neutralizing antibodies at all doses. The addition of M2 augmented these responses.

GEN-003-002: A Randomized, Double-Blind, Factorial Study to Compare the Safety and Efficacy of Varying Combinations of GEN-003 and Matrix-M2 in Subjects with Genital HSV-2 Infection Subjects aged 18 to 50 years with documented diagnosis of genital HSV-2 infection for >1 year were randomized in equal proportions to receive 3 IM doses of 1 of the following formulations at intervals of 21 days:

30 µg each GEN-003 antigen with 25 µg M2
30 µg each GEN-003 antigen with 50 µg M2
30 µg each GEN-003 antigen with 75 µg M2
60 µg each GEN-003 antigen with 25 µg M2
60 µg each GEN-003 antigen with 50 µg M2
60 µg each GEN-003 antigen with 75 µg M2
Placebo The study is complete; 310 subjects were enrolled.

Reduction in anogenital HSV-2 shedding was observed in all active treatment combinations immediately after the last dose and persisted to 12 months after the last dose. The most effective dose combinations (60 µg each GEN-003 antigen with 50 µg M2 and 60 µg each GEN-003 antigen with 75 µg M2) also reduced HSV-2 lesion rates (the % of days with subject-recorded HSV-2 lesions in a 28-day observation period). Risk ratios (95% confidence intervals [CIs]) compared to Baseline were 0.35 (0.18, 0.71; P=0.0033) and 0.53 (0.31, 0.89; P=0.0165), respectively. These 2 doses are currently being further evaluated in Study GEN-003-003.

GEN-003 exhibited an acceptable safety and tolerability profile for use as a therapeutic vaccine in all dose combinations. Ten SAEs in 8 subjects (femur facture, myocardial infarction, viral syndrome, post lumbar puncture syndrome, pyelonephritis, diverticulitis, bipolar disorder exacerbation [2 events], cholecystitis, and overdose) were reported during the course of the study, and none was considered associated with treatment. All of the SAEs resolved, and only one event (femur fracture) had sequelae. No AESIs were reported.

Six subjects discontinued dosing because of an adverse event (AE) or laboratory abnormality and 3 subjects discontinued because of a local reaction or systemic event, with no differences noted across the treatment groups (no more than 2 in any group). The frequency of Grade 3 AEs within 7 days of any dose was 4% for subjects who received placebo and ranged from 20% to 43% among active dose groups. The most common systemic events were fatigue and muscle aches, which were generally related to adjuvant dose GEN-003-002a: Rollover Trial for Placebo Subjects Previously Enrolled into GEN-003-002—A Randomized, Double-Blind, Factorial Study to Compare the Safety and Efficacy of Varying Combinations of GEN-003 and Matrix-M2 in Subjects with Genital HSV-2 Infection Subjects who received placebo in Study GEN-003-002 were offered enrollment in this open-label study of the same active dose combinations given in that study. A total of 37 subjects were enrolled and have completed the dosing period, and the study is ongoing.

No SAEs or AESIs have been reported.

GEN-003-003: A Randomized, Double-Blind Study to Evaluate a New Formulation of GEN-003 in Subjects with Genital HSV-2 Infection Subjects aged 18 to 50 with documented diagnosis of genital HSV-2 infection for >1 year were randomized in a 1:1:1 ratio to receive 3 IM doses of 1 of the following formulations at intervals of 21 days:

GEN-003: 60 µg each antigen and 50 µg M2
GEN-003: 60 µg each antigen and 75 µg M2
Placebo (normal saline)

A total of 131 subjects were enrolled and have completed the dosing period. Safety data are being reviewed by an independent Data Monitoring Committee (DMC) throughout the study. As of Jun. 13, 2016, the DMC has recommended continuing the trial as planned. Two SAEs in 2 subjects have been reported (meningitis, ductal carcinoma in situ), and neither were considered associated with treatment. No AESIs have been reported.

GEN-003-004 Study Rationale

The only currently approved medications for the prevention of outbreaks caused by genital HSV-2 are antiviral medications (Valtrex 2013, Famvir 2013). The endpoint by which these medications were studied and approved was the proportion of subjects initiating therapy who remained HSV-2 recurrence-free at 6 months or 12 months. For valacyclovir (the most commonly prescribed medication for recurrent genital HSV-2), the proportion of patients who remained recurrence-free at 6 months was 55% (compared to 7% for patients who received placebo) and at 12 months was 34% (compared to 4% for patients who received placebo). Thus, oral antiviral therapy only partially suppresses the recurrences of genital HSV-2.

In addition, antiviral suppressive therapy does not completely eliminate viral shedding (Johnston et al., Lancet. (2012) 379:641-7) and reduces transmission risk by only 48% (Corey et al., N Engl J Med. (2004) 350:11-20 2004). GEN-003 reduces viral shedding by over 50% and combination with suppressive therapy may show additional activity compared to valacyclovir alone, possibly because of the different mechanisms of action.

This study evaluates the combined activity of an optimized dose of GEN-003 in combination with valacyclovir suppressive therapy compared to valacyclovir suppressive therapy alone.

Objectives

The primary objective of the study is to compare the effect of GEN-003 versus placebo administered to subjects taking valacyclovir suppressive therapy to the proportion of subjects who are genital HSV-2 recurrence-free at 6 months after the Last Dose and 12 months after the Last Dose. A secondary objective of the study is to compare the effect of GEN-003 versus placebo administered to subjects taking valacyclovir suppressive therapy on clinical outcomes. The clinical outcomes include:

Proportion of subjects who are genital HSV-2 recurrence-free at 6 months after Dose 1 and 12 months after Dose 1;
Time to first genital HSV-2 recurrence after Dose 1 and after Last Dose;
Time to next genital HSV-2 recurrence after Dose 1 and after Last Dose;
Genital HSV-2 lesion rate;
Rate of genital HSV-2 outbreaks;
Duration of genital HSV-2 outbreaks;
Anogenital HSV-2 shedding rate and magnitude; and
Number of subjects who increase valacyclovir dose.

Another secondary objective of the study is to evaluate safety and tolerability of GEN-003 in subjects taking valacyclovir suppressive therapy. One exploratory objective of the study is to compare immune responses to GEN-003 versus placebo in subjects taking valacyclovir suppressive therapy. Another exploratory objective of the study is to compare duration, severity, and bother of genital herpes symptoms in subjects taking GEN-003 versus placebo and valacyclovir suppressive therapy. A third exploratory objective of the study is to assess health-related quality of life in the presence and absence of a genital herpes recurrence as measured by the EuroQol-5 Domains-5 Levels (EQ-5D-5L) questionnaire.

Study Design

This study is a randomized, double-blind, placebo-controlled clinical trial of GEN-003 in subjects taking valacyclovir suppressive therapy. Subjects aged 18 to 50 years with documented diagnosis of genital HSV-2 infection for >1 year and ≥6 months of use of a stable dose of valacyclovir suppressive therapy or willingness to start valacyclovir suppressive therapy are eligible for screening.

Subjects who pass initial screening begin the 14-day Baseline Period comprising once daily administration of valacyclovir, reporting use via a daily electronic tool of genital herpes lesions, genital herpes symptoms, and valacyclovir use; daily completion of the EQ-5D-5L questionnaire, and a daily single dose of valacyclovir. Subjects taking valacyclovir suppressive therapy before the Baseline Period continue using the same dose of valacyclovir (500 mg or 1 g once a day). Subjects initiating valacyclovir suppressive therapy during the Baseline Period take 500 mg once a day. Immediately after successful completion of the Baseline Period (e.g., entered data into the daily electronic reporting tool, took valacyclovir, and completed the EQ-5D-5L on ≥11 of 14 days), subjects who meet all inclusion and no exclusion criteria are randomized. Randomization is stratified by prior duration of valacyclovir suppressive therapy use (>6 months or initiated at Baseline Period only).

Up to 300 subjects are randomized in a 1:1 ratio to receive 3 IM doses of GEN-003 (60 µg of each antigen and 50 µg of M2) or placebo at intervals of 21 days (Days 1, 22, and 43). The subject remains on the same valacyclovir dose (500 mg once a day or 1 g once a day) through Day 71/Month 1. After Day 71/Month 1, a subject taking 500 mg once a day increases the dose to 1 g once a day if he/she experiences a genital HSV-2 outbreak and the Investigator agrees. Subjects continue to take valacyclovir once a day until the end of the study.

Subjects continue to use the daily electronic tool for reporting of genital herpes lesions, genital herpes symptoms, and valacyclovir use until the end of the study. The subject reports to the investigational site the first time he/she notes the presence of genital lesions, and a clinician examines the subject to confirm the presence of genital lesions consistent with HSV-2 and, if present, collects a lesion swab sample for detection of HSV-2 DNA. Subjects complete the EQ-5D-5L on each day of every outbreak during the study.

Subjects collect anogenital swabs for measurement of HSV-2 shedding twice a day for 28-day periods immediately after Dose 3 (Days 43 to 71), from Month 5 to 6, and from Month 11 to 12. Samples are analyzed for HSV-2 DNA by real-time quantitative PCR.

A serum sample is collected from each subject for evaluation of humoral responses before Dose 1, 7 days after Dose 3 (Day 50), 28 days after Dose 3 (Day 71/Month 1), and at Months 6 and 12. HSV-2 IgG is measured by enzyme-linked immunosorbent assay, and HSV-2 neutralizing antibody is measured by a colorimetric assay. At selected investigational sites, a whole blood sample is collected and processed to isolate peripheral blood mononuclear cells (PBMCs) for evaluation of cellular responses before Dose 1, 7 days after Doses 1 and 3 (Days 8 and 50), and at Months 6 and 12. Secretion of granzyme B (GrB) specific to the vaccine-specific antigens is measured by GrB enzyme-linked immunosorbent spot assay (ELISPOT).

Local reactions and systemic events are recorded 1 hour postdose at the investigational site and for the first 7 days after each dose on the Diary Card; if any event is ongoing after the 7-day diary reporting period, it is followed until resolution. All AEs and concomitant medications are recorded from Day 1 to Day 71/Month 1. After Day 71/Month 1 to the end of the study, only SAEs, AESIs, antivirals (other than valacyclovir), and vaccines are recorded. Symptom-driven physical examinations are performed at all visits from Day 1 to Day 71/Month 1 and at Months 6 and 12, and vital signs are measured at all visits from Day 1 to Day 71/Month 1, including before and 1 hour after each GEN-003/placebo dose. Hematology, serum chemistry, and urine samples are collected 7 days after each GEN-003/placebo dose (Days 8, 29, and 5) and 28 days after Dose 3 (Day 71/Month 1).

After Day 71/Month 1, the subjects visit the investigational site monthly for check of valacyclovir supply, review of daily electronic reporting tool data, collection of any completed EQ-5D-5L questionnaires, check of EQ-5D-5L questionnaire supply, and assessment of SAEs, AESIs, and antiviral medication and vaccine use.

A DMC reviews safety data at intervals of a minimum of 3 months until all subjects have completed the GEN-003/placebo dosing period. Any additional meetings and the specific safety monitoring plan are detailed in the DMC charter.

An interim analysis is conducted after all subjects have completed the Month 6 visit.

Study Population

The study population consists of patients with documented HSV-2 infection who have been taking valacyclovir suppressive therapy at a stable dose (either 500 mg or 1 g) once a day for at least 6 months or are willing to start valacyclovir suppressive therapy. Subjects who have been taking valacyclovir suppressive therapy have had at least 1 outbreak in the past 6 months. Subjects who start valacyclovir suppressive therapy for the study have had >5 outbreaks in the past 12 months. This study population represents a target population likely to benefit from a therapeutic HSV-2 vaccine.

Dosing Regimen

Among the antigen and adjuvant combinations tested in Study GEN-003-002, the largest reductions in HSV-2 shedding were observed in subjects who received 60 µg of each antigen with 50 or 75 µg of M2. The GEN-003 dose for this study is 60 µg of each antigen with 50 or 75 µg of M2.

Stratification

Subjects taking a stable dose (500 mg once a day or 1 g once a day) of valacyclovir suppressive therapy (for >6 months) are enrolled only if they have had an outbreak of genital HSV-2 and thus have demonstrated incomplete HSV-2 control regardless of valacyclovir dose. Consequently, there is no need to stratify subjects by dose (all subjects newly initiating valacyclovir take 500 mg once a day). Subjects are, however, stratified by prior duration of suppressive therapy use: (≥6 months or initiated at Baseline Period only). This stratification minimizes bias caused by potential variability in subject responses to antiviral suppression and uncertainty in long-term effectiveness of antiviral suppression.

Efficacy Endpoints

Proportion of subjects recurrence-free at 6 and 12 months post-treatment is a clinically important measure of efficacy that has been used as the primary efficacy measure for currently available treatments for HSV-2 genital infection (Valtrex 2013, Famvir 2013). Although both the proportion of subjects recurrence-free and time to first HSV-2 recurrence are important measures of clinical efficacy, the proportion of subjects recurrence-free fails to account for vaccine effect in prolonging the period between HSV-2 recurrences and time to HSV-2 recurrence after the first recurrence. Time to next recurrence accounts for the vaccine effect over the course of the 6-or 12-month period by measuring and averaging the intervals between all recurrences, thus providing a more complete picture of vaccine effect over the observed time period.

Viral shedding is a direct measurement of antiviral activity that has been used in previous studies of both vaccines and antiviral medications for genital HSV-2. It is an objective measure of antiviral activity against HSV-2.

Subjects report daily severity and bother for 5 HSV-2-related symptoms (itch, pain, burning sensation, tingling, irritation) if present. The purpose of collecting patient-reported assessment of symptoms is to identify episodes of HSV-2-related symptoms that may or may not coincide with patient-reported presence of genital lesions (e.g., prodrome). In addition, GEN-003 may reduce the severity of symptoms related to recurrent outbreaks of genital HSV-2.

The EQ-5D-5L is a self-administered questionnaire designed as a standardized measure of health-related quality of life and has been used to study a wide range of medical conditions.

Study Duration

The total duration of enrollment is 6 months; the actual duration of enrollment may be longer. The duration of each subject's participation (including Screening) is up to 14.5 months. Thus, the study lasts approximately 21 months.

Subject Population

Inclusion Criteria

Subjects who participate in the study meet the following inclusion criteria:
1. males and nonpregnant females, ages 18 to 50 years inclusive;
2. medical history consistent with genital herpes for >1 year;
   taking valacyclovir suppressive therapy at a stable dose (either 500 mg or 1 g) once a day for at least 6 months before the Baseline Period AND history of at least 1 outbreak in the 6 months before the Baseline Period
   OR
   willing to start 500 mg valacyclovir suppressive therapy at 500 mg once a day for the Baseline Period AND history of >5 outbreaks in the 12 months before the Baseline Period;
3. diagnosis of genital HSV-2 infection supported by ONE of the following documented in the medical history or performed at Screening:
   a) Western blot for HSV-2;
   b) type-specific PCR OR viral culture;
   c) compatible clinical history AND;
      i) positive HerpeSelect® 2 enzyme-linked immunosorbent assay (ELISA) IgG with an index value >3.5 OR;
      ii) positive LIAISON® HSV-2 Type Specific IgG;
4. completion of the daily electronic reporting tool, took once daily valacyclovir, and completed the EQ-5D-5L on at least 11 of 14 days in the Baseline Period;
5. willing and able to provide written informed consent;
6. willing to perform and comply with all study procedures including attending clinic visits as scheduled; and 7. willing to practice a highly effective method of contraception that may include, but is not limited to, abstinence, sex only with persons of the same sex, monogamous relationship with vasectomized partner, vasectomy, hysterectomy, bilateral tubal ligation, licensed hormonal methods, intrauterine device (IUD), or use of a spermicide combined with a barrier method (e.g., condom, diaphragm) for 28 days before and 90 days after receiving the investigational product (IP).

Exclusion Criteria

Subjects who meet any one of the following criteria are excluded from participation in the study:

1. use of tenofovir, lysine, or medication (other than valacyclovir) or supplement known or purported to affect HSV outbreak frequency or intensity within 14 days prior to Dose 1 of GEN-003/placebo;
2. history of any form of ocular HSV infection, HSV-related erythema multiforme, or herpes meningitis or encephalitis;
3. have active genital HSV-2 lesions (the subject may enter the study once lesions have re-epithelialized);
4. immunocompromised individuals, including those receiving any type of systemic immunosuppressive medication within 30 days prior to Dose 1 of GEN-003/placebo;
5. presence or history of autoimmune disease (see, Table 3), regardless of current treatment;
6. current infection with HIV or hepatitis B or C virus;
7. clinically significant laboratory abnormality or a value ≥Grade 2 except for (i) Grade 2 creatinine kinase in an individual with an identified exercise regimen and hepatic and renal enzyme levels within normal limits or (ii) isolated Grade 2 unconjugated bilirubin in fasting subject with history of Gilbert's syndrome;
8. history of hypersensitivity to any component of the vaccine;
9. prior receipt of GEN-003 or another vaccine containing HSV-2 antigens;
10. receipt of any IP within 30 days prior to Dose 1 of GEN-003/placebo;
11. receipt of any blood product within 90 days prior to Dose 1 of GEN-003/placebo;
12. receipt of a live vaccine within 28 days prior to or any other vaccine within 14 days prior to Dose 1 of GEN-003/placebo;
13. planned use of any vaccine from Dose 1 of GEN-003/placebo to 28 days after Dose 3 of GEN-003/placebo;
14. pregnant or nursing women;
15. history of drug or alcohol abuse that, in the opinion of the Investigator, would interfere with the subject's ability to comply with the requirements of the study;
16. other active, uncontrolled comorbidities that, in the opinion of the Investigator, would make the subject unsuitable for the study or unable to comply with the study requirements; or
17. changes to medication used to manage an underlying comorbidity within 60 days prior to Dose 1 of GEN-003/placebo.

TABLE 3

| Autoimmune Diseases |
| --- |
| Gastrointestinal disorders |
| Celiac disease |
| Crohn's disease |
| Ulcerative colitis |
| Ulcerative proctitis |

TABLE 3-continued

| Autoimmune Diseases |
| --- |
| Liver disorders |
| Autoimmune cholangitis |
| Autoimmune hepatitis |
| Primary biliary cirrhosis |
| Primary sclerosing cholangitis |
| Metabolic diseases |
| Addison's disease |
| Autoimmune thyroiditis (including Hashimoto thyroiditis) |
| Diabetes mellitus type I |
| Grave's or Basedow's disease |
| Musculoskeletal disorders |
| Antisynthetase syndrome |
| Dermatomyositis |
| Juvenile chronic arthritis (including Still's disease) |
| Mixed connective tissue disorder |
| Polymyalgia rheumatic |
| Polymyositis |
| Psoriatic arthropathy |
| Relapsing polychondritis |
| Rheumatoid arthritis |
| Scleroderma (including diffuse systemic form and CREST syndrome) |
| Spondyloarthritis (including ankylosing spondylitis, reactive arthritis [Reiter's Syndrome] and undifferentiated spondyloarthritis) |
| Systemic lupus erythematosus |
| Systemic sclerosis |
| Neuroinflammatory disorders |
| Acute disseminated encephalomyelitis (including site specific variants: e.g., noninfectious encephalitis, encephalomyelitis, myelitis, and myeloradiculomyelitis) |
| Cranial nerve disorders, including paralyses/paresis (e.g., Bell's palsy) |
| Guillain-Barre syndrome (including Miller Fisher syndrome and other variants) |
| Immune-mediated peripheral neuropathies and plexopathies (including chronic inflammatory demyelinating polyneuropathy, multifocal motor neuropathy, and polyneuropathies associated with monoclonal gammopathy) |
| Multiple sclerosis |
| Narcolepsy |
| Optic neuritis |
| Transverse myelitis |
| Skin disorders |
| Alopecia areata |
| Autoimmune bullous skin diseases (including pemphigus, pemphigold, and dermatitis herpetiformis) |
| Cutaneous lupus erythematosus |
| Erythema nodosum |
| Morphoea |
| Lichen planus |
| Psoriasis |
| Sweet's syndrome |
| Vitiligo |
| Vasculitides |
| Large vessels vasculitis (including giant cell arteritis such as Takayasu's arteritis and temporal arteritis) |
| Medium sized and/or small vessels vasculitis (including polyarteritis nodosa, Kawasaki's disease, microscopic polyangiitis, Wegener's granulomatosis, Churg-Strauss syndrome [allergic granulomatous angiitis], Buerger's disease [thromboangiitis obliterans], necrotizing vasculitis and antineutrophil cytoplasmic antibody positive vasculitis [type unspecified], Henoch- Schonlein purpura, Behcet's syndrome, and leukocytoclastic vasculitis) |
| Antiphospholipid syndrome |
| Autoimmune hemolytic anemia |
| Autoimmune glomerulonephritis (including immunoglobuiln A nephropathy, glomerulonephritis rapidly progressive, membranous glomerulonephritis, membranoproliferative glomerulonephritis, and mesangioproliferative glomerulonephritis) |
| Autoimmune myocarditis/cardiomyopathy |
| Autoimmune thrombocytopenia |
| Goodpasture syndrome |
| Idiopathic pulmonary fibrosis |
| Pernicious anemia |

TABLE 3-continued

Autoimmune Diseases

Raynaud's phenomenon
Sarcoidosis
Sjogren's syndrome
Stevens-Johnson syndrome
Uveitis Investigational Products Formulation GEN-003 consists of 2 recombinant antigens corresponding to 2 distinct HSV-2 proteins (GB208 and GB217) in combination with M2 and diluent. These components are detailed in Table 4.

TABLE 4

Composition of GEN-003

| Ingredient | Description | Dose |
| --- | --- | --- |
| GB208 | Corresponds to a ~39 kDa internal fragment of the ICP4 protein | 60 µg |
| GB217 | A recombinant version of the glycoprotein gD modified by a deletion of the transmembrane region | 60 µg |
| Matrix-M2 Adjuvant | An immune stimulating complex-based adjuvant containing saponin fractions purified from *Quillaja saponaria* (soapbark tree) bark, phosphatidylcholine, and cholesterol | 50 µg |
| Diluent | 0.9% normal saline | Not applicable |

Packing and Labeling of Vaccine Formulation

GEN-003/placebo is prepared from the following 3 components before injection:
(1) GB208 and GB217 antigens in a lyophilized form are supplied in a 3 mL glass vial containing 125 µg, at a concentration of 0.25 mg/mL when reconstituted to a volume of 0.5 mL.
(2) M2 is supplied in a second 3 mL glass vial containing 0.75 mL of M2 at a concentration of 1 mg/mL.
(3) Normal saline (0.9% sodium chloride in water) from commercially available supply is supplied in a third vial for dilution of antigens to the desired concentration and for use as placebo.

The vaccine components are packaged and labeled as IPs in accordance with applicable legal and regulatory requirements.

Storage

The antigens and M2 are stored at 2° C. to 8° C. The site must report excursions above 10° C. to the Sponsor for an assessment of product quality. Normal saline is stored at ambient temperature.

Preparation and Administration

Preparation of GEN-003/placebo is performed by a designated unblinded site pharmacist (or otherwise qualified personnel) in accordance with the Pharmacy Manual provided by the Sponsor. Preparation requires approximately 30 minutes.

GEN-003/placebo is administered by trained study personnel. Each injection consists of a total volume of 0.5 mL administered IM to the deltoid muscle of either arm. Both 1.0-inch and 1.5-inch needles are provided. For obese subjects, a 1.5-inch needle is recommended.

Antiviral Therapy

Commericially available 500 mg valacyclovir tablets are supplied and provided to subjects in the original commerical packaging and labels as investigational products in accordance with applicable legal and regulatory requirements. Valacyclovir is stored at 15° C. to 25° C. (59° F. to 77° F.) in accordance with the Prescribing Information. Valacyclovir is dispensed at clinic visits as detailed in the Study Procedures Section. Valacyclovir is taken with or without food. Subjects are advised to maintain adequate hydration while taking valacyclovir.

Randomization and Dosing

Eligible subjects are randomized in a 1:1 ratio to receive 3 IM doses of GEN-003 (60 µg each antigen and 50 µg M2) or placebo at intervals of 21 days (Days 1, 22, and 43). Randomization is stratified by prior duration of valacyclovir suppressive therapy use (≥6 months or initiated at Baseline Period only).

Randomization is achieved using the randomization component of the electronic case report form (eCRF). After subject eligibility is confirmed on this form, the system sends an e-mail to the unblinded pharmacist (or otherwise qualified personnel) with instructions for accessing the treatment assignment.

The subject remains on the same valacyclovir dose (500 mg once a day or 1 g once a day) through Day 71/Month 1. After Day 71/Month 1, a subject taking 500 mg once a day increases the dose to 1 g once a day if he/she experiences a genital HSV-2 outbreak and the Investigator agrees.

Blinding and Unblinding

Investigators, subjects, and all study staff with direct subject contact are blinded to treatment assignment (GEN-003 vs placebo). A designated unblinded pharmacist (or otherwise qualified personnel) at each site prepares each dose. That individual has no contact with the subjects and minimize contact with other site study personnel.

Unblinding of treatment assignment is discouraged. In the event of a medical emergency, for which the identity of the treatment assignment is critical to the care of a subject, the Investigator calls the Medical Monitor to discuss. In the event that unblinding is deemed necessary, an unblinded statistician provides the treatment assignment to the Medical Monitor who provides the information to the Investigator. A decision to discontinue a subject from further IP administration is not a rationale for unblinding the treatment assignment An unblinded statistician is available to the DMC and Medical Monitor and reviews interim analyses.

Investigational Product Accountability, Dispensing and Destruction

The Investigator (or designee) maintains an accurate record of the receipt of the GEN-003 components and valacyclovir as shipped by the Sponsor (or designee), including the date received. In addition, an accurate GEN-003/placebo disposition record is kept, specifying the amount administered to each subject, and an accurate valacyclovir disposition record is kept, specifying the amount dispensed to each subject and the dates of dispensation and return.

At the completion of the study, all unused IP supplies are returned to the Sponsor (or designee) or disposed of by the site in accordance with the Sponsor's (or designee's) written instructions.

Concomitant Medications

All concomitant medications (not including valacyclovir), including over-the-counter medications and supplements, are recorded in the eCRF from Dose 1 to Day 71/Month 1. Use of antivirals (other than valacyclovir) and vaccines is recorded from Screening through the end of the study.

Medications and Supplements with Anti-HSV Activity

Use of tenofovir (except for postexposure prophylaxis for HIV-1), lysine, or medication (other than valacyclovir) or supplement known or purported to affect HSV outbreak frequency or intensity is prohibited from 14 days before Dose 1 to the end of the study.

Topical Steroids and Antiviral Medications

Use of topical steroids or antiviral medication in the anogenital region is prohibited from 14 days before the beginning of each swab collection period to the end of the swab collection period.

Immunosuppressive Medications

Systemic immunosuppressive medications are prohibited from 30 days before Dose 1 to the end of the study.

Vaccines

Subjects do not receive a live vaccine within 28 days prior to Dose 1 or any other vaccine within 14 days prior to Dose 1. In addition, subjects do not receive any vaccine from Dose 1 to 28 days after the last dose of GEN-003/placebo. It is particularly important to reinforce this information if the subject is receiving GEN-003/placebo during the influenza season Other Study Restrictions There are no restrictions on fluid or food intake during the study. However, because of the large volume of blood drawn on days when PBMCs are obtained, subjects are well-hydrated. Subjects should also maintain hydration while taking valacyclovir. Subjects refrain from excessive physical activity for 48 hours before each study visit from Screening through Day 71/Month 1. Male and female subjects practice a highly effective method of contraception that includes, but is not limited to, abstinence, sex only with persons of the same sex, monogamous relationship with vasectomized partner, vasectomy, hysterectomy, bilateral tubal ligation, licensed hormonal methods, IUD, or use of spermicide combined with barrier method (e.g., condom, diaphragm) for 28 days before Dose 1 through 90 days after the last dose of GEN-003/placebo3. Subjects are advised that GEN-003 has not been proven to reduce the likelihood of transmission of HSV-2 infection to an uninfected sexual partner. Valacyclovir has been shown to reduce but not eliminate the risk of transmission. In addition, the efficacy of condoms for the prevention of HSV-2 infection is limited.

Treatment Compliance

To ensure compliance with the dosing regimen, all doses of GEN-003/placebo are administered by trained study personnel in the clinic who have been delegated that responsibility by the Investigator. Subjects report valacyclovir use via the daily electronic reporting tool and are required to return all bottles at each clinic visit. Clinic visits are conducted within the windows of the specified date.

Study Procedures

Definitions and Descriptions of Assessments and Procedures

Complete physical examination—Examination of the following systems: cardiovascular; dermatological; ear, nose, and throat; extremities; gastrointestinal; genitourinary; musculoskeletal; neurological ophthalmological; neurological; respiratory.

Symptom-driven physical examination—Brief, focused examination of the subject following medical history.

Vital signs—Temperature, heart rate, blood pressure. Heart rate and blood pressure are obtained after subject is seated for 5 minutes.

Hematology—Hemoglobin, red blood cell count, white blood cell count and differential, platelet count.

Serum chemistry—Alanine aminotransferase, aspartate aminotransferase, creatinine, creatine kinase, potassium, sodium, total bilirubin.

Urinalysis—Glucose, occult blood, protein.

Serum/urine pregnancy tests—For all women regardless of menopausal status other than those that have been surgically sterilized (by hysterotomy or bilateral tubal ligation).

Anogenital swabs—Subjects are provided with a swab kit (containing Swab Log, swabs, collection tubes, labels, and storage boxes) for the swab collection period. Subjects are instructed to collect anogenital swabs twice a day for 28-day periods. Subjects do not collect swabs for more than 28 days (e.g., more than 56 swabs).

Swab Log—Subjects are provided with a Swab Log for the swab collection period to indicate date and time of each swab collected.

Genital herpes lesions—Papules, pustules, vesicles, or ulcers, including those that have crusted. Symptoms of prodrome, redness, itchiness, or postinflammatory hyperpigmentation of re-epithelialized ulcers do not constitute the presence of lesions.

Daily electronic reporting tool—Each day subjects report the presence or absence of genital lesions, genital herpes symptoms, and valacyclovir use. In addition, if genital herpes symptoms are present, subjects also rate the severity and bother of the symptoms using the questions from the Genital Herpes Signs and Symptoms Diary. Data is entered daily. A subject receives a daily text reminder if data are entered for that day. The investigational site receives a weekly e-mail notification if a subject misses any data, and the site makes contact with the subject to promote compliance.

First recurrence of HSV-2—The subject returns to the investigational site within 72 hours (preferably within 24 to 48 hours) of the first time he/she notes the presence of new genital lesions after Dose 1 for confirmation of lesions by the Investigator (or Subinvestigator) (see, Study Vaccine (GEN-003/Placebo) Dosing Period section).

EQ-5D-5L—Subjects completes the paper questionnaire each day during the Baseline Period and each day genital lesions are present.

Reactogenicity—Subjects are interviewed and examined at 1 hour after each dose and the following items is entered in the eCRF:

i) Local reactions: pain, tenderness, swelling, redness ii) Systemic events: headache, chills, fatigue, nausea, vomiting, diarrhea, muscle aches iii) Oral temperature The subjects also record these items on a Diary Card for the first 7 days after each dose, and the information is entered in the eCRF.

Diary Card—Subjects are provided a Diary Card to record local reactions, systemic events, and oral temperature for the 7 days following each dose. If there are any events ongoing after the 7-day diary reporting period these events are followed until resolution and the stop date recorded. The Investigator (or Subinvestigator) review Diary Cards with the subject. Any changes or comments to the subject's Diary Card are made on the Diary Card and initialed and dated by the Investigator (or Subinvestigator). The Diary Card and the Investigator's (or Subinvestigator's) assessment serve as the source document. An event recorded on the Diary Card is recorded on the AE eCRF unless it meets the criteria of an SAE.

AEs (including SAEs and AESIs)—see Adverse Events section below.

AESIs—refer to Table 3 for list

Screening (within 28 Days before Day 1 of Study)

The subject is screened to assess eligibility criteria. The following assessments and procedures are performed:
  written informed consent
  medical history, including complete history of HSV-2 infection (date of diagnosis, number of outbreaks per year, treatment, etc.), demographics, and medication and vaccine history
  complete physical examination including examination of genital area
  height and weight
  vital signs
  sample collection:
    hematology
    serum chemistry
    serum pregnancy test for all women (unless surgically sterilized)
    serum for HSV-1 and HSV-2 serology (if not previously available)
    serum for hepatitis C virus (HCV) and HIV serology and hepatitis B surface antigen (HBsAg) testing
    urinalysis (e.g., glucose, occult blood, protein)

Baseline Period (Day-14 to Day-1)

Subjects that the initial screening assessment, attend a clinic visit on the first day of the 14-day Baseline Period (Day -14). The following procedures are performed:
  Assessment of concomitant medications and vaccines
  Dispensing of valacyclovir and reminder to take valacyclovir once daily and to maintain adequate hydration and to bring all bottles to the next clinic visit
  Recording of valacyclovir dose, e.g., the previously prescribed dose (if previously taken for >6 months) or 500 mg if initiating suppressive antiviral therapy
  Provision of a pad of EQ-5D-5L questionnaires
  Instruction in use of the daily electronic reporting tool and EQ-5D-5L.
  On each day during the Baseline Period, the subject:
  Records the presence or absence of genital herpes lesions, genital herpes symptoms, and valacyclovir use via the daily electronic reporting tool
  Completes the EQ-5D-5L questionnaire
  Takes valacyclovir once a day
  If Dose 1 is delayed because of active genital HSV-2 lesions or because of vaccine receipt, these procedures are continued through the delayed Dose 1 (up to an additional 3 days).

Study Vaccine (GEN-003/Placebo) Dosing Period

Day 1 (Dose 1)

The visit takes approximately 2.5 hours, including observation for 1 hour after vaccination. The following procedures are performed before IP administration:
  Return of valacyclovir bottles and dispensing of valacyclovir, if required
  Review of daily electronic reporting tool data, including review of valacyclovir dosing
  Collection of completed EQ-5D-5L questionnaires and provision of a new pad, if needed
  Symptom-driven physical examination
  Vital signs
  Urine pregnancy test for all women (unless surgically sterilized)
  Sample collection:
    Serum for immunogenicity testing
    At selected investigational sites: whole blood for PBMC isolation for immunogenicity testing and human leukocyte antigen typing
  Assessment of concomitant medications and vaccines.
  Any subject presenting with active genital HSV-2 lesions has Dose 1 delayed until lesions have re-epithelialized. Dose 1 may be delayed for up to 3 days; completion of the daily electronic reporting tool and EQ-5D-5L and once daily valacyclovir is continued until delayed Dose 1.
  Day 1 is delayed if a subject has received a vaccine within the excluded time frame (see Comcomitant Medications section). Dose 1 may be delayed for up to 3 days; completion of the daily electronic reporting tool and EQ-5D-5L and once daily valacyclovir is continued until delayed Dose 1.
  Upon determination that a subject meets all eligibility criteria (including completion of the daily electronic reporting tool and the EQ-5D-5L and a daily valacyclovir dose on at least 11 of 14 days of the Baseline Period), the subject is randomized to treatment assignment (see, Randomization and Dosing section) and GEN-003/placebo administered.
  The following procedures are performed 1 hour after GEN-003/placebo administration:
    Vital signs
    Assessment of local reactions, systemic events, and AEs
    Before discharge from the clinic, the subject is given a Diary Card and instructed to record temperature, local reactions, and systemic events (at the same time each day). The subject is also instructed that, if any event is ongoing after the 7-day diary reporting period, to follow the event until resolution and report the stop date. The subject is instructed to bring the Diary Card back to the clinic at the next visit.
  The subject is reminded to:
    Continue use of the daily electronic reporting tool
    Contact the investigational site to schedule a visit immediately upon suspecting the first genital herpes outbreak on study
    Complete the EQ-5D-5L questionnaire on each day genital lesions are present during the study and return the questionnaires at the next study visit
    Take valacyclovir once daily and maintain adequate hydration
    Bring all valacyclovir bottles to the next clinic visit.

Recurrence of Genital HSV-2

The subject returns to the investigational site within 72 hours (preferably within 24 to 48 hours) of the first time he/she notes the presence of new genital lesions after Dose 1. A clinician examines the subject to confirm the presence of genital lesions consistent with HSV-2 and, if presence confirmed, collects a lesion swab sample for detection of HSV-2 DNA.

If the subject does not attend a clinic visit or the clinician determines that the lesion observed by the subject is not consistent with genital HSV-2 or is not able to determine if the lesion is consistent with genital HSV-2 (e.g., if the lesion is no longer present), the subject is instructed to return to the clinic at the next suspected recurrence.

Completed EQ-5D-5L questionnaires are collected and a new pad is provided, if needed. Subjects are reminded to complete the EQ-5D-5L questionnaire on each day genital lesions are present during the study and return the questionnaires at the next study visit.

Days 8 (+/−3 Days) and 29 (+/−3 Days)

The following procedures are performed:
  Return of valacyclovir bottles and dispensing of valacyclovir, if required
  Review of daily electronic reporting tool data, including review of valacyclovir dosing
  Collection of any completed EQ-5D-5L questionnaires and provision of a new pad, if needed
  Review of Diary Card
  Symptom-driven physical exam, including examination of the injection site
  Vital signs
  Sample collection:
    (a) Hematology
    (b) Serum chemistry (c) At selected investigational sites: whole blood for PBMC isolation for immunogenicity testing (Day 8 only); and
(d) Urinalysis Assessment of AEs
Assessment of concomitant medications and vaccines.
The subject are reminded to:
Continue use of the daily electronic reporting tool
Contact the investigational site to schedule a visit immediately upon suspecting the first genital herpes outbreak on study
Complete the EQ-5D-5L questionnaire on each day genital lesions are present during the study and return the questionnaires at the next study visit
Take valacyclovir once daily and maintain adequate hydration
Bring all valacyclovir bottles to the next clinic visit.

Doses 2 and 3 [Day 22 (+/−3 Days)/Day 43 (+/−3 Days)]
In no case is a dose be given within 14 days before or after another dose. The following procedures are performed before IP administration:
Return of valacyclovir bottles and dispensing of valacyclovir, if required
Review of daily electronic reporting tool data, including review of valacyclovir dosing
Collection of any completed EQ-5D-5L questionnaires and provision of a new pad, if needed
Symptom-driven physical exam
Vital signs
Urine pregnancy test for all women (unless surgically sterilized)
Assessment of AEs
Assessment of concomitant medications and vaccines.

Any subject who received a vaccine within the excluded time frame (see Concomitant Medications section) has dosing delayed until required time since vaccination has elapsed. If dosing is delayed more than 7 days after the due date, the dose is skipped.

The following procedures are performed 1 hour after GEN-003/placebo administration:
Vital signs
Assessment of local reactions, systemic events, and AEs.

Before discharge from the clinic, the subject is given a Diary Card and instructed to record temperature, local reactions, systemic events, and medication used for fever or pain for the first 7 days (at the same time each day). The subject is also instructed that, if any event is ongoing after the 7-day diary reporting period, to follow the event until resolution and report the stop date. The subject is instructed to bring the Diary Card back to the clinic at the next visit.
The subject is reminded to:
Continue use of the daily electronic reporting tool
Contact the investigational site to schedule a visit immediately upon suspecting the first genital herpes outbreak on study
Complete the EQ-5D-5L questionnaire on each day genital lesions are present during the study and return the questionnaires at the next study visit
Take valacyclovir once daily and maintain adequate hydration
Bring all valacyclovir bottles to the next clinic visit.
At Day 43, the subject is provided with a swab kit and instructed to collect anogenital swabs for the next 28 consecutive days (prior to the Day 71/Month 1 visit).

Day 50 (+/−3 Days)—Clinic Visit
The following procedures are performed:
Reconciliation of number of swabs collected with the number of days collected
Processing and storage of swabs in accordance with instructions in the Specialty Laboratory Manual
Return of valacyclovir bottles and dispensing of valacyclovir, if required
Review of daily electronic reporting tool data, including review of valacyclovir dosing
Collection of any completed EQ-5D-5L questionnaires and provision of a new pad, if needed
Review of Diary Card
Symptom-driven physical exam, including examination of the injection site
Vital signs
Sample collection:
  (a) Hematology
  (b) Serum chemistry
  (c) Serum for immunogenicity testing
  (d) At selected investigational sites: whole blood for PBMC isolation for immunogenicity testing
  (e) Urinalysis
Assessment of AEs
Assessment of concomitant medications and vaccines.
The subject is reminded to:
Continue use of the daily electronic reporting tool
Contact the investigational site to schedule a visit immediately upon suspecting the first genital herpes outbreak on study
Complete the EQ-5D-5L questionnaire on each day genital lesions are present during the study and return the questionnaires at the next study visit
Take valacyclovir once daily and maintain adequate hydration
Bring all valacyclovir bottles to the next clinic visit.

Day 71/Month 1 (+/−3 Days)—Clinic Visit
The following procedures are performed:
Review of swab collection procedures
Return of valacyclovir bottles and dispensing of valacyclovir, if required
Review of daily electronic reporting tool data, including review of valacyclovir dosing
Collection of any completed EQ-5D-5L questionnaires and provision of a new pad, if needed
Symptom-driven physical exam
Vital signs
Sample collection:
  (a) Hematology
  (b) Serum chemistry
  (c) Serum pregnancy test for all women (unless surgically sterilized)
  (d) Serum for immunogenicity testing
  (e) Urinalysis
Assessment of AEs
Assessment of concomitant medications and vaccines
The subject are reminded to:
Continue use of the daily electronic reporting tool
Contact the investigational site to schedule a visit immediately upon suspecting the first genital herpes outbreak on study
Complete the EQ-5D-5L questionnaire on each day genital lesions are present during the study and return the questionnaires at the next study visit
Take valacyclovir once daily and maintain adequate hydration; and
Bring all valacyclovir bottles to the next clinic visit Follow-up Period
Month 2 (Day 99±7 Days)/Month 3 (Day 127+/−7 Days)/Month 4 (Day 155+/−7 Days)
The following procedures are performed:
Return of valacyclovir bottles and dispensing of valacyclovir, if required Review of daily electronic reporting tool data, including review of valacyclovir dosing
Collection of any completed EQ-5D-5L questionnaires and provision of a new pad, if needed
Assessment of SAEs and AESIs
Assessment of antiviral and vaccine use.
The subject is reminded to:
Continue use of the daily electronic reporting tool
Contact the investigational site to schedule a visit immediately upon suspecting the first genital herpes outbreak on study
Complete the EQ-5D-5L questionnaire on each day genital lesions are present during the study
Take valacyclovir once daily and maintain adequate hydration
Bring all valacyclovir bottles to the next clinic visit.
Month 5 (Day 183±7 Days)
The following procedures are performed:
Return of valacyclovir bottles and dispensing of valacyclovir, if required
Review of daily electronic reporting tool data, including review of valacyclovir dosing
Collection of any completed EQ-5D-5L questionnaires and provision of a new pad, if needed
Assessment of SAEs and AESIs
Assessment of antiviral and vaccine use.
The subject is provided with a swab kit and instructed to collect anogenital swabs for the next 28 consecutive days (prior to the Month 6 visit).
The subject is reminded to:
Continue use of the daily electronic reporting tool
Contact the investigational site to schedule a visit immediately upon suspecting the first genital herpes outbreak on study and return the questionnaires at the next study visit
Complete the EQ-5D-5L questionnaire on each day genital lesions are present during the study
Take valacyclovir once daily and maintain adequate hydration
Bring all valacyclovir bottles to the next clinic visit.
Month 6 (Day 211±14 Days)
The following procedures are performed:
Reconciliation of number of swabs collected with the number of days collected
Processing and storage of swabs in accordance with instructions in the Specialty Laboratory Manual
Return of valacyclovir bottles and dispensing of valacyclovir, if required
Review of daily electronic reporting tool data, including review of valacyclovir dosing
Collection of any completed EQ-5D-5L questionnaires and provision of a new pad, if needed
Symptom-driven physical examination
Sample collection:
  (a) Serum for immunogenicity testing
  (b) At selected investigational sites: whole blood for PBMC isolation for immunogenicity testing
Assessment of SAEs and AESIs
Assessment of antiviral and vaccine use.
The subject is reminded to:
Continue use of the daily electronic reporting tool
Contact the investigational site to schedule a visit immediately upon suspecting the first genital herpes outbreak on study
Complete the EQ-5D-5L questionnaire on each day genital lesions are present during the study and return the questionnaires at the next study visit
Take valacyclovir once daily and maintain adequate hydration
Bring all valacyclovir bottles to the next clinic visit.
Month 7 (Day 239±14 Days)/Month 8 (Day 267±14 Days)/Month 9 (Day 295±14 Days)/Month 10 (Day323±14 Days)
The following procedures are performed:
Return of valacyclovir bottles and dispensing of valacyclovir, if required
Review of daily electronic reporting tool data, including review of valacyclovir dosing
Collection of any completed EQ-5D-5L questionnaires and provision of a new pad, if needed
Assessment of SAEs and AESIs
Assessment of antiviral and vaccine use.
The subject is reminded to:
Continue use of the daily electronic reporting tool
Contact the investigational site to schedule a visit immediately upon suspecting the first genital herpes outbreak on study
Complete the EQ-5D-5L questionnaire on each day genital lesions are present during the study and return the questionnaires at the next study visit
Take valacyclovir once daily and maintain adequate hydration
Bring all valacyclovir bottles to the next clinic visit
Month 11 (Day 351±14 Days)
The following procedures are performed:
Return of valacyclovir bottles and dispensing of valacyclovir, if required
Review of daily electronic reporting tool data, including review of valacyclovir dosing
Collection of any completed EQ-5D-5L questionnaires and provision of a new pad, if needed
Assessment of SAEs and AESIs
Assessment of antiviral and vaccine use.
The subject is provided with a swab kit and instructed to collect anogenital swabs for the next 28 consecutive days (prior to the Month 12 visit). The subject is reminded to:
Continue use of the daily electronic reporting tool
Contact the investigational site to schedule a visit immediately upon suspecting the first genital herpes outbreak on study
Complete the EQ-5D-5L questionnaire on each day genital lesions are present during the study and return the questionnaires at the next study visit
Take valacyclovir once daily and maintain adequate hydration
Bring all valacyclovir bottles to the next clinic visit.
Month 12 (Day 379±14 Days)—Clinic Visit
The following procedures are performed:
Reconciliation of number of swabs collected with the number of days collected
Processing and storage of swabs in accordance with instructions in the Specialty Laboratory Manual
Return of valacyclovir bottles
Review of daily electronic reporting tool data, including review of valacyclovir dosing
Collection of any completed EQ-5D-5L questionnaires
Symptom-driven physical exam
Sample collection:
  Serum for immunogenicity testing
  At selected investigational sites: whole blood for PBMC isolation for immunogenicity testing
Assessment of SAEs and AESIs
Assessment of antiviral and vaccine use.

Adverse Events

AEs will be reported in a manner consistent with the FDA Guidance for Industry and Investigators, "Safety Reporting Requirements for IND and BA/BE Studies," December 2012(on the FDA web site on the World Wide Web, at the hypertyext protocol transfer address of "fda.gov/downloads/Drugs/GuidanceComplianceRegulatoryInformation/Guidances/UCM227351.pdf").

Reporting Responsibilities

All AEs (including AESIs and SAEs) will be recorded from Dose 1 to Day 71/Month 1. After Day 71/Month 1 to the end of study, only AESIs and SAEs will be recorded. It is the responsibility of the Investigator or Subinvestigator(s) to perform periodic assessment of AEs. Data describing AEs will be entered in the subject's medical record and eCRF, and as appropriate, an SAE/AESI report form. SAEs and AESIs will be reported to the Sponsor as described in below.

Definitions

Adverse Event: An AE is any untoward medical occurrence in a patient or clinical investigation subject administered a pharmaceutical product and which does not necessarily have a causal relationship with this treatment. An AE can therefore be any unfavorable and unintended sign (including an abnormal laboratory finding), symptom, or disease temporally associated with the use of an IP, whether or not related to the IP.

Adverse Event of Special Interest: Table 3 for the list of AESIs.

Serious Adverse Event: an AE or suspected adverse reaction is considered serious (an SAE) if, in the view of either the Investigator or Sponsor, it results in any of the following outcomes:
  death
  life-threatening: an AE is considered "life-threatening" if, in the view of either the Investigator or Sponsor, its occurrence places the patient or subject at immediate risk of death; does not include an AE that, had it occurred in a more severe form, might have caused death
  inpatient hospitalization or prolongation of existing hospitalization
  a persistent or significant incapacity or substantial disruption of the ability to conduct normal life functions
  a congenital anomaly/birth defect.

Important medical events that may not result in death, be life-threatening, or require hospitalization may be considered serious when, based upon appropriate medical judgment, they may jeopardize the patient or subject and may require medical or surgical intervention to prevent one of the outcomes listed in this definition. Examples of such medical events include allergic bronchospasm requiring intensive treatment in an emergency room or at home, blood dyscrasias or convulsions that do not result in inpatient hospitalization, or the development of drug dependency or drug abuse. If it is not certain that an event meets the above definitions of an SAE, the Medical Monitor is contacted to discuss.

Relatedness (Causality): causality (relationship to GEN-003/placebo and to valacyclovir) assessment is required for all AEs that occur during clinical studies. The following terms are used during this study:
  Likely—reasons to consider an AE likely related to treatment may include, but are not limited, to the following:
    timing of the event relative to the administration of the IP
    location of the AE relative to the site of IP administration
    likelihood based on experience with similar products
    a biologically plausible explanation based on the mechanism of action or mode of delivery of the treatment
    the AE is repeated on subsequent treatments
    no other explanation is likely.
  Unlikely—an AE with no temporal association with the IP but rather related to other etiologies such as concomitant medications or conditions or subject's known clinical state.

Severity: severity for al AEs including laboratory abnormalities is reported in accordance with Toxicity Grading Scale for Healthy Adult and Adolescent Volunteers Enrolled in Preventive Vaccine Clinical Trials (FIGS. 1A-1D). If an appropriate listing is not present in this table for an AE, the AE is graded as follows:
  Grade 1 (Mild)—no interference with daily activity
  Grade 2 (Moderate)—some interference with daily activity but medical intervention not required (e.g., doctor visit and/or prescription medicine); over-the-counter medicine permitted
  Grade 3 (Severe)—prevents daily activity and requires medical intervention (e.g., doctor visit and/or prescription medicine)
  Grade 4 (Potentially Life-threatening)—emergency room visit or hospitalization Clinical Laboratory Abnormalities Any laboratory abnormality deemed clinically significant by the Investigator is recorded as an AE. A clinically significant abnormality is a confirmed abnormality (by repeat test) that is changed sufficiently from Screening/Baseline so that in the judgment of the Investigator a change in management is warranted. This alteration includes, for example, monitoring the laboratory test further, initiating other diagnostic tests or procedures, changing ongoing treatment, or administering new treatment.

Whenever possible, the underlying medical diagnosis (e.g., anemia) is recorded as the AE term. Repeated additional tests and/or other evaluations required to establish the significance and etiology of an abnormal result are obtained when clinically indicated.

Physical Examination Abnormalities

Any physical examination abnormality deemed clinically significant by the Investigator at Screening or during the Baseline Period is reported as Medical History. Any new physical examination abnormality deemed clinically significant by the Investigator during the study is reported as an AE.

Pregnancy

The informed consent form (ICF) includes information regarding reporting of pregnancy to the Sponsor and collection of information through the end of pregnancy in both subjects and female partners of male subjects. If a female partner becomes pregnant, the Investigator requests consent from the partner to collect this information.

No additional doses of GEN-003/placebo are administered to a subject who becomes pregnant during the conduct of the trial. Subjects discuss with their health care provider the use of valacyclovir during pregnancy. All remaining safety assessments are performed. All pregnancies that occur during the study—including pregnancies in female partners of male subjects—are reported to the Sponsor on the Pregnancy eCRF and followed to conclusion. The outcome of each pregnancy is reported on the Pregnancy eCRF. Pregnancy alone is not an AE, nor is an induced elective abortion to terminate a pregnancy without medical reason. However, an induced therapeutic abortion to terminate a pregnancy due to complications or medical reasons is reported as an SAE. The underlying medical diagnosis for this procedure is reported as the SAE term. A spontaneous abortion is always considered an SAE.

Reporting of Serious Adverse Events and Adverse Events of Special Interest

SAEs and AESIs are reported to the Sponsor or designee within 1 business day of becoming aware of the event by entering the data on the AE eCRF. If at the time the Investigator submits an initial SAE/AESI report, the event has not resolved, the Investigator provides a follow up as soon as it resolves (or upon receipt of significant information if the event is still ongoing). All SAEs/AESIs are followed until resolution/stabilization or until a time that is mutually agreed upon between the Medical Monitor and the Investigator.

Upon checking serious or AESI on the AE eCRF, a notification is sent to the Medical Monitor and/or designee. Relevant eCRFs, including the subject's Medical History, Concomitant Medications, and other AEs are completed to provide supporting documentation for the SAE/AESI. Additional documents that support the SAE/AESI (e.g., clinic or hospital records or procedure reports), are uploaded to the AE eCRF.

After review of the initial SAE/AESI information, the Medical Monitor requests additional documentation.

The Sponsor is responsible for notifying the relevant Regulatory Authorities of certain events. It is the Investigator's responsibility to notify the IRB/EC of all SAEs that occur at his or her site. Investigators are notified of all unexpected, serious, IP-related events that occur during the clinical trial. Each site is responsible for notifying its IRB/EC of these additional SAEs.

Follow-Up of Adverse Events

A subject who experiences any AE, whether serious or not serious, is monitored at appropriate intervals and receives appropriate treatment and medical supervision as clinicaly indicated. All AEs are followed until resolution or stabilization or until a time that is mutually agreed upon between the Medical Monitor and the Investigator. Clinically significant laboratory abnormalities are confirmed within 48 hours or as soon as clinically indicated and then followed weekly until resolution.

Example 2

Sub-Study of GEN-003-003 Clinical Study: Genital Lesion Rate in Patients taking GEN-003 and an Antiviral Therapy Study Design Subjects had a documented diagnosis of genital HSV-2 infection for >1 year and a history of 3 to 9 reported clinical occurrences in the prior 12 months (or, if currently on suppressive antiviral therapy, history of at least 3 and no more than 9 reported clinical occurrences in the 12 months prior to initiation of suppressive therapy). The subjects started reporting presence or absence of genital lesions at the start of a 28-day baseline swab collection period. Following this, subjects were randomized in a 1:1:1 ratio to receive 3 IM doses of GEN-003 (described in Example 1) at a dose of 60 µg of each antigen and 50 µg of M2, or 60 µg of each antigen and 75 µg of M2, or placebo (normal saline) at intervals of 21 days (Days 1, 22, and 43).

Subjects reported to the investigational site the first time he/she noted the presence of genital lesions, and a clinician examined the subject to confirm the presence of genital lesions consistent with HSV-2 and, if present, collected a lesion swab sample for detection of HSV-2 DNA. Subjects reported daily the presence or absence of genital lesions, the severity and bother of genital herpes symptoms and antiviral use via an electronic diary for the duration of the study.

The lesion rate is the proportion of days with lesions present. Lesion rates were calculated for the following periods (in addition to Baseline): Day 1 to Day 183 (6 months), and Day 1 to Day 365 (12 months) post-dosing. Antiviral use is the days of reported antiviral use in the 6-month and 12-month periods after Dose 1.

Results

The genital herpes lesion rate in subjects who received antiviral therapy in addition to GEN-003 was examined. Among subjects who took antiviral therapy, the number of days on therapy ranged widely, with some subjects only taking the antiviral medication for a few days (episodically), while others reported treating themselves chronically. Table 5 shows the antiviral therapies taken and the number of subjects.

TABLE 5

| Antiviral Therapies Included in this Analysis | Number of subjects |
| --- | --- |
| ACICLOVIR | 21 |
| FAMCICLOVIR | 2 |
| VALACICLOVIR HYDROCHLORIDE | 31 |

A. Decreased Genital Lesion Rate in Subjects who took Anti-viral Therapy

The genital lesion rate of subjects in the 60 µg GEN-003+ 50 µg Matrix-M2 dose group who took any amount of antiviral during the study period was compared to the genital lesion rate of those who never took an antiviral. FIG. 2 shows the change from baseline genital lesion rates separately for those who never took antiviral therapy during the study period and those who took antiviral therapy at least once. The efficacy of the vaccine formulation is improved with the addition of antiviral therapy based on a lower median change from baseline lesion rate, as shown in Table 6.

TABLE 6

| Antiviral Use | Median Change From Baseline Lesion Rate |
| --- | --- |
| No | 0.0000000 |
| Yes | −8.906074 |

Figure 3:
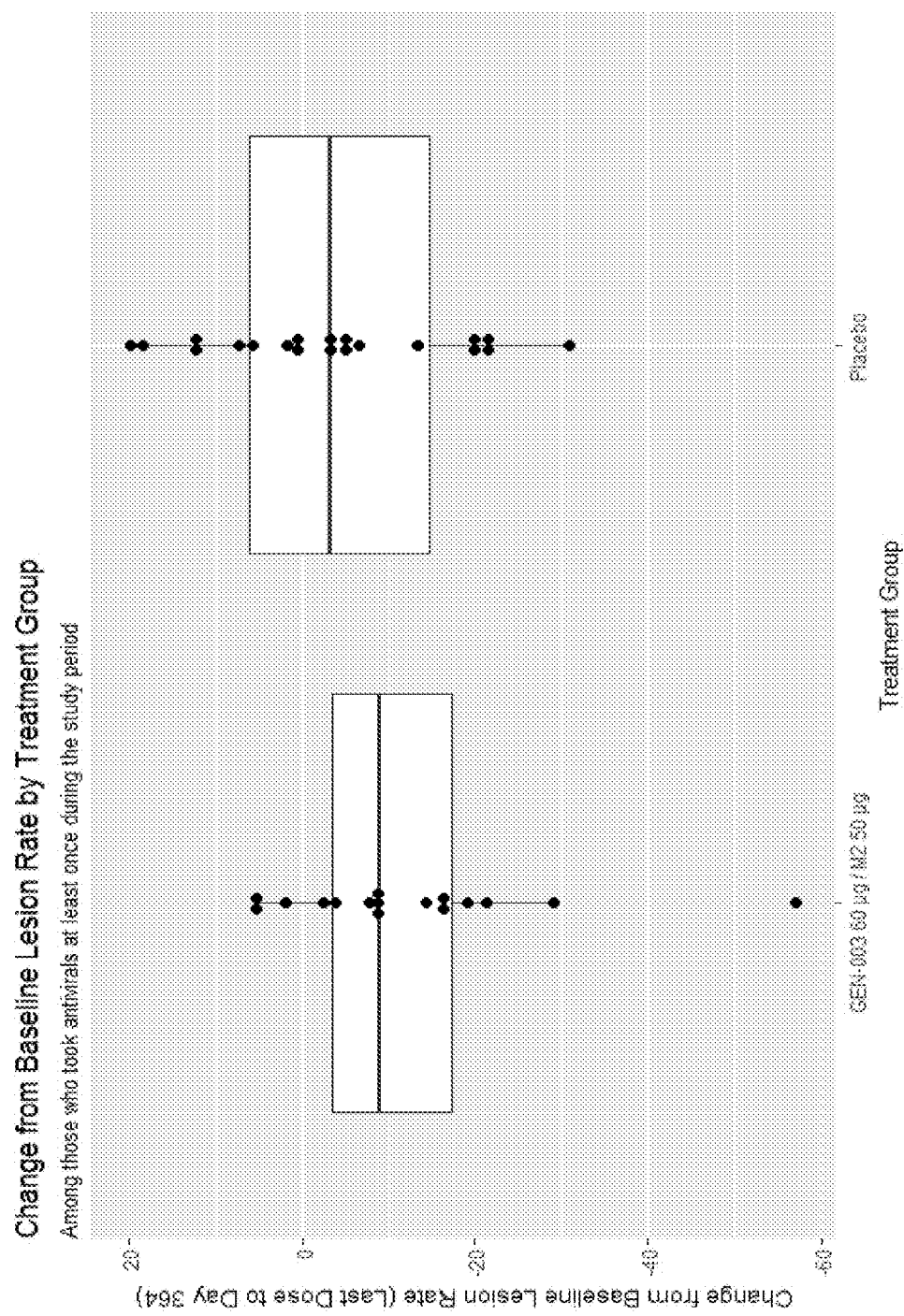
FIG. 3 depicts exemplary data comparing the genital lesion rate of subjects in the 60 μg GEN-003+50 μg Matrix-M2 dose group who took antiviral therapy at least once during the study period to the genital lesion rate of those in the placebo group who took antiviral therapy at least once during the study period.

The genital lesion rate of subjects in the 60 µg GEN-003+ 50 µg Matrix-M2 dose group was compared to the genital lesion rate of those in the placebo group. FIG. 3 shows the change from baseline genital lesion rate of subjects in each of these groups who took antiviral therapy at least once during the study period. The efficacy of antiviral therapy is improved with the addition of the vaccine based on a lower median change from baseline lesion rate, as shown in Table 7.

TABLE 7

| Treatment Group | Median Change From Baseline Lesion Rate |
| --- | --- |
| GEN-003 60 µg/M2 50 µg | −8.906074 |
| Placebo | −3.260018 |

B. Association between Days on Anti-viral Therapy and Decreased Genital Lesion Rate.

Figure 4:
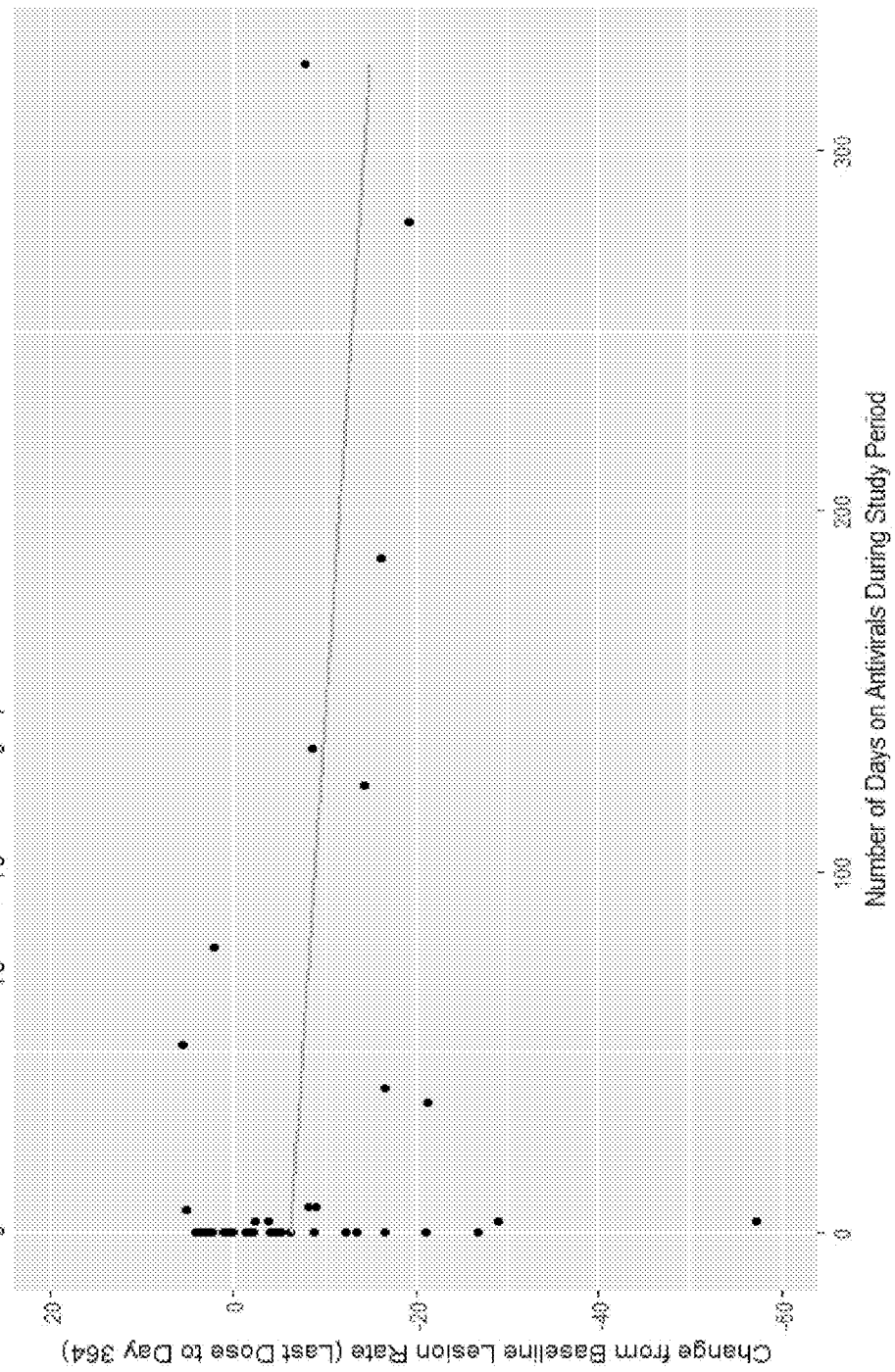
FIG. 4 depicts exemplary data showing an association between days on anti-viral therapy and change from baseline genital lesion rate among subjects receiving 60 μg GEN-003+50 μg Matrix-M2.

The relationship between the number of days on antiviral therapy and the change from baseline genital lesion rate was also examined. FIG. 4 demonstrates the association between days on anti-viral therapy and change from baseline genital lesion rate among those receiving GEN-003 60 μg/M2 50 μg. There is a downward trend in lesion rate as the number of days on antiviral therapy increases.

REFERENCES

Awasthi S, Friedman H M. Status of prophylactic and therapeutic genital herpes vaccines. Curr Opin Virol. 2014; 6:6-12.

Benedetti J, Corey L, Ashley R. Recurrence rates in genital herpes after symptomatic first-episode infection. Ann Intern Med; 1994; 121:847-54.

Centers for Disease Control. Seroprevalence of herpes simplex virus type 2 among persons aged 14-49 years—United States, 2005-2008. MMWR Morb Mortal Wkly Rep. 2010; 59:456-9.

Corey L. Herpes simplex virus type 2 and HIV-1: the dialogue between the 2 organisms continues. J Infect Dis. 2007; 195:1242-4.

Corey L, Wald A, Patel R, et al. Once-daily valacyclovir to reduce the risk of transmission of genital herpes. N Engl J Med. 2004; 350:11-20.

de Bruyn G, Vargas-Cortez M, Vargas T, et al. A randomized controlled trial of a replication defective (gH deletion) herpes simplex virus vaccine for the treatment of recurrent genital herpes among immunocompetent subjects. Vaccine. 2006; 24:914-20.

Famvir [prescribing information]. East Hanover, N.J.: Novartis Pharmaceuticals Corporation; 2013.

Fife K H, Warren T J, Ferrera R D, et al. Effect of valacyclovir on viral shedding in immunocompetent patients with recurrent herpes simplex virus 2 genital herpes: a US-based randomized, double-blind, placebo-controlled clinical trial. Mayo Clin Proc. 2006; 81:1321-7.

Gupta R, Wald A, Krantz E, et al. Valacyclovir and acyclovir for suppression of shedding of herpes simplex virus in the genital tract. J Infect Dis. 2004; 190:1374-81.

Gupta R, Warren T, Wald A. Genital herpes. Lancet. 2007; 370:2127-37.

Johnston C, Saracino M, Kuntz S, et al. Standard-dose and high-dose daily antiviral therapy for short episodes of genital HSV-2 reactivation: three randomised, open-label, cross-over trials. Lancet. 2012; 379:641-7.

Kimberlin D W, Rouse D J. Clinical practice. Genital herpes. New Engl J Med. 2004; 350:1970-7.

Martens M G, Fife K H, Leone P A, et al. Once daily valacyclovir for reducing viral shedding in subjects newly diagnosed with genital herpes. Infect Dis Obstet Gynecol 2009:2009:105376.

Skoberne M, Cardin R, Lee A, et al. An adjuvanted herpes simplex virus 2 subunit vaccine elicits a T-cell response in mice and is an effective therapeutic vaccine in Guinea pigs. J Virol. 2013; 87:3930-42.

```
SEQUENCES
SEQ ID NO: 1 = ICP4
SAEQRKKKKTTTTTQGRGAEVAMADEDGGRLRAAAETTGGPGSPDPADGPPPTPNPDRRPAARPGFGWHGGPEENED

EADDAAADADADEAAPASGEAVDEPAADGVVSPRQLALLASMVDEAVRTIPSPPPERDGAQEEAARSPSPPRTPSMR

ADYGEENDDDDDDDDDDRDAGRWVRGPETTSAVRGAYPDPMASLSPRPPAPRRHHHHHHRRRRAPRRRSAASDSS

KSGSSSSASSASSSASSSSSASASSSDDDDDDDAARAPASAADHAAGGTLGADDEEAGVPARAPGAAPRPSPPRAEP

APARTPAATAGRLERRRARAAVAGRDATGRFTAGRPRRVELDADAASGAFYARYRDGYVSGEPWPGAGPPPPGRVLY

GGLGDSRPGLWGAPEAEEARARFEASGAPAPVWAPELGDAAQQYALITRLLYTPDAEAMGWLQNPRVAPGDVALDQA

CFRISGAARNSSSFISGSVARAVPHLGYAMAAGRFGWGLAHVAAAVAMSRRYDRAQKGFLLTSLRRAYAPLLARENA

ALTGARTPDDGGDANRHDGDDARGKPAAAAAPLPSAAASPADERAVPAGYGAAGVLAALGRLSAAPASAPAGADDDD

DDDGAGGGGGGRRAEAGRVAVECLAACRGILEALAEGFDGDLAAVPGLAGARPAAPPRPGPAGAAAPPHADAPRLRA

WLRELRFVRDALVLMRLRGDLRVAGGSEAAVAAVRAVSLVAGALGPALPRSPRLLSSAAAAAADLLFQNQSLRPLLA

DTVAAADSLAAPASAPREARKRKSPAPARAPPGGAPRPPKKSRADAPRPAAAPPAGAAPPAPPTPPPRPPRPAALTR

RPAEGPDPQGGWRRQPPGPSHTPAPSAAALEAYCAPRAVAELTDHPLFPAPWRPALMFDPRALASLAARCAAPPPGG

APAAFGPLRASGPLRRAAAWMRQVPDPEDVRVVILYSPLPGEDLAAGRAGGGPPPEWSAERGGLSCLLAALGNRLCG

PATAAWAGNWTGAPDVSALGAQGVLLLSTRDLAFAGAVEFLGLLAGACDRRLIVVNAVRAADWPADGPVVSRQHAYL

ACEVLPAVQCAVRWPAARDLRRTVLASGRVFGPGVFARVEAAHARLYPDAPPLRLCRGANVRYRVRTRFGPDTLVPM

SPREYRRAVLPALDGRAAASGAGDAMAPGAPDFCEDEAHSHRACARWGLGAPLRPVYVALGRDAVRGGPAELRGPRR

EFCARALLEPDGDAPPLVLRDDADAGPPPQIRWASAAGRAGTVLAAAGGGVEVVGTAAGLATPPRREPVDMDAELED

DDDGLFGE

SEQ ID NO: 2 = ICP4 internal fragment
MVLYGGLGDSRPGLWGAPEAEEARARFEASGAPAPVWAPELGDAAQQYALITRLLYTPDAEAMGWLQNPRVAPGDVA

LDQACFRISGAARNSSSFISGSVARAVPHLGYAMAAGRFGWGLAHVAAAVAMSRRYDRAQKGFLLTSLRRAYAPLLA

RENAALTGARTPDDGGDANRRDGDDARGKPAAAAAPLPSAAASPADERAVPAGYGAAGVLAALGRLSAAPASAPAGA
```

-continued

DDDDDDDDGAGGGGGGGGGGGGRRAEAGRVAVECLAACRGILEALAEGFDGDLAAVPGLAGARPAAPPRPGPAGAAA

PPHADAPRLRAWLRELRFVRDALVLMRLRGDLRVAGGSEAAVAAVRAVSLVAGALGPALPRSPRLLSSAAAAAADLL

FQNQSL

SEQ ID NO: 3 = gL2
MGFVCLFGLVVMGAWGAWGGSQATEYVLRSVIAKEVGDILRVPCMRTPADDVSWRYEAPSVIDYARIDGIFLRYHCP

GLDTFLWDRHAQRAYLVNPFLFAAGFLEDLSHSVFPADTQETTTRRALYKEIRDALGSRKQAVSHAPVRAGCVNFDY

SRTRRCVGRRDLRPANTTSTWEPPVSSDDEASSQSKPLATQPPVLALSNAPPRRVSPTRGRRRHTRLRRN

SEQ ID NO: 4 = gD2 internal deletion dD2ΔTMR encoded by construct US6ΔTMR
NRWKYALADPSLKMADPNRFRGKNLPVLDQLTDPPGVKRVYHIQPSLEDPFQPPSIPITVYYAVLERACRSVLLHAP

SEAPQIVRGASDEARKHTYNLTIAWYRMGDNCAIPITVMEYTECPYNKSLGVCPIRTQPRWSYYDSFSAVSEDNLGF

LMHAPAFETAGTYLRLVKINDWTEITQFILEHRARASCKYALPLRIPPAACLTSKAYQQGVTVDSIGMLPRFTPENQ

RTVALYSLKIAGWHGPKPPYTSTLLPPELSDTTNATQPELVPEDPEDSALLEDPAGTVSSQIPPNWHIPSIQDVAPH

HAPAAPSNPRRRAQMAPKRLRLPHIRDDDAPPSHQPLFY

SEQ ID NO: 5 = predicted sequence for gD2 encoded by US6
MGRLTSGVGTAALLVVAVGLRVVCAKYALADPSLKMADPNRFRGKNLPVLDQLTDPPGVKRVYHIQPSLEDPFQPPS

IPITVYYAVLERACRSVLLHAPSEAPQIVRGASDEARKHTYNLTIAWYRMGDNCAIPITVMEYTECPYNKSLGVCPI

RTQPRWSYYDSFSAVSEDNLGELMHAPAFETAGTYLRLVKINDWTEITQFILEHRARASCKYALPLRIPPAACLTSK

AYQQGVTVDSIGMLPRFTPENQRTVALYSLKIAGWHGPKPPYTSTLLPPELSDTTNATQPELVPEDPEDSALLEDPA

GTVSSQIPPNWHIPSIQDVAPHHAPAAPSNPGLIIGALAGSTLAVLVIGGIAFWVRRRAQMAPKRLRLPHIRDDDAP

PSHQPLFY

SEQ ID NO: 6 = ICP34.5 encoded by RL1
MSRRRGPRRRGPRRRPRPGAPAVPRPGAPAVPRPGALPTADSQMVPAYDSGTAVESAPAASSLLRRWLLVPQADDSD

DADYAGNDDAEWANSPPSEGGGKAPEAPHAAPAAACPPPPPRKERGPQRPLPPHLALRLRTTTEYLARLSLRRRRPP

ASPPADAPRGKVCFSPRVQVRHLVAWETAARLARRGSWARERADRDRFRRRVAAAEAVIGPCLEPEARARARARARA

HEDGGPAEEEEAAAAARGSSAAAGPGRRAV

SEQ ID NO: 7 = ICP0 encoded by RL2
MEPRPGTSSRADPGPERPPRQTPGTQPAAPHAWGMLNDMQWLASSDSEEETEVGISDDDLHRDSTSEAGSTDTEMFE

AGLMDAATPPARPPAERQGSPTPADAQGSCGGGPVGEEEAEAGGGGDVCAVCTDEIAPPLRCQSFPCLHPFCIPCMK

TWIPLRNTCPLCNTPVAYLIVGVTASGSESTIPIVNDPRTRVEAEAAVRAGTAVDFIWTGNPRTAPRSLSLGGHTVR

ALSPTPPWPGTDDEDDDLADVDYVPPAPRRAPRRGGGGAGATRGTSQPAATRPAPPGAPRSSSSGGAPLRAGVGSGS

GGGPAVAAVVPRVASLPPAAGGGRAQARRVGEDAAAAEGRTPPARQPRAAQEPPIVISDSPPPSPRRPAGPGPLSFV

SSSSAQVSSGPGGGGLPQSSGRAARPRAAVAPRVRSPPRAAAAPVVSASADAAGPAPPAVPVDAHRAPRSRMTQAQT

DTQAQSLGRAGATDARGSGGPGAEGGPGVPRGTNTPGAAPHAAEGAAARPRKRRGSDSGPAASSSASSSAAPRSPLA

PQGVGAKRAAPRRAPDSDSGDRGHGPLAPASAGAAPPSASPSSQAAVAAASSSSASSSSASSSSASSSSASSSSASS

SSASSSSASSSAGGAGGSVASASGAGERRETSLGPRAAAPRGPRKCARKTRHAEGGPEPGARDPAPGLTRYLPIAGV

SSVVALAPYVNKTVTGDCLPVLDMETGHIGAYVVLVDQTGNVADLLRAAAPAWSRRTLLPEHARNCVRPPDYPTPPA

SEWNSLWMTPVGNMLFDQGTLVGALDFHGLRSRHPWSREQGAPAPAGDAPAGHGE

SEQ ID NO: 8 = ICP4 internal fragment encoded by construct RS1.1 (#1-400)
MSAEQRKKKKTTTTTQGRGAEVAMADEDGGRLRAAAETTGGPGSPDPADGPPPTPNPDRRPAARPGFGWHGGPEENE

DEADDAAADADADEAAPASGEAVDEPAADGVVSPRQLALLASMVDEAVRTIPSPPPERDGAQEEAARSPSPPRTPSM

RADYGEENDDDDDDDDDDDDDDRDAGRWVRGPETTSAVRGAYPDPMASLSPRPPAPRRHHHHHHHRRRRAPRRRSAASDS

SKSGSSSSASSSASSSSASSSSSASASSSDDDDDDDAARAPASAADHAAGGTLGADDEEAGVPARAPGAAPRPSPPRAE

PAPARTPAATAGRLERRRARAAVAGRDATGRFTAGRPRRVELDADAASGAFYARYRDGYVSGEPWPGAGPPPPGRVL

YGGLGDSRPGLWGAP

-continued

SEQ ID NO: 9 = ICP4 internal fragment encoded by construct RS1.3.1
(#750-1024)
SSAAAAAADLLFQNQSLRPLLADTVAAADSLAAPASAPREARKRKSPAPARAPPGGAPRPPKKSRADAPRPAAAPPA

GAAPPAPPTPPPRPPRPAALTRRPAEGPDPQGGWRRQPPGPSHTPAPSAAALEAYCAPRAVAELTDHPLFPAPWRPA

LMFDPRALASLAARCAAPPPGGAPAAFGPLRASGPLRRAAAWMRQVPDPEDVRVVILYSPLPGEDLAAGRAGGGPPP

EWSAERGGLSCLLAALGNRLCGPATAAWAGNWTGAPDVSALGAQ

SEQ ID NO: 10 = ICP4 internal fragment encoded by construct RS1.3.2
(#1008-1319)
WAGNWTGAPDVSALGAQGVLLLSTRDLAFAGAVEFLGLLAGACDRRLIVVNAVRAADWPADGPVVSRQHAYLACEVL

PAVQCAVRWPAARDLRRTVLASGRVFGPGVFARVEAAHARLYPDAPPLRLCRGANVRYRVRTRFGPDTLVPMSPREY

RRAVLPALDGRAAASGAGDAMAPGAPDFCEDEAHSHRACARWGLGAPLRPVYVALGRDAVRGGPAELRGPRREFCAR

ALLEPDGDAPPLVLRDDADAGPPPQIRWASAAGRAGTVLAAAGGGVEVVGTAAGLATPPRREPVDMDAELEDDDDGL

FGE

SEQ ID NO: 11 = ICP4 internal fragment encoded by construct RS1.3 (#750-1319)
SSAAAAAADLLFQNQSLRPLLADTVAAADSLAAPASAPREARKRKSPAPARAPPGGAPRPPKKSRADAPRPAAAPPA

GAAPPAPPTPPPRPPRPAALTRRPAEGPDPQGGWRRQPPGPSHTPAPSAAALEAYCAPRAVAELTDHPLFPAPWRPA

LMFDPRALASLAARCAAPPPGGAPAAFGPLRASGPLRRAAAWMRQVPDPEDVRVVILYSPLPGEDLAAGRAGGGPPP

EWSAERGGLSCLLAALGNRLCGPATAAWAGNWTGAPDVSALGAQGVLLLSTRDLAFAGAVEFLGLLAGACDRRLIVV

NAVRAADWPADGPVVSRQHAYLACEVLPAVQCAVRWPAARDLRRTVLASGRVFGPGVFARVEAAHARLYPDAPPLRL

CRGANVRYRVRTRFGPDTLVPMSPREYRRAVLPALDGRAAASGAGDAMAPGAPDFCEDEAHSHRACARWGLGAPLRP

VYVALGRDAVRGGPAELRGPRREFCARALLEPDGDAPPLVLRDDADAGPPPQIRWASAAGRAGTVLAAAGGGVEVVG

TAAGLATPPRREPVDMDAELEDDDDGLFGE

SEQ ID NO: 12 = ICP4 internal fragment encoded by construct RS1.4 (#340-883)
TAGRPRRVELDADAASGAFYARYRDGYVSGEPWPGAGPPPPGRVLYGGLGDSRPGLWGAPEAEEARARFEASGAPAP

VWAPELGDAAQQYALITRLLYTPDAEAMGWLQNPRVAPGDVALDQACFRISGAARNSSSFISGSVARAVPHLGYAMA

AGRFGWGLAHVAAAVAMSRRYDRAQKGFLLTSLRRAYAPLLARENAALTGARTPDDGGDANRHDGDDARGKPAAAAA

PLPSAAASPADERAVPAGYGAAGVLAALGRLSAAPASAPAGADDDDDDGAGGGGGRRAEAGRVAVECLAACRGIL

EALAEGFDGDLAAVPGLAGARPAAPPRPGPAGAAAPPHADAPRLRAWLRELRFVRDALVLMRLRGDLRVAGGSEAAV

AAVRAVSLVAGALGPALPRSPRLLSSAAAAAADLLFQNQSLRPLLADTVAAADSLAAPASAPREARKRKSPAPARAP

PGGAPRPPKKSRADAPRPAAAPPAGAAPPAPPTPPPRPPRPAALTRRPAEGPDPQGGWRRQPPGPSHTPAPSAAALE

AYCA

SEQ ID NO: 13 = ICP4 internal fragment encoded by construct RS1.5 (#775-1318)
AAADSLAAPASAPREARKRKSPAPARAPPGGAPRPPKKSRADAPRPAAAPPAGAAPPAPPTPPPRPPRPAALTRRPA

EGPDPQGGWRRQPPGPSHTPAPSAAALEAYCAPRAVAELTDHPLFPAPWRPALMFDPRALASLAARCAAPPPGGAPA

AFGPLRASGPLRRAAAWMRQVPDPEDVRVVILYSPLPGEDLAAGRAGGGPPPEWSAERGGLSCLLAALGNRLCGPAT

AAWAGNWTGAPDVSALGAQGVLLLSTRDLAFAGAVEFLGLLAGACDRRLIVVNAVRAADWPADGPVVSRQHAYLACE

VLPAVQCAVRWPAARDLRRTVLASGRVFGPGVFARVEAAHARLYPDAPPLRLCRGANVRYRVRTRFGPDTLVPMSPR

EYRRAVLPALDGRAAASGAGDAMAPGAPDFCEDEAHSHRACARWGLGAPLRPVYVALGRDAVRGGPAELRGPRREFC

ARALLEPDGDAPPLVLRDDADAGPPPQIRWASAAGRAGTVLAAAGGGVEVVGTAAGLATPPRREPVDMDAELEDDDD

GLFGE

SEQ ID NO: 14 = ICP4 internal fragment encoded by construct RS1.6 (#210-1318)
HHHHHHHRRRRAPRRRSAASDSSKSGSSSSASSASSSASSSSASASSSDDDDDDAARAPASAADHAAGGTLGADD

EEAGVPARAPGAAPRPSPPRAEPAPARTPAATAGRLERRRARAAVAGRDATGRFTAGRPRRVELDADAASGAFYARY

RDGYVSGEPWPGAGPPPPGRVLYGGLGDSRPGLWGAPEAEEARARFEASGAPAPVWAPELGDAAQQYALITRLLYTP

DAEAMGWLQNPRVAPGDVALDQACFRISGAARNSSSFISGSVARAVPHLGYAMAAGRFGWGLAHVAAAVAMSRRYDR

AQKGFLLTSLRRAYAPLLARENAALTGARTPDDGGDANRHDGDDARGKPAAAAAPLPSAAASPADERAVPAGYGAAG

VLAALGRLSAAPASAPAGADDDDDDGAGGGGGGRRAEAGRVAVECLAACRGILEALAEGFDGDLAAVPGLAGARPA

APPRPGPAGAAAPPHADAPRLRAWLRELRFVRDALVLMRLRGDLRVAGGSEAAVAAVRAVSLVAGALGPALPRSPRL

LSSAAAAAADLLFQNQSLRPLLADTVAAADSLAAPASAPREARKRKSPAPARAPPGGAPRPPKKSRADAPRPAAAPP

AGAAPPAPPTPPPRPPRPAALTRRPAEGPDPQGGWRRQPPGPSHTPAPSAAALEAYCAPRAVAELTDHPLFPAPWRP

ALMFDPRALASLAARCAAPPPGGAPAAFGPLRASGPLRRAAAWMRQVPDPEDVRVVILYSPLPGEDLAAGRAGGGPP

PEWSAERGGLSCLLAALGNRLCGPATAAWAGNWTGAPDVSALGAQGVLLLSTRDLAFAGAVEFLGLLAGACDRRLIV

VNAVRAADWPADGPVVSRQHAYLACEVLPAVQCAVRWPAARDLRRTVLASGRVFGPGVFARVEAAHARLYPDAPPLR

LCRGANVRYRVRTRFGPDTLVPMSPREYRRAVLPALDGRAAASGAGDAMAPGAPDFCEDEAHSHRACARWGLGAPLR

PVYYVALGRDAVRGGPAELRGPRREFCARALLEPDGDAPPLVLRDDADAGPPPQIRWASAAGRAGTVLAAAGGGVEVV

GTAAGLATPPRREPVDMDAELEDDDDGLFGE

SEQ ID NO: 15 = ICP4 internal fragment encoded by construct RS1.7
(deletion of #391-544)
MSAEQRKKKKTTTTTQGRGAEVAMADEDGGRLRAAAETTGGPGSPDPADGPPPTPNPDRRPAARPGFGWHGGPEENE

DEADDAAADADADEAAPASGEAVDEPAADGVVSPRQLALLASMVDEAVRTIPSPPPERDGAQEEAARSPSPPRTPSM

RADYGEENDDDDDDDDDDDRDAGRWVRGPETTSAVRGAYPDPMASLSPRPPAPRRHHHHHHRRRRAPRRRSAASDS

SKSGSSSSASSASSSASSSSSASASSSDDDDDDDAARAPASAADHAAGGTLGADDEEAGVPARAPGAAPRPSPPRAE

PAPARTPAATAGRLERRRARAAVAGRDATGRFTAGRPRRVELDADAASGAFYARYRDGYVSGEPWPGAGPPPPGRVL

YGGLGARTPDDGGDANRHDGDDARGKPAAAAAPLPSAAASPADERAVPAGYGAAGVLAALGRLSAAPASAPAGADDD

DDDDGAGGGGGGRRAEAGRVAVECLAACRGILEALAEGFDGDLAAVPGLAGARPAAPPRPGPAGAAAPPHADAPRLR

AWLRELRFVRDALVLMRLRGDLRVAGGSEAAVAAVRAVSLVAGALGPALPRSPRLLSSAAAAAADLLFQNQSLRPLL

ADTVAAADSLAAPASAPREARKRKSPAPARAPPGGAPRPPKKSRADAPRPAAAPPAGAAPPAPPTPPPRPPRPAALT

RRPAEGPDPQGGWRRQPPGPSHTPAPSAAALEAYCAPRAVAELTDHPLFPAPWRPALMFDPRALASLAARCAAPPPG

GAPAAFGPLRASGPLRRAAAWMRQVPDPEDVRVVILYSPLPGEDLAAGRAGGGPPPEWSAERGGLSCLLAALGNRLC

GPATAAWAGNWTGAPDVSALGAQGVLLLSTRDLAFAGAVEFLGLLAGACDRRLIVVNAVRAADWPADGPVVSRQHAY

LACEVLPAVQCAVRWPAARDLRRTVLASGRVFGPGVFARVEAAHARLYPDAPPLRLCRGANVRYRVRTRFGPDTLVP

MSPREYRRAVLPALDGRAAASGAGDAMAPGAPDFCEDEAHSHRACARWGLGAPLRPVYYVALGRDAVRGGPAELRGPR

REFCARALLEPDGDAPPLVLRDDADAGPPPQIRWASAAGRAGTVLAAAGGGVEVVGTAAGLATPPRREPVDMDAELE

DDDDGLFGE

SEQ ID NO: 16 = ICP4 internal fragment encoded by construct RS1.8 (deletion
of #786-868)
MSAEQRKKKKTTTTTQGRGAEVAMADEDGGRLRAAAETTGGPGSPDPADGPPPTPNPDRRPAARPGFGWHGGPEENE

DEADDAAADADADEAAPASGEAVDEPAADGVVSPRQLALLASMVDEAVRTIPSPPPERDGAQEEAARSPSPPRTPSM

RADYGEENDDDDDDDDDDDRDAGRWVRGPETTSAVRGAYPDPMASLSPRPPAPRRHHHHHHRRRRAPRRRSAASDS

SKSGSSSSASSASSSASSSSSASASSSDDDDDDDAARAPASAADHAAGGTLGADDEEAGVPARAPGAAPRPSPPRAE

PAPARTPAATAGRLERRRARAAVAGRDATGRFTAGRPRRVELDADAASGAFYARYRDGYVSGEPWPGAGPPPPGRVL

YGGLGDSRPGLWGAPEAEEARARFEASGAPAPVWAPELGDAAQQYALITRLLYTPDAEAMGWLQNPRVAPGDVALDQ

ACFRISGAARNSSSFISGSVARAVPHLGYAMAAGRFGWGLAHVAAAVAMSRRYDRAQKGFLLTSLRRAYAPLLAREN

AALTGARTPDDGGDANRHDGDDARGKPAAAAAPLPSAAASPADERAVPAGYGAAGVLAALGRLSAAPASAPAGADDD

DDDDGAGGGGGGRRAEAGRVAVECLAACRGILEALAEGFDGDLAAVPGLAGARPAAPPRPGPAGAAAPPHADAPRLR

AWLRELRFVRDALVLMRLRGDLRVAGGSEAAVAAVRAVSLVAGALGPALPRSPRLLSSAAAAAADLLFQNQSLRPLL

ADTVAAADSLAAPASTPAPSAAALEAYCAPRAVAELTDHPLFPAPWRPALMFDPRALASLAARCAAPPPGGAPAAFG

PLRASGPLRRAAAWMRQVPDPEDVRVVILYSPLPGEDLAAGRAGGGPPPEWSAERGGLSCLLAALGNRLCGPATAAW

AGNWTGAPDVSALGAQGVLLLSTRDLAFAGAVEFLGLLAGACDRRLIVVNAVRAADWPADGPVVSRQHAYLACEVLP

AVQCAVRWPAARDLRRTVLASGRVFGPGVFARVEAAHARLYPDAPPLRLCRGANVRYRVRTRFGPDTLVPMSPREYR

RAVLPALDGRAAASGAGDAMAPGAPDFCEDEAHSHRACARWGLGAPLRPVYVALGRDAVRGGPAELRGPRREFCARA

LLEPDGDAPPLVLRDDADAGPPPQIRWASAAGRAGTVLAAAGGGVEVVGTAAGLATPPRREPVDMDAELEDDDDGLF

GE

SEQ ID NO: 17 = predicted sequence for uracil DNA glycosylase encoded by UL2
MESASTTPEQPLGLSGDATPPLPTSVPLDWAAFRRAFLIDDAWRPLLEPELANPLTARLLAEYDRRCQTEEVLPPRE

DVFSWTRYCTPDDVRVVIIGQDPYHHPGQAHGLAFSVRADVPVPPSLRNVLAAVKNCYPDARMSGRGCLEKWARDGV

LLLNTTLTVKRGAAASHSKLGWDRFVGGVVQRLAARRPGLVFMLWGAHAQNAIRPDPRQHYVLKFSHPSPLSKVPFG

TCQHFLAANRYLETRDIMPIDWSV

SEQ ID NO: 18 = predicted sequence for tegument protein encoded by UL11
MGLAFSGARPCCCRHNVITTDGGEVVSLTAHEFDVVDIESEEEGNFYVPPDVRVVTRAPGPQYRRASDPPSRHTRRR

DPDVARPPATLTPPLSDSE

SEQ ID NO: 19 = gL2 secreted v.1 encoded by construct UL1s v.1
NRWGFVCLFGLVVMGAWGAWGGSQATEYVLRSVIAKEVGDILRVPCMRTPADDVSWRYEAPSVIDYARIDGIFLRYH

CPGLDTFLWDRHAQRAYLVNPFLFAAGFLEDLSHSVFPADTQETTTRRALYKEIRDALGSRKQAVSHAPVRAGCVNF

DYSRTRRCVGRRDLRPANTTSTWEPPVSSDDEASSQSKPLATQPPVLALSNAPPRRVSPTRGRRRHTRLRRN

SEQ ID NO: 20 = predicted sequence for VP5 encoded by construct UL19a
DYDIPTTENLYFQGMAAPARDPPGYRYAAAMVPTGSILSTIEVASHRRLFDFFARVRSDENSLYDVEFDALLGSYCN

TLSLVRFLELGLSVACVCTKFPELAYMNEGRVQFEVHQPLIARDGPHPVEQPVHNYMTKVIDRRALNAAFSLATEAT

ALLTGEALDGTGISLHRQLRAIQQLARNVQAVLGAFERGTADQMLHVLLEKAPPLALLLPMQRYLDNGRLATRVARA

TLVAELKRSFCDTSFELGKAGHRREAIEAWLVDLTTATQPSVAVPRLTHADTRGRPVDGVLVTTAAIKQRLLQSFLK

VEDTEADVPVTYGEMVLNGANLVTALVMGKAVRSLDDVGRHLLEMQEEQLEANRETLDELESAPQTTRVRADLVAIG

DRLVFLEALEKRIYAATNVPYPLVGAMDLTFVLPLGLFNPAMERFAAHAGDLVPAPGHPEPRAFPPRQLFFWGKDHQ

VLRLSMENAVGTVCHPSLMNIDAAVGGVNHDPVEAANPYGAYVAAPAGPGADMQQRFLNAWRQRLAHGRVRWVAECQ

MTAEQFMQPDNANLALELHPAFDFFAGVADVELPGGEVPPAGPGAIQATWRVVNGNLPLALCPVAFRDARGLELGVG

RHAMAPATIAAVRGAFEDRSYPAVFYLLQAAIHGSEHVFCALARLVTQCITSYWNNTRCAAFVNDYSLVSYIVTYLG

GDLPEECMAVYRDLVAHVEALAQLVDDFTLPGPELGGQAQAELNHLMRDPALLPPLVWDCDGLMRHAALDRHRDCRI

DAGEHEPVYAAACNVATADFNRNDGRLLHNTQARAADAADDRPHRPADWTVHHKIYYYVLVPAFSRGRCCTAGVRFD

RVYATLQNMVVPEIAPGEECPSDPVTDPAHPLHPANLVANTVNAMFHNGRVVVDGPAMLTLQVLAHNMAERTTALLC

SAAPDAGANTASTANMRIFDGALHAGVLLMAPQHLDHTIQNGEYFYVLPVHALFAGADHVANAPNFPPALRDLARHV

PLVPPALGANYFSSIRQPVVQHARESAAGENALTYALMAGYFKMSPVALYHQLKTGLHPGEGFTVVRQDREVTENVL

FSERASEAYFLGQLQVARHETGGGVSFTLTQPRGNVDLGVGYTAVAATATVRNPVTDMGNLPQNFYLGRGAPPLLDN

AAAVYLRNAVVAGNRLGPAQPLPVFGCAQVPRRAGMDHGQDAVCEFIATPVATDINYFRRPCNPRGRAAGGVYAGDK

EGDVIALMYDHGQSDPARPFAATANPWASQRFSYGDLLYNGAYHLNGASPVLSPCFKFFTAADITAKHRCLERLIVE

TGSAVSTATAASDVQFKRPPGCRELVEDPCGLFQEAYPITCASDPALLRSARDGEAHARETHFTQYLIYDASPLKGL

SL

SEQ ID NO: 21 = VP5 encoded by construct UL19ΔTEV
MAAPARDPPGYRYAAAMVPTGSILSTIEVASHRRLFDFFARVRSDENSLYDVEFDALLGSYCNTLSLVRFLELGLSV

ACVCTKFPELAYMNEGRVQFEVHQPLIARDGPHPVEQPVHNYMTKVIDRRALNAAFSLATEAIALLTGEALDGTGIS

LHRQLRAIQQLARNVQAVLGAFERGTADQMLHVLLEKAPPLALLLPMQRYLDNGRLATRVARATLVAELKRSFCDTS

FELGKAGHRREAIEAWLVDLTTATQPSVAVPRLTHADTRGRPVDGVLVTTAAIKQRLLQSFLKVEDTEADVPVTYGE

MVLNGANLVTALVMGKAVRSLDDVGRHLLEMQEEQLEANRETLDELESAPQTTRVRADLVAIGDRLVFLEALEKRIY

-continued

```
AATNVPYPLVGAMDLTFVLPLGLFNPAMERFAAHAGDLVPAPGHPEPRAFPPRQLFFWGKDHQVLRLSMENAVGTVC

HPSLMNIDAAVGGVNHDPVEAANPYGAYVAAPAGPGADMQQRFLNAWRQRLAHGRVRWVAECQMTAEQFMQPDNANL

ALELHPAFDFFAGVADVELPGGEVPPAGPGAIQATWRVVNGNLPLALCPVAFRDARGLELGVGRHAMAPATIAAVRG

AFEDRSYPAVFYLLQAAIHGSEHVFCALARLVTQCITSYWNNTRCAAFVNDYSLVSYIVTYLGGDLPEECMAVYRDL

VAHVEALAQLVDDFTLPGPELGGQAQAELNHLMRDPALLPPLVWDCDGLMRHAALDRHRDCRIDAGEHEPVYAAACN

VATADFNRNDGRLLHNTQARAADAADDRPHRPADWTVHHKIYYYVLVPAFSRGRCCTAGVRFDRVYATLQNMVVPEI

APGEECPSDPVTDPAHPLHPANLVANTVNAMFHNGRVVVDGPAMLTLQVLAHNMAERTTALLCSAAPDAGANTASTA

NMRIFDGALHAGVLLMAPQHLDHTIQNGEYFYVLPVHALFAGADHVANAPNFPPALRDLARHVPLVPPALGANYFSS

IRQPVVQHARESAAGENALTYALMAGYFKMSPVALYHQLKTGLHPGFGFTVVRQDRFVTENVLFSERASEAYFLGQL

QVARHETGGGVSFTLTQPRGNVDLGVGYTAVAATATVRNPVTDMGNLPQNFYLGRGAPPLLDNAAAVYLRNAVVAGN

RLGPAQPLPVFGCAQVPRRAGMDHGQDAVCEFIATPVATDINYFRRPCNPRGRAAGGVYAGDKEGDVIALMYDHGQS

DPARPFAATANPWASQRFSYGDLLYNGAYHLNGASPVLSPCFKFFTAADITAKHRCLERLIVETGSAVSTATAASDV

QFKRPPGCRELVEDPCGLFQEAYPITCASDPALLRSARDGEAHARETHFTQYLIYDASPLKGLSL

SEQ ID NO: 22 = predicted sequence for ICP1/2 encoded by UL36
MIPAALPHPTMKRQGDRDIVVTGVRNQFATDLEPGGSVSCMRSSLSFLSLLFDVGPRDVLSAEAIEGCLVEGGEWTR

AAAGSGPPRMCSIIELPNFLEYPAARGGLRCVFSRVYGEVGFFGEPTAGLLETQCPAHTFFAGPWAMRPLSYTLLTI

GPLGMGLYRDGDTAYLFDPHGLPAGTPAFIAKVRAGDVYPYLTYYAHDRPKVRWAGAMVFFVPSGPGAVAPADLTAA

ALHLYGASETYLQDEPFVERRVAITHPLRGEIGGLGALFVGVVPRGDGEGSPVVPALPAPTHVQTPGADRPPEAPR

GASGPPDTPQAGHPNRPPDDVWAAALEGTPPAKPSAPDAAASGPPHAAPPPQTPAGDAAEEAEDLRVLEVGAVPVGR

HRARYSTGLPKRRRPTWTPPSSVEDLTSGERPAPKAPPAKAKKKSAPKKKAPVAAEVPASSPTPIAATVPPAPDTPP

QSGQGGGDDGPASPSSPSVLETLGARRPPEPPGADLAQLFEVHPNVAATAVRLAARDAALAREVAACSQLTINALRS

PYPAHPGLLELCVIFFFERVLAFLIENGARTHTQAGVAGPAAALLDFTLRMLPRKTAVGDFLASTRMSLADVAAHRP

LIQHVLDENSQIGRLALAKLVLVARDVIRETDAFYGDLADLDLQLRAAPPANLYARLGEWLLERSRAHPNTLFAPAT

PTHPEPLLHRIQALAQFARGEEMRVEAEAREMREALDALARGVDSVSQRAGPLTVMPVPAAPGAGGRAPCPPALGPE

AIQARLEDVRIQARRAIESAVKEYFHRGAVYSAKALQASDSHDCRFHVASAAVVPMVQLLESLPAFDQHTRDVAQRA

ALPPPPPLATSPQAILLRDLLQRGQPLDAPEDLAAWLSVLTDAATQGLIERKPLEELARSIHGINDQQARRSSGLAE

LQRFDALDAALAQQLDSDAAFVPATGPAPYVDGGGLSPEATRMAEDALRQARAMEAAKMTAELAPEARSRLRERAHA

LEAMLNDARERAKVAHDAREKFLHKLQGVLRPLPDFVGLKACPAVLATLRASLPAGWTDLADAVRGPPPEVTAALRA

DLWGLLGQYREALEHPTPDTATALAGLHPAFVVVLKTLFADAPETPVLVQFESDHAPTIAKAVSNAINAGSAAVATA

SPAATVDAAVRAHGALADAVSALGAAARDPASPLSFLAVLADSAAGYVKATRLALEARGAIDELTTLGSAAADLVVQ

ARRACAQPEGDHAALIDAAARATTAARESLAGHEAGFGGLLHAEGTAGDHSPSGRALQELGKVIGATRRRADELEAA

VADLTAKMAAQRARGSSERWAAGVEAALDRVENRAEFDVVELRRLQALAGTHGYNPRDFRKRAEQALAANAEAVTLA

LDTAFAFNPYTPENQRHPMLPPLAAIHRLGWSAAFHAAAETYADMFRVDAEPLARLLRIAEGLLEMAQAGDGFIDYH

EAVGRLADDMTSVPGLRRYVPFFQHGYADYVELRDRLDAIRADVHRALGGVPLDLAAAAEQISAARNDPEATAELVR

TGVTLPCPSEDALVACAAALERVDQSPVKNTAYAEYVAFVTRQDTAETKDAVVRAKQQRAEATERVMAGLREALAAR

ERRAQIEAEGLANLKTMLKVVAVPATVAKTLDQARSVAEIADQVEVLLDQTEKTRELDVPAVIWLEHAQRTFETHPL

SAARGDGPGPLARHAGRLGALFDTRRRVDALRRSLEEAEAEWDEVWGRFGRVRGGAWKSPEGFRAMHEQLRALQDTT

NTVSGLRAQPAYERLSARYQGVLGAKGAERAEAVEELGARVTKHTALCARLRDEVVRRVPWEMNFDALGGLLAEFDA

AAADLAPWAVEEFRGARELIQYRMGLYSAYARAGGQTGAGAESAPAPLLVDLRALDARARASSSPEGHEVDPQLLRR

RGEAYLRAGGDPGPLVLREAVSALDLPFATSFLAPDGTPLQYALCFPAVTDKLGALLMRPEAACVRPPLPTDVLESA

PTVTAMYVLTVVNRLQLALSDAQAANFQLFGRFVRHRQATWGASMDAAAELYVALVATTLTREFGCRWAQLGWASGA
```

-continued

AAPRPPPGPRGSQRHCVAFNENDVLVALVAGVPEHIYNFWRLDLVRQHEYMHLTLERAFEDAAESMLFVQRLTPHPD

ARIRVLPTFLDGGPPTRGLLFGTRLADWRRGKLSETDPLAPWRSALELGTQRRDVPALGKLSPAQALAAVSVLGRMC

LPSAALAALWTCMFPDDYTEYDSFDALLAARLESGQTLGPAGGREASLPEAPHALYRPTGQHVAVLAAATHRTPAAR

VTAMDLVLAAVLLGAPVVVALRNTTAFSRESELELCLTLFDSRPGGPDAALRDVVSSDIETWAVGLLHTDLNPIENA

CLAAQLPRLSALIAERPLADGPPCLVLVDISMTPVAVLWEAPEPPGPPDVRFVGSEATEELPFVATAGDVLAASAAD

ADPFFARAILGRPFDASLLTGELFPGHPVYQRPLADEAGPSAPTAARDPRDLAGGDGGSGPEDPAAPPARQADPGVL

APTLLTDATTGEPVPPRMWAWIHGLEELASDDAGGPTPNPAPALLPPPATDQSVPTSQYAPRPIGPAATARETRPSV

PPQQNTGRVPVAPRDDPRPSPPTPSPPADAALPPPAFSGSAAAFSAAVPRVRRSRRTRAKSRAPRASAPPEGWRPPA

LPAPVAPVAASARPPDQPPTPESAPPAWVSALPLPPGPASARGAFPAPTLAPIPPPPAEGAVVPGGDRRRGRRQTTA

GPSPTPPRGPAAGPPRRLTRPAVASLSASLNSLPSPRDPADHAAAVSAAAAAVPPSPGLAPPTSAVQTSPPPLAPGP

VAPSEPLCGWVVPGGPVARRPPPQSPATKPAARTRIRARSVPQPPLPQPPLPQPPLPQPPLPQPPLPQPPLPQPPLP

QPPLPQPPLPQPPLPQPPLPPVTRTLTPQSRDSVPTPESPTHTNTHLPVSAVTSWASSLALHVDSAPPPASLLQTLH

ISSDDEHSDADSLRFSDSDDTEALDPLPPEPHLPPADEPPGPLAADHLQSPHSQFGPLPVQANAVLSRRYVRSTGRS

ALAVLIRACRRIQQQLQRTRRALFQRSNAVLTSLHHVRMLLG

SEQ ID NO: 23 = ICP1/2 internal fragment encoded by construct UL36.3.4.1
AAQRARGSSERWAAGVEAALDRVENRAEFDVVELRRLQALAGTHGYNPRDFRKRAEQALAANAEAVTLALDTAFAFN

PYTPENQRHPMLPPLAAIHRLGWSAAFHAAAETYADMFRVDAEPLARLLRIAEGLLEMAQAGDGFIDYHEAVGRLAD

DMTSVPGLRRYVPFFQHGYADYVELRDRLDAIRADVHRALGGVPLDLAAAAEQISAARNDPEATAELVRTGVTLPCP

SEDALVACAAALERVDQSPVKNTAYAEYVAFVTRQDTAETKDAVVRAKQQRAEATERVMAGLREALAARERRAQIEA

EGLANLKTMLKVVAVPATVAKTLDQARSVAEIADQVEVLLDQTEKTRELDVPAVIWLEHAQRTFETHPLSAARGDGP

GPLARHAGRLGALFDTRRRVDALRRSLEEAEAEWDEVWGRFGRVRGGAWKSPEGFRAMHEQLRALQDTTNTVSGLRA

QPAYERLSARYQGVLGAKGAERAEAVEELGARVTKHTALCARLRDEVVRRVPWEMNFDALGGLLAEFDAAAADLAPW

AVEEFRGARELIQYRMGLYSAYARAGGQTGAGAESAPAPLLVDLRALDARARASSSPEGHEVDPQLLRRRGEAYLRA

GGDPGPLVLREAVSALDLPFATSFLAPDGTPLQYALCFPAVTDKLGALLMRPEAACVRPPLPTDVLESAPTVTAMYV

LTVVNRLQLALSDAQAANFQLFGRFVRHRQATWGASMDAAAELYVALVATTLTREFGCRWAQLGWASGAAAPRPPPG

PRGSQRHCVAFNENDVLVALVAGVPEHIYNFWRLDLVRQHEYMHLTLERAFEDAAESMLFVQRLTPHPDARTRVLPT

FLDGGPPTRGLLFGTRLADWRRGKLSETDPLAPWRSALELGTQRRDVPALGKLSPAQALAAVSVLGRMCLPSAALAA

LWTCMFPDDYTEYDSFDALLAARLESGQTLGPAGGREASL

SEQ ID NO: 24 = ICP1/2 internal fragment encoded by construct UL36.4.2.5
EYDSFDALLAARLESGQTLGPAGGREASLPEAPHALYRPTGQHVAVLAAATHRTPAARVTAMDLVLAAVLLGAPVVV

ALRNTTAFSRESELELCLTLFDSRPGGPDAALRDVVSSDIETWAVGLLHTDLNPIENACLAAQLPRLSALIAERPLA

DGPPCLVLVDISMTPVAVLWEAPEPPGPPDVRFVGSEATEELPFVATAGDVLAASAADADPFFARAILGRPFDASLL

TGELFPGHPVYQRPLADEAGPSAPTAARDPRDLAGGDGGSGPEDPAAPPARQADPGVLAPTLLTDATTGEPVPPRMW

AWIHGLEELASDDAGGPTPNPAPALLPPPATDQSVPTSQYAPRPIGPAATARETRPSVPPQQNTGRVPVAPRDDPRP

SPPTPSPPADAALPPPAFSGSAAAFSAAVPRVRRSRRTRAKSRAPRASAPPEGWRPPALPAPVAPVAASARPPDQPP

TPESAPPAWVSALPLPPGPASARGAFPAPTLAPIPPPPAEGAVVPGGDRRRGRRQTTAGPSPTPPRGPAAGPPRRLT

RPAVASLSASLNSLPSPRDPADHAAAVSAAAAAVPPSPGLAPPTSAVQTSPPPLAPGPVAPSEPLCGWVVPGGPVAR

RPPPQSPATKPAARTRIRARSVPQPPLPQPPLPQPPLPQPPLPQPPLPQPPLPQPPLPQPPLPQPPLPQPPLPQPPL

PPVTRTLTPQSRDSVPTPESPTHTNTHLPVSAVTSWASSLALHVDSAPPPASLLQTLHISSDDEHSDADSLRFSDSD

DTEALDPLPPEPHLPPADEPPGPLAADHLQSPHSQFGPLPVQANAVLSRRYVRSTGRSALAVLIRACRRIQQQLQRT

RRALFQRSNAVLTSLHHVRMLLG

-continued

SEQ ID NO: 25 = predicted sequence for reductase encoded by UL40
MDPAVSPASTDPLDTHASGAGAAPIPVCPTPERYFYTSQCPDINHLRSLSILNRWLETELVFVGDEEDVSKLSEGEL

GFYRFLFAFLSAADDLVTENLGGLSGLFEQKDILHYYVEQECIEVVHSRVYNIIQLVLFHNNDQARRAYVARTINHP

AIRVKVDWLEARVRECDSIPEKFILMILIEGVFFAASFAAIAYLRTNNLLRVTCQSNDLISRDEAVHTTASCYIYNN

YLGGHAKPEAARVYRLFREAVDIEIGFIRSQAPTDSSILSPGALAAIENYVRFSADRLLGLIHMQPLYSAPAPDASF

PLSLMSTDKHTNFFECRSTSYAGAVVNDL

SEQ ID NO: 26 = ICP47 encoded by US12
MSWALKTTDMFLDSSRCTHRTYGDVCAEIHKREREDREAARTAVTDPELPLLCPPDVRSDPASRNPTQQTRGCARSN

ERQDRVLAP

SEQ ID NO: 27 = gM2 encoded by UL10
MGRRAPRGSPEAAPGADVAPGARAAWWVWCVQVATFIVSAICVVGLLVLASVERDRFPCLYAPATSYAKANATVEVR

GGVAVPLRLDTQSLLATYAITSTLLLAAAVYAAVGAVTSRYERALDAARRLAAARMAMPHATLIAGNVCAWLLQITV

LLLAHRISQLAHLIYVLHFACLVYLAAHFCTRGVLSGTYLRQVHGLIDPAPTHHRIVGPVRAVMTNALLLGTLLCTA

AAAVSLNTIAALNENFSAPSMLICLTTLFALLVVSLLLVVEGVLCHYVRVLVGPHLGAIAATGIVGLACEHYHTGGY

YVVEQQWPGAQTGVRVALALVAAFALAMAVLRCTRAYLYHRRHHTKFFVRMRDTRHRAHSALRRVRSSMRGSRRGGP

PGDPGYAETPYASVSHHAEIDRYGDSDGDPIYDEVAPDHEAELYARVQRPGPVPDAEPIYDTVEGYAPRSAGEPVYS

TVRRW

SEQ ID NO: 28 = predicted sequence for cleavage/packaging protein encoded
by UL15
MFGQQLASDVQQYLERLEKQRQQKVGVDEASAGLTLGGDALRVPFLDFATATPKRHQTVVPGVGTLHDCCEHSPLFS

AVARRLLFNSLVPAQLRGRDFGGDHTAKLEFLAPELVRAVARLRFRECAPEDAVPQRNAYYSVLNTFQALHRSEAFR

QLVHFVRDFAQLLKTSERASSLAETTGPPKKRAKVDVATHGQTYGTLELFQKMILMHATYFLAAVLLGDHAEQVNTF

LRLVFEIPLFSDTAVRHFRQRATVELVPRRHGKTWFLVPLIALSLASFRGIKIGYTAHIRKATEPVFDEIDACLRGW

FGSSRVDHVKGETISFSFPDGSRSTIVFASSHNTNGIRGQDFNLLFVDEANFIRPDAVQTIMGFLNQANCKIIFVSS

TNTGKASTSFLYNLRGAADELLNVVTYICDDHMPRVVTHTNATACSCYILNKPVFITMDGAVRRTADLFLPDSFMQE

IIGGQARETGDDRPVLTKSAGERFLLYRPSTTTNSGLMAPELYVYVDPAFTANTRASGTGIAVVGRYRDDFIIFALE

HFFLRALTGSAPADIARCVVHSLAQVLALHPGAFRSVRVAVEGNSSQDSAVAIATHVHTEMHRILASAGANGPGPEL

LFYHCEPPGGAVLYPFFLLNKQKTPAFEYFIKKFNSGGVMASQELVSVTVRLQTDPVEYLSEQLNNLIETVSPNTDV

RMYSGKRNGAADDLMVAVIMAIYLAAPTGIPPAFFPITRTS

SEQ ID NO: 29 = predicted sequence for ICP35 encoded by UL26.5
MNPVSASGAPAPPPPGDGSYLWIPASHYNQLVTGQSAPRHPPLTACGLPAAGTVAYGHPGAGPSPHYPPPPAHPYPG

MLFAGPSPLEAQIAALVGAIAADRQAGGLPAAAGDHGIRGSAKRRRHEVEQPEYDCGRDEPDRDFPYYPGEARPEPR

PVDSRRAARQASGPHETITALVGAVTSLQQELAHMRARTHAPYGPYPPVGPYHHPHADTETPAQPPRYPAKAVYLPP

PHIAPPGPPLSGAVPPPSYPPVAVTPGPAPPLHQPSPAHAHPPPPPGPTPPPAASLPQPEAPGAEAGALVNASSAA

HVNVDTARAADLFVSQMMGSR

SEQ ID NO: 30 = predicted sequence for polymerase encoded by UL30
MFCAAGGPASPGGKPAARAASGFEAPHNPRGATQTAPPPCRRQNFYNPHLAQTGTQPKALGPAQRHTYYSECDEFRF

IAPRSLDEDAPAEQRTGVHDGRLRRAPKVYCGGDERDVLRVGPEGFWPRRLRLWGGADHAPEGFDPTVTVFHVYDIL

EHVEHAYSMRAAQLHERFMDAITPAGTVITLLGLTPEGHRVAVHVYGTRQYFYMNKAEVDRHLQCRAPRDLCERLAA

ALRESPGASFRGISADHFEAEVVERADVYYYETRPTLYYRVFVRSGRALAYLCDNFCPAIRKYEGGVDATTRFTLDN

PGFVTFGWYRLKPGRGNAPAQPRPPTAFGTSSDVEFNCTADNLAVEGAMCDLPAYKLMCFDIECKAGGEDELAFPVA

ERPEDLVIQISCLLYDLSTTALEHILLFSLGSCDLPESHLSDLASRGLPAPVVLEFDSEFEMLLAFMTFVKQYGPEF

VTGYNIINFDWPFVLTKLTEIYKVPLDGYGRMNGRGVERVWDIGQSHFQKRSKIKVNGMVNIDMYGIITDKVKLSSY

KLNAVAEAVLKDKKKDLSYRDIPAYYASGPAQRGVIGEYCVQDSLLVGQLFFKFLPHLELSAVARLAGINITRTIYD

```
GQQIRVFTCLLRLAGQKGFILPDTQGRFRGLDKEAPKRPAVPRGEGERPGDGNGDEDKDDDEDGDEDGDEREEVARE

TGGRHVGYQGARVLDPTSGEHVDPVVVEDFASLYPSIIQAHNLCFSTLSLRPEAVAHLEADRDYLEIEVGGRRLFFV

KAHVRESLLSILLRDWLAMRKQIRSRIPQSTPEEAVLLDKQQAAIKVVCNSVYGFTGVQHGLLPCLHVAATVTTIGR

EMLLATRAYVHARWAEFDQLLADFPEAAGMRAPGPYSMRIIYGDTDSIFVLCRGLTAAGLVAMGDKMASHISRALFL

PPIKLECEKTFTKLLLIAKKKYIGVICGGKMLIKGVDLVRKNNCAFINRTSRALVDLLFYDDTVSGAAAALAERPAE

EWLARPLPEGLQAFGAVLVDAHRRITDPERDIQDFVLTAELSRHPRAYTNKRLAHLTVYYKLMARRAQVPSIKDRIP

YVIVAQTREVEETVARLAALRELDAAAPGDEPAPPAALPSPAKRPRETPSHADPPGGASKPRKLLVSELAEDPGYAI

ARGVPLNTDYYFSHLLGAACVTFKALFGNNAKITESLLKRFIPETWHPPDDVAARLRAAGFGPAGAGATAEETRRML

HRAFDTLA

SEQ ID NO: 31 = predicted sequence for helicase/primase complex encoded
by UL5
MAASGGEGSRDVRAPGPPPQQPGARPAVRERDEAFLNFTSMHGVQPIIARIRELSQQQLDVTQVPRLQWFRDVAALE

VPTGLPLREFPFAAYLITGNAGSGKSTCVQTLNEVLDCVVTGATRIAAQNMYVKLSGAELSRPINTIFHEFGFRGNH

VQAQLGQHPYTLASSPASLEDLQRRDLTYYWEVILDITKRALAAHGGEDARNEFHALTALEQTLGLGQGALTRLASV

THGALPAFTRSNIIVIDEAGLLGRHLLTTVVYCWWMINALYHTPQYAGRLRPVLVCVGSPTQTASLESTFEHQKLRC

SVRQSENVLTYLICNRTLREYTRLSHSWATFINNKRCVEHEFGNLMKVLEYGLPITEEHMQFVDRFVVPESYITNPA

NLPGWTRLFSSHKEVSAYMAKLHAYLKVTREGEFVVFTLPVLTFVSVKEFDEYRRLTQQPTLTMEKWITANASRITN

YSQSQDQDAGHVRCEVHSKQQLVVARNDITYVLNSQVAVTARLRKMVEGEDGTFRTFEAVLRDDSFVKTQGETSVEF

AYRFLSRLMFGGLIHEYNFLQRPGLDATQRTLAYGRLGELTAELLSLRRDAAGASATRAADTSDRSPGERAFNFKHL

GPRDGGPDDFPDDDLDVIFAGLDEQQLDVFYCHYALEEPETTAAVHAQFGLLKRAFLGRYLILRELFGEVFESAPFS

TYVDNVIFRGCELLTGSPRGGLMSVALQTDNYTLMGYTYTRVFAFAEELRRRHATAGVAEFLEESPLPYIVLRDQHG

FMSVVNTNISEFVESIDSTELAMAINADYGISSKLAMTITRSQGLSLDKVAICFTPGNLRLNSAYVAMSRTTSSEFL

HMNLNPLRERHERDDVISEHILSALRDPNVVIVY

SEQ ID NO: 32 = predicted sequence for helicase/primase complex encoded
by UL8
MEAPGIVWVEESVSAITLYAVWLPPRTRDCLHALLYLVCRDAAGEARARFAEVSVGSSDLQDFYGSPDVSAPGAVAA

ARAATAPAASPLEPLGDPTLWRALYACVLAALERQTGRWALFVPLRLGWDPQTGLVVRVERASWGPPAAPRAALLDV

EAKVDVDPLALSARVAEHPGARLAWARLAAIRDSPQCASSASLAVTITTRTARFAREYTTLAFPPTRKEGAFADLVE

VCEVGLRPRGHPQRVTARVLLPRGYDYFVSAGDGFSAPALVALFRQWHTTVHAAPGALAPVFAFLGPGFEVRGGPVQ

YFAVLGFPGWPTFTVPAAAAAESARDLVRGAAATHAACLGAWPAVGARVVLPPRAWPAVASEAAGRLLPAFREAVAR

WHPTATTIQLLDPPAAVGPVWTARFCFSGLQAQLLAALAGLGEAGLPEARGRAGLERLDALVAAAPSEPWARAVLER

LVPDACDACPALRQLLGGVMAAVCLQIEQTASSVKFAVCGGTGAAFWGLENVDPGDADAAHGAIQDARRALEASVRA

VLSANGIRPRLAPSLAPEGVYTHVVTWSQTGAWFWNSRDDTDFLQGFPLRGAAYAAAAEVMRDALRRILRRPAAGPP

EEAVCAARGVMEDACDRFVLDAFGRRLDAEYWSVLTPPGEADDPLPQTAFRGGALLDAEQYWRRVVRVCPGGGESVG

VPVDLYPRPLVLPPVDCAHHLREILREIQLVFTGVLEGVWGEGGSFVYPFDEKIRFLFP

SEQ ID NO: 33 = predicted sequence for unknown protein encoded by UL15.5
MDGAVRRTADLFLPDSFMQEIIGGQARETGDDRPVLTKSAGERFLLYRPSTTTNSGLMAPELYVYVDPAFTANTRAS

GTGIAVVGRYRDDFIIFALEHFFLRALTGSAPADIARCVVHSLAQVLALHPGAFRSVRVAVEGNSSQDSAVAIATHV

HTEMHRILASAGANGPGPELLFYHCEPPGGAVLYPFFLLNKQKTPAFEYFIKKFNSGGVMASQELVSVTVRLQTDPV

EYLSEQLNNLIETVSPNTDVRMYSGKRNGAADDLMVAVIMAIYLAAPTGIPPAFFPITRTS

SEQ ID NO: 34 = predicted sequence for packaging protein encoded by UL32
MATSAPGVPSSAAVREESPGSSWKEGAFERPYVAFDPDLLALNEALCAELLAACHVVGVPPASALDEDVESDVAPAP

PRPRGAAREASGGRGPGSARGPPADPTAEGLLDTGPFAAASVDTFALDRPCLVCRTIELYKQAYRLSPQWVADYAFL

CAKCLGAPHCAASIEVAAFEEVYVMDHHFLRTKKATLVGSFARFALTINDIHRHEFLHCCERTDGGVPGRHAQKQPR
```

-continued

PTPSPGAAKVQYSNYSFLAQSATRALIGTLASGGDDGAGAGAGGGSGTQPSLTTALMNWKDCARLLDCTEGKRGGGD

SCCTRAAARNGEFEAAAGALAQGGEPETWAYADLILLLLAGTPAVWESGPRLRAAADARRAAVSESWEAHRGARMRD

AAPRFAQFAEPQPQPDLDLGPLMATVLKHGRGRGRTGGECLLCNLLLVRAYWLAMRRLRASVVRYSENNTSLFDCIV

PVVDQLEADPEAQPGDGGRFVSLLRAAGPEATFKHMECDPMCAITEMEVDPWVLFGHPRADHRDELQLHKAKLACGN

EFEGRVCIALRALIYTFKTYQVFVPKPTALATFVREAGALLRRHSISLLSLEHTLCTYV

SEQ ID NO: 35 = predicted sequence for ICP1/2 fragment encoded by construct
UL36.4.2
MEYDSFDALLAARLESGQTLGPAGGREASLPEAPHALYRPTGQHVAVLAAATHRTPAARVTAMDLVLAAVLLGAPVV

VALRNTTAFSRESELELCLTLFDSRPGGPDAALRDVVSSDIETWAVGLLHTDLNPIENACLAAQLPRLSALIAERPL

ADGPPCLVLVDISMTPVAVLWEAPEPPGPPDVRFVGSEATEELPFVATAGDVLAASAADADPFFARAILGRPFDASL

LTGELFPGHPVYQRPLADEAGPSAPTAARDPRDLAGGDGGSGPEDPAAPPARQADPGVLAPTLLTDATTGEPVPPRM

WAWIHGLEELASDDAGGPT

SEQ ID NO: 36 = predicted sequence for ICP27 encoded by UL54
MATDIDMLIDLGLDLSDSELEEDALERDEEGRRDDPESDSSGECSSSDEDMEDPCGDGGAEAIDAAIPKGPPARPED

AGTPEASTPRPAARRGADDPPPATTGVWSRLGTRRSASPREPHGGKVARIQPPSTKAPHPRGGRRGRRRGRGRYGPG

GADSTPKPRRRVSRNAHNQGGRHPASARTDGPGATHGEARRGGEQLDVSGGPRPRGTRQAPPPLMALSLTPPHADGR

APVPERKAPSADTIDPAVRAVLRSISERAAVERISESFGRSALVMQDPFGGMPFPAANSPWAPVLATQAGGFDAETR

RVSWETLVAHGPSLYRTFAANPRAASTAKAMRDCVLRQENLIEALASADETLAWCKMCIHHNLPLRPQDPIIGTAAA

VLENLATRLRPFLQCYLKARGLCGLDDLCSRRRLSDIKDIASFVLVILARLANRVERGVSEIDYTTVGVGAGETMHF

YIPGACMAGLIEILDTHRQECSSRVCELTASHTIAPLYVHGKYFYCNSLF

SEQ ID NO: 37 = virion protein encoded by UL49.5
MTGKPARLGRWVVLLFVALVAGVPGEPPNAAGARGVIGDAQCRGDSAGVVSVPGVLVPFYLGMTSMGVCMIAHVYQI

CQRALAAGSA

SEQ ID NO: 38 = gG2 encoded by US4
NRWGSGVPGPINPPNSDVVFPGGSPVAQYCYAYPRLDDPGPLGSADAGRQDLPRRVVRHEPLGRSFLTGGLVLLAPP

VRGFGAPNATYAARVTYYRLTRACRQPILLRQYGGCRGGEPPSPKTCGSYTYTYQGGGPPTRYALVNASLLVPIWDR

AAETFEYQIELGGELHVGLLWVEVGGEGPGPTAPPQAARAEGGPCVPPVPAGRPWRSVPPVWYSAPNPGFRGLRFRE

RCLPPQTPAAPSDLPRVAFAPQSLLVGITGRTFIRMARPTEDVGVLPPHWAPGALDDGPYAPEPPRPRERR

SEQ ID NO: 39 = RS1
ATGTCGTACTACCATCACCATCACCATCACAGTGCCGAACAGCGTAAAAAGAAAAAACCACCACCACGACCCAAGG

ACGTGGAGCTGAAGTTGCTATGGCGGATGAGGATGGAGGCCGCTTGAGAGCTGCTGCTGAGACTACTGGAGGACCTG

GATCACCGGACCCTGCCGATGACCCCCCCCTACACCAAACCCCGATCGTAGACCGGCTGCTAGACCTGGATTCGGA

TGGCATGGAGGACCCGAGGAAAACGAGGACGAGGCGGACGACGCCGCTGCCGACGCCGACGCCGATGAGGCTGCCCC

TGCTTCTGGAGAGGCGGTAGACGAACCTGCTGCCGATGGAGTTGTTAGCCCTAGGCAATTGGCTTTGTTGGCGAGCA

TGGTAGACGAGGCTGTGAGAACAATCCCTTCCCCTCCCCCTGAACGTGATGGAGCACAAGAGGAGGCGGCTAGGAGT

CCCTCACCACCCCGTACACCTTCTATGAGAGCGGATTACGGCGAGGAAAACGACGACGACGACGATGATGATGACGA

CGATGATCGTGATGCCGGACGCTGGGTTAGGGGACCTGAAACCACTTCTGCTGTCCGTGGAGCATACCCCGATCCTA

TGGCGAGTTTGAGCCCTAGACCACCTGCCCCGAGGAGACACCACCACCACCACCATCATAGGCGTAGACGTGCTCCT

AGACGTCGTTCTGCCGCTAGTGACTCTTCCAAATCTGGCTCTTCTTCATCTGCCTCTTCCGCTTCATCTTCGGCCTC

ATCGTCCTCTTCGGCATCCGCTTCGAGTAGTGATGATGATGATGACGACGACGCTGCTAGAGCCCCCGCTTCTGCTG

CCGACCACGCTGCTGGCGGAACTTTGGGAGCCGACGACGAGGAGGCGGGAGTTCCTGCTCGTGCCCCGGGAGCTGCT

CCGAGGCCTTCTCCACCCCGTGCTGAACCTGCTCCGGCTAGAACACCGGCCGCTACTGCTGGTAGACTGGAGCGTAG

ACGTGCCCGTGCTGCTGTGGCTGGTAGAGATGCTACTGGCCGCTTCACTGCTGGCCGTCCTAGACGTGTTGAACTGG

ACGCCGATGCTGCTTCTGGTGCTTTCTACGCCCGTTACCGTGATGGTTACGTGTCTGGTGAACCTTGGCCTGGCGCT

-continued

```
GGTCCACCTCCGCCCGGACGTGTACTCTACGGTGGATTGGGCGATTCTCGCCCTGGTCTGTGGGCGCTCCGGAGGC
TGAGGAGGCTAGAGCCCGTTTCGAGGCTTCTGGTGCCCCTGCTCCTGTTTGGGCTCCTGAATTGGGCGACGCTGCTC
AACAATACGCCCTCATCACACGCTTGCTGTACACTCCCGACGCCGAGGCTATGGGATGGCTCCAAAACCCTAGAGTT
GCCCCTGGTGATGTTGCTCTGGATCAGGCTTGTTTCCGTATCTCCGCGCTGCTCGTAACTCTTCTTCGTTCATCTC
CGGTTCTGTGGCTAGAGCTGTGCCTCACTTGGGATACGCCATGGCCGCTGGACGTTTCGGCTGGGGACTGGCTCATG
TTGCTGCCGCTGTAGCAATGTCTAGACGCTACGACCGTGCTCAAAAAGGATTCTTGCTCACGTCACTGAGGCGTGCT
TACGCCCCTTTGTTGGCCCGTGAAAACGCTGCCCTCACTGGCGCCCGTACCCCCGATGACGGTGGCGACGCCAACCG
CCACGATGGTGATGATGCTAGAGGCAAACCCGCTGCCGCTGCTGCTCCTTTGCCCTCTGCCGCCGCTTCCCCTGCCG
ATGAACGTGCTGTTCCTGCCGGTTACGGTGCCGCTGGTGTGTTGGCTGCTTTGGGACGCTTGAGTGCTGCCCCGGCT
AGTGCCCCGCTGGTGCCGATGACGATGACGATGACGATGGTGCTGGCGGAGGCGGTGGCGGTAGACGTGCTGAGGC
TGGACGTGTTGCTGTTGAATGCCTGGCTGCCTGTAGAGGAATCTTGGAGGCTCTGGCCGAGGGATTCGACGGAGACT
TGGCGGCTGTACCGGGACTGGCGGGAGCGAGGCCTGCCGCTCCACCTCGCCCCGGTCCTGCTGGTGCTGCCGCTCCT
CCTCATGCCGACGCTCCTAGACTCCGTGCTTGGCTCCGTGAACTCCGTTTCGTTCGTGACGCTTTGGTTCTGATGAG
ACTGAGAGGCGACTTGAGAGTGGCTGGAGGATCCGAGGCTGCTGTTGCTGCTGTCCGTGCTGTTTCTTTGGTTGCTG
GTGCTTTGGGCCCTGCTTTGCCGAGATCTCCCCGTTTGTTGTCGAGTGCCGCCGCTGCTGCCGCCGATTTGTTGTTC
CAAAACCAATCCCTCCGCCCTCTGCTCGCCGACACTGTTGCCGCTGCCGATTCTCTGGCTGCTCCGGCTTCTGCCCC
ACGTGAAGCTCGTAAACGTAAATCACCCGCTCCGGCTCGTGCTCCCCCTGGTGGCGCCCCTAGACCCCCTAAAAAAT
CCCGTGCCGATGCCCCTAGACCTGCTGCTGCTCCCCCCGCTGGTGCTGCTCCCCCCGCTCCCCCTACTCCCCCCCCA
CGCCCACCTCGTCCCGCTGCCCTCACACGCCGTCCTGCTGAGGGACCCGATCCACAAGGCGGCTGGCGTAGACAACC
TCCTGGCCCATCCCATACACCGGCACCATCTGCCGCTGCTTTGGAGGCTTACTGTGCTCCTCGTGCTGTGGCTGAAC
TCACCGATCATCCGCTGTTCCCTGCTCCCTGGCGTCCCGCCCTCATGTTCGATCCTAGAGCTTTGGCTTCCTTGGCC
GCTCGTTGTGCTGCCCCTCCCCCTGGCGGTGCTCCGGCTGCTTTCGGTCCTCTCCGTGCCTCTGGTCCACTCCGCCG
TGCCGCTGCCTGGATGAGACAAGTTCCCGACCCTGAGGATGTTAGAGTTGTGATCTTGTACTCGCCCTTGCCTGGCG
AGGATTTGGCCGCTGGTAGAGCTGGCGGTGGCCCCCCTCCTGAATGGTCTGCTGAACGTGGTGGTTTGTCTTGCTTG
TTGGCCGCCCTGGGAAACCGTCTGTGTGGTCCTGCTACTGCTGCTTGGGCTGGAAACTGGACTGGCGCTCCCGATGT
TTCTGCTCTCGGTGCTCAAGGAGTTTTGCTGCTCTCTACTCGTGACTTGGCATTCGCTGGAGCTGTTGAATTCCTGG
GACTCTTGGCTGGCGCTTGTGATAGGAGACTCATCGTCGTAAACGCTGTGAGAGCTGCCGATTGGCCTGCCGATGGT
CCTGTTGTGTCTCGTCAACACGCTTACTTGGCTTGTGAAGTGTTGCCCGCTGTCCAATGTGCTGTTCGCTGGCCTGC
TGCTCGTGATCTGAGGCGTACTGTTCTGGCTAGTGGTCGTGTTTTCGGACCTGGTGTTTTCGCTCGTGTCGAAGCTG
CTCACGCTAGACTGTACCCCGATGCCCCACCCCTCCGTTTGTGTCGTGGAGCAAACGTTCGCTACCGTGTCCGTACT
CGTTTCGGACCCGATACTCTGGTTCCAATGTCCCCTCGTGAATACCGTCGTGCTGTTCTGCCTGCCCTCGATGGACG
TGCTGCCGCTTCTGGCGCTGGTGACGCTATGGCTCCTGGCGCTCCGGACTTCTGTGAGGATGAGGCTCACTCACATC
GTGCCTGTGCCCGCTGGGGACTGGGCGCTCCATTGAGGCCTGTATACGTGGCACTGGGCCGTGATGCTGTTAGAGGC
GGACCCGCTGAATTGAGAGGCCCTCGTCGTGAATTCTGTGCTAGGGCTCTGCTCGAACCCGATGGAGATGCTCCTCC
TTTGGTACTCCGTGACGACGCCGATGCTGGTCCTCCCCCACAAATTCGCTGGGCTAGTGCTGCTGGACGTGCTGGTA
CTGTATTGGCTGCTGCTGGCGGTGGCGTTGAAGTTGTTGGTACTGCCGCTGGACTCGCTACACCTCCCCGCCGTGAA
CCTGTAGACATGGATGCTGAACTCGAGGATGATGACGACGGATTGTTCGGAGAGTAATAG
```

SEQ ID NO: 40 = construct US6ΔTMR

```
ATGAAGTTCCTCGTGAACGTGGCCCTGGTGTTCATGGTGGTGTACATCAGCTACATCTACGCCAACCGTTGGAAGTA
CGCTCTGGCTGACCCATCCCTGAAGATGGCTGACCCCAACCGTTTCCGTGGCAAGAACCTGCCCGTGCTGGACCAGC
TGACCGACCCCCCTGGCGTGAAGCGTGTGTACCACATCCAGCCATCCCTCGAAGACCCCTTCCAGCCCCCCTCCATC
```

```
-continued
CCCATCACCGTGTACTACGCTGTGCTGGAACGCGCTTGCCGTTCCGTGCTGCTGCACGCTCCTTCCGAGGCTCCCCA

GATCGTGCGTGGTGCTTCCGACGAGGCTCGCAAGCACACCTACAACCTGACTATCGCTTGGTACAGGATGGGTGACA

ACTGCGCTATCCCTATCACCGTCATGGAATACACCGAGTGCCCCTACAACAAGTCCCTGGGCGTGTGCCCTATCCGT

ACCCAGCCCCGTTGGTCCTACTACGACTCCTTCAGCGCTGTGTCCGAGGACAACCTGGGTTTCCTGATGCACGCTCC

CGCTTTCGAGACTGCTGGCACCTACCTGCGTCTGGTCAAGATCAACGACTGGACCGAGATCACCCAGTTCATCCTGG

AACACCGTGCTCGTGCTTCGTGCAAGTACGCCCTGCCCCTGCGTATCCCTCCTGCTGCTTGCCTGACCTCCAAGGCT

TACCAGCAGGGCGTGACCGTGGACTCCATCGGCATGCTGCCCCGTTTCATCCCCGAGAACCAGCGTACCGTGGCTCT

GTACTCTCTGAAGATCGCTGGCTGGCACGGTCCTAAGCCCCCCTACACCTCCACTCTGCTGCCCCCTGAGCTGTCCG

ACACCACCAACGCTACTCAGCCCGAGTTGGTGCCTGAGGACCCCGAGGACTCCGCTCTGTTGGAGGACCCCGCTGGA

ACCGTGTCCTCCCAGATCCCCCCCAACTGGCACATCCCTTCCATCCAGGACGTGGCCCCTCACCACGCTCCAGCTGC

TCCCTCCAACCCCCGTCGTCGTGCTCAGATGGCTCCCAAGCGTCTGCGTCTGCCCCACATCCGTGACGACGACGCTC

CTCCATCCCACCAGCCCCTGTTCTACCACCACCACCATCACCACTAATAA

SEQ ID NO: 41 = RL1
ATGTCTCGTCGTCGTGGTCCTCGTCGTCGTGGTCCTCGTCGTCGTCCGCGTCCGGGTGCGCCGGCGGTACCACGCCC

GGGTGCGCCGGCAGTGCCGCGTCCAGGCGCACTGCCTACCGCGGACTCTCAAATGGTGCCGGCGTATGATTCTGGTA

CTGCCGTCGAATCTGCTCCGGCAGCGAGCTCCCTGCTGCGTCGTTGGCTGCTGGTCCCTCAGGCGGACGATTCCGAT

GACGCAGACTACGCGGGCAACGACGACGCGGAGTGGGCTAACAGCCCGCCAAGCGAGGGTGGTGGCAAAGCGCCGGA

GGCTCCGCACGCAGCGCCTGCCGCAGCGTGCCCGCCTCCGCCTCCTCGTAAAGAACGTGGCCCTCAACGTCCTCTGC

CGCCGCACCTGGCTCTGCGTCTGCGTACTACCACTGAGTACCTGGCGCGTCTGTCTCTGCGTCGTCGCCGTCCGCCG

GCTAGCCCGCCGGCCGATGCACCGCGTGGCAAAGTGTGCTTCTCTCCACGTGTTCAAGTTCGTCACCTGGTGGCTTG

GGAAACGGCTGCCCGTCTGGCTCGCCGTGGCAGCTGGGCACGTGAGCGCGCAGACCGTGACCGCTTCCGTCGCCGTG

TGGCGGCTGCTGAAGCCGTTATCGGCCCGTGCCTGGAACCTGAGGCTCGCGCTCGCGCGTGCGCGCGCTCGTGCC

CACGAAGATGGCGGTCCAGCAGAGGAAGAAGAGGCAGCTGCAGCAGCGCGCGGTAGCTCCGCGGCTGCGGGTCCAGG

TCGTCGTGCCGTA

SEQ ID NO: 42 = RL2
ATGTCGTACTACCATCACCATCACCATCACATGGAGCCACGTCCTGGTACTTCTTCTCGCGCTGATCCTGGTCCTGA

ACGTCCGCCACGCCAGACTCCGGGCACCCAGCCGGCCGCCCCTCACGCTTGGGGCATGCTGAACGATATGCAGTGGC

TGGCGTCCTCTGATTCCGAAGAGGAGACTGAGGTTGGTATCAGCGATGATGATCTGCACCGCGACTCTACCAGCGAA

GCAGGTTCCACTGACACCGAAATGTTTGAAGCGGGCCTGATGGATGCCGCGACCCCGCCGGCTCGTCCGCCGGCTGA

ACGTCAGGGTAGCCCTACGCCTGCGGATGCGCAAGGCTCTTGTGGTGGTGGTCCAGTAGGCGAAGAGGAGGCTGAGG

CCGGTGGCGGCGGTGATGTGTGTGCGGTTTGTACCGATGAAATCGCACCGCCGCTGCGTTGTCAGTCTTTCCCGTGC

CTGCACCCGTTTTGCATTCCGTGCATGAAAACCTGGATCCCGCTGCGCAACACTTGCCCGCTGTGCAACACTCCGGT

TGCTTATCTGATCGTTGGTGTAACCGCATCTGGTTCCTTTTCTACCATCCCGATTGTCAACGACCCACGTACGCGTG

TTGAGGCGGAGGCGGCTGTACGTGCGGGCACCGCGGTGGACTTTATCTGGACCGGTAACCCGCGCACCGCGCCACGC

TCCCTGTCTCTGGGTGGCCATACCGTTCGTGCTCTGAGCCCGACCCCACCTTGGCCAGGCACCGATGACGAAGACGA

CGATCTGGCTGACGTTGACTATGTTCCGCCGGCACCGCGTCGCGCACCACGCCGTGGTGGCGGTGGCGCCGGTGCGA

CGCGCGGTACCTCCCAGCCGGCAGCAACTCGCCCAGCACCGCCGGGTGCCCCGCGTTCTAGCAGCTCCGGTGGCGCA

CCGCTGCGTGCTGGCGTGGGTTCTGGTTCCGGTGGTGGTCCGGCCGTGGCGGCTGTCGTCCCGCGTGTGGCTTCTCT

GCCACCGGCAGCTGGTGGCGGTCGTGCTCAAGCTCGTCGTGTCGGCGAGGACGCAGCGGCTGCTGAGGGCCGTACTC

CACCGGCCCGTCAACCGCGCGCAGCACAGGAACCGCCGATCGTGATCTCCGATTCCCCGCCACCGAGCCCGCGTCGC

CCGGCGGGTCCGGGTCCGCTGTCTTTTGTATCCTCCAGCTCTGCTCAGGTAAGCAGCGGTCCTGGCGGTGGCGGCCT

GCCACAGTCCTCTGGTCGTGCTGCTCGTCCTCGTGCGGCGGTTGCTCCTCGTGTACGTTCTCCGCCACGCGCTGCTG
```

-continued

CCGCGCCGGTCGTTTCTGCCTCTGCTGACGCGGCAGGTCCGGCTCCGCCTGCAGTTCCGGTTGATGCACACCGTGCA

CCGCGCTCTCGTATGACCCAGGCGCAGACTGATACCCAGGCACAATCCCTGGGTCGCGCGGGTGCGACTGACGCTCG

TGGTAGCGGTGGTCCGGGCGCTGAAGGTGGCCCGGGTGTTCCACGCGGTACTAACACTCCGGGCGCTGCGCCACACG

CGGCTGAAGGTGCGGCTGCACGTCCGCGTAAACGTCGTGGTTCCGACAGCGGTCCGGCTGCAAGCAGCAGCGCGAGC

TCTTCCGCTGCGCCTCGCAGCCCGCTGGCGCCGCAGGGTGTTGGCGCCAAGCGTGCTGCTCCGCGTCGTGCACCGGA

CTCCGATTCTGGCGACCGCGGTCACGGCCCGCTGGCCCCTGCTAGCGCAGGCGCTGCGCCGCCATCCGCCAGCCCGT

CTTCTCAGGCAGCTGTGGCTGCGGCGTCCTCTTCTTCCGCTAGCAGCTCTTCCGCCTCTTCTAGCAGCGCGTCCTCT

AGCAGCGCATCTTCCTCTTCTGCTTCTTCTTCTAGCGCTTCTAGCTCTTCCGCGTCCTCTTCCGCTGGCGGTGCAGG

CGGCTCTGTTGCTTCCGCCAGCGGCGCAGGTGAGCGTCGTGAAACGAGCCTGGGCCCACGTGCTGCTGCACCGCGTG

GCCCGCGTAAGTGTGCGCGCAAGACCCGCCACGCTGAAGGCGGTCCGGAGCCGGGTGCGCGTGATCCGGCTCCGGGT

CTGACCCGTTACCTGCCGATTGCGGGTGTGTCCTCCGTTGTGGCACTGGCGCCGTATGTGAACAAAACTGTCACGGG

CGATTGCCTGCCTGTTCTGGACATGGAAACCGGTCATATCGGCGCTTACGTCGTTCTGGTTGACCAAACCGGCAACG

TGGCGGATCTGCTGCGTGCGGCCGCTCCGGCTTGGTCCCGTCGTACCCTGCTGCCGGAACATGCTCGCAACTGTGTA

CGCCCACCGGATTACCCAACCCCGCCGGCCTCCGAGTGGAACTCCCTGTGGATGACCCCGGTTGGTAACATGCTGTT

CGACCAGGGCACGCTGGTTGGTGCTCTGGACTTTCACGGCCTGCGCTCCCGTCACCCGTGGTCCCGTGAGCAAGGCG

CTCCGGCCCCTGCGGGCGATGCCCCGGCTGGCCACGGCGAGAGTACTAGAGGATCATAA

SEQ ID NO: 43 = construct UL36.3.4.1
ATGTCGTACTACCATCACCATCACCATCACGCCGCTCAACGTGCTAGGGGATCCTCTGAACGCTGGGCTGCTGGTGT

CGAGGCTGCTTTGGATAGAGTGGAGAACCGTGCCGAATTCGATGTTGTCGAGCTGAGGAGACTCCAAGCTTTGGCTG

GTACTCACGGCTACAACCCTCGTGATTTCCGTAAACGTGCCGAACAGGCTTTGGCGGCAAACGCTGAGGCCGTAACA

TTGGCTCTGGACACTGCCTTCGCTTTCAACCCATACACGCCCGAAAACCAACGTCATCCTATGCTCCCACCTCTCGC

TGCTATTCACCGCCTGGGATGGAGCGCTGCTTTCCATGCTGCTGCTGAAACTTACGCCGACATGTTCCGTGTCGATG

CCGAACCACTGGCTAGACTGCTCCGTATCGCTGAGGGACTGCTGGAGATGGCTCAAGCTGGCGACGGATTCATCGAT

TACCATGAGGCTGTCGGTAGACTGGCCGATGATATGACTTCTGTGCCCGGATTGAGGCGCTACGTTCCTTTCTTCCA

ACATGGCTACGCCGATTACGTGGAACTGAGAGATCGCCTGGATGCTATTAGGGCCGACGTCCATAGAGCACTCGGTG

GTGTTCCGCTGGATTTGGCGGCTGCTGCCGAACAAATTTCCGCTGCTCGTAACGATCCTGAGGCTACTGCTGAATTG

GTCCGTACTGGTGTAACATTGCCTTGCCCTAGTGAGGACGCTCTCGTGGCTTGTGCTGCTGCCCTGGAGAGAGTCGA

TCAATCTCCCGTGAAAAACACGGCTTACGCCGAATACGTTGCCTTCGTGACCCGTCAAGACACTGCTGAGACTAAAG

ACGCTGTGGTCCGTGCTAAACAACAACGTGCTGAGGCCACTGAACGTGTTATGGCTGGCCTGAGAGAGGCTCTGGCT

GCTAGAGAACGTCGTGCTCAAATTGAGGCTGAGGGATTGGCAAACCTGAAAACCATGCTCAAAGTCGTGGCTGTACC

CGCTACTGTTGCTAAAACTCTCGACCAGGCTCGTAGTGTTGCCGAAATTGCCGATCAAGTCGAAGTGTTGCTGGATC

AAACCGAAAAAACTCGTGAACTGGATGTGCCTGCTGTGATCTGGCTCGAACACGCCCAAAGAACATTCGAGACACAC

CCTTTGTCTGCCGCTCGTGGTGATGGTCCTGGACCCTTGGCTCGTCATGCTGGCCGCCTCGGTGCCCTCTTCGATAC

TCGTCGTAGAGTAGACGCCTTGAGGAGATCCCTGGAGGAGGCTGAGGCTGAATGGGACGAAGTTTGGGGACGCTTCG

GTAGAGTGAGGGGCGGAGCGTGGAAATCTCCGGAGGGATTCCGTGCAATGCATGAGCAACTGAGGGCCCTCCAAGAC

ACAACAAACACCGTGTCTGGCCTGAGGGCTCAACCTGCTTACGAACGCTTGTCTGCTCGCTACCAAGGAGTACTCGG

AGCGAAAGGCGCTGAGAGAGCTGAGGCTGTTGAGGAACTCGGTGCTCGTGTCACTAAACACACCGCTCTGTGTGCTA

GGCTGAGAGATGAGGTCGTCCGTAGAGTGCCTTGGGAAATGAACTTCGATGCTCTGGGAGGATTGTTGGCTGAGTTC

GATGCCGCTGCTGCCGATTTGGCACCTTGGGCTGTAGAGGAATTCCGTGGTGCTAGAGAACTCATTCAATACCGTAT

GGGCCTGTACTCTGCCTACGCTAGAGCTGGAGGACAAACTGGTGCTGGAGCTGAATCTGCTCCTGCTCCTTTGCTCG

TGGATCTGAGGGCTTTGGATGCTCGTGCTCGTGCTTCTTCTTCCCCTGAGGGACATGAAGTGGACCCACAACTGCTG

-continued

AGGAGGCGTGGAGAGGCTTACTTGAGAGCTGGCGGCGACCCTGGACCTCTCGTGCTCCGTGAAGCTGTTTCTGCTTT

GGACCTGCCATTCGCCACATCTTTCTTGGCCCCCGATGGAACTCCCCTCCAATACGCTTTGTGCTTCCCTGCCGTAA

CGGACAAACTCGGAGCTTTGCTCATGAGGCCCGAGGCCGCTTGTGTTAGACCTCCTTTGCCTACCGATGTGCTGGAA

TCTGCCCCAACTGTGACTGCCATGTACGTACTCACTGTGGTCAACCGCCTCCAACTGGCATTGAGTGATGCTCAAGC

GGCAAACTTCCAACTGTTCGGTCGTTTCGTTCGTCATAGGCAGGCAACCTGGGGAGCGTCAATGGATGCCGCCGCTG

AATTGTACGTTGCCCTGGTGGCTACAACTCTCACACGTGAATTCGGTTGTCGCTGGGCACAATTGGGATGGGCTAGT

GGAGCTGCTGCTCCTAGACCCCCACCTGGACCCCGTGGCTCACAACGTCACTGTGTGGCATTCAACGAGAACGATGT

CCTCGTCGCTTTGGTTGCCGGTGTTCCCGAACACATCTACAACTTCTGGCGCCTGGACTTGGTCCGTCAACACGAGT

ACATGCACCTCACACTGGAGCGTGCCTTCGAGGATGCTGCCGAGTCTATGCTCTTCGTTCAACGCCTCACTCCACAT

CCCGACGCTCGTATTAGAGTTCTGCCGACCTTCTTGGATGGTGGTCCTCCTACACGTGGTCTGTTGTTCGGAACCCG

CTTGGCGGACTGGCGTCGTGGTAAACTGTCTGAAACCGACCCATTGGCCCCATGGAGATCTGCTTTGGAACTCGGAA

CCCAACGTCGTGACGTGCCTGCTTTGGGAAAACTGTCCCCTGCTCAAGCTTTGGCCGCTGTGTCGGTACTGGGCCGT

ATGTGCTTGCCCTCGGCTGCCTTGGCTGCTTTGTGGACCTGTATGTTCCCCGACGACTACACTGAATACGACTCATT

CGACGCCCTCTTGGCGGCTCGCCTGGAATCGGGACAAACATTGGGACCTGCTGGCGGTAGAGAGGCTTCATTGTAAT

AG

SEQ ID NO: 44 = construct UL36.4.2.5
ATGTCGTACTACCATCACCATCACCATCACGAATACGACTCCTTCGACGCTTTGTTGGCTGCTAGATGGAATCTGG

TCAAACCTTGGGACCCGCTGGCGGTAGAGAGGCTTCTTTGCCCGAGGCTCCTCATGCTTTGTACCGTCCAACCGGAC

AACATGTTGCTGTGTTGGCGGCTGCTACTCATAGAACCCCTGCTGCTCGTGTTACTGCTATGGACCTGGTCTTGGCG

GCCGTTTTGCTGGGCGCTCCTGTGGTGGTCGCTCTGAGAAACACTACTGCCTTCTCCCGTGAATCCGAATTGGAACT

GTGCCTCACCCTGTTCGATTCTCGTCCCGGCGGACCGGATGCTGCCCTGAGAGATGTGGTATCCTCCGACATTGAAA

CCTGGGCTGTGGGCTTGCTCCACACCGATTTGAACCCTATTGAGAACGCTTGCTTGGCGGCTCAACTGCCACGCTTG

TCTGCCCTCATTGCTGAACGTCCTTTGGCCGATGGACCCCCTTGTTTGGTGTTGGTGGACATTTCGATGACACCTGT

CGCTGTTTTGTGGGAGGCCCCTGAACCACCTGGCCCTCCCGATGTTCGTTTCGTCGGTAGCGAGGCCACTGAGGAAT

TGCCTTTCGTGGCTACTGCTGGTGATGTTTTGGCGGCGAGTGCTGCCGATGCCGATCCTTTCTTCGCTCGTGCTATC

CTGGGCCGTCCTTTCGATGCTTCTCTGCTCACTGGTGAACTGTTCCCTGGTCACCCCGTTTACCAACGTCCCCTGGC

GGATGAGGCTGGTCCTTCTGCTCCTACTGCCGCTCGTGATCCTAGAGATCTGGCTGGAGGCGACGGTGGATCCGGAC

CTGAGGATCCCGCTGCTCCACCTGCTAGACAGGCCGATCCTGGTGTTTTGGCTCCTACTCTGCTCACCGATGCTACT

ACTGGCGAACCTGTGCCACCCCGTATGTGGGCTTGGATTCATGGACTGGAGGAACTGGCTTCCGATGATGCCGGCGG

TCCTACCCCAAACCCTGCCCCGGCTTTGCTGCCCCCTCCTGCTACGGATCAATCTGTCCCCACTTCCCAATACGCCC

CTAGACCAATTGGCCCGGCTGCCACTGCTAGAGAAACTCGTCCTTCCGTTCCCCCTCAACAAAACACTGGTCGTGTC

CCTGTGGCTCCACGTGATGACCCTAGACCTTCCCCCCCTACTCCTTCCCCCCCTGCCGATGCTGCTTTGCCACCTCC

TGCCTTCTCTGGTTCTGCTGCTGCTTTCTCCGCTGCTGTTCCACGTGTTCGTCGTTCTAGGCGTACTCGTGCCAAAT

CCCGTGCCCCTCGTGCTTCTGCCCCACCCGAGGGATGCCGTCCCCCGCTTTGCCTGCCCCTGTTGCTCCTGTGGCG

GCTTCTGCTCGTCCCCCCGATCAACCTCCTACTCCCGAATCTGCTCCCCCGGCTTGGGTTTCCGCTCTGCCATTGCC

ACCCGGACCTGCTAGTGCTCGTGGTGCTTTCCCTGCTCCAACCTTGGCCCCTATTCCCCACCCCCCGCTGAGGGAG

CTGTTGTTCCCGGTGGTGATCGTAGACGTGGTCGCCGTCAAACAACTGCTGGACCATCCCCTACACCGCCACGTGGC

CCGGCTGCTGGTCCTCCTCGTCGCCTCACTAGGCCTGCTGTTGCTAGTCTGTCCGCTTCTTTGAACTCTCTGCCTTC

CCCCCGTGATCCTGCCGATCATGCTGCTGCCGTTTCTGCTGCCGCCGCTGCCGTACCACCTTCACCTGGACTGGCTC

CCCCAACTTCTGCTGTCCAAACCTCTCCTCCTCCCTTGGCGCCTGGTCCTGTTGCCCCATCTGAACCTTTGTGTGGC

TGGGTTGTGCCTGGAGGCCCTGTTGCTAGACGTCCCCCACCCCAATCTCCGGCTACTAAACCGGCTGCTCGTACCCG

-continued

TATTAGGGCTCGTTCTGTGCCCCAACCACCCTTGCCCCAACCTCCACTGCCTCAACCCCCTTGCCTCAACCCCCTC

TCCCCCAACCACCTCTGCCTCAACCTCCGCTGCCCCAACCTCCTTTGCCCCAACCTCCTTTGCCCCAACCTCCTTTG

CCCCAACCTCCGCTGCCCCAACCTCCGCTGCCACCTGTTACTCGTACACTCACTCCCCAATCTCGTGACTCTGTGCC

TACACCTGAGTCTCCAACTCACACAAACACCCACTTGCCCGTTAGTGCTGTGACTTCTTGGGCTTCGTCCCTGGCTC

TCCATGTGGATTCTGCCCCTCCCCCTGCTTCATTGCTCCAAACTCTCCACATTTCCTCCGATGATGAACACTCCGAC

GCCGACTCACTCCGCTTCTCCGATTCCGATGACACTGAGGCTCTCGATCCTTTGCCTCCTGAACCTCACTTGCCACC

TGCCGATGAACCCCCGGACCTCTGGCTGCCGACCATCTCCAATCACCTCACTCACAATTCGGTCCTTTGCCCGTTC

AAGCGAACGCTGTTCTGTCTCGTCGTTACGTGAGATCAACTGGCCGTTCTGCCTTGGCTGTGCTCATTAGAGCTTGT

CGCCGTATCCAACAACAACTCCAGCGTACTAGGAGAGCACTCTTCCAACGCTCAAACGCCGTGCTCACATCACTCCA

CCATGTCCGTATGCTCTTGGGATAATAG

SEQ ID NO: 45 = US12
ATGTCTTGGGCTCTGAAAACCACCGACATGTTCCTGGACTCTTCTCGTTGCACCCACCGTACCTACGGTGACGTTTG

CGCTGAAATCCACAAACGTGAACGTGAAGACCGTGAAGCTGCTCGTACCGCTGTTACCGACCCGGAACTGCCGCTGC

TGTGCCCGCCGGACGTTCGTTCTGACCCGGCTTCTCGTAACCCGACCCAGCAGACCCGTGGTTGCGCTCGTTCTAAC

GAACGTCAGGACCGTGTTCTGGCTCCGTGA

SEQ ID NO: 46 = US4
ATGAAGTTCCTCGTGAACGTGGCCCTGGTGTTCATGGTGGTGTACATCAGCTACATCTACGCTAACCGTTGGGGTTC

CGGCGTGCCCGGTCCCATCAACCCCCCCAACTCCGACGTGGTGTTCCCCGGTGGTTCCCCCGTGGCTCAGTACTGCT

ACGCTTACCCCCGTCTGGACGACCCTGGTCCCCTGGGTTCTGCTGACGCTGGTCGTCAGGACCTGCCCCGTCGTGTC

GTGCGTCACGAGCCCCTGGGTCGTAGCTTCCTGACCGGTGGCCTGGTGCTGTTGGCTCCCCCTGTGCGCGGTTTCGG

TGCTCCCAACGCTACCTACGCTGCTCGTGTGACCTACTACCGTCTGACCCGTGCTTGCCGTCAGCCCATCCTGCTGC

GTCAGTACGGTGGTTGCCGTGGTGGAGAGCCCCCATCCCCCAAGACCTGCGGTTCTTACACCTACACCTACCAGGGT

GGTGGTCCCCCTACCCGTTACGCTCTGGTCAACGCTTCCCTGCTGGTGCCCATCTGGGACCGTGCTGCTGAGACTTT

CGAGTACCAGATCGAGCTGGGTGGCGAGCTGCACGTGGGTCTGCTGTGGGTGGAAGTGGGTGGAGAGGGTCCCGGTC

CTACCGCTCCTCCTCAGGCTGCTCGTGCTGAGGGTGGTCCTTGCGTGCCACCCGTGCCTGCTGGTCGTCCTTGGCGT

TCCGTGCCCCCGTGTGGTACTCCGCTCCCAACCCCGGTTTCCGCGGTCTGCGTTTCCGTGAGCGTTGCCTGCCTCC

CCAGACCCCTGCTGCTCCTTCCGACCTGCCTCGTGTGGCTTTCGCTCCCCAGTCCCTGCTCGTGGGTATCACCGGTC

GTACCTTCATCCGTATGGCTCGTCCCACCGAGGACGTGGGTGTCCTGCCTCCTCACTGGGCTCCAGGTGCTCTGGAC

GACGGTCCCTACGCTCCCTTCCCCCCTCGTCCCCGTTTCCGTCGTCACCACCACCATCACCACTAATAA

SEQ ID NO: 117 = construct RS1.2
ATGTCGTACTACCATCACCATCACCATCACATGGTGCTGTACGGCGGGCTGGGCGACAGCCGCCCCGGCCTCTGGGG

GGCGCCCGAGGCGGAGGAGGCGCGGGCCCGGTTCGAGGCCTCGGGCGCCCCGGCGCCCGTGTGGGCGCCCGAGCTGG

GCGACGCGGCGCAGCAGTACGCCCTGATCACGCGGCTGCTGTACACGCCGGACGCGGAGGCGATGGGGTGGCTCCAG

AACCCGCGCGTGGCGCCCGGGGACGTGGCGCTGGACCAGGCCTGCTTCCGGATCTCGGGCGCGGCGCGCAACAGCAG

CTCCTTCATCTCCGGCAGCGTGGCGCGGGCCGTGCCCCACCTGGGGTACGCCATGGCGGCGGGCCGCTTCGGCTGGG

GCCTGGCGCACGTGGCGGCCGCCGTGGCCATGAGCCGCCGCTACGACGCGCGCAGAAGGGCTTCCTGCTGACCAGC

CTGCGCCGCGCCTACGCGCCCCTGCTGGCGCGCGAGAACGCGGCGCTGACCGGGGCGCGGACCCCCGACGACGGCGG

CGACGCCAACCGCCGCGACGGCGACGACGCCCGCGGGAAGCCCGCCGCCGCCGCCGCCCCGTTGCCGTCGGCGGCGG

CGTCGCCGGCCGACGAGCGCGCGGTGCCCGCCGGCTACGGCGCCGCGGGGGTGCTCGCCGCCCTGGGGCGCCTGAGC

GCCGCGCCCGCCTCCGCGCCGGCCGGGGCCGACGACGACGACGACGACGACGGCGCCGGCGGTGGTGGCGGTGG

TGGCGGTGGTGGCGGCGGCCGGCGCGCGGAGGCGGGCCGCGTGGCCGTGGAGTGCCTGGCCGCCTGCCGCGGGATCC

TGGAGGCGCTGGCGGAGGGCTTCGACGGCGACCTGGCGGCCGTGCCGGGGCTGGCCGGAGCCCGGCCCGCCGCGCCC

```
CCGCGCCCGGGGCCCGCGGGCGCGGCCGCCCCGCCGCACGCCGACGCGCCCCGCCTGCGCGCCTGGCTGCGCGAGCT
GCGGTTCGTGCGCGACGCGCTGGTGCTGATGCGCCTGCGCGGGGACCTGCGCGTGGCCGGCGGCAGCGAGGCCGCCG
TGGCCGCCGTGCGCGCCGTGAGCCTGGTCGCCGGGGCCCTGGGCCCGGCGCTGCCGCGGAGCCCGCGCCTGCTGAGC
TCCGCCGCCGCCGCCGCGGACCTGCTCTTCCAGAACCAGAGCCTGAGTACTAGAGGATCATAA
```

SEQ ID NO: 118 = UL1
```
ATGTCGTACTACCATCACCATCACCATCACATGGGGTTCGTCTGTCTGTTTGGGCTTGTCGTTATGGGAGCCTGGGG
GGCGTGGGGTGGGTCACAGGCAACCGAATATGTTCTTCGTAGTGTTATTGCCAAAGAGGTGGGGGACATACTAAGAG
TGCCTTGCATGCGGACCCCCGCGGACGATGTTTCTTGGCGCTACGAGGCCCCGTCCGTTATTGACTATGCCCGCATA
GACGGAATATTTCTTCGCTATCACTGCCCGGGGTTGGACACGTTTTTGTGGGATAGGCACGCCCAGAGGGCGTATCT
TGTTAACCCCTTTCTCTTTGCGGCGGGATTTTTGGAGGACTTGAGTCACTCTGTGTTTCCGGCCGACACCCAGGAAA
CAACGACGCGCCGGGCCCTTTATAAAGAGATACGCGATGCGTTGGGCAGTCGAAAACAGGCCGTCAGCCACGCACCC
GTCAGGGCCGGGTGTGTAAACTTTGACTACTCACGCACTCGCCGCTGCGTCGGGCGACGCGATTTACGGCCTGCCAA
CACCACGTCAACGTGGGAACCGCCTGTGTCGTCGGACGATGAAGCGAGCTCGCAGTCGAAGCCCCTCGCCACCCAGC
CGCCCGTCCTCGCCCTTTCGAACGCCCCCCCACGGCGGGTCTCCCCGACGCGAGGTCGGCGCCGGCATACTCGCCTC
CGACGCAACTGA
```

SEQ ID NO: 119 = construct UL1s
```
ATGAAGTTCCTCGTGAACGTGGCCCTGGTGTTCATGGTGGTGTACATCAGCTACATCTACGCCAACCGTTGGGGGTT
CGTCTGTCTGTTTGGGCTTGTCGTTATGGGAGCCTGGGGGGCGTGGGGTGGGTCACAGGCAACCGAATATGTTCTTC
GTAGTGTTATTGCCAAAGAGGTGGGGGACATACTAAGAGTGCCTTGCATGCGGACCCCCGCGGACGATGTTTCTTGG
CGCTACGAGGCCCCGTCCGTTATTGACTATGCCCGCATAGACGGAATATTTCTTCGCTATCACTGCCCGGGGTTGGA
CACGTTTTTGTGGGATAGGCACGCCCAGAGGGCGTATCTTGTTAACCCCTTTCTCTTTGCGGCGGGATTTTTGGAGG
ACTTGAGTCACTCTGTGTTTCCGGCCGACACCCAGGAAACAACGACGCGCCGGGCCCTTTATAAAGAGATACGCGAT
GCGTTGGGCAGTCGAAAACAGGCCGTCAGCCACGCACCCGTCAGGGCCGGGTGTGTAAACTTTGACTACTCACGCAC
TCGCCGCTGCGTCGGGCGACGCGATTTACGGCCTGCCAACACCACGTCAACGTGGGAACCGCCTGTGTCGTCGGACG
ATGAAGCGAGCTCGCAGTCGAAGCCCCTCGCCACCCAGCCGCCCGTCCTCGCCCTTTCGAACGCCCCCCCACGGCGG
GTCTCCCCGACGCGAGGTCGGCGCCGGCATACTCGCCTCCGACGCAACCATCACCATCACCATCACTGA
```

SEQ ID NO: 120 = construct UL19ΔTEV
```
ATGTCGTACTACCATCACCATCACCATCACATGGCCGCTCCTGCCCGCGACCCCCCGGGTTACCGGTACGCCGCGGC
CATGGTGCCCACCGGCTCCATCCTGAGTACGATCGAGGTGGCGTCCCACCGCAGACTCTTTGATTTTTTCGCCCGCG
TGCGCTCCGACGAAAACAGCCTGTATGACGTAGAGTTTGACGCCCTGCTGGGGTCCTACTGCAACACCCTGTCGCTC
GTGCGCTTTCTGGAGCTCGGCCTGTCCGTGGCGTGCGTGTGCACCAAGTTCCCGGAGCTGGCTTACATGAACGAAGG
GCGTGTGCAGTTCGAGGTCCACCAGCCCCTCATCGCCCGCGACGGCCCGCACCCCGTCGAGCAGCCCGTGCATAATT
ACATGACGAAGGTCATCGACCGCCGGGCCCTGAACGCCGCCTTCAGCCTGGCCACCGAGGCCATTGCCCTGCTCACG
GGGGAGGCCCTGGACGGGACGGGCATTAGCCTGCATCGCCAGCTGCGCGCCATCCAGCAGCTCGCGCGCAACGTCCA
GGCCGTCCTGGGGGCGTTTGAGCGCGGCACGGCCGACCAGATGCTGCACGTGCTGTTGGAGAAGGCGCCTCCCCTGG
CCCTGCTGTTGCCCATGCAACGATATCTCGACAACGGGCGCCTGGCGACCAGGGTTGCCCGGGCGACCCTGGTCGCC
GAGCTGAAGCGGAGCTTTTGCGACACGAGCTTCTTCCTGGGCAAGGCGGGCCATCGCCGCGAGGCCATCGAGGCCTG
GCTCGTGGACCTGACCACGGCGACGCAGCCGTCCGTGGCCGTGCCCCGCCTGACGCACGCCGACACGCGCGGGCGGC
CGGTCGACGGGGTGCTGGTCACCACCGCCGCCATCAAACAGCGCCTCCTGCAGTCCTTCCTGAAGGTGGAGGACACC
GAGGCCGACGTGCCGGTGACCTACGGCGAGATGGTCTTGAACGGGGCCAACCTCGTCACGGCGCTGGTGATGGGCAA
GGCCGTGCGGAGCCTGGACGACGTGGGCCGCCACCTGCTGGAGATGCAGGAGGAGCAACTCGAGGCGAACCGGGAGA
CGCTGGATGAACTCGAAAGCGCCCCCCAGACAACGCGCGTGCGCGCGGATCTGGTGGCCATAGGCGACAGGCTGGTC
```

-continued

```
TTCCTGGAGGCCCTGGAGAAGCGCATCTACGCCGCCACCAACGTGCCCTACCCCCTGGTGGGCGCCATGGACCTGAC
GTTCGTCCTGCCCCTGGGGCTGTTCAACCCGGCCATGGAGCGCTTCGCCGCGCACGCCGGGGACCTGGTGCCCGCCC
CCGGCCACCCGGAGCCCCGCGCGTTCCCTCCCCGGCAGCTGTTTTTTTGGGGAAAGGACCACCAGGTTCTGCGGCTG
TCCATGGAGAACGCGGTCGGGACCGTGTGTCATCCTTCGCTCATGAACATCGACGCGGCCGTCGGGGGCGTGAACCA
CGACCCCGTCGAGGCCGCGAATCCGTACGGGGCGTACGTCGCGGCCCCGGCCGGCCCCGGCGCGGACATGCAGCAGC
GTTTTCTGAACGCCTGGCGGCAGCGCCTCGCCCACGGCCGGGTCCGGTGGGTCGCCGAGTGCCAGATGACCGCGGAG
CAGTTCATGCAGCCCGACAACGCCAACCTGGCTCTGGAGCTGCACCCCGCGTTCGACTTCTTCGCGGGCGTGGCCGA
CGTCGAGCTTCCCGGCGGCGAAGTCCCCCCGGCCGGTCCGGGGCGATCCAGGCCACCTGGCGCGTGGTCAACGGCA
ACCTGCCCCTGGCGCTGTGTCCGGTGGCGTTTCGTGACGCCGGGGCCTGGAGCTCGGCGTTGGCCGCCACGCCATG
GCGCCGGCTACCATAGCCGCCGTCCGCGGGGCGTTCGAGGACCGCAGCTACCCGGCGGTGTTCTACCTGCTGCAAGC
CGCGATTCACGGCAGCGAGCACGTGTTCTGCGCCCTGGCGCGGCTCGTGACTCAGTGCATCACCAGCTACTGGAACA
ACACGCGATGCGCGGCGTTCGTGAACGACTACTCGCTGGTCTCGTACATCGTGACCTACCTCGGGGGCGACCTCCCC
GAGGAGTGCATGGCCGTGTATCGGGACCTGGTGGCCCACGTCGAGGCCCTGGCCCAGCTGGTGGACGACTTTACCCT
GCCGGGCCCGGAGCTGGGCGGGCAGGCTCAGGCCGAGCTGAATCACCTGATGCGCGACCCGGCGCTGCTGCCGCCCC
TCGTGTGGGACTGCGACGGCCTTATGCGACACGCGGCCCTGGACCGCCACCGAGACTGCCGGATTGACGCGGGGGAG
CACGAGCCCGTCTACGCGGCGGCGTGCAACGTGGCGACGGCCGACTTTAACCGCAACGACGGCCGGCTGCTGCACAA
CACCCAGGCCCGCGCGGCCGACGCCGCCGACGACCGGCCGCACCGGCCGGCCGACTGGACCGTCCACCACAAAATCT
ACTATTACGTGCTGGTGCCGGCCTTCTCGCGGGGCGCTGCTGCACCGCGGGGGTCCGCTTCGACCGCGTGTACGCC
ACGCTGCAGAACATGGTGGTCCCGGAGATCGCCCCCGGCGAGGAGTGCCCGAGCGATCCCGTGACCGACCCCGCCCA
CCCGCTGCATCCCGCCAATCTGGTGGCCAACACGGTCAACGCCATGTTCCACAACGGGCGCGTCGTCGTCGACGGGC
CCGCCATGCTCACGCTGCAGGTGCTGGCGCACAACATGGCCGAGCGCACGACGGCGCTGCTGTGCTCCGCGGCGCCC
GACGCGGGCGCCAACACCGCGTCGACGGCCAACATGCGCATCTTCGACGGGGCGCTGCACGCCGGCGTGCTGCTCAT
GGCCCCCCAGCACCTGGACCACACCATCCAAAATGGCGAATACTTCTACGTCCTGCCCGTCCACGCGCTGTTTGCGG
GCGCCGACCACGTGGCCAACGCGCCCAACTTCCCCCCGGCCCTGCGCGACCTGGCGCGCCACGTCCCCCTGGTCCCC
CCGGCCCTGGGGGCCAACTACTTCTCCTCCATCCGCCAGCCCGTGGTGCAGCACGCCCGCGAGAGCGCGGCGGGGGA
GAACGCGCTGACCTACGCGCTCATGGCGGGGTACTTCAAGATGAGCCCCGTGGCCCTGTATCACCAGCTCAAGACGG
GCCTCCACCCCGGGTTCGGGTTCACCGTCGTGCGGCAGGACCGCTTCGTGACCGAGAACGTGCTGTTTTCCGAGCGC
GCGTCGGAGGCGTACTTTCTGGGCCAGCTCCAGGTGGCCCGCCACGAAACGGGCGGGGGGTCAGCTTCACGCTCAC
CCAGCCGCGCGGAAACGTGGACCTGGGTGTGGGCTACACCGCCGTCGCGGCCACGGCCACCGTCCGCAACCCCGTTA
CGGACATGGGCAACCTCCCCCAAAACTTTTACCTCGGCCGCGGGCCCCCCCGCTGCTAGACAACGCGGCCGCCGTG
TACCTGCGCAACGCGGTCGTGGCGGGAAACCGGCTGGGGCCGGCCCAGCCCCTCCCGGTCTTTGGCTGCGCCCAGGT
GCCGCGGCGCGCCGGCATGGACCACGGGCAGGATGCCGTGTGTGAGTTCATCGCCACCCCCGTGGCCACGGACATCA
ACTACTTTCGCCGGCCCTGCAACCCGCGGGGACGCGCGGCCGGCGGCGTGTACGGGGGACAAGGAGGGGGACGTC
ATAGCCCTCATGTACGACCACGGCCAGAGCGACCCGGCGCGGCCCTTCGCGGCCACGGCCAACCCGTGGGCGTCGCA
GCGGTTCTCGTACGGGGACCTGCTGTACAACGGGGCCTATCACCTCAACGGGGCCTCGCCCGTCCTCAGCCCCTGCT
TCAAGTTCTTCACCGCGGCCGACATCACGGCCAAACATCGCTGCCTGGAGCGTCTTATCGTGGAAACGGGATCGGCG
GTATCCACGGCCACCGCTGCCAGCGACGTGCAGTTTAAGCGCCCGCCGGGGTGCCGCGAGCTCGTGGAAGACCCGTG
CGGCCTGTTTCAGGAAGCCTACCCGATCACCTGCGCCAGCGACCCCGCCCTGCTACGCAGCGCCCGCGATGGGGAGG
CCCACGCGCGAGAGACCCACTTTACGCAGTATCTCATCTACGACGCCTCCCCGCTAAAGGGCCTGTCTCTGTAA
```

-continued

SEQ ID NO: 121 = construct RS1.1
ATGAGTGCCGAACAGCGTAAAAAGAAAAAAACCACCACCACGACCCAAGGACGTGGAGCTGAAGTTGCTATGGCGGA

TGAGGATGGAGGCCGCTTGAGAGCTGCTGCTGAGACTACTGGAGGACCTGGATCACCGGACCCTGCCGATGGACCCC

CCCCTACACCAAACCCCGATCGTAGACCGGCTGCTAGACCTGGATTCGGATGGCATGGAGGACCCGAGGAAAACGAG

GACGAGGCGGACGACGCCGCTGCCGACGCCGACGCCGATGAGGCTGCCCCTGCTTCTGGAGAGGCGGTAGACGAACC

TGCTGCCGATGGAGTTGTTAGCCCTAGGCAATTGGCTTTGTTGGCGAGCATGGTAGACGAGGCTGTGAGAACAATCC

CTTCCCCTCCCCCTGAACGTGATGGAGCACAAGAGGAGGCGGCTAGGAGTCCCTCACCACCCCGTACACCTTCTATG

AGAGCGGATTACGGCGAGGAAAACGACGACGACGACGATGATGATGACGACGATGATCGTGATGCCGGACGCTGGGT

TAGGGGACCTGAAACCACTTCTGCTGTCCGTGGAGCATACCCCGATCCTATGGCGAGTTTGAGCCCTAGACCACCTG

CCCCGAGGAGACACCACCACCACCACCATCATAGGCGTAGACGTGCTCCTAGACGTCGTTCTGCCGCTAGTGACTCT

TCCAAATCTGGCTCTTCTTCATCTGCCTCTTCCGCTTCATCTTCGGCCTCATCGTCCTCTTCGGCATCCGCTTCGAG

TAGTGATGATGATGATGACGACGACGCTGCTAGAGCCCCCGCTTCTGCTGCCGACCACGCTGCTGGCGGAACTTTGG

GAGCCGACGACGAGGAGGCGGGAGTTCCTGCTCGTGCCCCGGGAGCTGCTCCGAGGCCTTCTCCACCCCGTGCTGAA

CCTGCTCCGGCTAGAACACCGGCCGCTACTGCTGGTAGACTGGAGCGTAGACGTGCCCGTGCTGCTGTGGCTGGTAG

AGATGCTACTGGCCGCTTCACTGCTGGCCGTCCTAGACGTGTTGAACTGGACGCCGATGCTGCTTCTGGTGCTTTCT

ACGCCCGTTACCGTGATGGTTACGTGTCTGGTGAACCTTGGCCTGGCGCTGGTCCACCTCCGCCCGGACGTGTACTC

TACGGTGGATTGGGCGATTCTCGCCCTGGTCTGTGGGGCGCTCCG

SEQ ID NO: 122 = construct RS1.3.1
TCGAGTGCCGCCGCTGCTGCCGCCGATTTGTTGTTCCAAAACCAATCCCTCCGCCCTCTGCTCGCCGACACTGTTGC

CGCTGCCGATTCTCTGGCTGCTCCGGCTTCTGCCCCACGTGAAGCTCGTAAACGTAAATCACCCGCTCCGGCTCGTG

CTCCCCCTGGTGGCGCCCCTAGACCCCCTAAAAAATCCCGTGCCGATGCCCCTAGACCTGCTGCTGCTCCCCCCGCT

GGTGCTGCTCCCCCCGCTCCCCCTACTCCCCCCCACGCCCACCTCGTCCCGCTGCCCTCACACGCCGTCCTGCTGA

GGGACCCGATCCACAAGGCGGCTGGCGTAGACAACCTCCTGGCCCATCCCATACACCGGCACCATCTGCCGCTGCTT

TGGAGGCTTACTGTGCTCCTCGTGCTGTGGCTGAACTCACCGATCATCCGCTGTTCCCTGCTCCCTGGCGTCCCGCC

CTCATGTTCGATCCTAGAGCTTTGGCTTCCTTGGCCGCTCGTTGTGCTGCCCCTCCCCCTGGCGGTGCTCCGGCTGC

TTTCGGTCCTCTCCGTGCCTCTGGTCCACTCCGCCGTGCCGCTGCCTGGATGAGACAAGTTCCCGACCCTGAGGATG

TTAGAGTTGTGATCTTGTACTCGCCCTTGCCTGGCGAGGATTTGGCCGCTGGTAGAGCTGGCGGTGGCCCCCCTCCT

GAATGGTCTGCTGAACGTGGTGGTTTGTCTTGCTTGTTGGCCGCCCTGGGAAACCGTCTGTGTGGTCCTGCTACTGC

TGCTTGGGCTGGAAACTGGACTGGCGCTCCCGATGTTTCTGCTCTCGGTGCTCAA

SEQ ID NO: 123 = construct RS1.3.2
TGGGCTGGAAACTGGACTGGCGCTCCCGATGTTTCTGCTCTCGGTGCTCAAGGAGTTTTGCTGCTCTCTACTCGTGA

CTTGGCATTCGCTGGAGCTGTTGAATTCCTGGGACTCTTGGCTGGCGCTTGTGATAGGAGACTCATCGTCGTAAACG

CTGTGAGAGCTGCCGATTGGCCTGCCGATGGTCCTGTTGTGTCTCGTCAACACGCTTACTTGGCTTGTGAAGTGTTG

CCCGCTGTCCAATGTGCTGTTCGCTGGCCTGCTGCTCGTGATCTGAGGCGTACTGTTCTGGCTAGTGGTCGTGTTTT

CGGACCTGGTGTTTTCGCTCGTGTCGAAGCTGCTCACGCTAGACTGTACCCCGATGCCCCACCCCTCCGTTTGTGTC

GTGGAGCAAACGTTCGCTACCGTGTCCGTACTCGTTTCGGACCCGATACTCTGGTTCCAATGTCCCCTCGTGAATAC

CGTCGTGCTGTTCTGCCTGCCCTCGATGGACGTGCTGCCGCTTCTGGCGCTGGTGACGCTATGGCTCCTGGCGCTCC

GGACTTCTGTGAGGATGAGGCTCACTCACATCGTGCCTGTGCCCGCTGGGGACTGGGCGCTCCATTGAGGCCTGTAT

ACGTGGCACTGGGCCGTGATGCTGTTAGAGGCGGACCCGCTGAATTGAGAGGCCCTCGTCGTGAATTCTGTGCTAGG

GCTCTGCTCGAACCCGATGGAGATGCTCCTCCTTTGGTACTCCGTGACGACGCCGATGCTGGTCCTCCCCCACAAAT

TCGCTGGGCTAGTGCTGCTGGACGTGCTGGTACTGTATTGGCTGCTGCTGGCGGTGGCGTTGAAGTTGTTGGTACTG

-continued

CCGCTGGACTCGCTACACCTCCCCGCCGTGAACCTGTAGACATGGATGCTGAACTCGAGGATGATGACGACGGATTG

TTCGGAGAG

SEQ ID NO: 124 = construct RS1.3
TCGAGTGCCGCCGCTGCTGCCGCCGATTTGTTGTTCCAAAACCAATCCCTCCGCCCTCTGCTCGCCGACACTGTTGC

CGCTGCCGATTCTCTGGCTGCTCCGGCTTCTGCCCCACGTGAAGCTCGTAAACGTAAATCACCCGCTCCGGCTCGTG

CTCCCCCTGGTGGCGCCCCTAGACCCCCTAAAAAATCCCGTGCCGATGCCCCTAGACCTGCTGCTGCTCCCCCCGCT

GGTGCTGCTCCCCCCGCTCCCCCTACTCCCCCCCCACGCCCACCTCGTCCCGCTGCCCTCACACGCCGTCCTGCTGA

GGGACCCGATCCACAAGGCGGCTGGCGTAGACAACCTCCTGGCCCATCCCATACACCGGCACCATCTGCCGCTGCTT

TGGAGGCTTACTGTGCTCCTCGTGCTGTGGCTGAACTCACCGATCATCCGCTGTTCCCTGCTCCCTGGCGTCCCGCC

CTCATGTTCGATCCTAGAGCTTTGGCTTCCTTGGCCGCTCGTTGTGCTGCCCCTCCCCCTGGCGGTGCTCCGGCTGC

TTTCGGTCCTCTCCGTGCCTCTGGTCCACTCCGCCGTGCCGCTGCCTGGATGAGACAAGTTCCCGACCCTGAGGATG

TTAGAGTTGTGATCTTGTACTCGCCCTTGCCTGGCGAGGATTTGGCCGCTGGTAGAGCTGGCGGTGGCCCCCCTCCT

GAATGGTCTGCTGAACGTGGTGGTTTGTCTTGCTTGTTGGCCGCCCTGGGAAACCGTCTGTGTGGTCCTGCTACTGC

TGCTTGGGCTGGAAACTGGACTGGCGCTCCCGATGTTTCTGCTCTCGGTGCTCAAGGAGTTTTGCTGCTCTCTACTC

GTGACTTGGCATTCGCTGGAGCTGTTGAATTCCTGGGACTCTTGGCTGGCGCTTGTGATAGGAGACTCATCGTCGTA

AACGCTGTGAGAGCTGCCGATTGGCCTGCCGATGGTCCTGTTGTGTCTCGTCAACACGCTTACTTGGCTTGTGAAGT

GTTGCCCGCTGTCCAATGTGCTGTTCGCTGGCCTGCTGCTCGTGATCTGAGGCGTACTGTTCTGGCTAGTGGTCGTG

TTTTCGGACCTGGTGTTTTCGCTCGTGTCGAAGCTGCTCACGCTAGACTGTACCCCGATGCCCCACCCCTCCGTTTG

TGTCGTGGAGCAAACGTTCGCTACCGTGTCCGTACTCGTTTCGGACCCGATACTCTGGTTCCAATGTCCCCTCGTGA

ATACCGTCGTGCTGTTCTGCCTGCCCTCGATGGACGTGCTGCCGCTTCTGGCGCTGGTGACGCTATGGCTCCTGGCG

CTCCGGACTTCTGTGAGGATGAGGCTCACTCACATCGTGCCTGTGCCCGCTGGGGACTGGGCGCTCCATTGAGGCCT

GTATACGTGGCACTGGGCCGTGATGCTGTTAGAGGCGGACCCGCTGAATTGAGAGGCCCTCGTCGTGAATTCTGTGC

TAGGGCTCTGCTCGAACCCGATGGAGATGCTCCTCCTTTGGTACTCCGTGACGACGCCGATGCTGGTCCTCCCCCAC

AAATTCGCTGGGCTAGTGCTGCTGGACGTGCTGGTACTGTATTGGCTGCTGCTGGCGGTGGCGTTGAAGTTGTTGGT

ACTGCCGCTGGACTCGCTACACCTCCCCGCCGTGAACCTGTAGACATGGATGCTGAACTCGAGGATGATGACGACGG

ATTGTTCGGAGAG

SEQ ID NO: 125 = construct RS1.4
ACTGCTGGCCGTCCTAGACGTGTTGAACTGGACGCCGATGCTGCTTCTGGTGCTTTCTACGCCCGTTACCGTGATGG

TTACGTGTCTGGTGAACCTTGGCCTGGCGCTGGTCCACCTCCGCCCGGACGTGTACTCTACGGTGGATTGGGCGATT

CTCGCCCTGGTCTGTGGGCGCTCCGGAGGCTGAGGAGGCTAGAGCCCGTTTCGAGGCTTCTGGTGCCCCTGCTCCT

GTTTGGGCTCCTGAATTGGGCGACGCTGCTCAACAATACGCCCTCATCACACGCTTGCTGTACACTCCCGACGCCGA

GGCTATGGGATGGCTCCAAAACCCTAGAGTTGCCCCTGGTGATGTTGCTCTGGATCAGGCTTGTTTCCGTATCTCCG

GCGCTGCTCGTAACTCTTCTTCGTTCATCTCCGGTTCTGTGGCTAGAGCTGTGCCTCACTTGGGATACGCCATGGCC

GCTGGACGTTTCGGCTGGGGACTGGCTCATGTTGCTGCCGCTGTAGCAATGTCTAGACGCTACGACCGTGCTCAAAA

AGGATTCTTGCTCACGTCACTGAGGCGTGCTTACGCCCCTTTGTTGGCCCGTGAAAACGCTGCCCTCACTGGCGCCC

GTACCCCCGATGACGGTGGCGACGCCAACCGCCACGATGGTGATGATGCTAGAGGCAAACCCGCTGCCGCTGCTGCT

CCTTTGCCCTCTGCCGCCGCTTCCCCTGCCGATGAACGTGCTGTTCCTGCCGGTTACGGTGCCGCTGGTGTGTTGGC

TGCTTTGGGACGCTTGAGTGCTGCCCCGGCTAGTGCCCCGCTGGTGCCGATGACGATGACGATGACGATGGTGCTG

GCGGAGGCGGTGGCGGTAGACGTGCTGAGGCTGGACGTGTTGCTGTTGAATGCCTGGCTGCCGTAGAGGAATCTTG

GAGGCTCTGGCCGAGGGATTCGACGGAGACTTGGCGGCTGTACCGGGACTGGCGGGAGCGAGGCCTGCCGCTCCACC

TCGCCCCGGTCCTGCTGGTGCTGCCGCTCCTCCTCATGCCGACGCTCCTAGACTCCGTGCTTGGCTCCGTGAACTCC

GTTTCGTTCGTGACGCTTTGGTTCTGATGAGACTGAGAGGCGACTTGAGAGTGGCTGGAGGATCCGAGGCTGCTGTT

```
GCTGCTGTCCGTGCTGTTTCTTTGGTTGCTGGTGCTTTGGGCCCTGCTTTGCCGAGATCTCCCCGTTTGTTGTCGAG

TGCCGCCGCTGCTGCCGCCGATTTGTTGTTCCAAAACCAATCCCTCCGCCCTCTGCTCGCCGACACTGTTGCCGCTG

CCGATTCTCTGGCTGCTCCGGCTTCTGCCCCACGTGAAGCTCGTAAACGTAAATCACCCGCTCCGGCTCGTGCTCCC

CCTGGTGGCGCCCCTAGACCCCCTAAAAAATCCCGTGCCGATGCCCCTAGACCTGCTGCTGCTCCCCCCGCTGGTGC

TGCTCCCCCCGCTCCCCCTACTCCCCCCCCACGCCCACCTCGTCCCGCTGCCCTCACACGCCGTCCTGCTGAGGGAC

CCGATCCACAAGGCGGCTGGCGTAGACAACCTCCTGGCCCATCCCATACACCGGCACCATCTGCCGCTGCTTTGGAG

GCTTACTGTGCT
```

SEQ ID NO: 126 = construct RS1.5
```
GCCGCTGCCGATTCTCTGGCTGCTCCGGCTTCTGCCCCACGTGAAGCTCGTAAACGTAAATCACCCGCTCCGGCTCG

TGCTCCCCCTGGTGGCGCCCCTAGACCCCCTAAAAAATCCCGTGCCGATGCCCCTAGACCTGCTGCTGCTCCCCCCG

CTGGTGCTGCTCCCCCCGCTCCCCCTACTCCCCCCCCACGCCCACCTCGTCCCGCTGCCCTCACACGCCGTCCTGCT

GAGGGACCCGATCCACAAGGCGGCTGGCGTAGACAACCTCCTGGCCCATCCCATACACCGGCACCATCTGCCGCTGC

TTTGGAGGCTTACTGTGCTCCTCGTGCTGTGGCTGAACTCACCGATCATCCGCTGTTCCCTGCTCCCTGGCGTCCCG

CCCTCATGTTCGATCCTAGAGCTTTGGCTTCCTTGGCCGCTCGTTGTGCTGCCCCTCCCCCTGGCGGTGCTCCGGCT

GCTTTCGGTCCTCTCCGTGCCTCTGGTCCACTCCGCCGTGCCGCTGCCTGGATGAGACAAGTTCCCGACCCTGAGGA

TGTTAGAGTTGTGATCTTGTACTCGCCCTTGCCTGGCGAGGATTTGGCCGCTGGTAGAGCTGGCGGTGGCCCCCCTC

CTGAATGGTCTGCTGAACGTGGTGGTTTGTCTTGCTTGTTGGCGCGCCCTGGGAAACCGTCTGTGTGGTCCTGCTACT

GCTGCTTGGGCTGGAAACTGGACTGGCGCTCCCGATGTTTCTGCTCTCGGTGCTCAAGGAGTTTTGCTGCTCTCTAC

TCGTGACTTGGCATTCGCTGGAGCTGTTGAATTCCTGGGACTCTTGGCTGGCGCTTGTGATAGGAGACTCATCGTCG

TAAACGCTGTGAGAGCTGCCGATTGGCCTGCCGATGGTCCTGTTGTGTCTCGTCAACACGCTTACTTGGCTTGTGAA

GTGTTGCCCGCTGTCCAATGTGCTGTTCGCTGGCCTGCTGCTCGTGATCTGAGGCGTACTGTTCTGGCTAGTGGTCG

TGTTTTCGGACCTGGTGTTTTCGCTCGTGTCGAAGCTGCTCACGCTAGACTGTACCCCGATGCCCCACCCCTCCGTT

TGTGTCGTGGAGCAAACGTTCGCTACCGTGTCCGTACTCGTTTCGGACCCGATACTCTGGTTCCAATGTCCCCTCGT

GAATACCGTCGTGCTGTTCTGCCTGCCCTCGATGGACGTGCTGCCGCTTCTGGCGCTGGTGACGCTATGGCTCCTGG

CGCTCCGGACTTCTGTGAGGATGAGGCTCACTCACATCGTGCCTGTGCCCGCTGGGGACTGGGCGCTCCATTGAGGC

CTGTATACGTGGCACTGGGCCGTGATGCTGTTAGAGGCGGACCCGCTGAATTGAGAGGCCCTCGTCGTGAATTCTGT

GCTAGGGCTCTGCTCGAACCCGATGGAGATGCTCCTCCTTTGGTACTCCGTGACGACGCCGATGCTGGTCCTCCCCC

ACAAATTCGCTGGGCTAGTGCTGCTGGACGTGCTGGTACTGTATTGGCTGCTGCTGGCGGTGGCGTTGAAGTTGTTG

GTACTGCCGCTGGACTCGCTACACCTCCCCGCCGTGAACCTGTAGACATGGATGCTGAACTCGAGGATGATGACGAC

GGATTGTTCGGAGAG
```

SEQ ID NO: 127 = construct RS1.6
```
CACCACCACCACCACCATCATAGGCGTAGACGTGCTCCTAGACGTCGTTCTGCCGCTAGTGACTCTTCCAAATCTGG

CTCTTCTTCATCTGCCTCTTCCGCTTCATCTTCGGCCTCATCGTCCTCTTCGGCATCCGCTTCGAGTAGTGATGATG

ATGATGACGACGACGCTGCTAGAGCCCCCGCTTCTGCTGCCGACCACGCTGCTGGCGGAACTTTGGGAGCCGACGAC

GAGGAGGCGGGAGTTCCTGCTCGTGCCCCGGGAGCTGCTCCGAGGCCTTCTCCACCCCGTGCTGAACCTGCTCCGGC

TAGAACACCGGCCGCTACTGCTGGTAGACTGGAGCGTAGACGTGCCCGTGCTGCTGTGGCTGGTAGAGATGCTACTG

GCCGCTTCACTGCTGGCCGTCCTAGACGTGTTGAACTGGACGCCGATGCTGCTTCTGGTGCTTTCTACGCCCGTTAC

CGTGATGGTTACGTGTCTGGTGAACCTTGGCCTGGCGCTGGTCCACCTCCGCCCGGACGTGTACTCTACGGTGGATT

GGGCGATTCTCGCCCTGGTCTGTGGGCGCTCCGGAGGCTGAGGAGGCTAGAGCCCGTTTCGAGGCTTCTGGTGCCC

CTGCTCCTGTTTGGGCTCCTGAATTGGGCGACGCTGCTCAACAATACGCCCTCATCACACGCTTGCTGTACACTCCC

GACGCCGAGGCTATGGGATGGCTCCAAAACCCTAGAGTTGCCCCTGGTGATGTTGCTCTGGATCAGGCTTGTTTCCG

TATCTCCGGCGCTGCTCGTAACTCTTCTTCGTTCATCTCCGGTTCTGTGGCTAGAGCTGTGCCTCACTTGGGATACG
```

```
CCATGGCCGCTGGACGTTTCGGCTGGGGACTGGCTCATGTTGCTGCCGCTGTAGCAATGTCTAGACGCTACGACCGT

GCTCAAAAAGGATTCTTGCTCACGTCACTGAGGCGTGCTTACGCCCCTTTGTTGGCCCGTGAAAACGCTGCCCTCAC

TGGCGCCCGTACCCCCGATGACGGTGGCGACGCCAACCGCCACGATGGTGATGATGCTAGAGGCAAACCCGCTGCCG

CTGCTGCTCCTTTGCCCTCTGCCGCCGCTTCCCCTGCCGATGAACGTGCTGTTCCTGCCGGTTACGGTGCCGCTGGT

GTGTTGGCTGCTTTGGGACGCTTGAGTGCTGCCCCGGCTAGTGCCCCGCTGGTGCCGATGACGATGACGATGACGA

TGGTGCTGGCGGAGGCGGTGGCGGTAGACGTGCTGAGGCTGGACGTGTTGCTGTTGAATGCCTGGCTGCCTGTAGAG

GAATCTTGGAGGCTCTGGCCGAGGGATTCGACGGAGACTTGGCGGCTGTACCGGGACTGGCGGGAGCGAGGCCTGCC

GCTCCACCTCGCCCCGGTCCTGCTGGTGCTGCCGCTCCTCCTCATGCCGACGCTCCTAGACTCCGTGCTTGGCTCCG

TGAACTCCGTTTCGTTCGTGACGCTTTGGTTCTGATGAGACTGAGAGGCGACTTGAGAGTGGCTGGAGGATCCGAGG

CTGCTGTTGCTGCTGTCCGTGCTGTTTCTTTGGTTGCTGGTGCTTTGGGCCCTGCTTTGCCGAGATCTCCCCGTTTG

TTGTCGAGTGCCGCCGCTGCTGCCGCCGATTTGTTGTTCCAAAACCAATCCCTCCGCCCTCTGCTCGCCGACACTGT

TGCCGCTGCCGATTCTCTGGCTGCTCCGGCTTCTGCCCCACGTGAAGCTCGTAAACGTAAATCACCCGCTCCGGCTC

GTGCTCCCCCTGGTGGCGCCCCTAGACCCCCTAAAAAATCCCGTGCCGATGCCCCTAGACCTGCTGCTGCTCCCCCC

GCTGGTGCTGCTCCCCCCGCTCCCCCTACTCCCCCCCCACGCCCACCTCGTCCCGCTGCCCTCACACGCCGTCCTGC

TGAGGGACCCGATCCACAAGGCGGCTGGCGTAGACAACCTCCTGGCCCATCCCATACACCGGCACCATCTGCCGCTG

CTTTGGAGGCTTACTGTGCTCCTCGTGCTGTGGCTGAACTCACCGATCATCCGCTGTTCCCTGCTCCCTGGCGTCCC

GCCCTCATGTTCGATCCTAGAGCTTTGGCTTCCTTGGCCGCTCGTTGTGCTGCCCCTCCCCCTGGCGGTGCTCCGGC

TGCTTTCGGTCCTCTCCGTGCCTCTGGTCCACTCCGCCGTGCCGCTGCCTGGATGAGACAAGTTCCCGACCCTGAGG

ATGTTAGAGTTGTGATCTTGTACTCGCCCTTGCCTGGCGAGGATTTGGCCGCTGGTAGAGCTGGCGGTGGCCCCCCT

CCTGAATGGTCTGCTGAACGTGGTGGTTTGTCTTGCTTGTTGGCCGCCCTGGGAAACCGTCTGTGTGGTCCTGCTAC

TGCTGCTTGGGCTGGAAACTGGACTGGCGCTCCCGATGTTTCTGCTCTCGGTGCTCAAGGAGTTTTGCTGCTCTCTA

CTCGTGACTTGGCATTCGCTGGAGCTGTTGAATTCCTGGGACTCTTGGCTGGCGCTTGTGATAGGAGACTCATCGTC

GTAAACGCTGTGAGAGCTGCCGATTGGCCTGCCGATGGTCCTGTTGTGTCTCGTCAACACGCTTACTTGGCTTGTGA

AGTGTTGCCCGCTGTCCAATGTGCTGTTCGCTGGCCTGCTGCTCGTGATCTGAGGCGTACTGTTCTGGCTAGTGGTC

GTGTTTTCGGACCTGGTGTTTTCGCTCGTGTCGAAGCTGCTCACGCTAGACTGTACCCCGATGCCCCACCCCTCCGT

TTGTGTCGTGGAGCAAACGTTCGCTACCGTGTCCGTACTCGTTTCGGACCCGATACTCTGGTTCCAATGTCCCCTCG

TGAATACCGTCGTGCTGTTCTGCCTGCCCTCGATGGACGTGCTGCCGCTTCTGGCGCTGGTGACGCTATGGCTCCTG

GCGCTCCGGACTTCTGTGAGGATGAGGCTCACTCACATCGTGCCTGTGCCCGCTGGGGACTGGGCGCTCCATTGAGG

CCTGTATACGTGGCACTGGGCCGTGATGCTGTTAGAGGCGGACCCGCTGAATTGAGAGGCCCTCGTCGTGAATTCTG

TGCTAGGGCTCTGCTCGAACCCGATGGAGATGCTCCTCCTTTGGTACTCCGTGACGACGCCGATGCTGGTCCTCCCC

CACAAATTCGCTGGGCTAGTGCTGCTGGACGTGCTGGTACTGTATTGGCTGCTGCTGGCGGTGGCGTTGAAGTTGTT

GGTACTGCCGCTGGACTCGCTACACCTCCCCGCCGTGAACCTGTAGACATGGATGCTGAACTCGAGGATGATGACGA

CGGATTGTTCGGAGAGTAA

SEQ ID NO: 128 = construct RS1.7
ATGAGTGCCGAACAGCGTAAAAAGAAAAAAACCACCACCACGACCCAAGGACGTGGAGCTGAAGTTGCTATGGCGGA

TGAGGATGGAGGCCGCTTGAGAGCTGCTGCTGAGACTACTGGAGGACCTGGATCACCGGACCCTGCCGATGGACCCC

CCCCTACACCAAACCCCGATCGTAGACCGGCTGCTAGACCTGGATTCGGATGGCATGGAGGACCCGAGGAAAACGAG

GACGAGGCGGACGACGCCGCTGCCGACGCCGACGCCGATGAGGCTGCCCCTGCTTCTGGAGAGGCGGTAGACGAACC

TGCTGCCGATGGAGTTGTTAGCCCTAGGCAATTGGCTTTGTTGGCGAGCATGGTAGACGAGGCTGTGAGAACAATCC

CTTCCCCTCCCCCTGAACGTGATGGAGCACAAGAGGAGGCGGCTAGGAGTCCCTCACCACCCCGTACACCTTCTATG

AGAGCGGATTACGGCGAGGAAAACGACGACGACGACGATGATGATGACGACGATGATCGTGATGCCGGACGCTGGGT
```

-continued

```
TAGGGGACCTGAAACCACTTCTGCTGTCCGTGGAGCATACCCCGATCCTATGGCGAGTTTGAGCCCTAGACCACCTG

CCCCGAGGAGACACCACCACCACCACCATCATAGGCGTAGACGTGCTCCTAGACGTCGTTCTGCCGCTAGTGACTCT

TCCAAATCTGGCTCTTCTTCATCTGCCTCTTCCGCTTCATCTTCGGCCTCATCGTCCTCTTCGGCATCCGCTTCGAG

TAGTGATGATGATGATGACGACGACGCTGCTAGAGCCCCGCTTCTGCTGCCGACCACGCTGCTGGCGGAACTTTGG

GAGCCGACGACGAGGAGGCGGGAGTTCCTGCTCGTGCCCCGGGAGCTGCTCCGAGGCCTTCTCCACCCCGTGCTGAA

CCTGCTCCGGCTAGAACACCGGCCGCTACTGCTGGTAGACTGGAGCGTAGACGTGCCCGTGCTGCTGTGGCTGGTAG

AGATGCTACTGGCCGCTTCACTGCTGGCCGTCCTAGACGTGTTGAACTGGACGCCGATGCTGCTTCTGGTGCTTTCT

ACGCCCGTTACCGTGATGGTTACGTGTCTGGTGAACCTTGGCCTGGCGCTGGTCCACCTCCGCCCGGACGTGTACTC

TACGGTGGATTGGGCGCCCGTACCCCCGATGACGGTGGCGACGCCAACCGCCACGATGGTGATGATGCTAGAGGCAA

ACCCGCTGCCGCTGCTGCTCCTTTGCCCTCTGCCGCCGCTTCCCCTGCCGATGAACGTGCTGTTCCTGCCGGTTACG

GTGCCGCTGGTGTGTTGGCTGCTTTGGGACGCTTGAGTGCTGCCCCGGCTAGTGCCCCCGCTGGTGCCGATGACGAT

GACGATGACGATGGTGCTGGCGGAGGCGGTGGCGGTAGACGTGCTGAGGCTGGACGTGTTGCTGTTGAATGCCTGGC

TGCCTGTAGAGGAATCTTGGAGGCTCTGGCCGAGGGATTCGACGGAGACTTGGCGGCTGTACCGGGACTGGCGGGAG

CGAGGCCTGCCGCTCCACCTCGCCCCGGTCCTGCTGGTGCTGCCGCTCCTCCTCATGCCGACGCTCCTAGACTCCGT

GCTTGGCTCCGTGAACTCCGTTTCGTTCGTGACGCTTTGGTTCTGATGAGACTGAGAGGCGACTTGAGAGTGGCTGG

AGGATCCGAGGCTGCTGTTGCTGCTGTCCGTGCTGTTTCTTTGGTTGCTGGTGCTTTGGGCCCTGCTTTGCCGAGAT

CTCCCCGTTTGTTGTCGAGTGCCGCCGCTGCTGCCGCCGATTTGTTGTTCCAAAACCAATCCCTCCGCCCTCTGCTC

GCCGACACTGTTGCCGCTGCCGATTCTCTGGCTGCTCCGGCTTCTGCCCCACGTGAAGCTCGTAAACGTAAATCACC

CGCTCCGGCTCGTGCTCCCCCTGGTGGCGCCCCTAGACCCCCTAAAAAATCCCGTGCCGATGCCCCTAGACCTGCTG

CTGCTCCCCCGCTGGTGCTGCTCCCCCCGCTCCCCCTACTCCCCCCCCACGCCCACCTCGTCCCGCTGCCCTCACA

CGCCGTCCTGCTGAGGGACCCGATCCACAAGGCGGCTGGCGTAGACAACCTCCTGGCCCATCCCATACACCGGCACC

ATCTGCCGCTGCTTTGGAGGCTTACTGTGCTCCTCGTGCTGTGGCTGAACTCACCGATCATCCGCTGTTCCCTGCTC

CCTGGCGTCCCGCCCTCATGTTCGATCCTAGAGCTTTGGCTTCCTTGGCCGCTCGTTGTGCTGCCCCTCCCCCTGGC

GGTGCTCCGGCTGCTTTCGGTCCTCTCCGTGCCTCTGGTCCACTCCGCCGTGCCGCTGCCTGGATGAGACAAGTTCC

CGACCCTGAGGATGTTAGAGTTGTGATCTTGTACTCGCCCTTGCCTGGCGAGGATTTGGCCGCTGGTAGAGCTGGCG

GTGGCCCCCTCCTGAATGGTCTGCTGAACGTGGTGGTTTGTCTTGCTTGTTGGCCGCCCTGGGAAACCGTCTGTGT

GGTCCTGCTACTGCTGCTTGGGCTGGAAACTGGACTGGCGCTCCCGATGTTTCTGCTCTCGGTGCTCAAGGAGTTTT

GCTGCTCTCTACTCGTGACTTGGCATTCGCTGGAGCTGTTGAATTCCTGGGACTCTTGGCTGGCGCTTGTGATAGGA

GACTCATCGTCGTAAACGCTGTGAGAGCTGCCGATTGGCCTGCCGATGGTCCTGTTGTGTCTCGTCAACACGCTTAC

TTGGCTTGTGAAGTGTTGCCCGCTGTCCAATGTGCTGTTCGCTGGCCTGCTGCTCGTGATCTGAGGCGTACTGTTCT

GGCTAGTGGTCGTGTTTTCGGACCTGGTGTTTTCGCTCGTGTCGAAGCTGCTCACGCTAGACTGTACCCCGATGCCC

CACCCCTCCGTTTGTGTCGTGGAGCAAACGTTCGCTACCGTGTCCGTACTCGTTTCGGACCCGATACTCTGGTTCCA

ATGTCCCCTCGTGAATACCGTCGTGCTGTTCTGCCTGCCCTCGATGGACGTGCTGCCGCTTCTGGCGCTGGTGACGC

TATGGCTCCTGGCGCTCCGGACTTCTGTGAGGATGAGGCTCACTCACATCGTGCCTGTGCCCGCTGGGGACTGGGCG

CTCCATTGAGGCCTGTATACGTGGCACTGGGCCGTGATGCTGTTAGAGGCGGACCCGCTGAATTGAGAGGCCCTCGT

CGTGAATTCTGTGCTAGGGCTCTGCTCGAACCCGATGGAGATGCTCCTCCTTTGGTACTCCGTGACGACGCCGATGC

TGGTCCTCCCCCACAAATTCGCTGGGCTAGTGCTGCTGGACGTGCTGGTACTGTATTGGCTGCTGCTGGCGGTGGCG

TTGAAGTTGTTGGTACTGCCGCTGGACTCGCTACACCTCCCCGCCGTGAACCTGTAGACATGGATGCTGAACTCGAG

GATGATGACGACGGATTGTTCGGAGAG
```

SEQ ID NO: 129 = construct RS1.8
ATGAGTGCCGAACAGCGTAAAAAGAAAAAAACCACCACCACGACCCAAGGACGTGGAGCTGAAGTTGCTATGGCGGA

TGAGGATGGAGGCCGCTTGAGAGCTGCTGCTGAGACTACTGGAGGACCTGGATCACCGGACCCTGCCGATGGACCCC

CCCCTACACCAAACCCCGATCGTAGACCGGCTGCTAGACCTGGATTCGGATGGCATGGAGGACCCGAGGAAAACGAG

GACGAGGCGGACGACGCCGCTGCCGACGCCGACGCCGATGAGGCTGCCCCTGCTTCTGGAGAGGCGGTAGACGAACC

TGCTGCCGATGGAGTTGTTAGCCCTAGGCAATTGGCTTTGTTGGCGAGCATGGTAGACGAGGCTGTGAGAACAATCC

CTTCCCCTCCCCCTGAACGTGATGGAGCACAAGAGGAGGCGGCTAGGAGTCCCTCACCACCCCGTACACCTTCTATG

AGAGCGGATTACGGCGAGGAAAACGACGACGACGACGATGATGATGACGACGATGATCGTGATGCCGGACGCTGGGT

TAGGGGACCTGAAACCACTTCTGCTGTCCGTGGAGCATACCCCGATCCTATGGCGAGTTTGAGCCCTAGACCACCTG

CCCCGAGGAGACACCACCACCACCACCATCATAGGCGTAGACGTGCTCCTAGACGTCGTTCTGCCGCTAGTGACTCT

TCCAAATCTGGCTCTTCTTCATCTGCCTCTTCCGCTTCATCTTCGGCCTCATCGTCCTCTTCGGCATCCGCTTCGAG

TAGTGATGATGATGATGACGACGACGCTGCTAGAGCCCCCGCTTCTGCTGCCGACCACGCTGCTGGCGGAACTTTGG

GAGCCGACGACGAGGAGGCGGGAGTTCCTGCTCGTGCCCGGGAGCTGCTCCGAGGCCTTCTCCACCCCGTGCTGAA

CCTGCTCCGGCTAGAACACCGGCCGCTACTGCTGGTAGACTGGAGCGTAGACGTGCCCGTGCTGCTGTGGCTGGTAG

AGATGCTACTGGCCGCTTCACTGCTGGCCGTCCTAGACGTGTTGAACTGGACGCCGATGCTGCTTCTGGTGCTTTCT

ACGCCCGTTACCGTGATGGTTACGTGTCTGGTGAACCTTGGCCTGGCGCTGGTCCACCTCCGCCCGGACGTGTACTC

TACGGTGGATTGGGCGATTCTCGCCCTGGTCTGTGGGGCGCTCCGGAGGCTGAGGAGGCTAGAGCCCGTTTCGAGGC

TTCTGGTGCCCCTGCTCCTGTTTGGGCTCCTGAATTGGGCGACGCTGCTCAACAATACGCCCTCATCACACGCTTGC

TGTACACTCCCGACGCCGAGGCTATGGGATGGCTCCAAAACCCTAGAGTTGCCCCTGGTGATGTTGCTCTGGATCAG

GCTTGTTTCCGTATCTCCGGCGCTGCTCGTAACTCTTCTTCGTTCATCTCCGGTTCTGTGGCTAGAGCTGTGCCTCA

CTTGGGATACGCCATGGCCGCTGGACGTTTCGGCTGGGGACTGGCTCATGTTGCTGCCGCTGTAGCAATGTCTAGAC

GCTACGACCGTGCTCAAAAAGGATTCTTGCTCACGTCACTGAGGCGTGCTTACGCCCCTTTGTTGGCCCGTGAAAAC

GCTGCCCTCACTGGCGCCCGTACCCCCGATGACGGTGGCGACGCCAACCGCCACGATGGTGATGATGCTAGAGGCAA

ACCCGCTGCCGCTGCTGCTCCTTTGCCCTCTGCCGCCGCTTCCCCTGCCGATGAACGTGCTGTTCCTGCCGGTTACG

GTGCCGCTGGTGTGTTGGCTGCTTTGGGACGCTTGAGTGCTGCCCCGGCTAGTGCCCCGCTGGTGCCGATGACGAT

GACGATGACGATGGTGCTGGCGGAGGCGGTGGCGGTAGACGTGCTGAGGCTGGACGTGTTGCTGTTGAATGCCTGGC

TGCCTGTAGAGGAATCTTGGAGGCTCTGGCCGAGGGATTCGACGGAGACTTGGCGGCTGTACCGGGACTGGCGGGAG

CGAGGCCTGCCGCTCCACCTCGCCCCGGTCCTGCTGGTGCTGCCGCTCCTCCTCATGCCGACGCTCCTAGACTCCGT

GCTTGGCTCCGTGAACTCCGTTTCGTTCGTGACGCTTTGGTTCTGATGAGACTGAGAGGCGACTTGAGAGTGGCTGG

AGGATCCGAGGCTGCTGTTGCTGCTGTCCGTGCTGTTTCTTTGGTTGCTGGTGCTTTGGGCCCTGCTTTGCCAGAT

CTCCCCGTTTGTTGTCGAGTGCCGCCGCTGCTGCCGCCGATTTGTTGTTCCAAAACCAATCCCTCCGCCCTCTGCTC

GCCGACACTGTTGCCGCTGCCGATTCTCTGGCTGCTCCGGCTTCTACACCGGCACCATCTGCCGCTGCTTTGGAGGC

TTACTGTGCTCCTCGTGCTGTGGCTGAACTCACCGATCATCCGCTGTTCCCTGCTCCCTGGCGTCCCGCCCTCATGT

TCGATCCTAGAGCTTTGGCTTCCTTGGCCGCTCGTTGTGCTGCCCCTCCCCTGGCGGTGCTCCGGCTGCTTTCGGT

CCTCTCCGTGCCTCTGGTCCACTCCGCCGTGCCGCTGCCTGGATGAGACAAGTTCCCGACCCTGAGGATGTTAGAGT

TGTGATCTTGTACTCGCCCTTGCCTGGCGAGGATTTGGCCGCTGGTAGAGCTGGCGGTGGCCCCCCTCCTGAATGGT

CTGCTGAACGTGGTGGTTTGTCTTGCTTGTTGGCCGCCCTGGGAAACCGTCTGTGGTCCTGCTACTGCTGCTTGG

GCTGGAAACTGGACTGGCGCTCCCGATGTTTCTGCTCTCGGTGCTCAAGGAGTTTTGCTGCTCTCTACTCGTGACTT

GGCATTCGCTGGAGCTGTTGAATTCCTGGGACTCTTGGCTGGCGCTTGTGATAGGAGACTCATCGTCGTAAACGCTG

TGAGAGCTGCCGATTGGCCTGCCGATGGTCCTGTTGTGTCTCGTCAACACGCTTACTTGGCTTGTGAAGTGTTGCCC

GCTGTCCAATGTGCTGTTCGCTGGCCTGCTGCTCGTGATCTGAGGCGTACTGTTCTGGCTAGTGGTCGTGTTTTCGG

```
ACCTGGTGTTTTCGCTCGTGTCGAAGCTGCTCACGCTAGACTGTACCCCGATGCCCCACCCCTCCGTTTGTGTCGTG
GAGCAAACGTTCGCTACCGTGTCCGTACTCGTTTCGGACCCGATACTCTGGTTCCAATGTCCCCTCGTGAATACCGT
CGTGCTGTTCTGCCTGCCCTCGATGGACGTGCTGCCGCTTCTGGCGCTGGTGACGCTATGGCTCCTGGCGCTCCGGA
CTTCTGTGAGGATGAGGCTCACTCACATCGTGCCTGTGCCCGCTGGGGACTGGGCGCTCCATTGAGGCCTGTATACG
TGGCACTGGGCCGTGATGCTGTTAGAGGCGGACCCGCTGAATTGAGAGGCCCTCGTCGTGAATTCTGTGCTAGGGCT
CTGCTCGAACCCGATGGAGATGCTCCTCCTTTGGTACTCCGTGACGACGCCGATGCTGGTCCTCCCCCACAAATTCG
CTGGGCTAGTGCTGCTGGACGTGCTGGTACTGTATTGGCTGCTGCTGGCGGTGGCGTTGAAGTTGTTGGTACTGCCG
CTGGACTCGCTACACCTCCCCGCCGTGAACCTGTAGACATGGATGCTGAACTCGAGGATGATGACGACGGATTGTTC
GGAGAG

SEQ ID NO: 130 = His tag
HHHHHH

SEQ ID NO: 131 = Tag
MSYYHHHHHH

SEQ ID NO: 132 = Secretion Signal
MKFLVNVALVFMVVYISYIYA

SEQ ID NO: 133 = UL49.5
ATGTCGTACTACCATCACCATCACCATCACATGACGGGGAAACCCGCAAGACTGGGCCGCTGGGTGGTGCTGTTGTT
CGTCGCGCTCGTCGCGGGCGTGCCCGGGGAGCCGCCGAACGCGGCAGGCGCACGCGGCGTTATCGGGGACGCGCAAT
GCCGGGGCGACAGCGCCGGTGTGGTGTCCGTCCCGGGGGTCCTGGTGCCCTTTTATCTAGGCATGACCTCGATGGGC
GTATGTATGATCGCGCACGTGTATCAGATATGCCAGCGGGCACTGGCCGCCGGGTCAGCCTGA

SEQ ID NO: 134 = UL10
ATGGGACGCCGGGCCCCAGGGGATCCCCCGAGGCCGCGCCGGGCGCCGACGTCGCGCCCGGGGCGCGGGCGGCGTG
GTGGGTCTGGTGTGTGCAGGTGGCGACGTTCATCGTCTCGGCCATCTGCGTCGTGGGGCTCCTGGTGCTGGCCTCTG
TGTTCCGGGACAGGTTTCCCTGCCTTTACGCCCCCGCGACCTCTTATGCGAAGGCGAACGCCACGGTCGAGGTGCGC
GGGGGTGTAGCCGTCCCCCTCCGGTTGGACACGCAGAGCCTGCTGGCCACGTACGCAATTACGTCTACGCTGTTGCT
GGCGGCGGCCGTGTACGCCGCGGTGGGCGCGGTGACCTCGCGCTACGAGCGCGCGCTGGATGCGCCCGTCGCCTGG
CGGCGGCCCGTATGGCGATGCCACACGCCACGCTAATCGCCGGAAACGTCTGCGCGTGGCTGTTGCAGATCACAGTC
CTGCTGCTGGCCCACCGCATCAGCCAGCTGGCCCACCTTATCTACGTCCTGCACTTTGCGTGCCTCGTGTATCTCGC
GGCCCATTTTTGCACCAGGGGGGTCCTGAGCGGGACGTACCTGCGTCAGGTTCACGGCCTGATTGACCCGGCGCCGA
CGCACCATCGTATCGTCGGTCCGGTGCGGGCAGTAATGACAAACGCCTTATTACTGGGCACCCTCCTGTGCACGGCC
GCCGCCGCGGTCTCGTTGAACACGATCGCCGCCCTGAACTTCAACTTTTCCGCCCCGAGCATGCTCATCTGCCTGAC
GACGCTGTTCGCCCTGCTTGTCGTGTCGCTGTTGTTGGTGGTCGAGGGGGTGCTGTGTCACTACGTGCGCGTGTTGG
TGGGCCCCCACCTCGGGGCCATCGCCGCCACCGGCATCGTCGGCCTGGCCTGCGAGCACTACCACACCGGTGGTTAC
TACGTGGTGGAGCAGCAGTGGCCGGGGGCCCAGACGGGAGTCCGCGTCGCCCTGGCGCTCGTCGCCGCCTTTGCCCT
CGCCATGGCCGTGCTTCGGTGCACGCGCGCCTACCTGTATCACCGGCGACACCACACTAAATTTTTCGTGCGCATGC
GCGACACCCGGCACCGCGCCCATTCGGCGCTTCGACGCGTACGCAGCTCCATGCGCGGTTCTAGGCGTGGCGGGCCG
CCCGGAGACCCGGGCTACGCGGAAACCCCCTACGCGAGCGTGTCCCACCACGCCGAGATCGACCGGTATGGGGATTC
CGACGGGGACCCGATCTACGACGAAGTGGCCCCCGACCACGAGGCCGAGCTCTACGCCCGAGTGCAACGCCCCGGGC
CTGTGCCCGACGCCGAGCCCATTTACGACACCGTGGAGGGGTATGCGCCAAGGTCCGCGGGGAGCCGGTGTACAGC
ACCGTTCGGCGATGGTAG

SEQ ID NO: 135 = uracil DNA glycosylase encoded by UL2
MKRARSRSPSPPSRPSSPERTPPHGGSPRREVGAGILASDATSHVCIASHPGSGAGQPTRLAAGSAVQRRRPRGCPP
GVMFSASTTPEQPLGLSGDATPPLPTSVPLDWAAFRRAFLIDDAWRPLLEPELANPLTARLLAEYDRRCQTEEVLPP
REDVFSWTRYCTPDDVRVVIIGQDPYHHPGQAHGLAFSVRADVPVPPSLRNVLAAVKNCYPDARMSGRGCLEKWARD
```

-continued

GVLLLNTTLTVKRGAAASHSKLGWDRFVGGVVQRLAARRPGLVFMLWGAHAQNAIRPDPRQHYVLKFSHPSPLSKVP

FGTCQHFLAANRYLETRDIMPIDWSV

SEQ ID NO: 136 = gL2 secreted v.2 encoded by construct UL1s v.2
AGSQATEYVLRSVIAKEVGDILRVPCMRTPADDVSWRYEAPSVIDYARIDGIFLRYHCPGLDTFLWDRHAQRAYLVN

PFLFAAGFLEDLSHSVFPADTQETTTRRALYKEIRDALGSRKQAVSHAPVRAGCVNFDYSRTRRCVGRRDLRPANTT

STWEPPVSSDDEASSQSKPLATQPPVLALSNAPPRRVSPTRGRRRHTRLRRN

SEQ ID NO: 137 = UL1s v.2
ATGAAGTTCCTCGTGAACGTGGCCCTGGTGTTCATGGTGGTGTACATCAGCTACATCTACGCCGCCGGGTCACAGGC

AACCGAATATGTTCTTCGTAGTGTTATTGCCAAAGAGGTGGGGGACATACTAAGAGTGCCTTGCATGCGGACCCCCG

CGGACGATGTTTCTTGGCGCTACGAGGCCCCGTCCGTTATTGACTATGCCCGCATAGACGGAATATTTCTTCGCTAT

CACTGCCCGGGGTTGGACACGTTTTTGTGGGATAGGCACGCCCAGAGGGCGTATCTTGTTAACCCCTTTCTCTTTGC

GGCGGGATTTTTGGAGGACTTGAGTCACTCTGTGTTTCCGGCCGACACCCAGGAAACAACGACGCGCCGGGCCCTTT

ATAAAGAGATACGCGATGCGTTGGGCAGTCGAAAACAGGCCGTCAGCCACGCACCCGTCAGGGCCGGGTGTGTAAAC

TTTGACTACTCACGCACTCGCCGCTGCGTCGGGCGACGCGATTTACGGCCTGCCAACACCACGTCAACGTGGGAACC

GCCTGTGTCGTCGGACGATGAAGCGAGCTCGCAGTCGAAGCCCCTCGCCACCCAGCCGCCCGTCCTCGCCCTTTCGA

ACGCCCCCCACGGCGGGTCTCCCCGACGCGAGGTCGGCGCCGGCATACTCGCCTCCGACGCAACCATCACCATCAC

CATCACTGA

SEQ ID NO: 138 = ICP4 internal fragment encoded by construct RS1.9
(deletion of #391-544 and #786-821)
MSAEQRKKKTTTTQGRGAEVAMADEDGGRLRAAAETTGGPGSPDPADGPPPTPNPDRRPAARPGFGWHGGPEENE

DEADDAAADADADEAAPASGEAVDEPAADGVVSPRQLALLASMVDEAVRTIPSPPPERDGAQEEAARSPSPPRTPSM

RADYGEENDDDDDDDDDDRDAGRWVRGPETTSAVRGAYPDPMASLSPRPPAPRRHHHHHHRRRRAPRRRSAASDS

SKSGSSSSASSASSSASSSSSASASSSDDDDDDDAARAPASAADHAAGGTLGADDEEAGVPARAPGAAPRPSPPRAE

PAPARTPAATAGRLERRRARAAVAGRDATGRFTAGRPRRVELDADAASGAFYARYRDGYVSGEPWPGAGPPPPGRVL

YGGLGRTPDDGGDANRHDGDDARGKPAAAAAPLPSAAASPADERAVPAGYGAAGVLAALGRLSAAPASAPAGADDDD

DDDGAGGGGGRRAEAGRVAVECLAACRGILEALAEGFDGDLAAVPGLAGARPAAPPRPGPAGAAAPPHADAPRLRA

WLRELRFVRDALVLMRLRGDLRVAGGSEAAVAAVRAVSLVAGALGPALPRSPRLLSSAAAAAADLLFQNQSLRPLLA

DTVAAADSLAAPASAAAPPAGAAPPAPPTPPPRPPRPAALTRRPAEGPDPQGGWRRQPPGPSHTPAPSAAALEAYCA

PRAVAELTDHPLFPAPWRPALMFDPRALASLAARCAAPPPGGAPAAFGPLRASGPLRRAAAWMRQVPDPEDVRVVIL

YSPLPGEDLAAGRAGGGPPPEWSAERGGLSCLLAALGNRLCGPATAAWAGNWTGAPDVSALGAQGVLLLSTRDLAFA

GAVEFLGLLAGACDRRLIVVNAVRAADWPADGPVVSRQHAYLACEVLPAVQCAVRWPAARDLRRTVLASGRVFGPGV

FARVEAAHARLYPDAPPLRLCRGANVRYRVRTRFGPDTLVPMSPREYRRAVLPALDGRAAASGAGDAMAPGAPDFCE

DEAHSHRACARWGLGAPLRPVYVALGRDAVRGGPAELRGPRREFCARALLEPDGDAPPLVLRDDADAGPPPQIRWAS

AAGRAGTVLAAAGGGVEVVGTAAGLATPPRREPVDMDAELEDDDDGLFGE

SEQ ID NO: 139 = ICP4 internal fragment encoded by construct RS1.10
(deletion of #391-508 and #786-821)
MSAEQRKKKTTTTQGRGAEVAMADEDGGRLRAAAETTGGPGSPDPADGPPPTPNPDRRPAARPGFGWHGGPEENE

DEADDAAADADADEAAPASGEAVDEPAADGVVSPRQLALLASMVDEAVRTIPSPPPERDGAQEEAARSPSPPRTPSM

RADYGEENDDDDDDDDDDRDAGRWVRGPETTSAVRGAYPDPMASLSPRPPAPRRHHHHHHRRRRAPRRRSAASDS

SKSGSSSSASSASSSASSSSSASASSSDDDDDDDAARAPASAADHAAGGTLGADDEEAGVPARAPGAAPRPSPPRAE

PAPARTPAATAGRLERRRARAAVAGRDATGRFTAGRPRRVELDADAASGAFYARYRDGYVSGEPWPGAGPPPPGRVL

YGGLGAMSRRYDRAQKGFLLTSLRRAYAPLLARENAALTGARTPDDGGDANRHDGDDARGKPAAAAAPLPSAAASPA

DERAVPAGYGAAGVLAALGRLSAAPASAPAGADDDDDDGAGGGGGRRAEAGRVAVECLAACRGILEALAEGFDGD

LAAVPGLAGARPAAPPRPGPAGAAAPPHADAPRLRAWLRELRFVRDALVLMRLRGDLRVAGGSEAAVAAVRAVSLVA

-continued

GALGPALPRSPRLLSSAAAAAADLLFQNQSLRPLLADTVAAADSLAAPASA<u>AAPPA</u>GAAPPAPPTPPPRPPRPAALT

RRPAEGPDPQGGWRRQPPGPSHTPAPSAAALEAYCAPRAVAELTDHPLFPAPWRPALMFDPRALASLAARCAAPPPG

GAPAAFGPLRASGPLRRAAAWMRQVPDPEDVRVVILYSPLPGEDLAAGRAGGGPPPEWSAERGGLSCLLAALGNRLC

GPATAAWAGNWTGAPDVSALGAQGVLLLSTRDLAFAGAVEFLGLLAGACDRRLIVVNAVRAADWPADGPVVSRQHAY

LACEVLPAVQCAVRWPAARDLRRTVLASGRVFGPGVFARVEAAHARLYPDAPPLRLCRGANVRYRVRTRFGPDTLVP

MSPREYRRAVLPALDGRAAASGAGDAMAPGAPDFCEDEAHSHRACARWGLGAPLRPVYVALGRDAVRGGPAELRGPR

REFCARALLEPDGDAPPLVLRDDADAGPPPQIRWASAAGRAGTVLAAAGGGVEVVGTAAGLATPPRREPVDMDAELE

DDDDGLFGE

SEQ ID NO: 140 = construct RS1.9
ATGAGTGCCGAACAGCGTAAAAAGAAAAAAACCACCACCACGACCCAAGGACGTGGAGCTGAAGTTGCTATGGCGGA

TGAGGATGGAGGCCGCTTGAGAGCTGCTGCTGAGACTACTGGAGGACCTGGATCACCGGACCCTGCCGATGGACCCC

CCCCTACACCAAACCCCGATCGTAGACCGGCTGCTAGACCTGGATTCGGATGGCATGGAGGACCCGAGGAAAACGAG

GACGAGGCGGACGACGCCGCTGCCGACGCCGACGCCGATGAGGCTGCCCCTGCTTCTGGAGAGGCGGTAGACGAACC

TGCTGCCGATGGAGTTGTTAGCCCTAGGCAATTGGCTTTGTTGGCGAGCATGGTAGACGAGGCTGTGAGAACAATCC

CTTCCCCTCCCCCTGAACGTGATGGAGCACAAGAGGAGGCGGCTAGGAGTCCCTCACCACCCCGTACACCTTCTATG

AGAGCGGATTACGGCGAGGAAAACGACGACGACGACGATGATGATGACGACGATGATCGTGATGCCGGACGCTGGGT

TAGGGGACCTGAAACCACTTCTGCTGTCCGTGGAGCATACCCCGATCCTATGGCGAGTTTGAGCCCTAGACCACCTG

CCCCGAGGAGACACCACCACCACCACCATCATAGGCGTAGACGTGCTCCTAGACGTCGTTCTGCCGCTAGTGACTCT

TCCAAATCTGGCTCTTCTTCATCTGCCTCTTCCGCTTCATCTTCGGCCTCATCGTCCTCTTCGGCATCCGCTTCGAG

TAGTGATGATGATGATGACGACGACGCTGCTAGAGCCCCCGCTTCTGCTGCCGACCACGCTGCTGGCGGAACTTTGG

GAGCCGACGACGAGGAGGCGGGAGTTCCTGCTCGTGCCCGGGAGCTGCTCCGAGGCCTTCTCCACCCCGTGCTGAA

CCTGCTCCGGCTAGAACACCGGCCGCTACTGCTGGTAGACTGGAGCGTAGACGTGCCCGTGCTGCTGTGGCTGGTAG

AGATGCTACTGGCCGCTTCACTGCTGGCCGTCCTAGACGTGTTGAACTGGACGCCGATGCTGCTTCTGGTGCTTTCT

ACGCCCGTTACCGTGATGGTTACGTGTCTGGTGAACCTTGGCCTGGCGCTGGTCCACCTCCGCCCGGACGTGTACTC

TACGGTGGATTGGGCCGTACCCCCGATGACGGTGGCGACGCCAACCGCCACGATGGTGATGATGCTAGAGGCAAACC

CGCTGCCGCTGCTGCTCCTTTGCCCTCTGCCGCCGCTTCCCCTGCCGATGAACGTGCTGTTCCTGCCGGTTACGGTG

CCGCTGGTGTGTTGGCTGCTTTGGGACGCTTGAGTGCTGCCCCGGCTAGTGCCCCCGCTGGTGCCGATGACGATGAC

GATGACGATGGTGCTGGCGGAGGCGGTGGCGGTAGACGTGCTGAGGCTGGACGTGTTGCTGTTGAATGCCTGGCTGC

CTGTAGAGGAATCTTGGAGGCTCTGGCCGAGGGATTCGACGGAGACTTGGCGGCTGTACCGGGACTGGCGGGAGCGA

GGCCTGCCGCTCCACCTCGCCCCGGTCCTGCTGGTGCTGCCGCTCCTCCTCATGCCGACGCTCCTAGACTCCGTGCT

TGGCTCCGTGAACTCCGTTTCGTTCGTGACGCTTTGGTTCTGATGAGACTGAGAGGCGACTTGAGAGTGGCTGGAGG

ATCCGAGGCTGCTGTTGCTGCTGTCCGTGCTGTTTCTTTGGTTGCTGGTGCTTTGGGCCCTGCTTTGCCGAGATCTC

CCCGTTTGTTGTCGAGTGCCGCCGCTGCTGCCGCCGATTTGTTGTTCCAAAACCAATCCCTCCGCCCTCTGCTCGCC

GACACTGTTGCCGCTGCCGATTCTCTGGCTGCTCCGGCTTCTGCTGCTGCTCCCCCGCTGGTGCTGCTCCCCCCGC

TCCCCCTACTCCCCCCCCACGCCCACCTCGTCCCGCTGCCCTCACACGCCGTCCTGCTGAGGGACCCGATCCACAAG

GCGGCTGGCGTAGACAACCTCCTGGCCCATCCCATACACCGGCACCATCTGCCGCTGCTTTGGAGGCTTACTGTGCT

CCTCGTGCTGTGGCTGAACTCACCGATCATCCGCTGTTCCCTGCTCCCTGGCGTCCCGCCCTCATGTTCGATCCTAG

AGCTTTGGCTTCCTTGGCCGCTCGTTGTGCTGCCCCTCCCCCTGGCGGTGCTCCGGCTGCTTTCGGTCCTCTCCGTG

CCTCTGGTCCACTCCGCCGTGCCGCTGCCTGGATGAGACAAGTTCCCGACCCTGAGGATGTTAGAGTTGTGATCTTG

TACTCGCCCTTGCCTGGCGAGGATTTGGCCGCTGGTAGAGCTGGCGGTGGCCCCCCTCCTGAATGGTCTGCTGAACG

TGGTGGTTTGTCTTGCTTGTTGGCCGCCCTGGGAAACCGTCTGTGTGGTCCTGCTACTGCTGCTTGGGCTGGAAACT

```
                          -continued
GGACTGGCGCTCCCGATGTTTCTGCTCTCGGTGCTCAAGGAGTTTTGCTGCTCTCTACTCGTGACTTGGCATTCGCT

GGAGCTGTTGAATTCCTGGGACTCTTGGCTGGCGCTTGTGATAGGAGACTCATCGTCGTAAACGCTGTGAGAGCTGC

CGATTGGCCTGCCGATGGTCCTGTTGTGTCTCGTCAACACGCTTACTTGGCTTGTGAAGTGTTGCCCGCTGTCCAAT

GTGCTGTTCGCTGGCCTGCTGCTCGTGATCTGAGGCGTACTGTTCTGGCTAGTGGTCGTGTTTTCGGACCTGGTGTT

TTCGCTCGTGTCGAAGCTGCTCACGCTAGACTGTACCCCGATGCCCCACCCCTCCGTTTGTGTCGTGGAGCAAACGT

TCGCTACCGTGTCCGTACTCGTTTCGGACCCGATACTCTGGTTCCAATGTCCCCTCGTGAATACCGTCGTGCTGTTC

TGCCTGCCCTCGATGGACGTGCTGCCGCTTCTGGCGCTGGTGACGCTATGGCTCCTGGCGCTCCGGACTTCTGTGAG

GATGAGGCTCACTCACATCGTGCCTGTGCCCGCTGGGGACTGGGCGCTCCATTGAGGCCTGTATACGTGGCACTGGG

CCGTGATGCTGTTAGAGGCGGACCCGCTGAATTGAGAGGCCCTCGTCGTGAATTCTGTGCTAGGGCTCTGCTCGAAC

CCGATGGAGATGCTCCTCCTTTGGTACTCCGTGACGACGCCGATGCTGGTCCTCCCCCACAAATTCGCTGGGCTAGT

GCTGCTGGACGTGCTGGTACTGTATTGGCTGCTGCTGGCGGTGGCGTTGAAGTTGTTGGTACTGCCGCTGGACTCGC

TACACCTCCCCGCCGTGAACCTGTAGACATGGATGCTGAACTCGAGGATGATGACGACGGATTGTTCGGAGAG

SEQ ID NO: 141 = construct RS1.10
ATGAGTGCCGAACAGCGTAAAAAGAAAAAAACCACCACCACGACCCAAGGACGTGGAGCTGAAGTTGCTATGGCGGA

TGAGGATGGAGGCCGCTTGAGAGCTGCTGCTGAGACTACTGGAGGACCTGGATCACCGGACCCTGCCGATGGACCCC

CCCCTACACCAAACCCCGATCGTAGACCGGCTGCTAGACCTGGATTCGGATGGCATGGAGGACCCGAGGAAAACGAG

GACGAGGCGGACGACGCCGCTGCCGACGCCGACGCCGATGAGGCTGCCCCTGCTTCTGGAGAGGCGGTAGACGAACC

TGCTGCCGATGGAGTTGTTAGCCCTAGGCAATTGGCTTTGTTGGCGAGCATGGTAGACGAGGCTGTGAGAACAATCC

CTTCCCCTCCCCCTGAACGTGATGGAGCACAAGAGGAGGCGGCTAGGAGTCCCTCACCACCCCGTACACCTTCTATG

AGAGCGGATTACGGCGAGGAAAACGACGACGACGACGATGATGATGACGACGATGATCGTGATGCCGGACGCTGGGT

TAGGGGACCTGAAACCACTTCTGCTGTCCGTGGAGCATACCCCGATCCTATGGCGAGTTTGAGCCCTAGACCACCTG

CCCCGAGGAGACACCACCACCACCACCATCATAGGCGTAGACGTGCTCCTAGACGTCGTTCTGCCGCTAGTGACTCT

TCCAAATCTGGCTCTTCTTCATCTGCCTCTTCCGCTTCATCTTCGGCCTCATCGTCCTCTTCGGCATCCGCTTCGAG

TAGTGATGATGATGATGACGACGACGCTGCTAGAGCCCCCGCTTCTGCTGCCGACCACGCTGCTGGCGGAACTTTGG

GAGCCGACGACGAGGAGGCGGGAGTTCCTGCTCGTGCCCCGGGAGCTGCTCCGAGGCCTTCTCCACCCCGTGCTGAA

CCTGCTCCGGCTAGAACACCGGCCGCTACTGCTGGTAGACTGGAGCGTAGACGTGCCCGTGCTGCTGTGGCTGGTAG

AGATGCTACTGGCCGCTTCACTGCTGGCCGTCCTAGACGTGTTGAACTGGACGCCGATGCTGCTTCTGGTGCTTTCT

ACGCCCGTTACCGTGATGGTTACGTGTCTGGTGAACCTTGGCCTGGCGCTGGTCCACCTCCGCCCGGACGTGTACTC

TACGGTGGATTGGGCGCAATGTCTAGACGCTACGACCGTGCTCAAAAAGGATTCTTGCTCACGTCACTGAGGCGTGC

TTACGCCCCTTTGTTGGCCCGTGAAAACGCTGCCCTCACTGGCGCCCGTACCCCGATGACGGTGGCGACGCCAACC

GCCACGATGGTGATGATGCTAGAGGCAAACCCGCTGCCGCTGCTGCTCCTTTGCCCTCTGCCGCCGCTTCCCCTGCC

GATGAACGTGCTGTTCCTGCCGGTTACGGTGCCGCTGGTGTGTTGGCTGCTTTGGGACGCTTGAGTGCTGCCCCGGC

TAGTGCCCCCGCTGGTGCCGATGACGATGACGATGACGATGGTGCTGGCGGAGGCGGTGGCGGTAGACGTGCTGAGG

CTGGACGTGTTGCTGTTGAATGCCTGGCTGCCTGTAGAGGAATCTTGGAGGCTCTGGCCGAGGGATTCGACGGAGAC

TTGGCGGCTGTACCGGGACTGGCGGGAGCGAGGCCTGCCGCTCCACCTCGCCCCGGTCCTGCTGGTGCTGCCGCTCC

TCCTCATGCCGACGCTCCTAGACTCCGTGCTTGGCTCCGTGAACTCCGTTTCGTTCGTGACGCTTTGGTTCTGATGA

GACTGAGAGGCGACTTGAGAGTGGCTGGAGGATCCGAGGCTGCTGTTGCTGCTGTCCGTGCTGTTTCTTTGGTTGCT

GGTGCTTTGGGCCCTGCTTTGCCGAGATCTCCCCGTTTGTTGTCGAGTGCCGCCGCTGCTGCCGCCGATTTGTTGTT

CCAAAACCAATCCCTCCGCCCTCTGCTCGCCGACACTGTTGCCGCTGCCGATTCTCTGGCTGCTCCGGCTTCTGCTG

CTGCTCCCCCCGCTGGTGCTGCTCCCCCCGCTCCCCCTACTCCCCCCCCACGCCCACCTCGTCCCGCTGCCCTCACA

CGCCGTCCTGCTGAGGGACCCGATCCACAAGGCGGCTGGCGTAGACAACCTCCTGGCCCATCCCATACACCGGCACC
```

```
                              -continued
ATCTGCCGCTGCTTTGGAGGCTTACTGTGCTCCTCGTGCTGTGGCTGAACTCACCGATCATCCGCTGTTCCCTGCTC

CCTGGCGTCCCGCCCTCATGTTCGATCCTAGAGCTTTGGCTTCCTTGGCCGCTCGTTGTGCTGCCCCTCCCCCTGGC

GGTGCTCCGGCTGCTTTCGGTCCTCTCCGTGCCTCTGGTCCACTCCGCCGTGCCGCTGCCTGGATGAGACAAGTTCC

CGACCCTGAGGATGTTAGAGTTGTGATCTTGTACTCGCCCTTGCCTGGCGAGGATTTGGCCGCTGGTAGAGCTGGCG

GTGGCCCCCTCCTGAATGGTCTGCTGAACGTGGTGGTTTGTCTTGCTTGTTGGCCGCCCTGGGAAACCGTCTGTGT

GGTCCTGCTACTGCTGCTTGGGCTGGAAACTGGACTGGCGCTCCCGATGTTTCTGCTCTCGGTGCTCAAGGAGTTTT

GCTGCTCTCTACTCGTGACTTGGCATTCGCTGGAGCTGTTGAATTCCTGGGACTCTTGGCTGGCGCTTGTGATAGGA

GACTCATCGTCGTAAACGCTGTGAGAGCTGCCGATTGGCCTGCCGATGGTCCTGTTGTGTCTCGTCAACACGCTTAC

TTGGCTTGTGAAGTGTTGCCCGCTGTCCAATGTGCTGTTCGCTGGCCTGCTGCTCGTGATCTGAGGCGTACTGTTCT

GGCTAGTGGTCGTGTTTTCGGACCTGGTGTTTTCGCTCGTGTCGAAGCTGCTCACGCTAGACTGTACCCCGATGCCC

CACCCCTCCGTTTGTGTCGTGGAGCAAACGTTCGCTACCGTGTCCGTACTCGTTTCGGACCCGATACTCTGGTTCCA

ATGTCCCCTCGTGAATACCGTCGTGCTGTTCTGCCTGCCCTCGATGGACGTGCTGCCGCTTCTGGCGCTGGTGACGC

TATGGCTCCTGGCGCTCCGGACTTCTGTGAGGATGAGGCTCACTCACATCGTGCCTGTGCCCGCTGGGGACTGGGCG

CTCCATTGAGGCCTGTATACGTGGCACTGGGCCGTGATGCTGTTAGAGGCGGACCCGCTGAATTGAGAGGCCCTCGT

CGTGAATTCTGTGCTAGGGCTCTGCTCGAACCCGATGGAGATGCTCCTCCTTTGGTACTCCGTGACGACGCCGATGC

TGGTCCTCCCCCACAAATTCGCTGGGCTAGTGCTGCTGGACGTGCTGGTACTGTATTGGCTGCTGCTGGCGGTGGCG

TTGAAGTTGTTGGTACTGCCGCTGGACTCGCTACACCTCCCCGCCGTGAACCTGTAGACATGGATGCTGAACTCGAG

GATGATGACGACGGATTGTTCGGAGAG
```

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Thus, for example, reference to "a cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antigen, any method of administration, any prophylactic and/or therapeutic application, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

Other Embodiments

Those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims.

What is claimed is:

1. A method of treating HSV-1 and/or HSV-2 infection in a subject, the method comprising:
   administering an antiviral therapy to a subject receiving a vaccine formulation, so that efficacy of the vaccine formulation and/or the antiviral therapy is improved in the subject over a specified time period relative to a subject receiving only the vaccine formulation or the antiviral therapy;
   wherein the vaccine formulation comprises an HSV-2 gD2 polypeptide, wherein the gD2 polypeptide has an internal deletion of all or part of the transmembrane domain, and an HSV-2 ICP4 polypeptide or an immunogenic fragment comprising at least 8 contiguous amino acids of HSV-2 ICP4 polypeptide;

wherein the antiviral therapy comprises famciclovir, valaciclovir, aciclovir or a combination thereof;

wherein the antiviral therapy is administered during and/or prior to the subject receiving the vaccine formulation; and wherein the efficacy of the vaccine formulation and/or the antiviral therapy is measured or indicated by a decrease of one or more herpes signs or symptoms or increased health-related quality of life.

2. The method of claim 1, further comprising administering the antiviral therapy to one or more additional subjects receiving the vaccine formulation, wherein the antiviral therapy is administered during and/or prior to the subject receiving the vaccine formulation.

3. The method of claim 2, wherein the efficacy of the vaccine formulation and/or the antiviral therapy is improved in the one or more additional subjects over a specified time period relative to subjects receiving only the vaccine formulation or the antiviral therapy.

4. The method of claim 3, wherein the efficacy of the vaccine formulation and/or the antiviral therapy is measured or indicated by an increase in a proportion of subjects who exhibit a decrease in one or more herpes signs or symptoms, and/or an increase in health-related quality of life.

5. A method of treating HSV-1 and/or HSV-2 infection in a subject, the method comprising:
  administering a vaccine formulation to a subject receiving or who has received an antiviral therapy, so that efficacy of the vaccine formulation and/or antiviral therapy is improved in the subject over a specified time period relative to a subject receiving only the vaccine formulation or the antiviral therapy;
  wherein the vaccine formulation comprises an HSV-2 gD2 polypeptide, wherein the gD2 polypeptide has an internal deletion of all or part of the transmembrane domain and an HSV-2 ICP4 polypeptide or an immunogenic fragment comprising at least 8 contiguous amino acids of HSV-2 ICP4 polypeptide;
  wherein the antiviral therapy comprises famciclovir, valaciclovir, aciclovir or a combination thereof;
  wherein the vaccine formulation is administered during the subject receiving and/or after the subject has received the antiviral therapy; and
  wherein the efficacy of the vaccine formulation and/or the antiviral therapy is measured or indicated by a decrease of one or more herpes signs or symptoms or increased health-related quality of life.

6. The method of claim 5, further comprising administering the vaccine formulation to one or more additional subjects receiving or who have received the antiviral therapy.

7. The method of claim 6, wherein the efficacy of the vaccine formulation and/or the antiviral therapy is improved in the one or more additional subjects over a specified time period relative to subjects receiving only the vaccine formulation or the antiviral therapy.

8. The method of claim 7, wherein the efficacy of the vaccine formulation and/or the antiviral therapy is measured or indicated by an increase in one or more herpes signs or symptoms and/or an increase in health-related quality of life.

9. A method of treating HSV-1 and/or HSV 2 infection in a subject, the method comprising:
  administering a vaccine formulation to a subject receiving or who has received antiviral therapy, so that efficacy of the antiviral therapy is improved in the subject over a specified time period relative to a subject receiving only the antiviral therapy;
  wherein the vaccine formulation comprises an HSV-2 gD2 polypeptide, wherein the gD2 polypeptide has an internal deletion of all or part of the transmembrane domain and an HSV-2 ICP4 polypeptide or an immunogenic fragment comprising at least 8 contiguous amino acids of HSV-2 ICP4 polypeptide;
  wherein the antiviral therapy comprises famciclovir, valaciclovir, aciclovir or a combination thereof;
  wherein the vaccine formulation is administered during the subject receiving and/or after the subject has received the antiviral therapy; and
  wherein the efficacy of the antiviral therapy is measured or indicated by decreased lesion score.

10. The method of claim 9, further comprising administering the vaccine formulation to one or more additional subjects receiving or who have received the antiviral therapy.

11. The method of claim 10, wherein the efficacy of the antiviral therapy is improved in the one or more additional subjects over a specified time period relative to subjects receiving only the antiviral therapy.

12. The method of claim 11, wherein the efficacy of the antiviral therapy is measured or indicated by an increased proportion of subjects who exhibit decreased lesion score.

13. The method of claim 1, wherein the efficacy of the vaccine formulation and/or antiviral therapy is assessed at, at least 3 months, 6 months, 12 months, 18 months, 24 months, 3 years, 4 years, 5 years, 6 years, 7 years, 8 years, 9 years, 10 years after administration of therapy.

14. The method of claim 1, wherein the decrease in one or more herpes signs or symptoms is a decrease in the percentage of days with herpes-related signs or symptoms and/or a decrease in the magnitude of herpes-related signs or symptoms.

15. The method of claim 1, wherein the efficacy of the vaccine formulation is measured or indicated by an increase in humoral response and/or an increase in cellular response.

16. The method of claim 1, wherein the subject: is not receiving therapy comprising tenofovir, lysine, a supplement or medication, other than valacyclovir; does not have a history of ocular herpes infection, herpes-related erythema multiforme, herpes meningitis or herpes encephalitis; does not have active genital HSV-2 lesions; is not immunocompromised; is not receiving systemic immunosuppressive medication; does not have an autoimmune disease; has not previously had an autoimmune disease; does not have HIV, hepatitis B or hepatitis C; does not have history of hypersensitivity to any component of the vaccine formulation; does not have a clinically significant laboratory abnormality except for (i) creatinine kinase in subjects with an identified exercise regimen and hepatic and renal enzyme levels within normal limits or (ii) isolated Grade 2 unconjugated bilirubin in fasting subjects with a history of Gilbert's syndrome; has not received any other vaccine containing an HSV-2 antigen; has not received an investigational product within 30 days prior to the first dose of the vaccine formulation; has not received a blood product within 90 days prior to the first dose of the vaccine formulation; has not received a live vaccine within 28 days prior to the first dose of the vaccine formulation; has not received any other vaccine within 14 days prior to the first dose of the vaccine formulation; does not receive any other vaccine from the first dose until 28 days after the third dose; is not pregnant or nursing; or any combination thereof.

17. The method of claim 1, wherein the subject: is male, female or non-pregnant female; is at least 18 years old and less than 51 years old, is at least 10, 11, 12, 13, 14, 15, 16 or 17 years old, or is 51 years or older; is receiving antiviral therapy; has a history of at least one genital herpes outbreak while on antiviral therapy within 6 months of treatment; has a history of greater than 5 outbreaks of genital herpes within one year if not receiving antiviral therapy; has been diagnosed with genital herpes infection for greater than 1 year; uses contraception for 28 days before and 90days after treatment with the vaccine formulation; or any combination thereof.

18. The method of claim 1, further comprising administering the vaccine formulation concurrently with or following administration of the antiviral therapy.

19. The method of claim 1, wherein the vaccine formulation comprises an HSV-2 gD2 polypeptide comprising an amino acid sequence having at least 85%, 90%, 95%, 97%, 98%, or 99% identity to SEQ ID NO:4, and an HSV-2 ICP4 polypeptide comprising an amino acid sequence having at least 85%, 90%, 95%, 97%, 98%, or 99% identity to SEQ ID NO:2.

20. The method of claim 1, wherein the vaccine formulation comprises an adjuvant.

21. The vaccine formulation of claim 20, wherein the adjuvant comprises one or more saponin fractions.

22. The method of claim 1, wherein the subject receives suppressive antiviral therapy.

23. The method of claim 18, wherein the vaccine formulation is administered in at least one dose, at least two doses, at least three doses, at least four doses, at least 5 doses or more.

24. The method of claim 18, wherein the vaccine formulation is administered at intervals of about 7 days, 14 days, 21 days, 28 days, 35 days, 42 days, 49 days, 56 days or longer.

25. The method of claim 1, wherein the HSV-1 and/or HSV-2 infection is a genital herpes infection.

26. The method of claim 1, wherein the vaccine formulation comprises about 10 μg, 20 μg, 30 μg, 60 μg, or 100 μg of each of the gD2 polypeptide and the ICP4 polypeptide and/or about 25 μg, 50 μg or 75 μg of adjuvant.

27. The method of claim 26, wherein the vaccine formulation comprises about 60 μg of the gD2 polypeptide, about 60 μg of the ICP4 polypeptide and about 50 μg of adjuvant.

* * * * *

UNITED STATES PATENT AND TRADEMARK OFFICE
CERTIFICATE OF CORRECTION

PATENT NO. : 10,350,288 B2
APPLICATION NO. : 15/717849
DATED : July 16, 2019
INVENTOR(S) : Seth Vollmer Hetherington Page 1 of 1

It is certified that error appears in the above-identified patent and that said Letters Patent is hereby corrected as shown below:

In the Claims

In Claim 8, Column 363, Line 48, replace "an increase in one or more herpes signs" with -- a decrease in one or more herpes signs --;

In Claim 17, Column 364, Line 65, replace "90days" with -- 90 days --.

Signed and Sealed this
Fourteenth Day of April, 2020

Andrei Iancu
*Director of the United States Patent and Trademark Office*